US011737355B2

(12) United States Patent
Uno

(10) Patent No.: US 11,737,355 B2
(45) Date of Patent: Aug. 22, 2023

(54) ORGANIC ELECTROLUMINESCENCE DEVICE AND AMINE COMPOUND FOR ORGANIC ELECTROLUMINESCENCE DEVICE

(71) Applicant: Samsung Display Co., Ltd., Yongin-si (KR)

(72) Inventor: Takuya Uno, Tsurumi-ku (JP)

(73) Assignee: Samsung Display Co., Ltd., Yongin-si (KR)

( * ) Notice: Subject to any disclaimer, the term of this patent is extended or adjusted under 35 U.S.C. 154(b) by 532 days.

(21) Appl. No.: 16/455,353

(22) Filed: Jun. 27, 2019

(65) Prior Publication Data

US 2020/0106022 A1 Apr. 2, 2020

(30) Foreign Application Priority Data

Sep. 28, 2018 (KR) ........................ 10-2018-0115457

(51) Int. Cl.
*C07D 471/04* (2006.01)
*H10K 50/11* (2023.01)
(Continued)

(52) U.S. Cl.
CPC ......... *H10K 85/636* (2023.02); *C07D 471/04* (2013.01); *C09K 11/06* (2013.01);
(Continued)

(58) Field of Classification Search
None
See application file for complete search history.

(56) References Cited

U.S. PATENT DOCUMENTS 6,461,538 B2 10/2002 Taguchi
9,997,724 B2 6/2018 Kim et al.

FOREIGN PATENT DOCUMENTS

KR 10-2010-0113204 A 10/2010
KR 10-2012-0083243 A 7/2012
(Continued)

OTHER PUBLICATIONS

KR-20190033218 machine translation, from Google patents, downloaded Nov. 29, 2021.*
(Continued)

*Primary Examiner* — Clinton A Brooks
(74) *Attorney, Agent, or Firm* — Lewis Roca Rothgerber Christie LLP

(57) ABSTRACT

An organic electroluminescence device according to embodiments of the present disclosure includes a first electrode, a second electrode opposite the first electrode, and at least one organic layer between the first electrode and the second electrode, wherein the at least one organic layer includes an amine compound represented by Formula 1, and HT in Formula 1 includes a pyridoindole moiety represented by Formula 2. Improved device efficiency and life characteristics may be achieved when the amine compound represented by Formula 1 is included in the organic electroluminescence device.

Formula 1

(Continued)

-continued

Formula 2

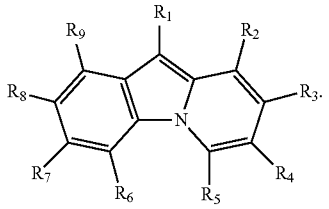

25 Claims, 2 Drawing Sheets

(51) Int. Cl.
*H10K 50/15* (2023.01)
*H10K 50/17* (2023.01)
*H10K 85/60* (2023.01)
*C09K 11/06* (2006.01)

(52) U.S. Cl.
CPC .... *H10K 85/633* (2023.02); *C09K 2211/1018* (2013.01); *H10K 50/11* (2023.02); *H10K 50/15* (2023.02); *H10K 50/17* (2023.02); *H10K 85/615* (2023.02); *H10K 85/626* (2023.02); *H10K 85/6572* (2023.02); *H10K 85/6574* (2023.02); *H10K 85/6576* (2023.02)

(56) References Cited

FOREIGN PATENT DOCUMENTS

| | | | |
|---|---|---|---|
| KR | 10-1560674 | B1 | 10/2015 |
| KR | 10-1576570 | B1 | 12/2015 |
| KR | 10-2016-0028979 | A | 3/2016 |
| KR | 10-1603387 | B1 | 3/2016 |
| KR | 10-2016-0037788 | A | 4/2016 |
| KR | 10-2016-0041695 | A | 4/2016 |
| KR | 10-2017-0111539 | A | 10/2017 |
| KR | 10-2019-0033218 | A | 3/2019 |
| WO | WO 2014/142488 | A1 | 9/2014 |
| WO | WO 2015/125986 | A1 | 8/2015 |
| WO | WO 2016/036171 | A1 | 3/2016 |

OTHER PUBLICATIONS

KR-20100113204 machine translation, from Google patents, downloaded Nov. 29, 2021.*

Rogness, Donald C. et al., "Synthesis of Pyrido[1,2-a]indole Malonates and Amines through Aryne Annulation," The Journal of Organic Chemistry, vol. 77, 2012, 13 pages.

Shukla, Satya Prakash et al., "Palladium-Catalyzed Sonogashira-Coupling Conjoined C—H Activation: A Regioselective Tandem Strategy to Access Indolo- and Pyrrolo[1,2-a]quinolines," The Journal of Organic Chemistry, vol. 77, 2012, 11 pages.

Verma, Akhilesh Kumar et al., "Syntheis of 5-lodopyrrolo[1,2-a]quinolines and Indolo[1,2-a]quinolines via Iodine-Mediated Electrophilic and Regioselective 6-endo-dig Ring Closure," The Journal of Organic Chemistry, vol. 76, 2011, 15 pages.

Verma, Akhilesh Kumar et al., "A Copper-Catalyzed Tandem Synthesis of Indolo- and Pyrrolo[2,1-a]isoquinolines," Angewandte Chemie International Edition, vol. 48, 2009, 6 pages.

EPO Extended Search Report dated Jan. 28, 2020, for corresponding European Patent Application No. 19192956.1 (10 pages).

EPO Examination Report dated Mar. 24, 2021 for EP Application No. 19 192 956.1, 6 pgs.

Rajeev Ranjan Jha et al., Synthesis of fused heterocycles via preferential hydroamination of o-haloarylalkynes over N-arylation and successive intramolecular C—C bond formation, Tetrahedron Letters, 2014, pp. 4724-4730, vol. 55, Elsevier.

* cited by examiner

ORGANIC ELECTROLUMINESCENCE DEVICE AND AMINE COMPOUND FOR ORGANIC ELECTROLUMINESCENCE DEVICE

CROSS-REFERENCE TO RELATED APPLICATION

This application claims priority to and the benefit of Korean Patent Application No. 10-2018-0115457, filed on Sep. 28, 2018, the entire content of which is incorporated herein by reference.

BACKGROUND

One or more aspects of example embodiments of the present disclosure are related to an amine compound and an organic electroluminescence device including the same, and more particularly, to an amine compound used in a hole transport region and an organic electroluminescence device including the same.

Organic electroluminescence display devices are being actively developed as image display devices. An organic electroluminescence display device differs from a liquid crystal display device in that it is a so-called self-luminescent display device, in which holes and electrons injected from a first electrode and a second electrode, respectively, recombine in an emission layer, and a light emission material including an organic compound in the emission layer emits light to attain display.

In the application of an organic electroluminescence device to a display device, a decrease in driving voltage, an increase in emission efficiency, and an increased lifetime of the organic electroluminescence device are desired, and materials for organic electroluminescence devices that can stably attain these requirements are being developed.

In order to achieve an organic electroluminescence device with high efficiency, materials for a hole transport layer that can restrain the diffusion, etc. of the exciton energy of an emission layer are being developed.

SUMMARY

One or more aspects of example embodiments of the present disclosure are directed toward an amine compound as a material for an organic electroluminescence device that is capable of improving emission efficiency and/or device life.

One or more aspects of example embodiments of the present disclosure are directed toward an organic electroluminescence device having improved thermal charge tolerance by including an amine compound including pyridoindole.

One or more example embodiments of the present disclosure provide an organic electroluminescence device including a first electrode; a second electrode on the first electrode; and a plurality of organic layers between the first electrode and the second electrode, wherein at least one organic layer of the plurality of organic layers includes an amine compound represented by Formula 1:

Formula 1

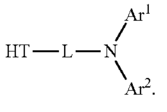

In Formula 1, $Ar_1$ and $Ar_2$ may each independently be a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms; L may be a direct linkage, a substituted or unsubstituted arylene group of 6 to 30 carbon atoms for forming a ring, or a substituted or unsubstituted heteroarylene group of 2 to 30 carbon atoms for forming a ring; and HT may be represented by Formula 2:

Formula 2

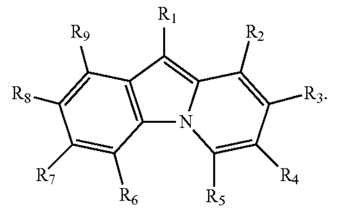

In Formula 2, $R_1$ to $R_9$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms. At least one pair of $R_2$ and $R_3$, $R_3$ and $R_4$, $R_4$ and $R_5$, $R_6$ and $R_7$, $R_7$ and $R_8$, and $R_8$ and $R_9$ may be combined with each other (linked) to form a hexagonal (six-membered) hydrocarbon ring, and when at least one pair of $R_2$ and $R_3$, $R_3$ and $R_4$, and $R_4$ and $R_5$ forms a hexagonal hydrocarbon ring, $R_8$ may be a hydrogen atom.

In some embodiments, the plurality of organic layers may include an emission layer; and a hole transport region between the first electrode and the emission layer, wherein the hole transport region may include the amine compound represented by Formula 1.

In some embodiments, the emission layer may be to emit blue light and/or green light.

In some embodiments, the plurality of organic layers may include an emission layer; a hole injection layer between the first electrode and the emission layer; and a hole transport layer between the hole injection layer and the emission layer, wherein the hole transport layer may include the amine compound represented by Formula 1.

In some embodiments, one or two pairs selected from $R_2$ and $R_3$, $R_3$ and $R_4$, and $R_4$ and $R_5$ may each form the hexagonal hydrocarbon ring.

In some embodiments, one or two pairs selected from $R_6$ and $R_7$, $R_7$ and $R_8$, and $R_8$ and $R_9$ may each form the hexagonal hydrocarbon ring.

In some embodiments, the hexagonal hydrocarbon ring may be represented by Formula 3:

Formula 3

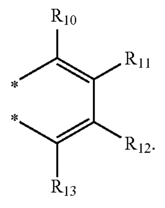

In Formula 3, $R_{10}$ to $R_{13}$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms, and * indicates a combining part (points of connection) with Formula 2.

In some embodiments, any one of $R_2$ to $R_9$ and $R_{10}$ to $R_{13}$ that is not a part of the hexagonal hydrocarbon ring may be combined with L in Formula 1.

In some embodiments, HT (Formula 2) may be further represented by one of Formula 2-1a to Formula 2-1d:

Formula 2-1a

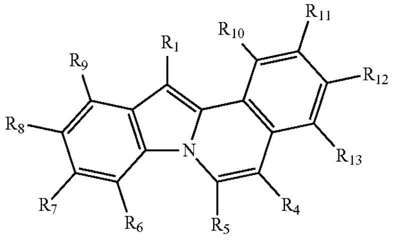

Formula 2-1b

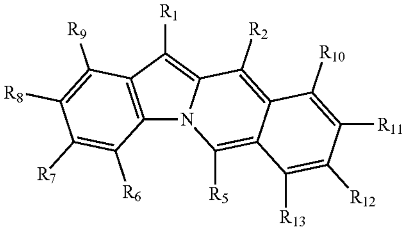

Formula 2-1c

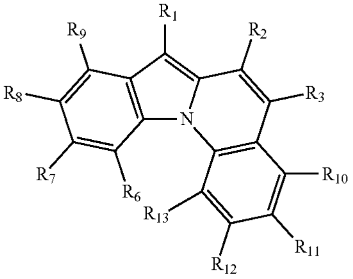

Formula 2-1d

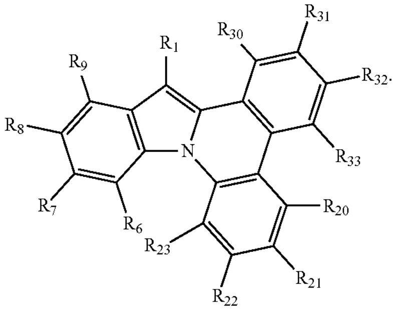

In Formula 2-1d, $R_{20}$ to $R_{23}$ and $R_{30}$ to $R_{33}$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms; and in Formula 2-1a to Formula 2-1d, $R_1$ to $R_9$ may be the same as defined in Formula 2, and $R_{10}$ to $R_{13}$ may be the same as defined in Formula 3.

In some embodiments, HT may be represented by one of Formula 2-2a to Formula 2-2d:

Formula 2-2a

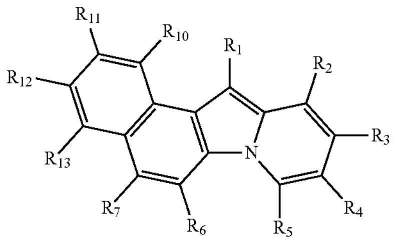

Formula 2-2b

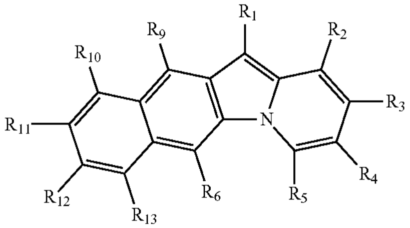

Formula 2-2c

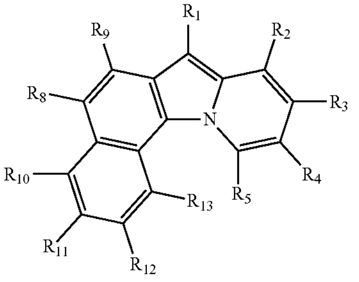

Formula 2-2d

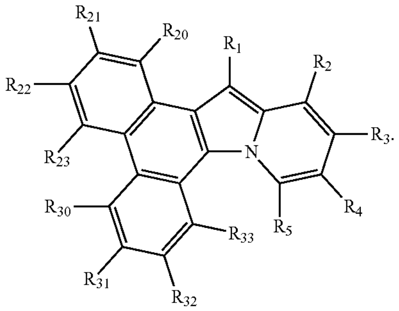

In Formula 2-2d, $R_{20}$ to $R_{23}$ and $R_{30}$ to $R_{33}$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms; and in Formula 2-2a to Formula 2-2d, $R_1$ to $R_9$ may be the same as defined in Formula 2, and $R_{10}$ to $R_{13}$ may be the same as defined in Formula 3.

In some embodiments, $R_1$ may be an unsubstituted phenyl group, an unsubstituted naphthyl group, an unsubstituted biphenyl group, an unsubstituted dibenzofuranyl group, or an unsubstituted dibenzothiophene group.

In some embodiments, L may be a direct linkage, a substituted or unsubstituted phenylene group, a substituted or unsubstituted divalent biphenyl group, a substituted or unsubstituted divalent terphenyl group, a substituted or unsubstituted divalent phenanthrene group, a substituted or unsubstituted naphthylene group, or a substituted or unsubstituted divalent dibenzofuran group.

One or more example embodiments of the present disclosure provide an amine compound represented by Formula 1:

Formula 1

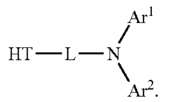

In Formula 1, $Ar_1$ and $Ar_2$ may each independently be a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms; L may be a direct linkage, a substituted or unsubstituted arylene group of 6 to 30 carbon atoms for forming a ring, or a substituted or unsubstituted heteroarylene group of 2 to 30 carbon atoms for forming a ring; and HT may be represented by Formula 2:

Formula 2

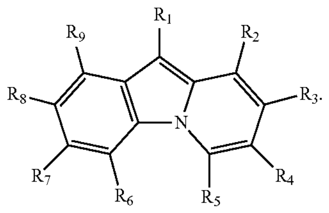

In Formula 2, $R_1$ to $R_9$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms; at least one pair of $R_2$ and $R_3$, $R_3$ and $R_4$, $R_4$ and $R_5$, $R_6$ and $R_7$, $R_7$ and $R_8$, and $R_8$ and $R_9$ may be combined with each other to form a hexagonal (six-membered) hydrocarbon ring; and when at least one pair of $R_2$ and $R_3$, $R_3$ and $R_4$, and $R_4$ and $R_5$ forms a hexagonal hydrocarbon ring, $R_8$ is a hydrogen atom.

In some embodiments, one or two pairs selected from $R_2$ and $R_3$, $R_3$ and $R_4$, and $R_4$ and $R_5$ may each form the hexagonal hydrocarbon ring.

In some embodiments, one or two pairs selected from $R_6$ and $R_7$, $R_7$ and $R_8$, and $R_8$ and $R_9$ may each form the hexagonal hydrocarbon ring.

In some embodiments, the hexagonal hydrocarbon ring may be represented by Formula 3:

Formula 3

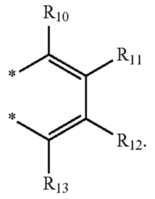

In Formula 3, $R_{10}$ to $R_{13}$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms, and * indicates a combining part (points of connection) with Formula 2.

In some embodiments, any one of $R_2$ to $R_9$ and $R_{10}$ to $R_{13}$ that is not a part of the hexagonal hydrocarbon ring may be combined with L in Formula 1.

In some embodiments, HT (Formula 2) may be further represented by one of Formula 2-1a to Formula 2-1d:

Formula 2-1a

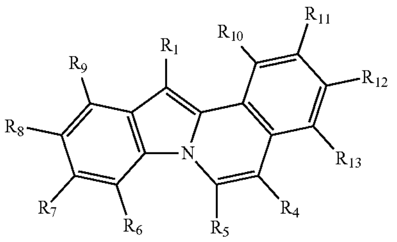

Formula 2-1b

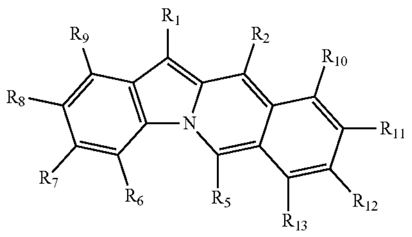

Formula 2-1c

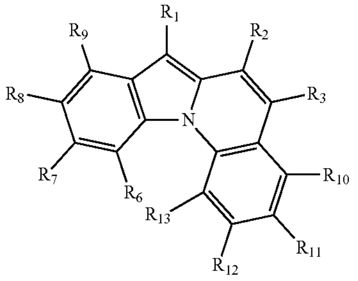

-continued

Formula 2-1d

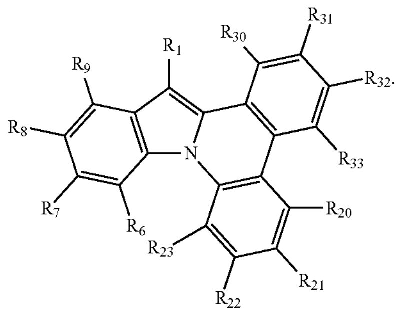

In Formula 2-1d, $R_{20}$ to $R_{23}$ and $R_{30}$ to $R_{33}$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms; and in Formula 2-1a to Formula 2-1d, $R_1$ to $R_9$ may be the same as defined in Formula 2, and $R_{10}$ to $R_{13}$ may be the same as defined in Formula 3.

In some embodiments, HT may be represented by one of Formula 2-2a to Formula 2-2d:

Formula 2-2a

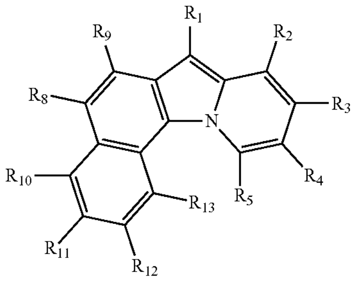

Formula 2-2b

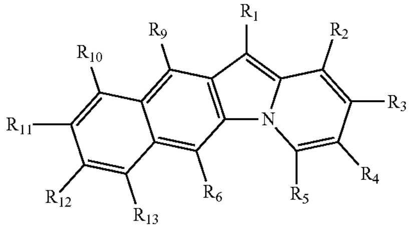

Formula 2-2c

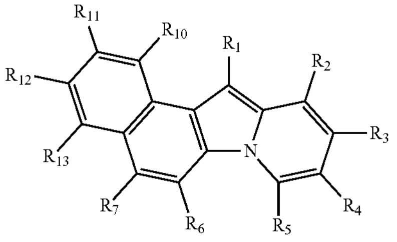

-continued

Formula 2-2d

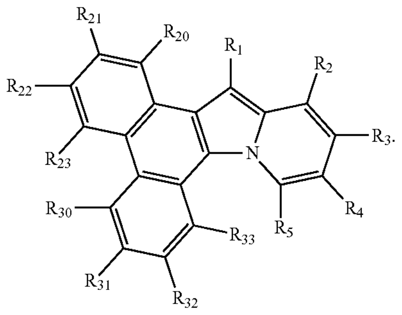

In Formula 2-2d, $R_{20}$ to $R_{23}$ and $R_{30}$ to $R_{33}$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms; and in Formula 2-2a to Formula 2-2d, $R_1$ to $R_9$ may be the same as defined in Formula 2, and $R_{10}$ to $R_{13}$ may be the same as defined in Formula 3.

In some embodiments, $R_1$ may be an unsubstituted phenyl group, an unsubstituted naphthyl group, an unsubstituted biphenyl group, an unsubstituted dibenzofuranyl group, or an unsubstituted dibenzothiophene group.

In some embodiments, L may be a direct linkage, a substituted or unsubstituted phenylene group, a substituted or unsubstituted divalent biphenyl group, a substituted or unsubstituted divalent terphenyl group, a substituted or unsubstituted divalent phenanthrene group, a substituted or unsubstituted naphthylene group, or a substituted or unsubstituted divalent dibenzofuran group.

In some embodiments, $Ar_1$ and $Ar_2$ may each independently be a substituted or unsubstituted phenyl group, a substituted or unsubstituted biphenyl group, a substituted or unsubstituted terphenyl group, a substituted or unsubstituted phenanthrene group, a substituted or unsubstituted triphenylene group, a substituted or unsubstituted naphthyl group, a substituted or unsubstituted fluorenyl group, a substituted or unsubstituted adamantyl group, a substituted or unsubstituted dibenzofuran group, a substituted or unsubstituted dibenzothiophene group, or a substituted or unsubstituted pyridinyl group.

In some embodiments, $Ar_1$ and $Ar_2$ may each independently be: an aryl group of 6 to 40 carbon atoms for forming a ring, which may be unsubstituted or substituted with at least one substituent selected from a halogen atom, a cyano group, an alkyl group of 1 to 20 carbon atoms, an alkoxy group of 1 to 10 carbon atoms, an aryloxy group of 1 to 20 carbon atoms, an aryl group of 6 to 30 carbon atoms, a triarylsilyl group of 18 to 50 carbon atoms, and an adamantyl group; or a heteroaryl group of 2 to 40 carbon atoms for forming a ring, which may be unsubstituted or substituted with at least one substituent selected from a halogen atom, a cyano group, an alkyl group of 1 to 20 carbon atoms, an alkoxy group of 1 to 10 carbon atoms, an aryloxy group of 1 to 20 carbon atoms, an aryl group of 6 to 30 carbon atoms, a triarylsilyl group of 18 to 50 carbon atoms, and an adamantyl group.

BRIEF DESCRIPTION OF THE DRAWINGS

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
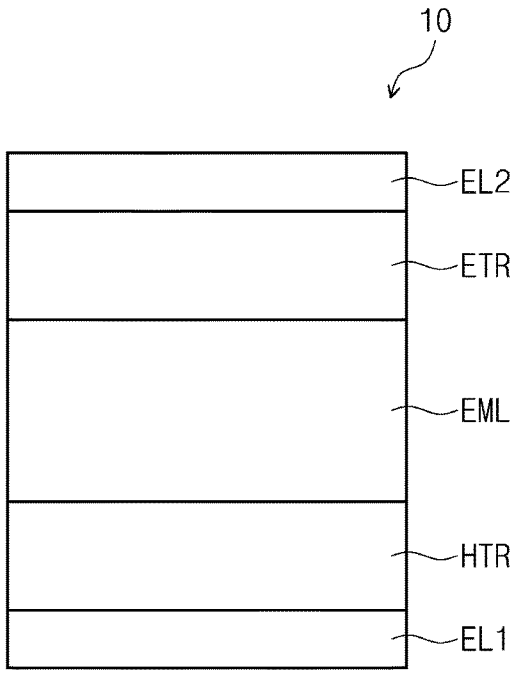
FIG. 1 is a cross-sectional view schematically illustrating an organic electroluminescence device according to an embodiment of the present disclosure.

The present disclosure may include various modifications and may be embodied in different forms, and example embodiments thereof will be explained in more detail with reference to the accompany drawings. The present disclosure may, however, be embodied in various suitable forms, and should not be construed as being limited to the embodiments set forth herein. Rather, all modifications, equivalents, and substituents within the spirit and technical scope of the present disclosure are understood to be included in the present disclosure.

Like reference numerals refer to like elements throughout, and duplicative descriptions thereof may not be provided. In the drawings, the dimensions of structures may be exaggerated for clarity of illustration. It will be understood that, although the terms first, second, etc. may be used herein to describe various elements, those elements should not be limited by these terms. These terms are only used to distinguish one element from another element. Thus, a first element could be alternatively termed a second element without departing from the teachings of the present disclosure. Similarly, a second element could be alternatively termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or combinations thereof, but do not preclude the presence or addition of one or more other features, numerals, steps, operations, elements, parts, or combinations thereof. It will also be understood that when a layer, a film, a region, a plate, etc. is referred to as being "on" another part, it can be "directly on" the other part, or intervening layers may also be present. In contrast, when an element is referred to as being "directly on" another element, no intervening elements are present.

Expressions such as "at least one of", "one of", "selected from", "at least one selected from", and "one selected from", when preceding a list of elements, modify the entire list of elements and do not modify the individual elements of the list. Further, the use of "may" when describing embodiments of the present disclosure refers to "one or more embodiments of the present disclosure."

In the description, "—*" indicates a connecting position or point of connection (e.g., to another formula or moiety).

In the description, the term "substituted or unsubstituted", for example, as used to describe a group, indicates that the group may be unsubstituted, or substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an alkoxy group, an aryloxy group, an alkylthio group, an arylthio group, a hydrocarbon ring, an aryl group, and a heterocyclic group. Each of the substituents may be further substituted or unsubstituted. For example, a biphenyl group may be interpreted as an aryl group or a phenyl group substituted with a phenyl group.

In the description, the term "halogen atom" may include a fluorine atom, a chlorine atom, a bromine atom, and/or an iodine atom.

In the description, the term "alkyl" may indicate a linear, branched, and/or cyclic alkyl. The carbon number of the alkyl may be 1 to 50, 1 to 30, 1 to 20, 1 to 10, or 1 to 6. Non-limiting examples of the alkyl include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the description, the term "hydrocarbon ring" may refer to a functional group or substituent derived from an aliphatic hydrocarbon ring, or a functional group or substituent derived from an aromatic hydrocarbon ring. The hydrocarbon ring does not include a heteroatom (e.g., includes only carbon and hydrogen atoms), and may include 5 to 20 carbon atoms for forming a ring. The hydrocarbon ring may be a monocyclic ring, and for example, a hexagonal hydrocarbon ring in the description may be a benzene ring.

In the description, the term "aryl group" may refer to a functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Non-limiting examples of the aryl group include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc.

In the description, the fluorenyl group may be substituted or bisubstituted (e.g. at the 9H position), and two substituents may be combined with each other (e.g., linked) to form a spiro structure. Non-limiting examples of a substituted fluorenyl group are as follows. However, embodiments of the present disclosure are not limited thereto:

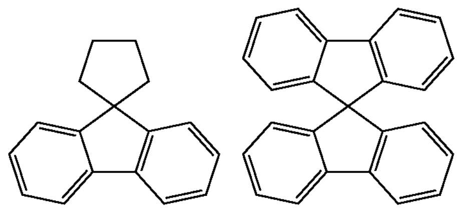

-continued

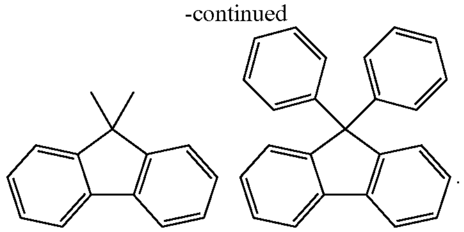

In the description, the term "heteroaryl" may refer to a heteroaryl group including at least one selected from oxygen (O), nitrogen (N), phosphorus (P), silicon (Si), and sulfur (S) as a heteroatom. The carbon number for forming a ring of the heteroaryl may be 2 to 30 or 2 to 20. The heteroaryl may be a monocyclic heteroaryl group or a polycyclic heteroaryl group. The polycyclic heteroaryl may have a dicyclic or tricyclic structure. Non-limiting examples of the heteroaryl include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc.

In the description, the term "silyl group" may refer to an alkyl silyl group or an aryl silyl group. Non-limiting examples of the silyl group include trimethylsilyl, triethylsilyl, t-butyldimethylsilyl, vinyldimethylsilyl, propyldimethylsilyl, triphenylsilyl, diphenylsilyl, phenylsilyl, etc. However, embodiments of the present disclosure are not limited thereto.

In the description, the term "oxy group" may refer to alkoxy group or an aryloxy group. The alkoxy group may include a linear, branched, or cyclic chain. The carbon number of the alkoxy group is not specifically limited and may be, for example, 1 to 20, or 1 to 10. Non-limiting examples of the oxy group include methoxy, ethoxy, n-propoxy, isopropoxy, butoxy, pentyloxy, hexyloxy, octyloxy, nonyloxy, decyloxy, benzyloxy, etc. However, embodiments of the present disclosure are not limited thereto.

In the description, the carbon number of the amino group is not specifically limited, but may be 1 to 30. Non-limiting examples of the amino group include an alkyl amino group and an aryl amino group. Non-limiting examples of the amino group include a methylamino group, a dimethylamino group, a phenylamino group, a diphenylamino group, a naphthylamino group, a 9-methyl-anthracenylamino group, a triphenylamino group, etc. However, embodiments of the present disclosure are not limited thereto.

Hereinafter, an organic electroluminescence device according to an embodiment of the present disclosure and an amine compound included therein according to an embodiment of the present disclosure will be explained.

Figure 2:
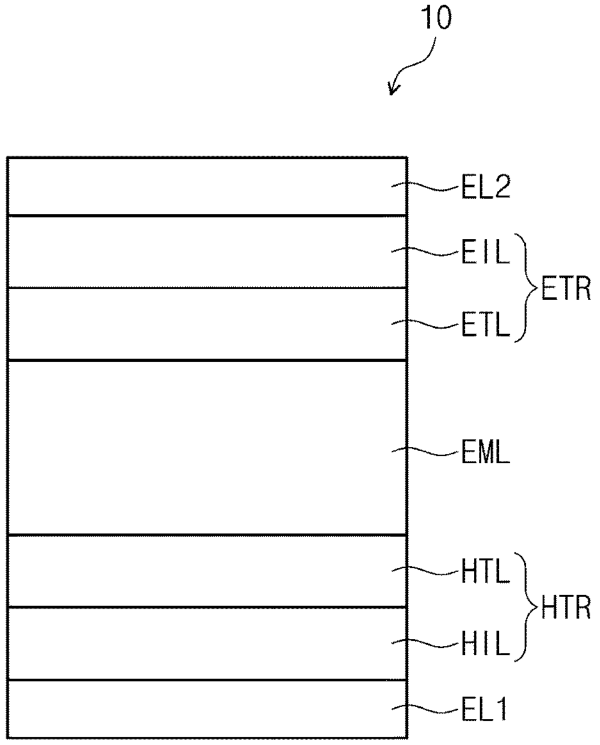
FIG. 2 is a cross-sectional view schematically illustrating an organic electroluminescence device according to an embodiment of the present disclosure.
Figure 3:
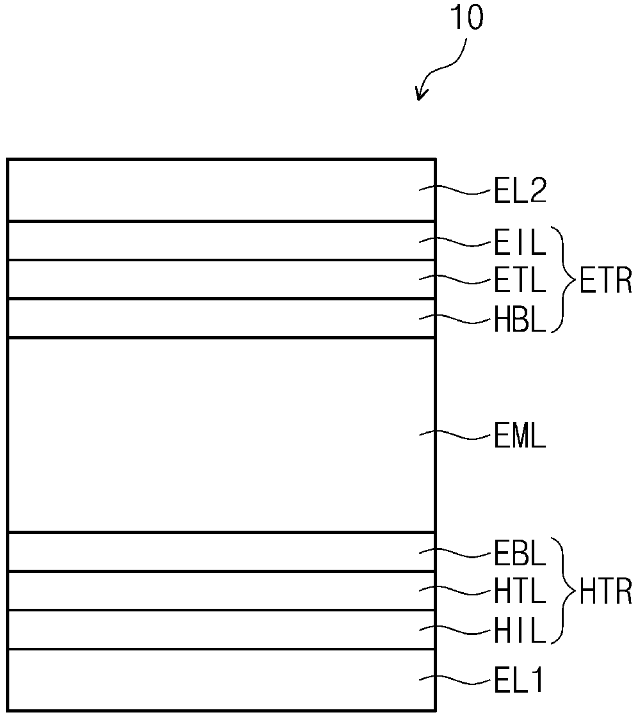
FIG. 3 is a cross-sectional view schematically illustrating an organic electroluminescence device according to an embodiment of the present disclosure.

FIG. 1-FIG. 3 are cross-sectional views schematically illustrating organic electroluminescence devices according to example embodiments of the present disclosure. Referring to FIG. 1-FIG. 3, an organic electroluminescence device 10 according to an embodiment of the present disclosure may include a first electrode EL1, a hole transport region HTR, an emission layer EML, an electron transport region ETR, and a second electrode EL2, each laminated (stacked) in this listed order.

The first electrode EL1 and the second electrode EL2 are opposite to each other, and a plurality of organic layers may be between the first electrode EL1 and the second electrode EL2. The plurality of the organic layers may include a hole transport region HTR, an emission layer EML, and/or an electron transport region ETR.

The organic electroluminescence device 10 according to an embodiment of the present disclosure may include an amine compound according to an embodiment of the present disclosure, which will be described later, in at least one organic layer of the plurality of the organic layers between the first electrode EL1 and the second electrode EL2. For example, an amine compound according to an embodiment of the present disclosure may be included in the hole transport region HTR.

FIG. 2 differs from FIG. 1 in that FIG. 2 shows a cross-sectional view of an organic electroluminescence device 10 according to an embodiment of the present disclosure, in which a hole transport region HTR includes a hole injection layer HIL and a hole transport layer HTL, and an electron transport region ETR includes an electron injection layer EIL and an electron transport layer ETL. FIG. 3 differs from FIG. 1 in that FIG. 3 shows a cross-sectional view of an organic electroluminescence device 10 according to an embodiment of the present disclosure, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. The hole transport layer HTL in the organic electroluminescence device 10 according to an embodiment of the present disclosure may include an amine compound according to an embodiment of the present disclosure.

Meanwhile, in the organic electroluminescence device 10 according to an embodiment of the present disclosure, the hole transport layer HTL may include a plurality of hole transport sub-layers, among which a hole transport sub-layer adjacent to the emission layer EML may include the amine compound according to an embodiment of the present disclosure.

The first electrode EL1 may be conductive. The first electrode EL1 may be formed using a metal alloy and/or a conductive compound. The first electrode EL1 may be an anode. In some embodiments, the first electrode EL1 may be a pixel electrode. The first electrode EL1 may be a transmissive electrode, a transflective (semi-transmissive) electrode, or a reflective electrode. When the first electrode EL1 is a transmissive electrode, the first electrode EL1 may be formed using a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or a mixture thereof (for example, a mixture of Ag and Mg). In some embodiments, the first electrode EL1 may have a structure including a plurality of layers, including a reflective layer or a transflective layer formed using the above materials, and a transmissive conductive layer formed using ITO, IZO, ZnO, or ITZO. For example, the first electrode EL1 may have a three-layer structure of ITO/Ag/ITO. However, embodiments of the present disclosure are not limited thereto. The thickness of the first electrode EL1 may be about 1,000 Å to about 10,000 Å, for example, about 1,000 Å to about 3,000 Å.

The hole transport region HTR may be on the first electrode EL1. The hole transport region HTR may include at least one selected from a hole injection layer HIL, a hole transport layer HTL, a hole buffer layer, and an electron blocking layer EBL.

The hole transport region HTR may have a single layer structure formed using a single material, a single layer structure formed using a plurality of different materials, or a multilayer structure including a plurality of layers formed using a plurality of different materials.

For example, the hole transport region HTR may have the structure of a single layer of a hole injection layer HIL or a hole transport layer HTL, and may have a structure of a single layer formed using a hole injection material and a hole transport material. Alternatively, the hole transport region HTR may have a structure of a single layer formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using any suitable method available in the art (such as a vacuum deposition method, a spin coating method, a cast method, a Langmuir-Blodgett (LB) method, an inkjet printing method, a laser printing method, and/or a laser induced thermal imaging (LITI) method).

In the organic electroluminescence device 10 according to an embodiment of the present disclosure, at least one of the organic layers between the first electrode EL1 and the second electrode EL2 may include an amine compound represented by Formula 1. In the organic electroluminescence device 10 according to an embodiment of the present disclosure, a hole transport region HTR may include an amine compound represented by Formula 1:

Formula 1

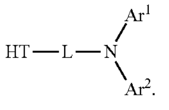

In Formula 1, $Ar_1$ and $Ar_2$ may each independently be a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms; and L may be a direct linkage, a substituted or unsubstituted arylene group of 6 to 30 carbon atoms for forming a ring, or a substituted or unsubstituted heteroarylene group of 2 to 30 carbon atoms for forming a ring.

In some embodiments, in Formula 1, $Ar_1$ and $Ar_2$ may each independently be an aryl group of 6 to 40 carbon atoms for forming a ring, which may be unsubstituted or substituted with at least one substituent selected from a halogen atom, a cyano group, an alkyl group of 1 to 20 carbon atoms, an alkoxy group of 1 to 10 carbon atoms, an aryloxy group of 1 to 20 carbon atoms, an aryl group of 6 to 30 carbon atoms, a triarylsilyl group of 18 to 50 carbon atoms, and an adamantyl group.

In some embodiments, $Ar_1$ and $Ar_2$ may each independently be a heteroaryl group of 2 to 40 carbon atoms for forming a ring, which may be unsubstituted or substituted with at least one substituent selected from a halogen atom, a cyano group, an alkyl group of 1 to 20 carbon atoms, an alkoxy group of 1 to 10 carbon atoms, an aryloxy group of 1 to 20 carbon atoms, an aryl group of 6 to 30 carbon atoms, a triarylsilyl group of 18 to 50 carbon atoms, and an adamantyl group. However, the case in which $Ar_1$ and $Ar_2$ include a pyridoindole moiety

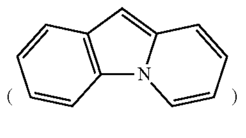 [SMILES: c1ccc2c(c1)cc1ccccn12]

is excluded.

$Ar_1$ and $Ar_2$ may each independently be a substituted or unsubstituted phenyl group, a substituted or unsubstituted biphenyl group, a substituted or unsubstituted terphenyl group, a substituted or unsubstituted phenanthrene group, a substituted or unsubstituted triphenylene group, a substituted or unsubstituted naphthyl group, a substituted or unsubstituted fluorenyl group, a substituted or unsubstituted adamantyl group, a substituted or unsubstituted dibenzofuran group, a substituted or unsubstituted dibenzothiophene group, or a substituted or unsubstituted pyridinyl group.

For example, $Ar_1$ and $Ar_2$ may each independently be an unsubstituted phenyl group, a phenyl group substituted with a naphthyl group, a phenyl group substituted with a phenyl group, a phenyl group substituted with deuterium, a phenyl group substituted with a halogen atom, a phenyl group substituted with an aryloxy group, a phenyl group substituted with an adamantyl group, an unsubstituted biphenyl group, a biphenyl group substituted with a phenyl group, an unsubstituted terphenyl group, an unsubstituted phenanthrene group, an unsubstituted triphenylene group, an unsubstituted naphthyl group, a naphthyl group substituted with a phenyl group, an unsubstituted fluorenyl group, a fluorenyl group substituted with a phenyl group, an unsubstituted dibenzofuran group, a dibenzofuran group substituted with a phenyl group, a substituted or unsubstituted dibenzothiophene group, a dibenzothiophene group substituted with a phenyl group, or an unsubstituted pyridinyl group. However, embodiments of the present disclosure are not limited thereto.

In Formula 1, $Ar_1$ and $Ar_2$ may be the same or different.

In Formula 1, L may be a direct linkage, a substituted or unsubstituted phenylene group, a substituted or unsubstituted divalent biphenyl group, a substituted or unsubstituted divalent terphenyl group, a substituted or unsubstituted divalent phenanthrene group, a substituted or unsubstituted naphthylene group, or a substituted or unsubstituted divalent dibenzofuran group.

For example, in Formula 1, L may be a direct linkage, an unsubstituted phenylene group, an unsubstituted divalent biphenyl group, an unsubstituted divalent terphenyl group, a substituted or unsubstituted divalent phenanthrene group, an unsubstituted naphthylene group, or an unsubstituted divalent dibenzofuran group. However, embodiments of the present disclosure are not limited thereto.

In Formula 1, HT may be further represented by Formula 2. For example, the amine compound represented by Formula 1 may include a pyridoindole part (moiety) represented by Formula 2:

Formula 2

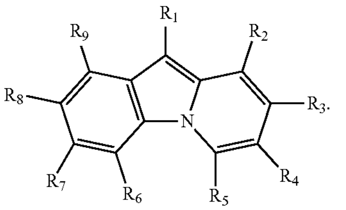

In Formula 2, $R_1$ to $R_9$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms. $R_1$ to $R_9$ may each be the same, or at least one thereof may be different.

Two neighboring substituents selected from $R_2$ to $R_9$ may be combined with each other to form a hexagonal (six-membered) hydrocarbon ring. As used herein, the term “form a hexagonal hydrocarbon ring” refers to a case in which the two named substituent groups in the pair are replaced with a four-carbon linker so that the two carbons underlying the named substituent groups and the four carbons in the linker thereby form a ring structure. The hexagonal hydrocarbon ring formed by the combination of two substituents may be an aromatic ring not including a heteroatom. In some embodiments, the hexagonal hydrocarbon ring may be a benzene ring.

In Formula 2, any one of the remaining groups of $R_2$ to $R_9$ that are not combined with each other to form a hexagonal hydrocarbon ring, and of $R_{10}$ to $R_{13}$ on the hexagonal hydrocarbon ring formed by the combination of two substituents, may be combined with L in Formula 1. In some embodiments, in Formula 2, the remaining groups not combined with L in Formula 1 may all be hydrogen atoms.

In Formula 2, at least one pair selected from $R_2$ and $R_3$, $R_3$ and $R_4$, $R_4$ and $R_5$, $R_6$ and $R_7$, $R_7$ and $R_8$, and $R_8$ and $R_9$ may be combined with each other to form a hexagonal hydrocarbon ring. For example, one or two pairs selected from $R_2$ and $R_3$, $R_3$ and $R_4$, $R_4$ and $R_5$, $R_6$ and $R_7$, $R_7$ and $R_8$, and $R_8$ and $R_9$ may be combined with each other to form one or two hexagonal hydrocarbon rings, respectively.

Any of the remaining groups of $R_2$ to $R_9$ that do not form the hexagonal hydrocarbon ring may be combined with L in Formula 1. In some embodiments, a group on the hexagonal hydrocarbon ring formed by the combination of $R_2$ and $R_3$, $R_3$ and $R_4$, $R_4$ and $R_5$, $R_6$ and $R_7$, $R_7$ and $R_8$, or $R_8$ and $R_9$ may be combined with L in Formula 1. In some embodiments, when at least one pair selected from $R_2$ and $R_3$, $R_3$ and $R_4$, and $R_4$ and $R_5$ forms a hexagonal hydrocarbon ring, $R_8$ may be a hydrogen atom.

For example, in an amine compound according to an embodiment of the present disclosure, when at least one pair selected from $R_2$ and $R_3$, $R_3$ and $R_4$, and $R_4$ and $R_5$ is combined with each other to form a hexagonal hydrocarbon ring, $R_8$ is excluded from being combined with L in Formula 1.

In Formula 2, $R_1$ may be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms. For example, $R_1$ may be an unsubstituted phenyl group, an unsubstituted naphthyl group, an unsubstituted biphenyl group, an unsubstituted dibenzofuranyl group, or an unsubstituted dibenzothiophene group. However, embodiments of the present disclosure are not limited thereto.

In Formula 2, at least one pair selected from $R_2$ and $R_3$, $R_3$ and $R_4$, $R_4$ and $R_5$, $R_6$ and $R_7$, $R_7$ and $R_8$, and $R_8$ and $R_9$ may be combined with each other to form a hexagonal hydrocarbon ring represented by Formula 3:

Formula 3

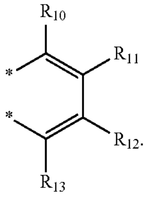

In Formula 3, $R_{10}$ to $R_{13}$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms. In Formula 3, * may be a combining part (point of connection) with Formula 2.

For example, in Formula 2, at least one pair selected from $R_2$ and $R_3$, $R_3$ and $R_4$, $R_4$ and $R_5$, $R_6$ and $R_7$, $R_7$ and $R_8$, and $R_8$ and $R_9$ may be combined with each other and with a moiety represented by Formula 3 to form a benzene ring. In some embodiments, for example, at least one pair selected from $R_2$ and $R_3$, $R_3$ and $R_4$, $R_4$ and $R_5$, $R_6$ and $R_7$, $R_7$ and $R_8$, and $R_8$ and $R_9$ in Formula 2 may be combined with each other and with Formula 3 to form a benzene ring that is coupled to a pyridoindole moiety.

Referring to Formula 1 to Formula 3, an amine compound according to an embodiment of the present disclosure may include, as a substituent, a condensed ring having four or five rings including a pyridoindole moiety. The amine compound according to an embodiment of the present disclosure may be a monoamine compound including, as a substituent, a condensed ring having four or five rings including a pyridoindole moiety.

The amine compound according to an embodiment of the present disclosure may include both a pyridoindole moiety ( 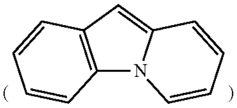 [SMILES: c1ccc2c(c1)cc1ccccn12] )

and an arylamine moiety

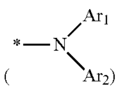

(e.g., simultaneously). When the amine compound according to an embodiment of the present disclosure includes both a pyridoindole moiety and an arylamine moiety (e.g., simultaneously), an organic electroluminescence device including the amine compound may show long life characteristics and/or high emission efficiency.

The amine compound according to an embodiment of the present disclosure includes a pyridoindole moiety having excellent thermal/charge tolerance, along with an arylamine moiety having long life characteristics, thereby improving tolerance to high temperature and charge. Accordingly, the amine compound may be used as a material for an organic electroluminescence device having an improved device lifetime (e.g., lifespan). In some embodiments, the nitrogen atom included in the pyridoindole moiety may improve the hole transport capacity of the entire amine compound molecule, and the recombination probability of holes and electrons in an emission layer of an organic electroluminescence device may be increased. Thus, the amine compound according to an embodiment of the present disclosure may provide an organic electroluminescence device with improved emission efficiency.

In Formula 2, one or two pairs selected from $R_2$ and $R_3$, $R_3$ and $R_4$, and $R_4$ and $R_5$ may form a hexagonal hydrocarbon ring represented by Formula 3. For example, in Formula 2, one pair selected from $R_2$ and $R_3$, $R_3$ and $R_4$, $R_4$ and $R_5$ may form a hexagonal hydrocarbon ring, or each of $R_2$ and $R_3$, and $R_4$ and $R_5$ may form a hexagonal hydrocarbon ring.

Formula 2 may be represented by one selected from Formula 2-1a to Formula 2-1d:

Formula 2-1a

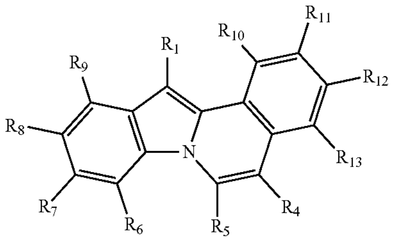

Formula 2-1b

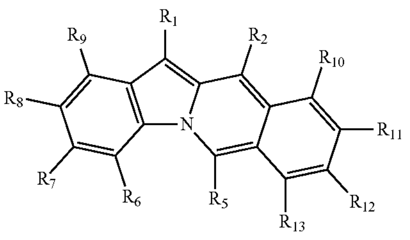

-continued

Formula 2-1c

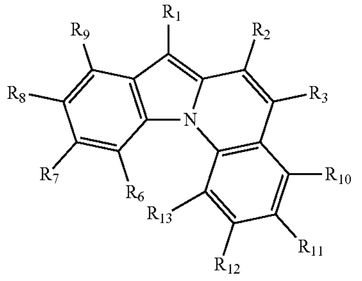

Formula 2-1d

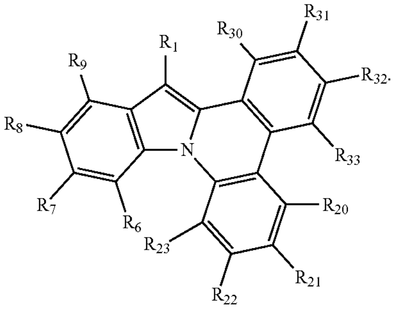

Each of Formula 2-1a to Formula 2-1c represents a structure in which one pair selected from $R_2$ and $R_3$, $R_3$ and $R_4$, or $R_4$ and $R_5$, respectively, forms a hexagonal hydrocarbon ring, and Formula 2-1d represents a structure in which two pairs, $R_2$ and $R_3$ and $R_4$ and $R_5$, each form a hexagonal hydrocarbon ring.

In Formula 2-1d, $R_{20}$ to $R_{23}$ and $R_{30}$ to $R_{33}$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms. $R_{20}$ to $R_{23}$ and $R_{30}$ to $R_{33}$ may be the same, or at least one thereof may be different.

In Formula 2-1a to Formula 2-1d, the same explanation referring to Formula 2 may be applied to $R_1$ to $R_9$, and the same explanation referring to Formula 3 may be applied to $R_{10}$ to $R_{13}$.

In some embodiments, in Formula 2-1a to Formula 2-1d, $R_8$ may be a hydrogen atom. In Formula 2-1a to Formula 2-1d, $R_8$ may not be connected with L in Formula 1.

In Formula 2-1a, the position combined with L in Formula 1 may be one selected from $R_4$, $R_5$, $R_6$, $R_7$, $R_9$, and $R_{10}$ to $R_{13}$, and in Formula 2-1b, the position combined with L in Formula 1 may be one selected from $R_2$, $R_5$, $R_6$, $R_7$, $R_9$, and $R_{10}$ to $R_{13}$. In Formula 2-1c, the position combined with L in Formula 1 may be one selected from $R_2$, $R_3$, $R_6$, $R_7$, $R_9$, and $R_{10}$ to $R_{13}$, and in Formula 2-1d, the position combined with L in Formula 1 may be one selected from $R_6$, $R_7$, $R_9$, $R_{20}$ to $R_{23}$, and $R_{30}$ to $R_{33}$. For example, in the amine compound represented by Formula 2-1a to Formula 2-1d, $R_1$ and $R_8$ may not be combined with L in Formula 1.

Formula 2-1a to Formula 2-1c represent structures in which one benzene ring is condensed with a pyridoindole moiety so that "HT" in Formula 1 has four condensed rings. Formula 2-1d represents a structure in which two benzene rings are condensed with a pyridoindole moiety so that "HT" in Formula 1 has five condensed rings.

Meanwhile, Formula 2-1a to Formula 2-1d may represent structures in which an aromatic hydrocarbon group (e.g., a benzene ring) is condensed with the pyridine ring of a pyridoindole moiety.

In some embodiments, in Formula 2, one or two pairs selected from $R_6$ and $R_7$, $R_7$ and $R_8$, and $R_8$ and $R_9$ may form hexagonal hydrocarbon rings represented by Formula 3. For example, in Formula 2, one pair selected from $R_6$ and $R_7$, $R_7$ and $R_8$, and $R_8$ and $R_9$ may form a hexagonal hydrocarbon ring, or each of $R_6$ and $R_7$, and $R_8$ and $R_9$ may form a hexagonal hydrocarbon ring.

Formula 2 may be further represented by one selected from Formula 2-2a to Formula 2-2d:

Formula 2-2a

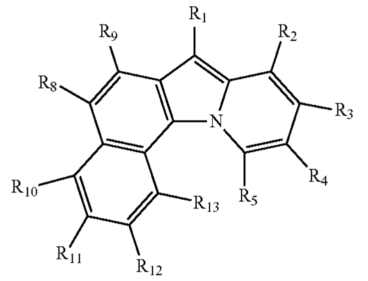

Formula 2-2b

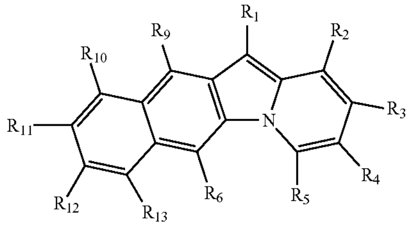

Formula 2-2c

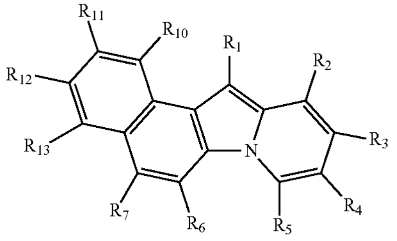

Formula 2-2d

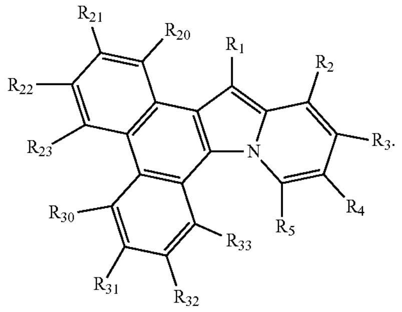

Each of Formula 2-2a to Formula 2-2c represents a structure in which one pair selected from $R_6$ and $R_7$, $R_7$ and $R_8$, and $R_8$ and $R_9$, respectively, forms a hexagonal hydrocarbon ring, and Formula 2-2d represents a structure in which two pairs, $R_6$ and $R_7$ and $R_8$ and $R_9$, each form a hexagonal hydrocarbon ring.

In Formula 2-2d, $R_{20}$ to $R_{23}$ and $R_{30}$ to $R_{33}$ may each independently be a hydrogen atom, a deuterium atom, a halogen atom, a cyano group, a nitro group, an amino group, a substituted or unsubstituted aryl group of 6 to 40 carbon atoms for forming a ring, a substituted or unsubstituted heteroaryl group of 2 to 40 carbon atoms for forming a ring, or a substituted or unsubstituted alkyl group of 1 to 20 carbon atoms.

In Formula 2-2a to Formula 2-2d, the same explanation referring to Formula 2 may be applied to $R_1$ to $R_9$, and the same explanation referring to Formula 3 may be applied to $R_{10}$ to $R_{13}$.

In Formula 2-2a, the position combined with L in Formula 1 may be one selected from $R_2$ to $R_5$, $R_8$, $R_9$, and $R_{10}$ to $R_{13}$, and in Formula 2-2b, the position combined with L in Formula 1 may be one selected from $R_2$ to $R_5$, $R_6$, $R_9$, and $R_{10}$ to $R_{13}$. In Formula 2-2c, the position combined with L in Formula 1 may be one selected from $R_2$ to $R_5$, $R_6$, $R_7$, and $R_{10}$ to $R_{13}$, and in Formula 2-2d, the position combined with L in Formula 1 may be one selected from $R_2$ to $R_5$, $R_{20}$ to $R_{23}$, and $R_{30}$ to $R_{33}$.

Formula 2-2a to Formula 2-2c represent structures in which one benzene ring is condensed with a pyridoindole moiety so that "HT" in Formula 1 has four condensed rings. Formula 2-2d represents a structure in which two benzene rings are condensed with a pyridoindole moiety so that "HT" in Formula 1 has five condensed rings.

Meanwhile, Formula 2-2a to Formula 2-2d may represent structures in which an aromatic hydrocarbon group is condensed with the indole part of a pyridoindole moiety.

In Formula 2-1a to Formula 2-1d and Formula 2-2a to Formula 2-2d, $R_1$ may be an unsubstituted phenyl group, and all substituents $R_2$ to $R_{13}$, $R_{20}$ to $R_{23}$, and $R_{30}$ to $R_{33}$ that are not combined with (linked to) Formula 1 may each be a hydrogen atom.

The amine compound represented by Formula 1 according to an embodiment of the present disclosure may be further represented by at least one selected from the compounds represented in Compound Group 1 and Compound Group 2. For example, the organic electroluminescence device according to an embodiment of the present disclosure may include at least one selected from the compounds represented in Compound Group 1 and Compound Group 2 in at least one organic layer.

Compound Group 1 represents amine compounds in which the HT moiety in Formula 1 is represented by one selected from Formula 2-1a to Formula 2-1d. Compound Group 2 represents amine compounds in which the HT moiety in Formula 1 is represented by one selected from Formula 2-2a to Formula 2-2d:

Compound Group 1
A1
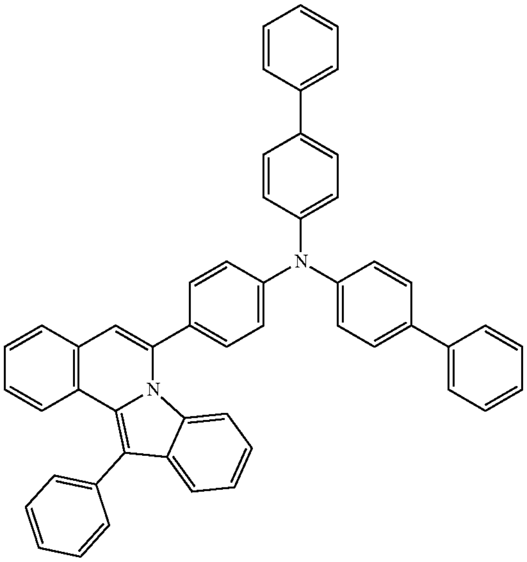
A2
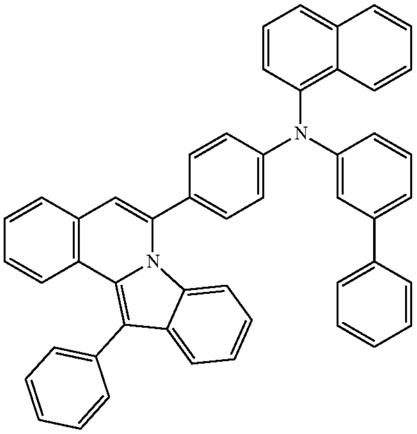
A3
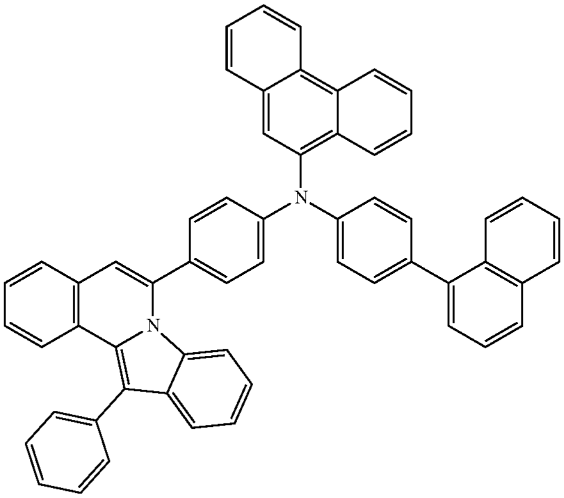
A4
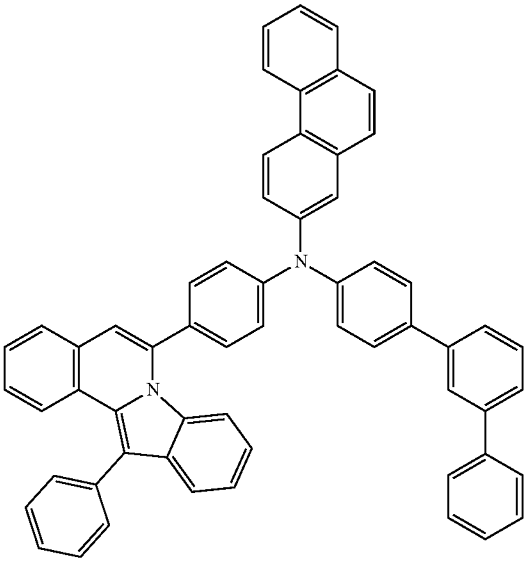

-continued
A5
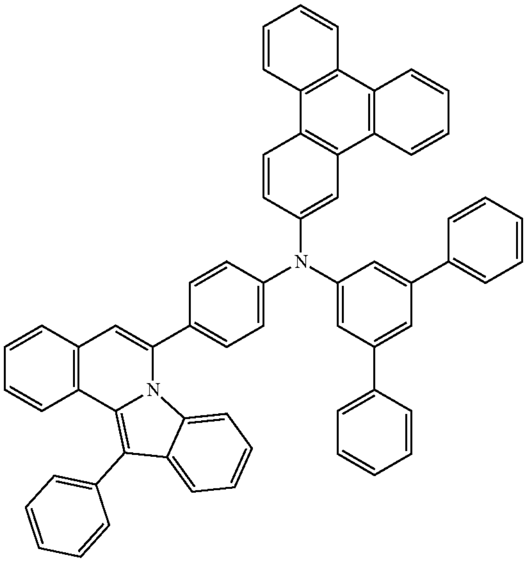
A6
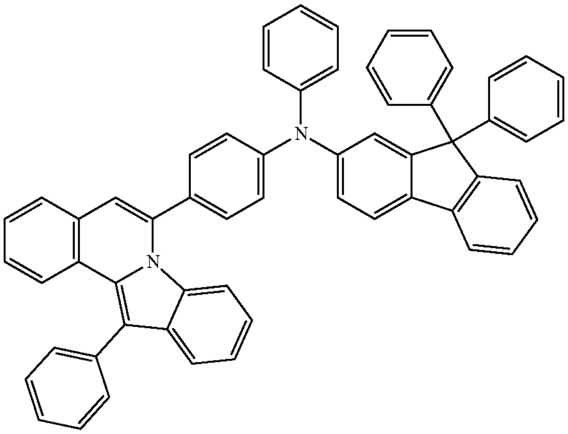
A7
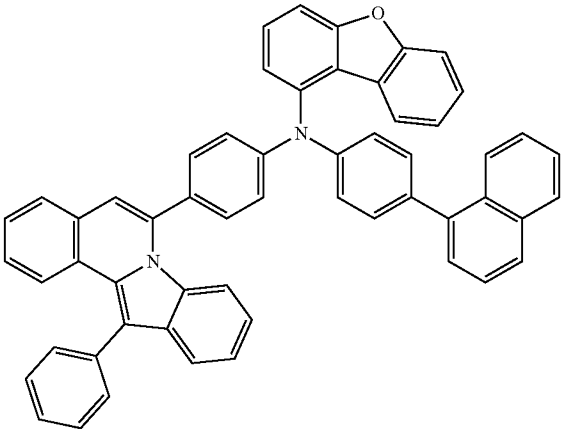
A8
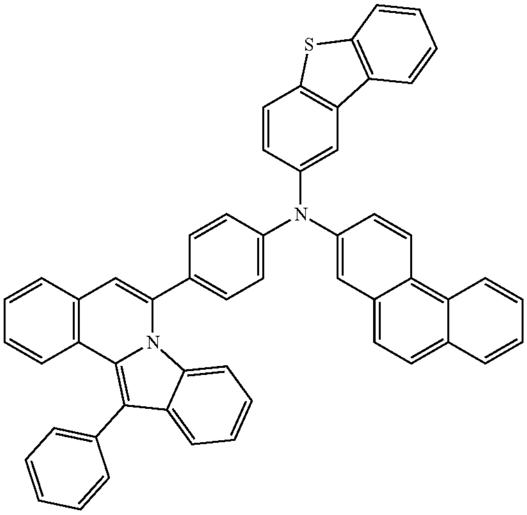
A9
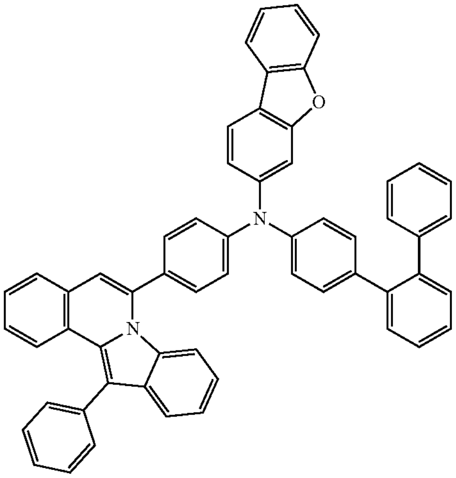
A10
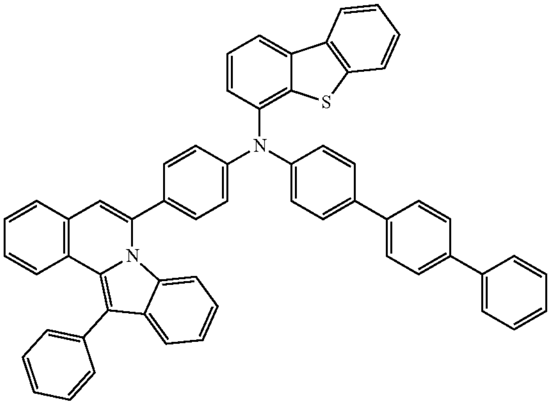

-continued
A11
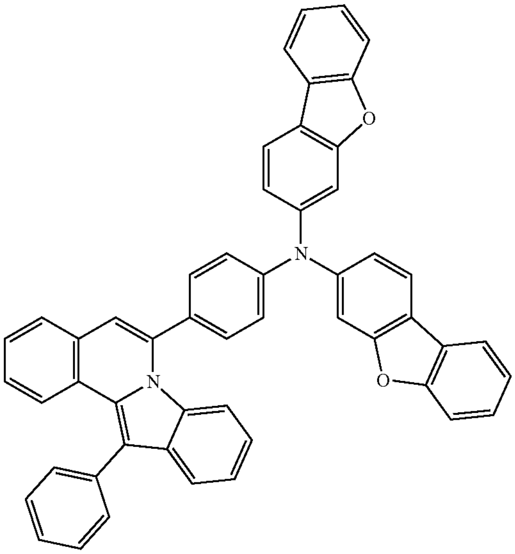
A12
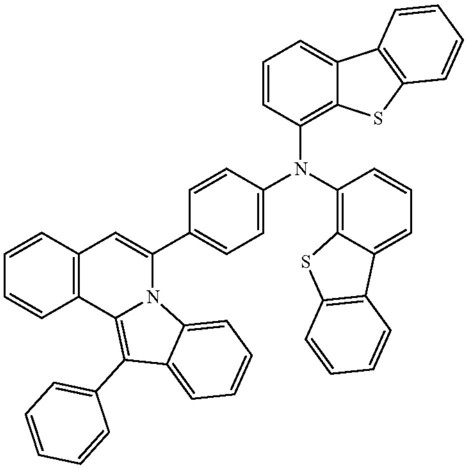
A13
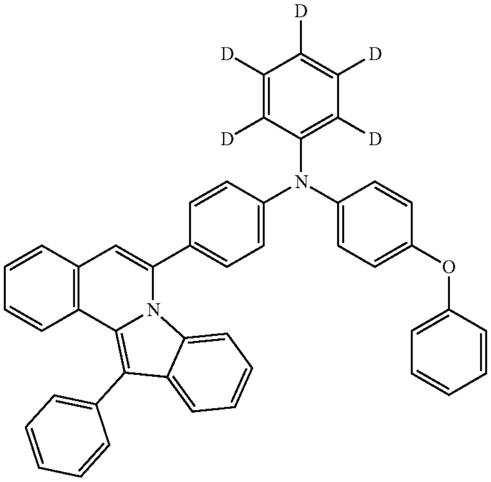
A14
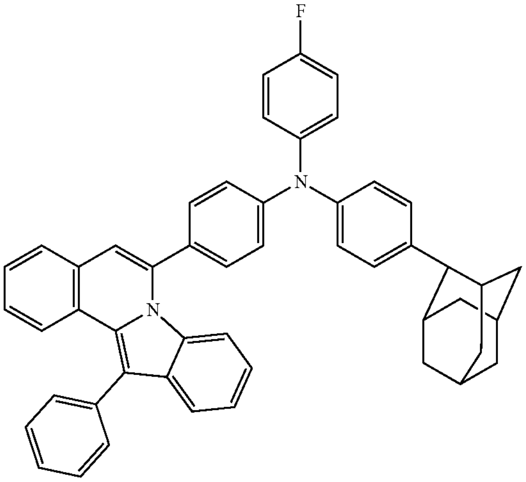
A15
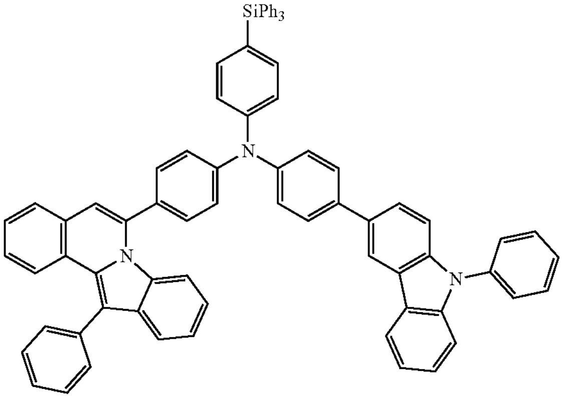
A16
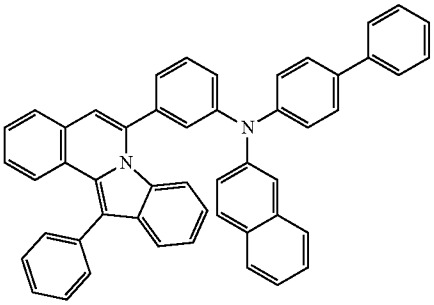

-continued
A17
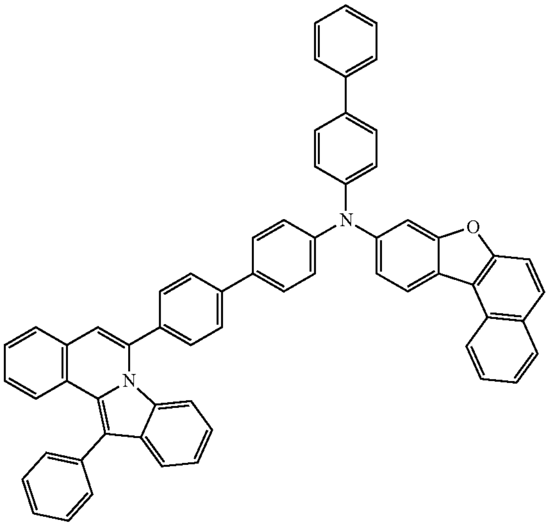
A18
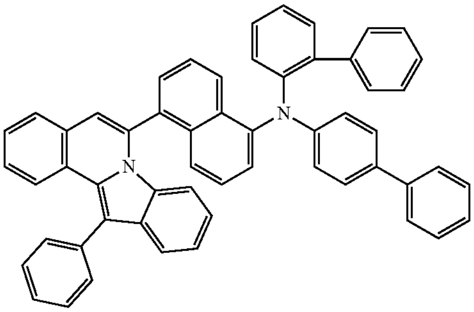
A19
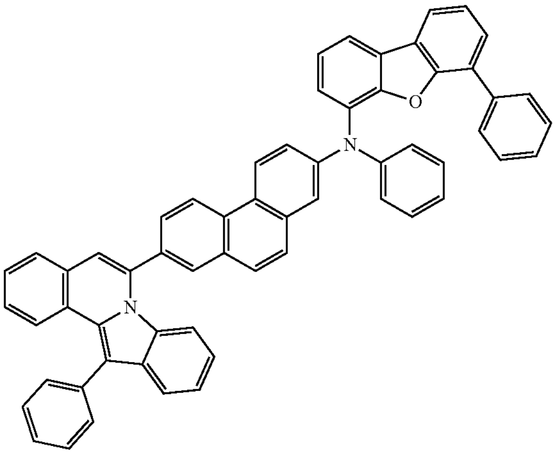
A20
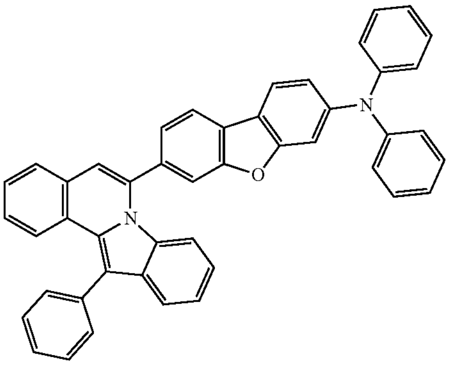
A21
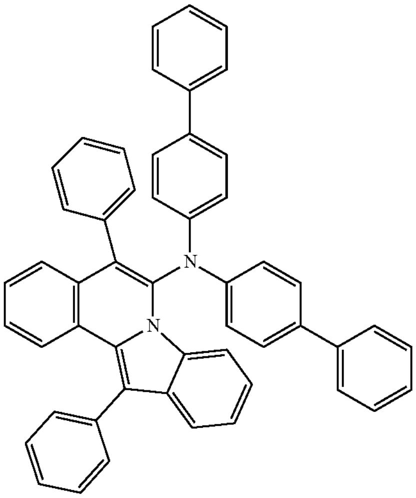
A22
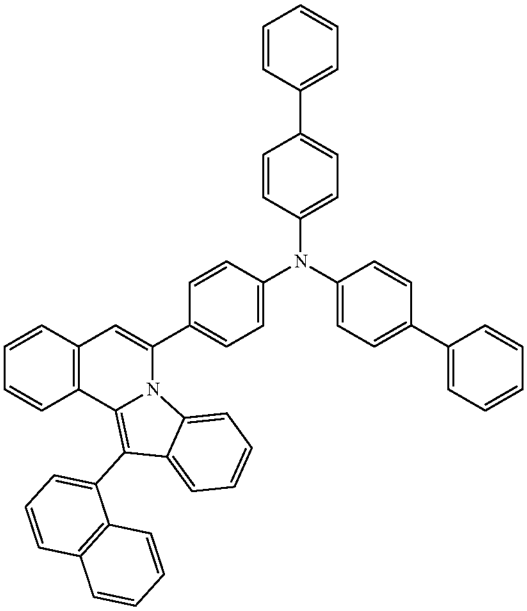

-continued
A23
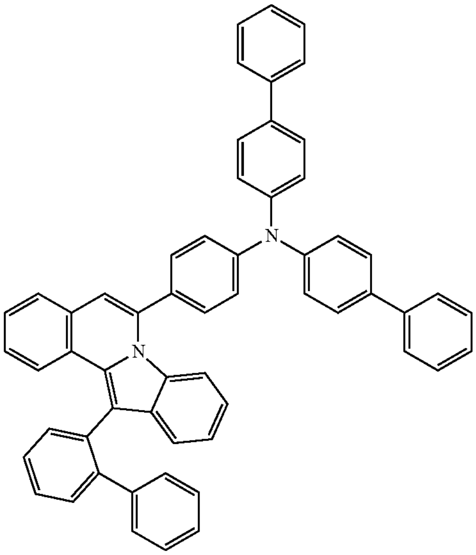
A24
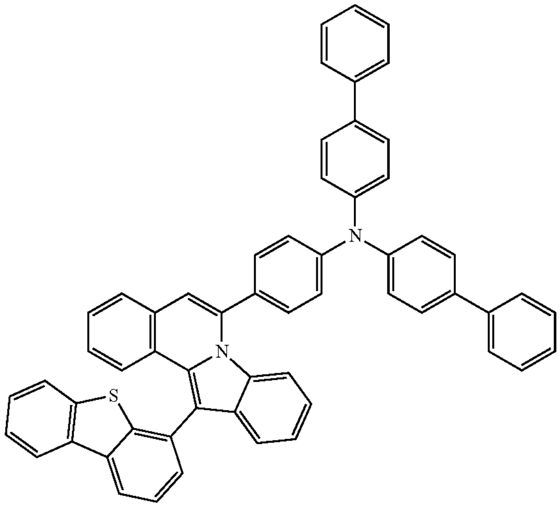
A25
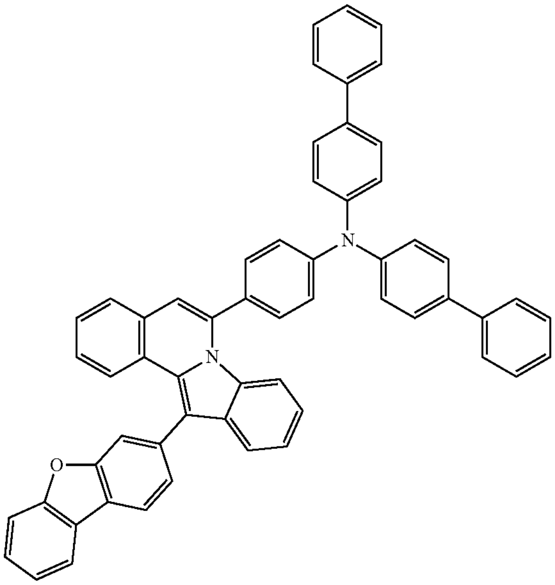
A26
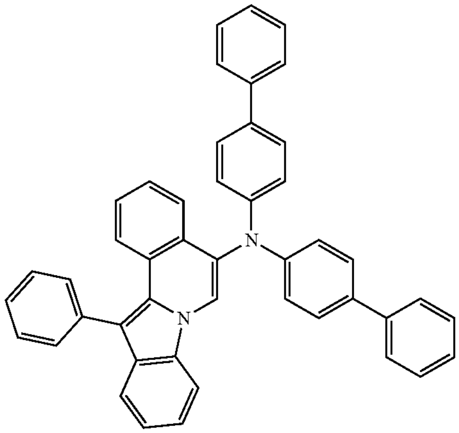
A27
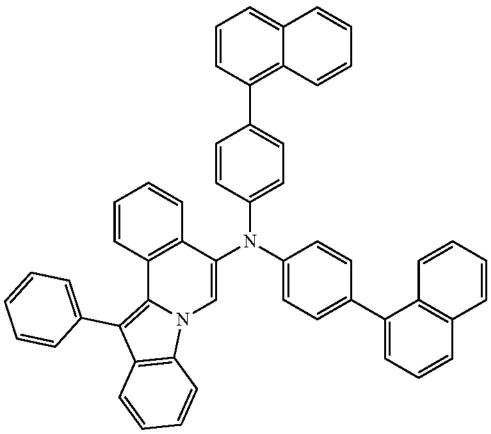
A28
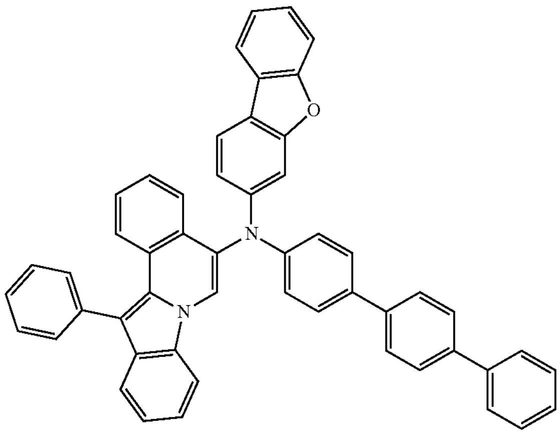

-continued
A29
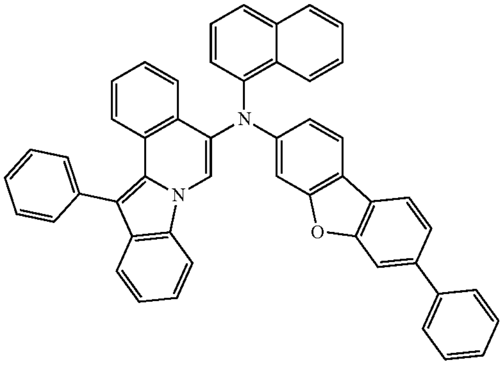
A30
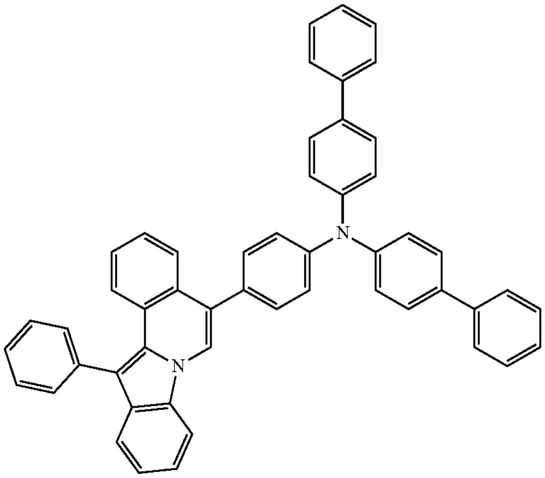
A31
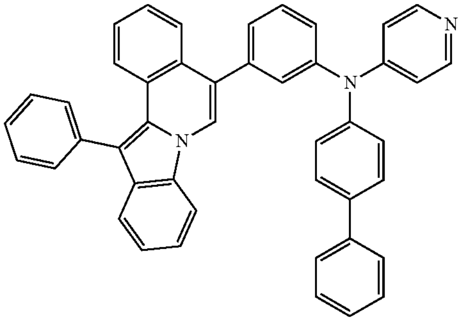
A32
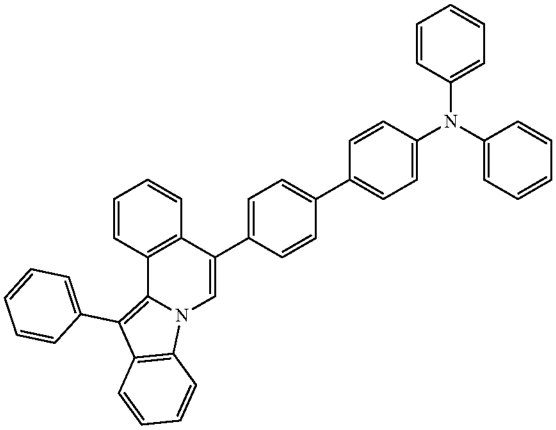
A33
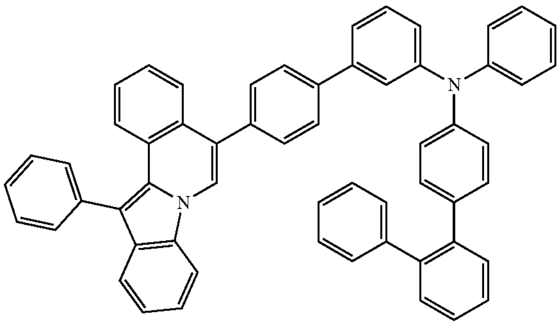
A34
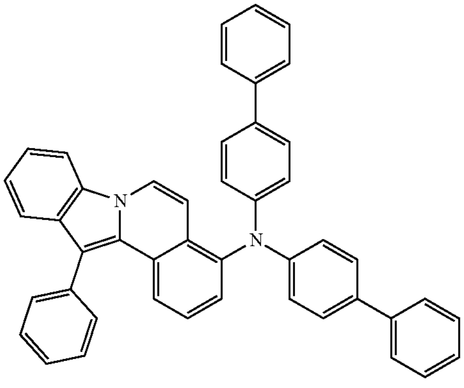

-continued
A35
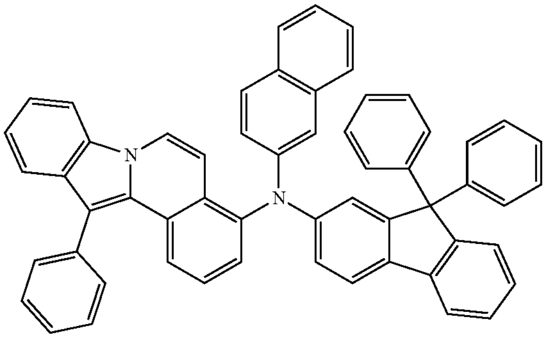
A36
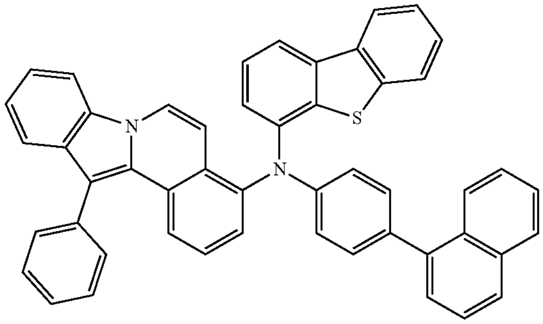
A37
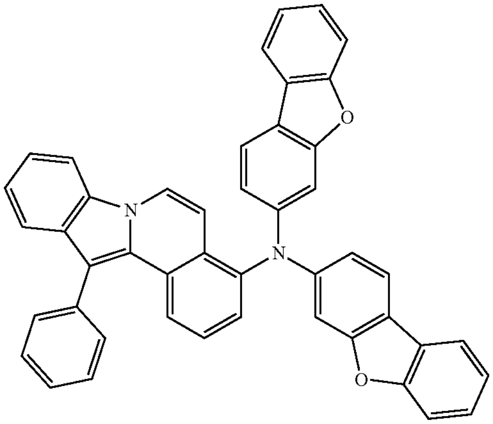
A38
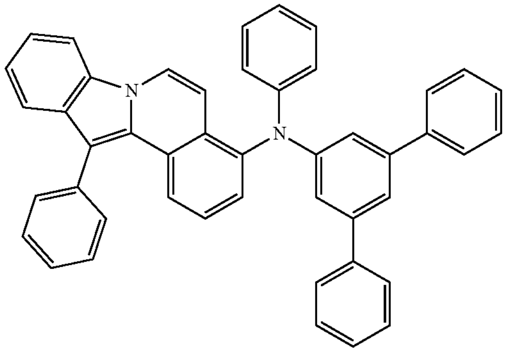
A39
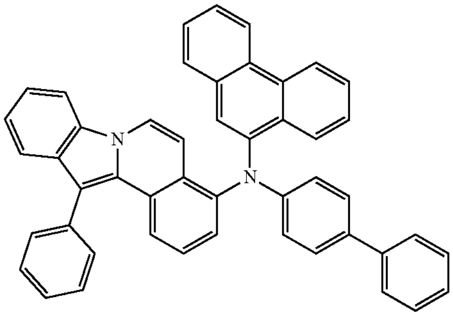
A40
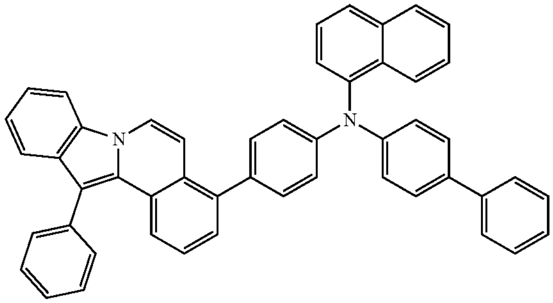
A41
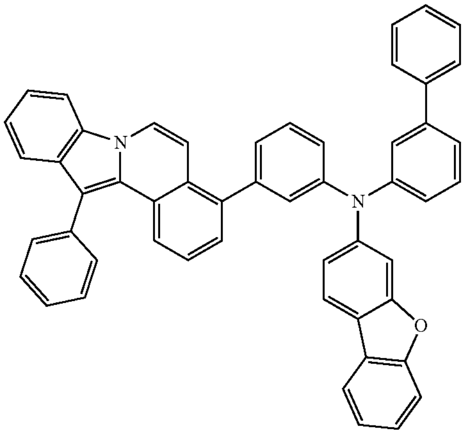
A42
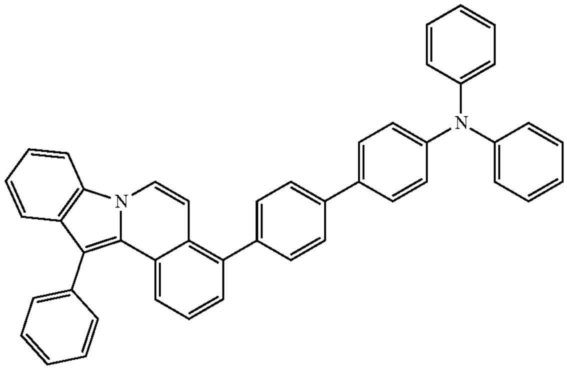

-continued
A43
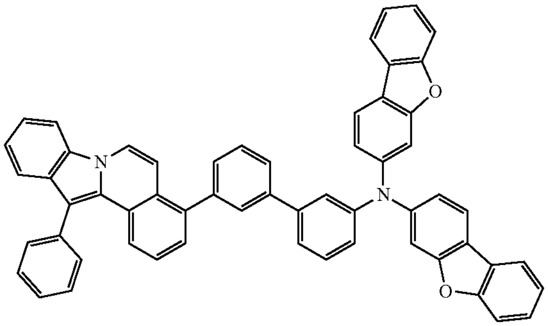
A44
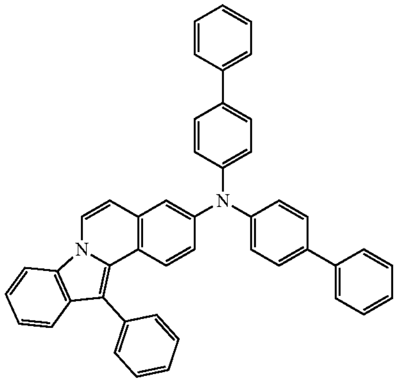
A45
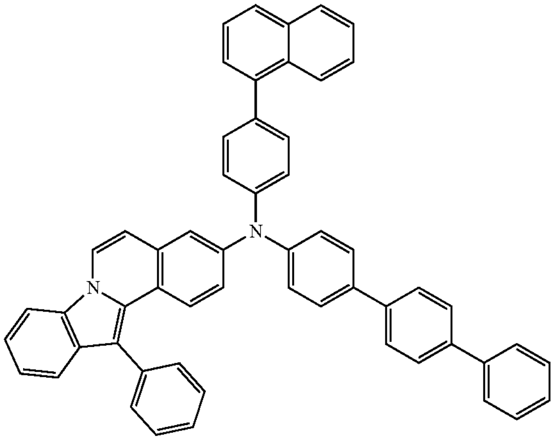
A46
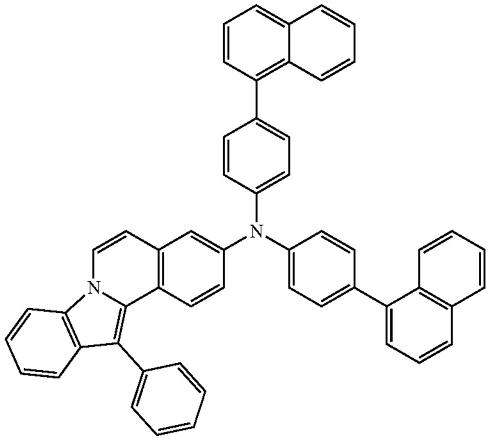
A47
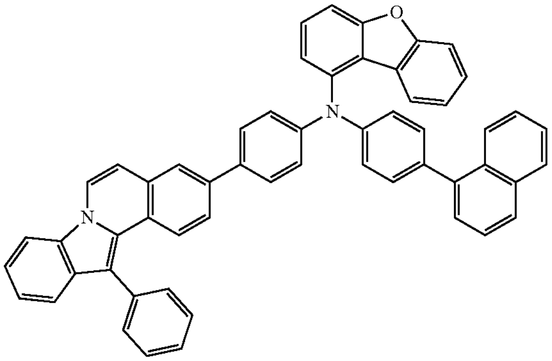
A48
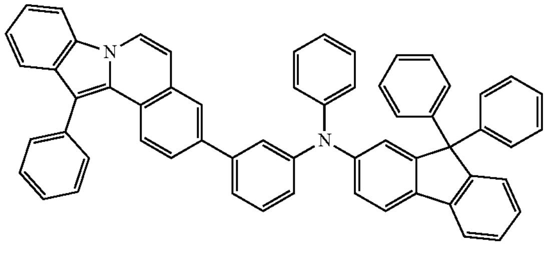

-continued
A49
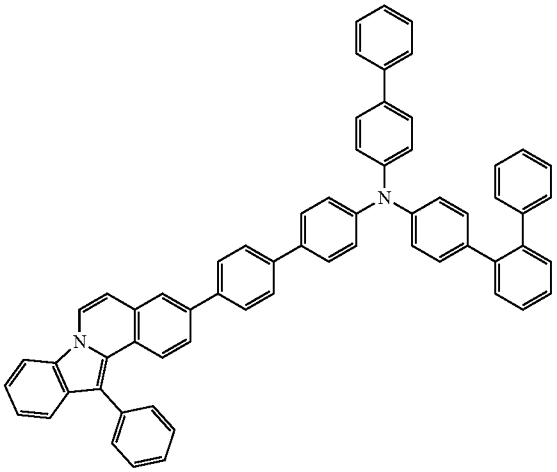
A50
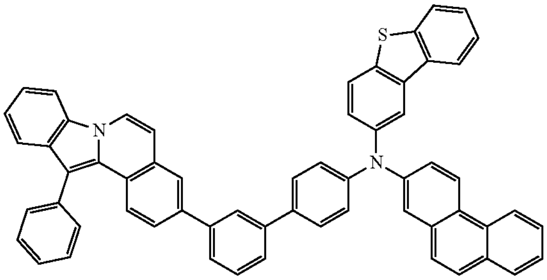
A51
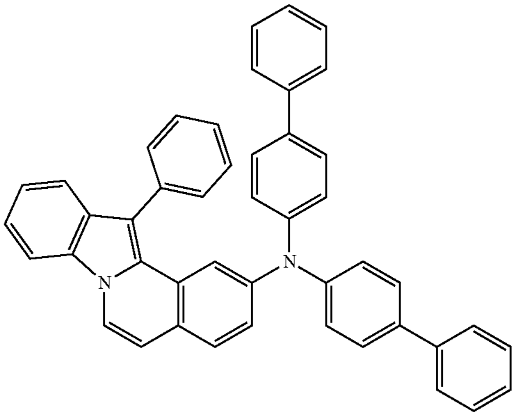
A52
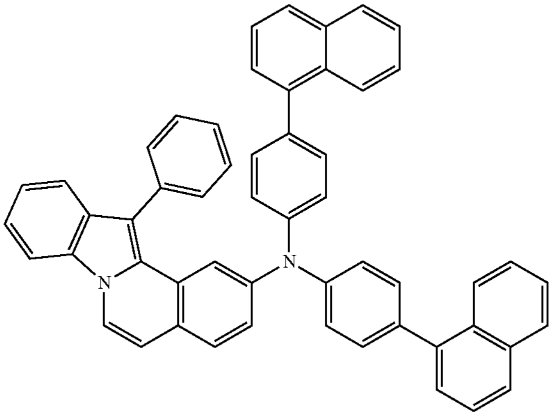
A53
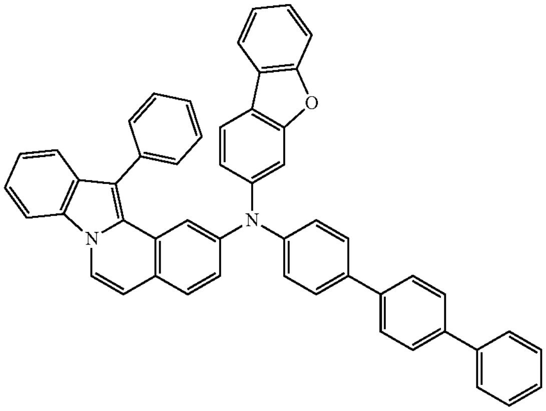
A54
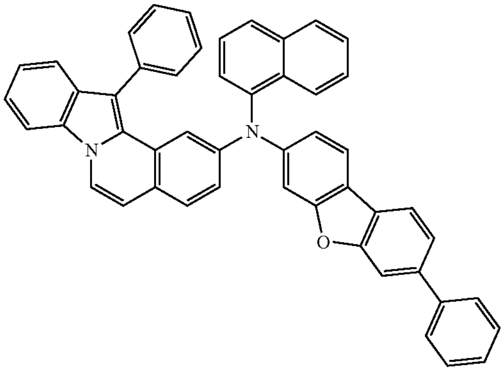

-continued
A55
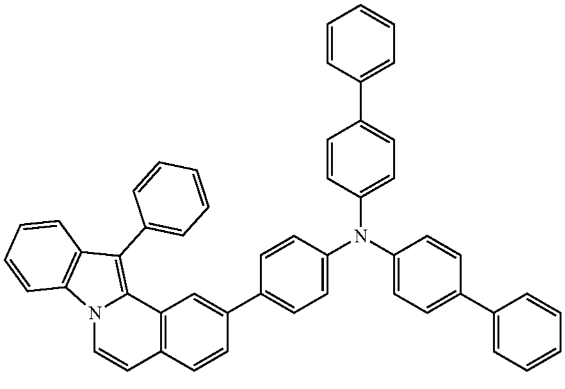
A56
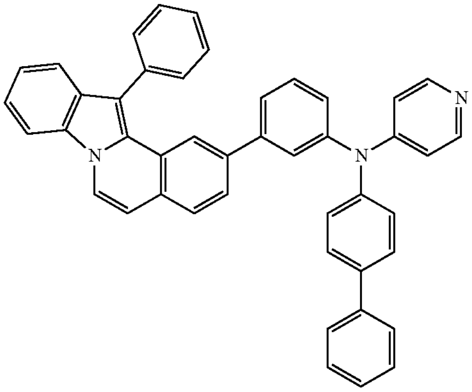
A57
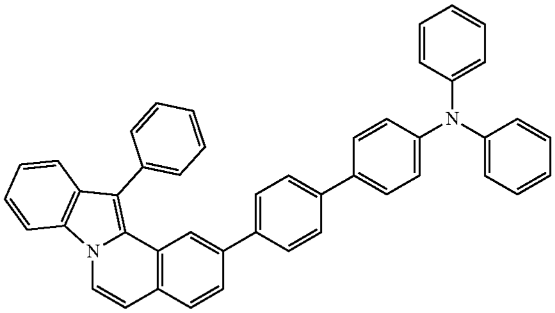
A58
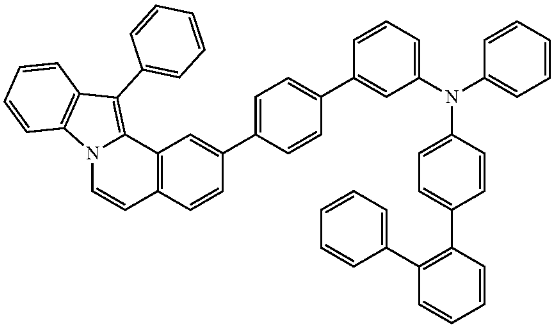
A59
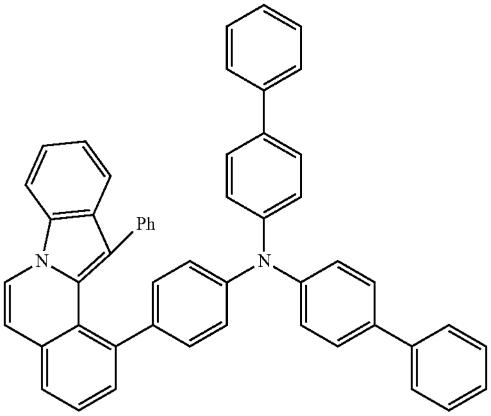
A60
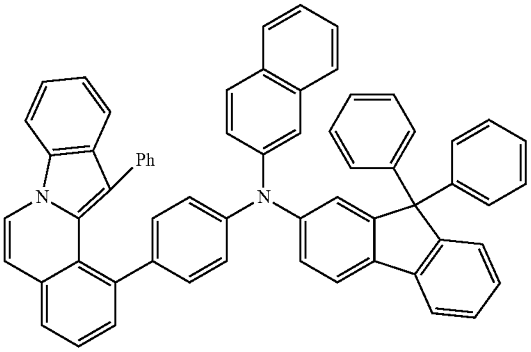
A61
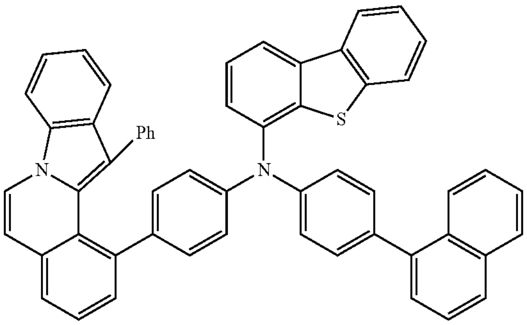
A62
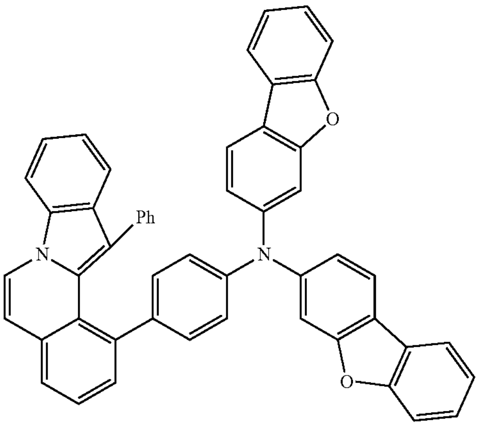

-continued
A63
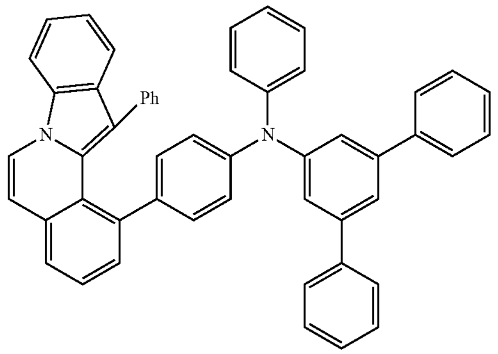
A64
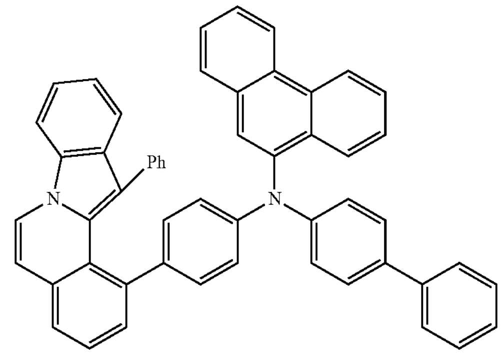
A65
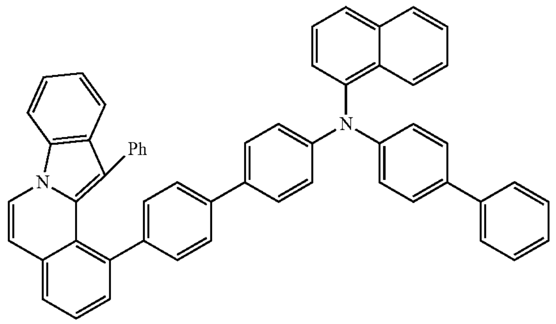
A66
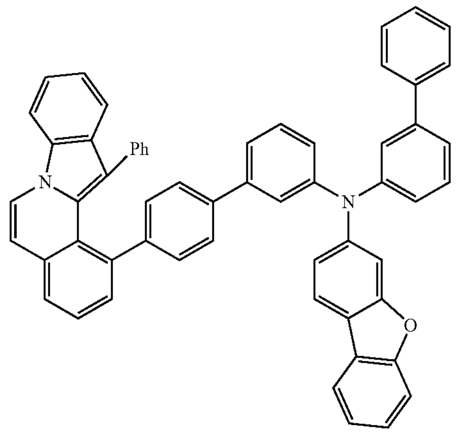
A67
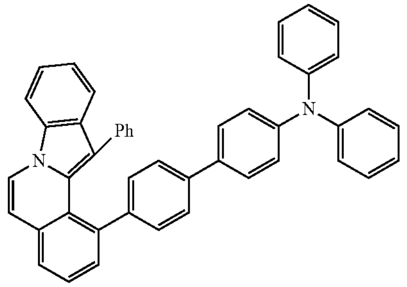
A68
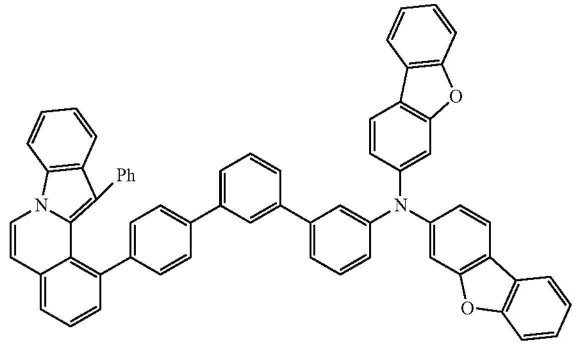
A69
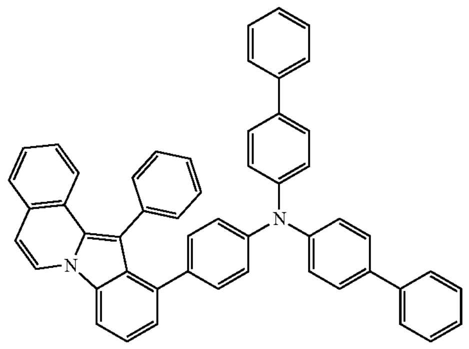
A70
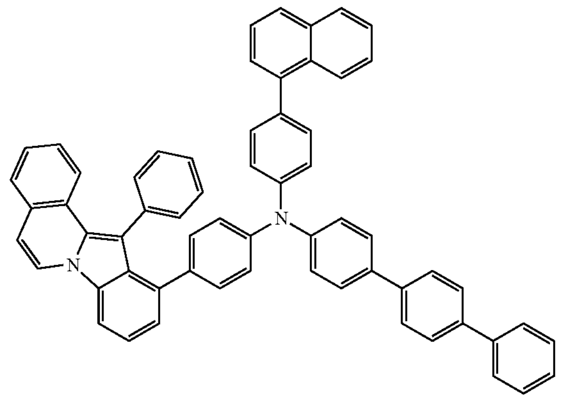

-continued
A71
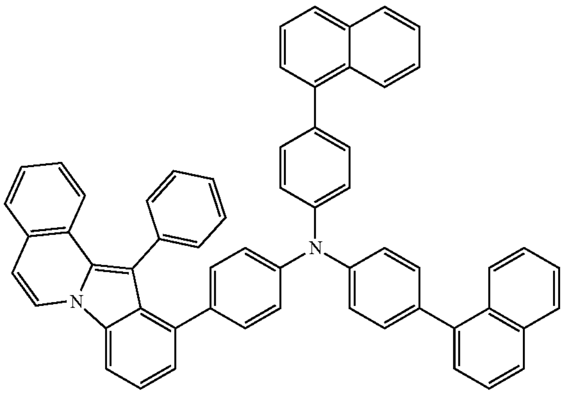
A72
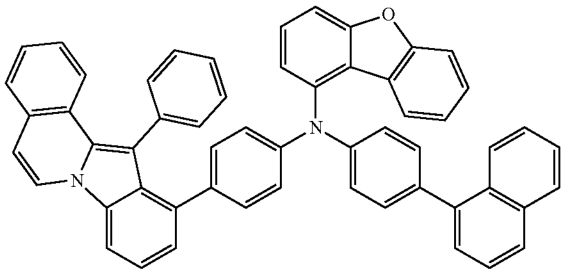
A73
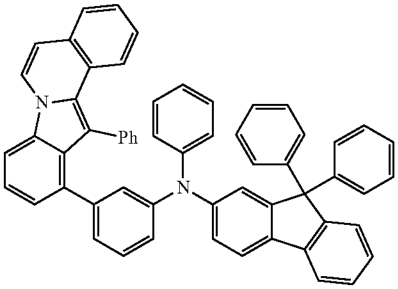
A74
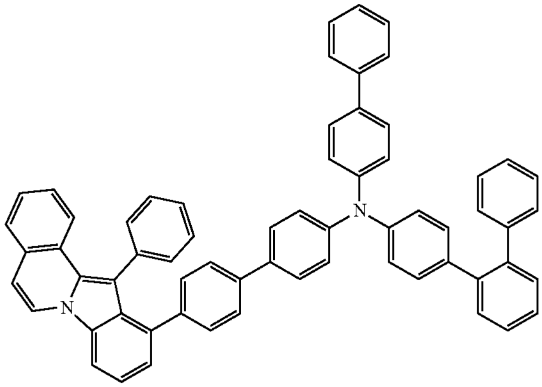
A75
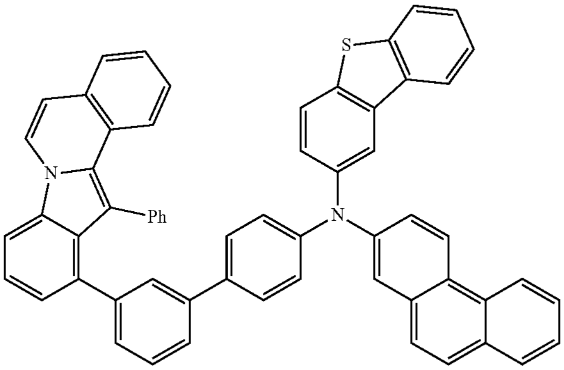
A76
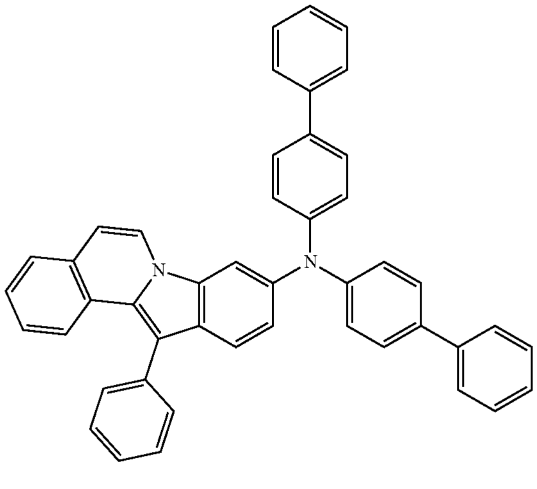

-continued
A77
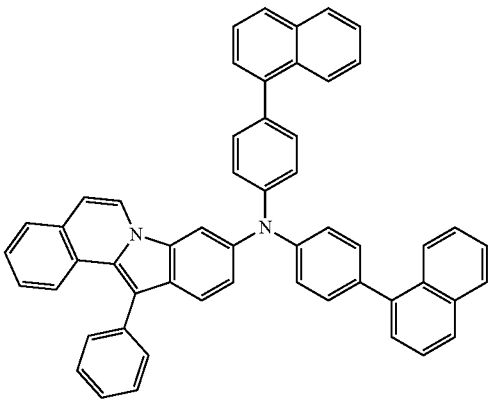
A78
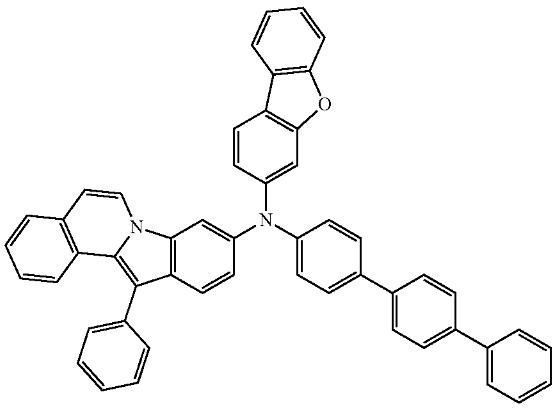
A79
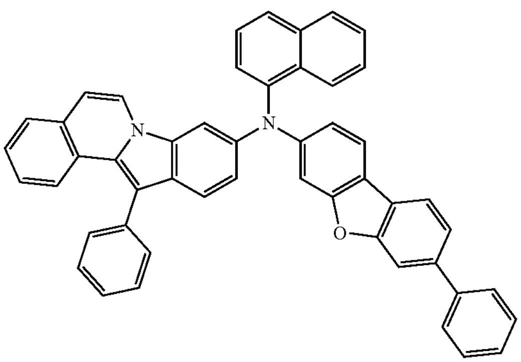
A80
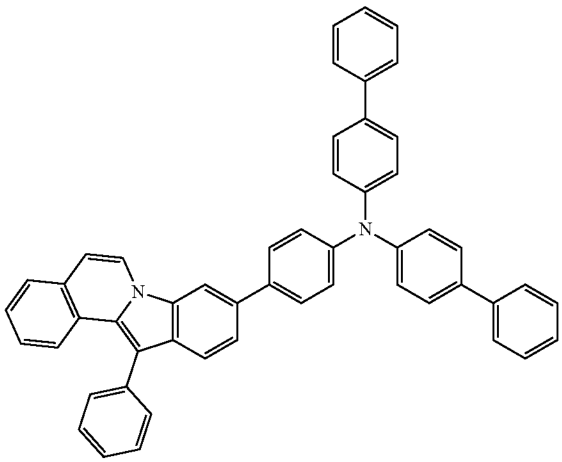
A81
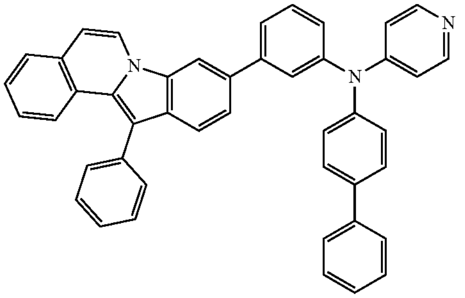
A82
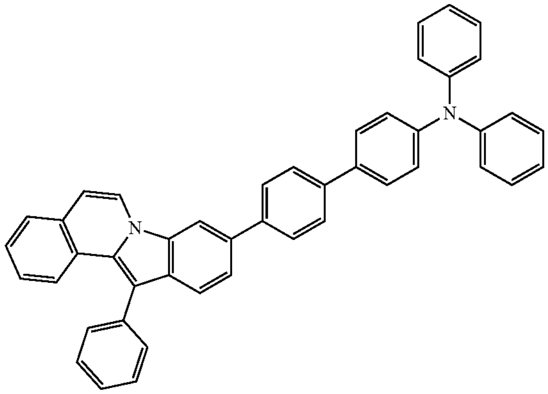

-continued
A83
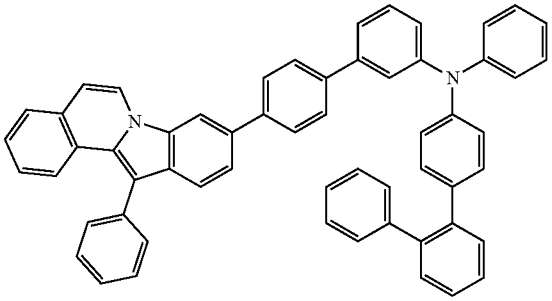
A84
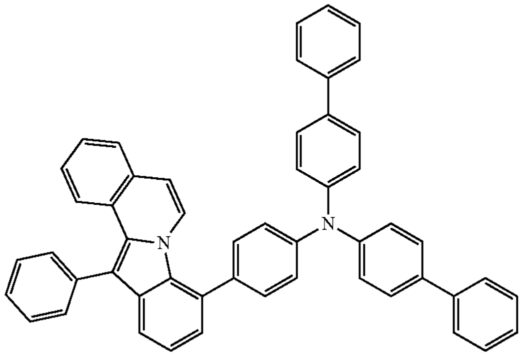
A85
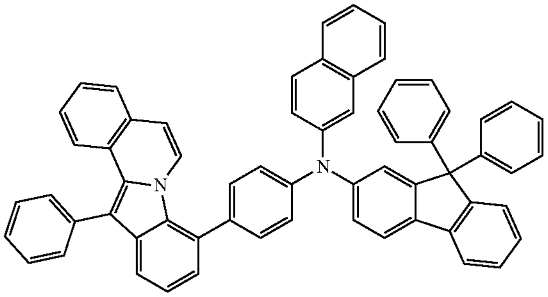
A86
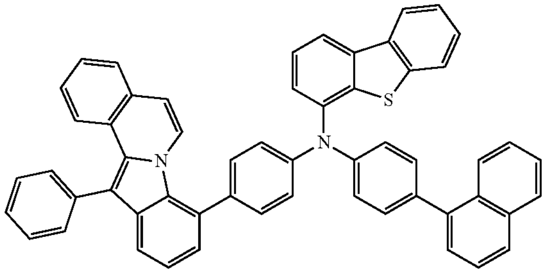
A87
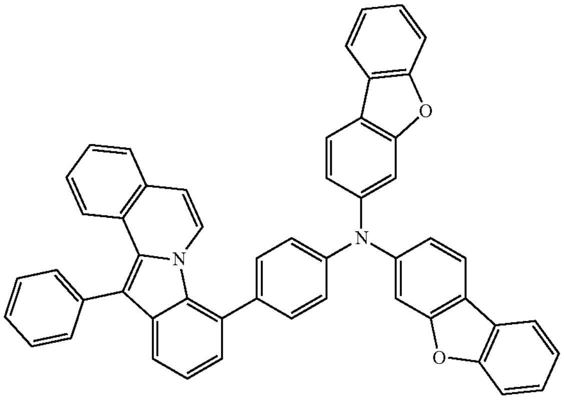
A88
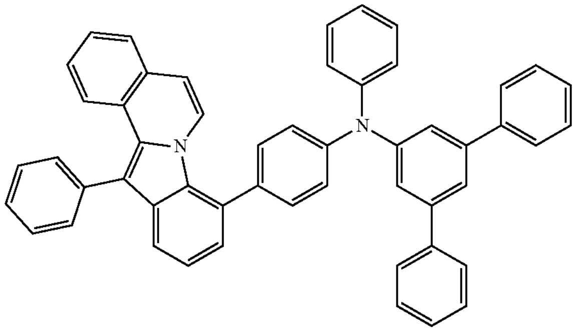
A89
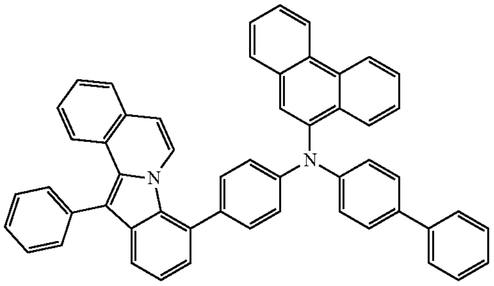
A90
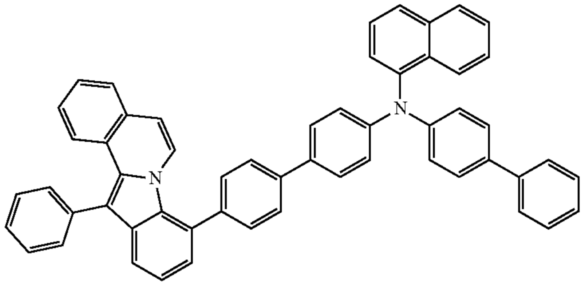

-continued
A91
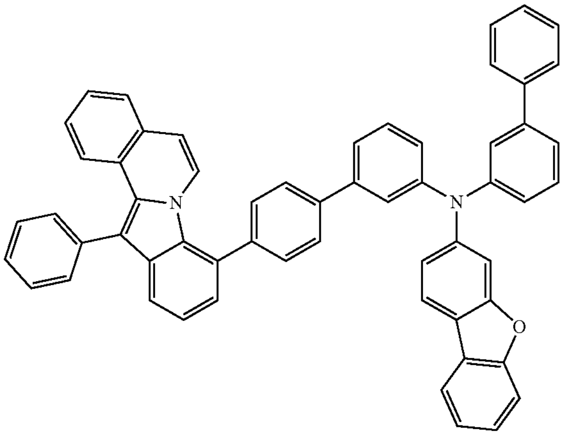
A92
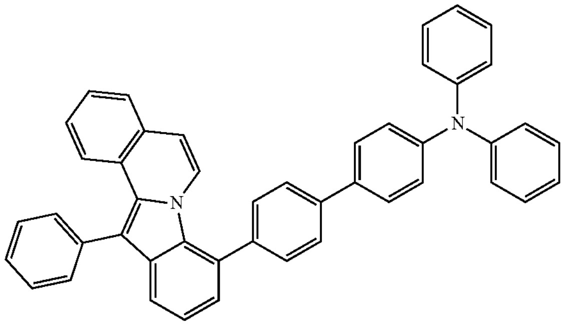
A93
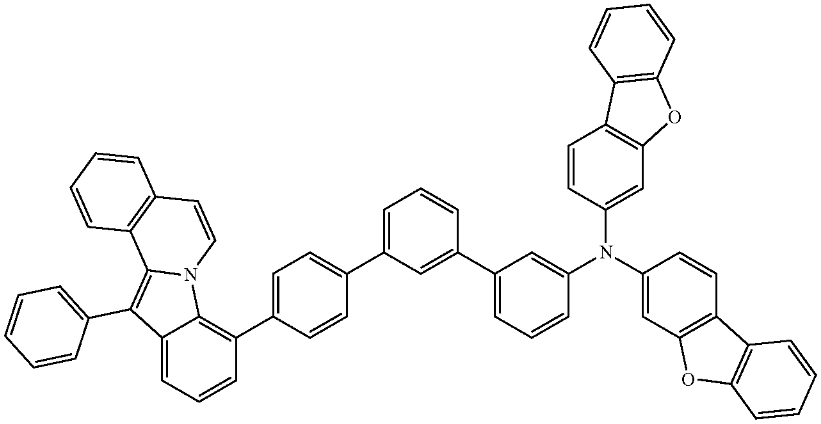
A94
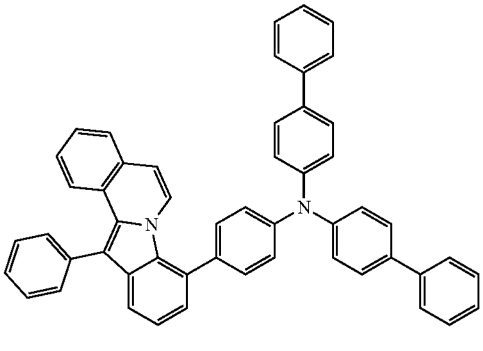
A95
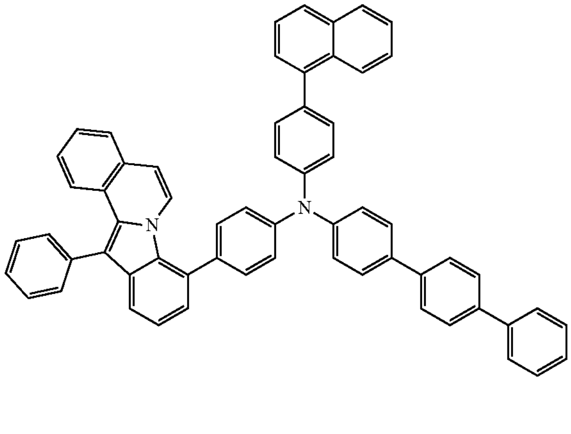

-continued
A96
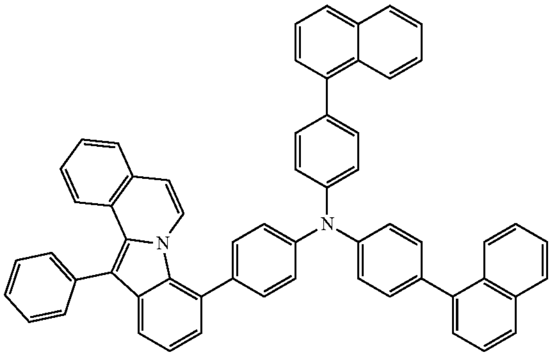
A97
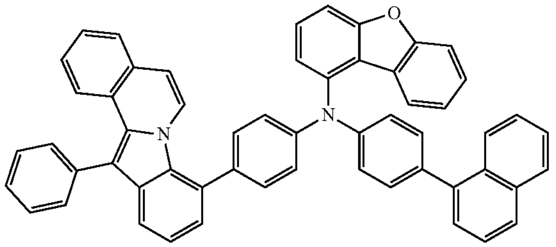
B1
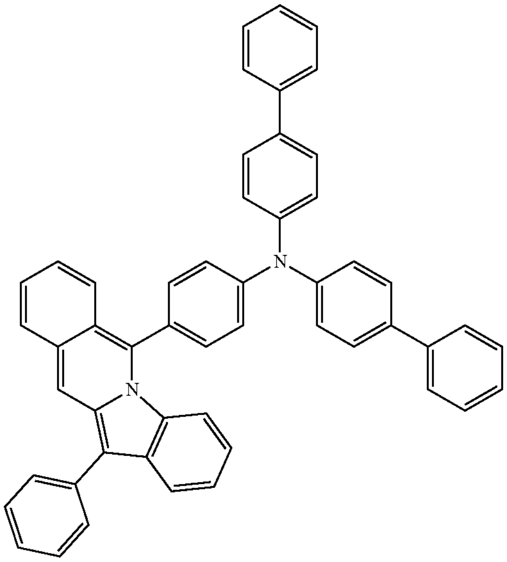
B2
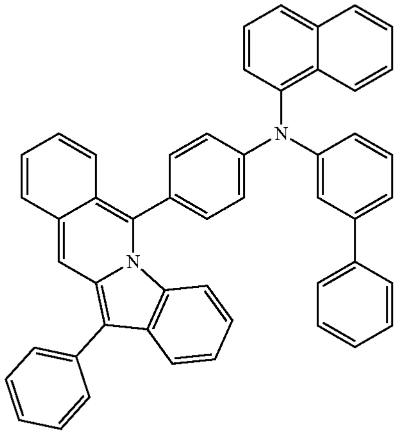
B3
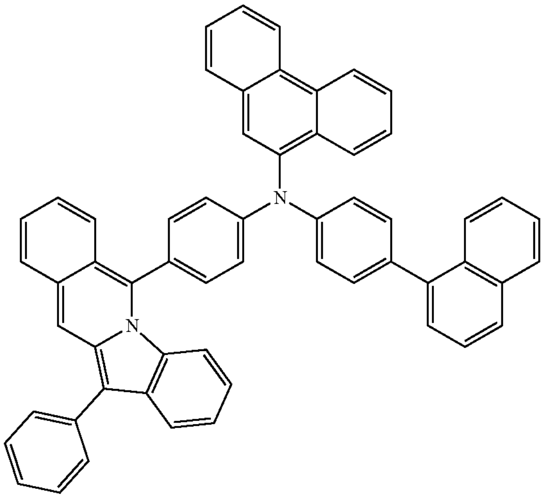
B4
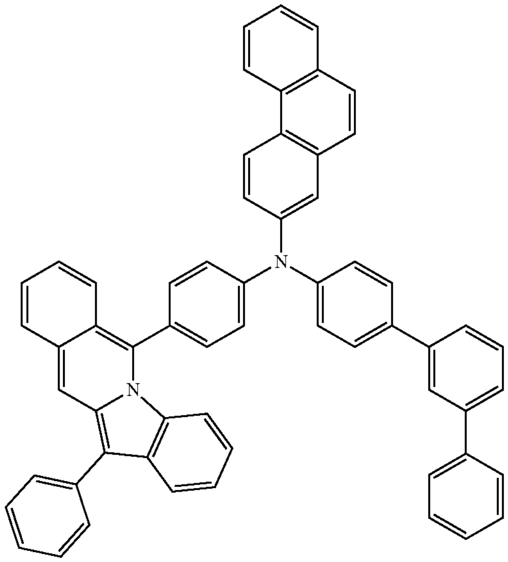

-continued
B5
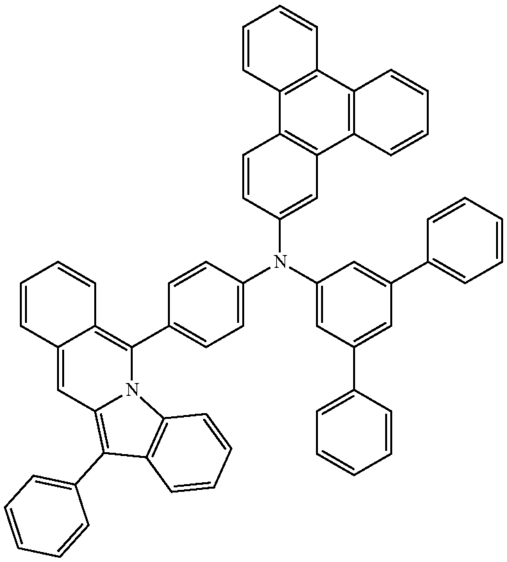
B6
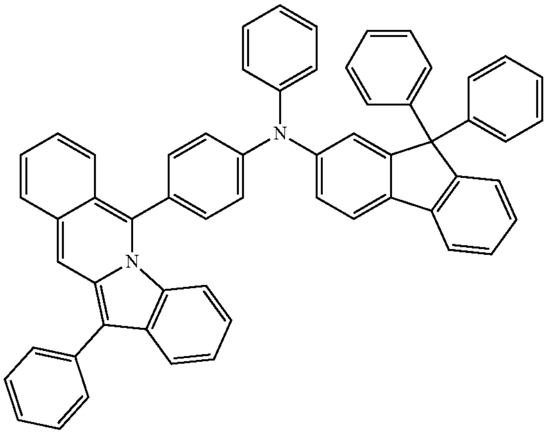
B7
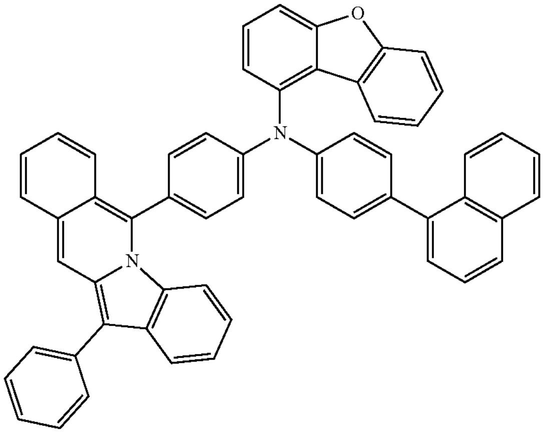
B8
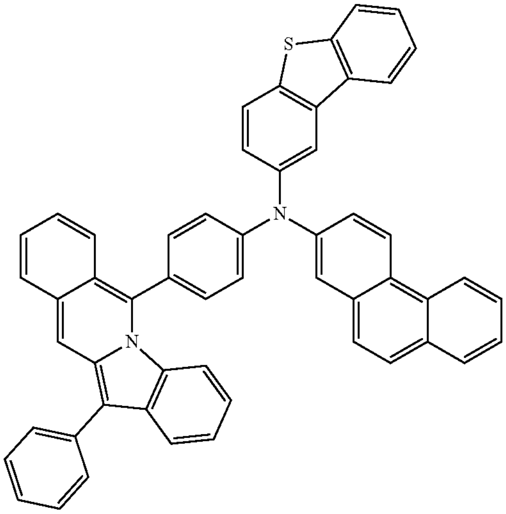
B9
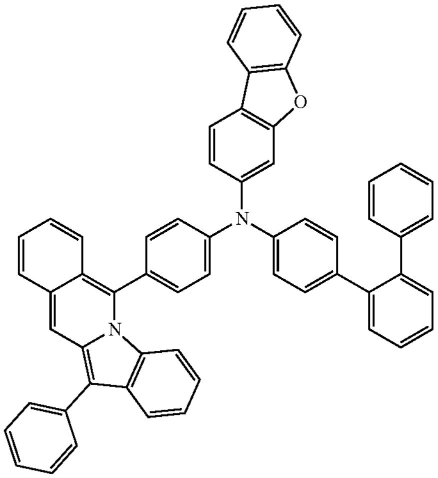
B10
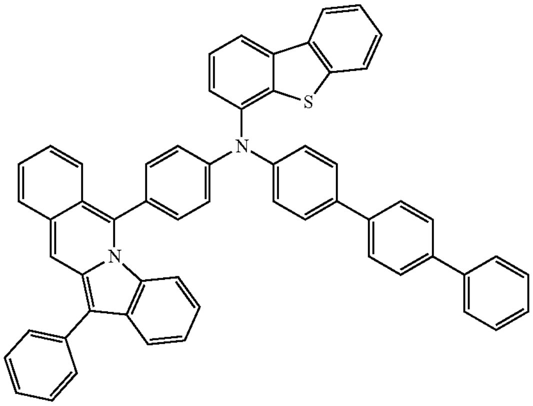

-continued
B11
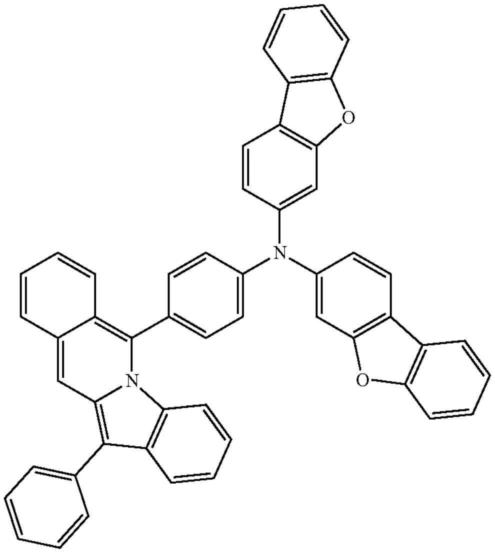
B12
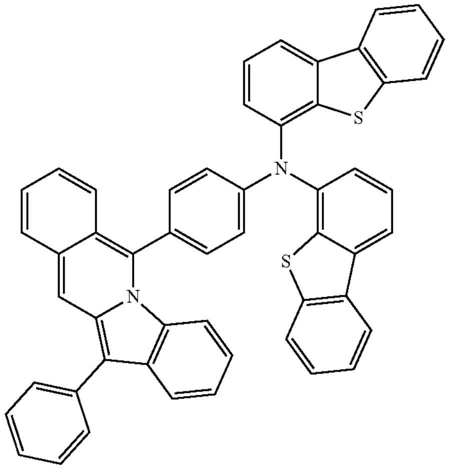
B13
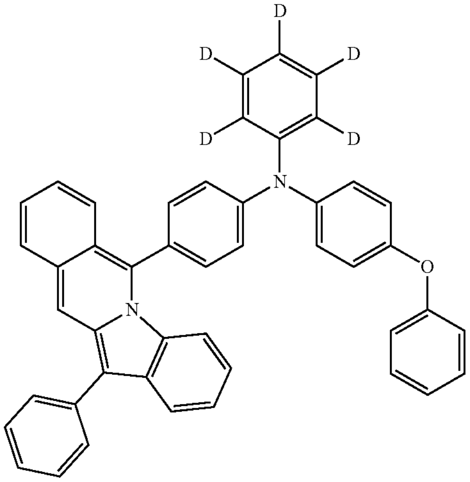
B14
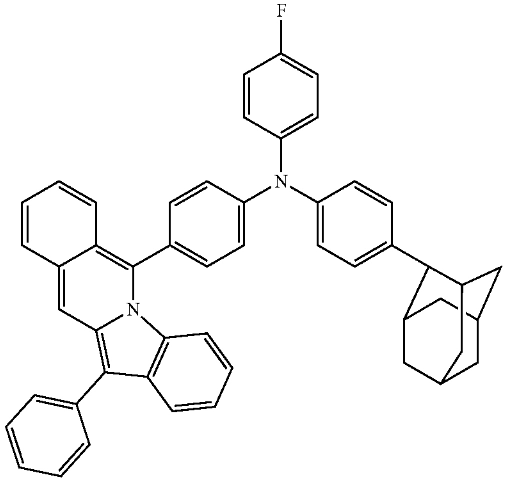
B15
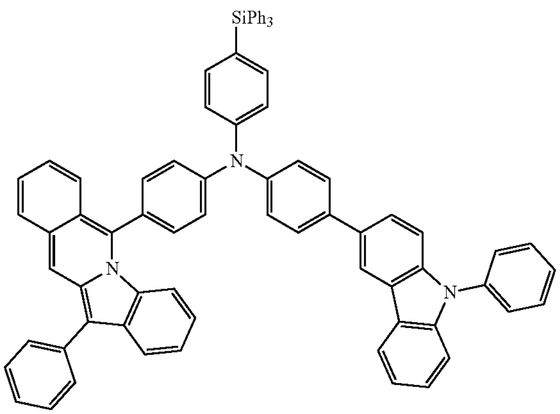
B16
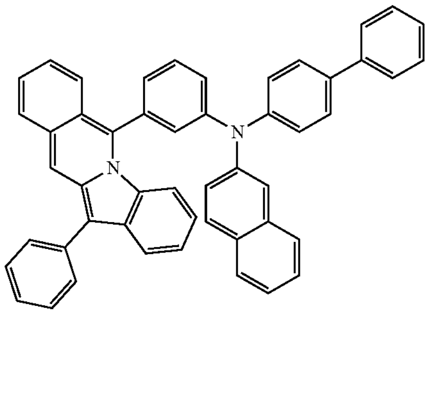

-continued
B17
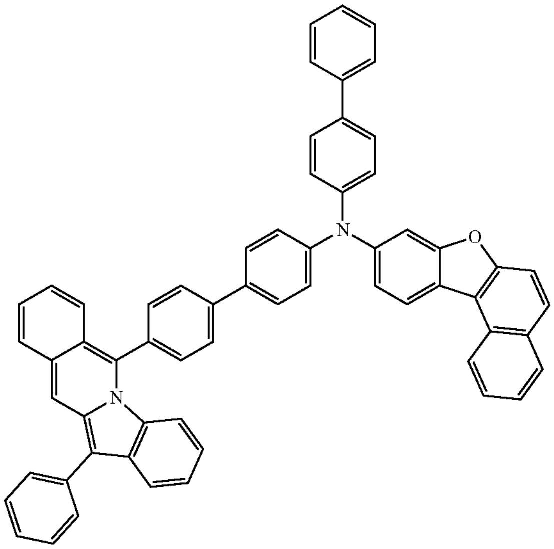
B18
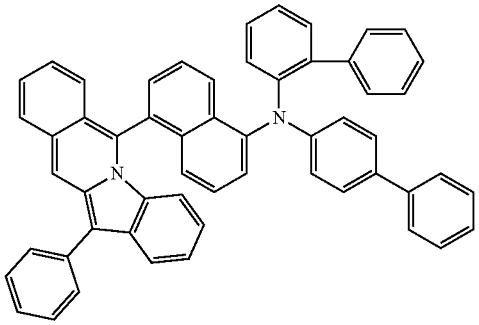
B19
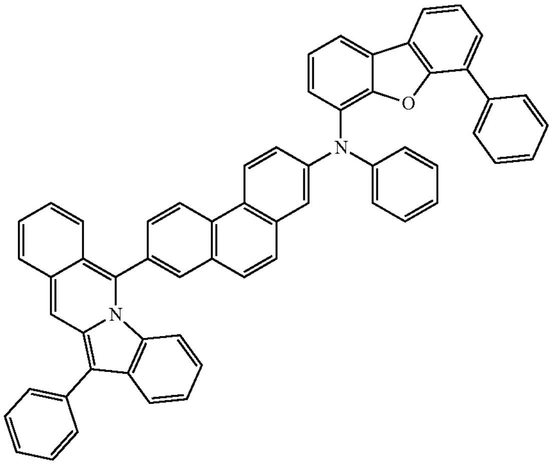
B20
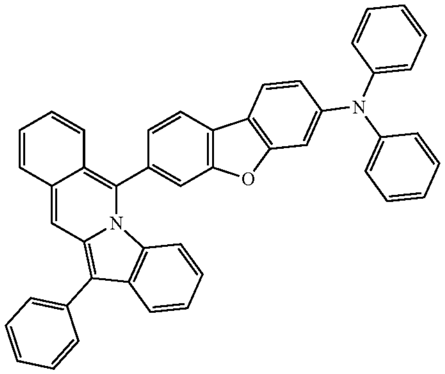
B21
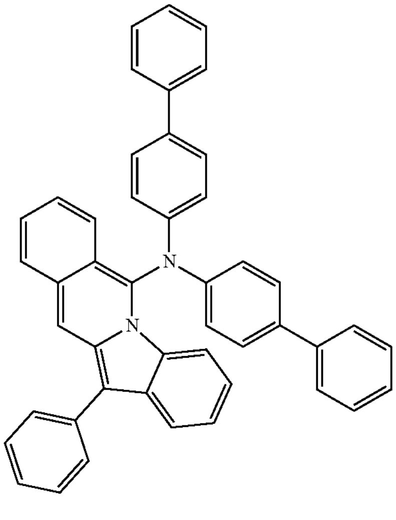
B22
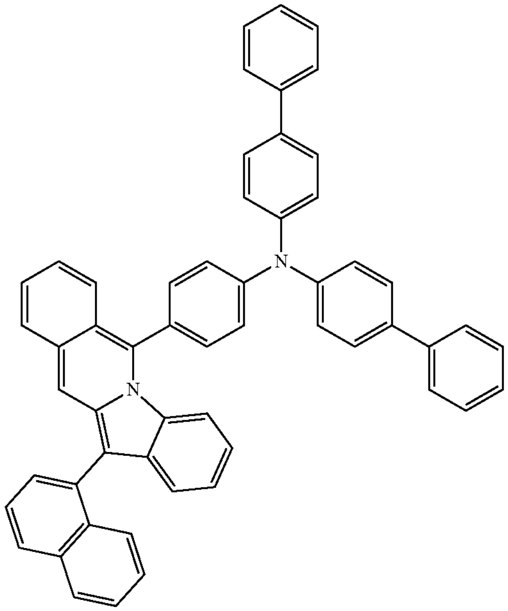

-continued
B23
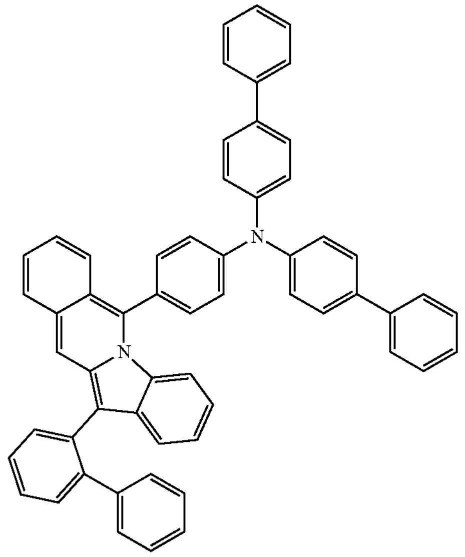
B24
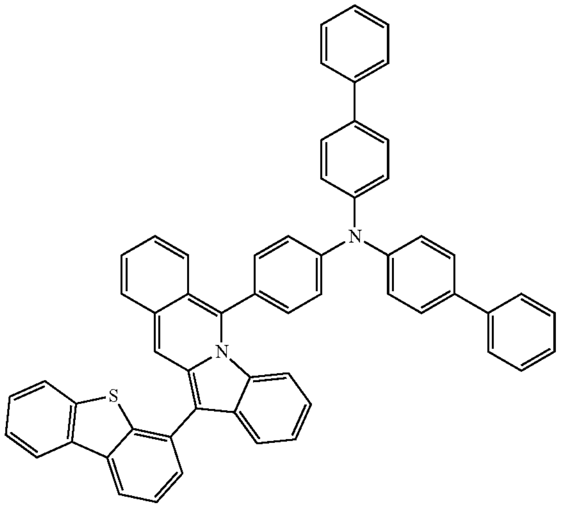
B25
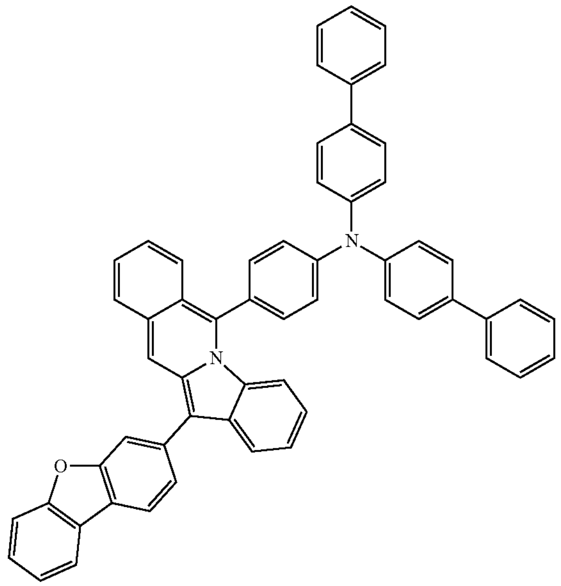
B26
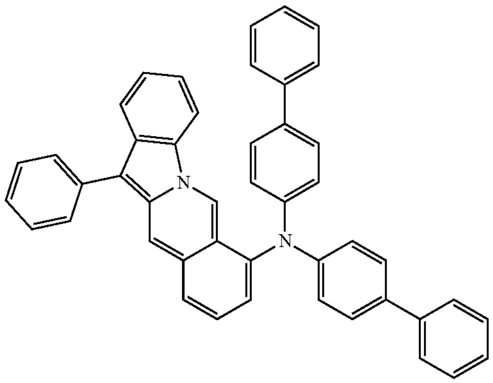
B27
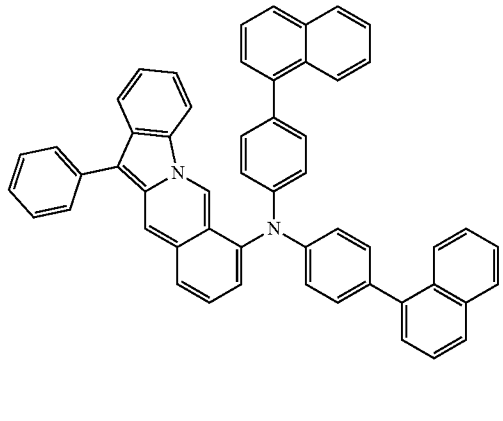
B28
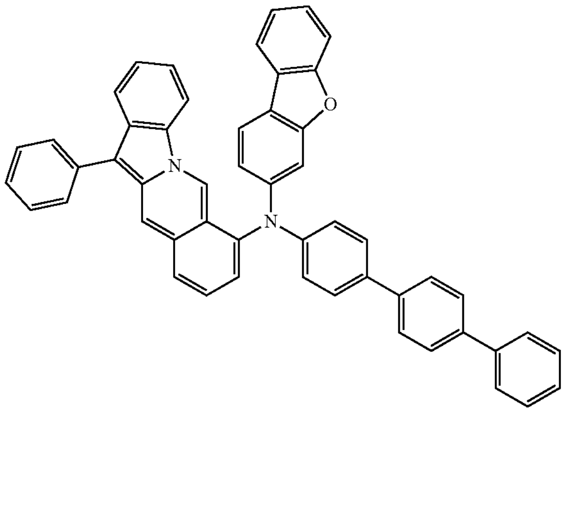

-continued
B29
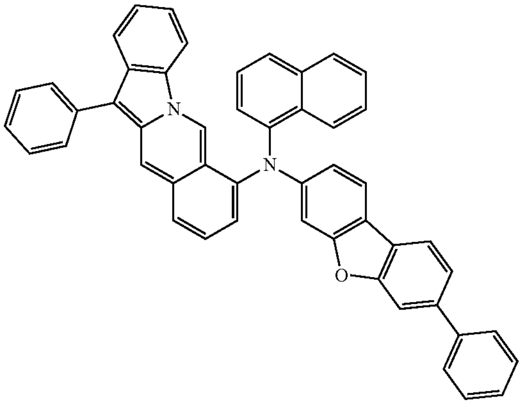
B30
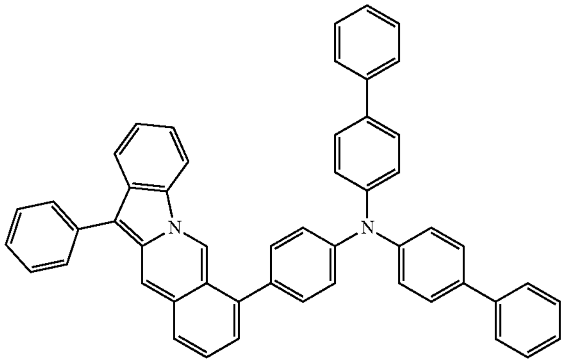
B31
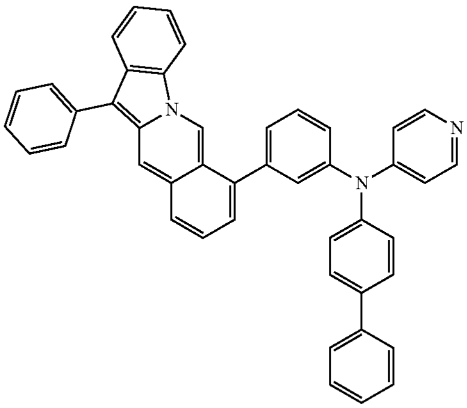
B32
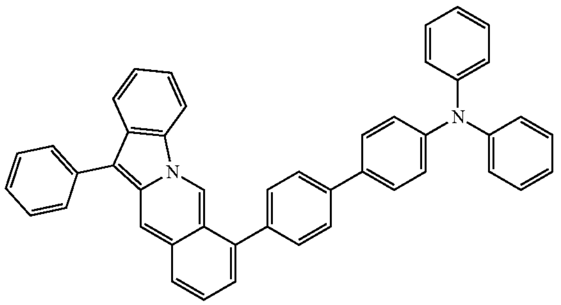
B33
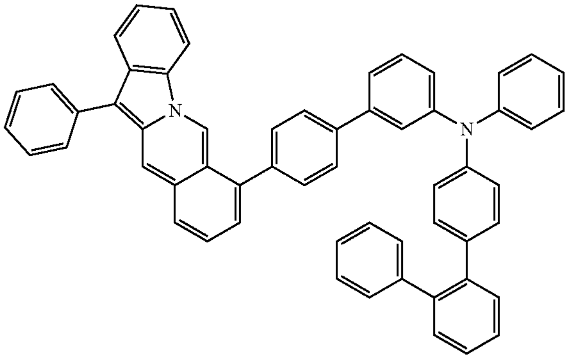
B34
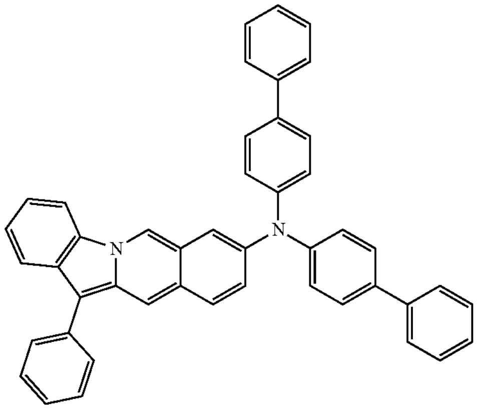

-continued
B35
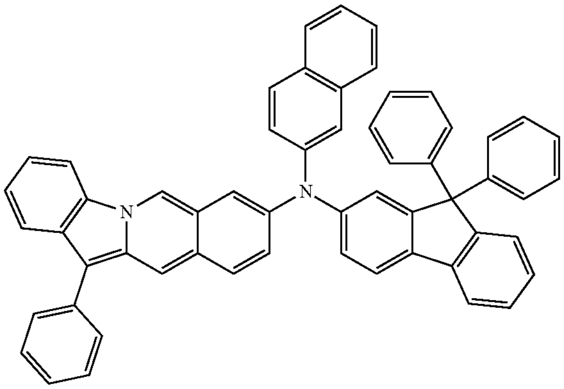
B36
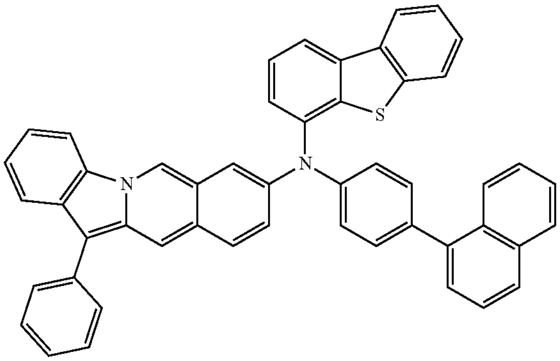
B37
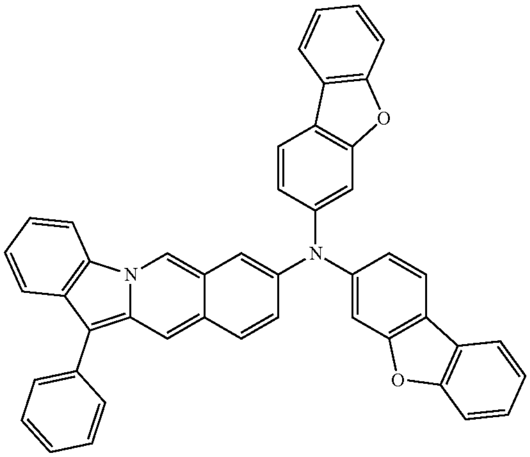
B38
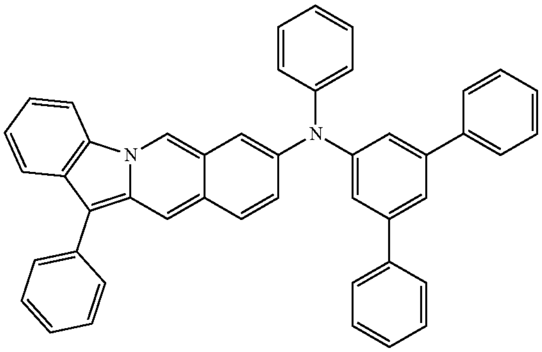
B39
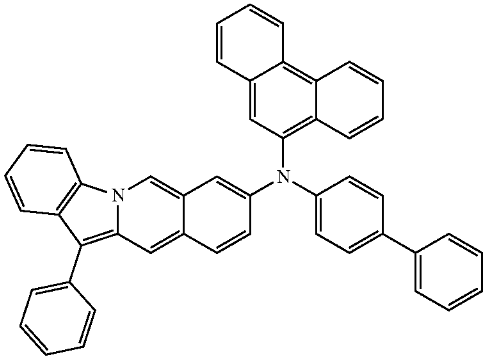
B40
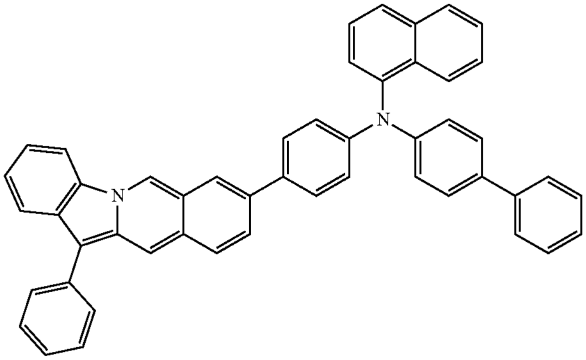

-continued
B41
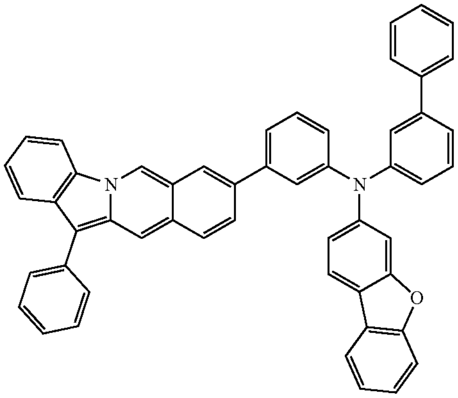
B42
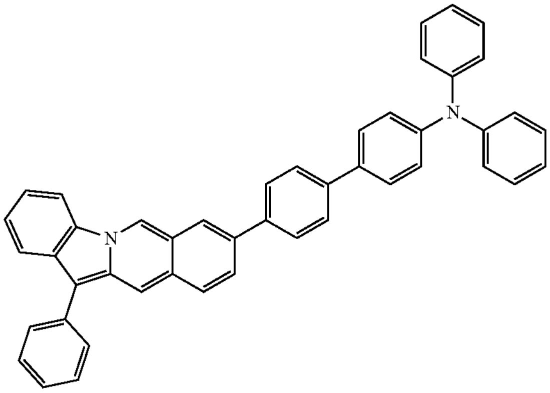
B43
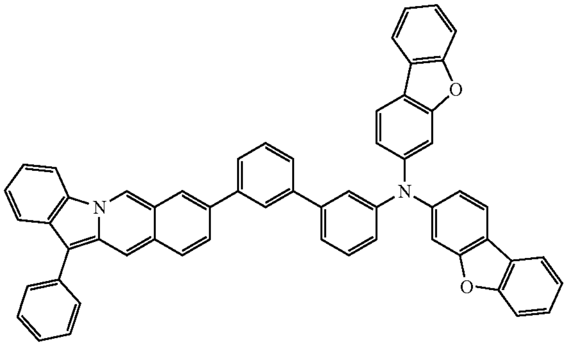
B44
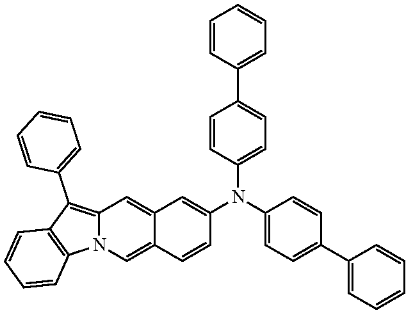
B45
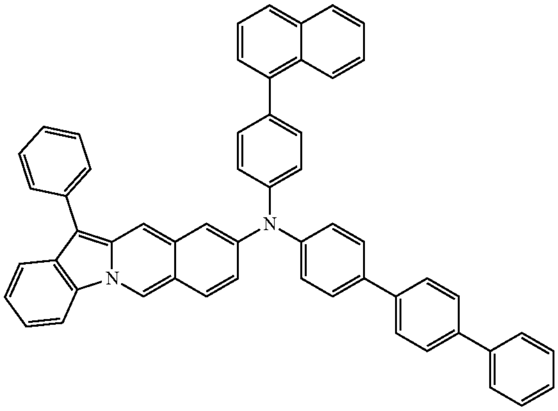
B46
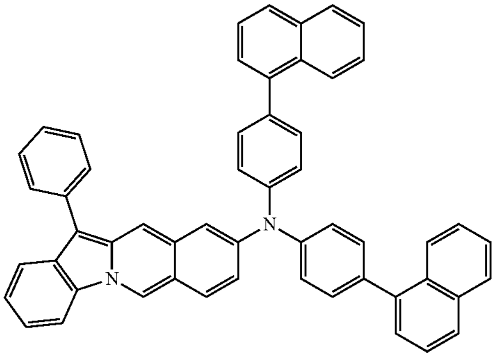
B47
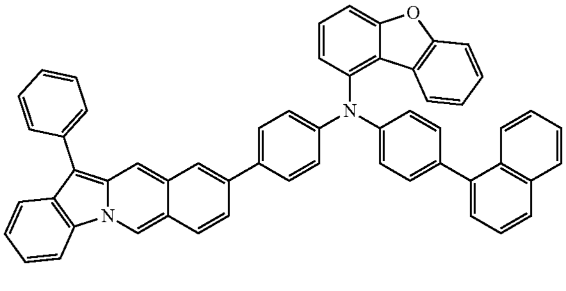
B48
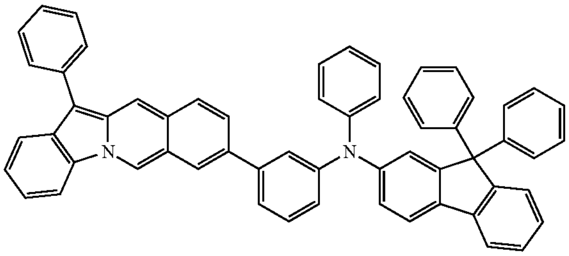

-continued
B49
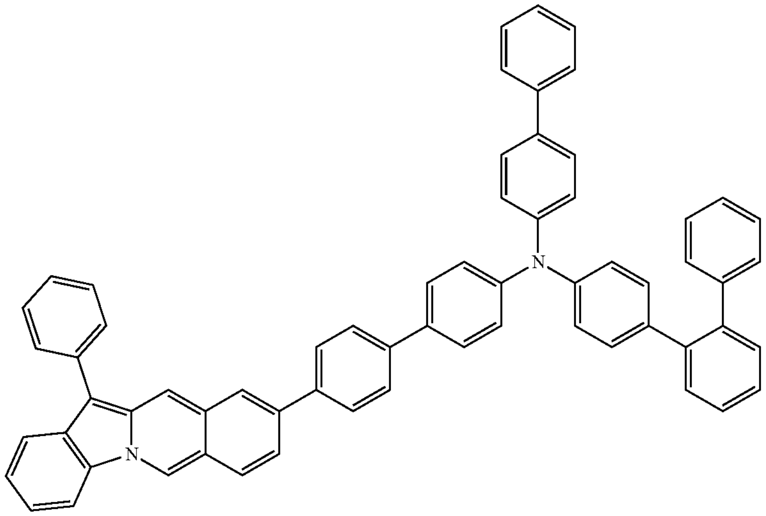
B50
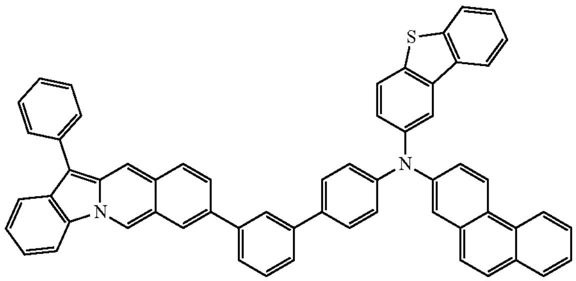
B51
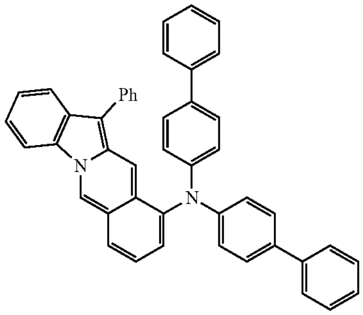
B52
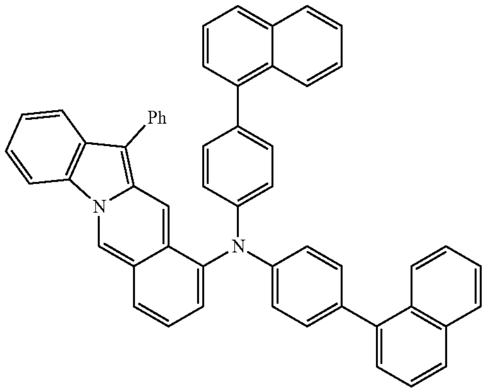
B53
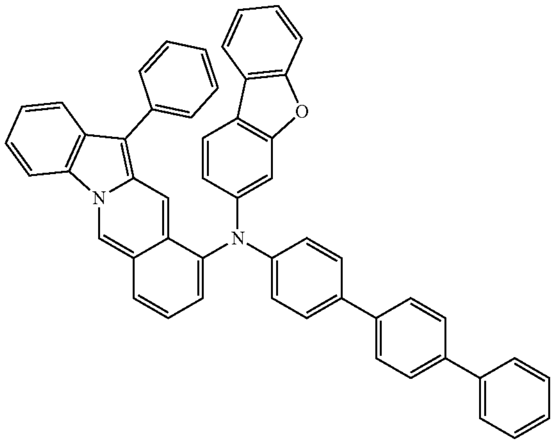

-continued
B54
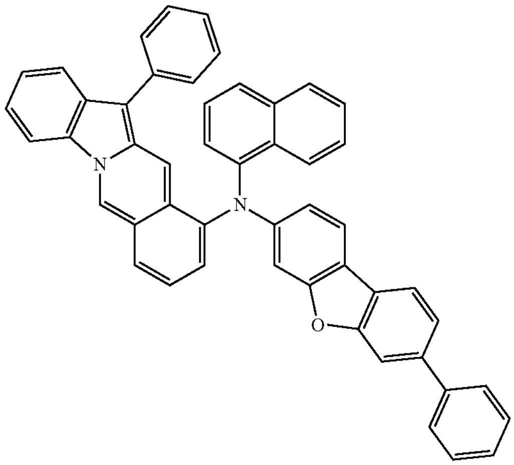
B55
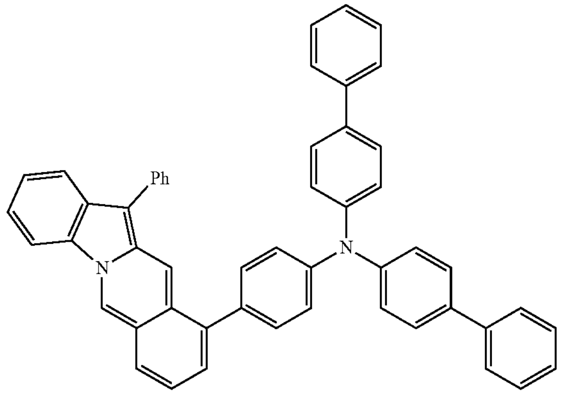
B56
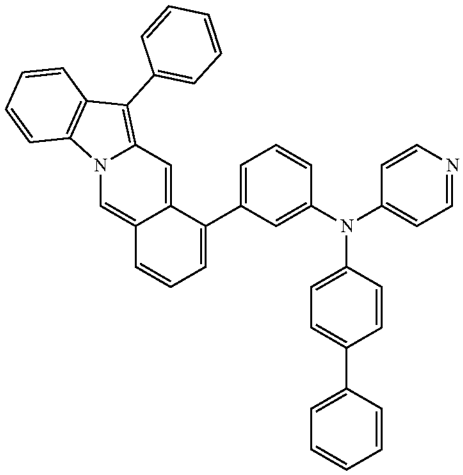
B57
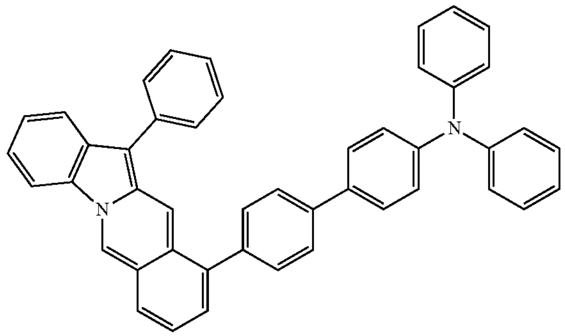
B58
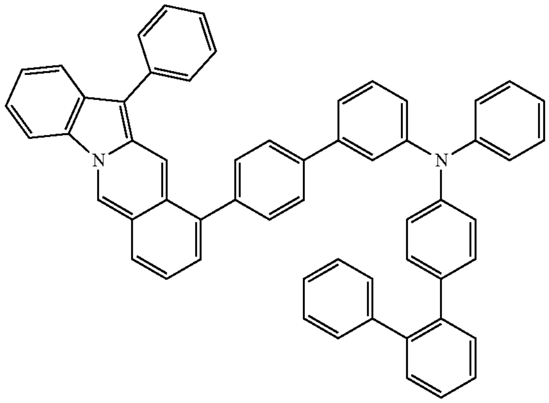
B59
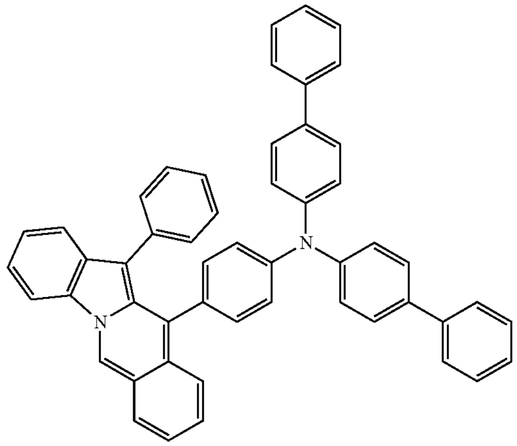

-continued
B60
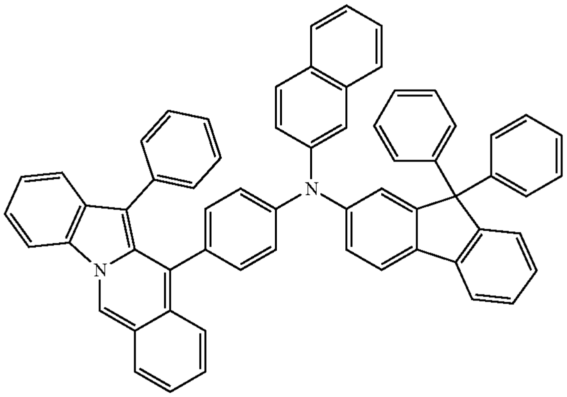
B61
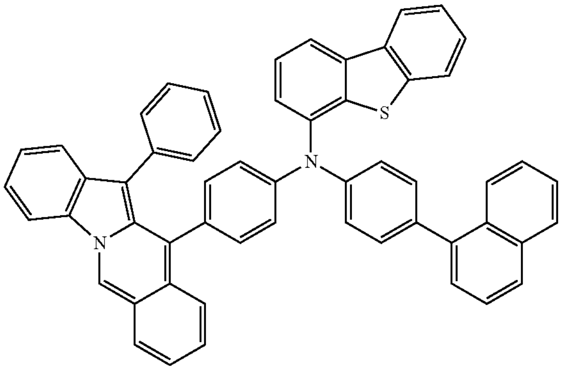
B62
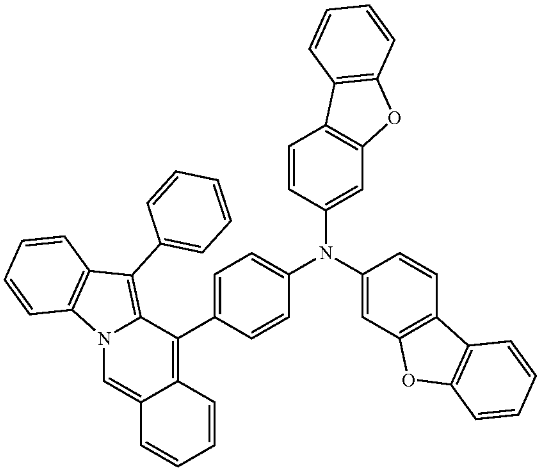
B63
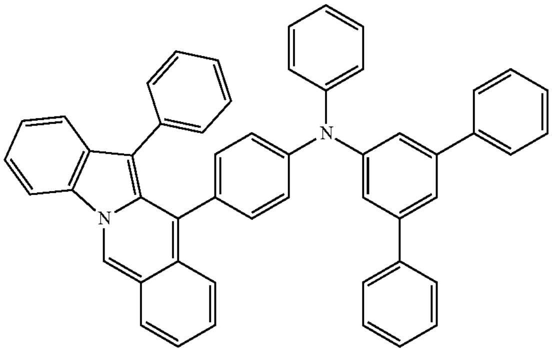
B64
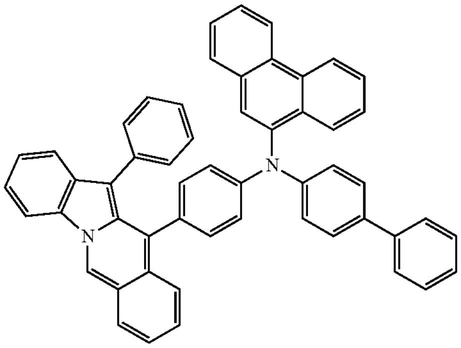
B65
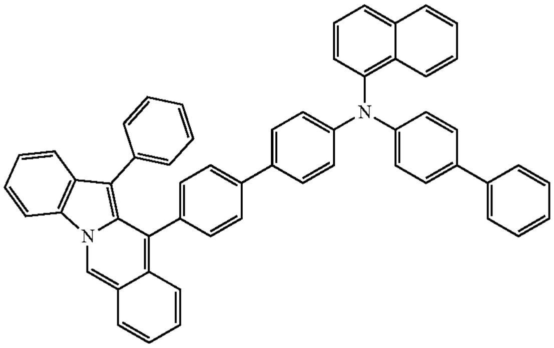

-continued
B66
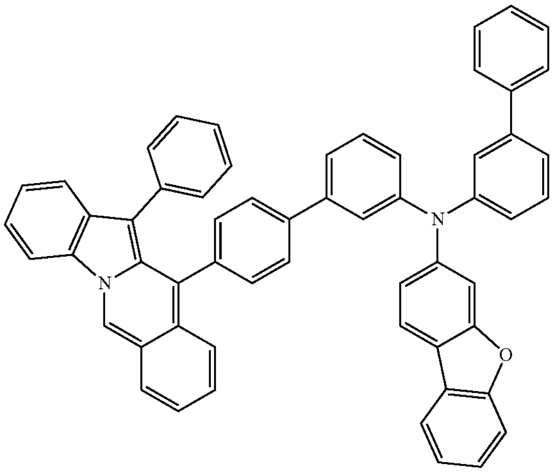
B67
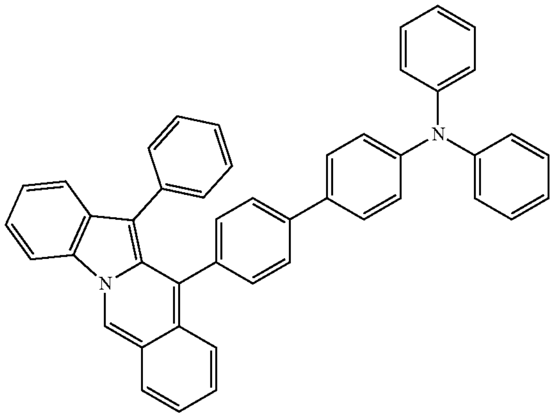
B68
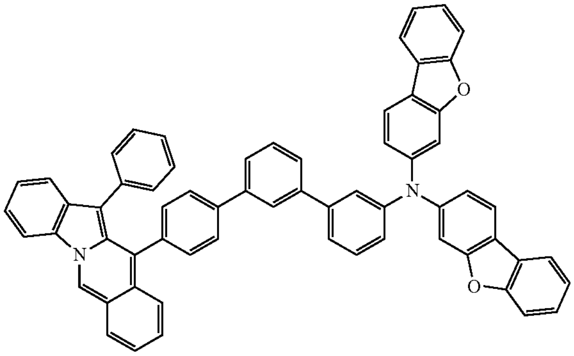
B69
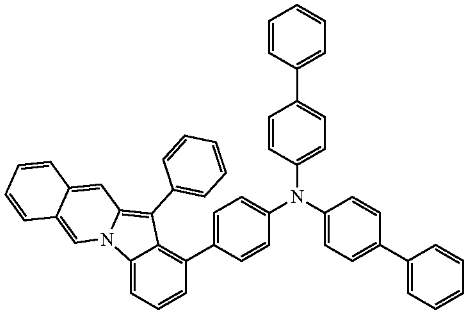
B70
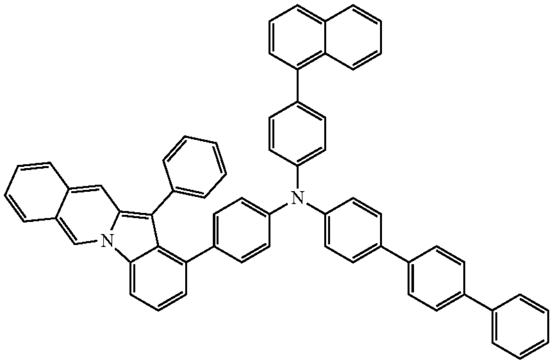
B71
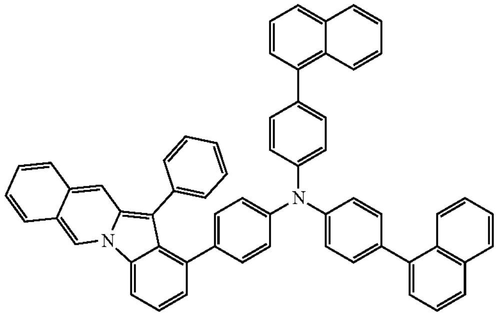
B72
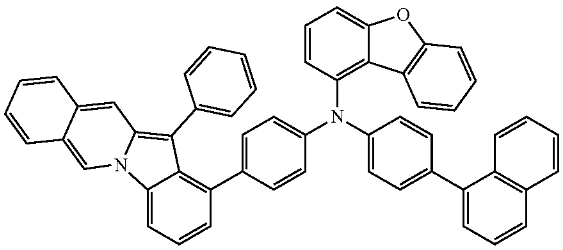
B73
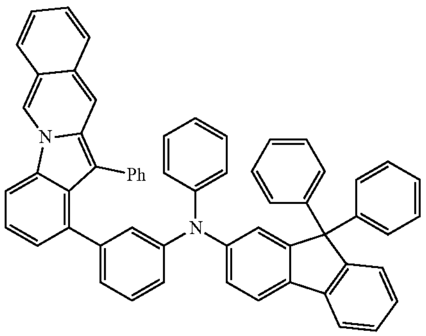

-continued
B74
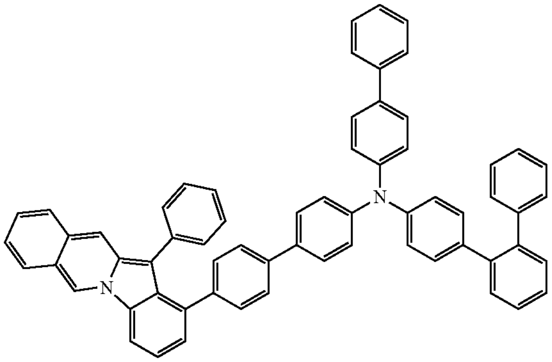
B75
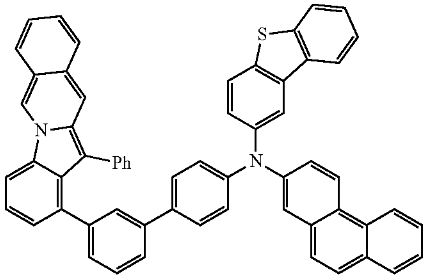
B76
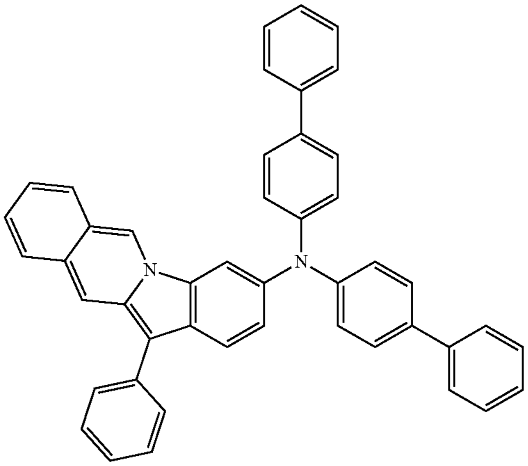
B77
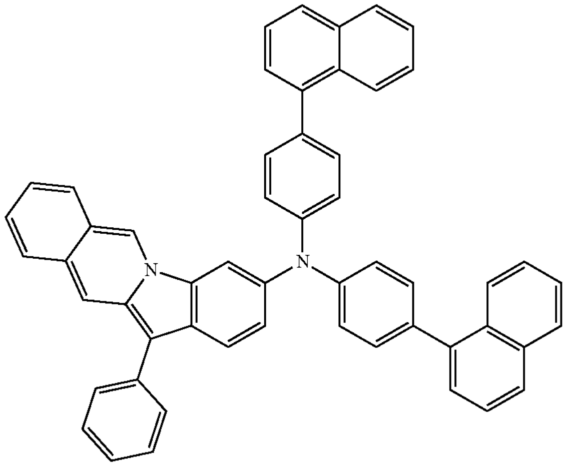
B78
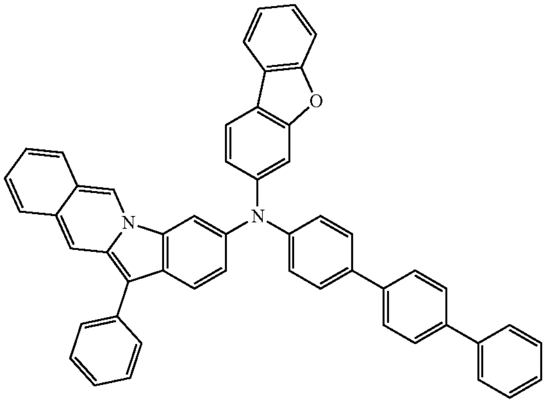
B79
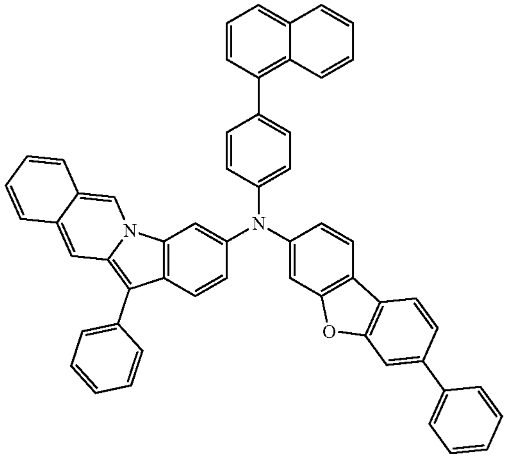

-continued
B80
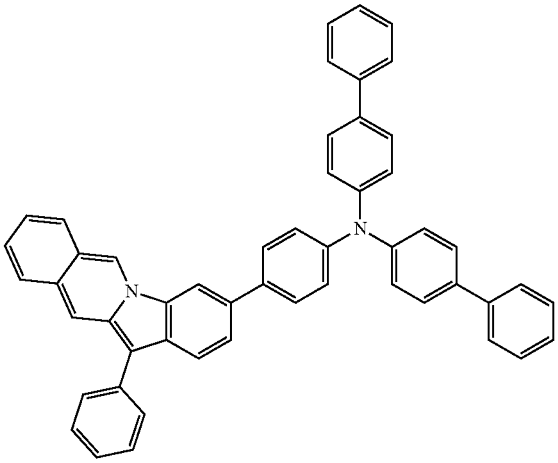
B81
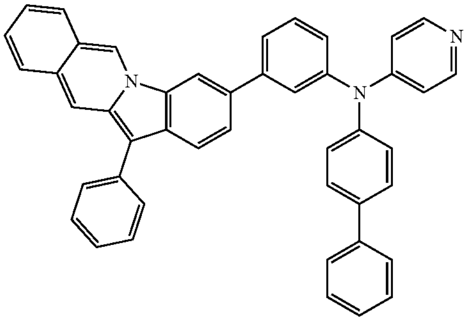
B82
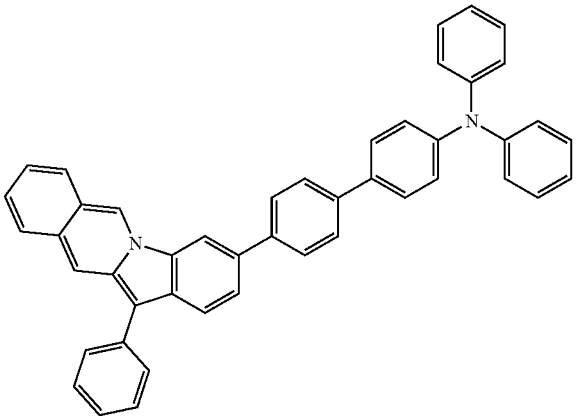
B83
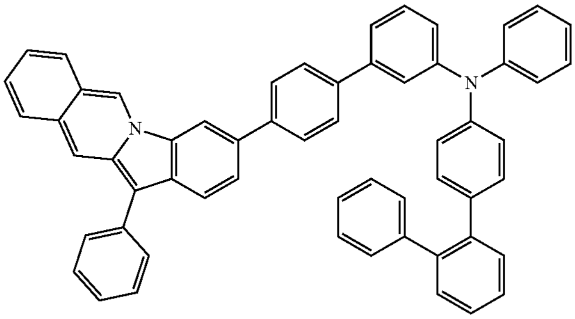
B84
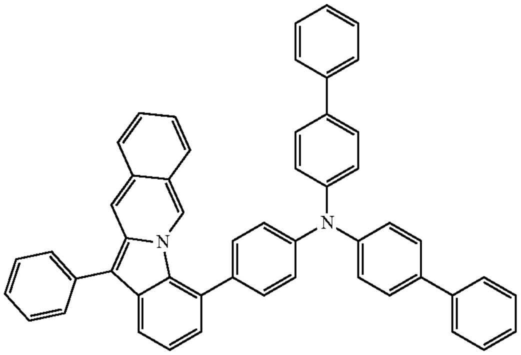
B85
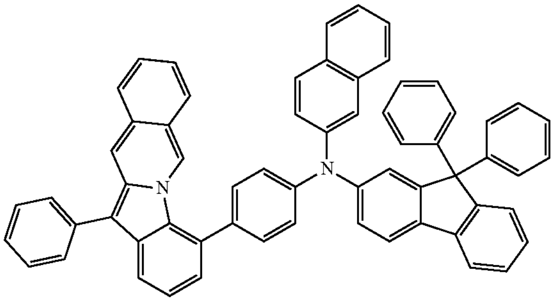

-continued
B86
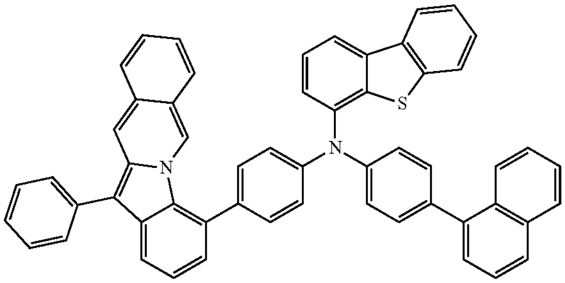
B87
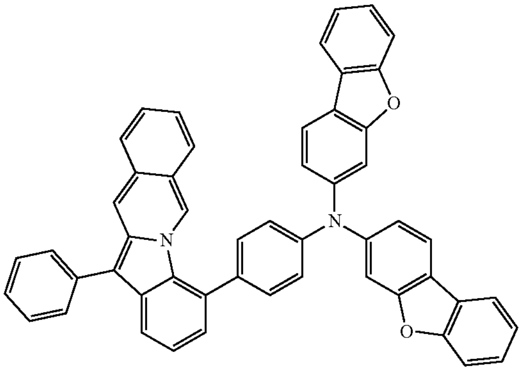
B88
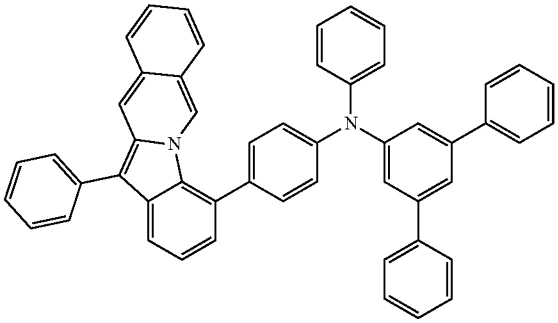
B89
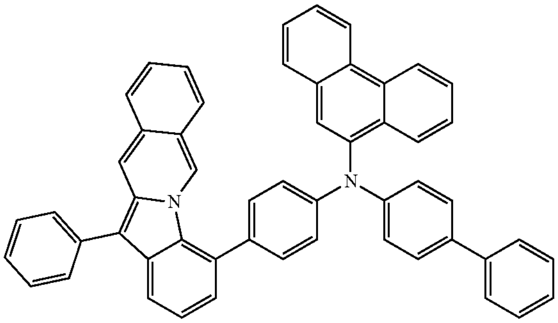
B90
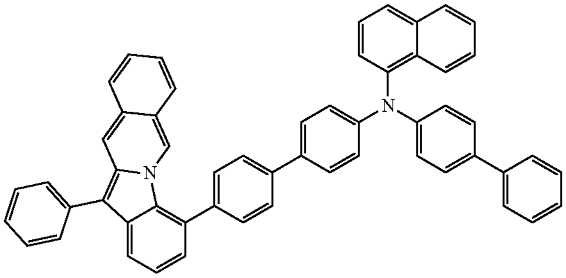
B91
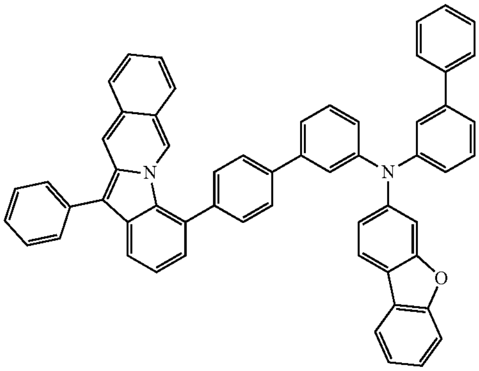
B92
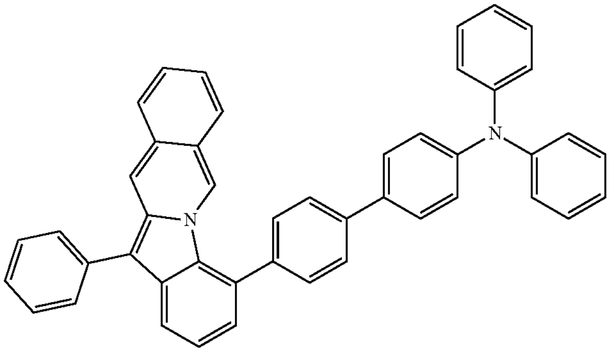

-continued
B93
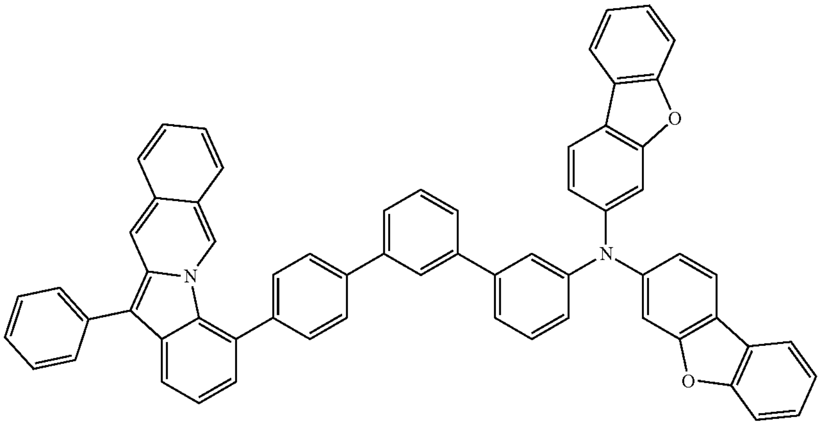
B94
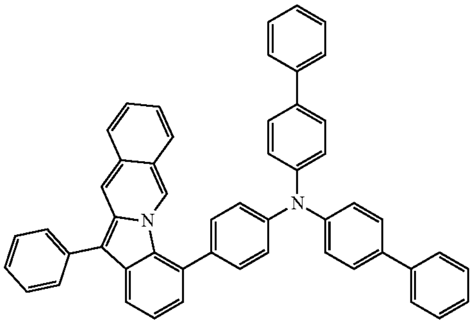
B95
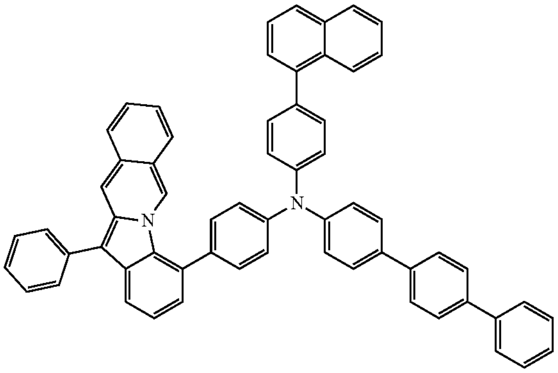
B96
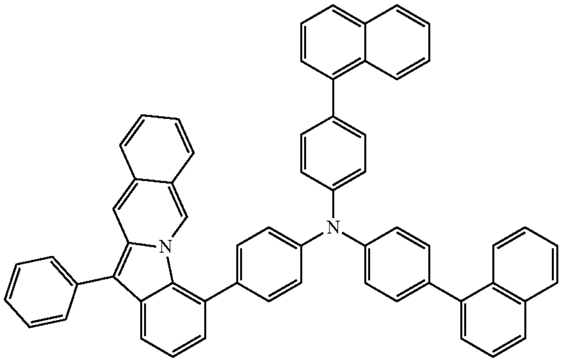
B97
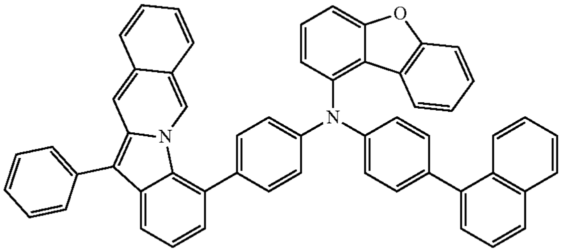
C1
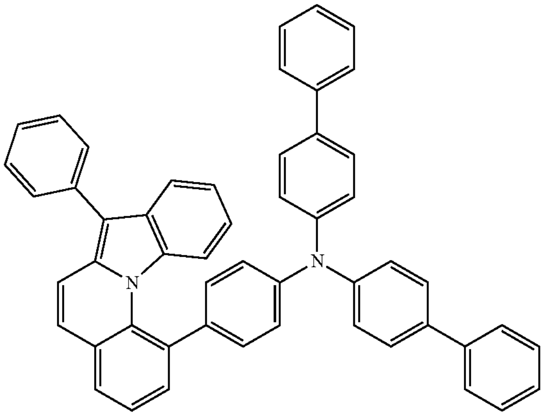
C2
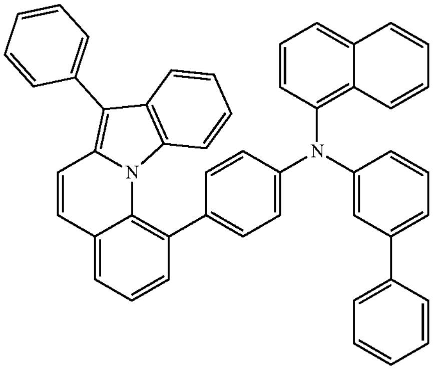

-continued
C3
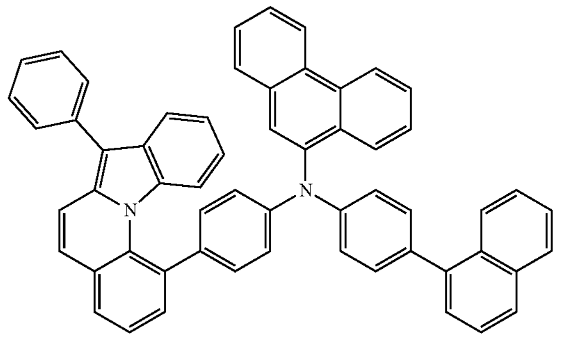
C4
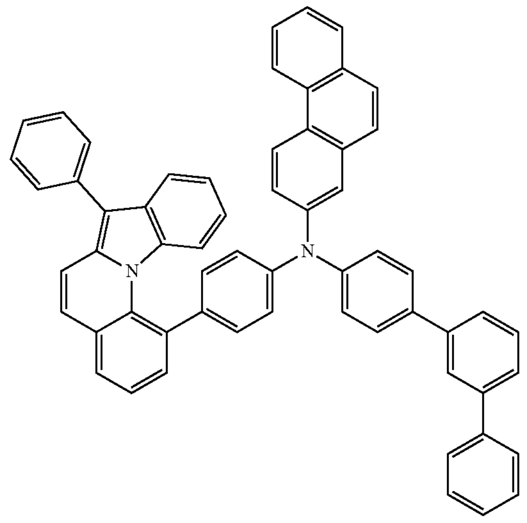
C5
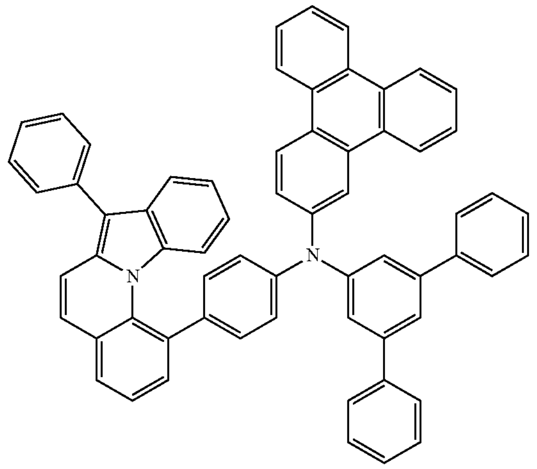
C6
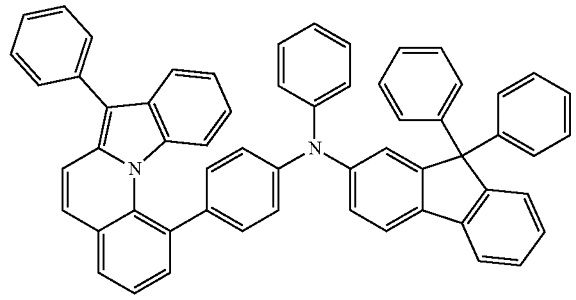
C7
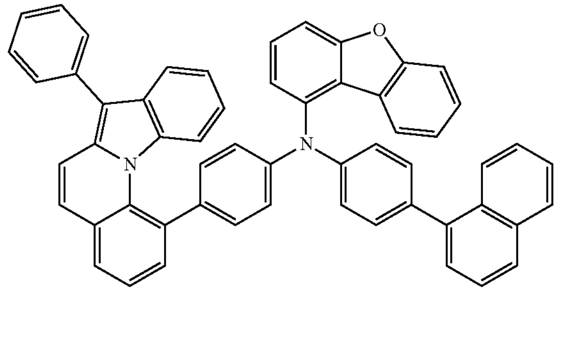
C8
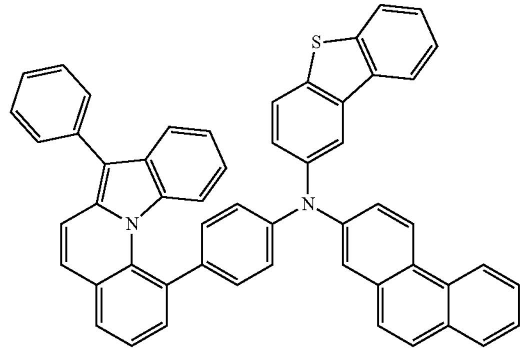

-continued
C9
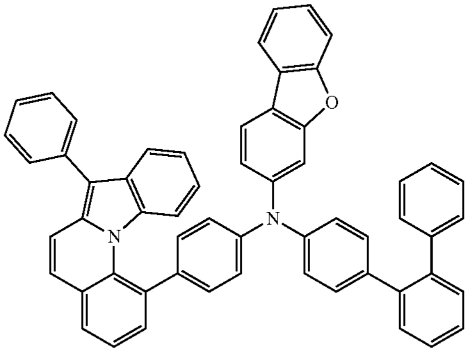
C10
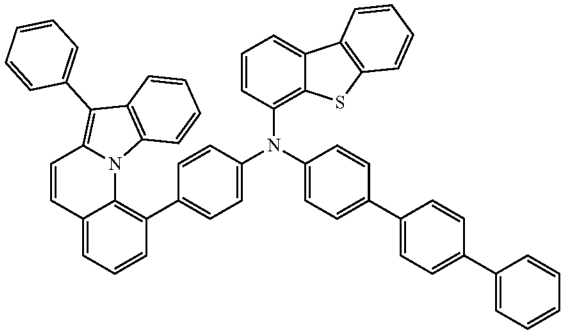
C11
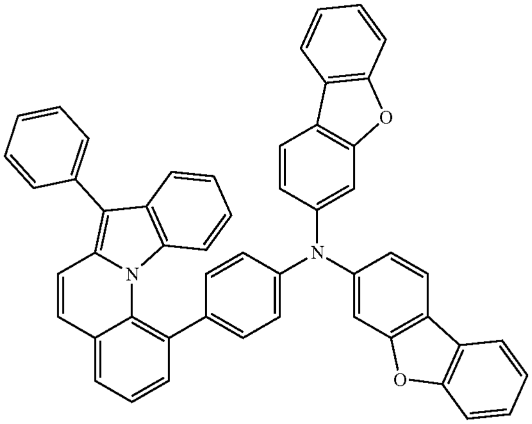
C12
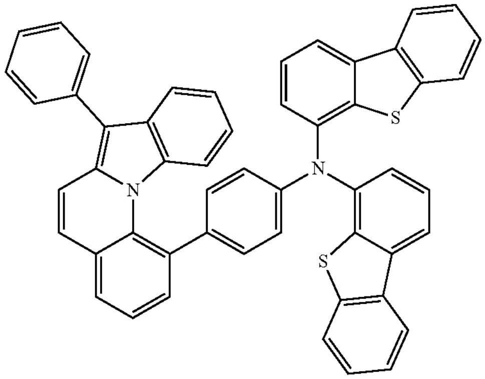
C13
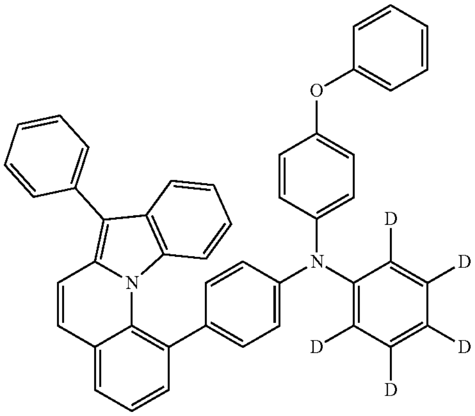
C14
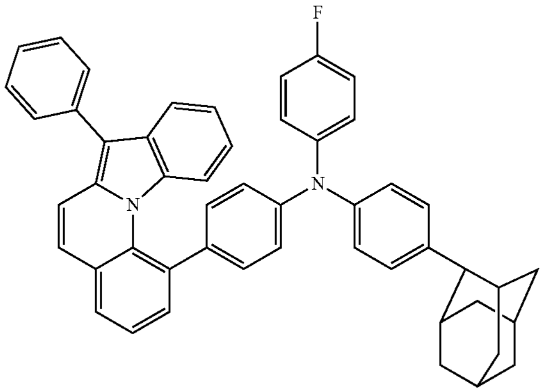
C15
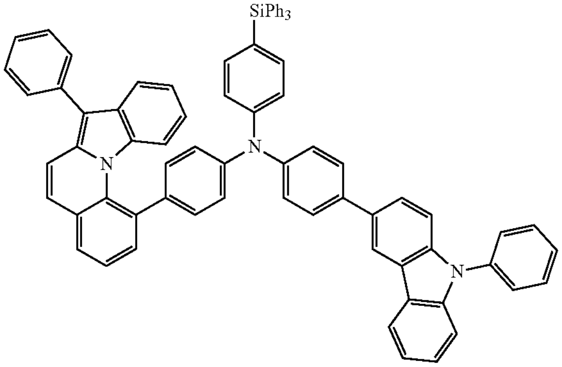
C16
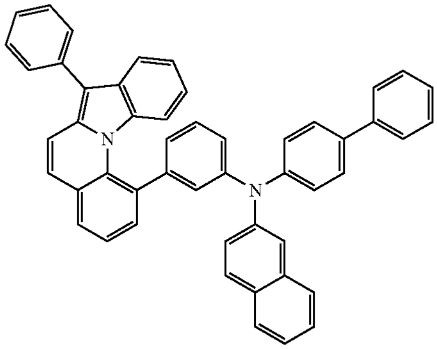

-continued
C17
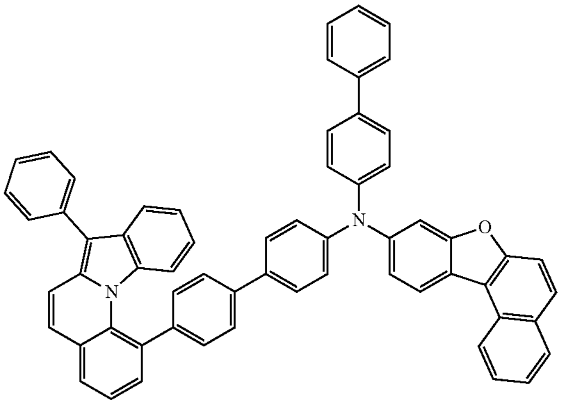
C18
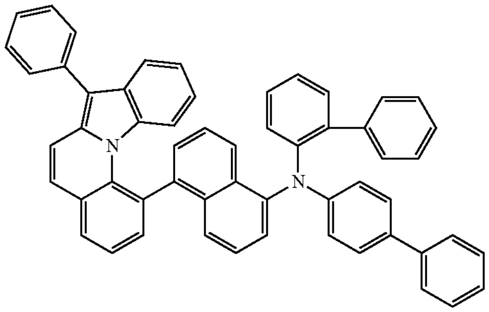
C19
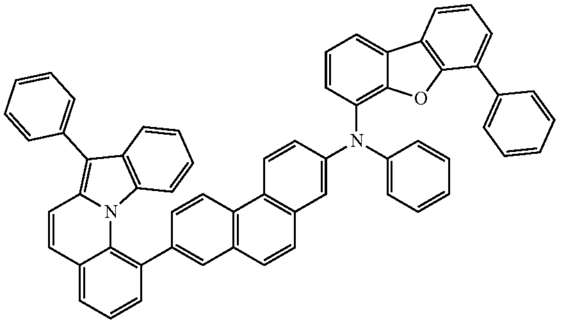
C20
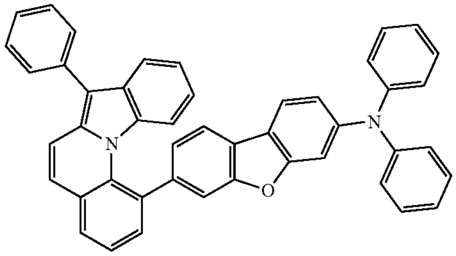
C21
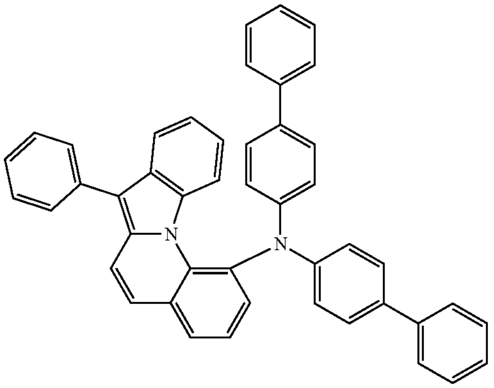
C22
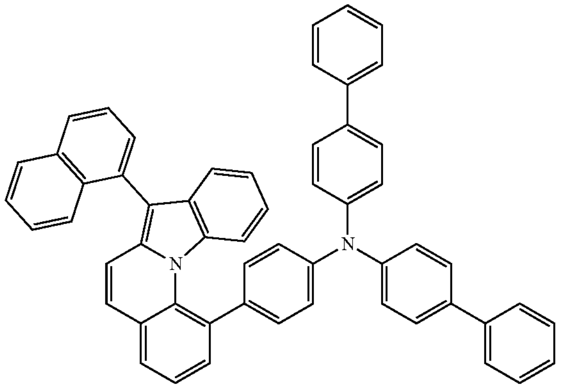
C23
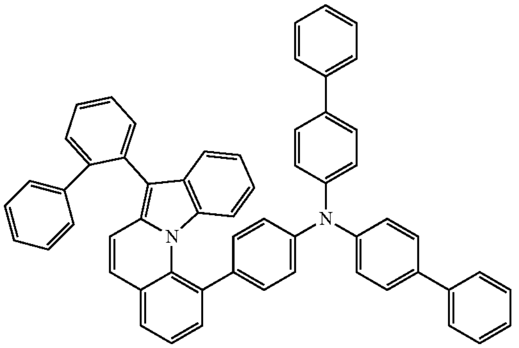
C24
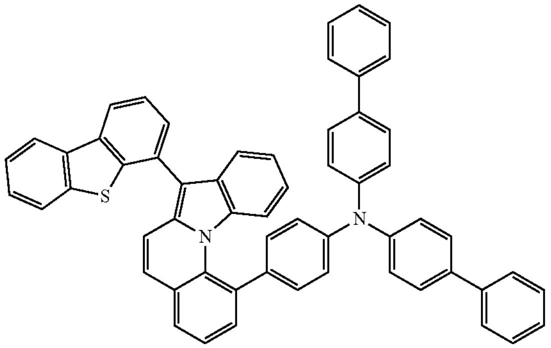

-continued
C25
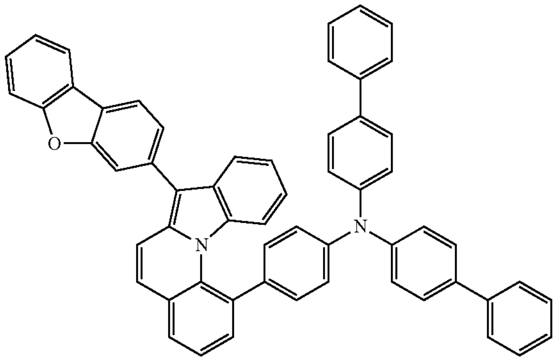
C26
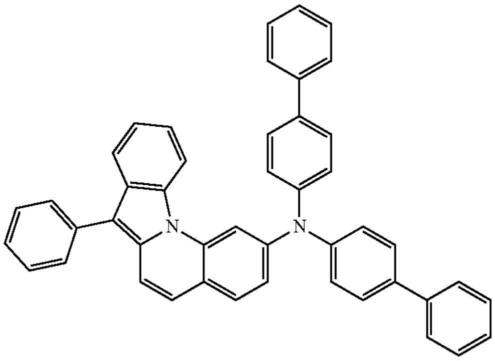
C27
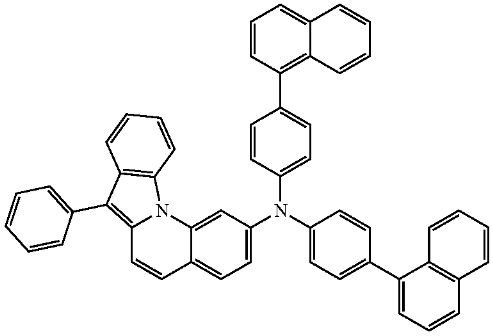
C28
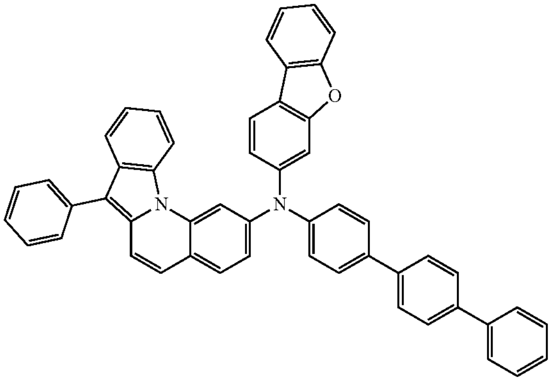
C29
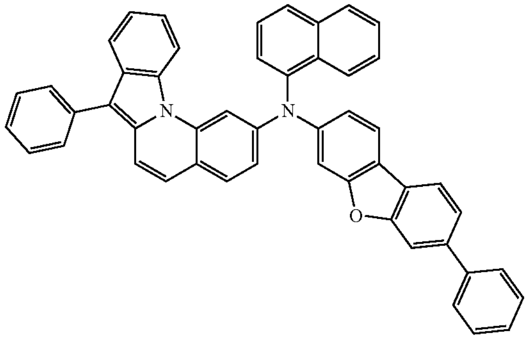
C30
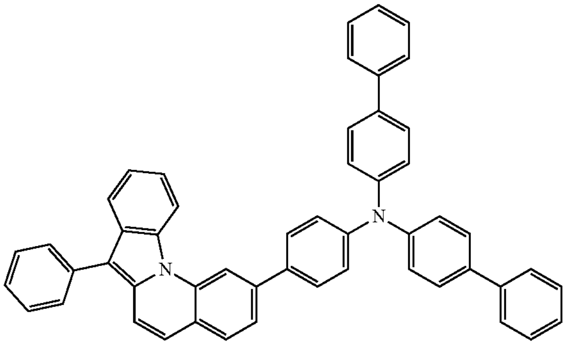
C31
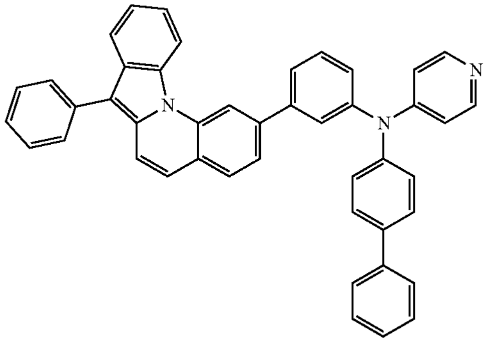
C32
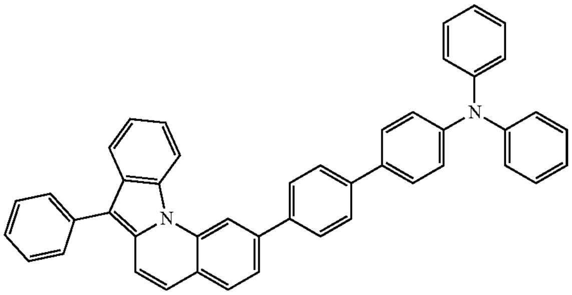

-continued
C33
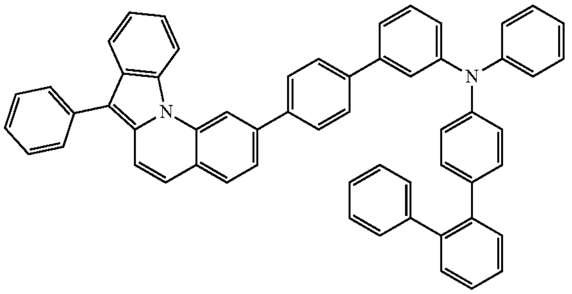
C34
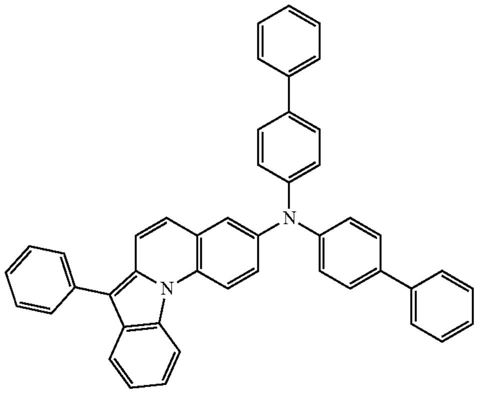
C35
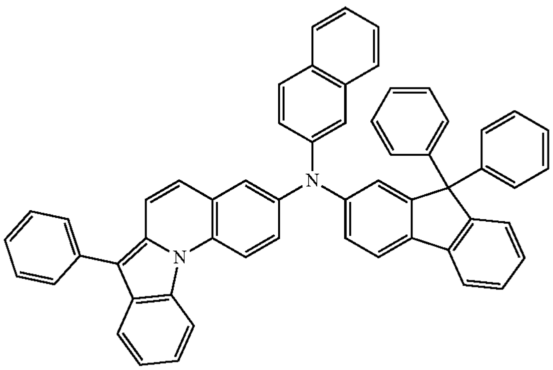
C36
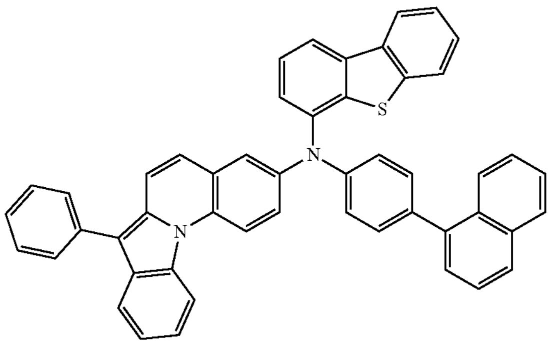
C37
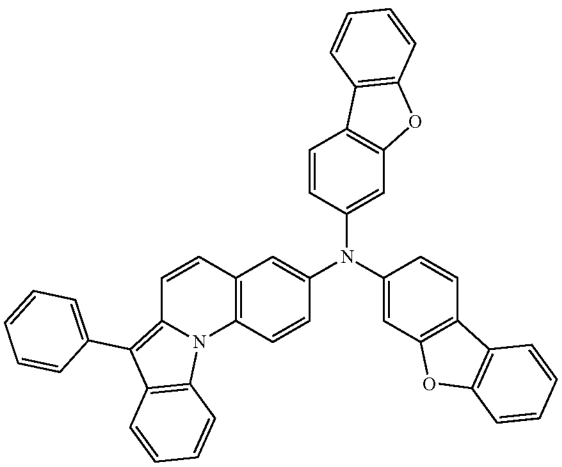
C38
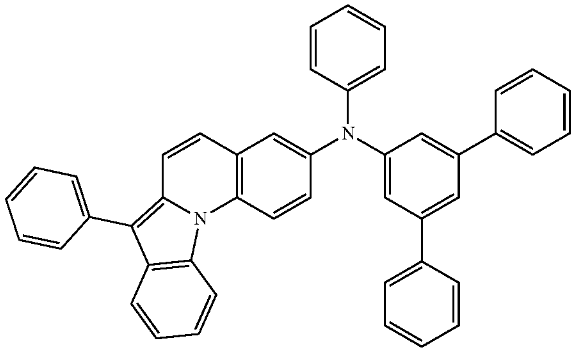
C39
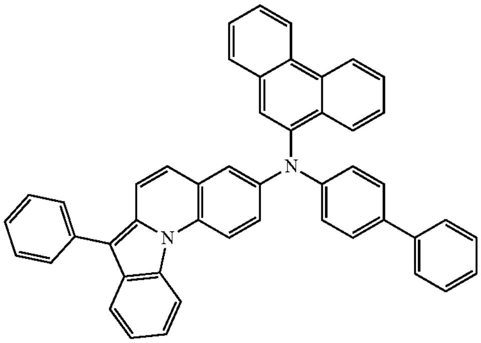
C40
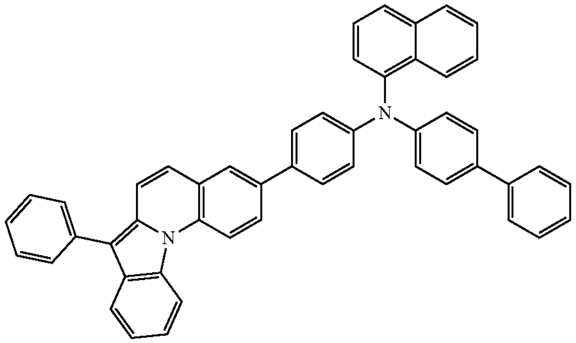

-continued
C41
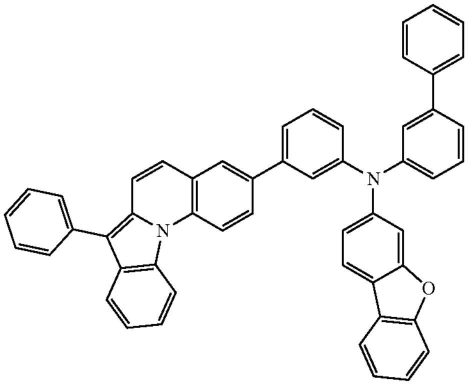
C42
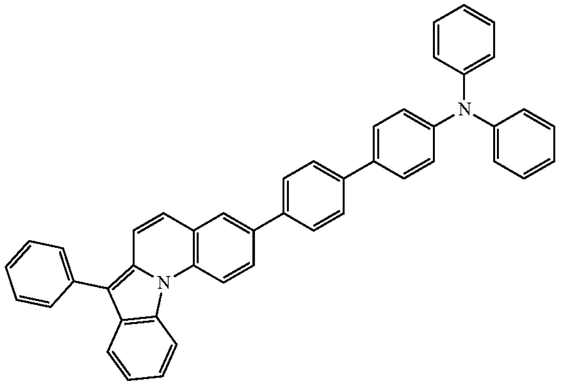
C43
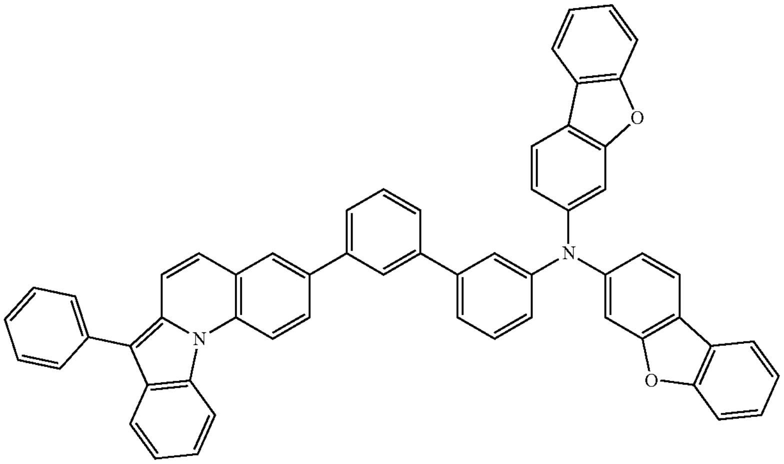
C44
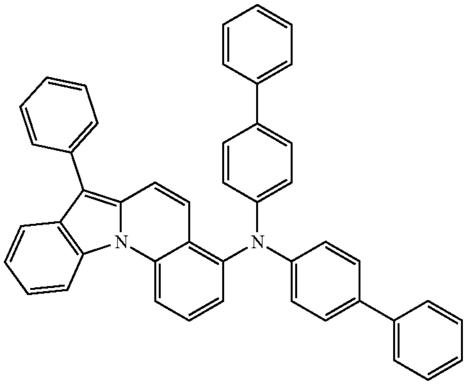
C45
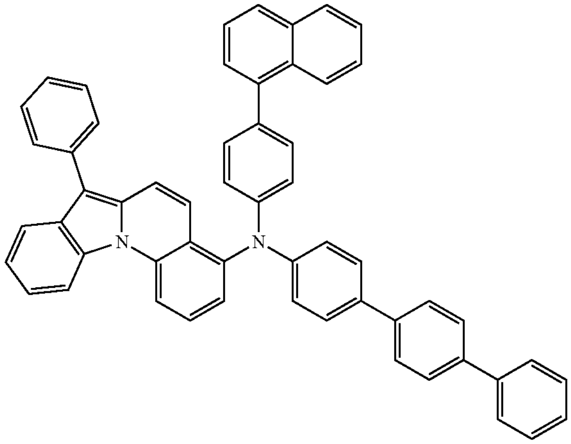

-continued
C46
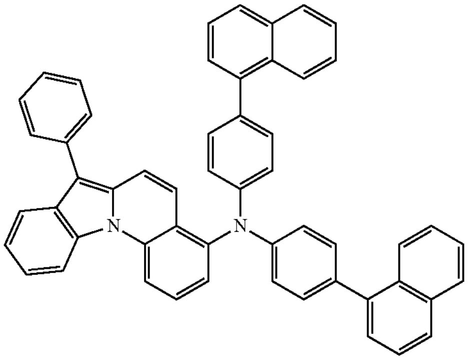
C47
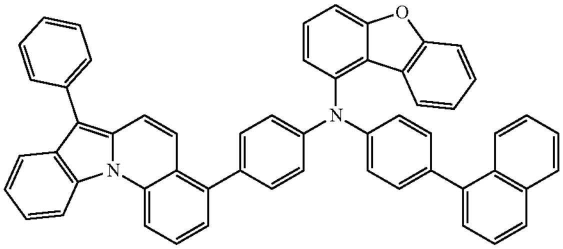
C48
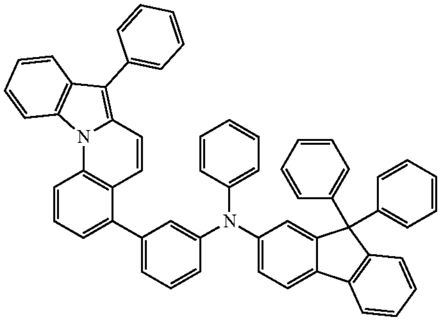
C49
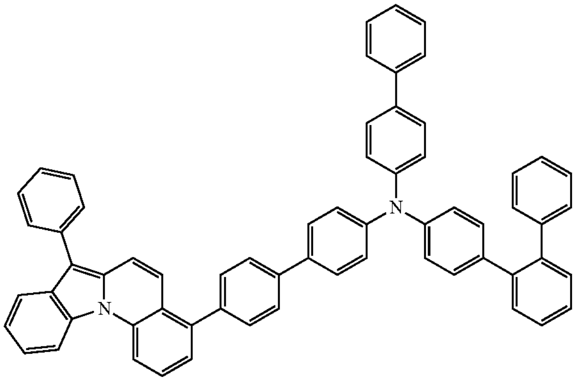
C50
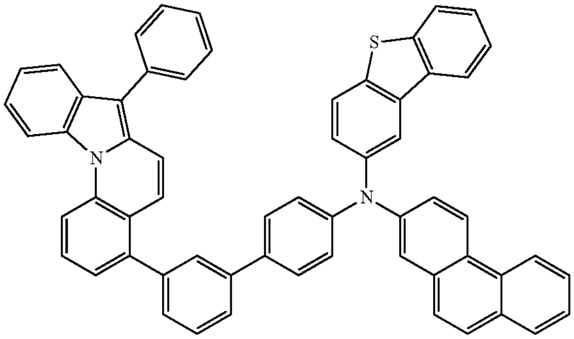
C51
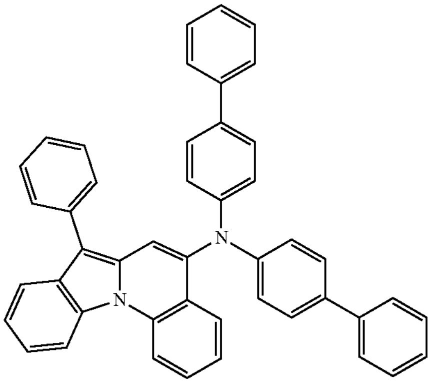

-continued
C52
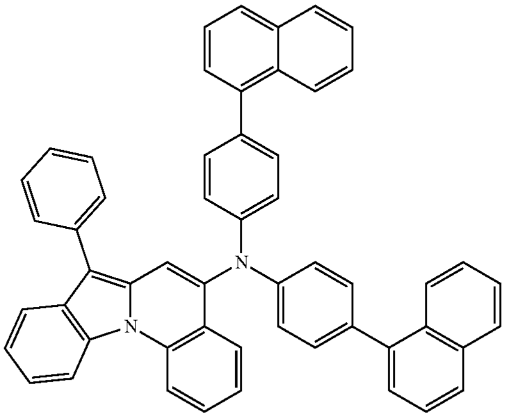
C53
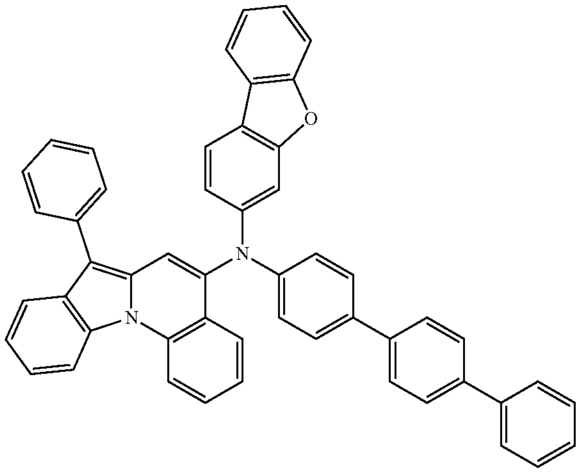
C54
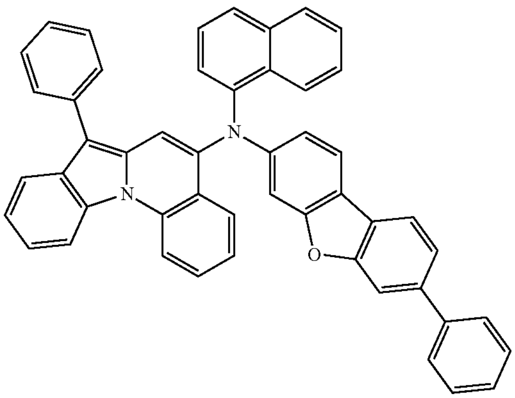
C55
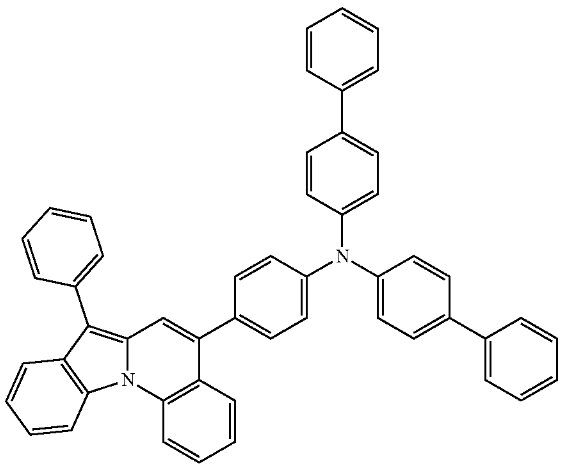
C56
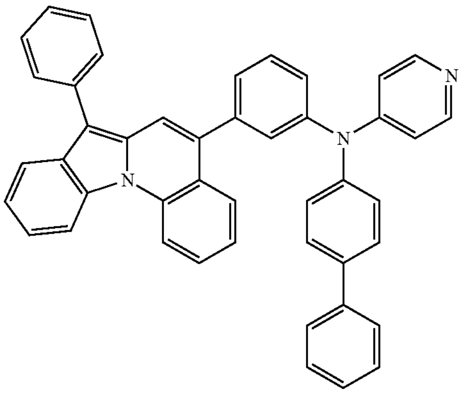
C57
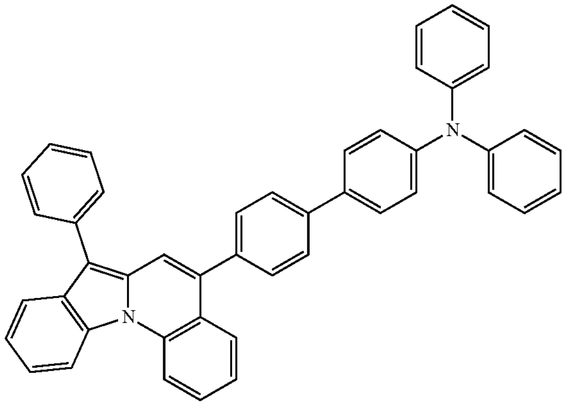

-continued
C58
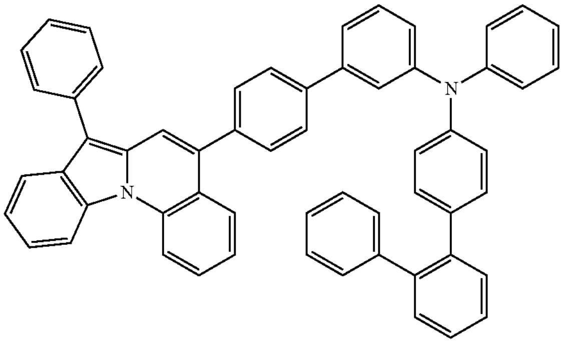
C59
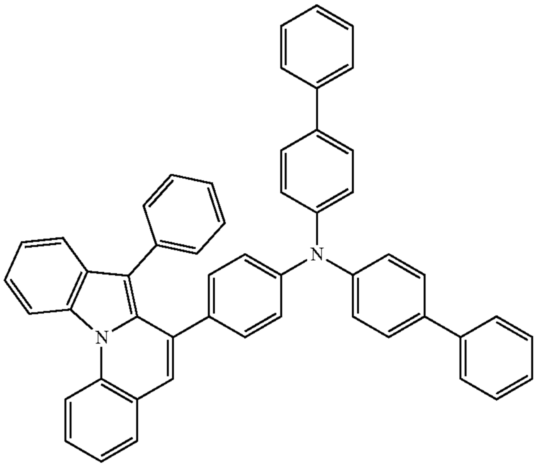
C60
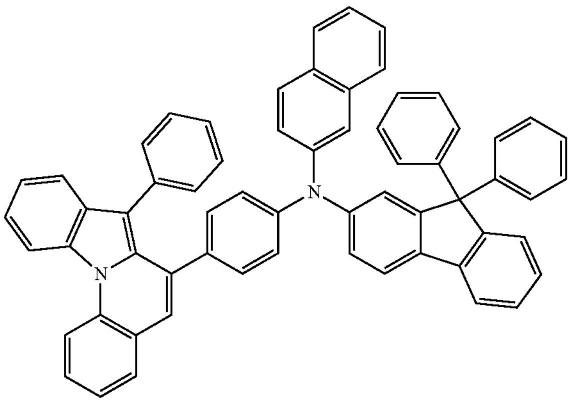
C61
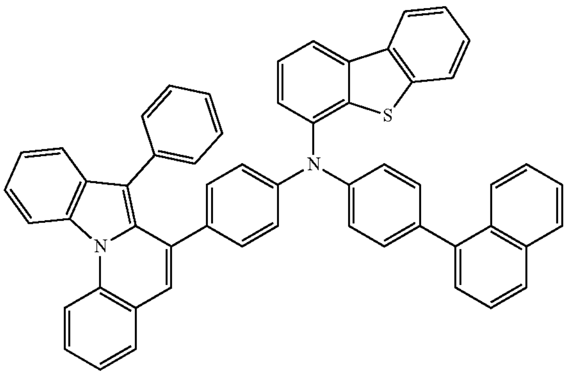
C62
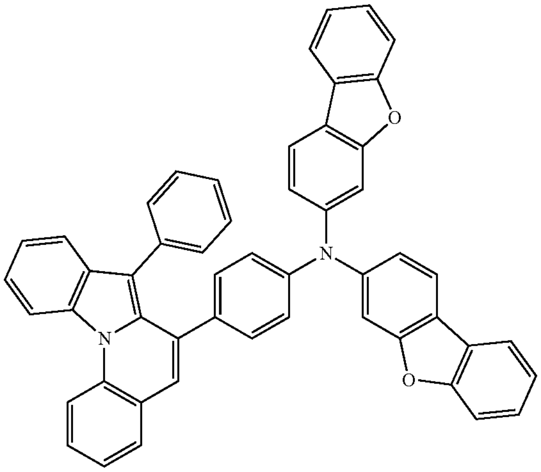
C63
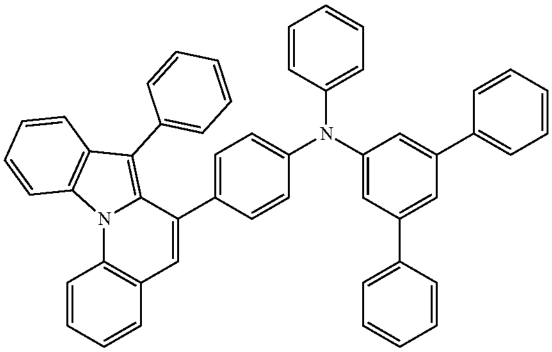

-continued
C64
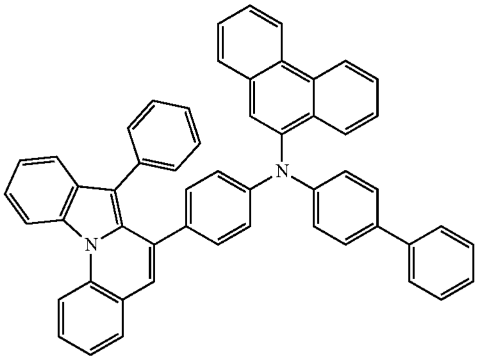
C65
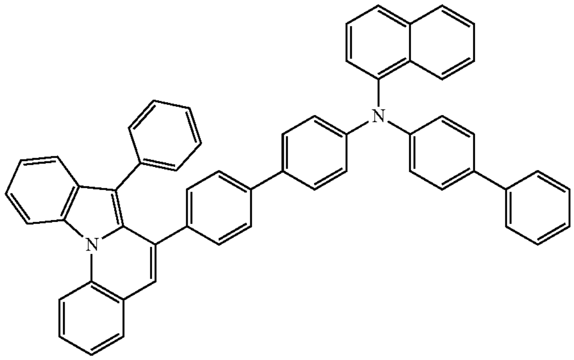
C66
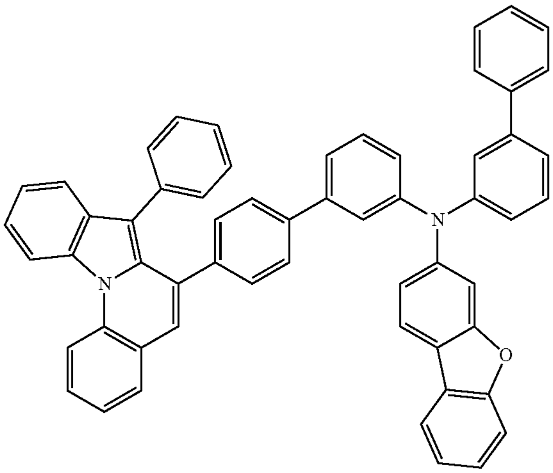
C67
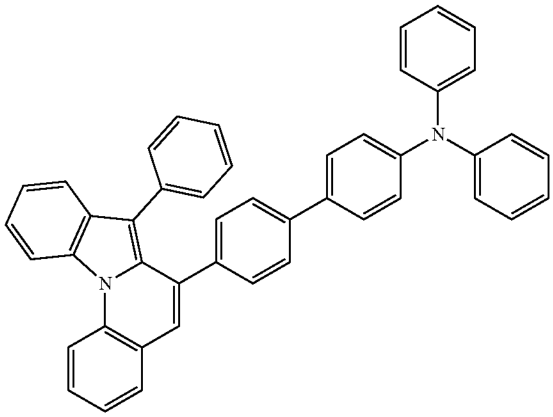
C68
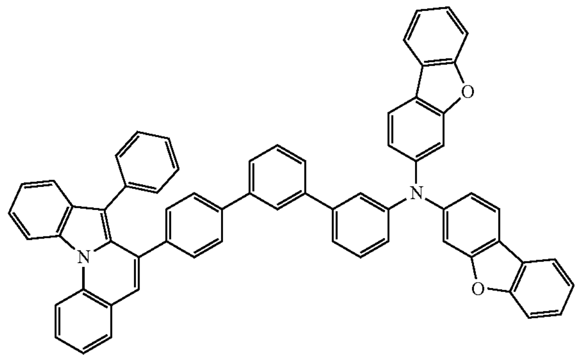
C69
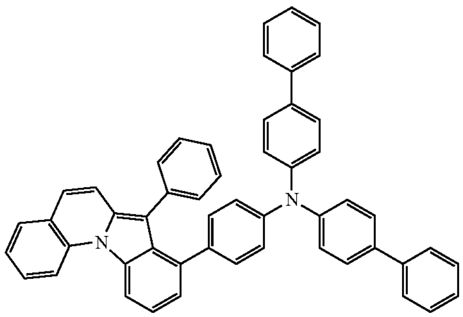
C70
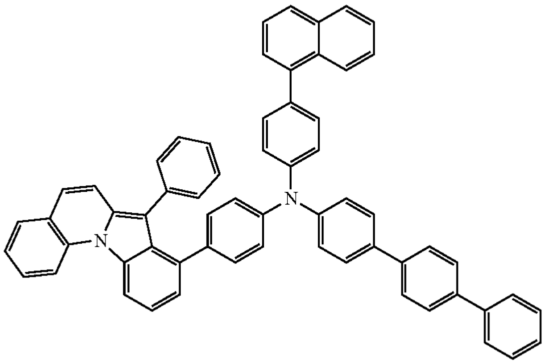
C71
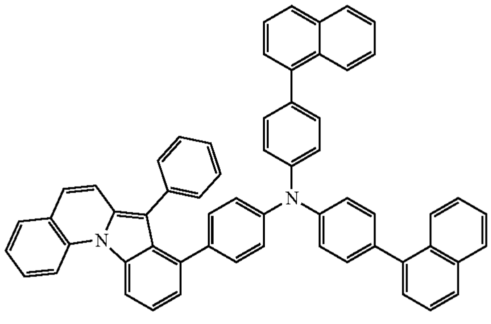

-continued
C72
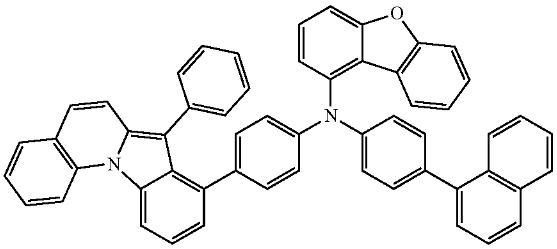
C73
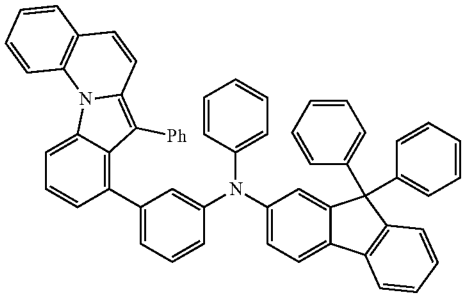
C74
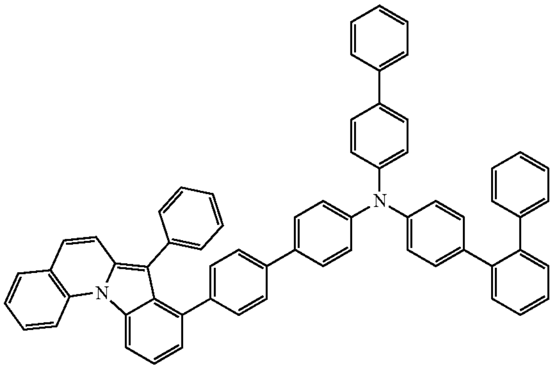
C75
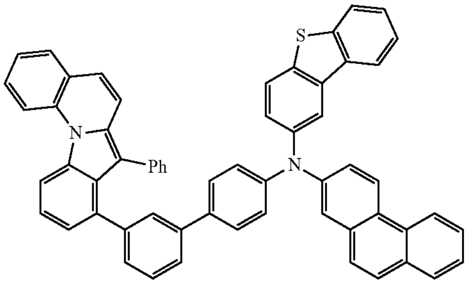
C76
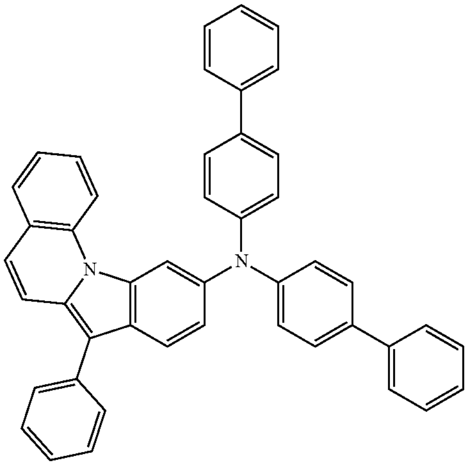
C77
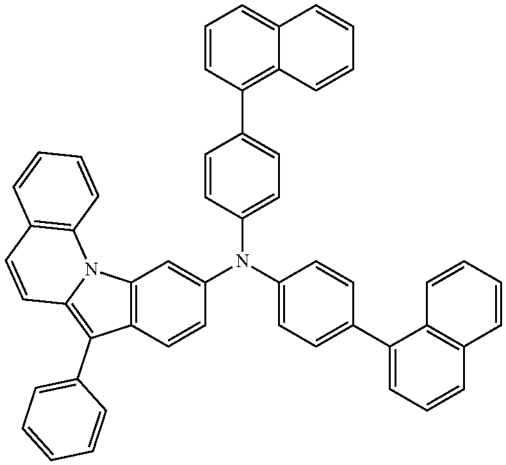
C78
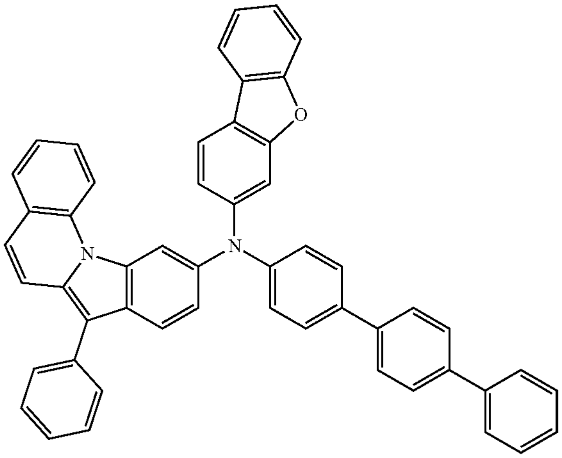
C79
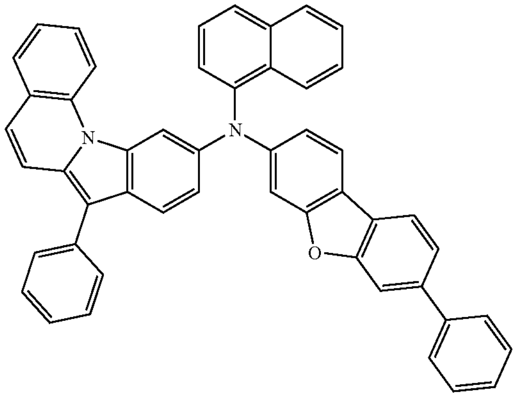

-continued
C80
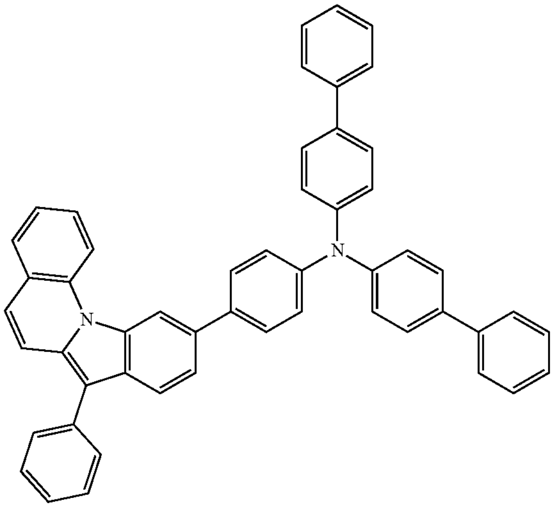
C81
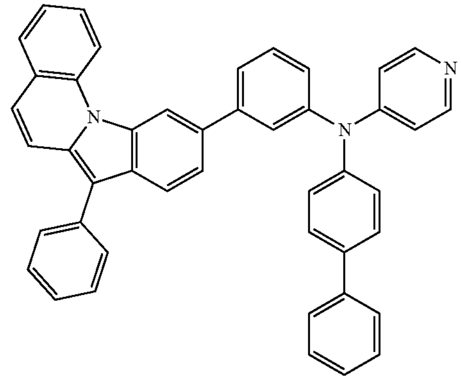
C82
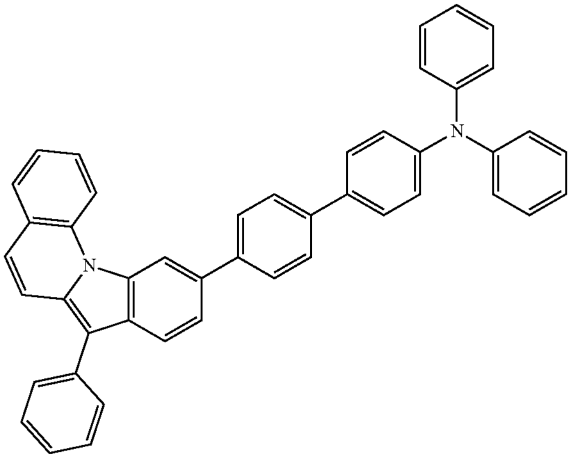
C83
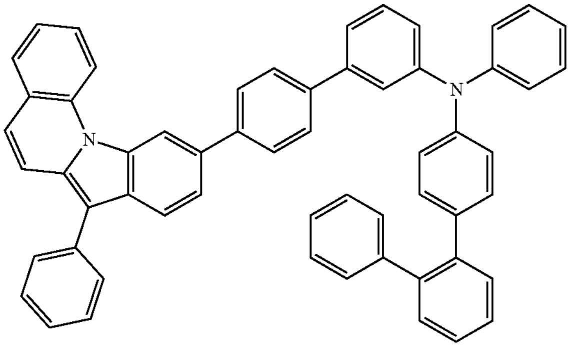
C84
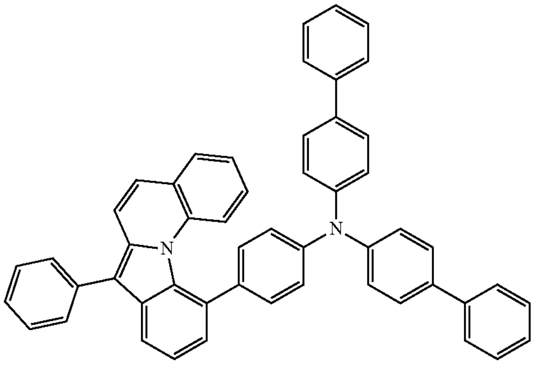
C85
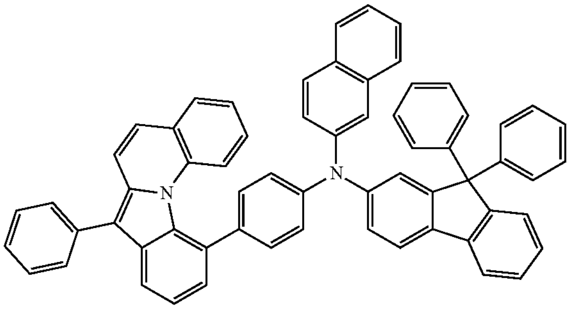

-continued
C86
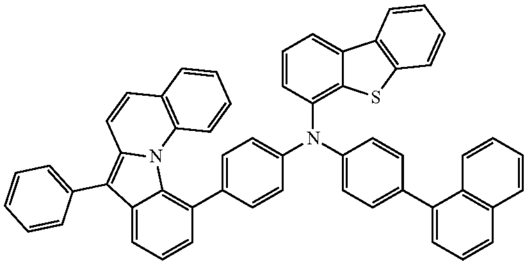
C87
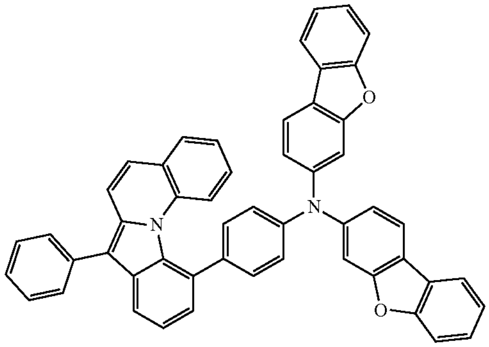
C88
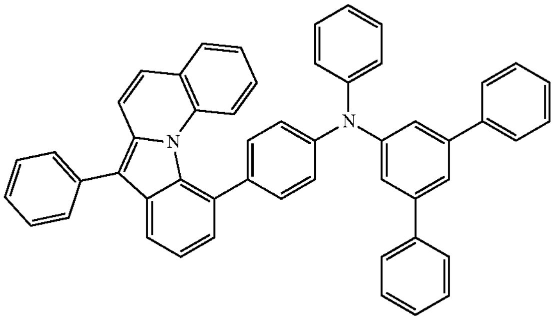
C89
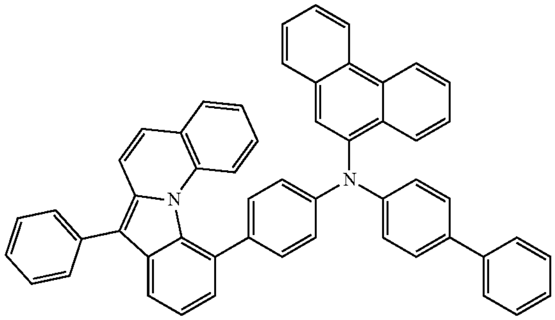
C90
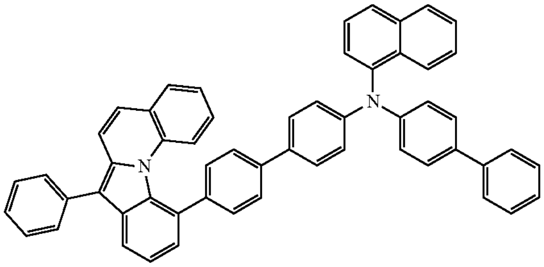
C91
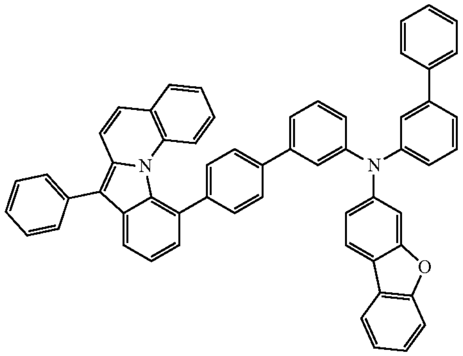
C92
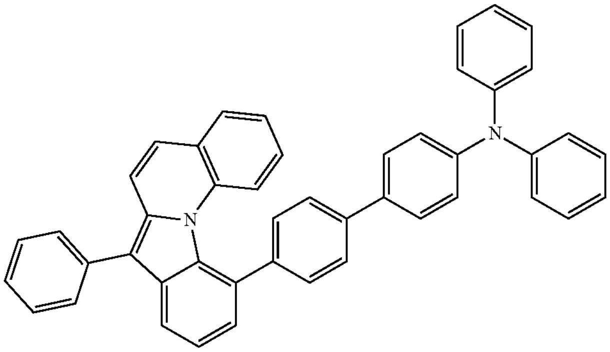

-continued
C93
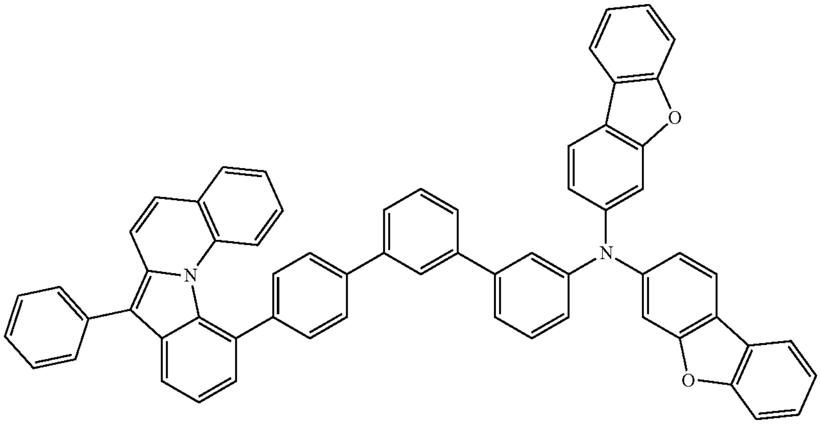
C94
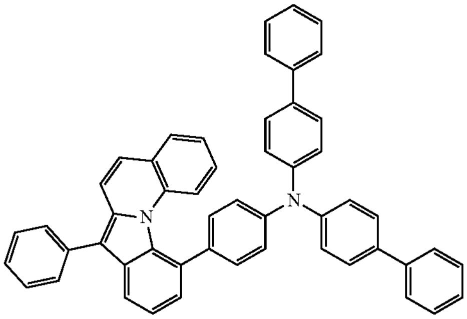
C95
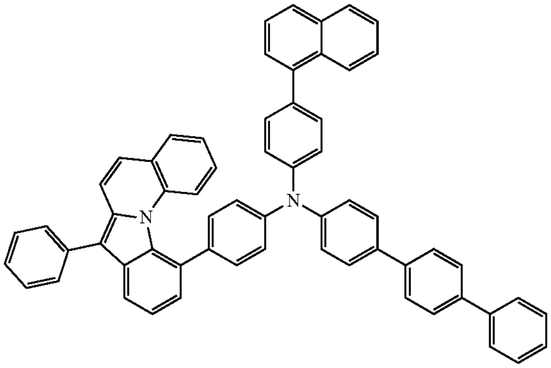
C96
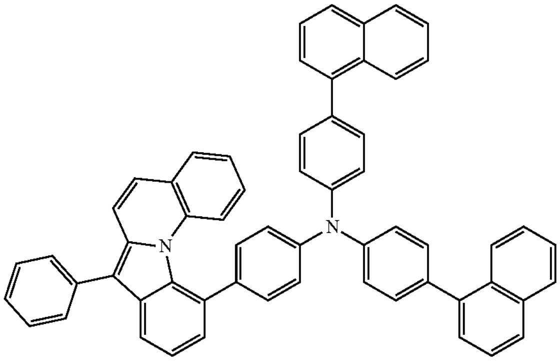
C97
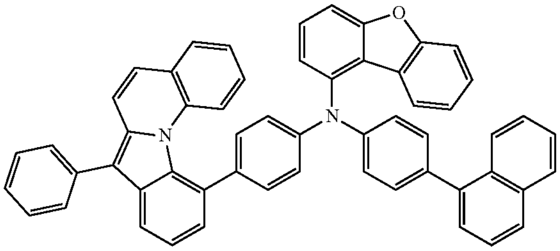

D1
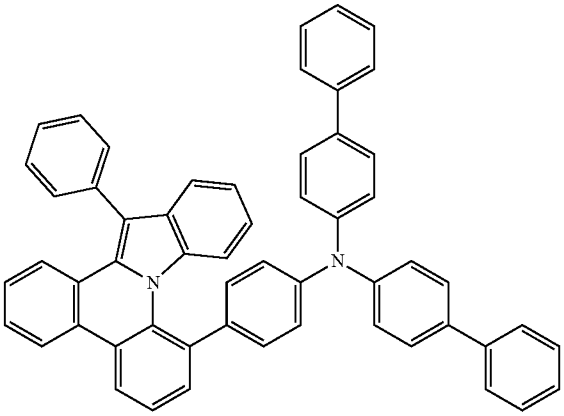
D2
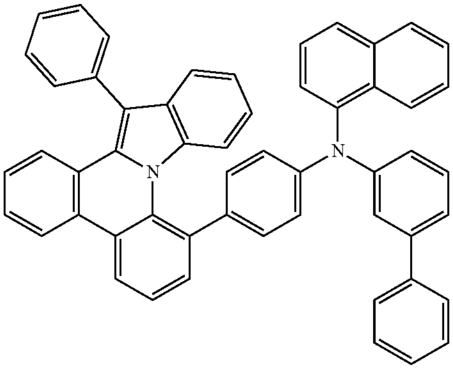
D3
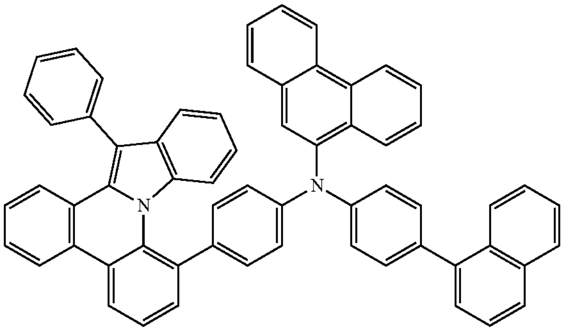
D4
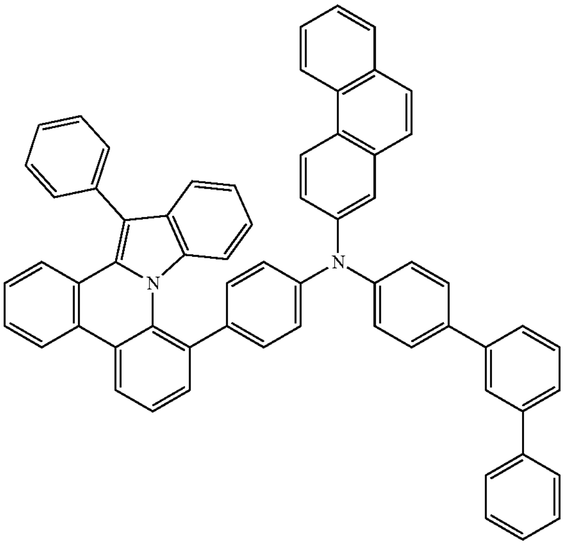
D5
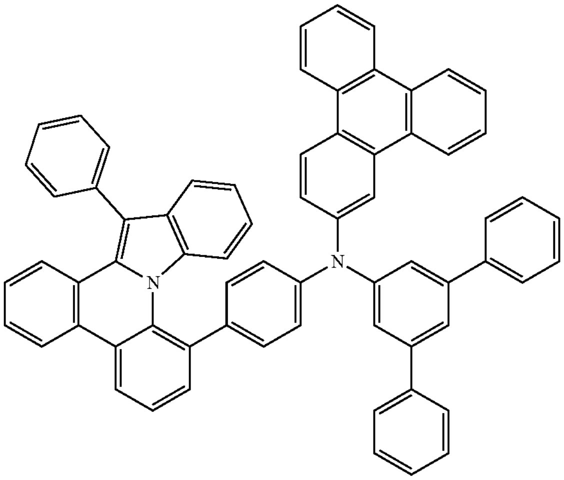
D6
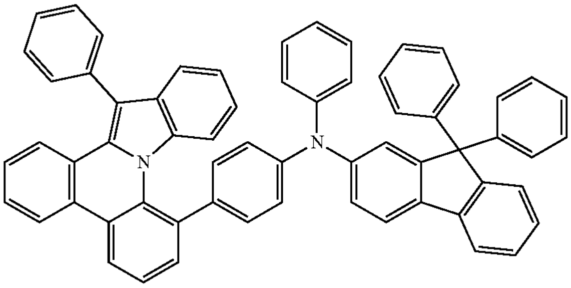

-continued
D7
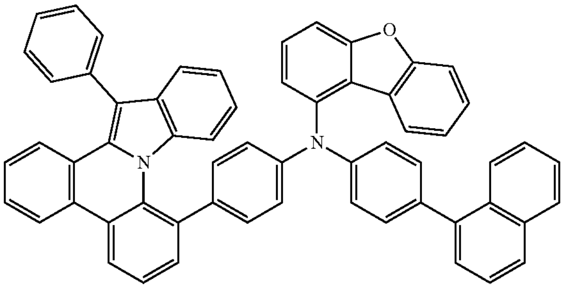
D8
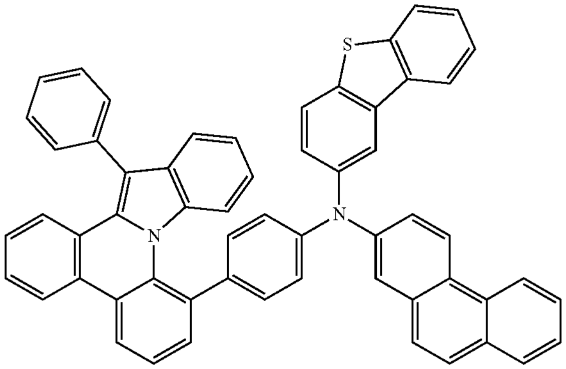
D9
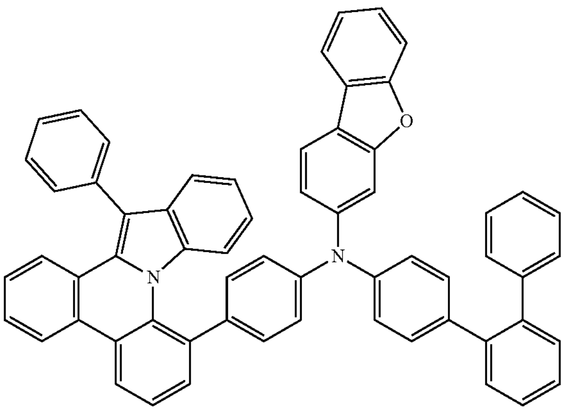
D10
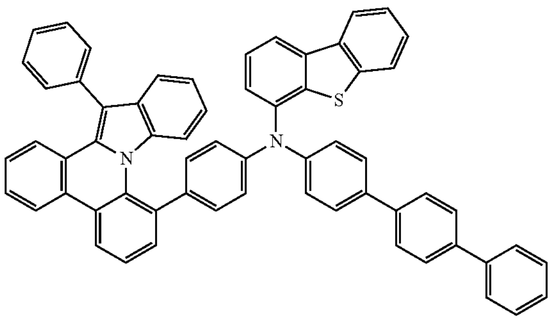
D11
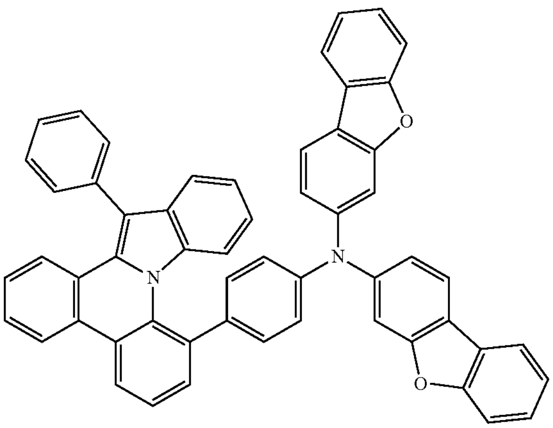
D12
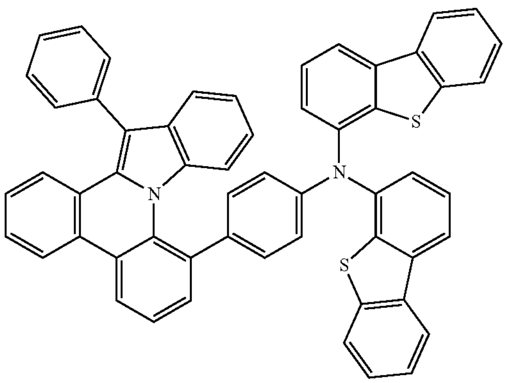

-continued
D13
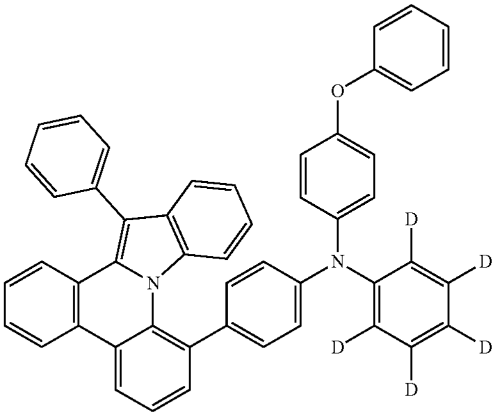
D14
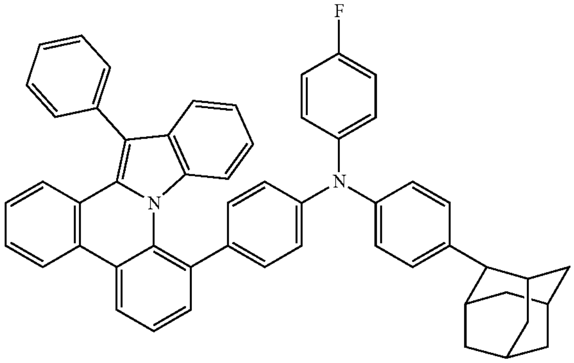
D15
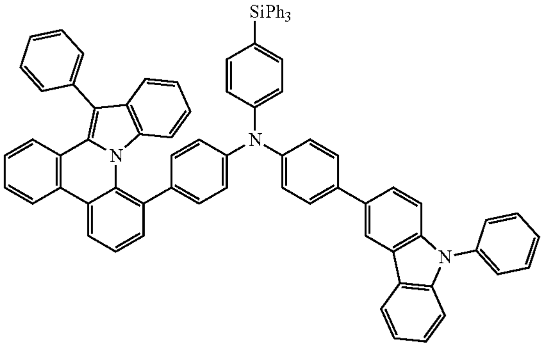
D16
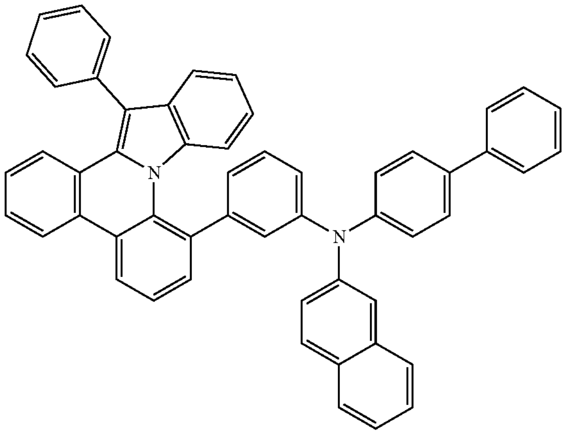
D17
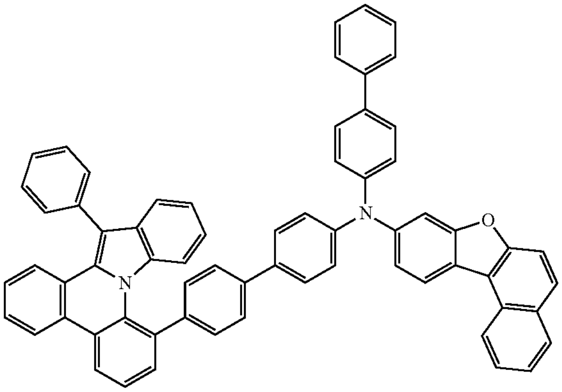
D18
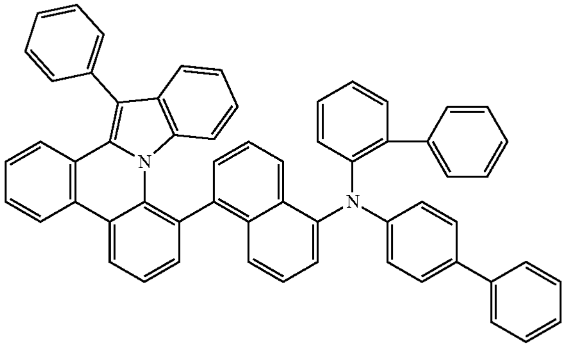
D19
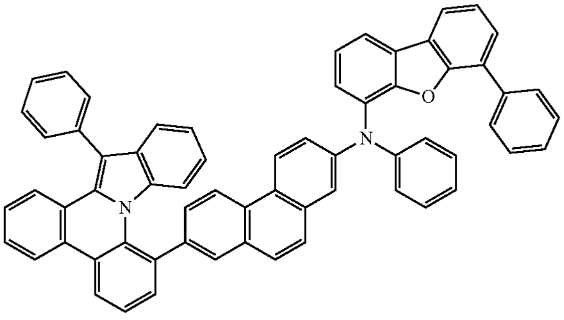
D20
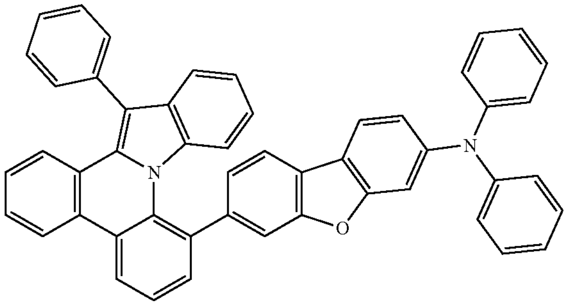

-continued
D21
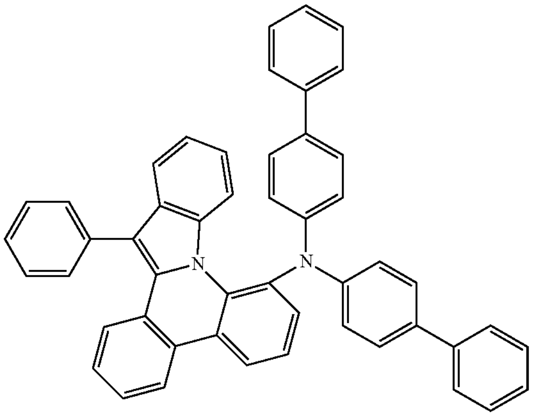
D22
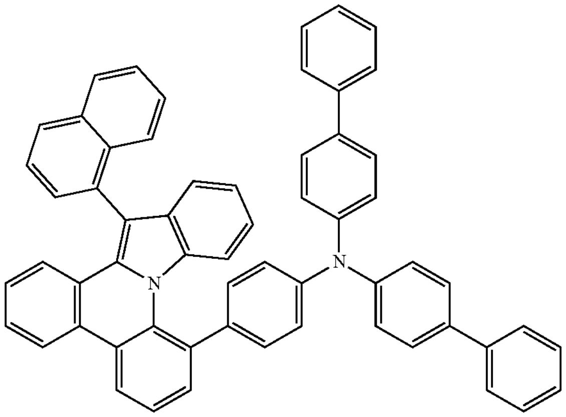
D23
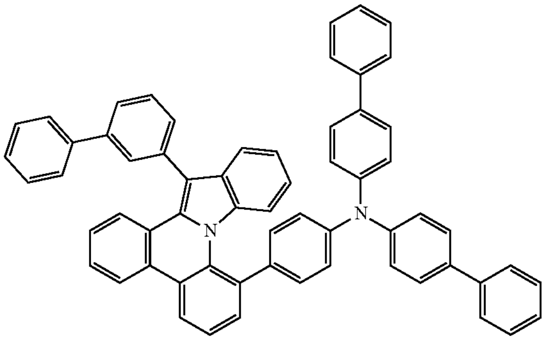
D24
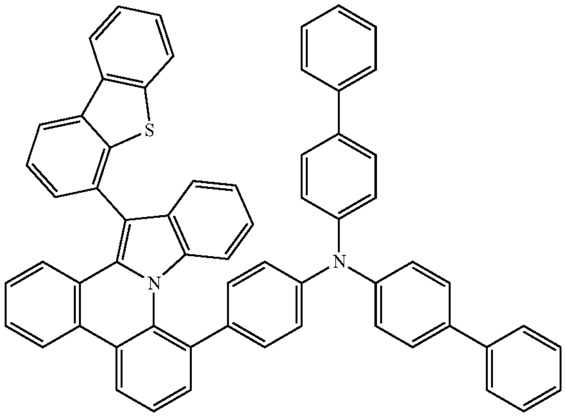
D25
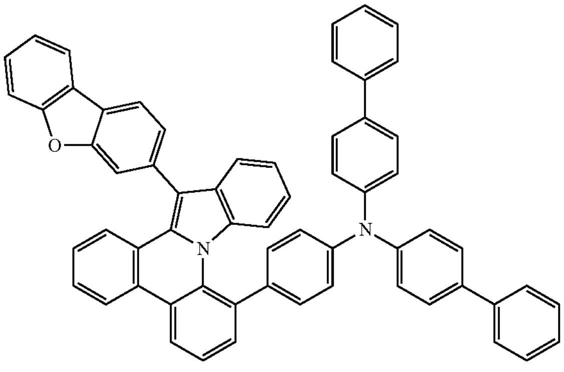
D26
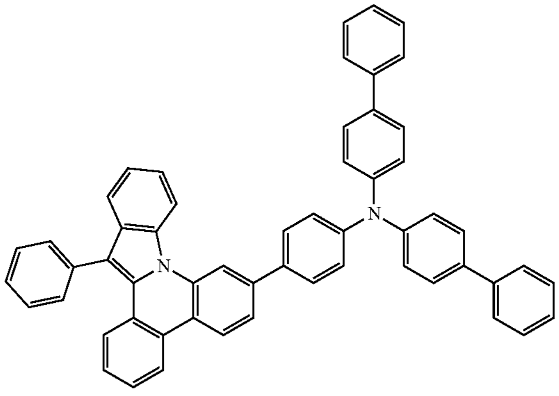

-continued
D27
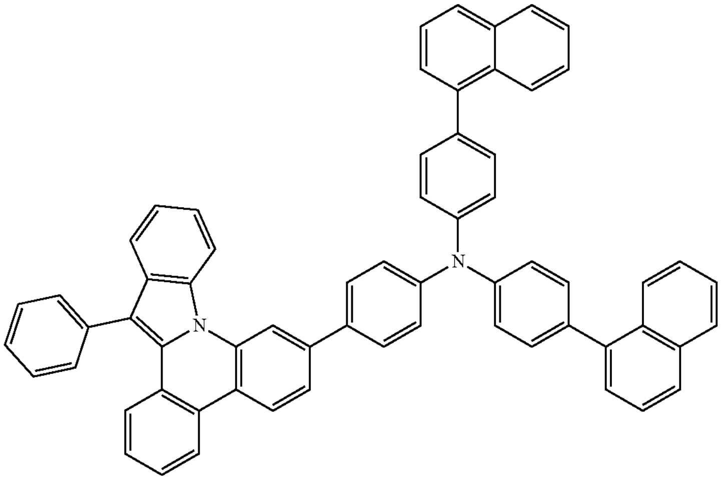
D28
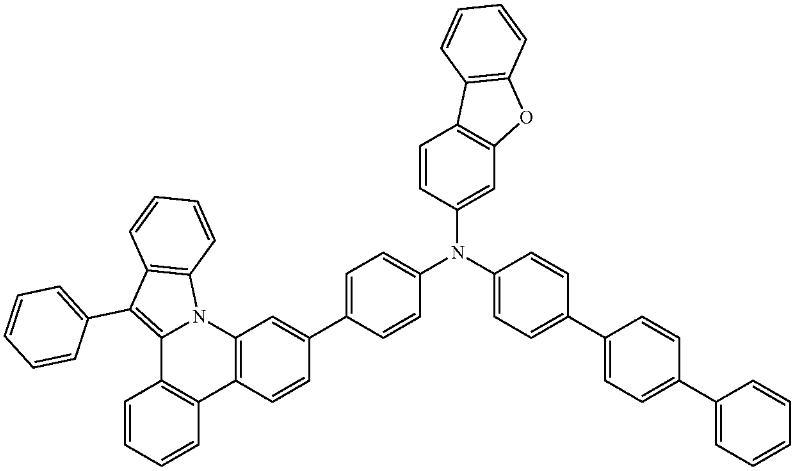
D29
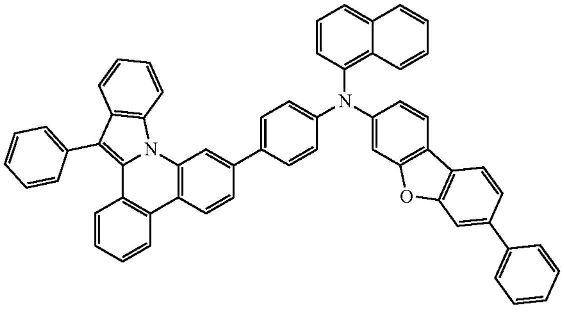
D30
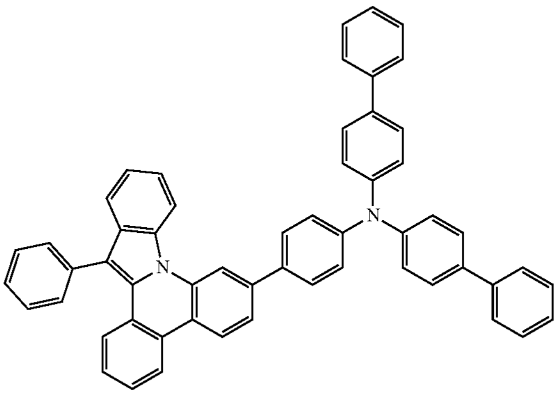

-continued
D31
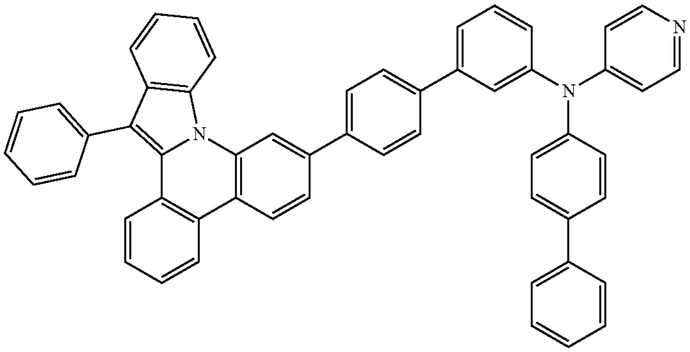
D32
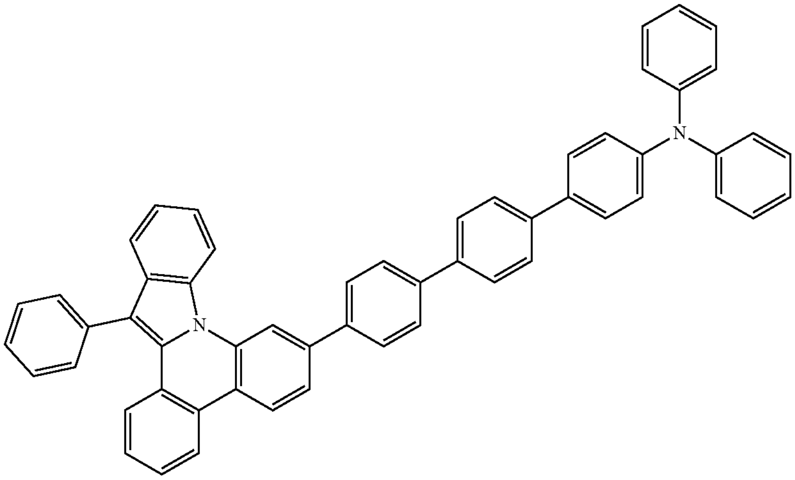
D33
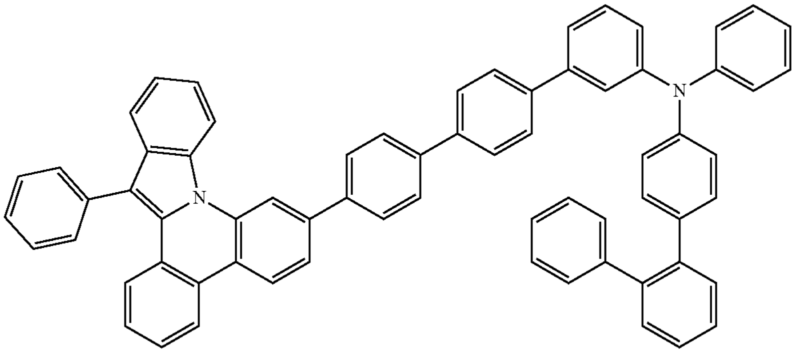
D34
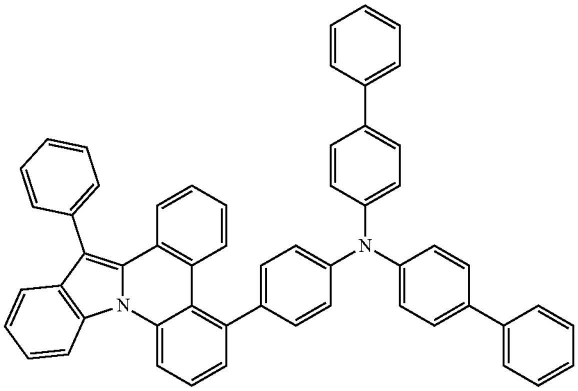
D35
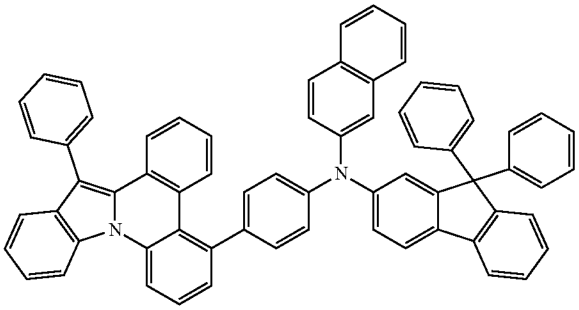

-continued
D36
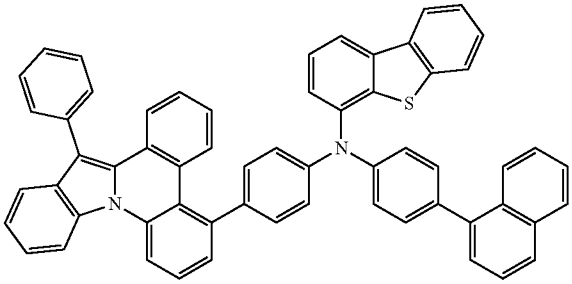
D37
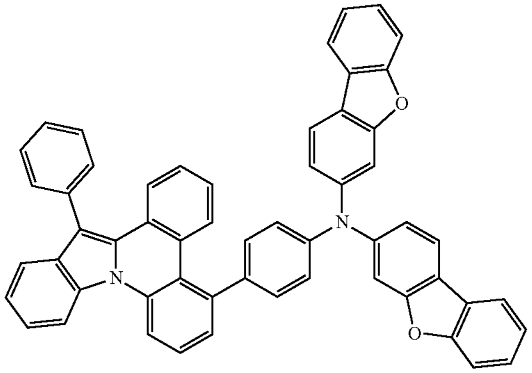
D38
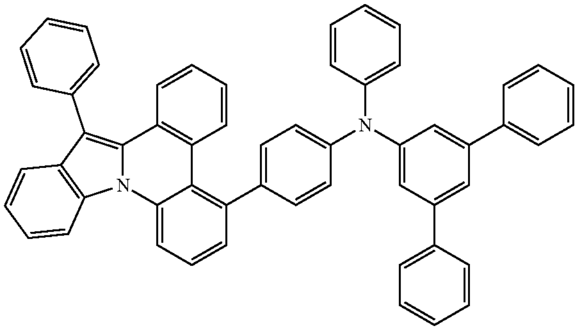
D39
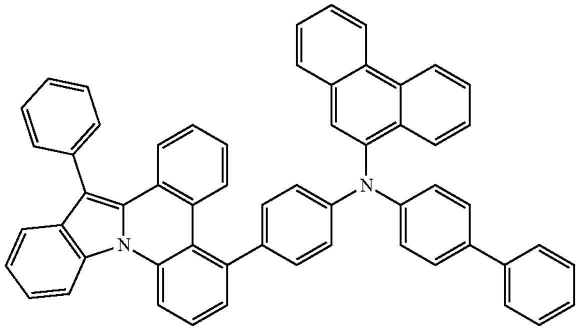
D40
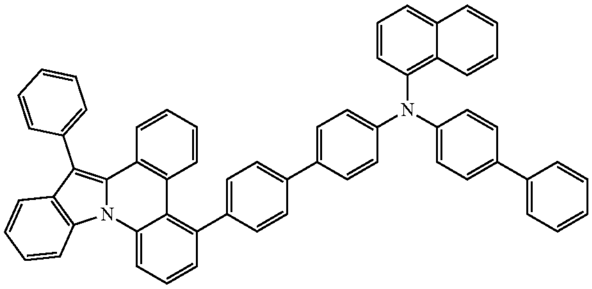
D41
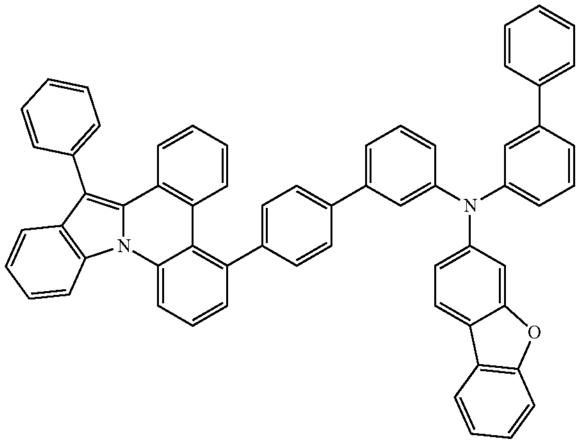
D42
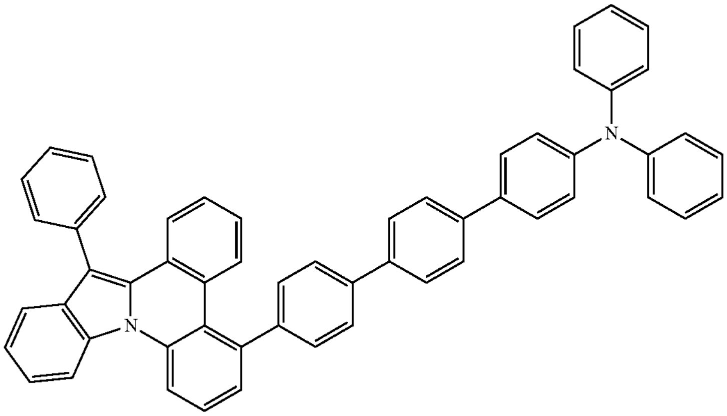

-continued
D43
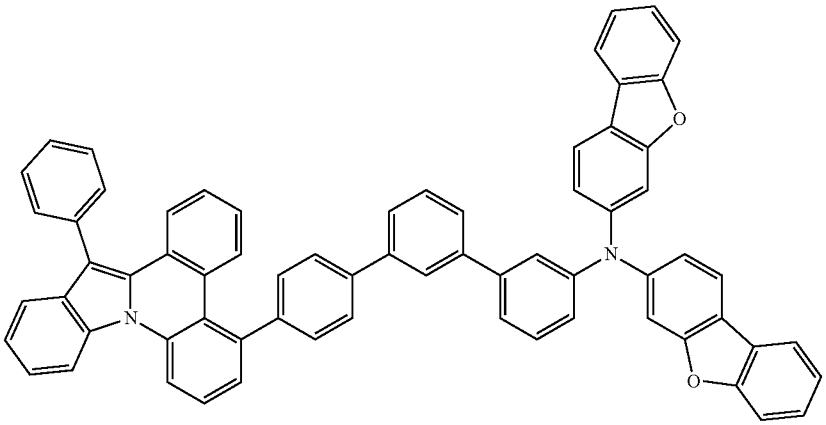
D44
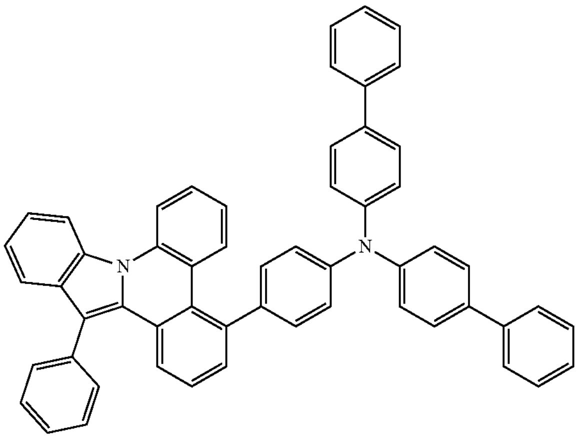
D45
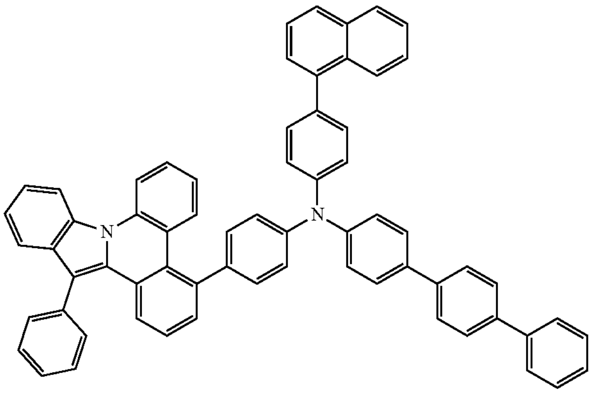
D46
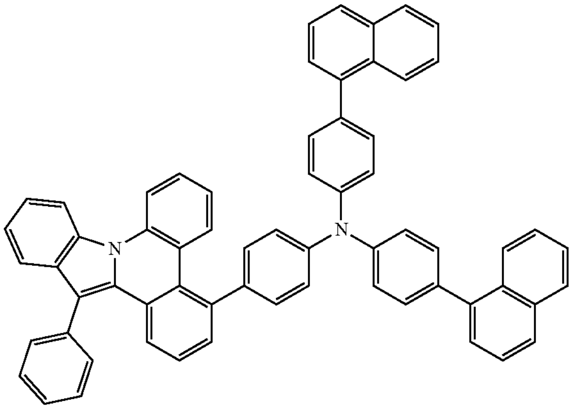
D47
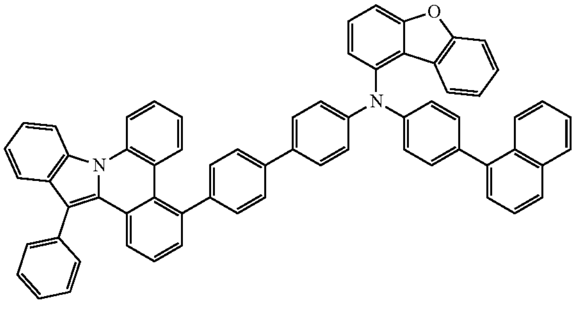

-continued
D48
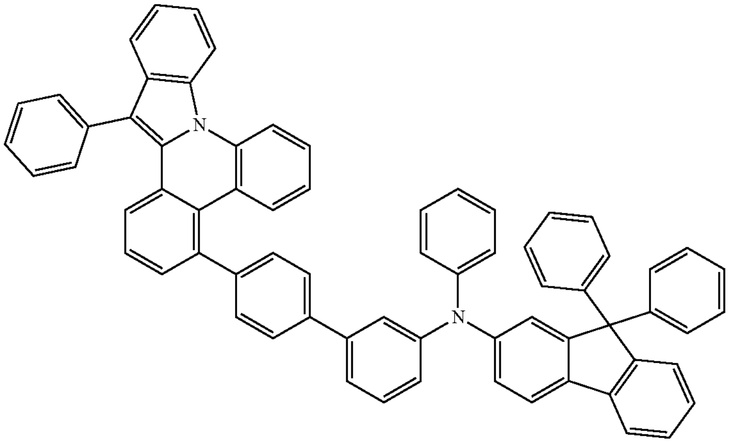
D49
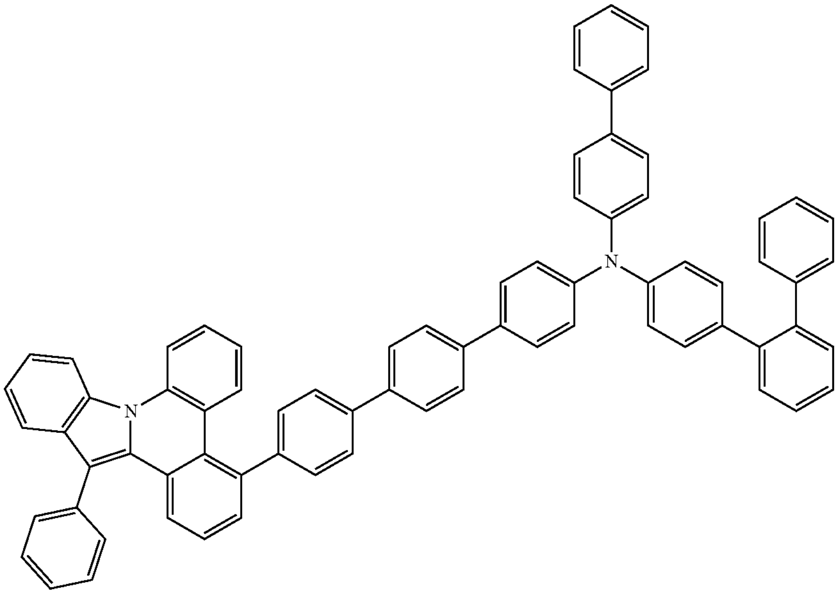
D50
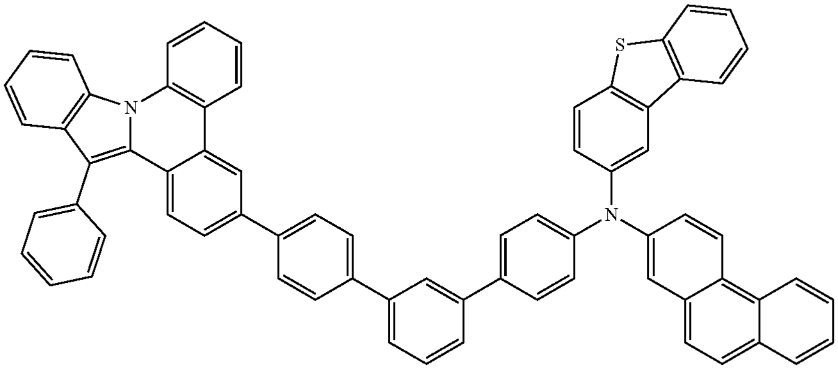

-continued
D51
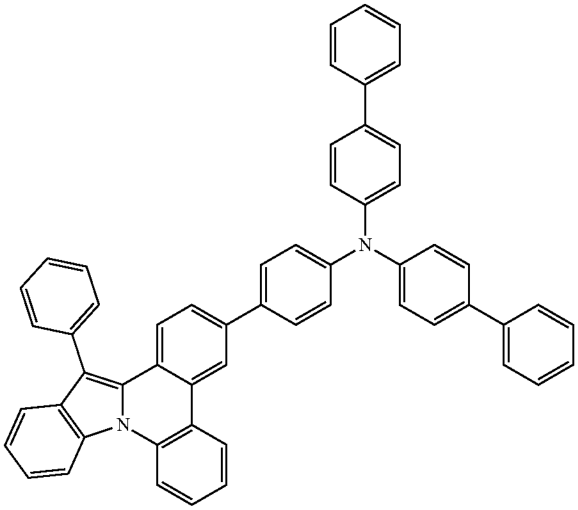
D52
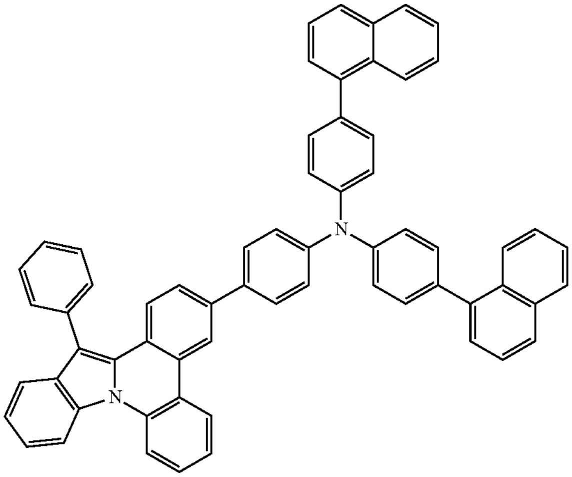
D53
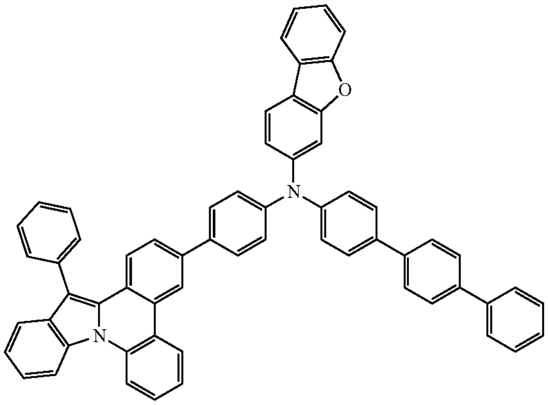
D54
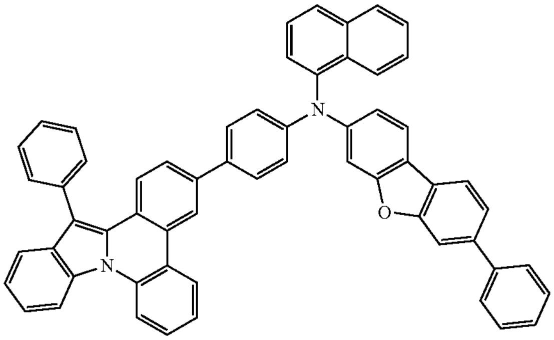
D55
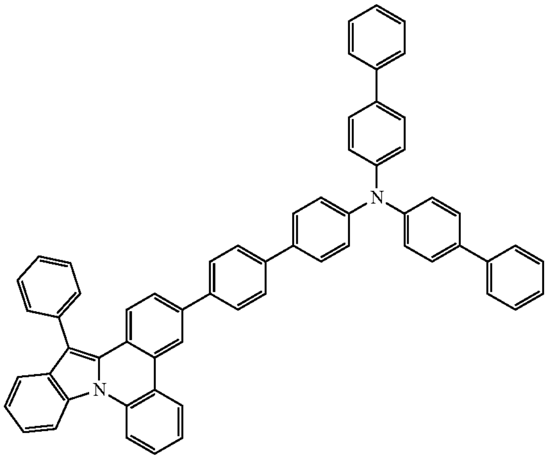
D56
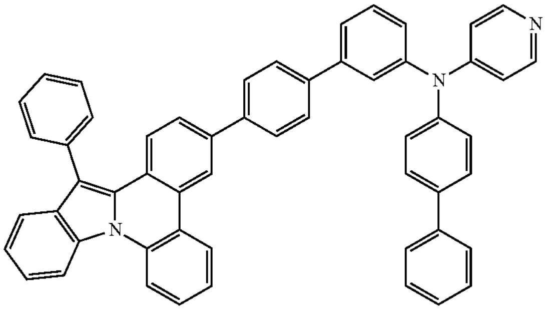

-continued
D57
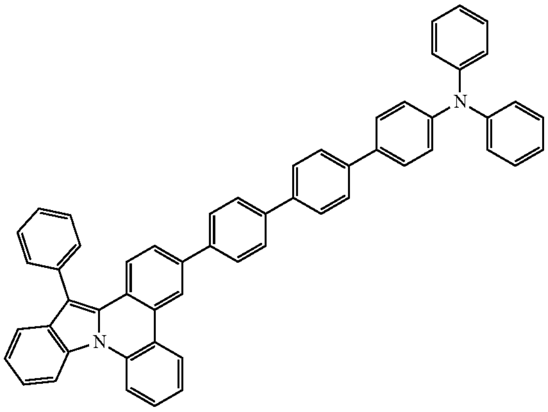
D58
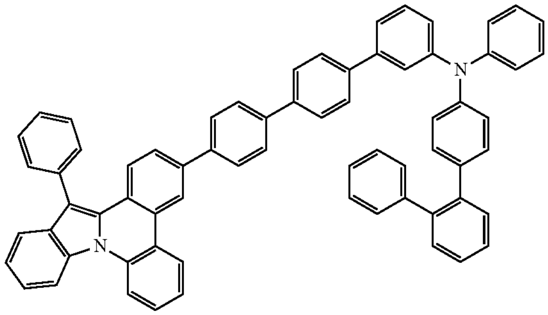
D59
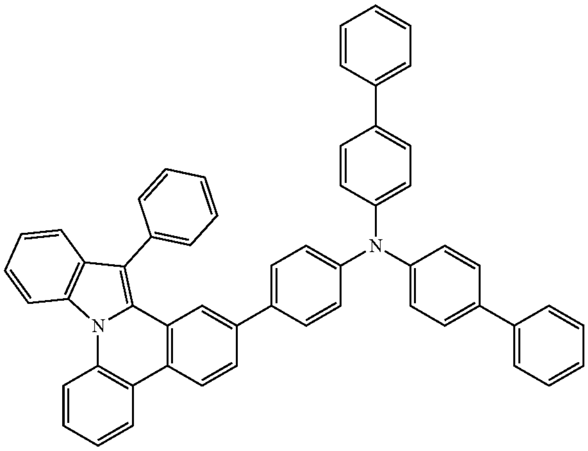
D60
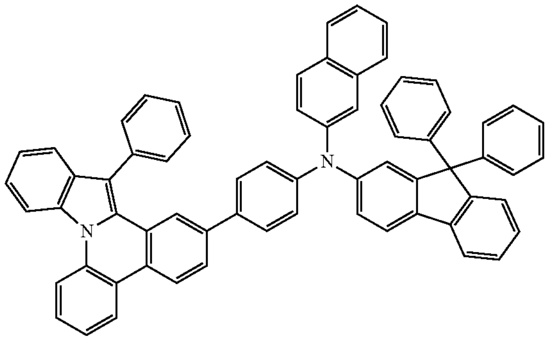
D61
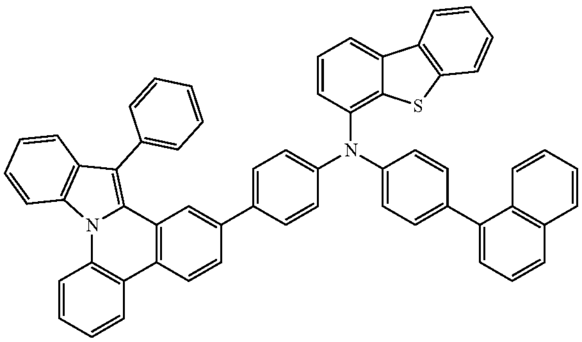
D62
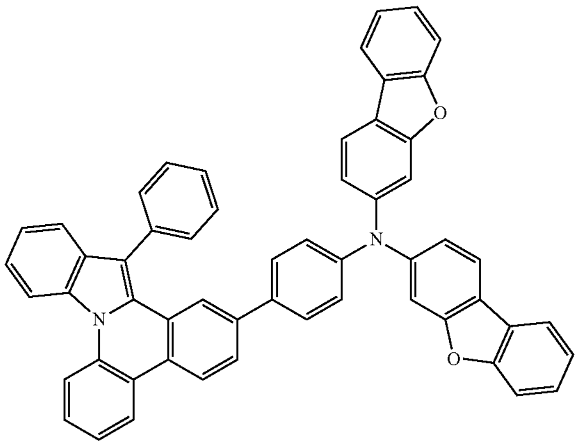

-continued
D63
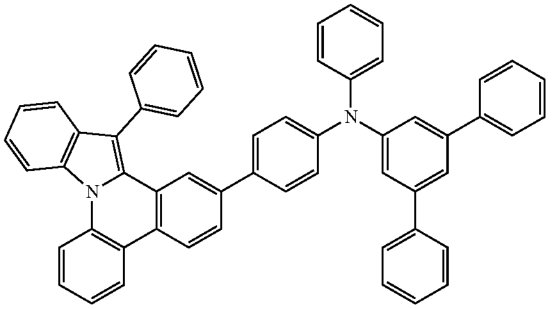
D64
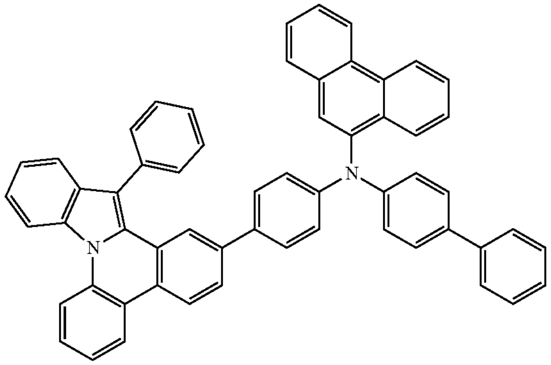
D65
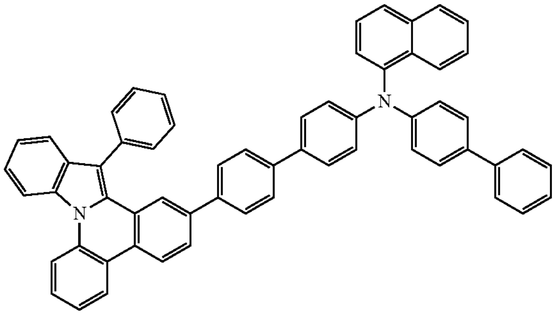
D66
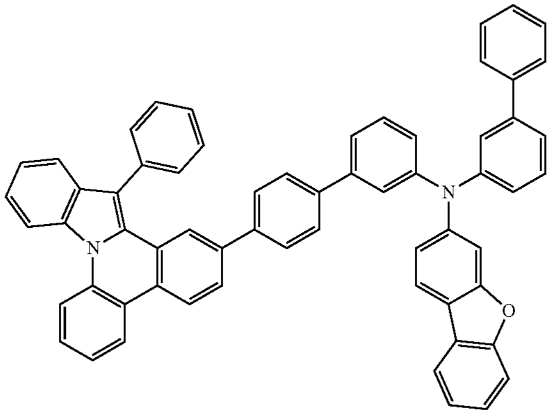
D67
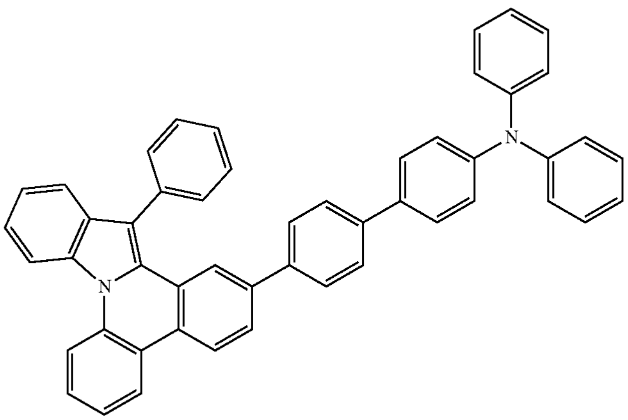

-continued
D68
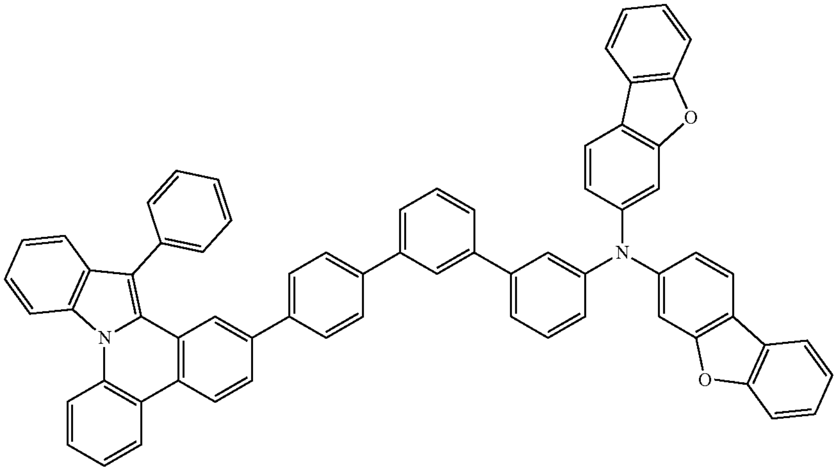
D69
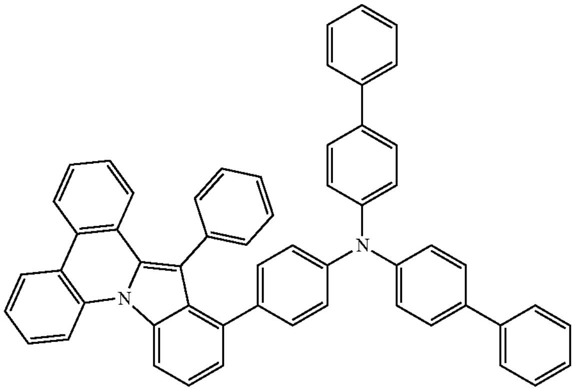
D70
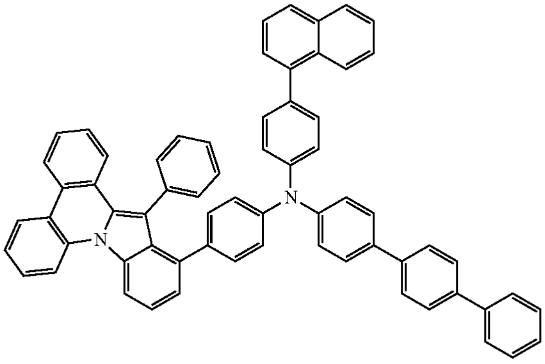
D71
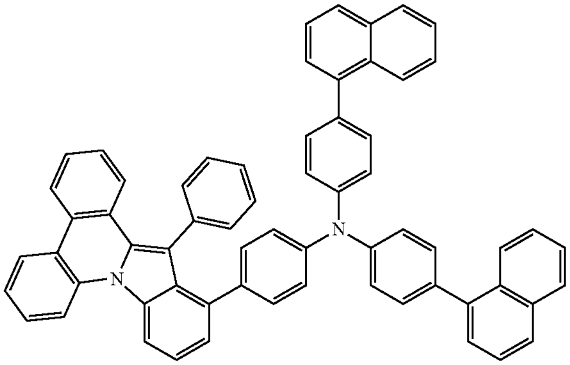
D72
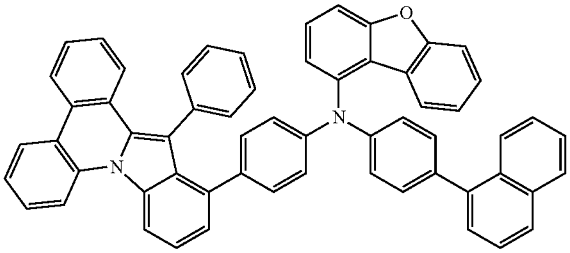
D73
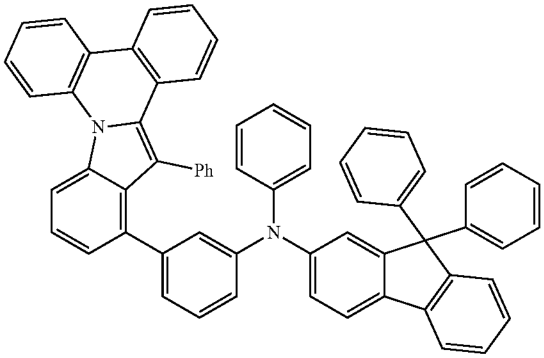
D74
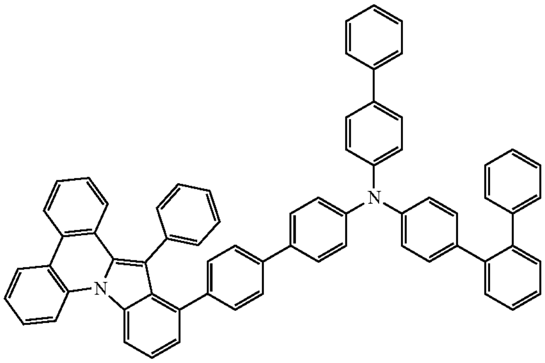

-continued
D75
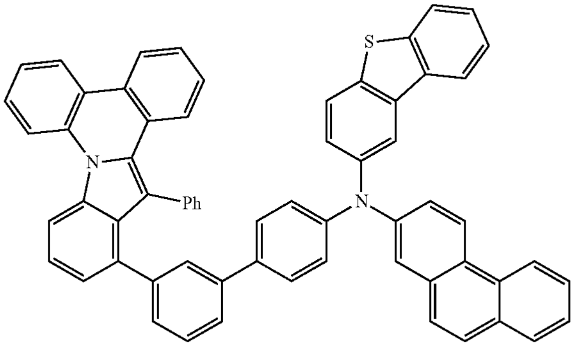
D76
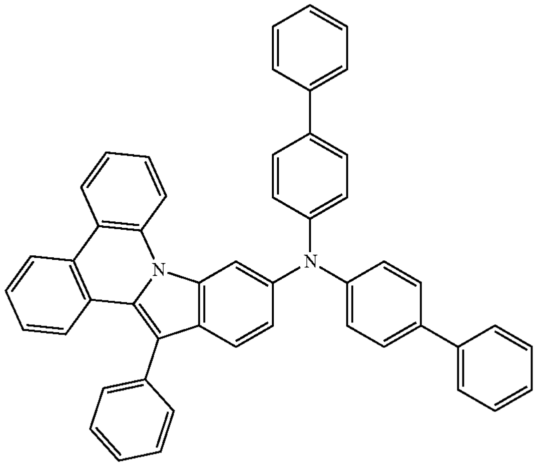
D77
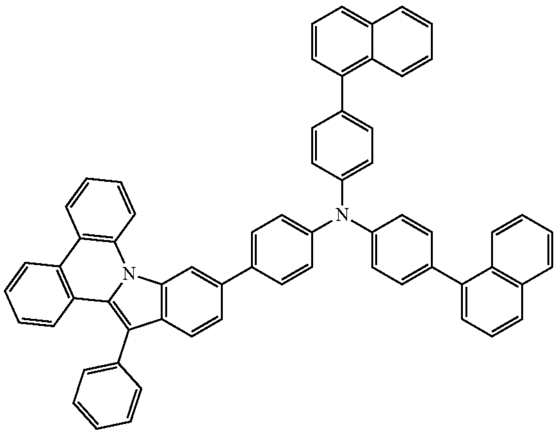
D78
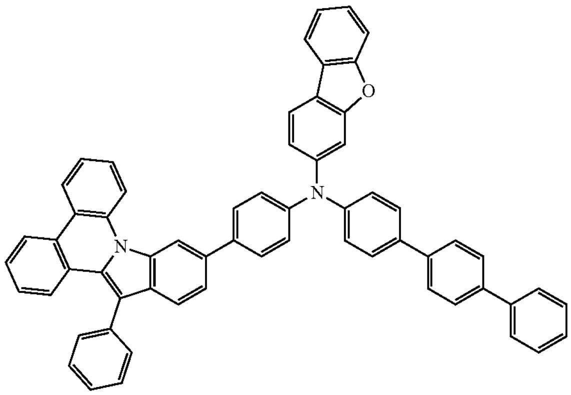
D79
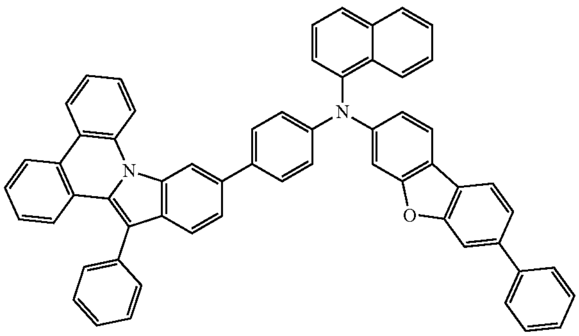
D80
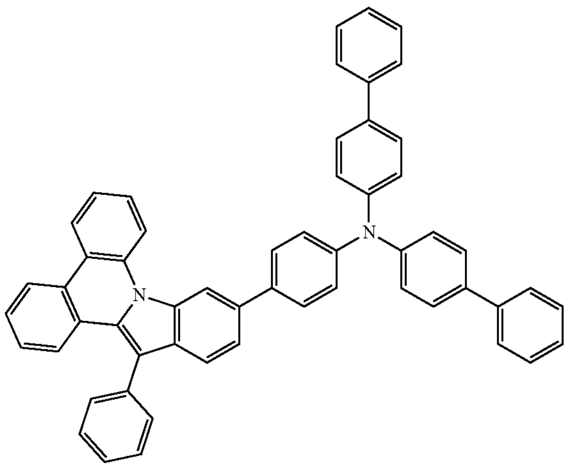

-continued
D81
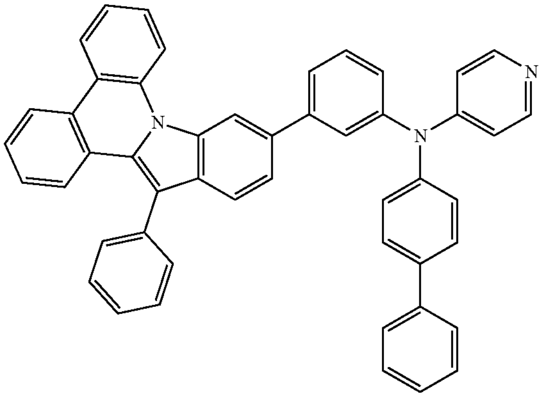
D82
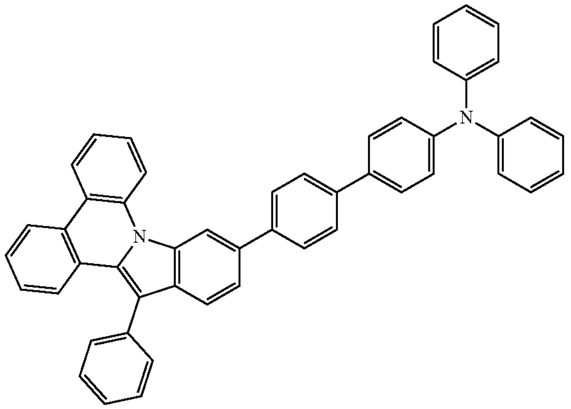
D83
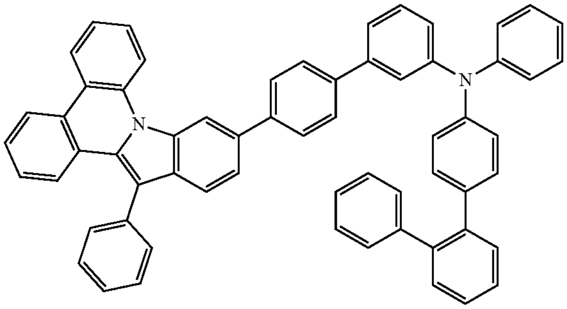
D84
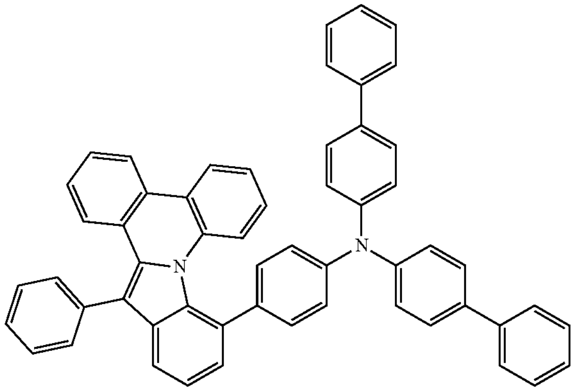
D85
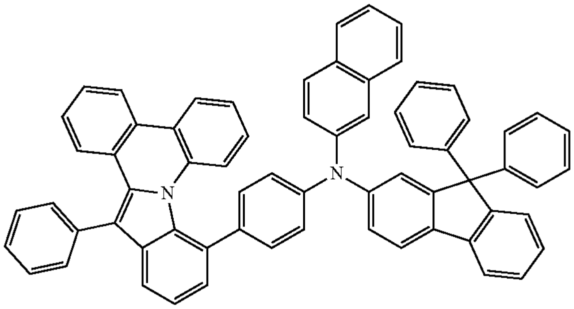
D86
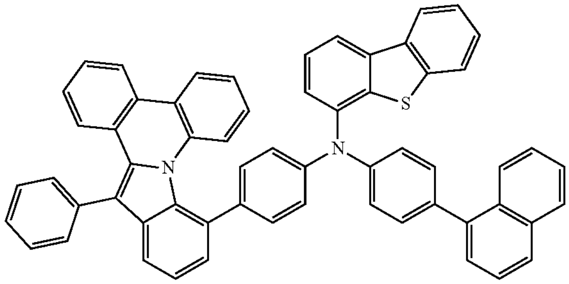
D87
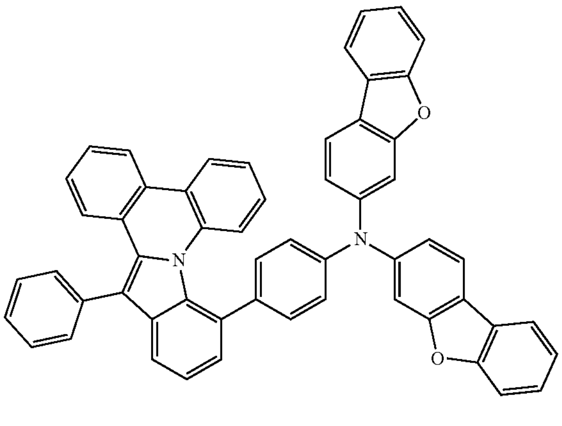
D88
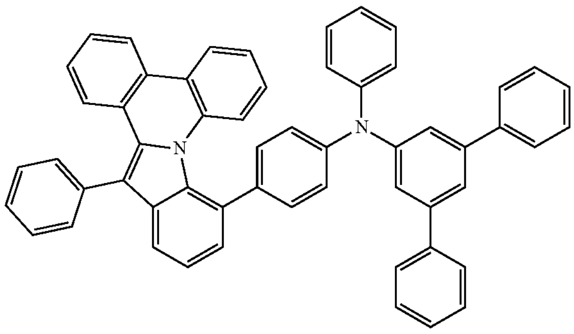

-continued
D89
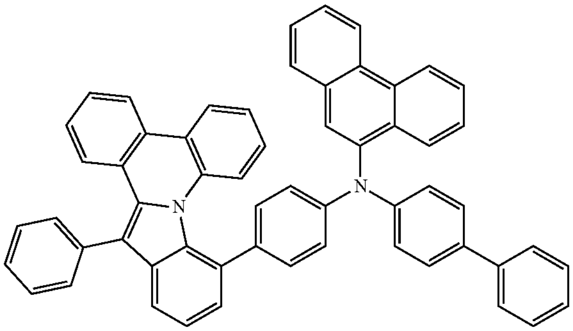
D90
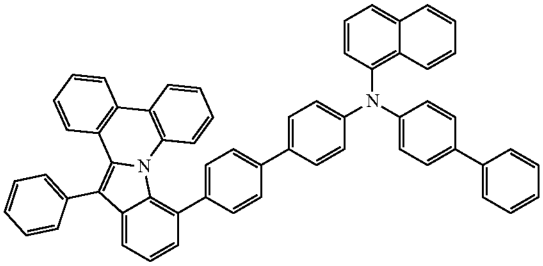
D91
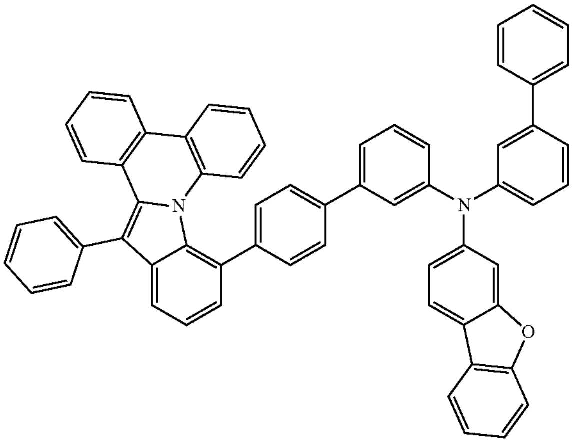
D92
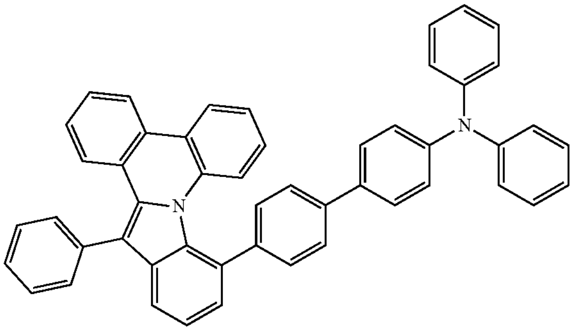
D93
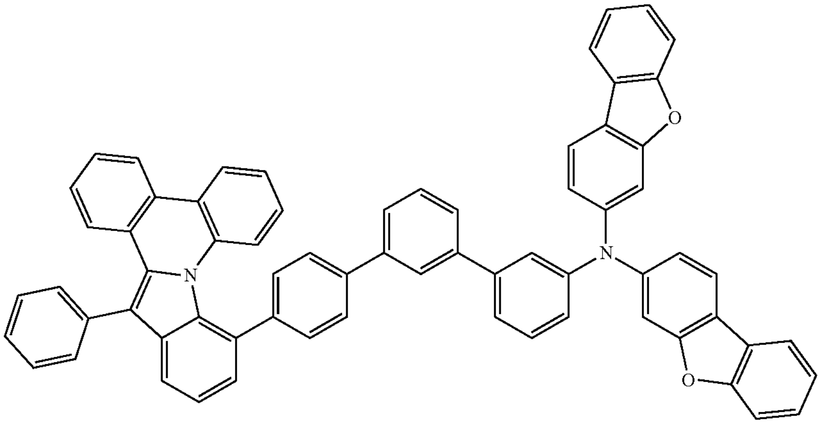
D94
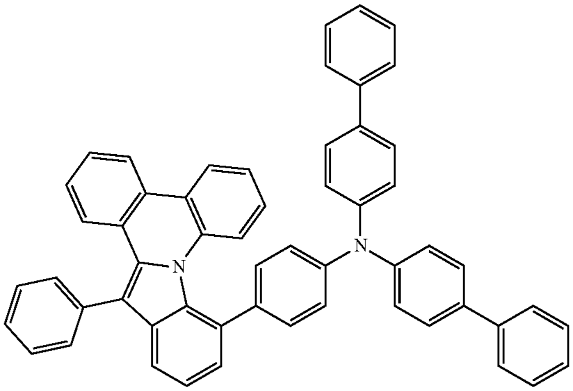
D95
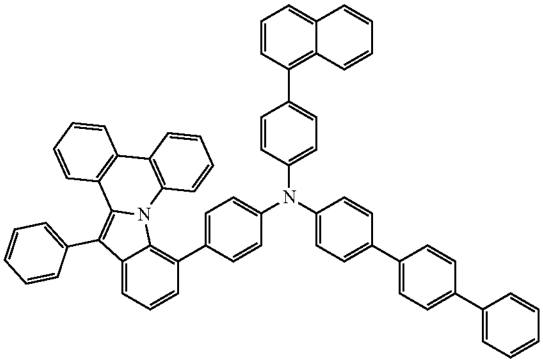

-continued
D96
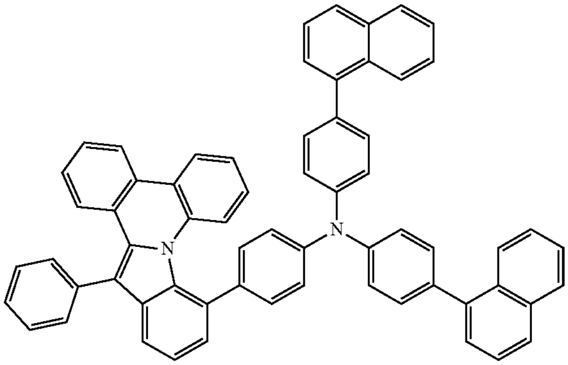
D97
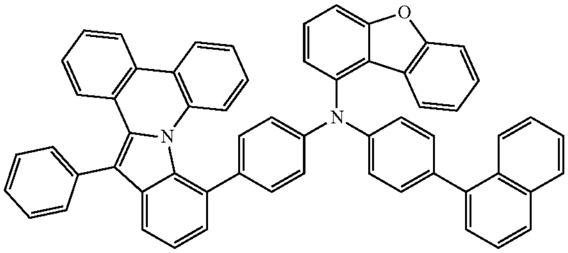
D98
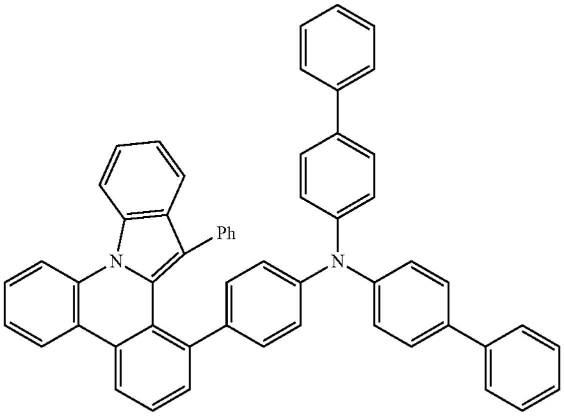
D99
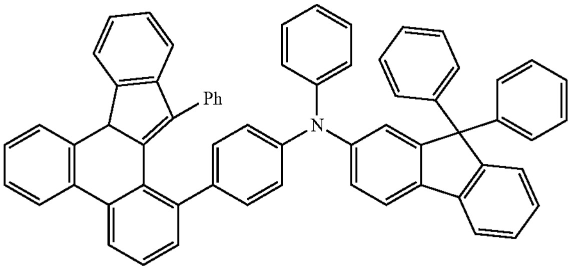
D100
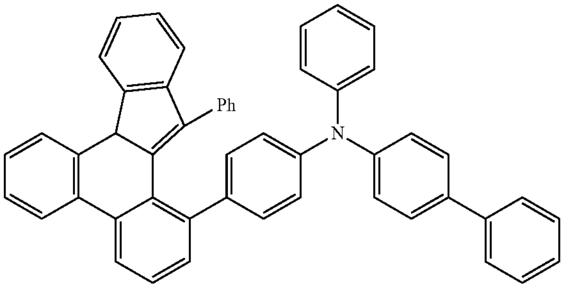
Compound Group 2
E1
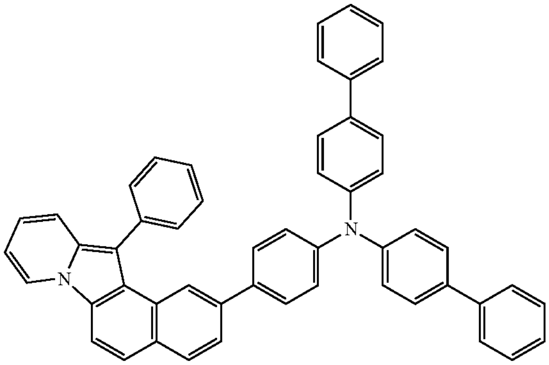
E2
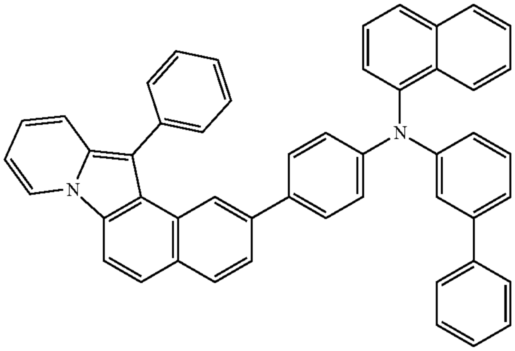

-continued
E3
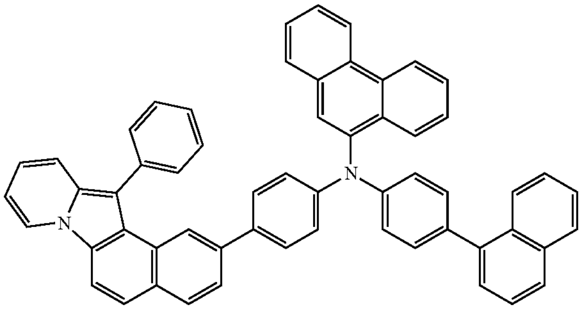
E4
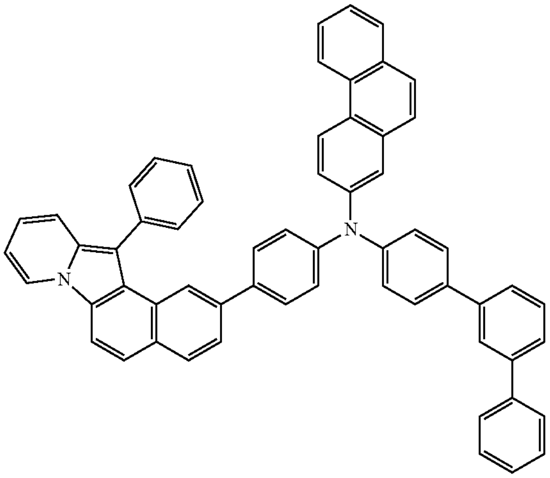
E5
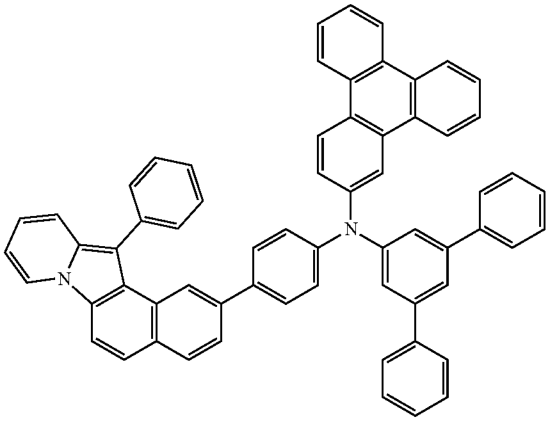
E6
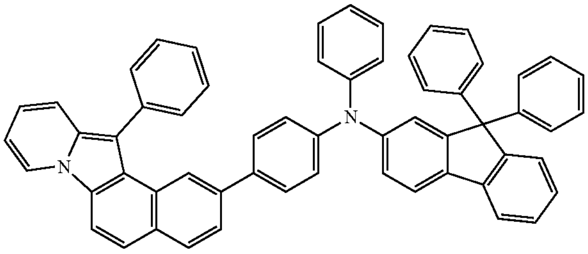
E7
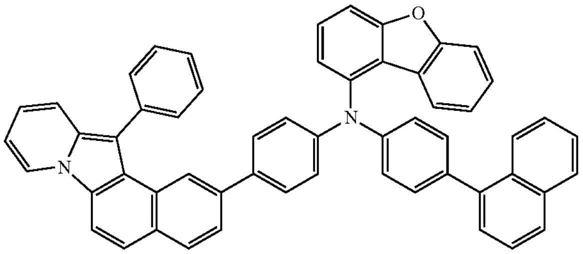
E8
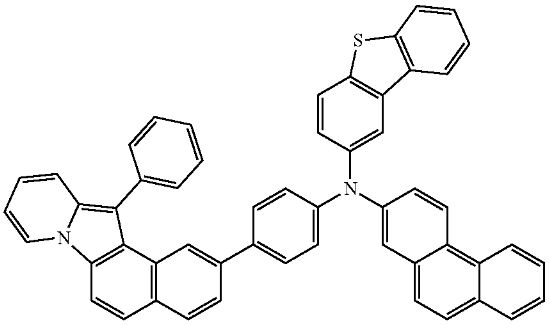

-continued
E9
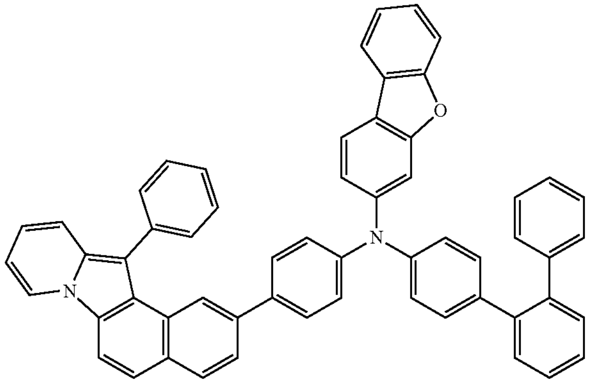
E10
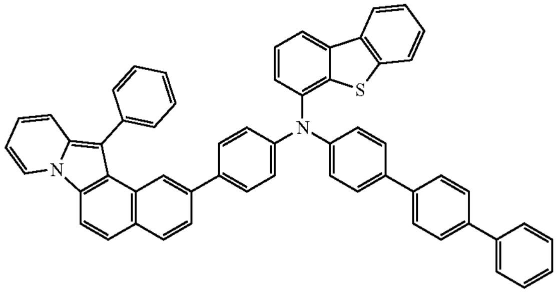
E11
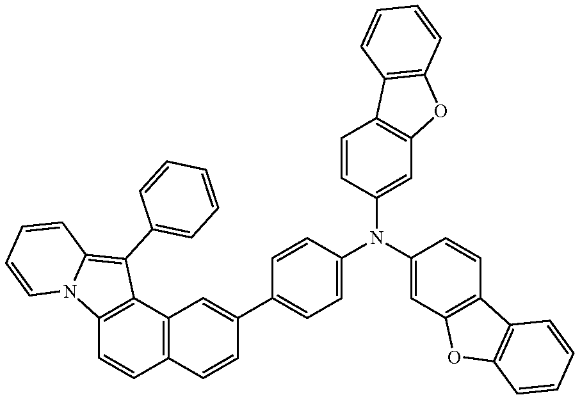
E12
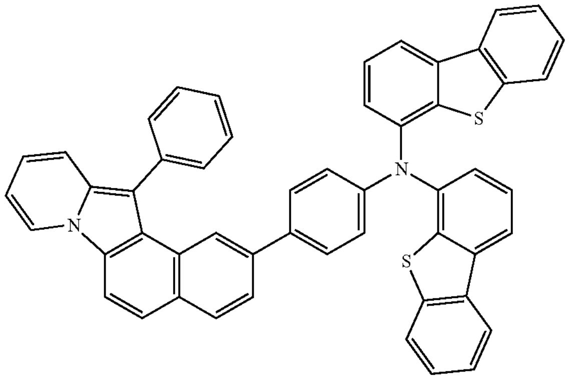
E13
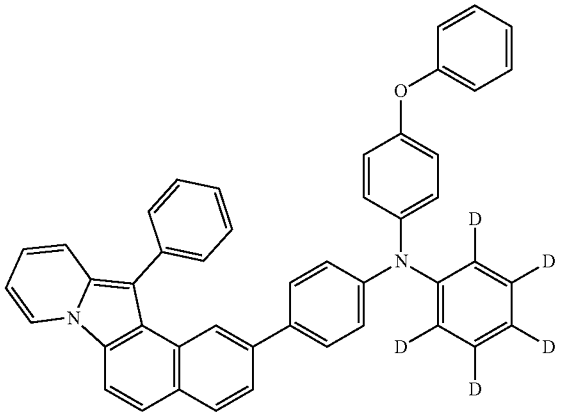
E14
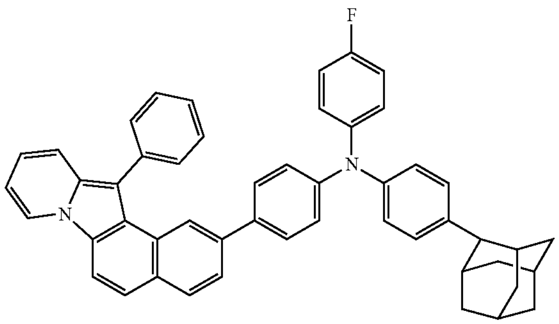
E15
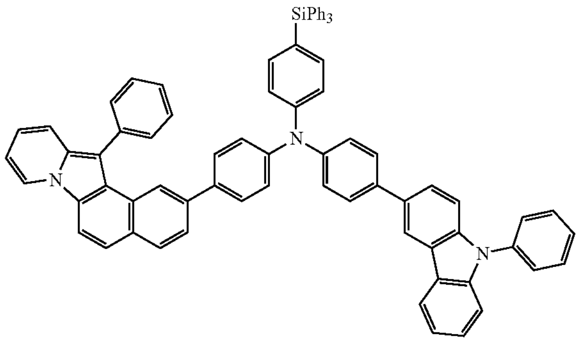
E16
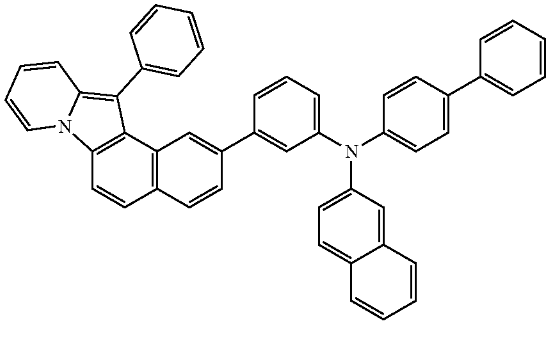

-continued
E17
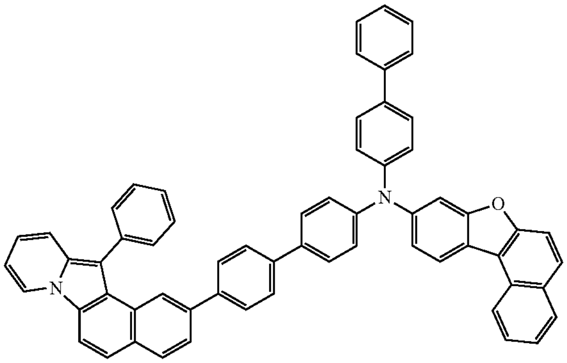
E18
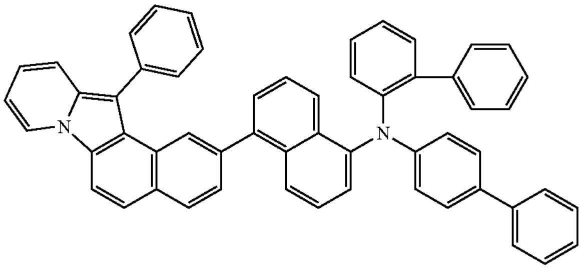
E19
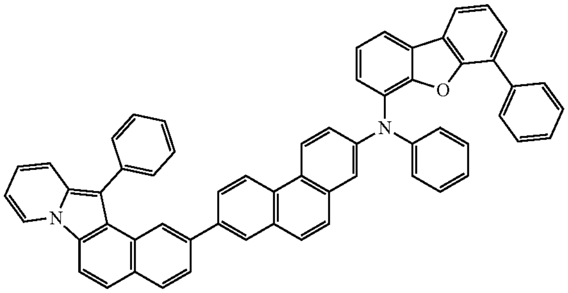
E20
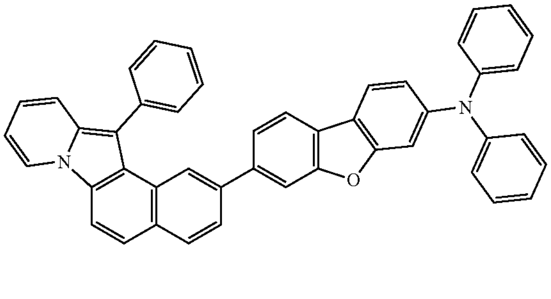
E21
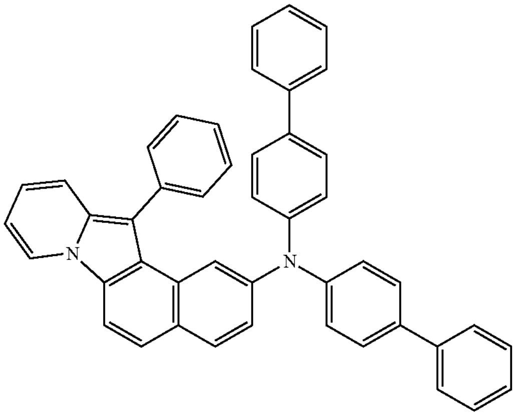
E22
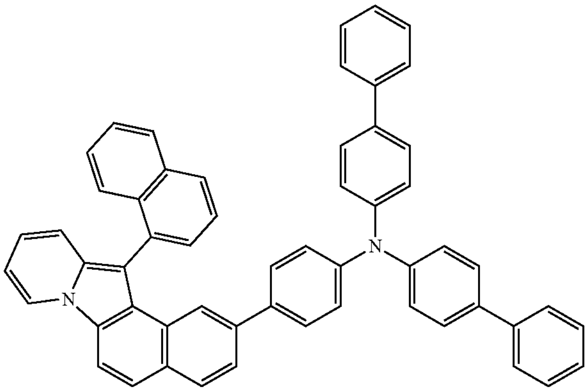
E23
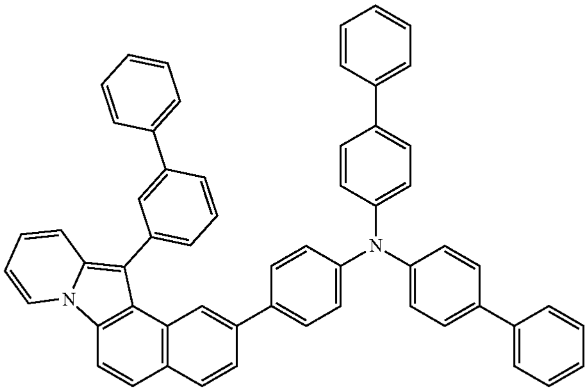
E24
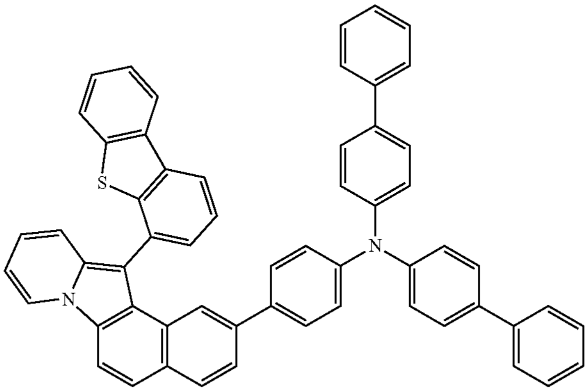

-continued
E25
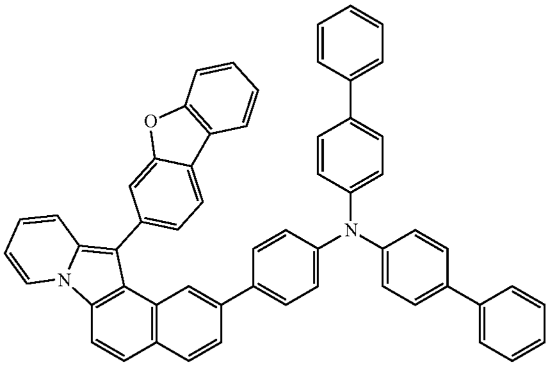
E26
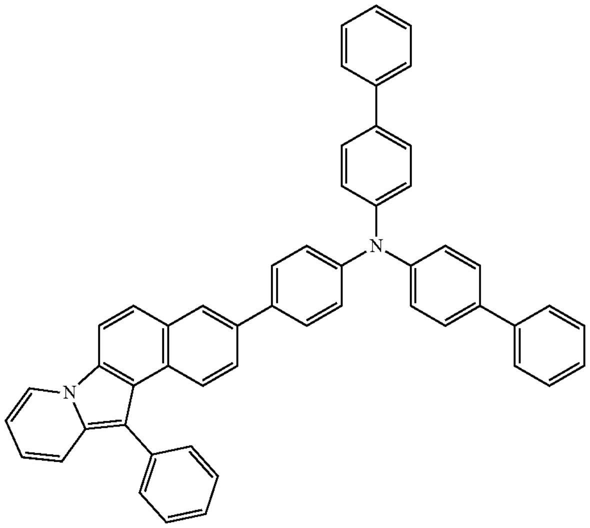
E27
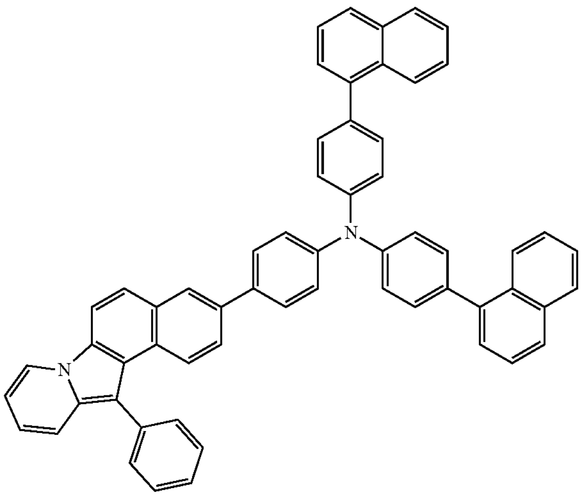
E28
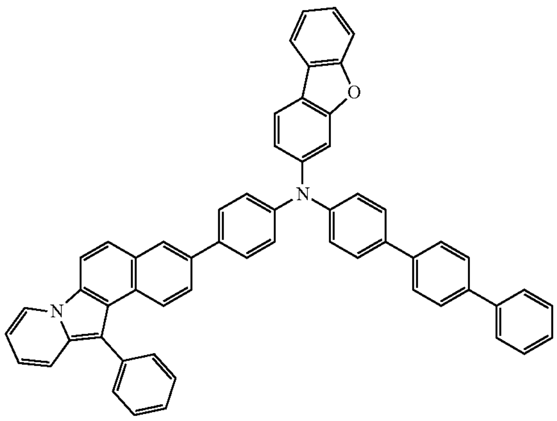
E29
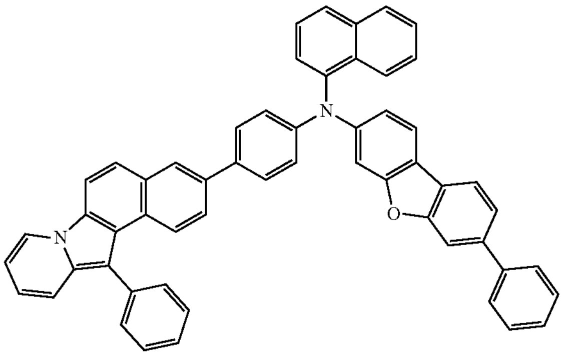
E30
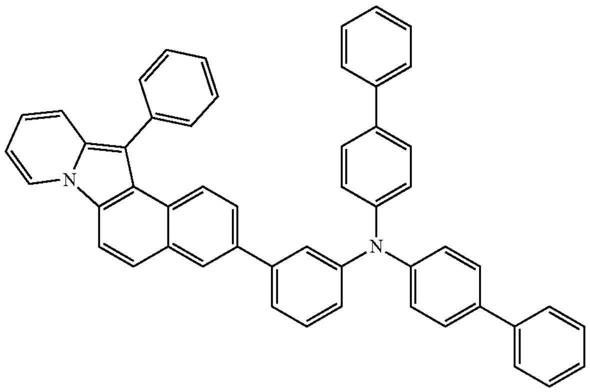

-continued
E31
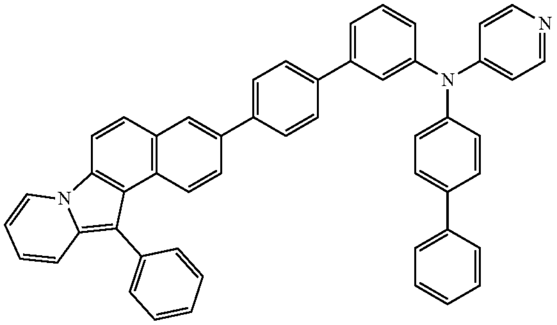
E32
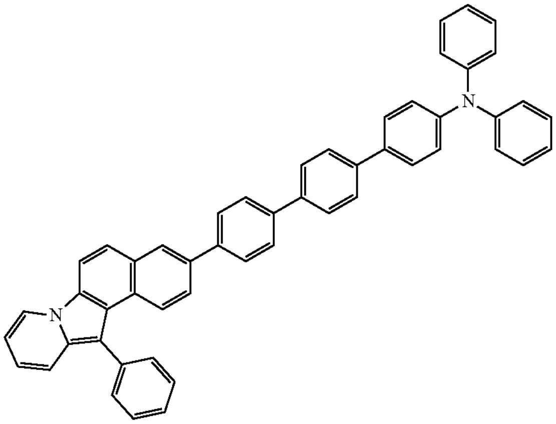
E33
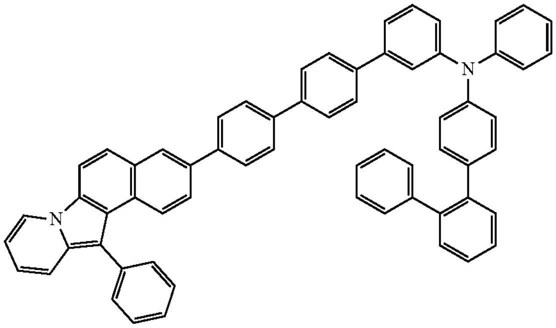
E34
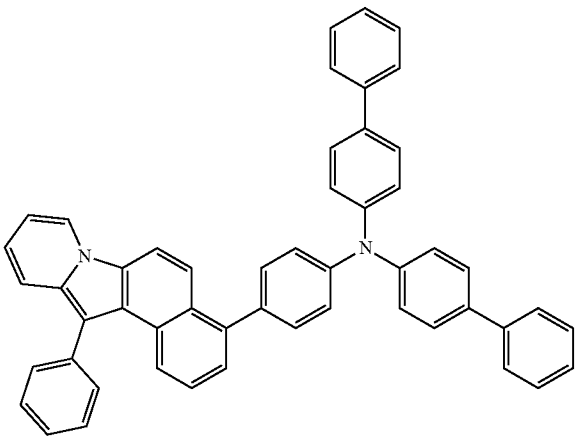
E35
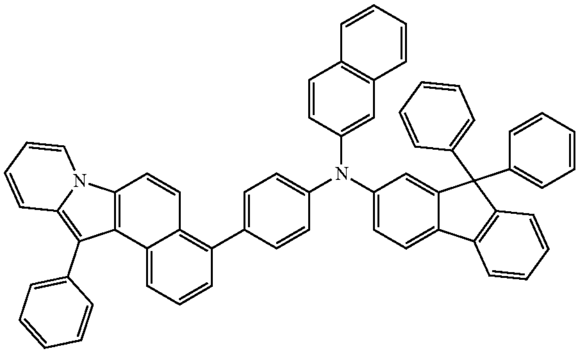
E36
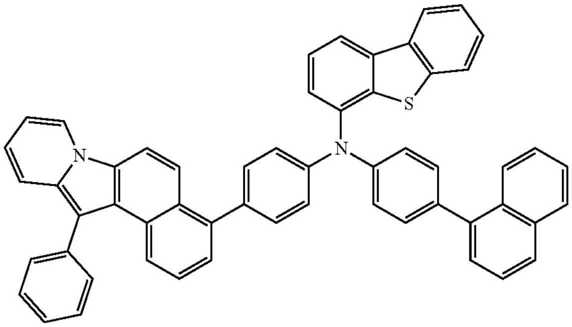

-continued
E37
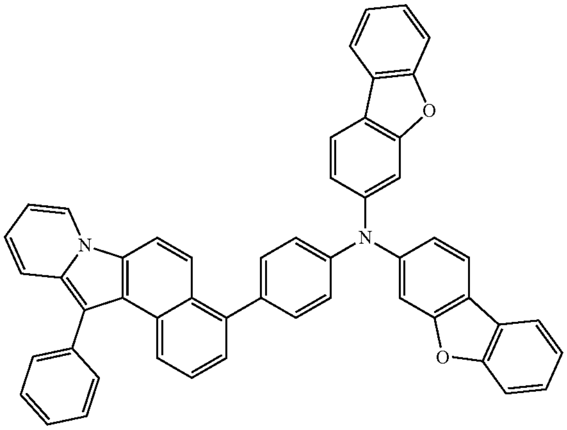
E38
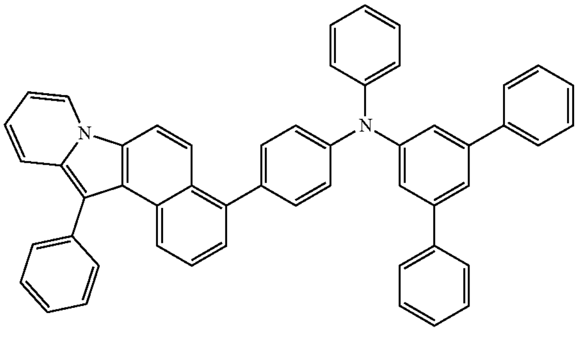
E39
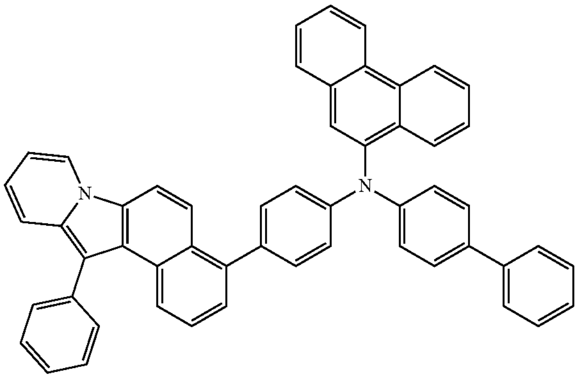
E40
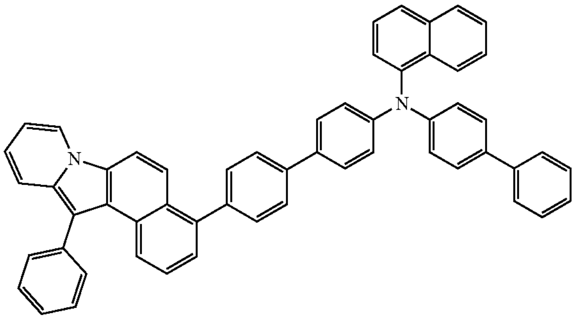
E41
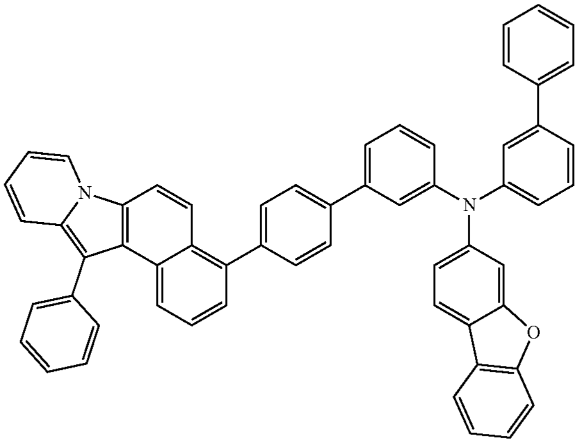
E42
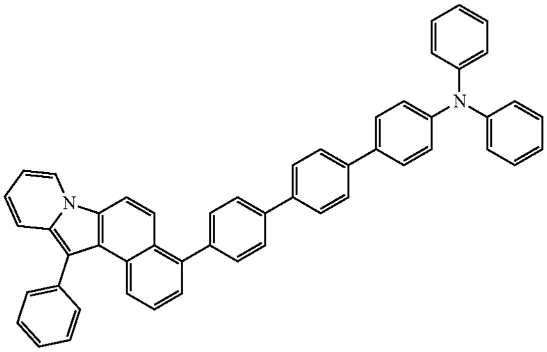

-continued
E43
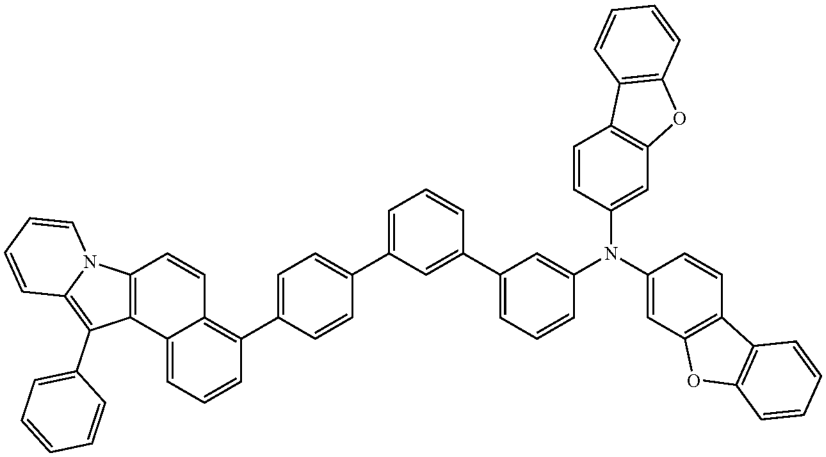
E44
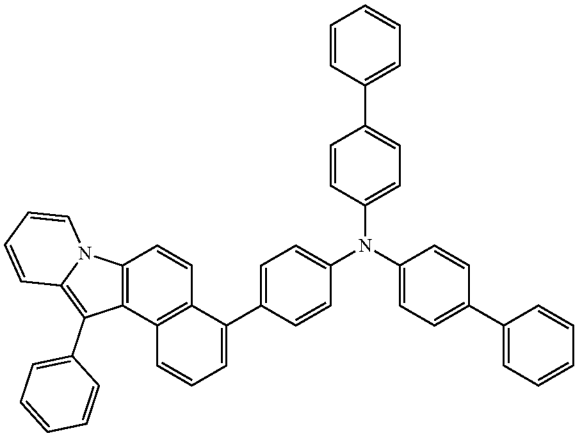
E45
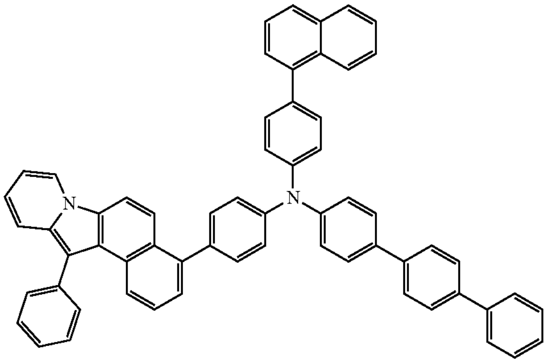
E46
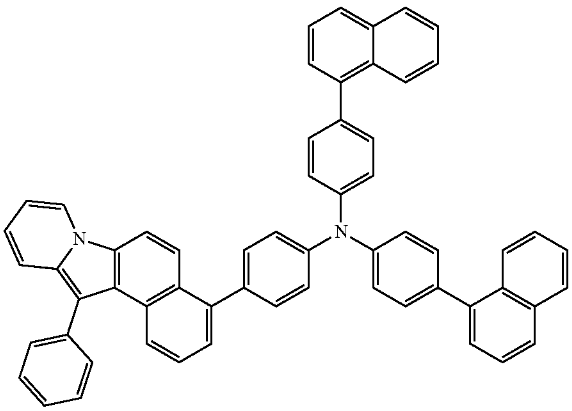
E47
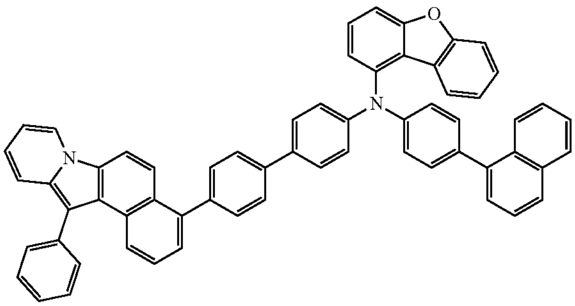

-continued
E48
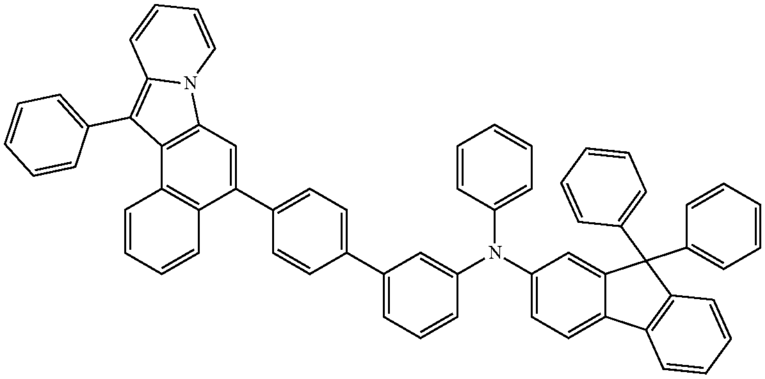
E49
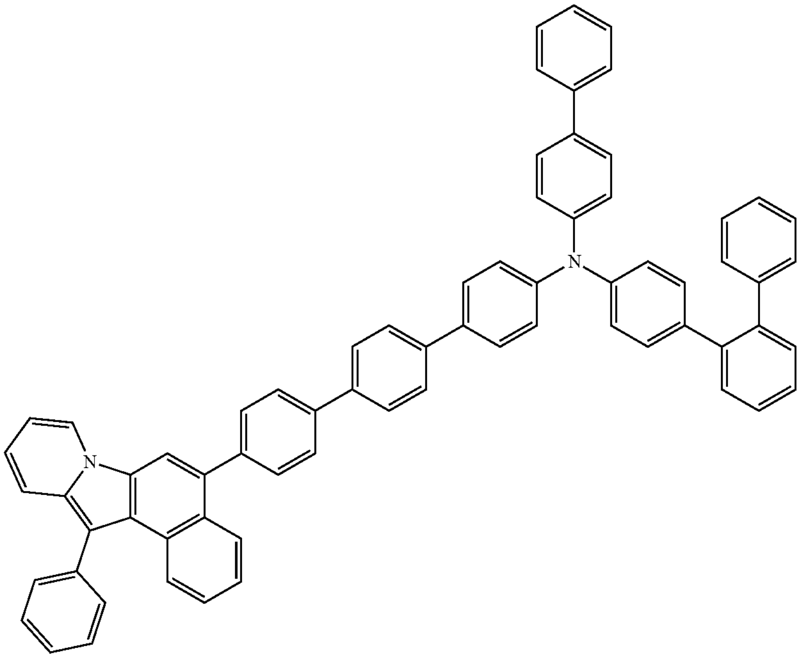
E50
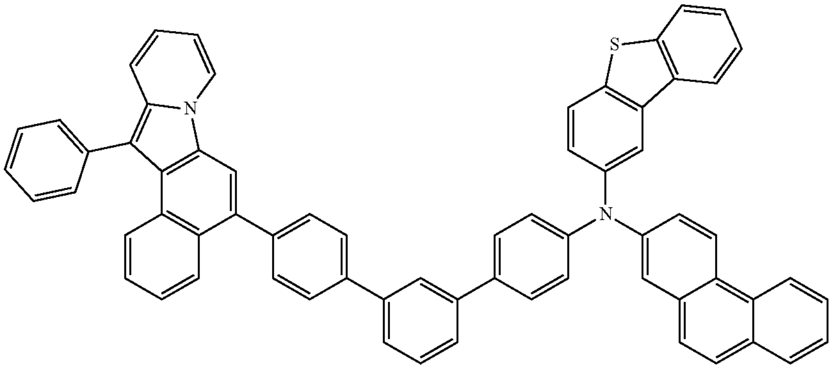

-continued
E51
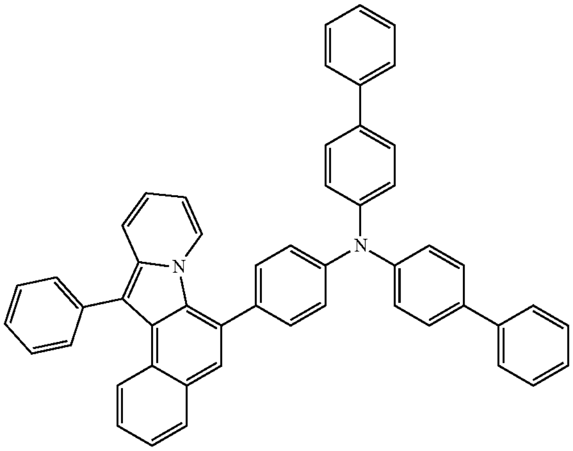
E52
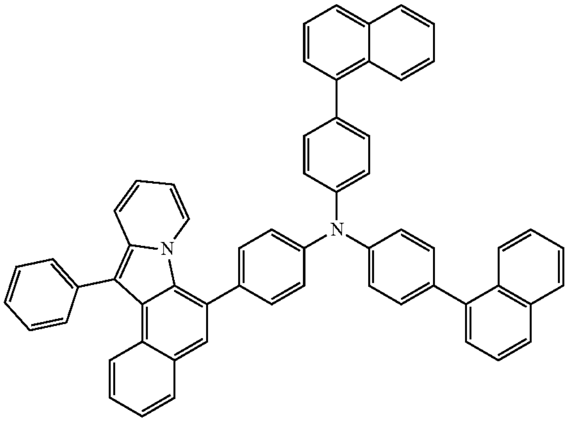
E53
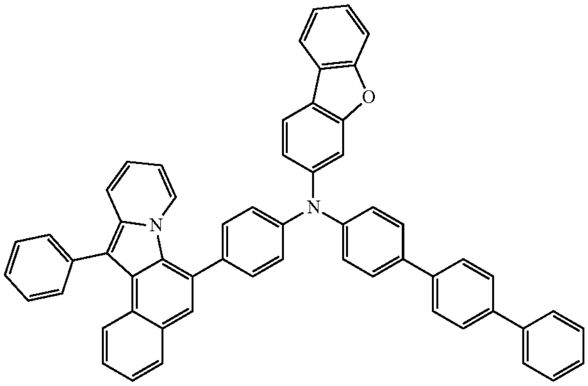
E54
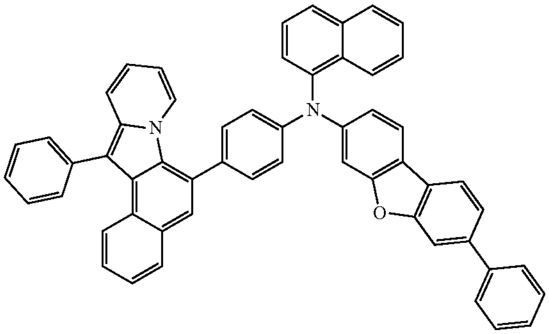
E55
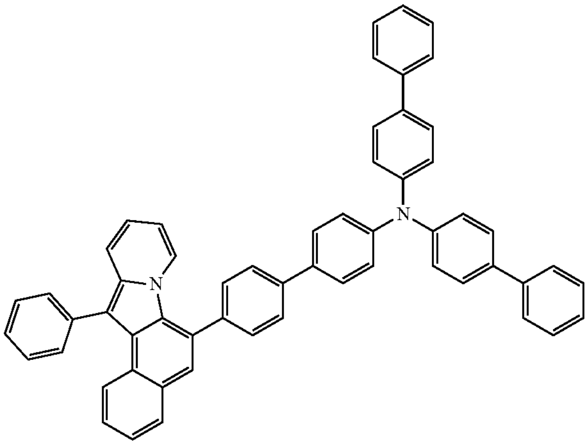
E56
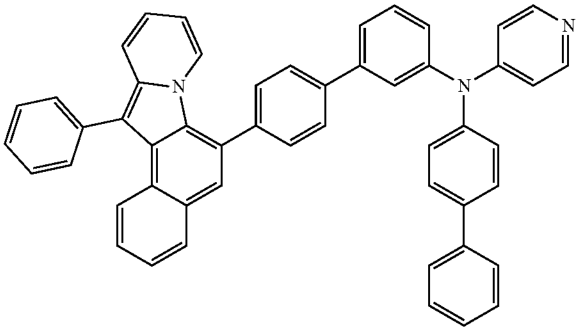

-continued
E57
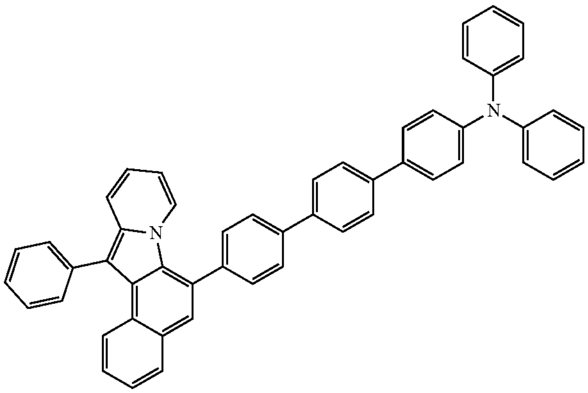
E58
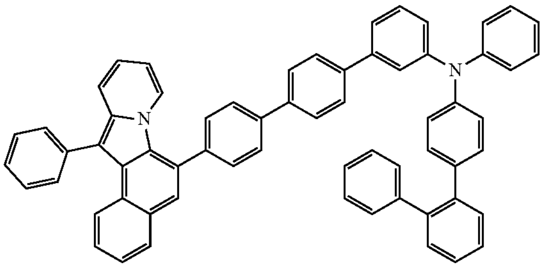
E59
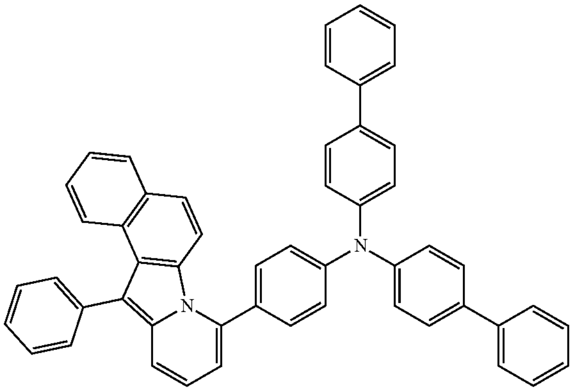
E60
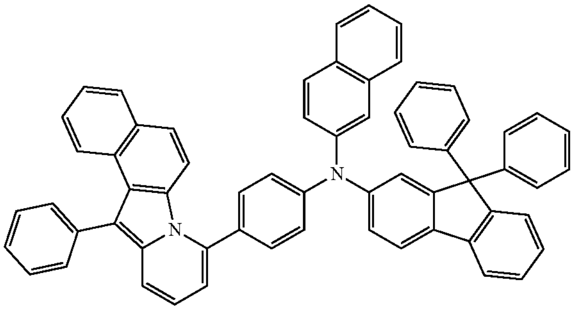
E61
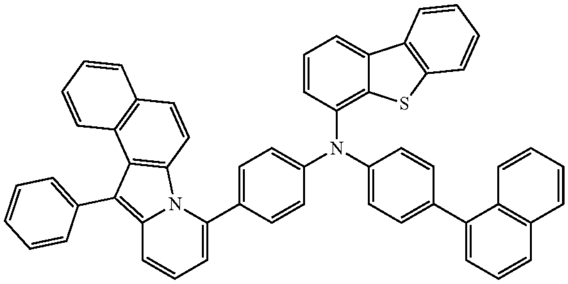
E62
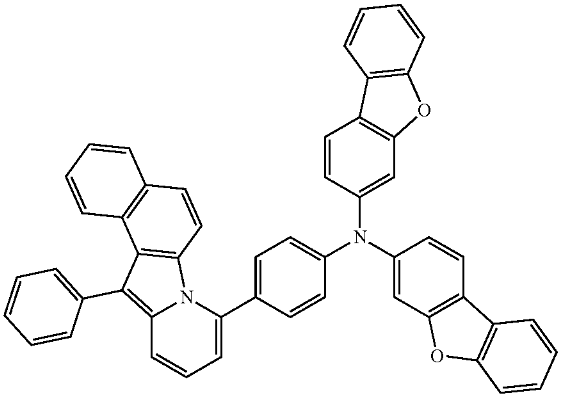
E63
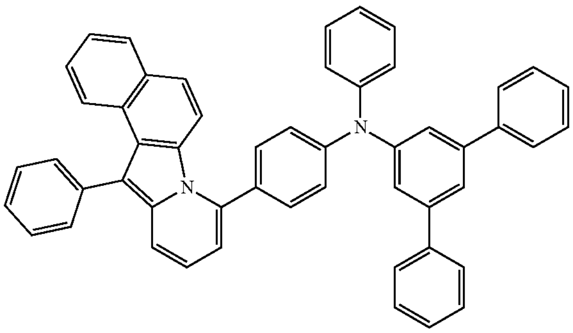
E64
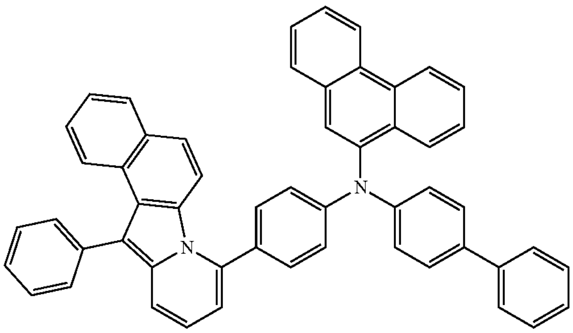

-continued
E65
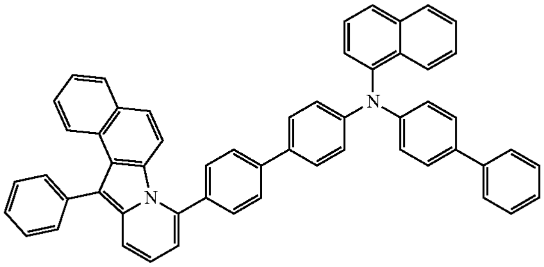
E66
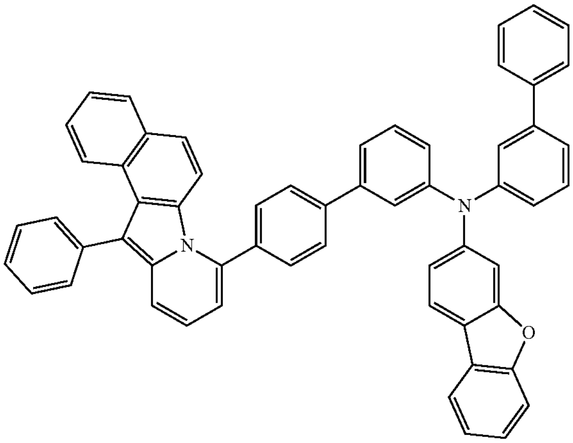
E67
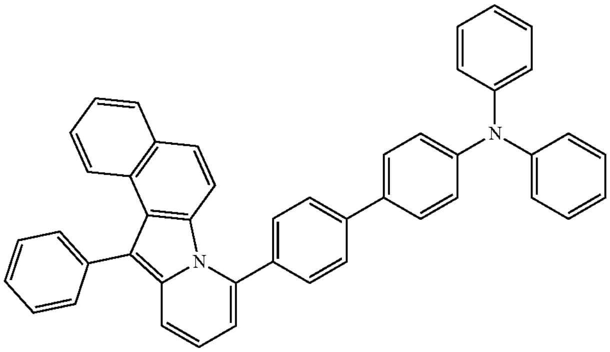
E68
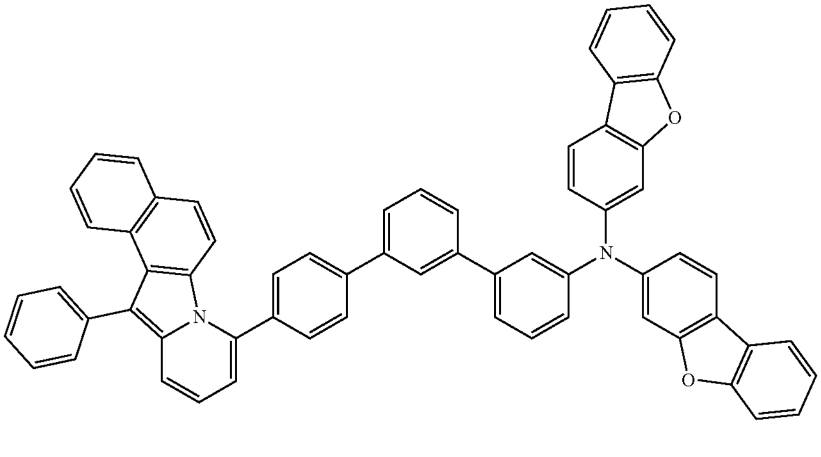

-continued
E69
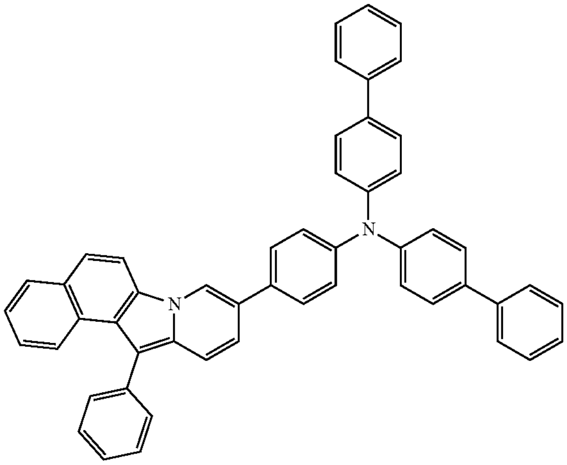
E70
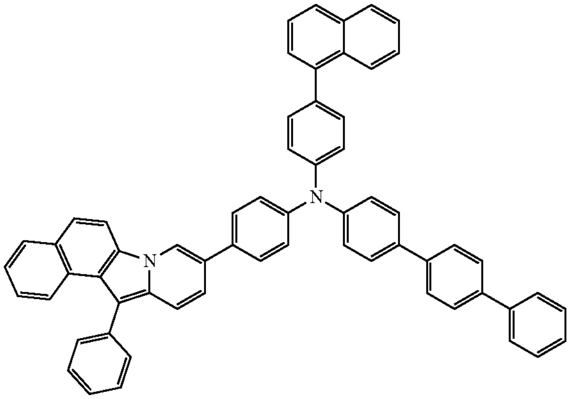
E71
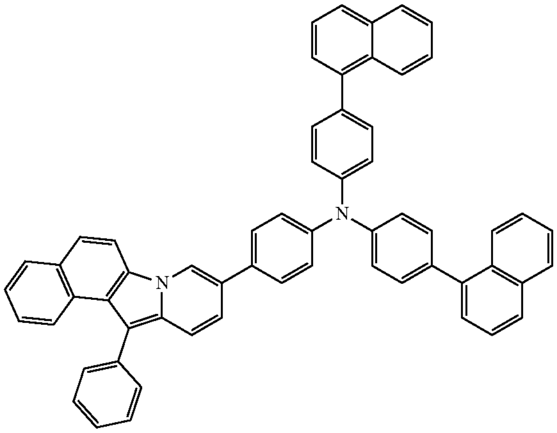
E72
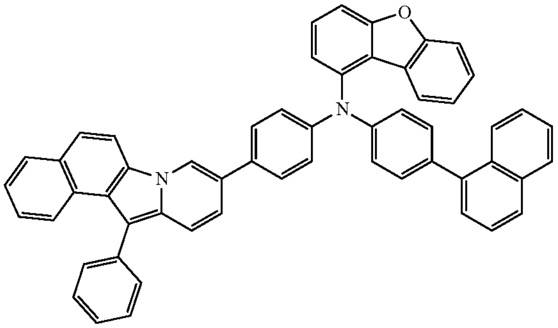
E73
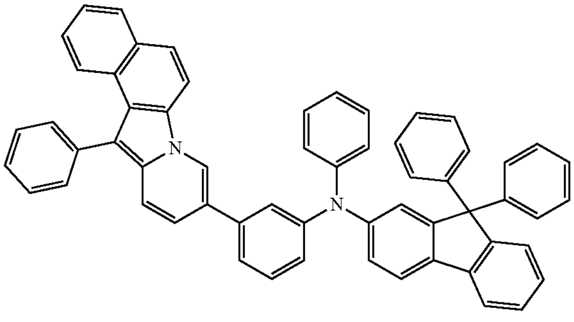
E74
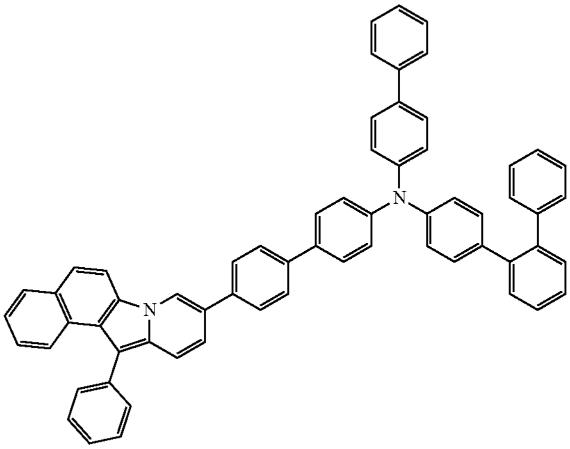

-continued
E75
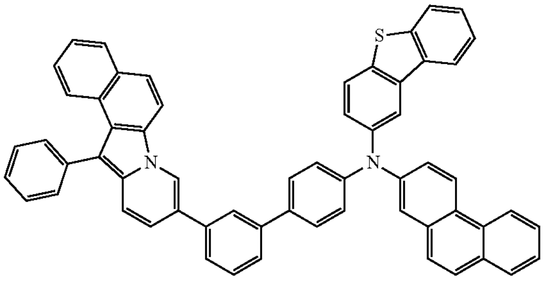
E76
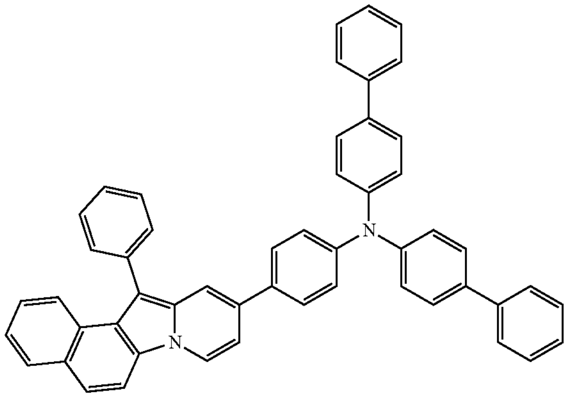
E77
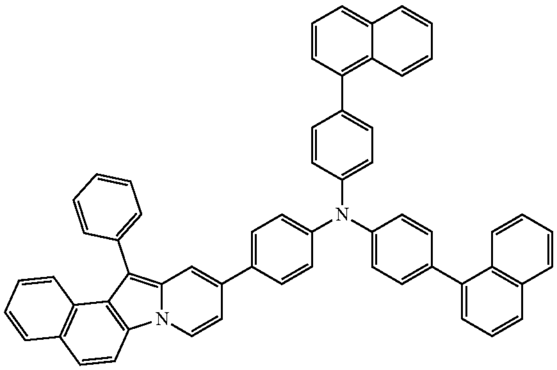
E78
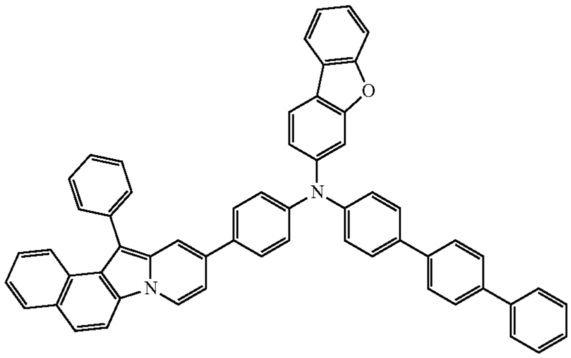
E79
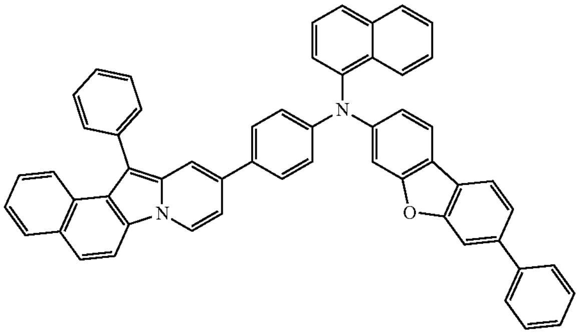
E80
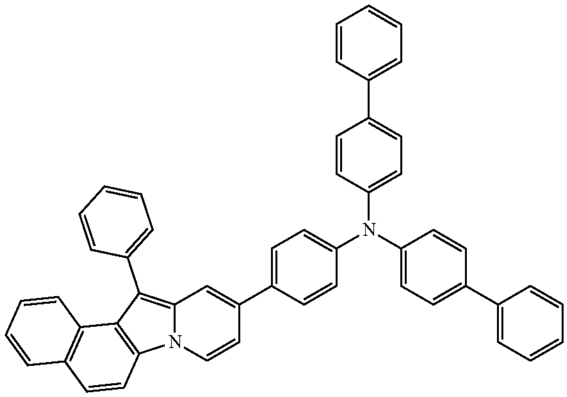
E81
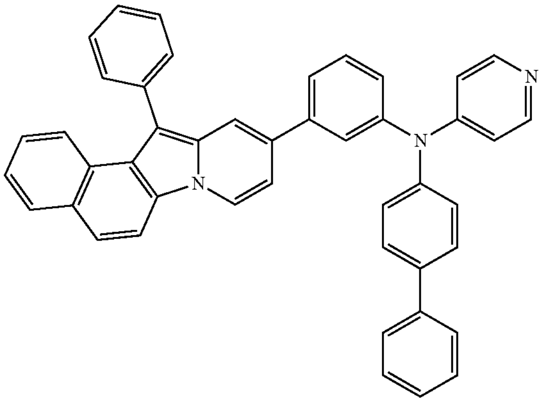
E82
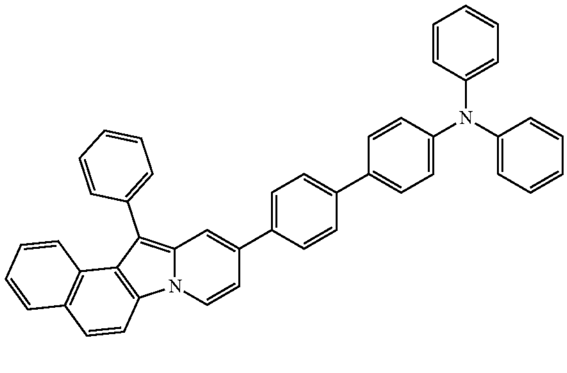

-continued
E83
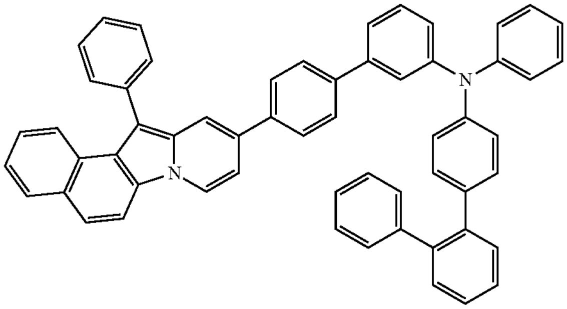
E84
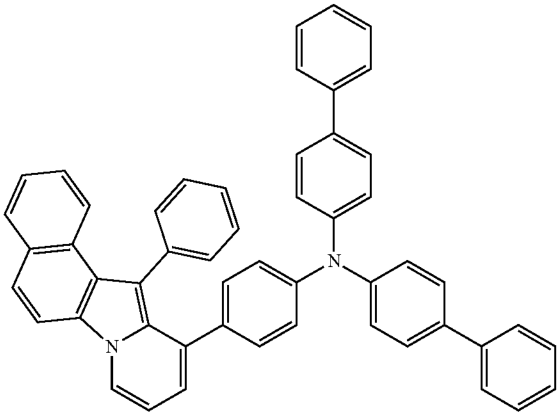
E85
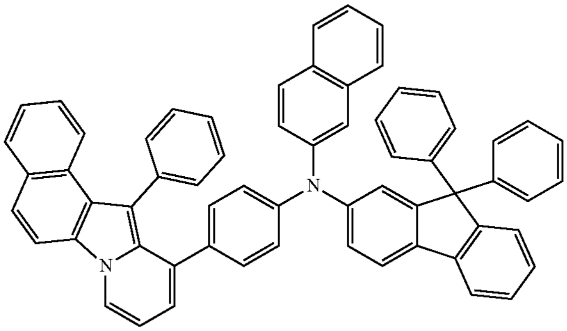
E86
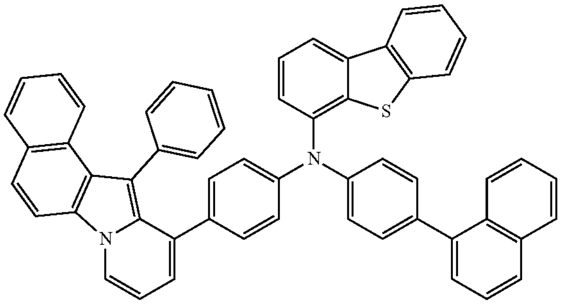
E87
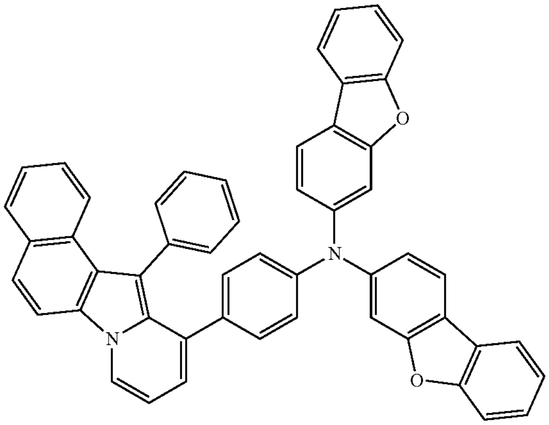
E88
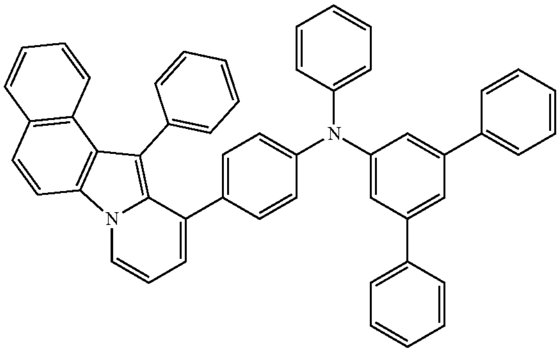
E89
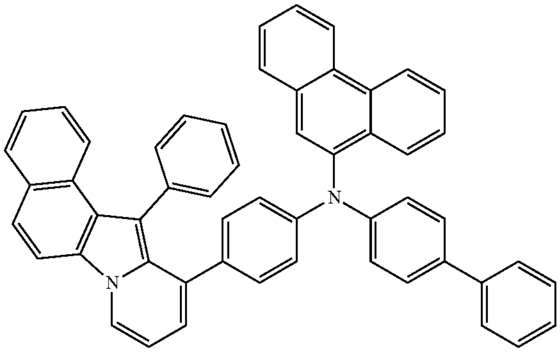
E90
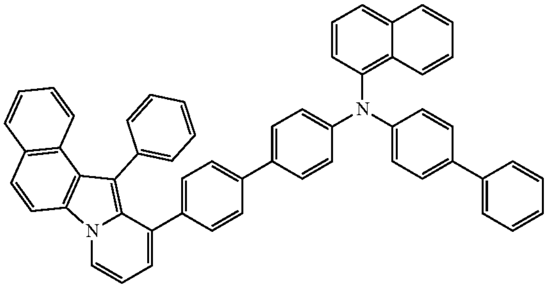

-continued
E91
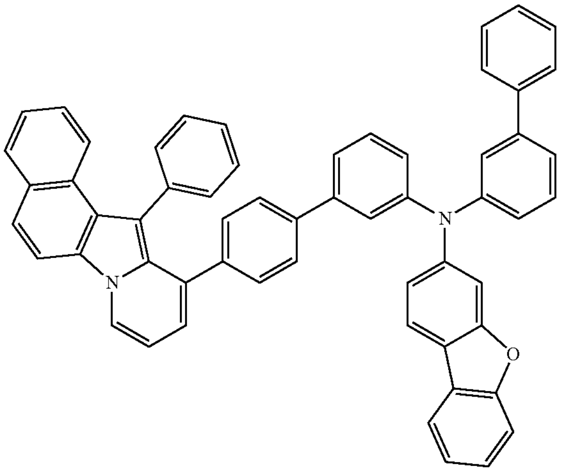
E92
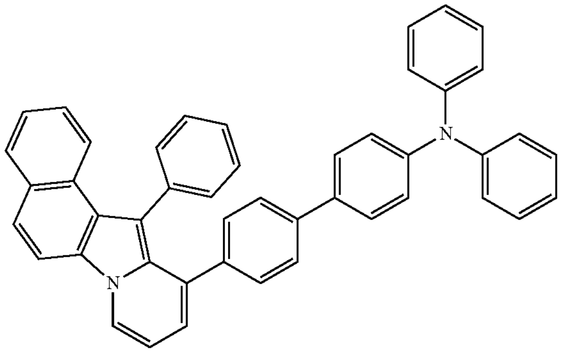
E93
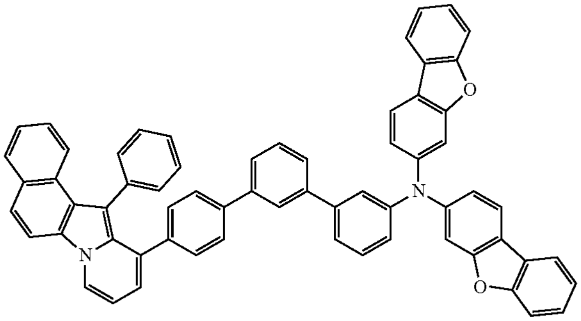
E94
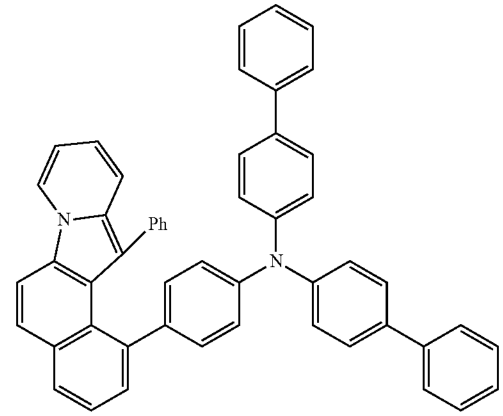
E95
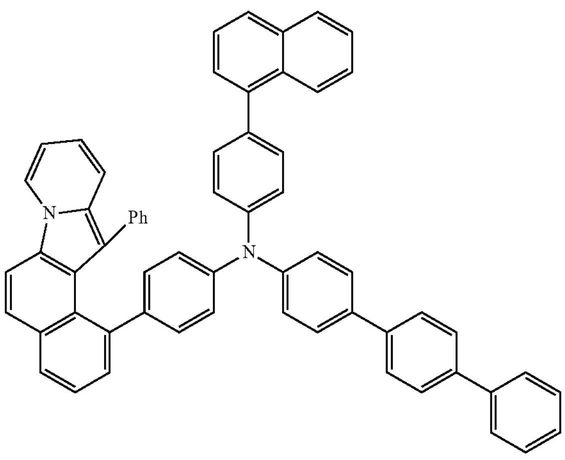
E96
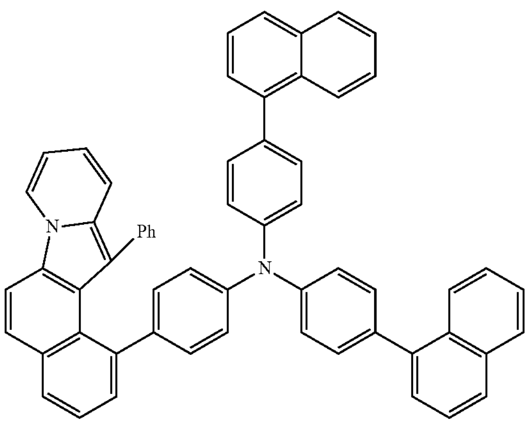

-continued
E97
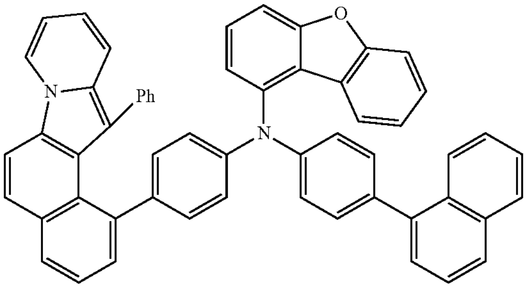
E98
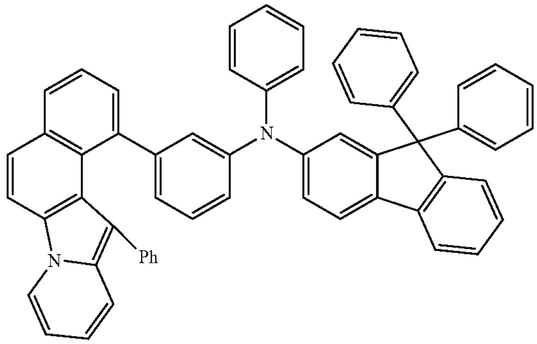
E99
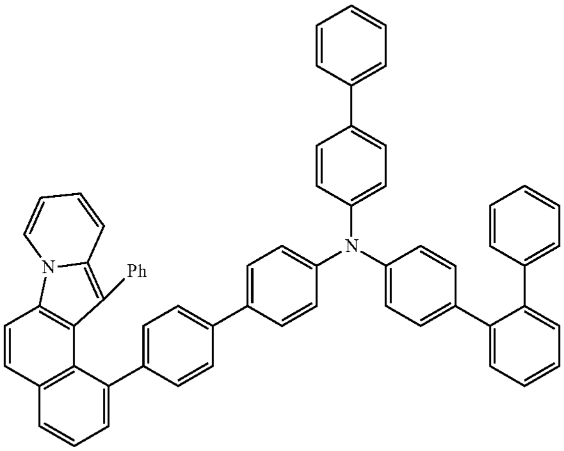
E100
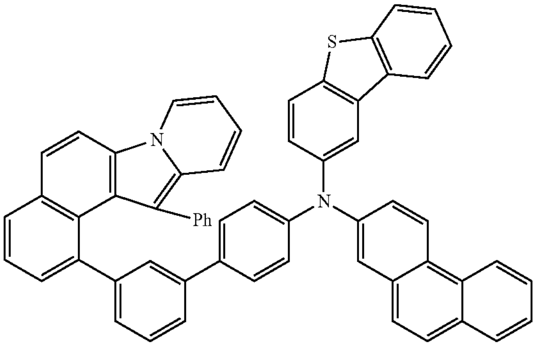
F1
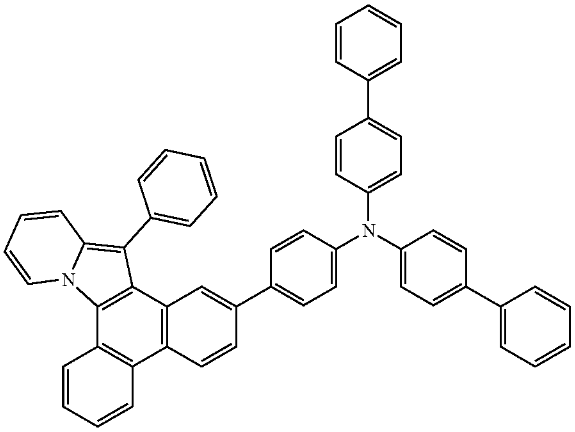
F2
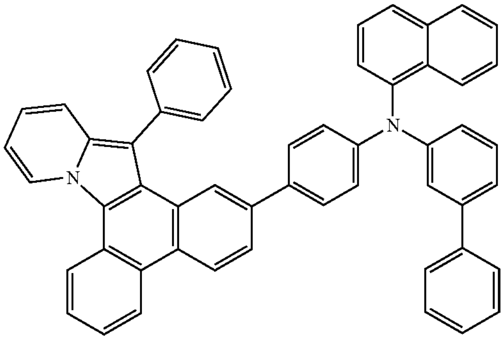

-continued
F3
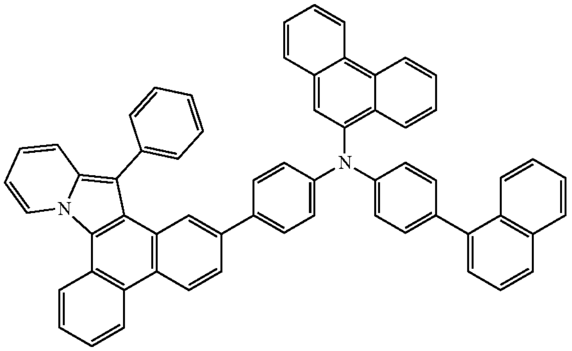
F4
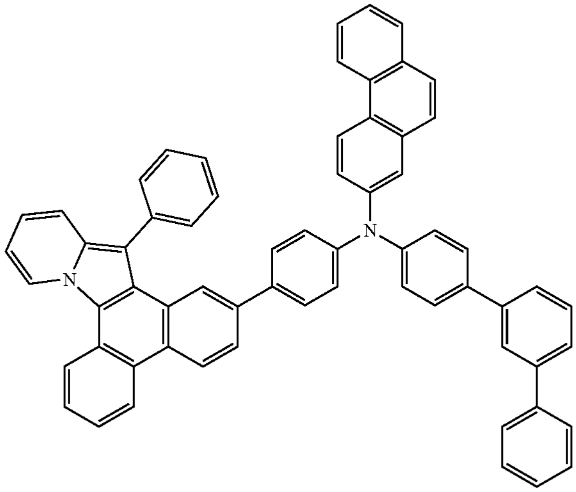
F5
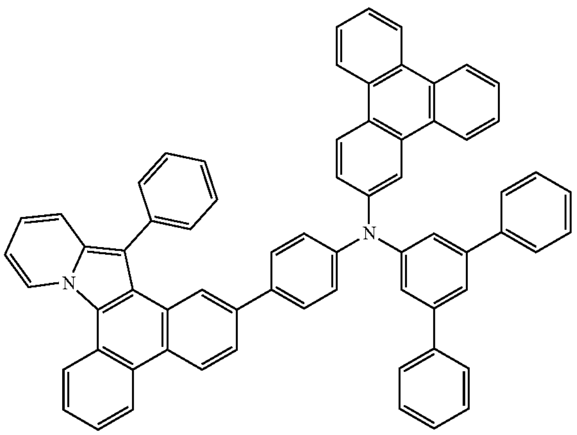
F6
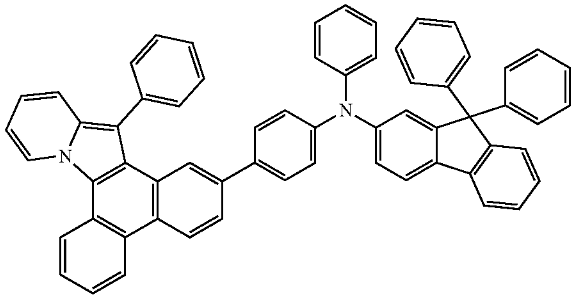
F7
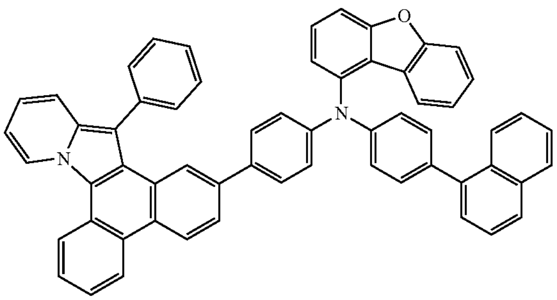
F8
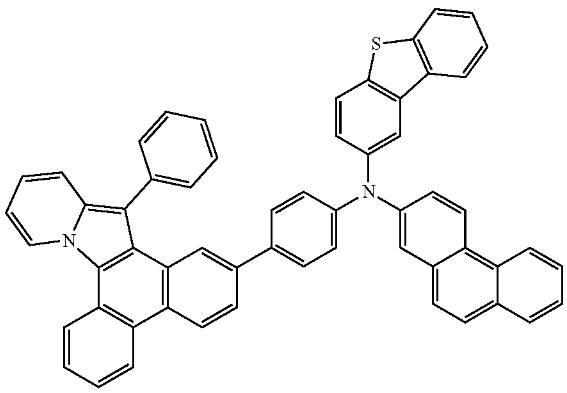

-continued
F9
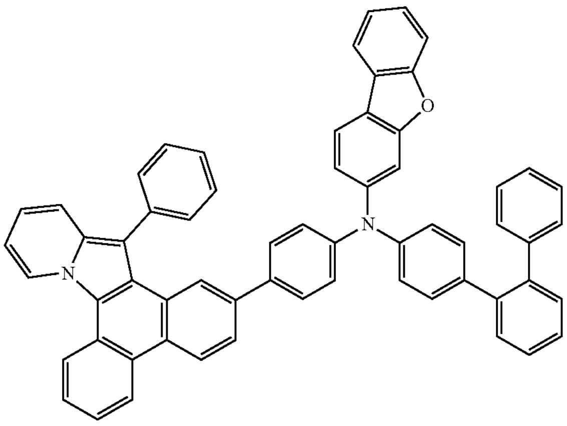
F10
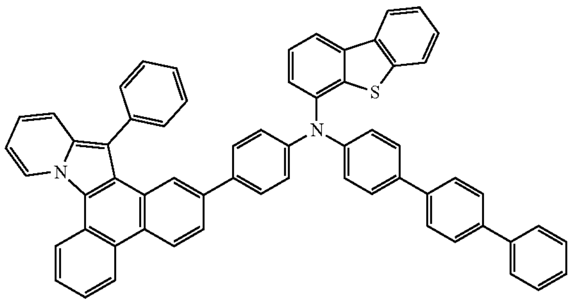
F11
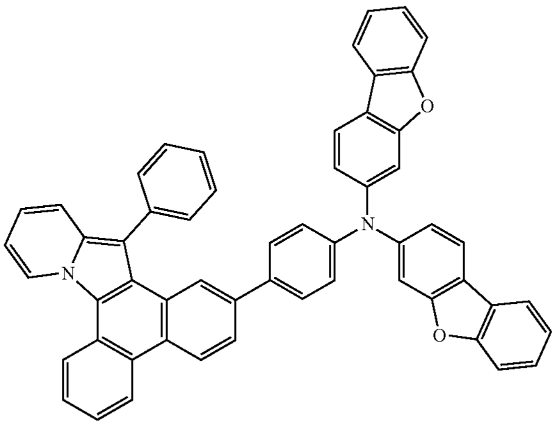
F12
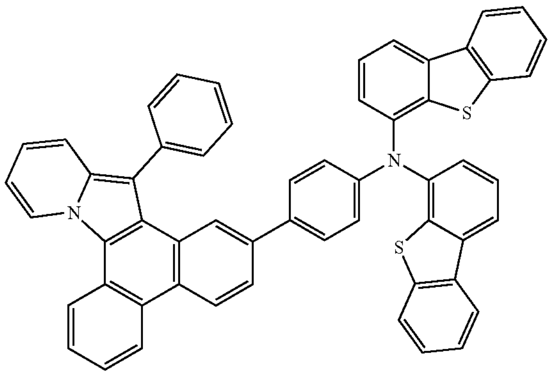
F13
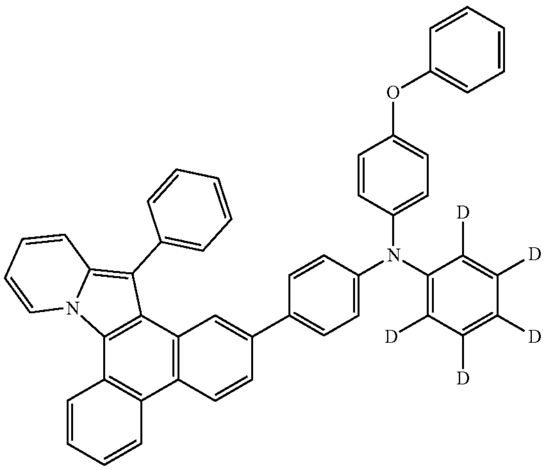
F14
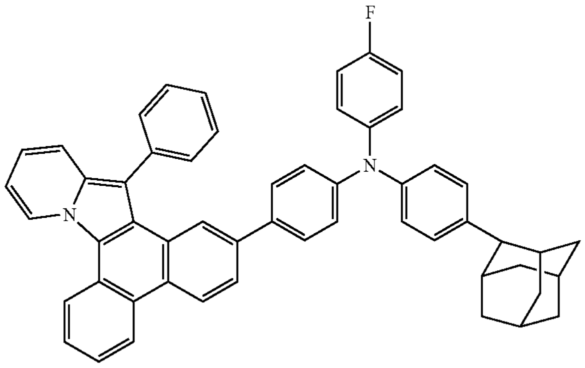

-continued
F15
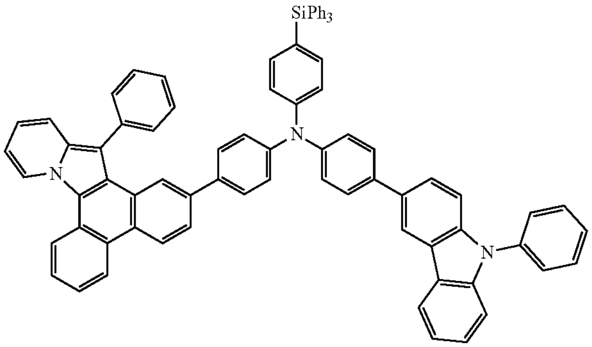
F16
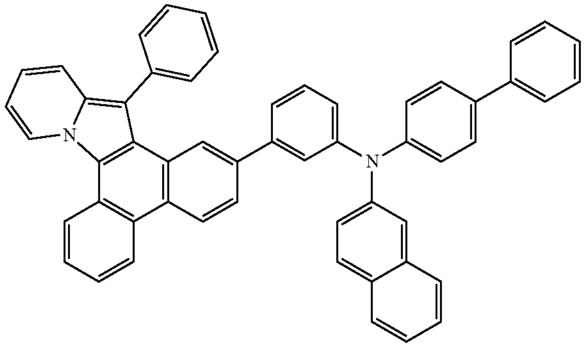
F17
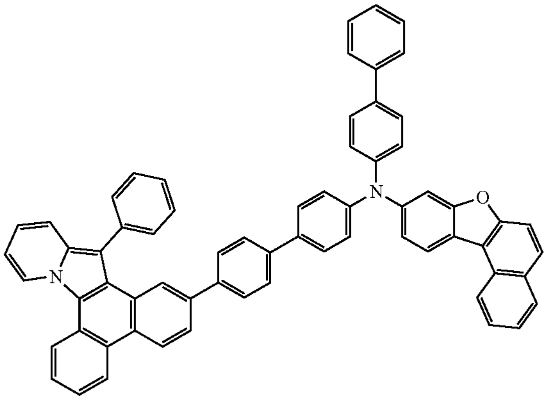
F18
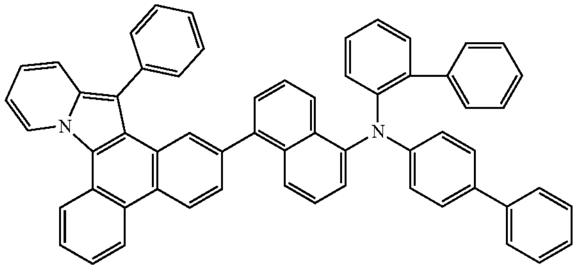
F19
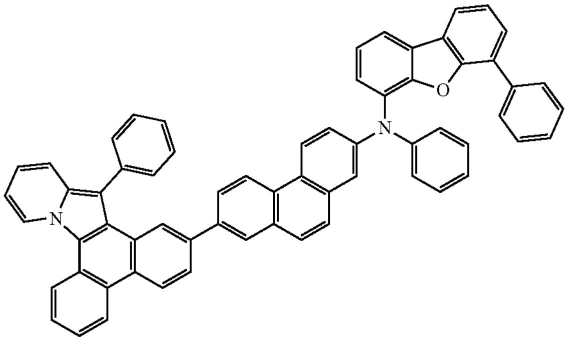
F20
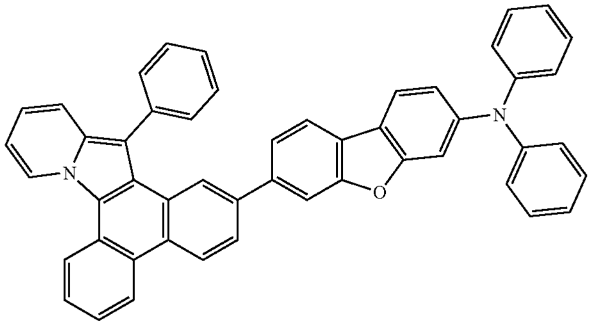
F21
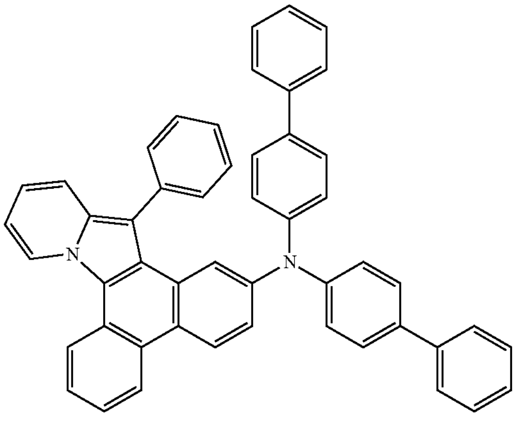
F22
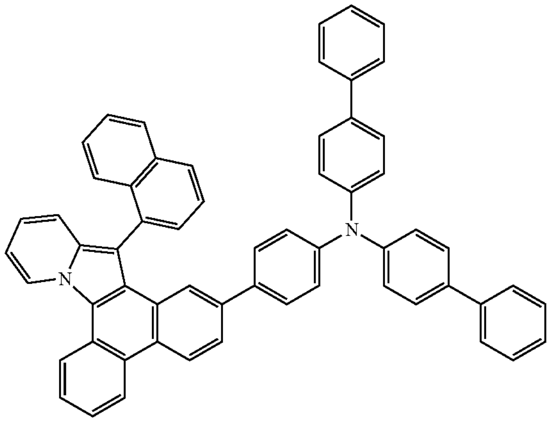

-continued
F23
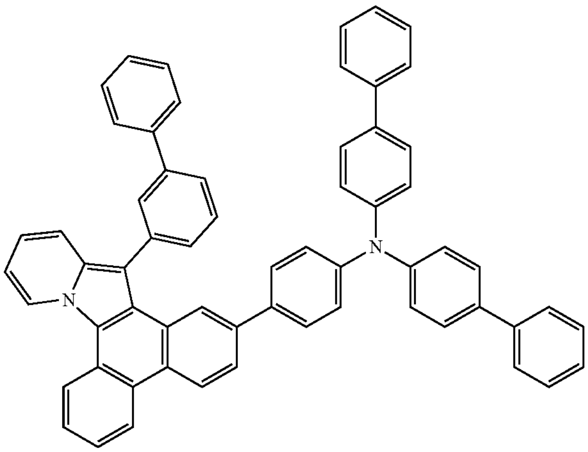
F24
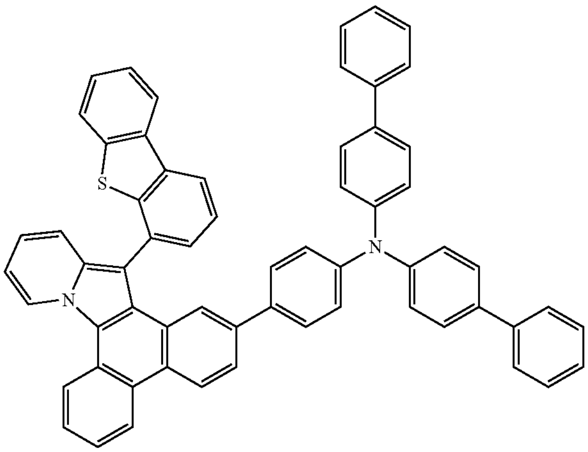
F25
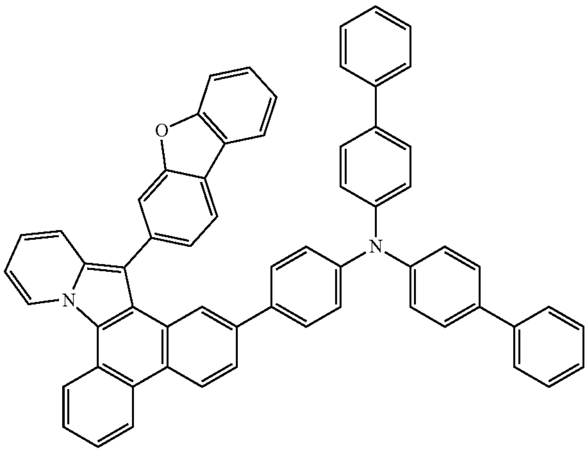
F26
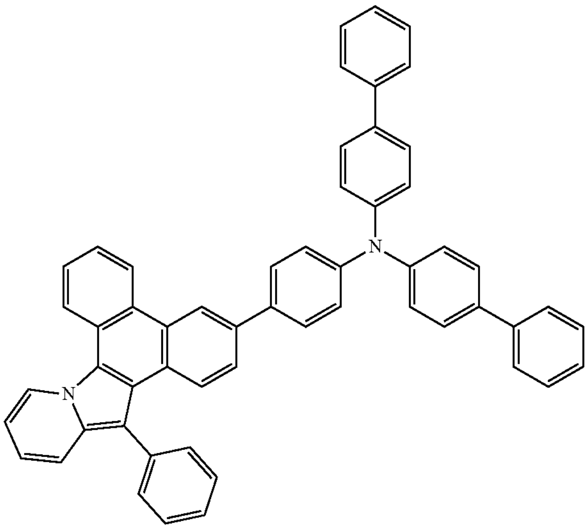
F27
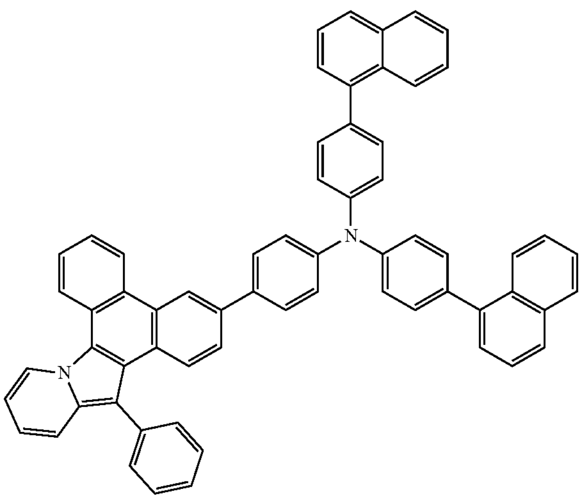
F28
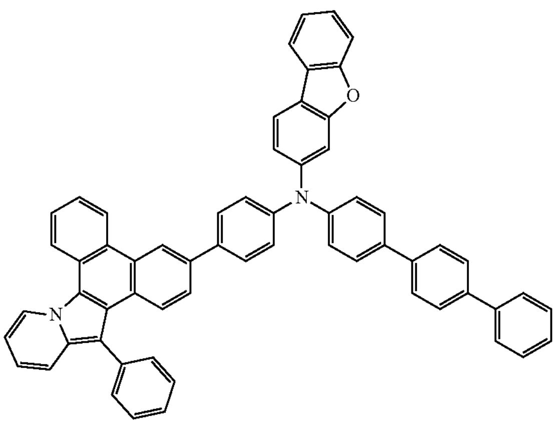

-continued
F29
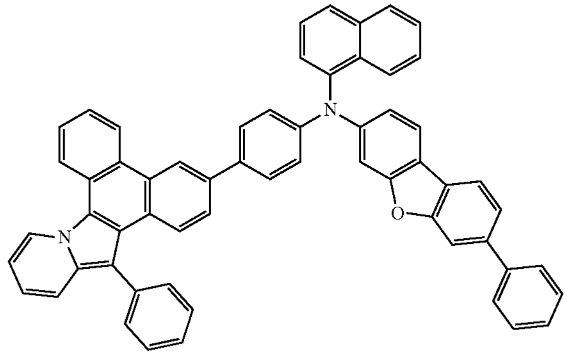
F30
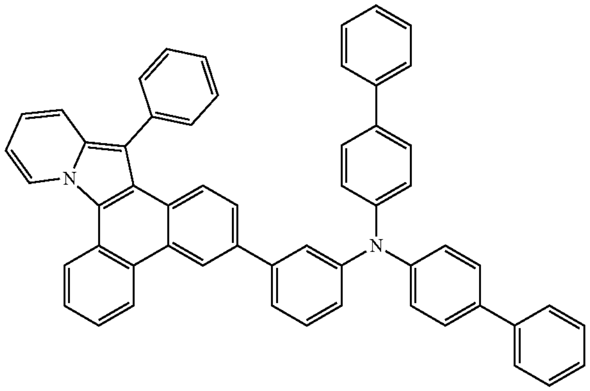
F31
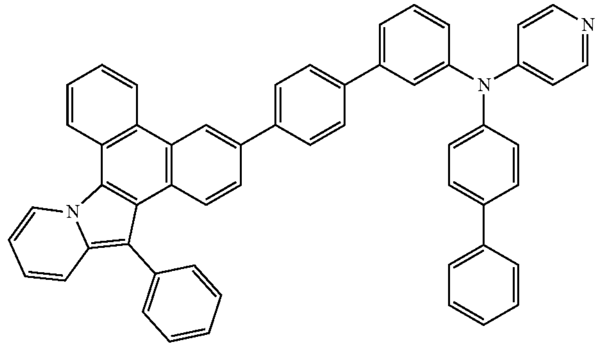
F32
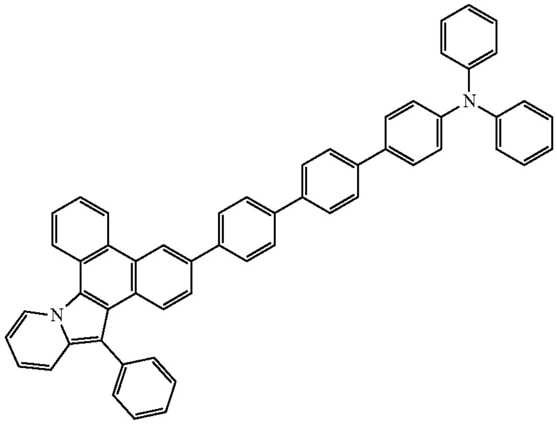
F33
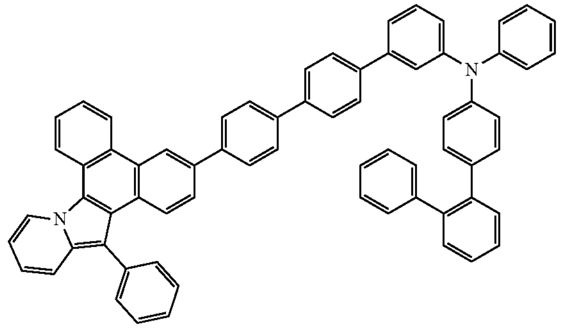
F34
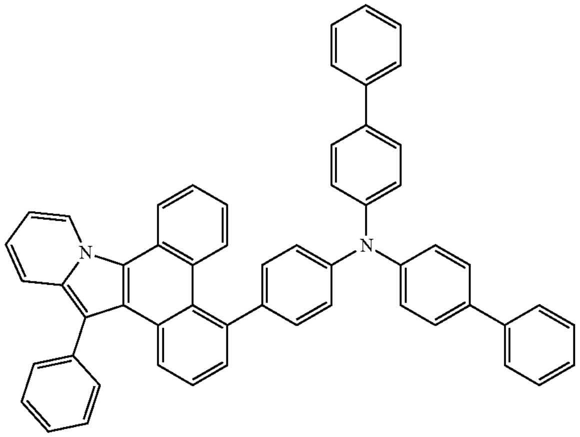

-continued
F35
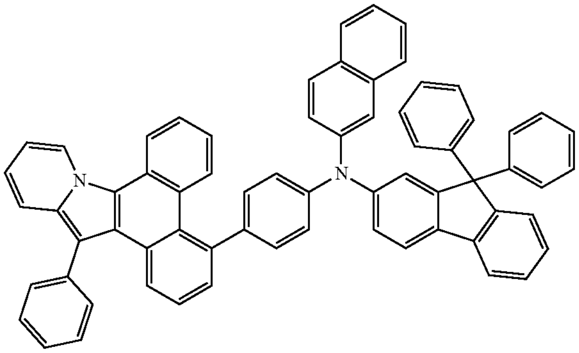
F36
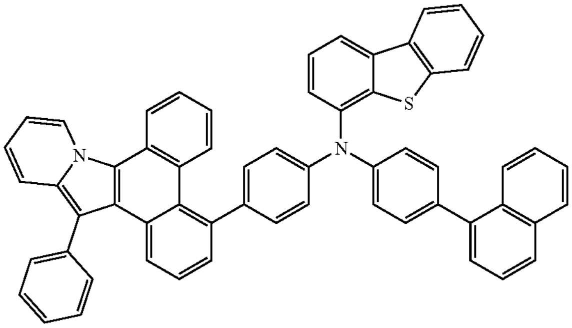
F37
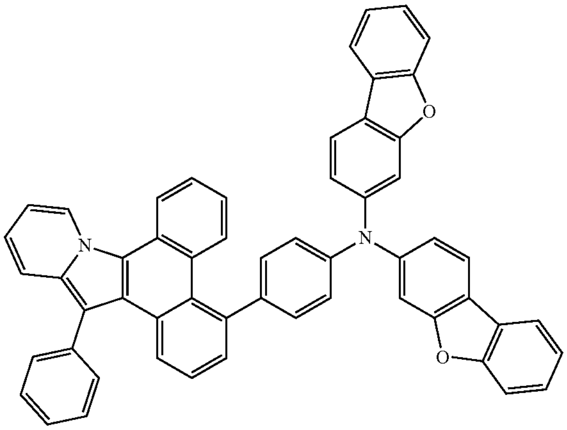
F38
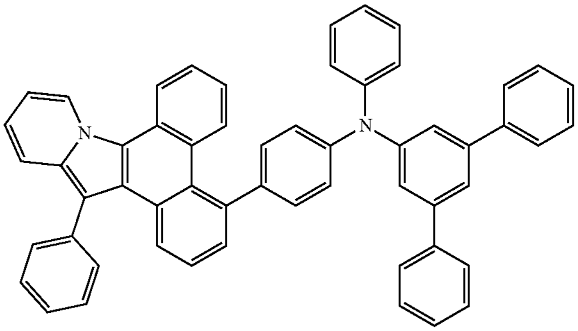
F39
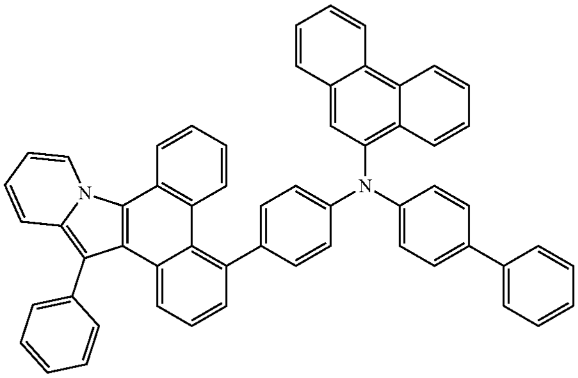
F40
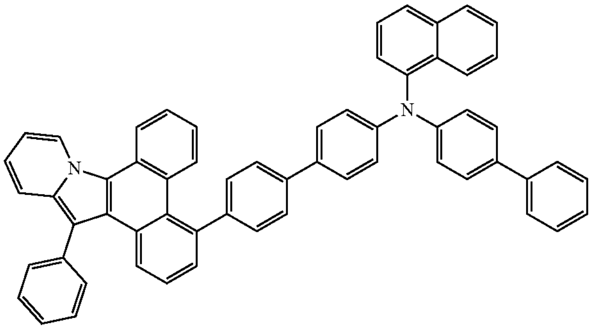

-continued
F41
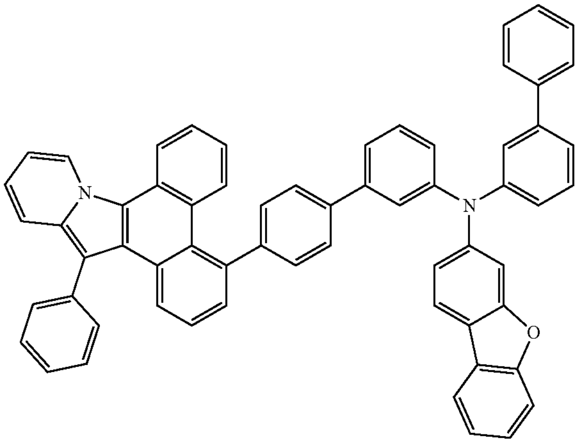
F42
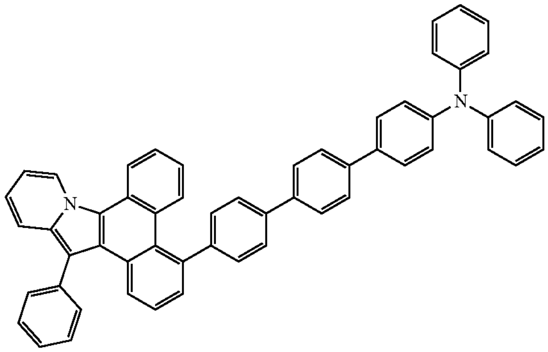
F43
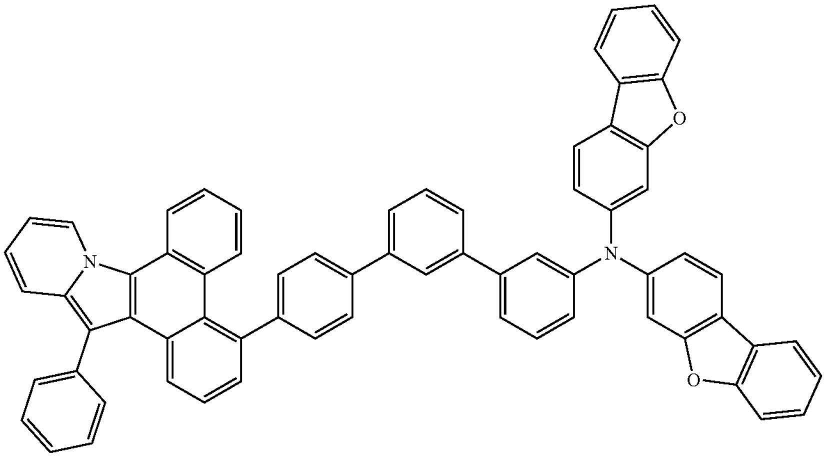
F44
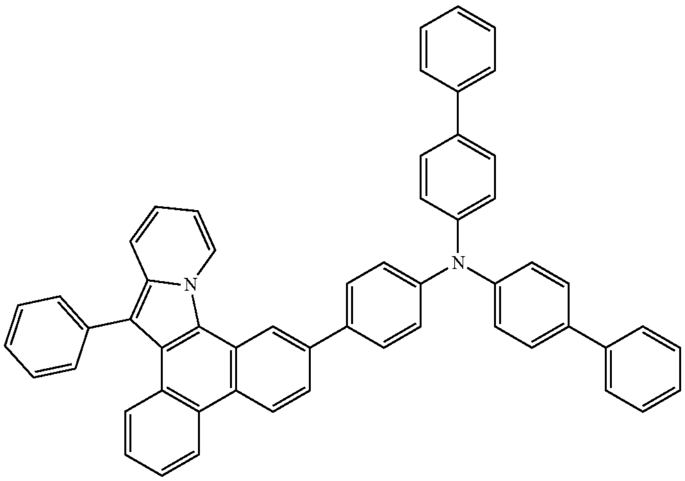

-continued
F45
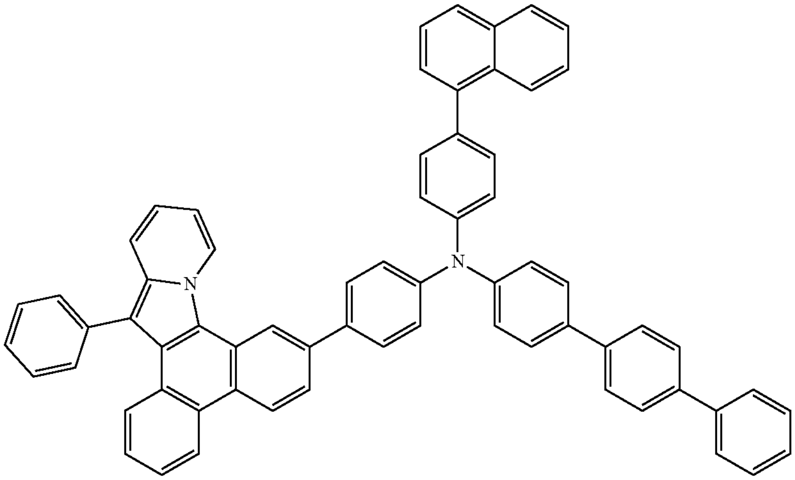
F46
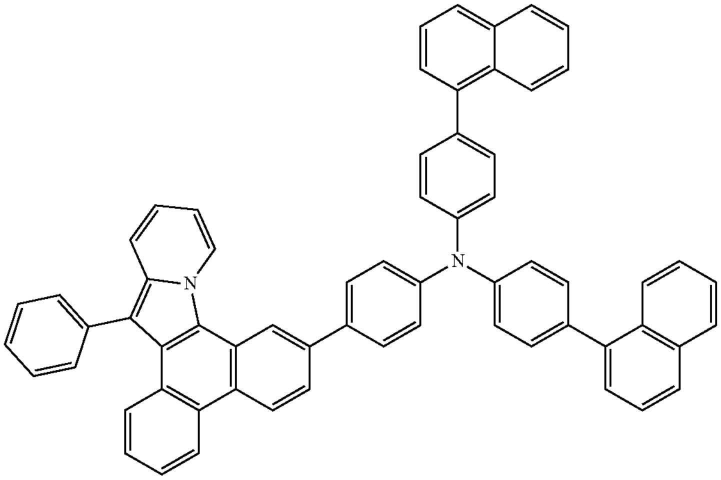
F47
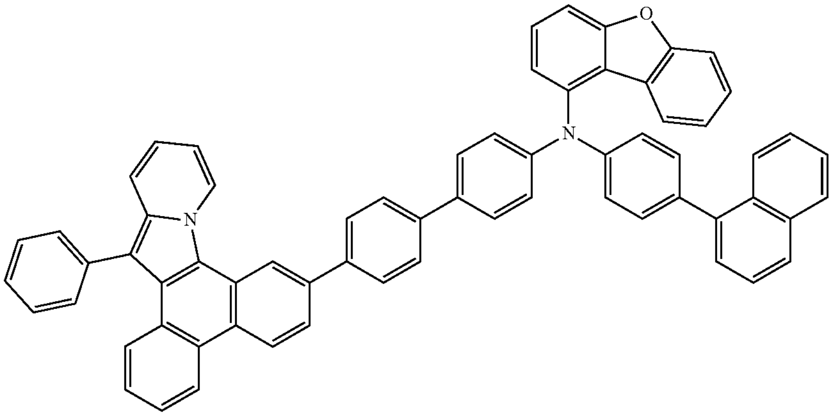

-continued
F48
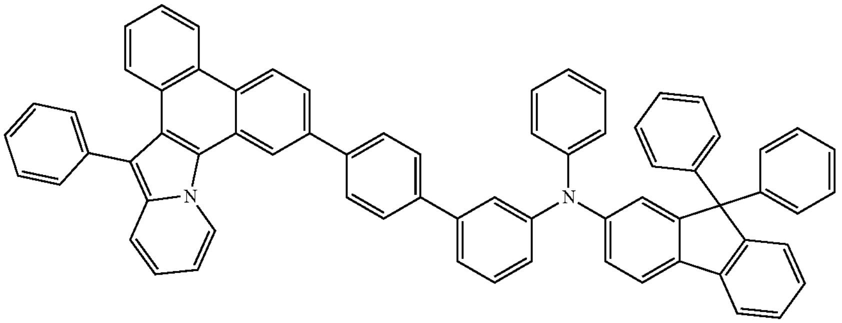
F49
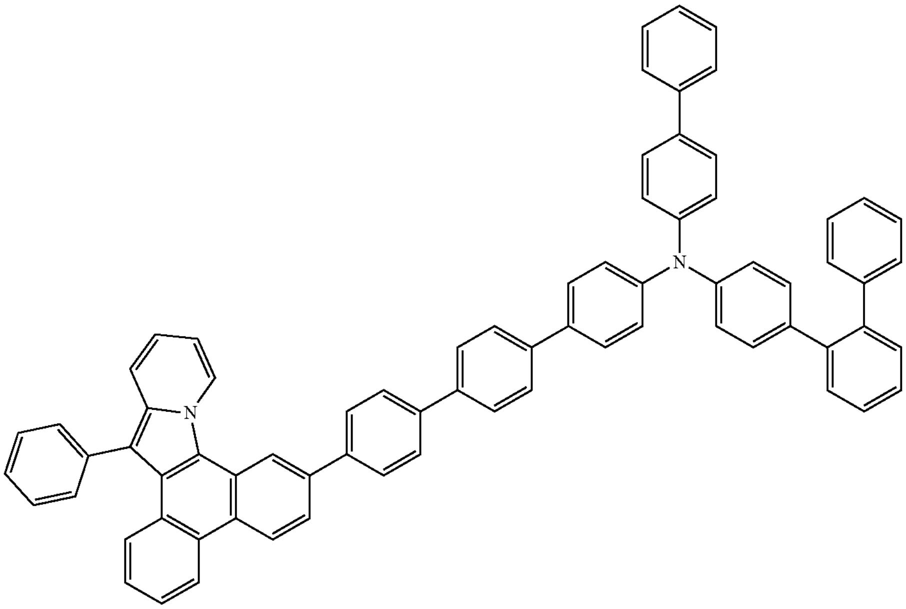
F50
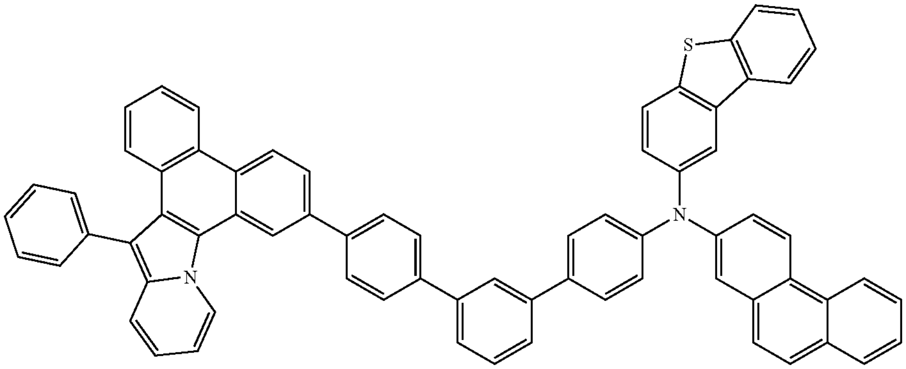

-continued
F51
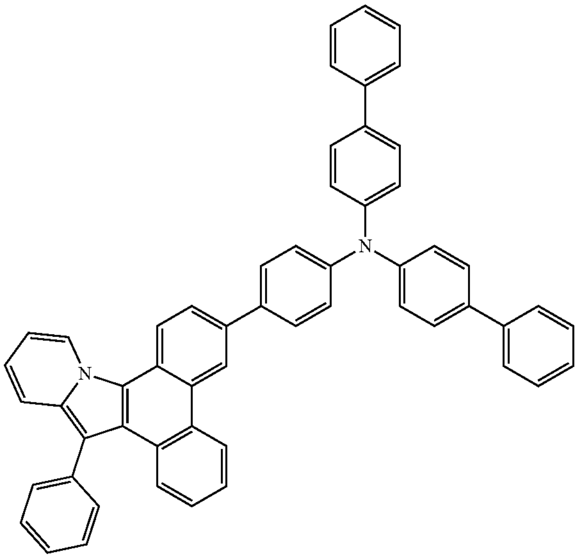
F52
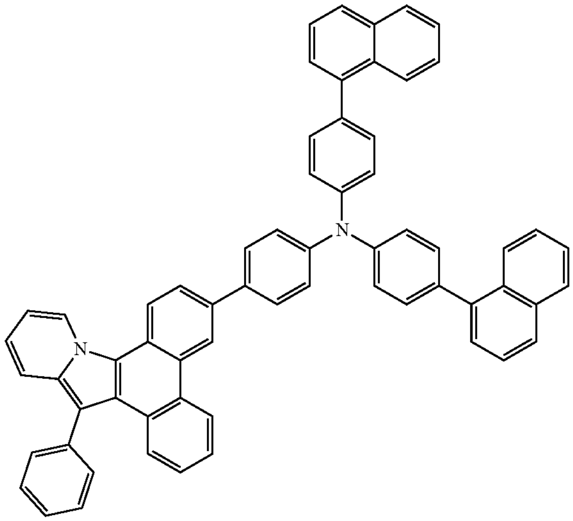
F53
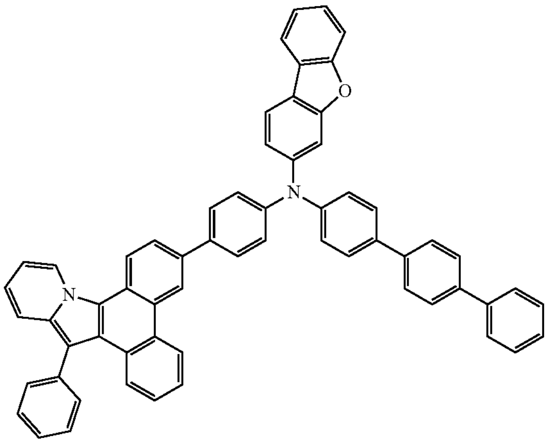
F54
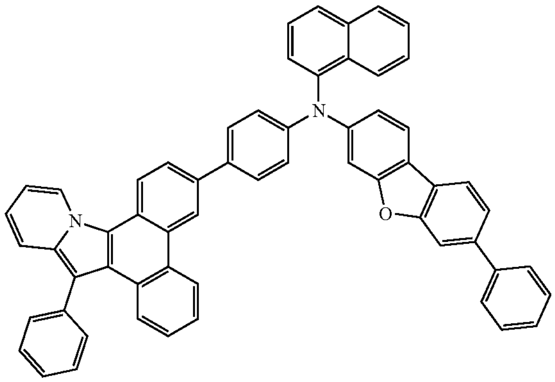
F55
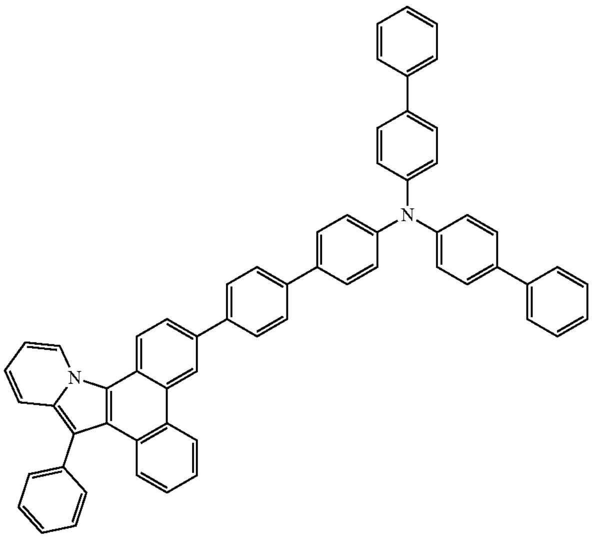
F56
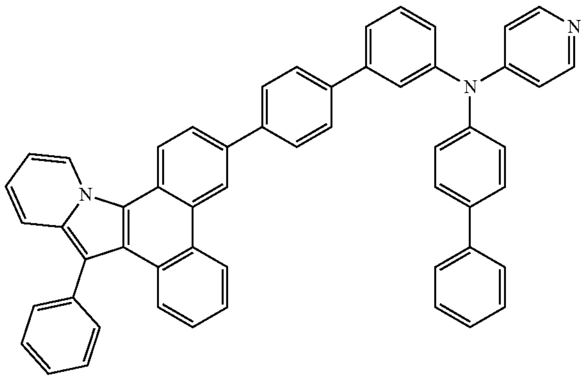

-continued
F57
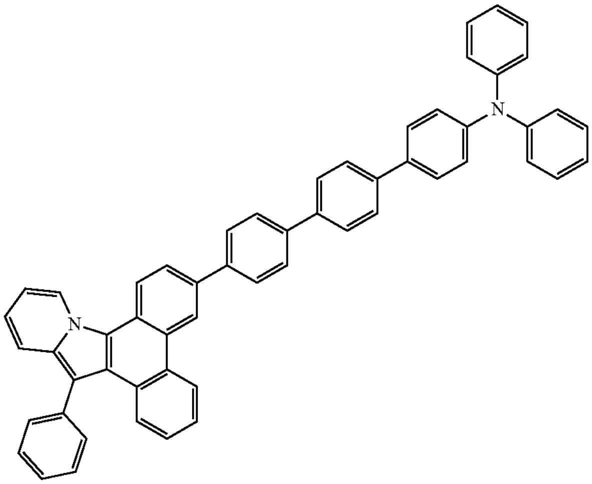
F58
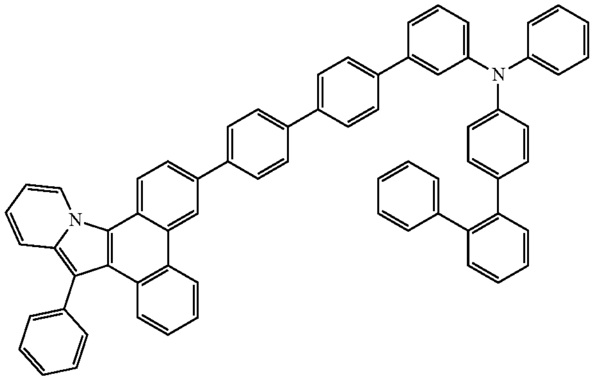
F59
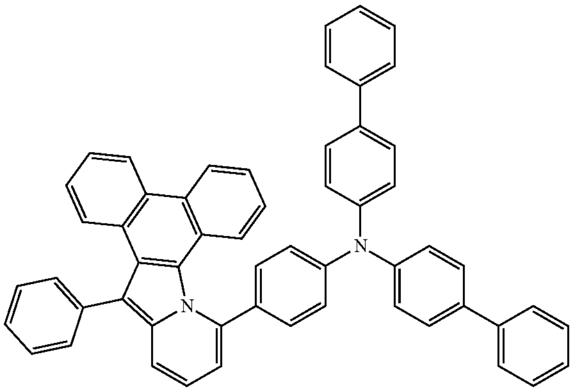
F60
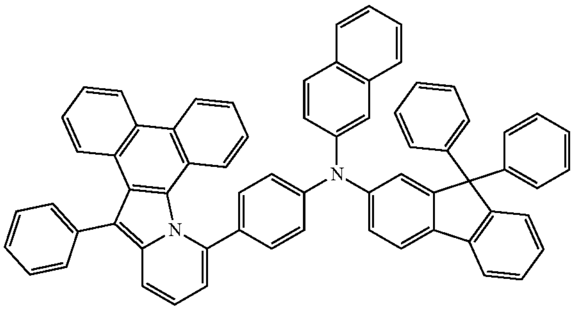
F61
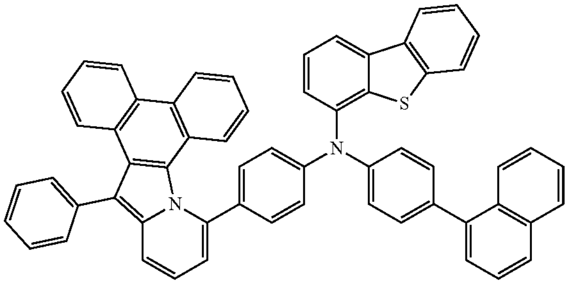
F62
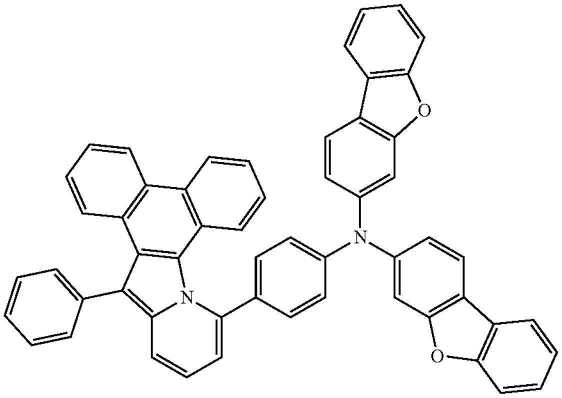

-continued
F63
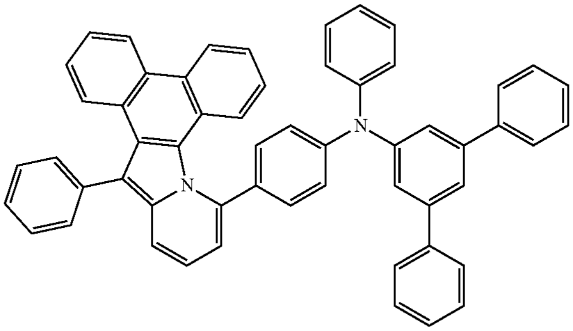
F64
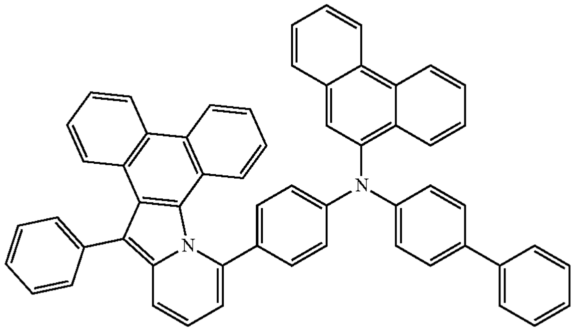
F65
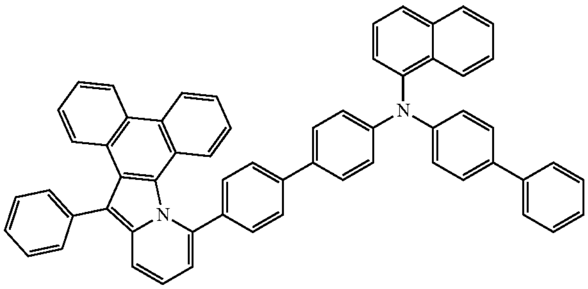
F66
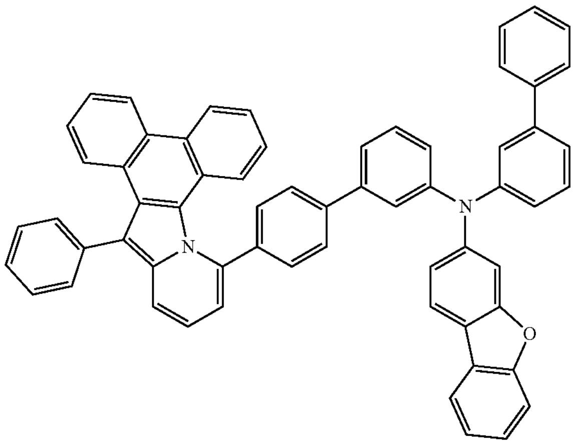
F67
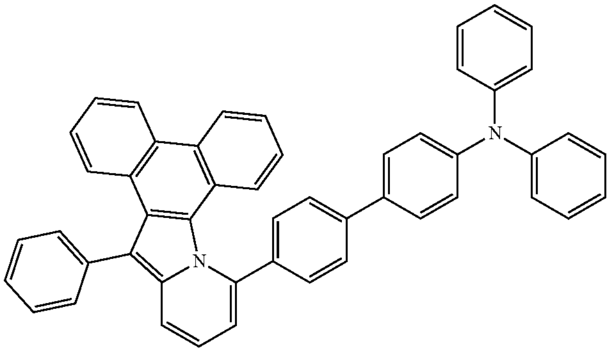
F68
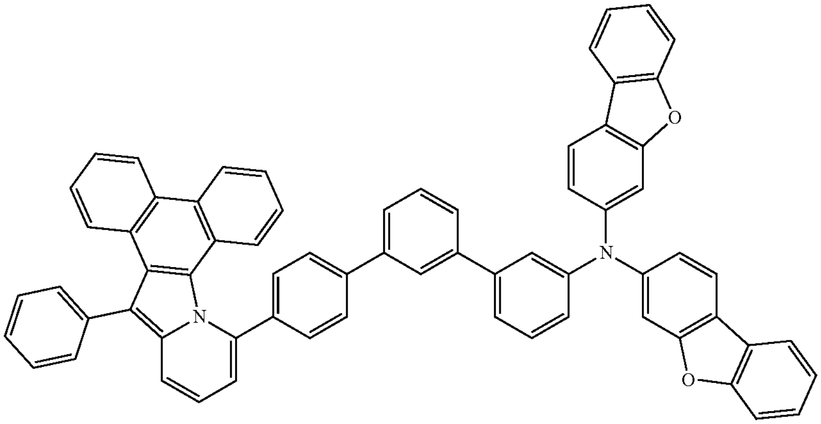

-continued
F69
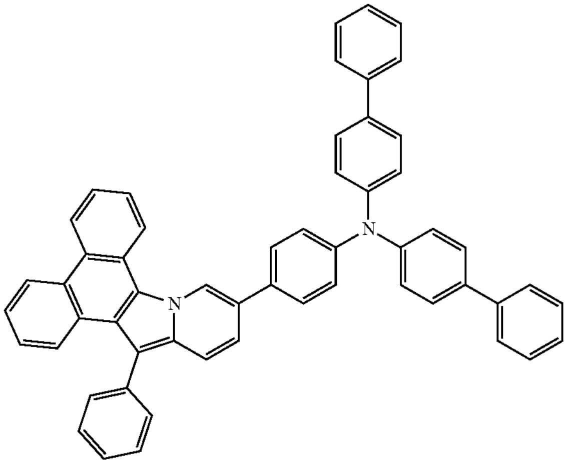
F70
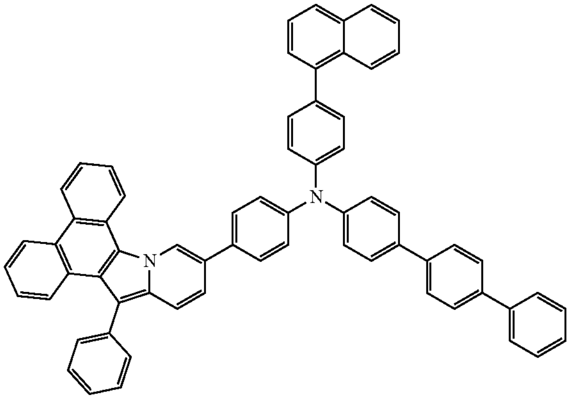
F71
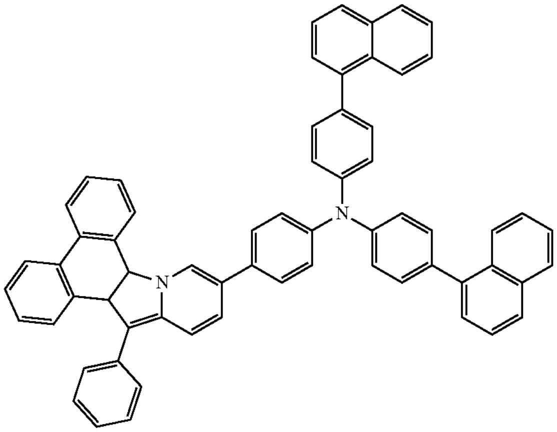
F72
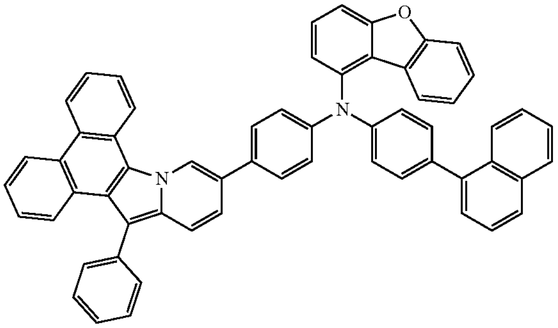
F73
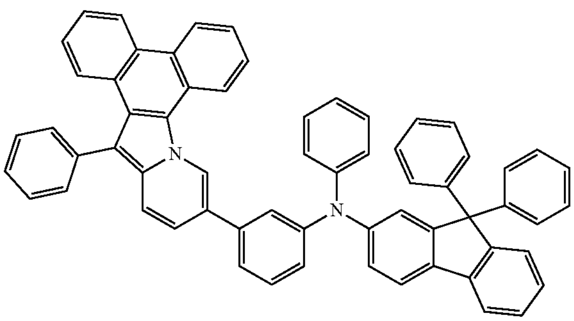
F74
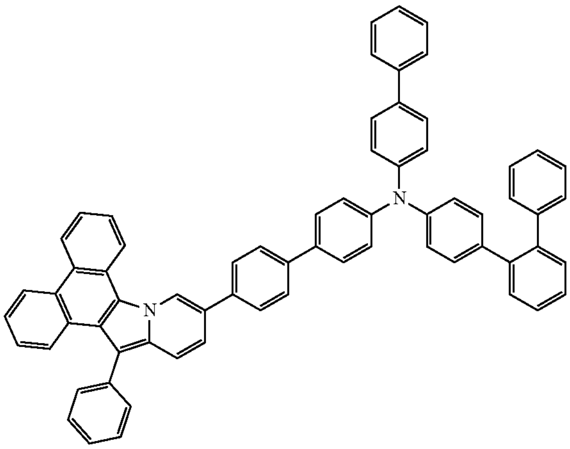

-continued
F75
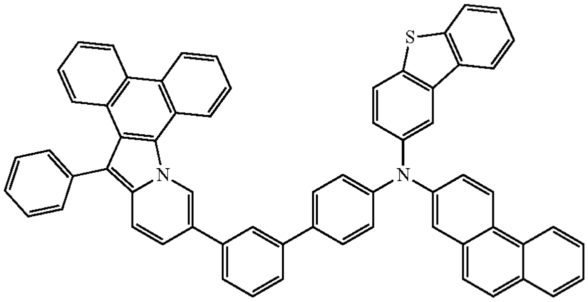
F76
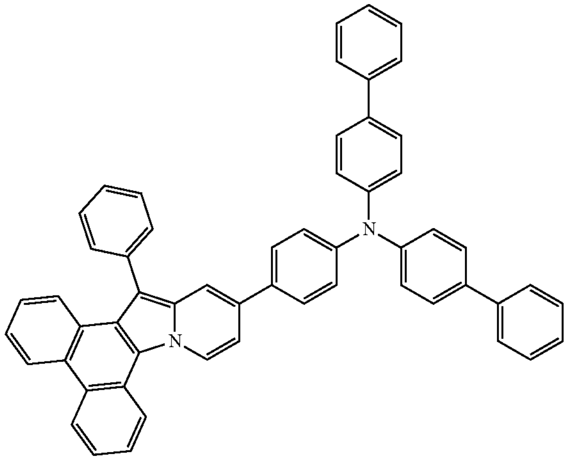
F77
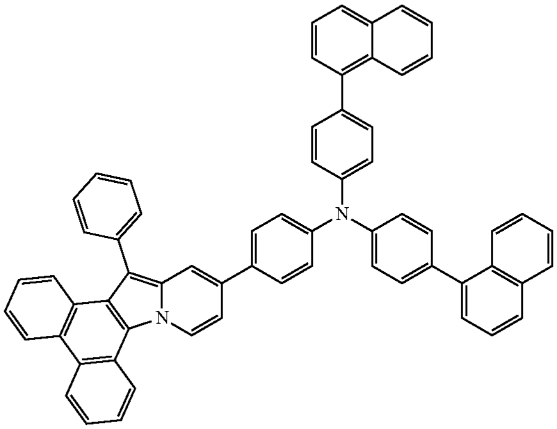
F78
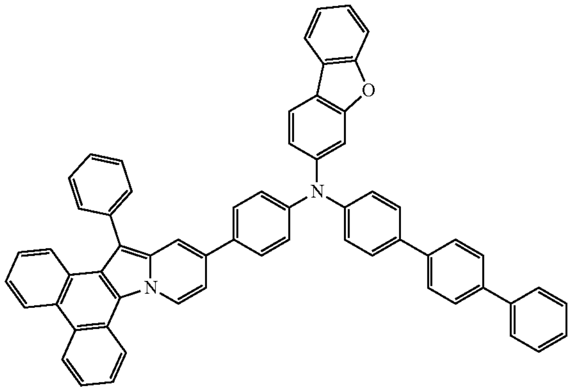
F79
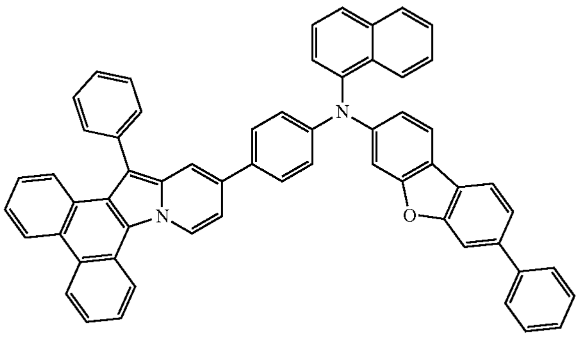
F80
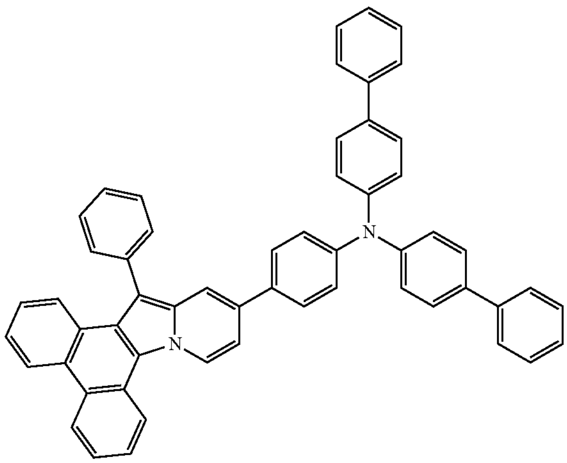

-continued
F81
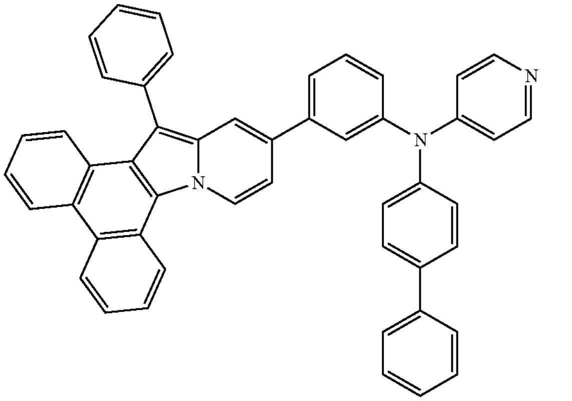
F82
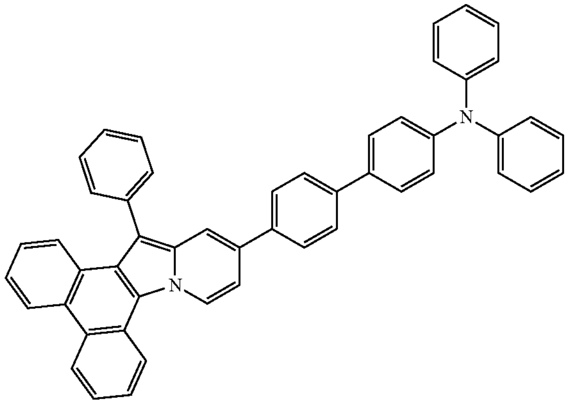
F83
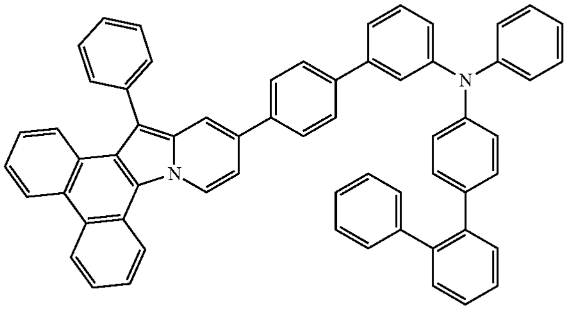
F84
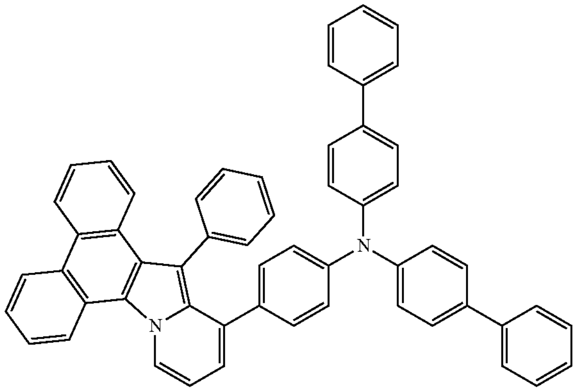
F85
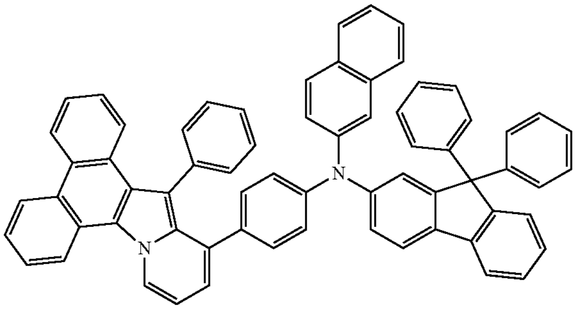
F86
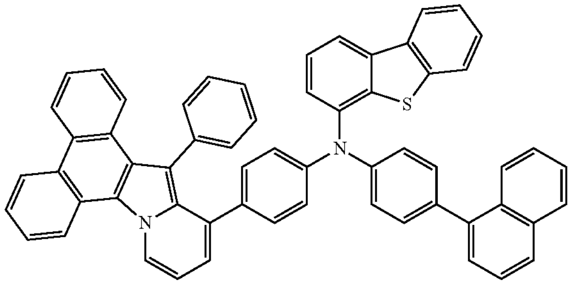
F87
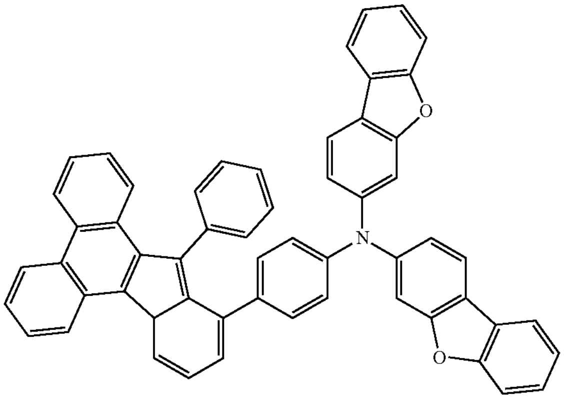
F88
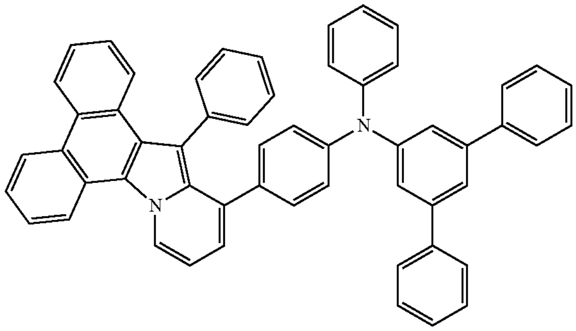

-continued
F89
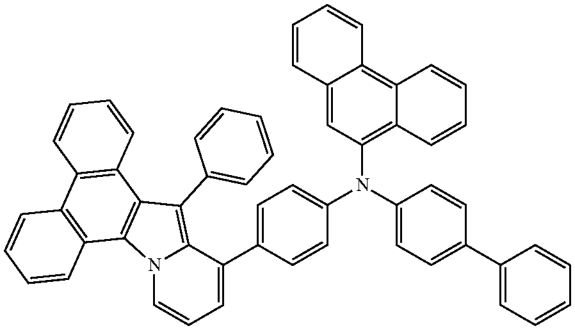
F90
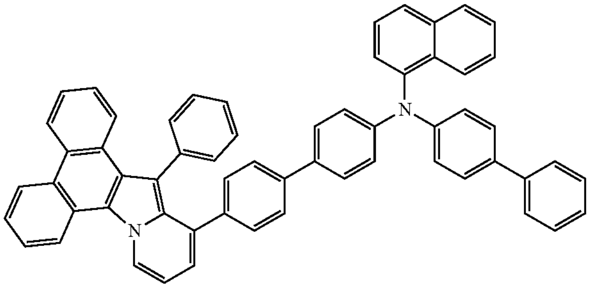
F91
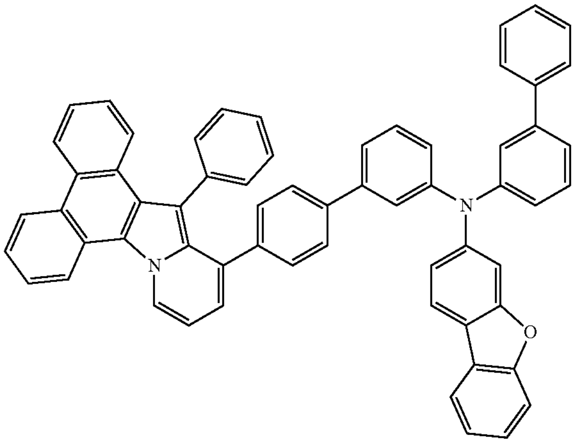
F92
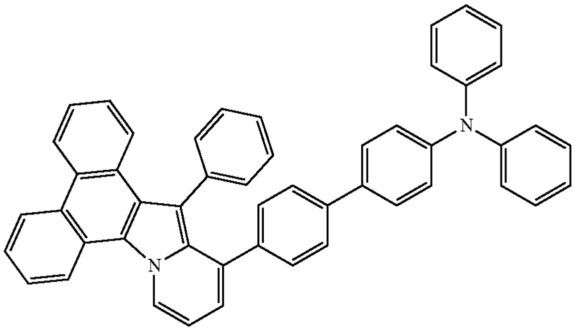
F93
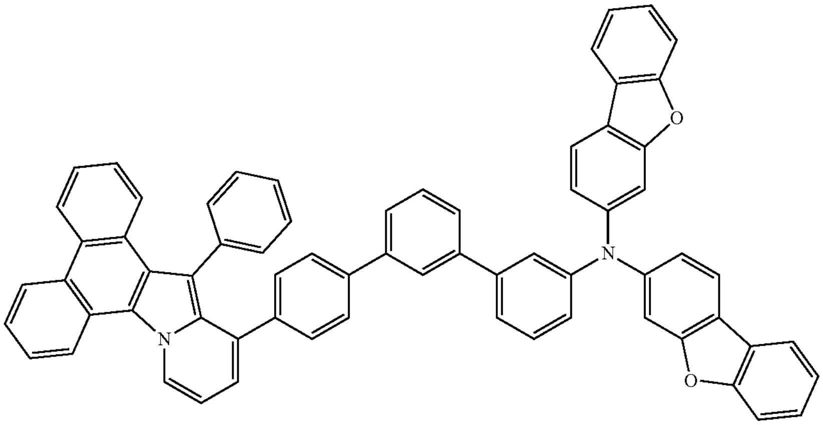

-continued
F94
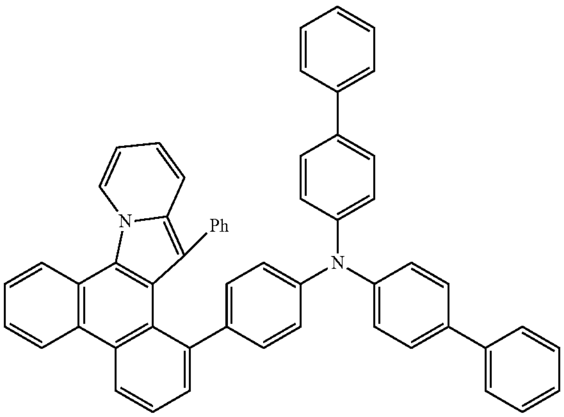
F95
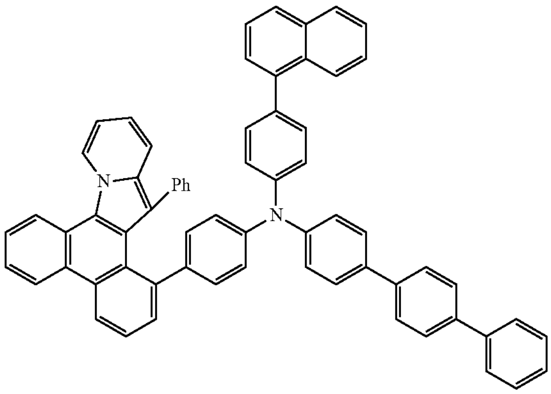
F96
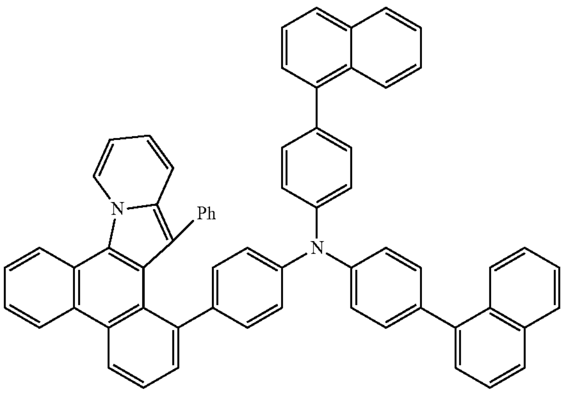
F97
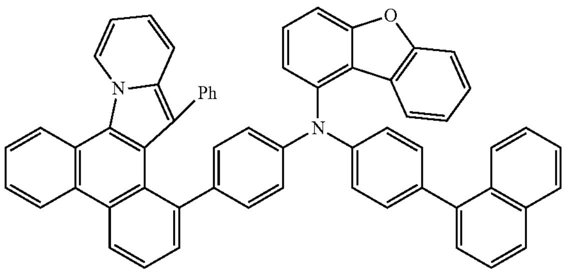
F98
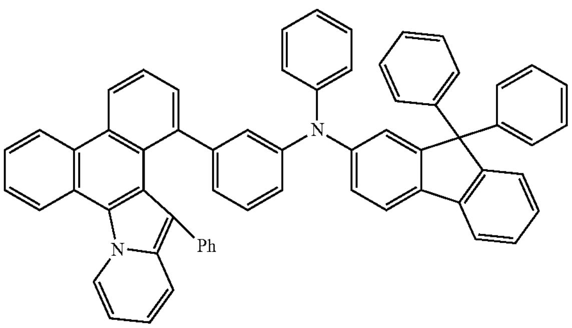
F99
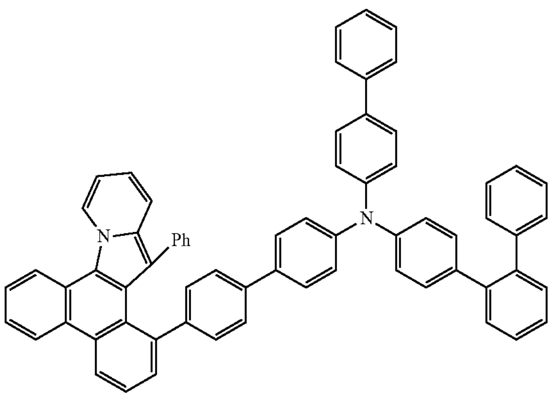

-continued

F100

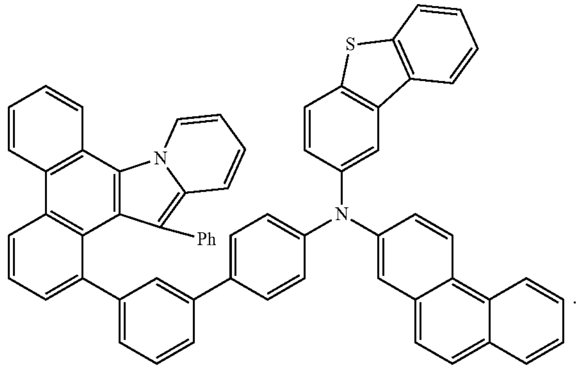

Compound A1 to Compound A97 in Compound Group 1 correspond to structures in which $R_2$ and $R_3$ are combined with each other to form a hexagonal hydrocarbon ring represented by Formula 3. Compound B1 to Compound B97 in Compound Group 1 correspond to structures in which $R_3$ and $R_4$ are combined with each other to form a hexagonal hydrocarbon ring represented by Formula 3. Compound C1 to Compound C97 in Compound Group 1 correspond to structures in which $R_4$ and $R_5$ are combined with each other to form a hexagonal hydrocarbon ring represented by Formula 3. Compound D1 to Compound D100 in Compound Group 1 correspond to structures in which $R_2$ and $R_3$, and $R_4$ and $R_5$ are respectively combined with each other to form hexagonal hydrocarbon rings represented by Formula 3.

Compound E1 to Compound E100 in Compound Group 2 correspond to structures in which $R_8$ and $R_9$ are combined with each other to form a hexagonal hydrocarbon ring represented by Formula 3. Compound F1 to Compound F100 in Compound Group 2 correspond to structures in which $R_6$ and $R_7$, and $R_8$ and $R_9$ are respectively combined with each other to form hexagonal hydrocarbon rings represented by Formula 3.

The amine compound according to an embodiment of the present disclosure includes a condensed ring including a pyridoindole moiety, and may be used as a material for an organic electroluminescence device showing good thermal/charge tolerance and/or excellent emission efficiency. When position $R_8$ in the pyridoindole moiety represented by Formula 2 is not substituted with an arylamine moiety, the compound may have a stable molecular structure. When position $R_1$ in the pyridoindole moiety represented by Formula 2 is not substituted with an arylamine moiety, the efficiency and life characteristics of an organic electroluminescence device including the amine compound may be improved.

Formula 2

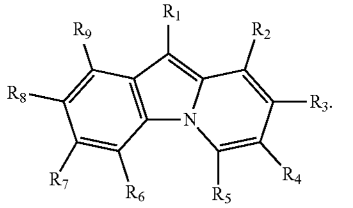

In the organic electroluminescence device 10 according to an embodiment of the present disclosure, as shown in FIG. 1 to FIG. 3, a hole transport region HTR may include one kind (species), or two or more kinds (species) of the amine compounds represented in Compound Group 1 and Compound Group 2. The hole transport region HTR may further include any suitable material available in the art, in addition to the amine compound.

The hole transport region HTR of the organic electroluminescence device 10 according to an embodiment of the present disclosure may include the amine compound according to an embodiment of the present disclosure. When the hole transport region HTR includes a plurality of organic layers, the amine compound according to an embodiment of the present disclosure may be included in an organic layer that is adjacent to the emission layer EML.

For example, the amine compound according to an embodiment of the present disclosure may be included in the hole transport layer HTL of the hole transport region HTR. When the hole transport layer HTL includes a plurality of organic layers, the amine compound according to an embodiment of the present disclosure may be included in an organic layer that is adjacent to the emission layer EML.

For example, when the hole transport region HTR of the organic electroluminescence device 10 according to an embodiment of the present disclosure includes a hole injection layer HIL and a hole transport layer HTL, the amine compound according to an embodiment of the present disclosure may be included in the hole transport layer HTL. When the hole transport region HTR of the organic electroluminescence device according to an embodiment of the present disclosure includes a hole injection layer HIL, a hole transport layer HTL, and an electron blocking layer EBL, the amine compound according to an embodiment of the present disclosure may be included in the electron blocking layer EBL.

In the organic electroluminescence device 10 according to an embodiment of the present disclosure, if the hole transport layer HTL includes the amine compound according to an embodiment of the present disclosure, the hole injection layer HIL may include any suitable hole injection material. For example, the hole injection layer HIL may include triphenylamine-containing polyetherketone (TPAPEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-phenyl-4,4'-diamine (DNTPD), a phthalocyanine compound (such as copper phthalocyanine), 4,4',4"-tris(3-methyl phenyl phenylamino)triphenylamine (m-MTDATA), N,N'-di(1-naphthyl)-N,N'-diphenylbenzidine (NPB), N,N'-bis(1-naphthyl)-N,N'-diphenyl-4,4'-diamine (α-NPD), 4,4',4"-tris(N,N-diphenylamino)

triphenylamine (TDATA), 4,4',4"-tris(N,N-2-naphthyl phenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or dipyrazino[2,3-f: 2',3'-h]quinoxaline-2,3,6,7,10,11-hexacarbonitrile (HAT-CN). However, embodiments of the present disclosure are not limited thereto.

Meanwhile, the hole transport layer HTL of the organic electroluminescence device 10 according to an embodiment of the present disclosure may further include any suitable hole transport material in addition to the amine compound. For example, the hole transport layer HTL may include 1,1-bis[(di-4-tolylamino)phenyl]cyclohexane (TAPC), carbazole derivatives (such as N-phenyl carbazole and/or polyvinyl carbazole), fluorine-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalene)-1-yl)-N,N'-diphenylbenzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc. However, embodiments of the present disclosure are not limited thereto.

As described above, in the organic electroluminescence device 10 according to an embodiment of the present disclosure, the hole transport region HTR may further include at least one selected from a hole butter layer and an electron blocking layer EBL, in addition to the hole injection layer HIL and the hole transport layer HTL. The hole buffer layer may compensate for an optical resonance distance according to the wavelength of light emitted from an emission layer EML (e.g., be used to adjust the optical resonance distance to match the wavelength of light emitted from the EML), and may thereby increase light emission efficiency. Materials that may be included in a hole transport region HTR may be included in a hole buffer layer.

When a hole transport region HTR further includes an electron blocking layer EBL between a hole transport layer HTL and an emission layer EML, the electron blocking layer EBL may play the role of preventing or reducing electron injection from an electron transport region ETR to a hole transport region HTR.

In the organic electroluminescence device 10 according to an embodiment of the present disclosure, when the hole transport region HTR includes an electron blocking layer EBL, the electron blocking layer EBL may include the amine compound according to an embodiment of the present disclosure. The electron blocking layer EBL may include any suitable material available in the art in addition to the amine compound. The electron blocking layer EBL may include, for example, carbazole derivatives (such as N-phenylcarbazole and/or polyvinyl carbazole), fluorine-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), mCP, etc.

For example, in the organic electroluminescence device 10 according to an embodiment of the present disclosure, if the hole transport region HTR is a single layer, the hole transport region HTR may include the amine compound according to an embodiment of the present disclosure. In this case, the hole transport region HTR may further include any suitable hole injection material and/or hole transport material.

In some embodiments, in the organic electroluminescence device 10 according to an embodiment of the present disclosure, when the hole transport region HTR includes a plurality of layers, at least one layer among the plurality of layers included in the hole transport region HTR may include the amine compound according to an embodiment of the present disclosure. For example, the layer adjacent to the emission layer EML among the plurality of layers included in the hole transport region HTR may include the amine compound according to an embodiment of the present disclosure. Meanwhile, the layer(s) not including the amine compound according to an embodiment of the present disclosure may include any suitable hole injection material and/or hole transport material. In some embodiments, the layer including the amine compound according to an embodiment of the present disclosure may further include any suitable hole injection material and/or hole transport material.

The thickness of the hole transport region HTR may be about 100 Å to about 10,000 Å, for example, about 100 Å to about 5,000 Å. The thickness of the hole injection region HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL, and the electron blocking layer EBL satisfy the above-described ranges, satisfactory hole transport properties may be achieved without a substantial increase in driving voltage.

In some embodiments, the hole transport region HTR may further include a charge generating material in addition to the above-described materials to increase conductivity. The charge generating material may be dispersed uniformly (e.g., substantially uniformly) or non-uniformly in the hole transport region HTR. The charge generating material may be, for example, a p-dopant. The p-dopant may be a quinone derivative, metal oxide, or cyano group-containing compound, without limitation. For example, non-limiting examples of the p-dopant include quinone derivatives (such as tetracyanoquinodimethane (TCNQ) and/or 2,3,5,6-tetrafluoro-7,7,8,8-tetracyanoquinodimethane (F4-TCNQ)), and metal oxides (such as tungsten oxide and/or molybdenum oxide), without limitation.

The emission layer EML is on the hole transport region HTR. The thickness of the emission layer EML may be, for example, about 100 Å to about 300 Å. The emission layer EML may have a single layer structure formed using a single material, a single layer structure formed using a plurality of different materials, or a multilayer structure having a plurality of layers formed using a plurality of different materials.

The emission layer EML may be to emit at least one selected from red, green, blue, white, yellow, and cyan light. The emission layer EML may include a fluorescence-emitting material and/or a phosphorescence-emitting material.

In the organic electroluminescence device 10 according to an embodiment of the present disclosure, the emission layer EML may include anthracene derivatives, pyrene derivatives, fluoranthene derivatives, fluoranthene derivatives, chrysene derivatives, dihydrobenzanthracene derivatives, and/or triphenylene derivatives. For example, the emission layer EML may include an anthracene derivative and/or a pyrene derivative.

In some embodiments, the emission layer EML may include an anthracene derivative represented by Formula 4:

Formula 4

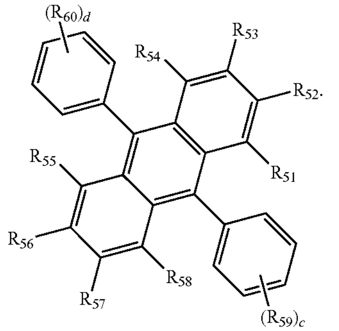

In Formula 4, $R_{51}$ to $R_{60}$ may each independently be a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 carbon atoms for forming a ring, or a substituted or unsubstituted heteroaryl group of 2 to 30 carbon atoms for forming a ring, or may be combined with an adjacent group to form a ring. In some embodiments, $R_{51}$ to $R_{60}$ may be combined with an adjacent group to form a saturated hydrocarbon ring or an unsaturated hydrocarbon ring.

In Formula 4, “c” and “d” may each independently be an integer of 0 to 5.

In some embodiments, the anthracene derivative represented by Formula 4 may be further represented by one of Formula 4-1 to Formula 4-6:

4-1

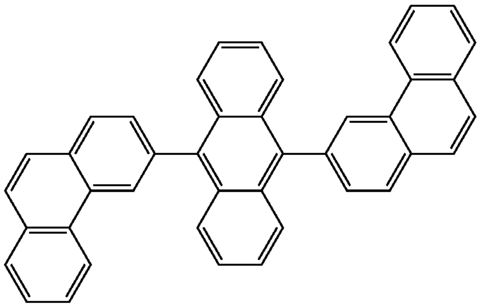

4-2

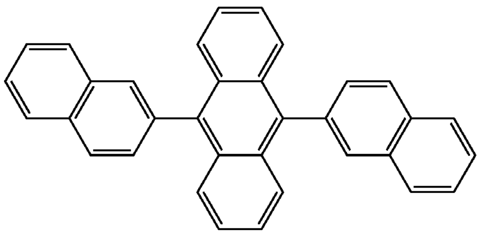

-continued 4-3

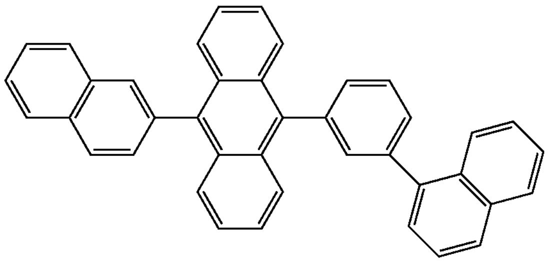

4-4

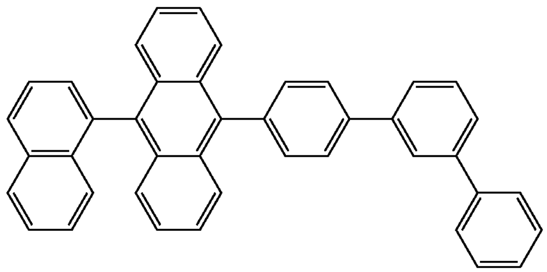

4-5

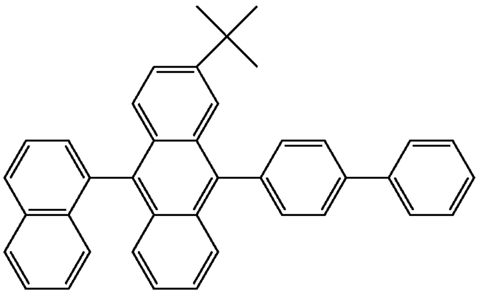

4-6

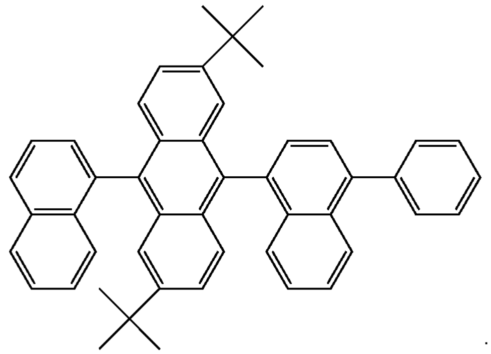

In the organic electroluminescence device 10 according to an embodiment of the present disclosure, as shown in FIG. 1 to FIG. 3, the emission layer EML may include a host and a dopant, and the emission layer EML may include the compound represented by Formula 4 as a host material.

The emission layer EML may further include any suitable material in the art as a host material. For example, at least one selected from bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TcTa), 1,3,5-tris(N-phenylbenzimidazole-2-yl)benzene (TPBi), tris(8-hydroxyquinolinato)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino) phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), and 2,8-bis(diphenylphosphoryl)dibenzofuran (PPF), etc. may be used as the host material. However, embodiments of the present disclosure are not limited thereto.

In some embodiments, the emission layer EML may include any suitable dopant material, for example, styryl derivatives (such as 1,4-bis[2-(3-N-ethylcarbazolyl)vinyl] benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-Avinyl)phenyl)-N-phenylbenzenamine (N-BDAVBi)), perylene and derivatives thereof (such as, 2,5,8,11-tetra-t-butylperylene (TBP)), pyrene and derivatives thereof (such as, 1,1-dipyrene, 1,4-dipyrenylbenzene, and/or 1,4-bis(N,N-diphenylamino)pyrene), etc.

In some embodiments, when the emission layer EML is to emit red light, the emission layer EML may further include a fluorescence material including tris(dibenzoylmethanato) phenanthroline europium (PBD:Eu$(DBM)_3$(Phen)) and/or perylene. If the emission layer EML is to emit red light, the dopant included in the emission layer EML may be selected from, for example, a metal complex or organometallic complex (such as bis(1-phenylisoquinoline)acetylacetonate iridium (PIQIr(acac)), bis(1-phenylquinoline)acetylacetonate iridium (PQIr(acac)), tris(1-phenylquinoline)iridium (PQIr), and octaethylporphyrin platinum (PtOEP)), rubrene and derivatives thereof, and 4-dicyanomethylene-2-(p-dimethylaminostyryl)-6-methyl-4H-pyran (DCM) and derivatives thereof.

In some embodiments, when the emission layer EML is to emit green light, the emission layer EML may further include a fluorescence material including tris(8-hydroxyquinolinato)aluminum (Alq3). If the emission layer EML is to emit green light, the dopant included in the emission layer EML may be selected from, for example, a metal complex or organometallic complex (such as fac-tris(2-phenylpyridine)iridium ($Ir(ppy)_3$)), and coumarin and derivatives thereof.

In some embodiments, when the emission layer EML is to emit blue light, the emission layer EML may further include a fluorescence material including, for example, one selected from the group consisting of spiro-DPVBi, spiro-6P, distyryl-benzene (DSB), distyryl-arylene (DSA), a polyfluorene (PFO)-based polymer, and a poly(p-phenylene vinylene) (PPV)-based polymer. If the emission layer EML is to emit blue light, the dopant included in the emission layer EML may be selected from a metal complex or organometallic complex (such as $(4,6\text{-F2ppy})_2$Irpic), and perylene and derivatives thereof.

In some embodiments, the emission layer EML of the organic electroluminescence device 10 according to an embodiment of the present disclosure may be to emit blue light and/or green light. The emission layer EML may emit blue light at a wavelength of about 450 nm to about 480 nm and/or green light at a wavelength of about 490 nm to about 560 nm.

In the organic electroluminescence device 10 according to an embodiment of the present disclosure, the electron transport region ETR is provided on the emission layer EML. The electron transport region ETR may include at least one selected from a hole blocking layer HBL, an electron transport layer ETL, and an electron injection layer EIL. However, embodiments of the present disclosure are not limited thereto.

The electron transport region ETR may have a single layer formed using a single material, a single layer formed using a plurality of different materials, or a multilayer structure having a plurality of layers formed using a plurality of different materials.

In some embodiments, for example, the electron transport region ETR may have a single layer structure including an electron injection layer EIL or an electron transport layer ETL, or a single layer structure formed using both of an electron injection material and an electron transport material. In some embodiments, the electron transport region ETR may have a single layer structure composed of a plurality of different materials, or a multi-layer structure laminated on the emission layer EML of electron transport layer ETL/electron injection layer EIL, or hole blocking layer HBL/electron transport layer ETL/electron injection layer EIL, without limitation. The thickness of the electron transport region ETR may be, for example, about 100 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

In some embodiments, when the electron transport region ETR includes an electron transport layer ETL, the electron transport region ETR may include, for example, tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinato-N1,O8)-(1,1'-biphenyl-4-olato) aluminum (BAlq), beryllium bis(benzoquinolin-10-olate (Bebq2), 9,10-di(naphthalene-2-yl)anthracene (ADN), or a mixture thereof, without limitation.

In some embodiments, when the electron transport region ETR includes the electron transport layer ETL, the thickness of the electron transport layer ETL may be about 100 Å to about 1,000 Å, for example, about 150 Å to about 500 Å. When the thickness of the electron transport layer ETL satisfies the above-described range, satisfactory electron transport properties may be obtained without a substantial increase in driving voltage.

In some embodiments, when the electron transport region ETR includes the electron injection layer EIL, the electron transport region ETR may include, for example, LiF, 8-hydroxyquinolinato-lithium (LiQ), $Li_2O$, BaO, NaCl, CsF, a lanthanide metal (such as Yb), and/or a metal halide (such as RbCl, RbI, and/or KI). However, embodiments of the present disclosure are not limited thereto. The electron injection layer EIL may be formed using a mixture of an electron transport material and an insulating organo metal salt. The organo metal salt may have an energy band gap of about 4 eV or more. The organo metal salt may include, for example, metal acetates, metal benzoates, metal acetoacetates, metal acetylacetonates, and/or metal stearates.

In some embodiments, when the electron transport region ETR includes the electron injection layer EIL, the thickness of the electron injection layer EIL may be about 1 Å to about 100 Å, or about 3 Å to about 90 Å. When the thickness of the electron injection layer EIL satisfies the above described range, suitable electron injection properties may be obtained without inducing a substantial increase in driving voltage.

The electron transport region ETR may include a hole blocking layer HBL as described above. The hole blocking layer HBL may include, for example, at least one selected from 2,9-dimethyl-4,7-diphenyl-1,10-phenanthroline (BCP) and 4,7-diphenyl-1,10-phenanthroline (Bphen). However, embodiments of the present disclosure are not limited thereto.

The second electrode EL2 is on the electron transport region ETR. The second electrode EL2 may be conductive. The second electrode EL2 may be formed using a metal alloy and/or a conductive compound. The second electrode EL2 may be a cathode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials, and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In the organic electroluminescence device 10, upon application of a voltage across the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes may recombine in the emission layer EML to produce excitons, and the excitons may emit light upon transition from an excited state to the ground state.

In some embodiments, when the organic electroluminescence device 10 is a top emission device, the first electrode EL1 may be a reflective electrode and the second electrode EL2 may be a transmissive electrode or a transflective electrode. In some embodiments, when the organic electroluminescence device 10 is a bottom emission device, the first electrode EL1 may be a transmissive electrode or a transflective electrode and the second electrode EL2 may be a reflective electrode.

The amine compound according to an embodiment of the present disclosure may be included in the organic electroluminescence device 10 according to an embodiment of the present disclosure. The organic electroluminescence device 10 according to an embodiment of the present disclosure may include the amine compound in at least one organic layer between the first electrode EL1 and the second electrode EL2, or in a capping layer on the second electrode EL2.

In some embodiments, the organic electroluminescence device 10 according to an embodiment of the present disclosure may include the amine compound in at least one organic layer between the first electrode EL1 and the second electrode EL2, and excellent emission efficiency and high reliability may be achieved. For example, the organic electroluminescence device 10 according to an embodiment of the present disclosure may include the amine compound in a hole transport region HTR and may show high emission efficiency and/or improved life characteristics.

For example, when the organic electroluminescence device according to an embodiment of the present disclosure includes the amine compound according to an embodiment of the present disclosure in an organic layer adjacent to the emission layer, the hole transport region may maintain high hole transport capacity while restraining the movement of electrons, thereby enabling improved emission efficiency.

When an amine compound including both a pyridoindole moiety and an arylamine moiety (e.g., simultaneously) is included in a hole transport region, the amine compound may have excellent reliability, and the organic electroluminescence device according to an embodiment of the present disclosure may thus show excellent life characteristics. In some embodiments, the nitrogen atom included in the pyridoindole moiety may improve the hole transport capacity of the entire amine compound structure, and the probability of recombination of holes and electrons in the emission layer of an organic electroluminescence device may be increased. Accordingly, the amine compound according to an embodiment of the present disclosure may enable improved emission efficiency.

Hereinafter, an amine compound according to embodiments of the present disclosure and an organic electroluminescence device including the amine compound according to an embodiment of the present disclosure will be explained in more detail with reference to example embodiments and comparative embodiments. The following embodiments are provided only as illustrations to assist the understanding of the present disclosure, and the scope of embodiments of the present disclosure is not limited thereto.

EXAMPLES

1. Synthesis of Amine Compound

Suitable synthetic methods for the amine compound according to embodiments of the present disclosure will be explained with reference to Compound A1, Compound A28, Compound A57, Compound B36, Compound B46, Compound C47, Compound C87, Compound D47, Compound D60, Compound D74, Compound E6, Compound E25, Compound E55, Compound E73, Compound E89, Compound F21, Compound F63, and Compound F82 in Compound Group 1. The synthetic methods are provided as example embodiments, and synthetic methods of an amine compound according to an embodiment of the present disclosure are not limited thereto.

Synthesis of Compound A1

Amine Compound A1 according to an embodiment of the present disclosure may be synthesized, for example, by Reaction 1:

Reaction 1

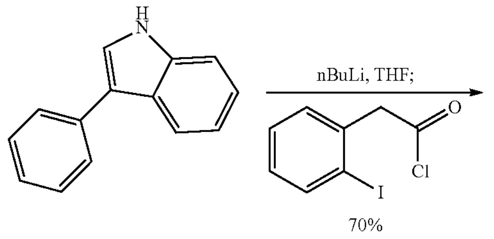

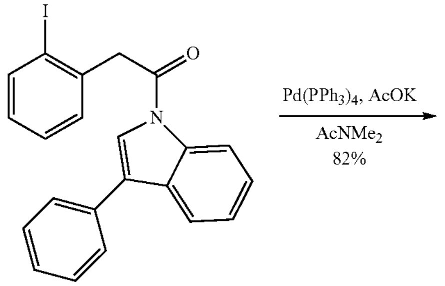

IM-1

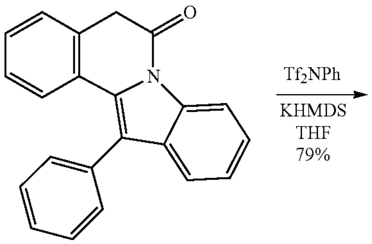

IM-2

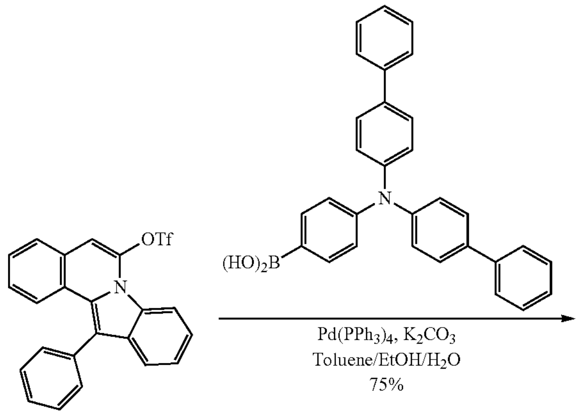

IM-3

-continued

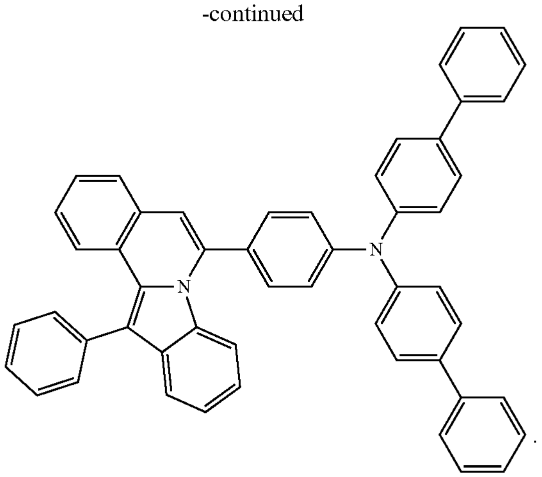

A1

Synthesis of Intermediate IM-1

Under an argon atmosphere, to a three-neck, 1,000 mL flask, 20.00 g (103.5 mmol) of 3-phenyl-1H-indole and 345 mL (0.3 M) of THF were added while stirring at a temperature of about −78° C., and 72 mL (1.1 eq) of a nBuLi/n-hexane solution of 1.6 mol/L was added dropwise thereto. After stirring for about 1 hour at the same temperature conditions, a THF solution (28.5 mL, 1 mol/L) of 31.94 g (1.1 eq, 113.8 mmol) of 2-(2-iodophenyl)acetyl chloride was added dropwise thereto and stirred for about 30 minutes at the same temperature. Then, the temperature was increased to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-1 (31.68 g, yield 70%). As measured by FAB-MS, mass number m/z=437 was observed as a molecular ion peak and Intermediate IM-1 was identified.

Synthesis of Intermediate IM-2

Under an argon atmosphere, to a three-neck, 500 mL flask, 25.00 g (57.2 mmol) of Intermediate IM-1, 8.42 g (1.5 eq, 85.8 mmol) of potassium acetate, 3.30 g (0.05 eq, 2.9 mmol) of $Pd(PPh_3)_4$, and 228 mL (0.25 M) of N,N-dimethylacetamide were added in order, and stirred while heating at about 80° C. After securing the disappearance of raw materials, the reaction solution was air cooled to room temperature, water was added to the reaction solution, and extraction with toluene was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-2 (14.50 g, yield 82%). As measured by FAB-MS, mass number m/z=309 was observed as a molecular ion peak and Intermediate IM-2 was identified.

Synthesis of Intermediate IM-3

Under an argon atmosphere, to a three-neck, 500 mL flask, 10.00 g (32.3 mmol) of IM-2 and 108 mL (0.3 M) of THF were added, and while stirring at about −78° C., 35.6 mL (1.1 eq) of a KHMDS/THF solution of 1.0 mol/L was added dropwise thereto. After stirring for about 1 hour at the same temperature, a THF solution (10.0 mL, 1 mol/L) of 13.86 g (1.2 eq, 38.8 mmol) of N,N'-bis(trifluoromethane-sulfonyl)aniline was added dropwise thereto and stirred for about 30 minutes at the same temperature. Then, the temperature was increased to room temperature and additional stirring was performed. After that, 10% NaOH aqueous solution was added thereto, and the reaction solution was extracted with AcOEt. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained, i.e., Intermediate IM-3 (11.27 g, yield 79%) was used without further purification in the subsequent reaction. As measured by FAB-MS, mass number m/z=441 was observed as a molecular ion peak and Intermediate IM-3 was identified.

Synthesis of Compound A1

Under an argon atmosphere, to a three-neck, 500 mL flask, 10.00 g (22.7 mmol) of Intermediate IM-3, 11.00 g (1.1 eq, 24.9 mmol) of 4-{di[(1,1'-biphenyl)-4-yl]amino}phenylboronic acid, 9.39 g (3.0 eq, 68.0 mmol) of $K_2CO_3$, 1.31 g (0.05 eq, 1.1 mmol) of $Pd(PPh_3)_4$, and 159 mL of a mixture of toluene/ethanol (EtOH)/water (4/2/1) were added in order and stirred while heating to about 80° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound A1 (11.70 g, yield 75%) as a white solid. As measured by FAB-MS, mass number m/z=688 was observed as a molecular ion peak and Compound A1 was identified.

Synthesis of Compound A28

Amine Compound A28 according to an embodiment of the present disclosure may be synthesized, for example, by Reaction 2:

Reaction 2

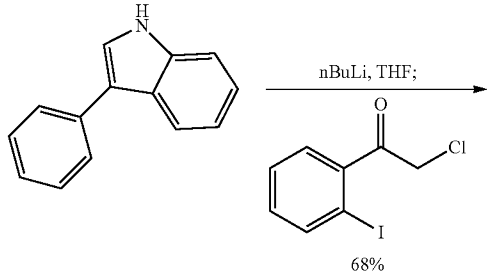

-continued

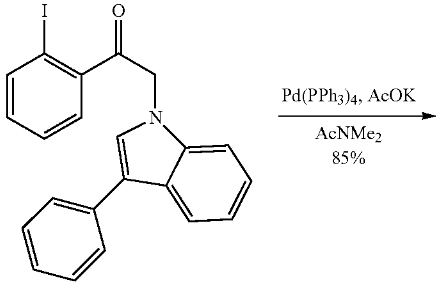

IM-4

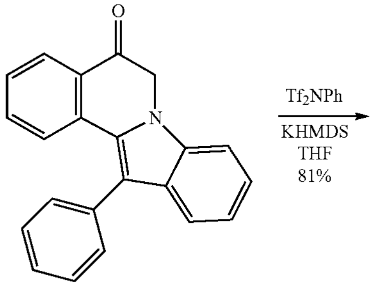

IM-5

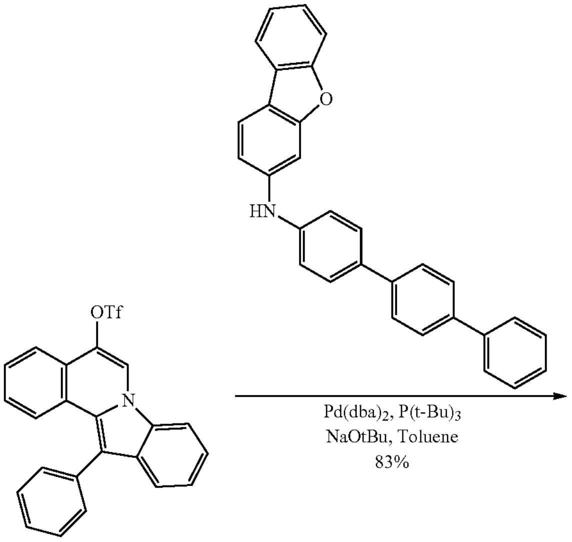

IM-6

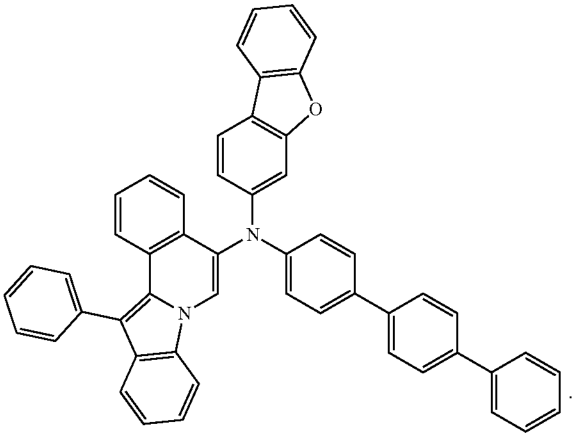

A28

Synthesis of Intermediate IM-4

Under an argon atmosphere, to a three-neck, 1,000 mL flask, 20.00 g (103.5 mmol) of 3-phenyl-1H-indole and 345 mL (0.3 M) of THF were added, and while stirring at about −78° C., 72 mL (1.1 eq) of a nBuLi/n-hexane solution of 1.6 mol/L was added dropwise thereto. After stirring for about 1 hour at the same temperature, a THF solution (28.5 ml, 1 mol/L) of 31.94 g (1.1 eq, 113.8 mmol) of 2-chloro-1-(2-iodophenyl)ethanone was added dropwise thereto and stirred for about 30 minutes at the same temperature. Then, the temperature was increased to room temperature and stirring was additionally performed for about 2 hours. After securing the disappearance of raw materials, the reaction solution was cooled with water and extraction with toluene was performed. Then, the aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-4 (30.77 g, yield 68%). As measured by FAB-MS, mass number m/z=437 was observed as a molecular ion peak and Intermediate IM-4 was identified.

Synthesis of Intermediate IM-5

Under an argon atmosphere, to a three-neck, 500 mL flask, 25.00 g (57.2 mmol) of Intermediate IM-4, 8.42 g (1.5 eq, 85.8 mmol) of potassium acetate, 3.30 g (0.05 eq, 2.9 mmol) of $Pd(PPh_3)_4$, and 228 mL (0.25 M) of N,N-dimethylacetamide were added in order, and stirred while heating at about 80° C. After securing the disappearance of raw materials, the reaction solution was air cooled to room temperature, water was added to the reaction solution, and extraction with toluene was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-5 (15.03 g, yield 85%). As measured by FAB-MS, mass number m/z=309 was observed as a molecular ion peak and Intermediate IM-5 was identified.

Synthesis of Intermediate IM-6

Under an argon atmosphere, to a three-neck, 500 mL flask, 10.00 g (32.3 mmol) of IM-5 and 108 mL (0.3 M) of THF were added, and 35.6 mL (1.1 eq) of a KHMDS/THF solution of 1.0 mol/L was added dropwise thereto while stirring at about −78° C. After stirring for about 1 hour at the same temperature, a THF solution (10.0 mL, 1 mol/L) of 13.86 g (1.2 eq, 38.8 mmol) of N,N'-bis(trifluoromethanesulfonyl)aniline was added dropwise thereto and stirred for about 30 minutes at the same temperature. Then, the temperature was increased to room temperature and additional stirring was performed. After that, 10% NaOH aqueous solution was added thereto, and the reaction solution was extracted with AcOEt. The aqueous layer was removed, and the organic layer was washed with an aqueous sodium bicarbonate solution and a saturated saline solution and dried over $MgSO_4$. $MgSO_4$ was filtered and an organic layer was concentrated, and the crude product thus obtained, i.e., Intermediate IM-6 (11.56 g, yield 81%) was used without further purification in the subsequent reaction. As measured by FAB-MS, mass number m/z=441 was observed as a molecular ion peak and Intermediate IM-6 was identified.

Synthesis of Compound A28

Under an argon atmosphere, to a three-neck, 200 mL flask, 10.00 g (18.5 mmol) of Intermediate IM-6, 0.39 g (0.03 eq, 0.7 mmol) of $Pd(dba)_2$, 4.35 g (2.0 eq, 45.3 mmol) of $NaO^tBu$, 113 mL of toluene, 10.25 g (1.1 eq, 24.9 mmol) of N-[(1,1':4',1"-terphenyl)-4-yl]dibenzofuran-3-amine, and 0.46 g (0.1 eq, 2.3 mmol) of $^tBu_3P$ were added in order, followed by refluxing while heating and stirring. The reaction solution was air cooled to room temperature. Water was added to the reaction solution and the organic layer was isolated. Toluene was added to the aqueous solution and additional organic layers were extracted. The organic layers were collected and washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound A28 (13.22 g, yield 83%) as a white solid. As measured by FAB-MS, mass number m/z=702 was observed as a molecular ion peak and Compound A28 was identified.

Synthesis of Compound A57

Amine Compound A57 according to an embodiment of the present disclosure may be synthesized, for example, by Reaction 3:

Reaction 3

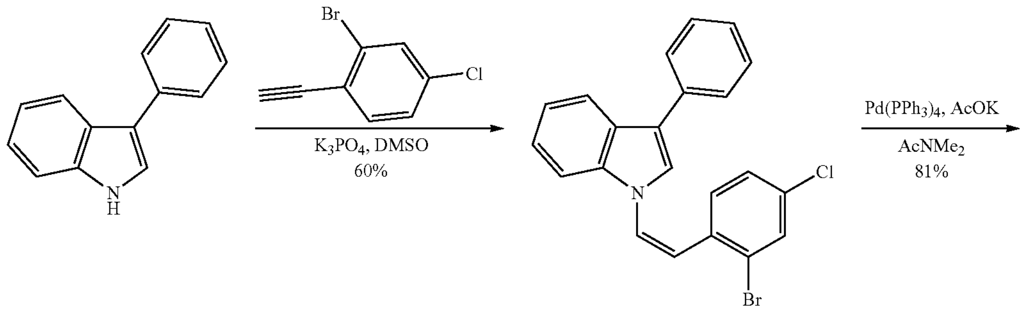

IM-7

-continued

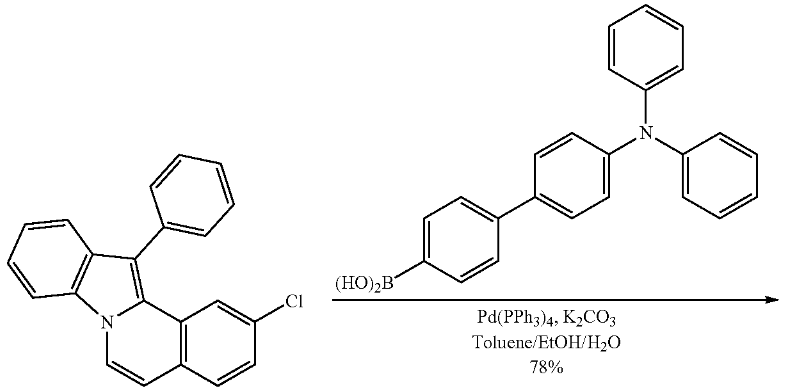

IM-8

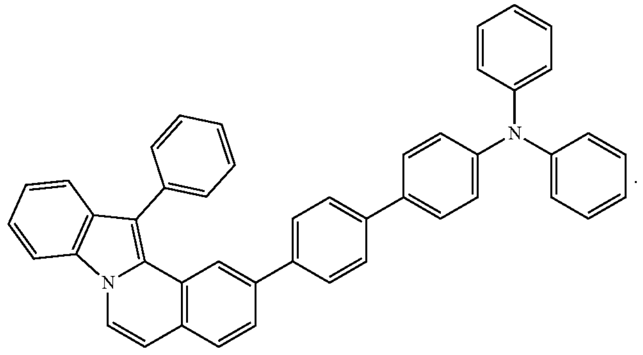

A57

Synthesis of Intermediate IM-7

Under an argon atmosphere, to a three-neck, 500 mL flask, 15.00 g (77.6 mmol) of 3-phenyl-1H-indole, 25.09 g (1.5 eq, 116.4 mmol) of 1-bromo-5-chloro-2-ethynylbenzene, 32.97 g (2.0 eq, 155.2 mmol) of $K_3PO_4$, and 215 mL (0.2 M) of DMSO were added in order and heated to 120° C. while stirring. After securing the disappearance of raw materials, the reaction solution was air cooled to room temperature, water was added to the reaction solution, and extraction with toluene was performed. The aqueous layer was removed, and the organic layer was washed with a saturated saline solution and dried over $MgSO_4$. $MgSO_4$ was filtered and an organic layer was concentrated, and the crude product thus obtained was separated by silica gel column chromatography (using a mixture of hexane and toluene as a developing solution) to obtain Intermediate IM-7 (19.03 g, yield 60%). As measured by FAB-MS, mass number m/z=408 was observed as a molecular ion peak and Intermediate IM-7 was identified.

Synthesis of Intermediate IM-8

Under an argon atmosphere, to a three-neck, 500 mL flask, 15.00 g (36.7 mmol) of Intermediate IM-7, 5.40 g (1.5 eq, 55.0 mmol) of potassium acetate, 2.12 g (0.05 eq, 1.8 mmol) of $Pd(PPh_3)_4$, and 146 mL (0.25 M) of N,N-dimethylacetamide were added in order, and stirred while heating to about 80° C. After securing the disappearance of raw materials, the reaction solution was air cooled to room temperature, water was added to the reaction solution, and extraction with toluene was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-8 (9.74 g, yield 81%). As measured by FAB-MS, mass number m/z=327 was observed as a molecular ion peak and Intermediate IM-8 was identified.

Synthesis of Compound A57

Under an argon atmosphere, to a three-neck, 500 mL flask, 8.00 g (24.4 mmol) of Intermediate IM-8, 9.80 g (1.1 eq, 26.8 mmol) of [4'-(diphenylamino)-1(1,1'-biphenyl)-4-yl]boronic acid, 10.12 g (3.0 eq, 73.2 mmol) of $K_2CO_3$, 1.41 g (0.05 eq, 1.2 mmol) of $Pd(PPh_3)_4$, and 170 mL of a mixture of toluene/ethanol (EtOH)/water (4/2/1) were added in order, followed by heating and stirring at about 80° C. The reaction solution was air cooled to room temperature and extraction with toluene was performed. The aqueous layer was removed and the organic layer was washed with a saturated saline solution and dried over $MgSO_4$. $MgSO_4$ was filtered and an organic layer was concentrated, and the crude product thus obtained was separated by silica gel column chromatography (using a mixture of hexane and toluene as a developing solution) to obtain Compound A57 (11.66 g, yield 78%) as a white solid. As measured by FAB-MS, mass number m/z=612 was observed as a molecular ion peak and Compound A57 was identified.

Synthesis of Compound B36

Amine Compound B36 according to an embodiment of the present disclosure may be synthesized, for example, by Reaction 4:

Reaction 4

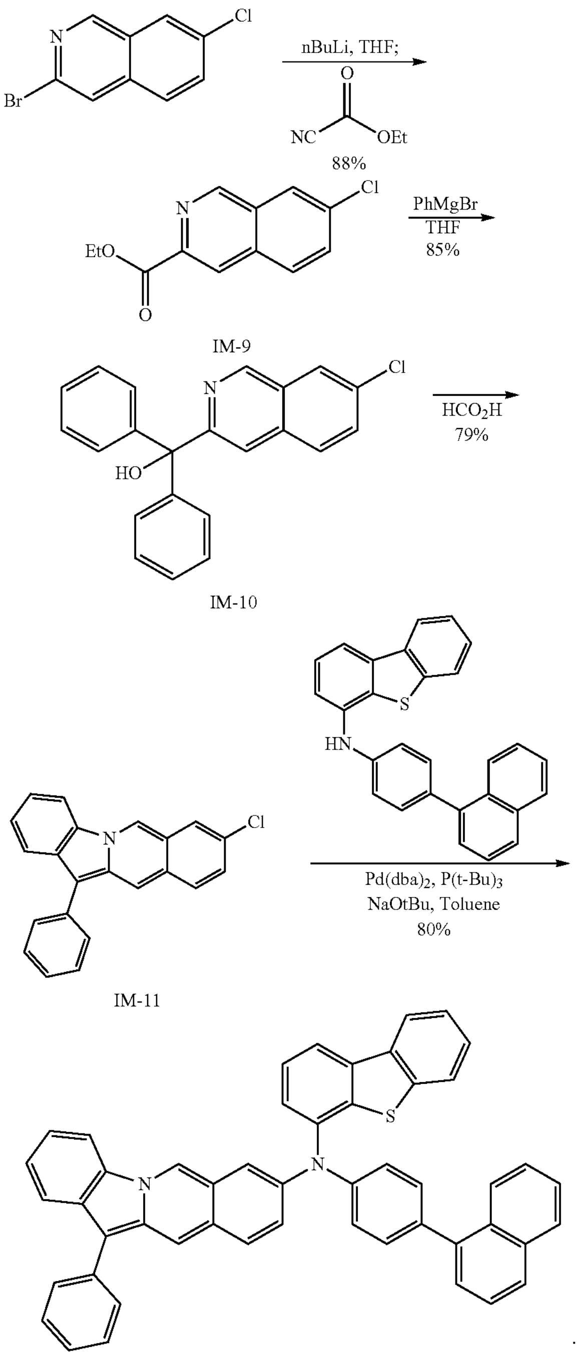

IM-9

IM-10

IM-11

B36

Synthesis of Intermediate IM-9

Under an argon atmosphere, to a three-neck, 500 mL flask, 20.00 g (82.5 mmol) of 3-bromo-7-chloroisoquinoline and 275 mL (0.3 M) of THF were added and while stirring at about −78° C., 56.7 mL (1.1 eq) of a nBuLi/n-hexane solution of 1.6 mol/L was added dropwise thereto. After stirring for about 1 hour at the same temperature, a THF solution (23 mL, 1 mol/L) of 8.99 g (1.1 eq, 90.7 mmol) of ethyl cyanoformate was added dropwise thereto and stirred for about 30 minutes at the same temperature. Then, the temperature was increased to room temperature and stirring was additionally performed. After securing the disappearance of raw materials, the reaction solution was cooled with water and extraction with toluene was performed. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-9 (17.10 g, yield 88%). As measured by FAB-MS, mass number m/z=235 was observed as a molecular ion peak and Intermediate IM-9 was identified.

Synthesis of Intermediate IM-10

Under an argon atmosphere, to a three-neck, 500 mL flask, 15.00 g (63.6 mmol) of Intermediate IM-9 and 213 mL (0.3 M) of THF were added, and while stirring at about −78° C., 159 mL (2.5 eq) of a PhMgBr/THF solution of 1.0 mol/L was added dropwise thereto. The stirring was performed at the same temperature for about 1 hour, and the temperature was elevated to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and an organic layer was concentrated, and the crude product thus obtained was separated by silica gel column chromatography (using a mixture of hexane and toluene as a developing solution) to obtain Intermediate IM-10 (18.71 g, yield 85%). As measured by FAB-MS, mass number m/z=345 was observed as a molecular ion peak and Intermediate IM-10 was identified.

Synthesis of Intermediate IM-11

Under an argon atmosphere, to a three-neck, 300 mL flask, 15.00 g (43.4 mmol) of IM-10 and 145 mL (0.3 M) of formic acid were added, followed by heating and stirring at about 120° C. The reaction solution was air cooled to room temperature, further cooled with water, and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-11 (11.23 g, yield 79%). As measured by FAB-MS, mass number m/z=327 was observed as a molecular ion peak and Intermediate IM-11 was identified.

Synthesis of Compound B36

Under an argon atmosphere, to a three-neck, 200 mL flask, 5.00 g (15.3 mmol) of Intermediate IM-11, 0.26 g (0.03 eq, 0.5 mmol) of $Pd(dba)_2$, 2.93 g (2.0 eq, 30.5 mmol)

of NaO$^t$Bu, 76 mL of toluene, 6.74 g (1.1 eq, 16.8 mmol) of N-[4-(naphthalen-1-yl)phenyl]dibenzothiophene-4-amine, and 0.31 g (0.1 eq, 1.5 mmol) of $^t$Bu$_3$P were added in order, followed by refluxing while heating and stirring. The reaction solution was air cooled to room temperature. Water was added to the reaction solution and the organic layer was isolated. Toluene was added to the aqueous solution and additional organic layers were extracted. The organic layers were collected, washed with a saturated saline solution, and dried over $MgSO_4$. $MgSO_4$ was filtered and an organic layer was concentrated, and the crude product thus obtained was separated by silica gel column chromatography (using a mixture of hexane and toluene as a developing solution) to obtain Compound B36 (8.45 g, yield 80%) as a white solid. As measured by FAB-MS, mass number m/z=692 was observed as a molecular ion peak and Compound B36 was identified.

Synthesis of Compound B46

Amine Compound B46 according to an embodiment of the present disclosure may be synthesized, for example, by Reaction 5:

Reaction 5

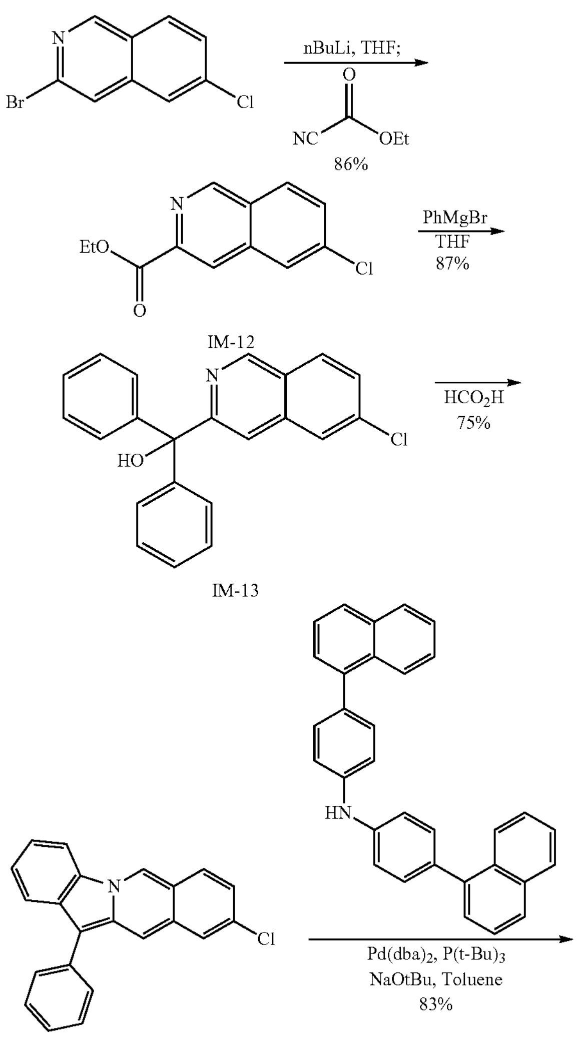

IM-12

IM-13

IM-14

-continued

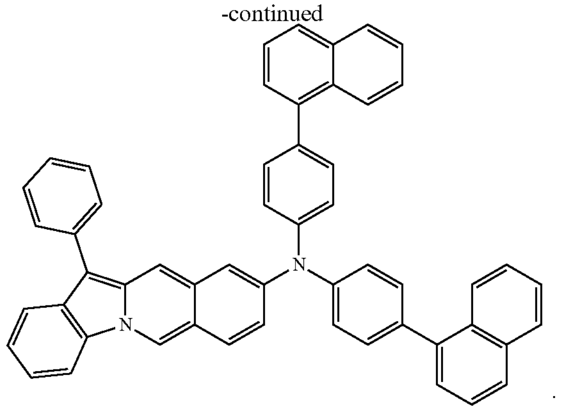

B46

Synthesis of Intermediate IM-12

Under an argon atmosphere, to a three-neck, 500 mL flask, 20.00 g (82.5 mmol) of 3-bromo-7-chloroisoquinoline and 275 mL (0.3 M) of THF were added, and while stirring at about −78° C., 56.7 mL (1.1 eq) of a nBuLi/n-hexane solution of 1.6 mol/L was added dropwise thereto. After stirring for about 1 hour at the same temperature, a THF solution (23 mL, 1 mol/L) of 8.99 g (1.1 eq, 90.7 mmol) of ethyl cyanoformate was added dropwise thereto and stirred for about 30 minutes at the same temperature. Then, the temperature was increased to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and an organic layer was concentrated, and the crude product thus obtained was separated by silica gel column chromatography (using a mixture of hexane and toluene as a developing solution) to obtain Intermediate IM-12 (16.72 g, yield 86%). As measured by FAB-MS, mass number m/z=235 was observed as a molecular ion peak and Intermediate IM-12 was identified.

Synthesis of Intermediate IM-13

Under an argon atmosphere, to a three-neck, 500 mL flask, 15.00 g (63.6 mmol) of Intermediate IM-12, and 213 mL (0.3 M) of THF were added and while stirring at about −78° C., 159 mL (2.5 eq) of a PhMgBr/THF solution of 1.0 mol/L was added dropwise thereto. The stirring was performed at the same temperature for about 1 hour, the temperature was elevated to room temperature, and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-13 (19.15 g, yield 87%). As measured by FAB-MS, mass number m/z=345 was observed as a molecular ion peak and Intermediate IM-13 was identified.

Synthesis of Intermediate IM-14

Under an argon atmosphere, to a three-neck, 300 mL flask, 15.00 g (43.4 mmol) of IM-13 and 145 mL (0.3 M) of formic acid were added, followed by heating and stirring at about 120° C. The reaction solution was air cooled to room temperature, further cooled with water, and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-14 (10.66 g, yield 75%). As measured by FAB-MS, mass number m/z=327 was observed as a molecular ion peak and Intermediate IM-14 was identified.

Synthesis of Compound B46

Under an argon atmosphere, to a three-neck, 200 mL flask, 5.00 g (15.3 mmol) of Intermediate IM-14, 0.26 g (0.03 eq, 0.5 mmol) of $Pd(dba)_2$, 2.93 g (2.0 eq, 30.5 mmol) of NaO$^t$Bu, 76 mL of toluene, 7.07 g (1.1 eq, 16.8 mmol) of bis[4-(naphthalen-1-yl)phenyl]amine, and 0.31 g (0.1 eq, 1.5 mmol) of $^tBu_3P$ were added in order, followed by refluxing while heating and stirring. The reaction solution was air cooled to room temperature. Water was added to the reaction solution and the organic layer was isolated. Toluene was added to the aqueous solution and additional organic layers were extracted. The organic layers were collected and washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound B46 (9.03 g, yield 83%) as a white solid. As measured by FAB-MS, mass number m/z=712 was observed as a molecular ion peak and Compound B46 was identified.

Synthesis of Compound C47

Amine Compound C47 according to an embodiment of the present disclosure may be synthesized, for example, by Reaction 6:

Reaction 6

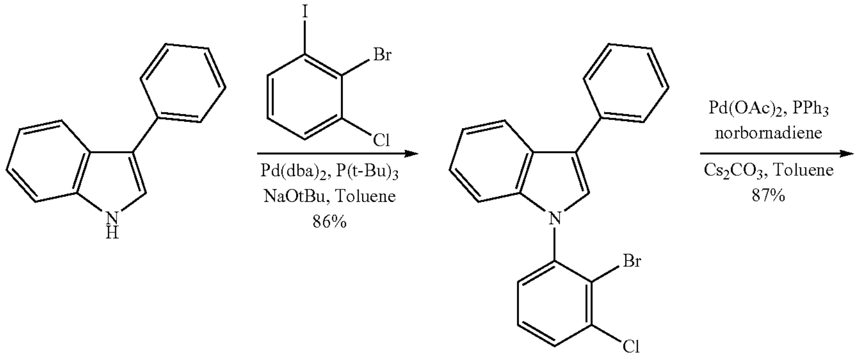

IM-15

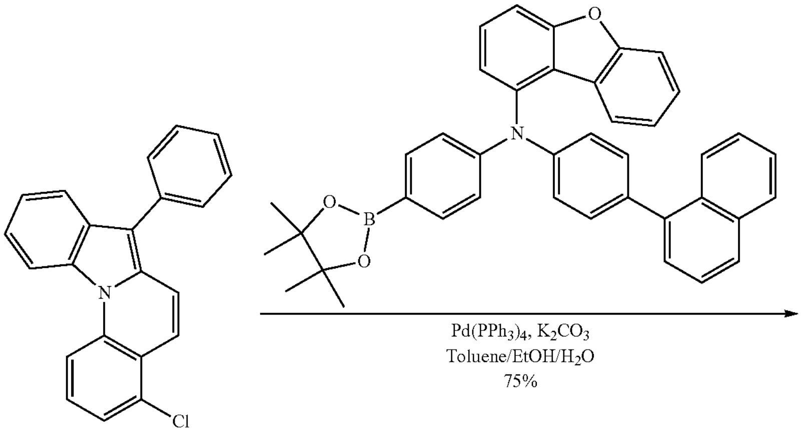

IM-16

-continued

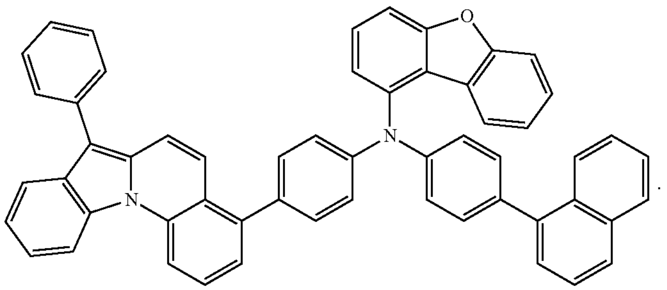

C47

Synthesis of Intermediate IM-15

Under an argon atmosphere, to a three-neck, 500 mL flask, 15.00 g (77.6 mmol) of 3-phenyl-1H-indole, 1.34 g (0.03 eq, 2.3 mmol) of $Pd(dba)_2$, 8.95 g (1.2 eq, 93.1 mmol) of $NaO^tBu$, 388 ml of toluene, 27.10 g (1.1 eq, 85.4 mmol) of 2-bromo-1-chloro-3-iodobenzene, and 1.57 g (0.1 eq, 7.8 mmol) of $^tBu_3P$ were added in order, followed by refluxing while heating and stirring. The reaction solution was air cooled to room temperature. Water was added to the reaction solution and an organic layer was isolated. Toluene was added to the aqueous solution and additional organic layers were extracted. The organic layers were collected and washed with a saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-15 (25.55 g, yield 86%). As measured by FAB-MS, mass number m/z=382 was observed as a molecular ion peak and Intermediate IM-15 was identified.

Synthesis of Intermediate IM-16

Under an argon atmosphere, to a three-neck, 500 mL flask, 15.00 g (39.2 mmol) of Intermediate IM-15, 0.88 g (0.1 eq, 3.9 mmol) of $Pd(OAc)_2$, 19.16 g (1.5 eq, 58.8 mmol) of $Cs_2CO_3$, 196 mL of toluene, 14.45 g (4.0 eq, 156.8 mmol) of norbornadiene, and 2.26 g (0.22 eq, 8.6 mmol) of $PPh_3$ were added in order and refluxed at about 120° C. while stirring. After air cooling the reaction solution to room temperature, water was added to the reaction solution and an organic layer was isolated. Toluene was added to the aqueous solution and additional organic layers were extracted. The organic layers were collected, washed with a saline solution, and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-16 (11.18 g, yield 87%). As measured by FAB-MS, mass number m/z=327 was observed as a molecular ion peak and Intermediate IM-16 was identified.

Synthesis of Compound C47

Under an argon atmosphere, to a three-neck, 500 mL flask, 8.00 g (24.4 mmol) of Intermediate IM-16, 15.77 g (1.1 eq, 26.8 mmol) of N-[4-(naphthalen-1-yl)phenyl]-N-[4-(4,4,5,5-tetramethyl-1,3,2-dioxaborolan-2-yl)phenyl]dibenzofuran-1-amine, 10.12 g (3.0 eq, 73.2 mol) of $K_2CO_3$, 1.41 g (0.05 eq, 1.2 mmol) of $Pd(PPh_3)_4$, and 170 mL of a mixture of toluene/ethanol (EtOH)/water (4/2/1) were added in order, followed by heating and stirring at about 80° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound C47 (13.78 g, yield 75%) as a white solid. As measured by FAB-MS, mass number m/z=752 was observed as a molecular ion peak and Intermediate C47 was identified.

Synthesis of Compound C87

Amine Compound C87 according to an embodiment of the present disclosure may be synthesized, for example, by Reaction 7:

Reaction 7

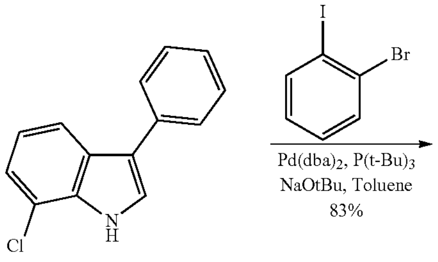

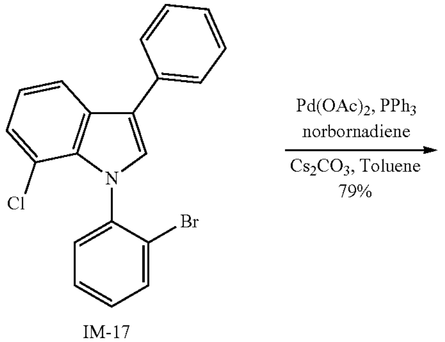

IM-17

-continued

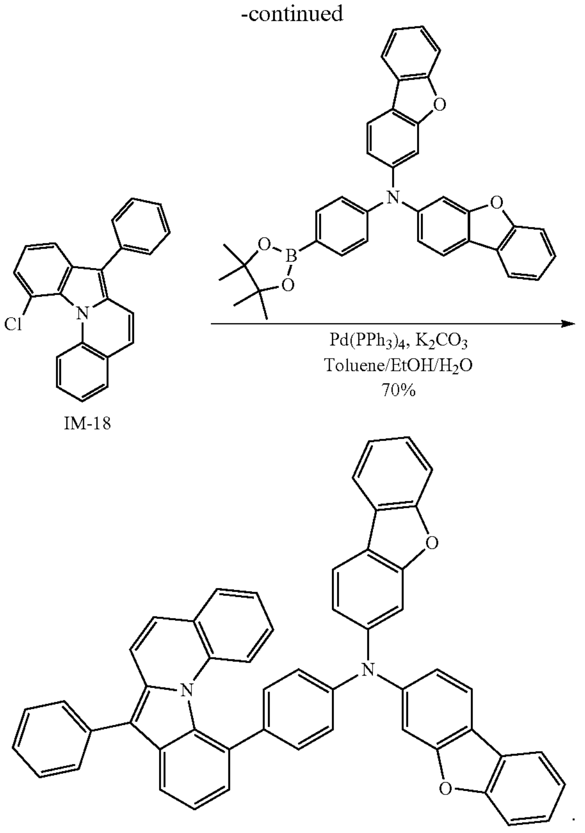

IM-18

C-87

Synthesis of Intermediate IM-17

Under an argon atmosphere, to a three-neck, 500 mL flask, 15.00 g (65.9 mmol) of 7-chloro-3-phenyl-1H-indole, 1.14 g (0.03 eq, 2.0 mmol) of $Pd(dba)_2$, 7.60 g (1.2 eq, 79.1 mmol) of $NaO^tBu$, 388 mL of toluene, 20.50 g (1.1 eq, 72.5 mmol) of 1-bromo-2-iodobenzene, and 1.33 g (0.1 eq, 6.6 mmol) of $^tBu_3P$ were added in order, followed by refluxing while heating and stirring. After air cooling the reaction solution to room temperature, water was added to the reaction solution and an organic layer was isolated. Toluene was added to the aqueous solution and additional organic layers were extracted. The organic layers were collected, washed with a saline solution, and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-17 (20.92 g, yield 83%). As measured by FAB-MS, mass number m/z=382 was observed as a molecular ion peak and Intermediate IM-17 was identified.

Synthesis of Intermediate IM-18

Under an argon atmosphere, to a three-neck, 500 mL flask, 15.00 g (39.2 mmol) of Intermediate IM-17, 0.88 g (0.1 eq, 3.9 mmol) of $Pd(OAc)_2$, 19.16 g (1.5 eq, 58.8 mmol) of $Cs_2CO_3$, 196 mL of toluene, 14.45 g (4.0 eq, 156.8 mmol) of norbornadiene and 2.26 g (0.22 eq, 8.6 mmol) of $PPh_3$ were added in order and refluxed at about 120° C. while stirring. After air cooling the reaction solution to room temperature, water was added to the reaction solution and the organic layer was isolated. Toluene was added to the aqueous solution and additional organic layers were extracted. The organic layers were collected, washed with a saline solution, and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-18 (10.15 g, yield 79%). As measured by FAB-MS, mass number m/z=327 was observed as a molecular ion peak and Intermediate IM-18 was identified.

Synthesis of Compound C87

Under an argon atmosphere, to a three-neck, 500 mL flask, 8.00 g (24.4 mmol) of Intermediate IM-18, 14.80 g (1.1 eq, 26.8 mmol) of N-(dibenzofuran-3-yl)-N-[4-(4,4,5,5-tetramethyl-1,3,2-dioxaborolan-2-yl)phenyl]dibenzofuran-3-amine, 10.12 g (3.0 eq, 73.2 mol) of $K_2CO_3$, 1.41 g (0.05 eq, 1.2 mmol) of $Pd(PPh_3)_4$, and 170 mL of a mixture of toluene/ethanol (EtOH)/water (4/2/1) were added in order, followed by heating and stirring at about 80° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound C87 (12.25 g, yield 70%) as a white solid. As measured by FAB-MS, mass number m/z=716 was observed as a molecular ion peak and Intermediate C87 was identified.

Synthesis of Compound D47

Amine Compound D47 according to an embodiment of the present disclosure may be synthesized, for example, by Reaction 8:

Reaction 8

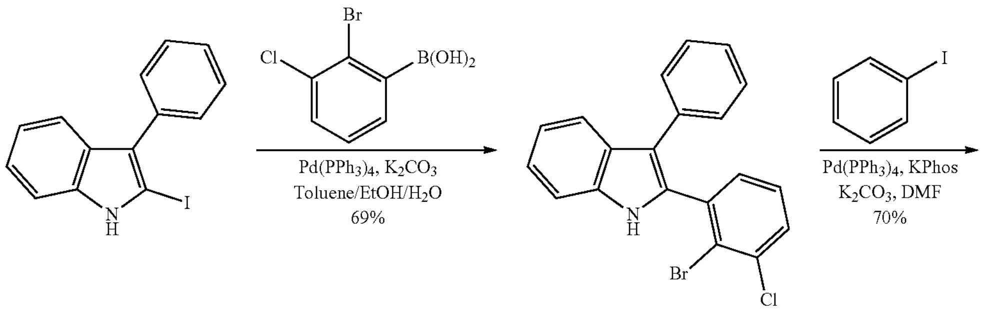

IM-19

-continued

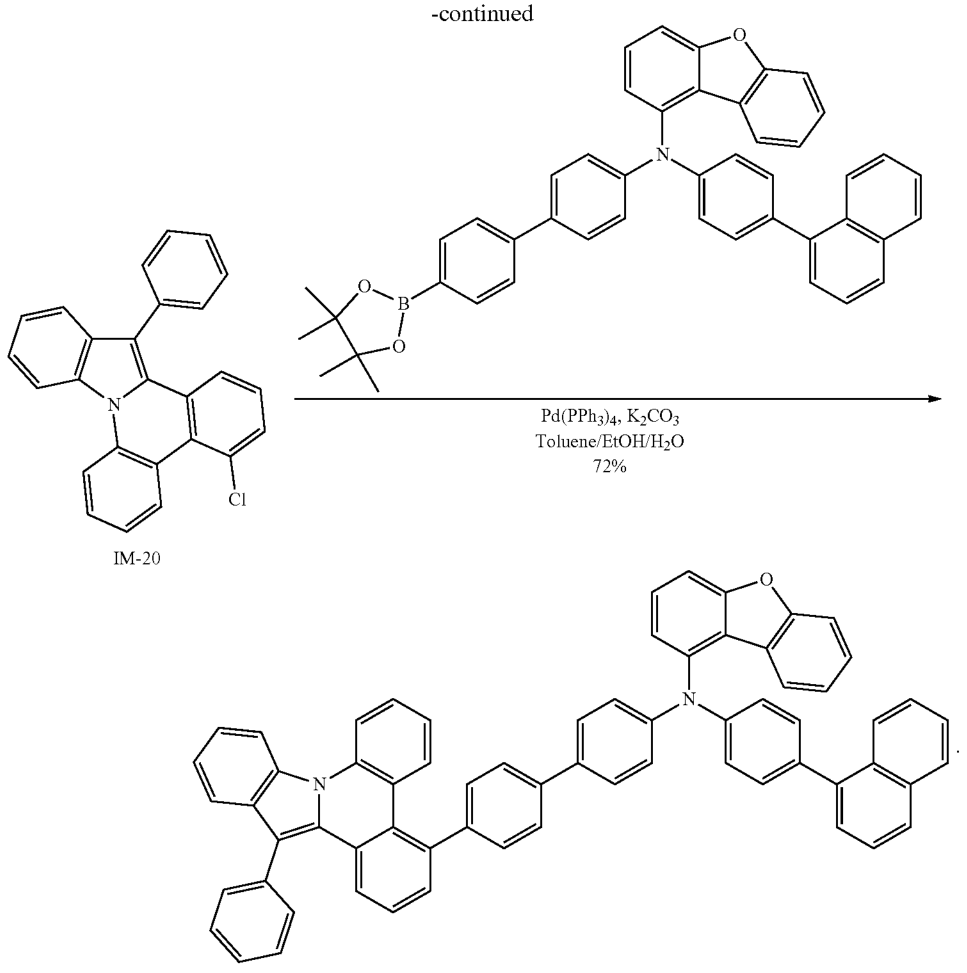

IM-20

D47

Synthesis of Intermediate IM-19

Under an argon atmosphere, to a three-neck, 500 mL flask, 15.00 g (47.00 mmol) of 2-iodo-3-phenyl-1H-indole, 12.16 g (1.1 eq, 51.7 mmol) of 2-bromo-3-chlorophenylboronic acid, 19.49 g (3.0 eq, 141.0 mmol) of $K_2CO_3$, 2.72 g (0.05 eq, 2.3 mmol) of $Pd(PPh_3)_4$, and 329 mL of a mixture of toluene/ethanol (EtOH)/water (4/2/1) were added in order, followed by heating and stirring at about 80° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-19 (12.41 g, yield 69%). As measured by FAB-MS, mass number m/z=382 was observed as a molecular ion peak and Intermediate IM-19 was identified.

Synthesis of Intermediate IM-20

Under an argon atmosphere, to a three-neck, 500 mL flask, 10.00 g (26.1 mmol) of Intermediate IM-19, 5.86 g (1.1 eq, 28.7 mmol) of iodobenzene, 10.83 g (3.0 eq, 78.4 mmol) of $K_2CO_3$, 3.02 g (0.1 eq, 2.6 mmol) of $Pd(PPh_3)_4$, 1.25 g (0.1 eq, 2.6 mmol) of XPhos, and 105 mL of DMF were added in order, followed by heating and stirring at about 140° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-20 (6.91 g, yield 70%). As measured by FAB-MS, mass number m/z=377 was observed as a molecular ion peak and Intermediate IM-20 was identified.

Synthesis of Compound D47

Under an argon atmosphere, to a three-neck, 300 mL flask, 5.00 g (13.2 mmol) of Intermediate IM-20, 9.66 g (1.1 eq, 14.6 mmol) of N-[4-(naphthalen-1-yl)phenyl]-N-[4'-(4,4,5,5-tetramethyl-1,3,2-dioxaborolan-2-yl)-(1,1'-biphenyl)-4-yl]dibenzofuran-1-amine, 5.49 g (3.0 eq, 39.7 mol) of $K_2CO_3$, 0.76 g (0.05 eq, 0.7 mmol) of $Pd(PPh_3)_4$, and 93 mL of a mixture of toluene/ethanol (EtOH)/water (4/2/1) were added in order, followed by heating and stirring at about 80° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound D47 (8.38 g, yield 72%) as a white solid. As measured by FAB-MS, mass number m/z=879 was observed as a molecular ion peak and Compound D47 was identified.

Synthesis of Compound D60

Amine Compound D60 according to an embodiment of the present disclosure may be synthesized, for example, by Reaction 9:

Reaction 9

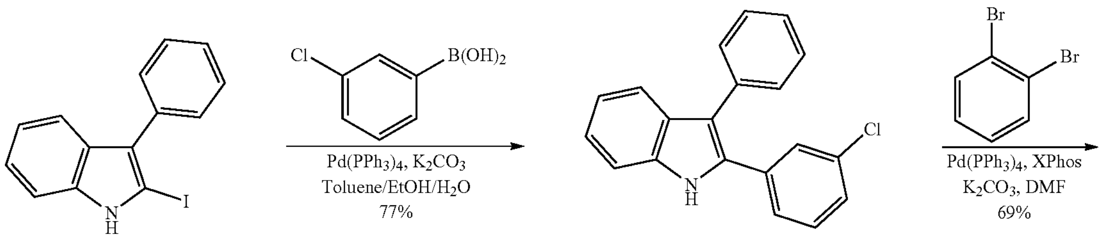

IM-21

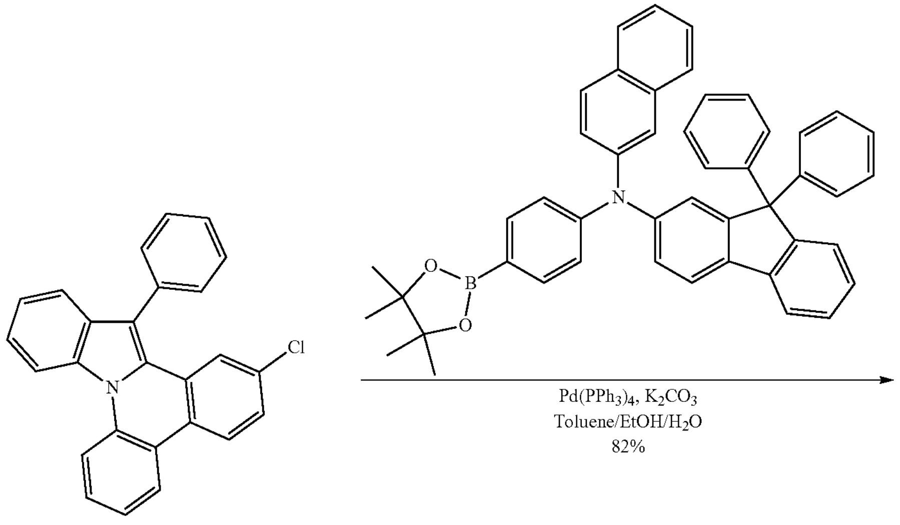

IM-22

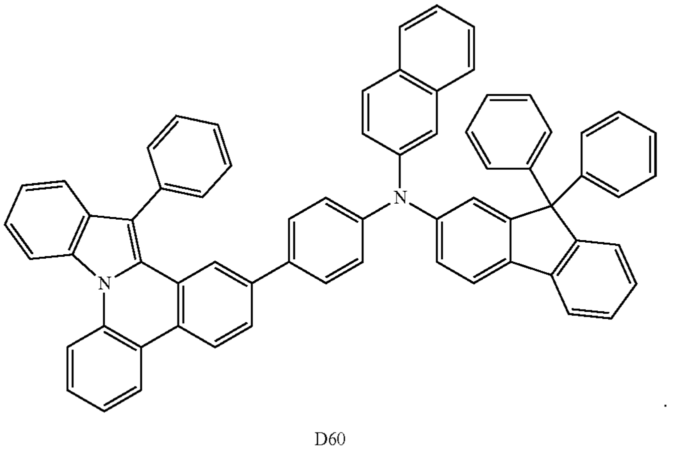

D60

Synthesis of Intermediate IM-21

Under an argon atmosphere, to a three-neck, 500 mL flask, 15.00 g (47.00 mmol) of 2-iodo-3-phenyl-1H-indole, 8.08 g (1.1 eq, 51.7 mmol) of 3-chlorophenylboronic acid, 19.49 g (3.0 eq, 141.0 mmol) of $K_2CO_3$, 2.72 g (0.05 eq, 2.3 mmol) of $Pd(PPh_3)_4$, and 329 mL of a mixture of toluene/ethanol (EtOH)/water (4/2/1) were added in order, followed by heating and stirring at about 80° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-21 (10.99 g, yield 77%). As measured by FAB-MS, mass number m/z=303 was observed as a molecular ion peak and Intermediate IM-21 was identified.

Synthesis of Intermediate IM-22

Under an argon atmosphere, to a three-neck, 500 mL flask, 10.00 g (32.9 mmol) of Intermediate IM-21, 8.54 g (1.1 eq, 36.2 mmol) of 1,2-dibromobenzene, 13.65 g (3.0 eq, 98.8 mmol) of $K_2CO_3$, 3.80 g (0.1 eq, 3.3 mmol) of $Pd(PPh_3)_4$, 1.57 g (0.1 eq, 3.3 mmol) of XPhos, and 132 mL of DMF were added in order, followed by heating and stirring at about 140° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-22 (8.58 g, yield 69%). As measured by FAB-MS, mass number m/z=377 was observed as a molecular ion peak and Intermediate IM-22 was identified.

Synthesis of Compound D60

Under an argon atmosphere, to a three-neck, 300 mL flask, 5.00 g (13.2 mmol) of Intermediate IM-22, 9.63 g (1.1 eq, 14.6 mmol) of N-(naphthalen-2-yl)-9,9-diphenyl-N-[4-(4,4,5,5-tetramethyl-1,3,2-dioxaborolan-2-yl)phenyl]-9H-fluoren-2-amine, 5.49 g (3.0 eq, 39.7 mol) of $K_2CO_3$, 0.76 g (0.05 eq, 0.7 mmol) of $Pd(PPh_3)_4$, and 93 mL of a mixture of toluene/ethanol (EtOH)/water (4/2/1) were added in order, followed by heating and stirring at about 80° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound D60 (9.52 g, yield 82%) as a white solid. As measured by FAB-MS, mass number m/z=877 was observed as a molecular ion peak and Compound D60 was identified.

Synthesis of Compound D74

Amine Compound D74 according to an embodiment of the present disclosure may be synthesized, for example, by Reaction 10:

Reaction 10

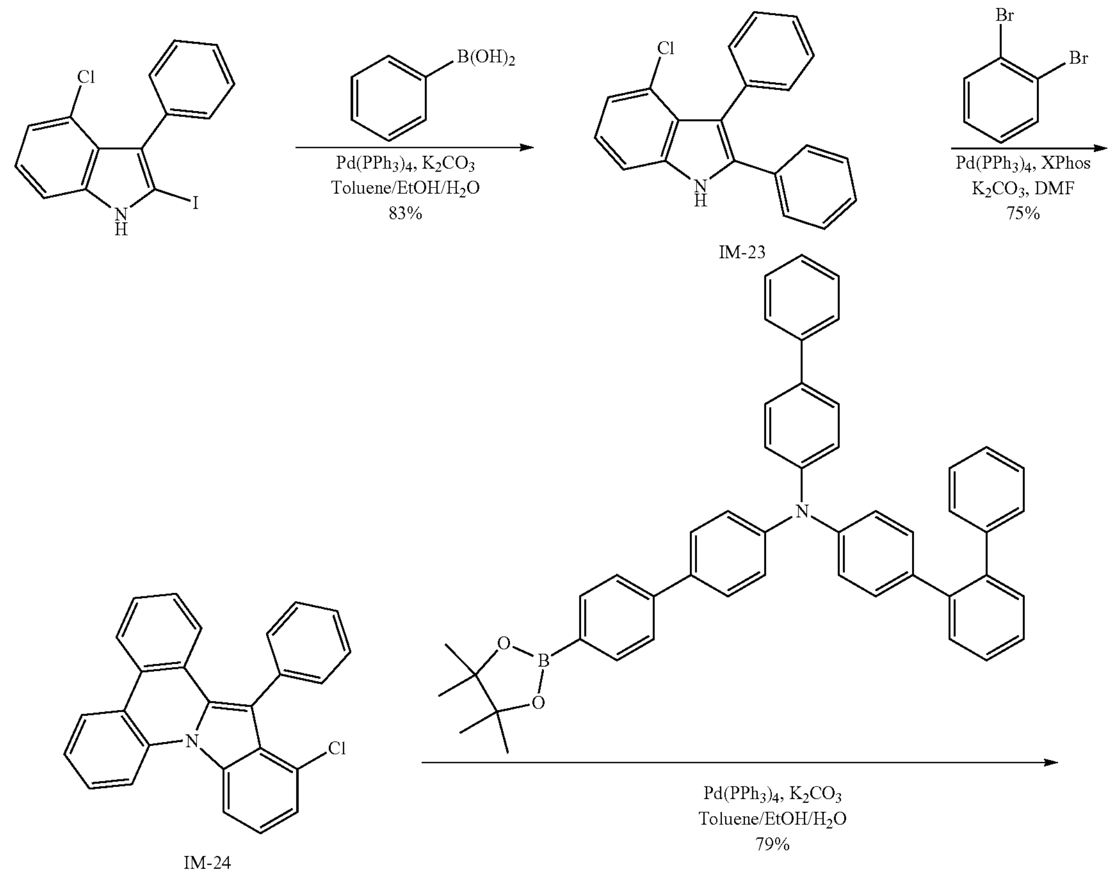

-continued

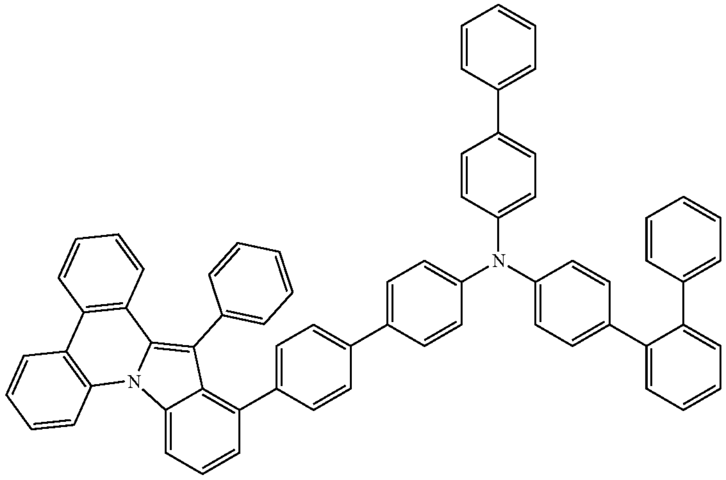

D74

Synthesis of Intermediate IM-23

Under an argon atmosphere, to a three-neck, 500 mL flask, 15.00 g (42.4 mmol) of 4-chloro-2-iodo-3-phenyl-1H-indole, 5.69 g (1.1 eq, 46.7 mmol) of boronic acid, 17.59 g (3.0 eq, 127.3 mmol) of $K_2CO_3$, 2.45 g (0.05 eq, 2.1 mmol) of $Pd(PPh_3)_4$, and 296 mL of a mixture of toluene/ethanol (EtOH)/water (4/2/1) were added in order, followed by heating and stirring at about 80° C. After cooling in the air to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-23 (10.70 g, yield 83%). As measured by FAB-MS, mass number m/z=303 was observed as a molecular ion peak and Intermediate IM-23 was identified.

Synthesis of Intermediate IM-24

Under an argon atmosphere, to a three-neck, 500 mL flask, 10.00 g (32.9 mmol) of Intermediate IM-23, 8.54 g (1.1 eq, 36.2 mmol) of 1,2-dibromobenzene, 13.65 g (3.0 eq, 98.8 mmol) of $K_2CO_3$, 3.80 g (0.1 eq, 3.3 mmol) of $Pd(PPh_3)_4$, 1.57 g (0.1 eq, 3.3 mmol) of XPhos, and 132 mL of DMF were added in order, followed by heating and stirring at about 140° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-24 (9.33 g, yield 75%). As measured by FAB-MS, mass number m/z=377 was observed as a molecular ion peak and Intermediate IM-24 was identified.

Synthesis of Compound D74

Under an argon atmosphere, to a three-neck, 300 mL flask, 5.00 g (13.2 mmol) of Intermediate IM-24, 9.83 g (1.1 eq, 14.6 mmol) of N-[(1,1'-biphenyl)-4-yl]-N-[4'-(4,4,5,5-tetramethyl-1,3,2-dioxaborolan-2-yl)-(1,1'-biphenyl)-4-yl]-(1,1': 2',1"-terphenyl)-4-amine, 5.49 g (3.0 eq, 39.7 mol) of $K_2CO_3$, 0.76 g (0.05 eq, 0.7 mmol) of $Pd(PPh_3)_4$, and 93 mL of a mixture of toluene/ethanol (EtOH)/water (4/2/1) were added in order, followed by heating and stirring at about 80° C. After cooling in the air to room temperature, the reaction solution was extracted with toluene. The aqueous layer was removed, and the organic layer was washed with a saturated saline solution and dried over $MgSO_4$. $MgSO_4$ was filtered and an organic layer was concentrated, and the crude product thus obtained was separated by silica gel column chromatography (using a mixture of hexane and toluene as a developing solution) to obtain Compound D74 (9.32 g, yield 79%) as a white solid. As measured by FAB-MS, mass number m/z=891 was observed as a molecular ion peak and Compound D74 was identified.

Synthesis of Compound E6

Amine Compound E6 according to an embodiment of the present disclosure may be synthesized, for example, by Reaction 11:

Reaction 11

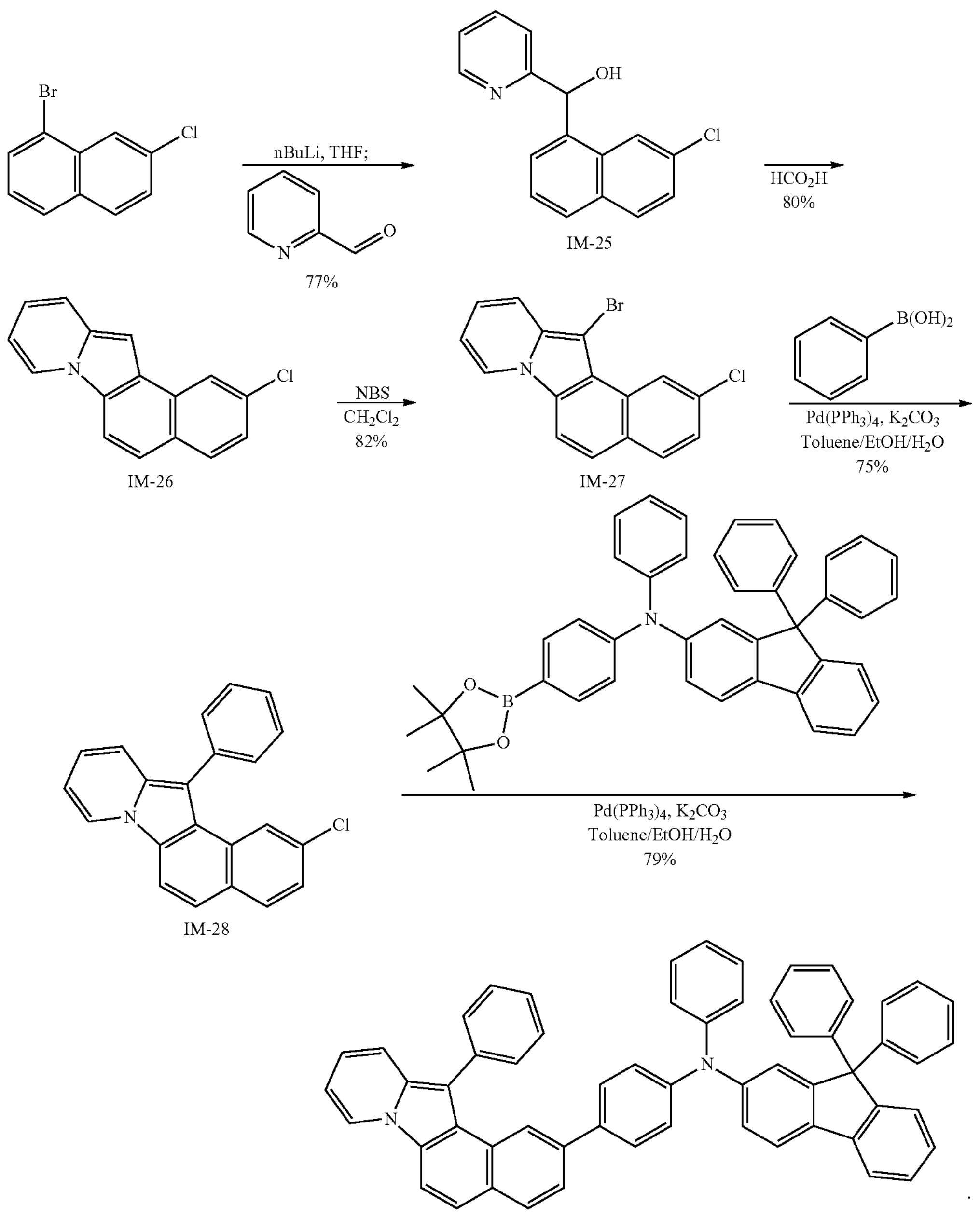

E6

Synthesis of Intermediate IM-25

Under an argon atmosphere, to a three-neck, 1,000 mL flask, 25.00 g (103.5 mmol) of 1-bromo-7-chloronaphthalene and 345 mL (0.3 M) of THF were added, and while stirring at about −78° C., 71.2 mL (1.1 eq) of a nBuLi/n-hexane solution of 1.6 mol/L was added dropwise thereto. After stirring for about 1 hour at the same temperature, a THF solution (29 mL, 1 mol/L) of 12.20 g (1.1 eq, 113.9 mmol) of picolinaldehyde was added dropwise thereto and stirred for about 30 minutes at the same temperature. Then, the temperature was increased to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-25 (21.50 g, yield 77%). As measured by FAB-MS, mass number m/z=269 was observed as a molecular ion peak and Intermediate IM-25 was identified.

Synthesis of Intermediate IM-26

Under an argon atmosphere, to a three-neck, 500 mL flask, 20.00 g (74.1 mmol) of Intermediate IM-25 and 247 mL (0.3 M) of formic acid were added, followed by stirring and heating at about 120° C. After air cooling the reaction solution to room temperature, the reaction solution was cooled and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-26 (14.93 g, yield 80%). As measured by FAB-MS, mass number m/z=251 was observed as a molecular ion peak and Intermediate IM-26 was identified.

Synthesis of Intermediate IM-27

Under an argon atmosphere, to a three-neck, 500 mL flask, 12.00 g (47.7 mmol) of IM-26, 239 mL of $CH_2Cl_2$, and 10.18 g (1.2 eq, 57.2 mmol) of N-bromosuccinimide were added in order and stirred at room temperature. Water was added to the reaction solution, and extraction with $CHCl_3$ was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-27 (12.92 g, yield 82%). As measured by FAB-MS, mass number m/z=330 was observed as a molecular ion peak and Intermediate IM-27 was identified.

Synthesis of Intermediate IM-28

Under an argon atmosphere, to a three-neck, 500 mL flask, 10.00 g (30.2 mmol) of Intermediate IM-27, 4.06 g (1.1 eq, 33.3 mmol) of phenylboronic acid, 12.54 g (3.0 eq, 90.7 mmol) of $K_2CO_3$, 1.75 g (0.05 eq, 1.5 mmol) of $Pd(PPh_3)_4$, and 212 mL of a mixture solution of toluene/ethanol (EtOH)/water (4/2/1) were added in order and stirred while heating at about 80° C. The reaction solution was air cooled and then extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-28 (7.44 g, yield 75%). As measured by FAB-MS, mass number m/z=327 was observed as a molecular ion peak and Intermediate IM-28 was identified.

Synthesis of Compound E6

Under an argon atmosphere, to a three-neck, 300 mL flask, 5.00 g (13.2 mmol) of Intermediate IM-28, 8.90 g (1.1 eq, 14.6 mmol) of N,9,9-triphenyl-N-[4-(4,4,5,5-tetramethyl-1,3,2-dioxaborolan-2-yl)phenyl]-9H-fluoren-2-amine, 5.49 g (3.0 eq, 39.7 mmol) of $K_2CO_3$, 0.76 g (0.05 eq, 0.7 mmol) of $Pd(PPh_3)_4$, and 93 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound E6 (7.20 g, yield 70%) as a white solid. As measured by FAB-MS, mass number m/z=776 was observed as a molecular ion peak and Compound E6 was identified.

Synthesis of Compound E25

Amine Compound E25 according to an embodiment of the present disclosure may be synthesized, for example, by Reaction 12:

Reaction 12

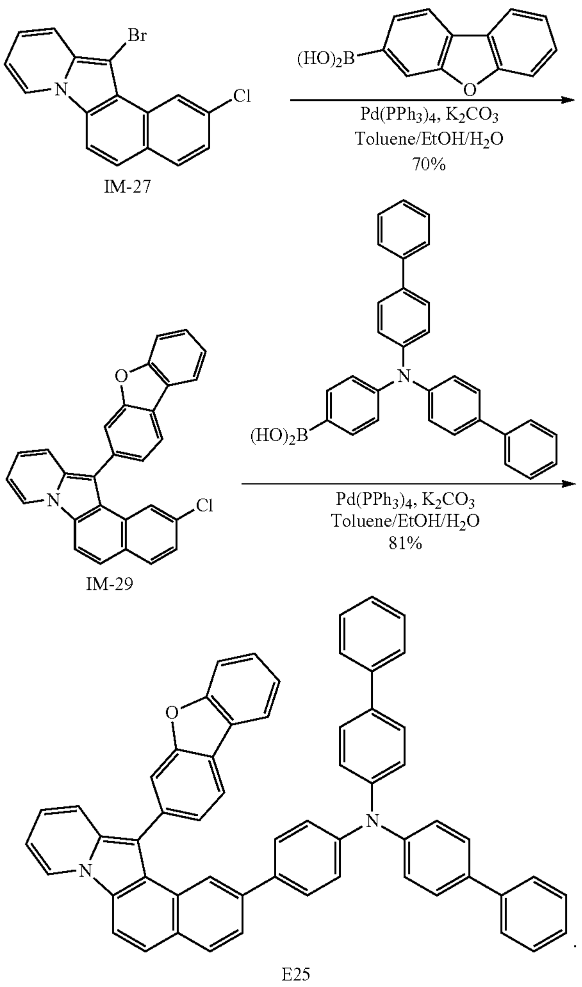

Synthesis of Intermediate IM-29

Under an argon atmosphere, to a three-neck, 500 mL flask, 10.00 g (30.2 mmol) of IM-27, 7.05 g (1.1 eq, 33.3 mmol) of dibenzofuran-3-ylboronic acid, 12.54 g (3.0 eq, 90.7 mmol) of $K_2CO_3$, 1.75 g (0.05 eq, 1.5 mmol) of $Pd(PPh_3)_4$, and 212 mL of a mixture of toluene/ethanol (EtOH)/water (4/2/1) were added in order, followed by heating and stirring at about 80° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-29 (8.85 g, yield 70%). As measured by FAB-MS, mass number m/z=417 was observed as a molecular ion peak and Intermediate IM-29 was identified.

Synthesis of Compound E25

Under an argon atmosphere, to a three-neck, 300 mL flask, 5.00 g (12.0 mmol) of Intermediate IM-29, 5.81 g (1.1 eq, 13.2 mmol) of 4-di[(1,1'-biphenyl)-4-yl]aminophenylboronic acid, 4.96 g (3.0 eq, 35.9 mmol) of $K_2CO_3$, 0.69 g (0.05 eq, 0.6 mmol) of $Pd(PPh_3)_4$, and 84 mL of a mixture of toluene/ethanol (EtOH)/water (4/2/1) were added in order, followed by heating and stirring at about 80° C. After air cooling to room temperature, the reaction solution was extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound E25 (7.55 g, yield 81%) as a white solid. As measured by FAB-MS, mass number m/z=778 was observed as a molecular ion peak and Compound E25 was identified.

Synthesis of Compound E55

Amine Compound E55 according to an embodiment of the present disclosure may be synthesized, for example, by Reaction 13:

Reaction 13

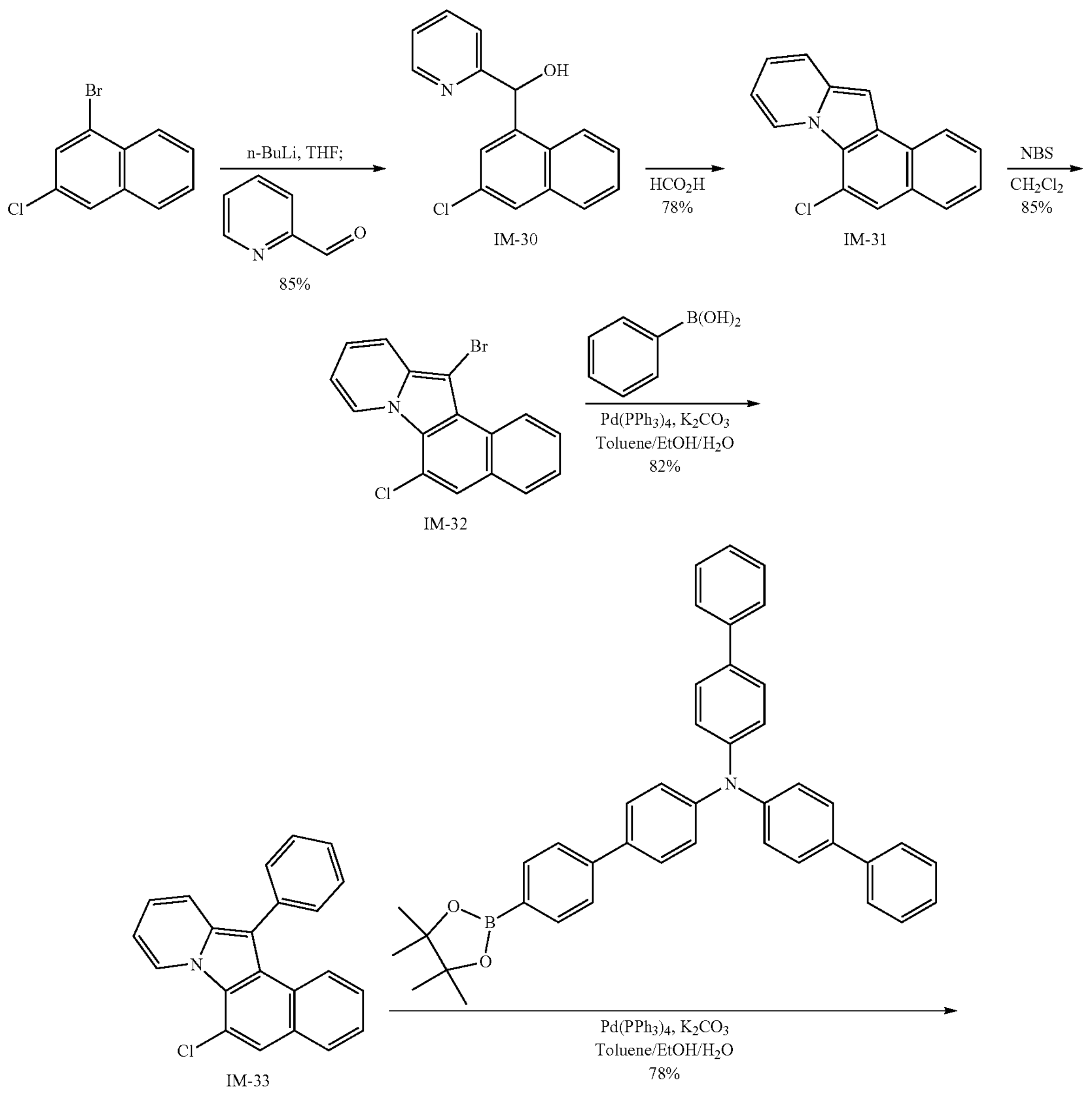

IM-30

IM-31

IM-32

IM-33

-continued

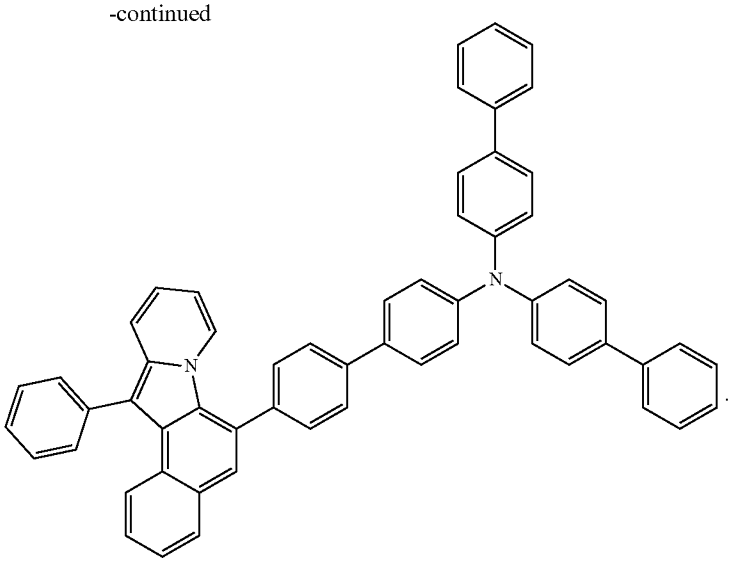

E55

Synthesis of Intermediate IM-30

Under an argon atmosphere, to a three-neck, 1,000 mL flask, 25.00 g (103.5 mmol) of 1-bromo-3-chloronaphthalene and 345 mL (0.3 M) of THF were added, and while stirring at about −78° C., 71.2 mL (1.1 eq) of a nBuLi/n-hexane solution of 1.6 mol/L was added dropwise thereto. After stirring for about 1 hour at the same temperature, a THF solution (29 mL, 1 mol/L) of 12.20 g (1.1 eq, 113.9 mmol) of picolinaldehyde was added dropwise thereto and stirred for about 30 minutes at the same temperature. Then, the temperature was increased to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-30 (23.73 g, yield 85%). As measured by FAB-MS, mass number m/z=269 was observed as a molecular ion peak and Intermediate IM-30 was identified.

Synthesis of Intermediate IM-31

Under an argon atmosphere, to a three-neck, 500 mL flask, 20.00 g (74.1 mmol) of Intermediate IM-30 and 247 mL (0.3 M) of formic acid were added, followed by stirring and heating at about 120° C. After air cooling to room temperature, the reaction solution was further cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-31 (14.56 g, yield 78%). As measured by FAB-MS, mass number m/z=251 was observed as a molecular ion peak and Intermediate IM-31 was identified.

Synthesis of Intermediate IM-32

Under an argon atmosphere, to a three-neck, 500 mL flask, 12.00 g (47.7 mmol) of IM-31, 239 mL of $CH_2Cl_2$, and 10.18 g (1.2 eq, 57.2 mmol) of N-bromosuccinimide were added in order and stirred at room temperature. Water was added to the reaction solution, and extraction with $CHCl_3$ was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-32 (13.40 g, yield 85%). As measured by FAB-MS, mass number m/z=330 was observed as a molecular ion peak and Intermediate IM-32 was identified.

Synthesis of Intermediate IM-33

Under an argon atmosphere, to a three-neck, 500 mL flask, 10.00 g (30.2 mmol) of Intermediate IM-33, 4.06 g (1.1 eq, 33.3 mmol) of phenylboronic acid, 12.54 g (3.0 eq, 90.7 mmol) of $K_2CO_3$, 1.75 g (0.05 eq, 1.5 mmol) of $Pd(PPh_3)_4$, and 212 mL of a mixture of toluene/ethanol (EtOH)/water (4/2/1) were added in order and stirred while heating at about 80° C. The reaction solution was air cooled to room temperature and then extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-33 (7.44 g, yield 75%). As measured by FAB-MS, mass number m/z=327 was observed as a molecular ion peak and Intermediate IM-33 was identified.

Synthesis of Compound E55

Under an argon atmosphere, to a three-neck, 300 mL flask, 5.00 g (13.2 mmol) of Intermediate IM-33, 10.06 g (1.1 eq, 14.6 mmol) of N,N-di[(1,1'-biphenyl)-4-yl]-4'-(4,4,5,5-tetramethyl-1,3,2-dioxaborolan-2-yl)-(1,1'-biphenyl)-4-amine, 5.49 g (3.0 eq, 39.7 mmol) of $K_2CO_3$, 0.76 g (0.05 eq, 0.7 mmol) of $Pd(PPh_3)_4$, and 93 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound E55 (9.10 g, yield 78%) as a white solid. As measured by FAB-MS, mass number m/z=764 was observed as a molecular ion peak and Compound E55 was identified.

Synthesis of Compound E73

Amine Compound E73 according to an embodiment of the present disclosure may be synthesized, for example, by Reaction 14:

Reaction 14

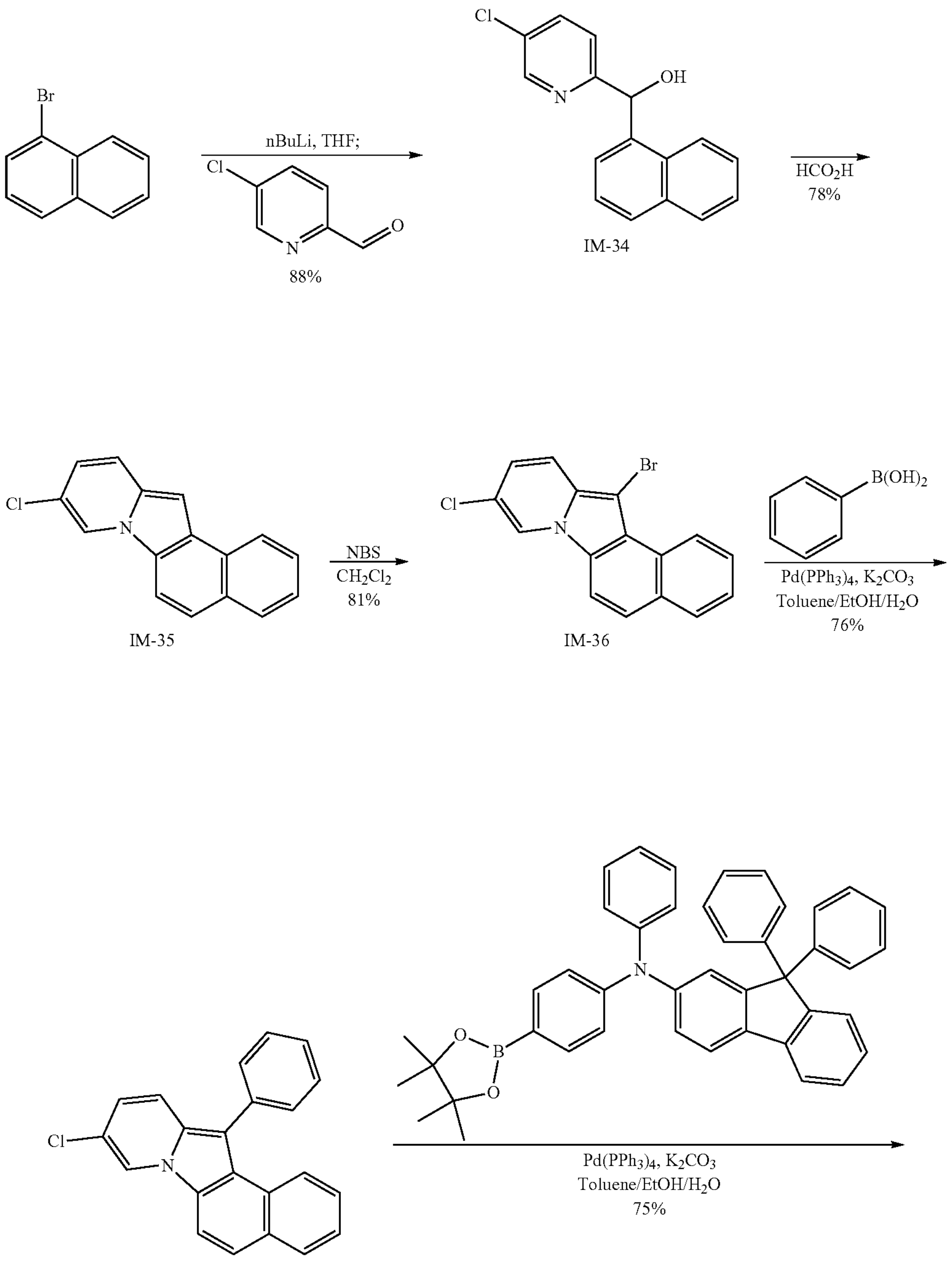

IM-34

IM-35

IM-36

IM-37

-continued

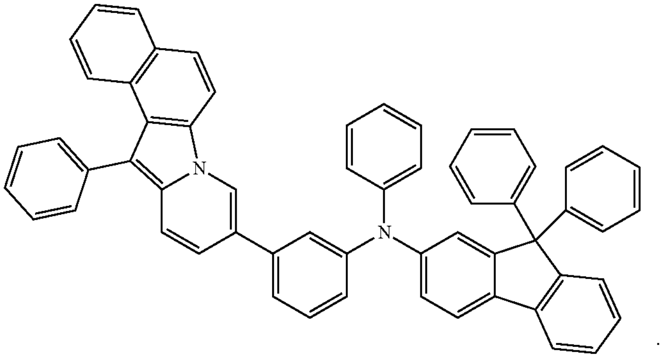

E73

Synthesis of Intermediate IM-34

Under an argon atmosphere, to a three-neck, 1,000 mL flask, 20.00 g (96.6 mmol) of 1-bromonaphthalene and 322 mL (0.3 M) of THF were added, and while stirring at about −78° C., 66.4 mL (1.1 eq) of a nBuLi/n-hexane solution of 1.6 mol/L was added dropwise thereto. After stirring for about 1 hour at the same temperature, a THF solution (27 mL, 1 mol/L) of 15.04 g (1.1 eq, 106.2 mmol) of 5-chloropicolinaldehyde was added dropwise thereto and stirred for about 30 minutes at the same temperature. Then, the temperature was increased to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-34 (22.93 g, yield 88%). As measured by FAB-MS, mass number m/z=269 was observed as a molecular ion peak and Intermediate IM-34 was identified.

Synthesis of Intermediate IM-35

Under an argon atmosphere, to a three-neck, 500 mL flask, 20.00 g (74.1 mmol) of Intermediate IM-34 and 247 mL (0.3 M) of formic acid were added, followed by stirring and heating at about 120° C. After air cooling the reaction solution to room temperature, the reaction solution was further cooled and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-35 (14.56 g, yield 78%). As measured by FAB-MS, mass number m/z=251 was observed as a molecular ion peak and Intermediate IM-35 was identified.

Synthesis of Intermediate IM-36

Under an argon atmosphere, to a three-neck, 500 mL flask, 12.00 g (47.7 mmol) of IM-35, 239 mL of $CH_2Cl_2$, and 10.18 g (1.2 eq, 57.2 mmol) of N-bromosuccinimide were added in order and stirred at room temperature. Water was added to the reaction solution, and extraction with $CHCl_3$ was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-36 (12.77 g, yield 81%). As measured by FAB-MS, mass number m/z=330 was observed as a molecular ion peak and Intermediate IM-36 was identified.

Synthesis of Intermediate IM-37

Under an argon atmosphere, to a three-neck, 500 mL flask, 10.00 g (30.2 mmol) of Intermediate IM-36, 4.06 g (1.1 eq, 33.3 mmol) of phenylboronic acid, 12.54 g (3.0 eq, 90.7 mmol) of $K_2CO_3$, 1.75 g (0.05 eq, 1.5 mmol) of $Pd(PPh_3)_4$, and 212 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-37 (7.73 g, yield 78%). As measured by FAB-MS, mass number m/z=327 was observed as a molecular ion peak and Intermediate IM-37 was identified.

Synthesis of Compound E73

Under an argon atmosphere, to a three-neck, 300 mL flask, 5.00 g (13.2 mmol) of Intermediate IM-37, 10.06 g (1.1 eq, 14.6 mmol) of N,9,9-triphenyl-N-[4-(4,4,5,5-tetramethyl-1,3,2-dioxaborolan-2-yl)phenyl]-9H-fluoren-2-amine, 5.49 g (3.0 eq, 39.7 mmol) of $K_2CO_3$, 0.76 g (0.05 eq, 0.7 mmol) of $Pd(PPh_3)_4$, and 93 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound E73 (8.88 g, yield 75%) as a white solid. As measured by FAB-MS, mass number m/z=776 was observed as a molecular ion peak and Compound E73 was identified.

Synthesis of Compound E89

Amine Compound E89 according to an embodiment of the present disclosure may be synthesized, for example, by Reaction 15:

Reaction 15

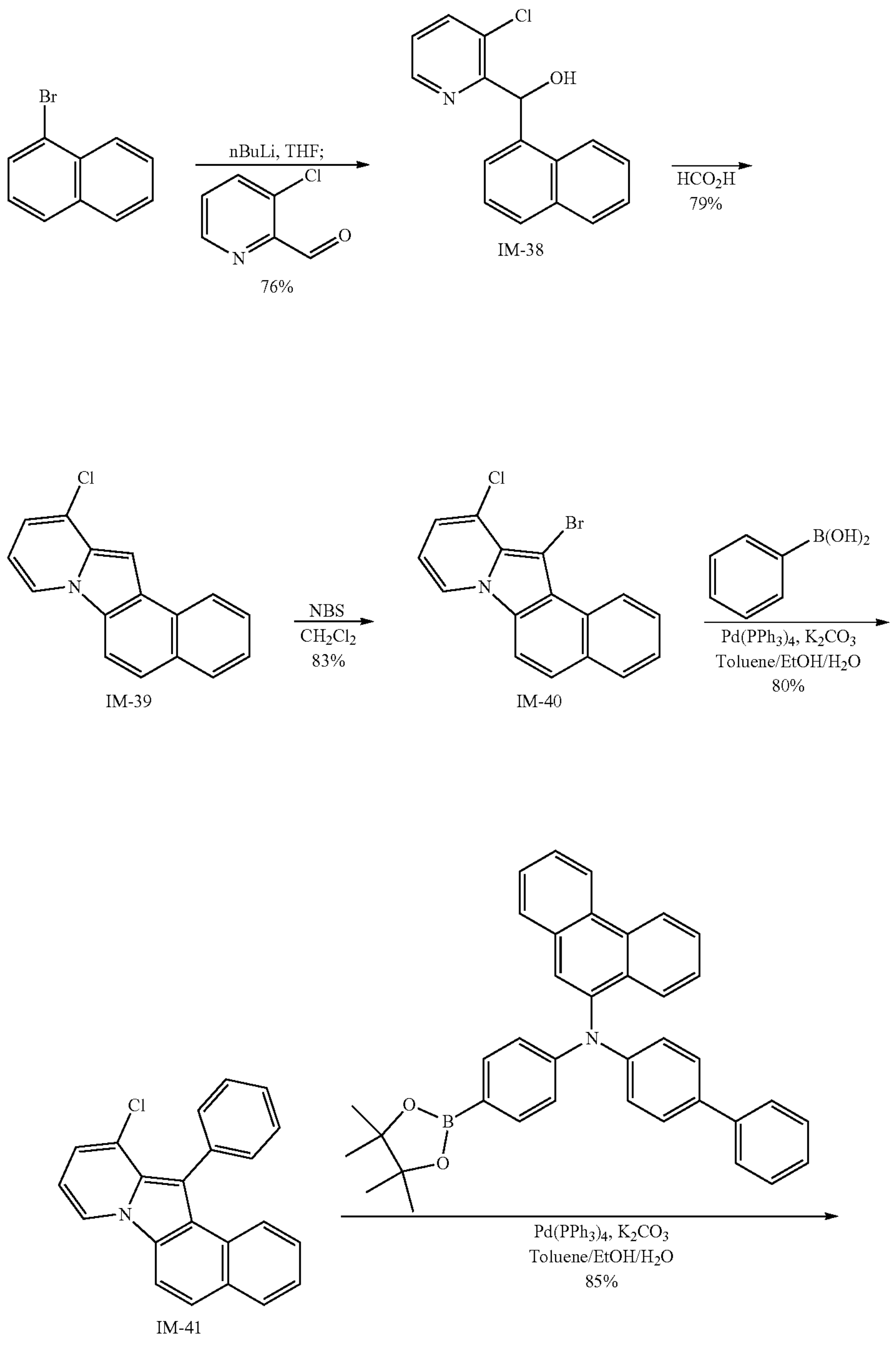

-continued

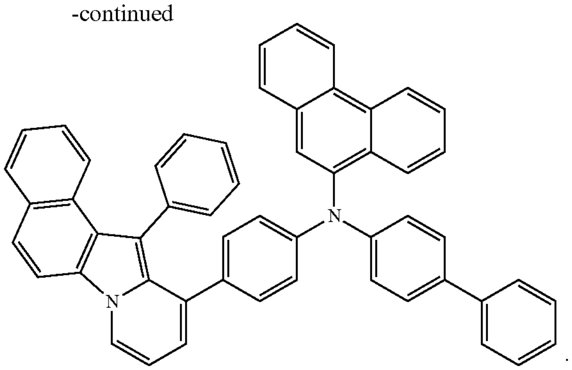

E89

Synthesis of Intermediate IM-38

Under an argon atmosphere, to a three-neck, 1,000 mL flask, 20.00 g (96.6 mmol) of 1-bromonaphthalene and 322 mL (0.3 M) of THF were added, and while stirring at about −78° C., 66.4 mL (1.1 eq) of a nBuLi/n-hexane solution of 1.6 mol/L was added dropwise thereto. After stirring for about 1 hour at the same temperature, a THF solution (27 mL, 1 mol/L) of 15.04 g (1.1 eq, 106.2 mmol) of 3-chloropicolinaldehyde was added dropwise thereto and stirred for about 30 minutes at the same temperature. Then, the temperature was increased to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-38 (19.80 g, yield 76%). As measured by FAB-MS, mass number m/z=269 was observed as a molecular ion peak and Intermediate IM-38 was identified.

Synthesis of Intermediate IM-39

Under an argon atmosphere, to a three-neck, 500 mL flask, 20.00 g (74.1 mmol) of Intermediate IM-38 and 247 mL (0.3 M) of formic acid were added, followed by stirring and heating at about 120° C. After air cooling to room temperature, the reaction solution was further cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-39 (14.74 g, yield 78%). As measured by FAB-MS, mass number m/z=251 was observed as a molecular ion peak and Intermediate IM-39 was identified.

Synthesis of Intermediate IM-40

Under an argon atmosphere, to a three-neck, 500 mL flask, 12.00 g (47.7 mmol) of Intermediate IM-39, 239 mL of $CH_2Cl_2$, and 10.18 g (1.2 eq, 57.2 mmol) of N-bromosuccinimide were added in order and stirred at room temperature. Water was added to the reaction solution, and extraction with $CHCl_3$ was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-40 (13.08 g, yield 83%). As measured by FAB-MS, mass number m/z=330 was observed as a molecular ion peak and Intermediate IM-40 was identified.

Synthesis of Intermediate IM-41

Under an argon atmosphere, to a three-neck, 500 mL flask, 10.00 g (30.2 mmol) of Intermediate IM-40, 4.06 g (1.1 eq, 33.3 mmol) of phenylboronic acid, 12.54 g (3.0 eq, 90.7 mmol) of $K_2CO_3$, 1.75 g (0.05 eq, 1.5 mmol) of $Pd(PPh_3)_4$, and 212 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-41 (7.93 g, yield 80%). As measured by FAB-MS, mass number m/z=327 was observed as a molecular ion peak and Intermediate IM-41 was identified.

Synthesis of Compound E89

Under an argon atmosphere, to a three-neck, 300 mL flask, 5.00 g (13.2 mmol) of Intermediate IM-41, 9.19 g (1.1 eq, 14.6 mmol) of N-[(1,1'-biphenyl)-4-yl]-N-[4-(4,4,5,5-tetramethyl-1,3,2-dioxaborolan-2-yl)phenyl]phenanthren-9-amine, 5.49 g (3.0 eq, 39.7 mmol) of $K_2CO_3$, 0.76 g (0.05 eq, 0.7 mmol) of $Pd(PPh_3)_4$, and 93 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound E89 (9.24 g, yield 85%) as a white solid. As measured by FAB-MS, mass number m/z=712 was observed as a molecular ion peak and Compound E89 was identified.

Synthesis of Compound F21

Amine Compound F21 according to an embodiment of the present disclosure may be synthesized, for example, by Reaction 16:

Reaction 16

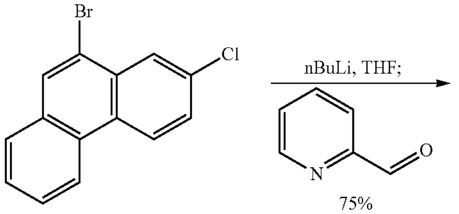

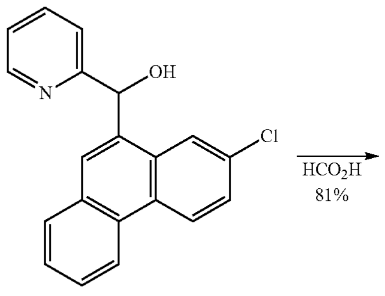

IM-42

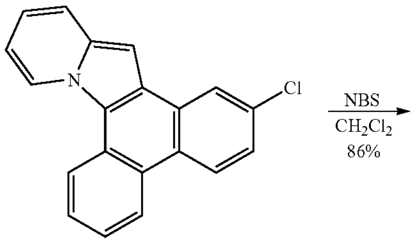

IM-43

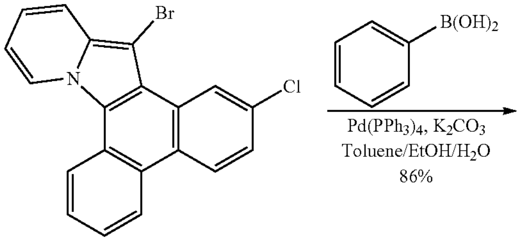

IM-44

-continued

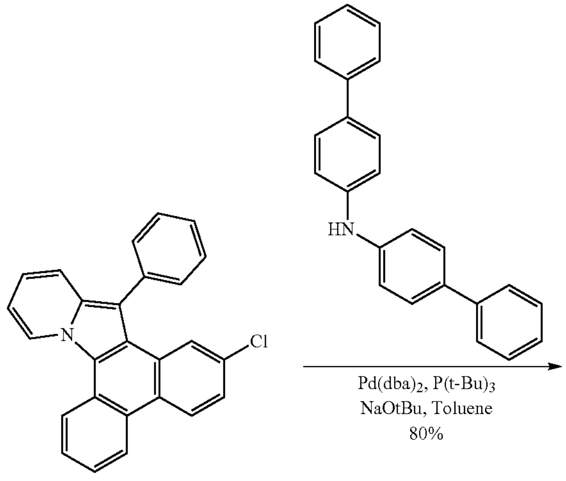

IM-45

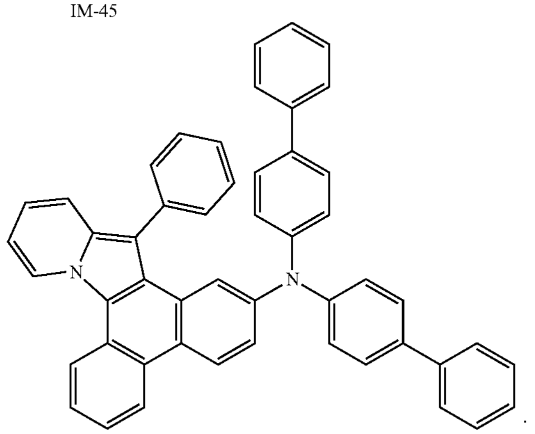

F21

Synthesis of Intermediate IM-42

Under an argon atmosphere, to a three-neck, 1,000 mL flask, 25.00 g (85.7 mmol) of 10-bromo-2-chloro-phenanthrene and 286 mL (0.3 M) of THF were added, and while stirring at about −78° C., 59.0 mL (1.1 eq) of a nBuLi/n-hexane solution of 1.6 mol/L was added dropwise thereto. After stirring for about 1 hour at the same temperature, a THF solution (24 mL, 1 mol/L) of 10.10 g (1.1 eq, 94.3 mmol) of picolinaldehyde was added dropwise thereto and stirred for about 30 minutes at the same temperature. Then, the temperature was increased to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-42 (20.57 g, yield 75%). As measured by FAB-MS, mass number m/z=319 was observed as a molecular ion peak and Intermediate IM-42 was identified.

Synthesis of Intermediate IM-43

Under an argon atmosphere, to a three-neck, 500 mL flask, 20.00 g (62.5 mmol) of Intermediate IM-42 and 208 mL (0.3 M) of formic acid were added, followed by stirring and heating at about 120° C. After air cooling the reaction solution to room temperature, the reaction solution was further cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-43 (15.29 g, yield 81%). As measured by FAB-MS, mass number m/z=301 was observed as a molecular ion peak and Intermediate IM-43 was identified.

Synthesis of Intermediate IM-44

Under an argon atmosphere, to a three-neck, 500 mL flask, 12.00 g (39.8 mmol) of Intermediate IM-43, 199 mL of $CH_2Cl_2$, and 8.49 g (1.2 eq, 47.7 mmol) of N-bromosuccinimide were added in order and stirred at room temperature. Water was added to the reaction solution, and extraction with $CHCl_3$ was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-44 (13.02 g, yield 86%). As measured by FAB-MS, mass number m/z=380 was observed as a molecular ion peak and Intermediate IM-44 was identified.

Synthesis of Intermediate IM-45

Under an argon atmosphere, to a three-neck, 500 mL flask, 10.00 g (26.3 mmol) of Intermediate IM-44, 3.52 g (1.1 eq, 28.9 mmol) of phenylboronic acid, 10.89 g (3.0 eq, 78.8 mmol) of $K_2CO_3$, 1.52 g (0.05 eq, 1.3 mmol) of $Pd(PPh_3)_4$, and 184 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-45 (8.54 g, yield 86%). As measured by FAB-MS, mass number m/z=377 was observed as a molecular ion peak and Intermediate IM-45 was identified.

Synthesis of Compound F21

Under an argon atmosphere, to a three-neck, 200 mL flask, 5.00 g (13.2 mmol) of Intermediate IM-45, 0.23 g (0.03 eq, 0.4 mmol) of $Pd(dba)_2$, 2.54 g (2.0 eq, 26.5 mmol) of NaO$^t$Bu, 66 mL of toluene, 4.68 g (1.1 eq, 14.6 mmol) of di[(1,1'-biphenyl)-4-yl]amine, and 0.27 g (0.1 eq, 1.3 mmol) of $^t$Bu$_3$P were added in order, followed by refluxing while heating and stirring. After cooling the reaction solution in the air to room temperature, water was added to the reaction solution and the organic layer was isolated. Toluene was added to the aqueous solution and additional organic layers were extracted. The organic layers were collected and washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound F21 (7.01 g, yield 80%) as a white solid. As measured by FAB-MS, mass number m/z=662 was observed as a molecular ion peak and Compound F21 was identified.

Synthesis of Compound F63

Amine Compound F63 according to an embodiment of the present disclosure may be synthesized, for example, by Reaction 17:

Reaction 17

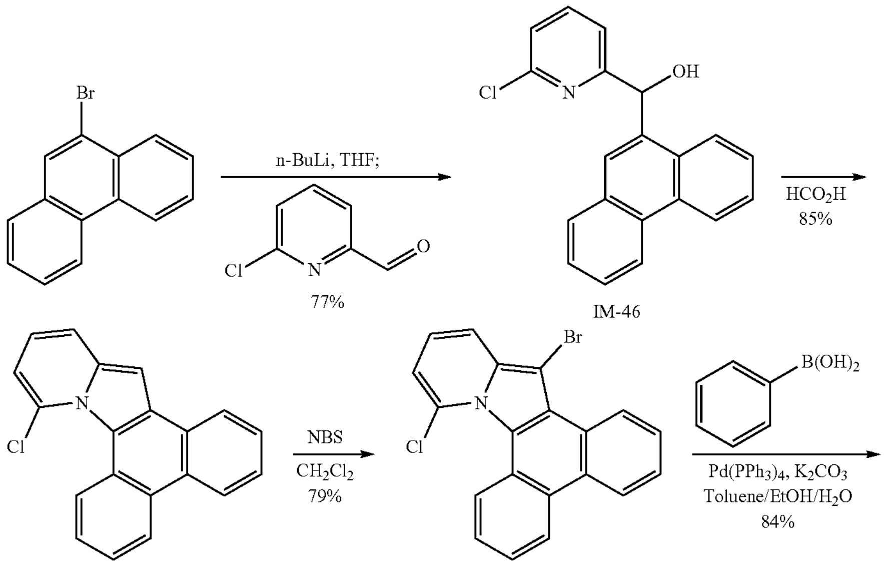

IM-46

IM-47

IM-48

-continued

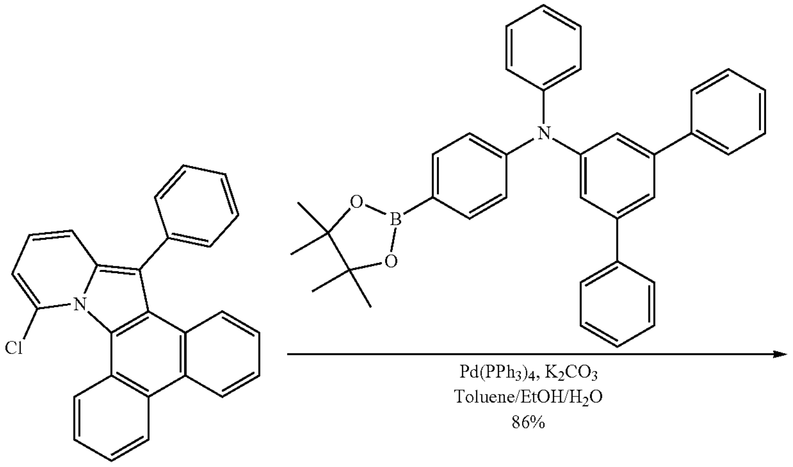

IM-49

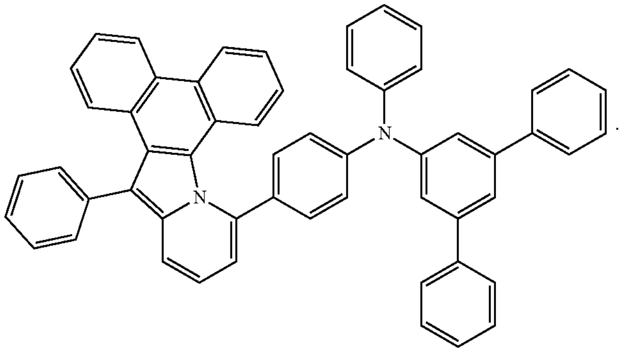

F63

Synthesis of Intermediate IM-46

Under an argon atmosphere, to a three-neck, 1,000 mL flask, 25.00 g (97.2 mmol) of 9-bromophenanthrene and 324 mL (0.3 M) of THF were added, and while stirring at about −78° C., 66.8 mL (1.1 eq) of a nBuLi/n-hexane solution of 1.6 mol/L was added dropwise thereto. After stirring for about 1 hour at the same temperature, a THF solution (27 mL, 1 mol/L) of 15.14 g (1.1 eq, 106.9 mmol) of 6-chloropicolinaldehyde was added dropwise thereto and stirred for about 30 minutes at the same temperature. Then, the temperature was increased to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-46 (23.94 g, yield 77%). As measured by FAB-MS, mass number m/z=319 was observed as a molecular ion peak and Intermediate IM-46 was identified.

Synthesis of Intermediate IM-47

Under an argon atmosphere, to a three-neck, 500 mL flask, 20.00 g (62.5 mmol) of Intermediate IM-46 and 208 mL (0.3 M) of formic acid were added, followed by stirring and heating at about 120° C. After air cooling the reaction solution to room temperature, the reaction solution was further cooled with water and extracted with toluene. The aqueous layer was removed, and the organic layer was washed with an aqueous sodium bicarbonate solution and a saturated saline solution and dried over $MgSO_4$. $MgSO_4$ was filtered and an organic layer was concentrated, and the crude product thus obtained was separated by silica gel column chromatography (using a mixture of hexane and toluene as a developing solution) to obtain Intermediate IM-47 (16.04 g, yield 85%). As measured by FAB-MS, mass number m/z=301 was observed as a molecular ion peak and Intermediate IM-47 was identified.

Synthesis of Intermediate IM-48

Under an argon atmosphere, to a three-neck, 500 mL flask, 12.00 g (39.8 mmol) of IM-47, 199 mL of $CH_2Cl_2$, and 8.49 g (1.2 eq, 47.7 mmol) of N-bromosuccinimide were added in order and stirred at room temperature. Water was added to the reaction solution, and extraction with $CHCl_3$ was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-48 (11.96 g, yield 79%). As measured by FAB-MS, mass number m/z=380 was observed as a molecular ion peak and Intermediate IM-48 was identified.

Synthesis of Intermediate IM-49

Under an argon atmosphere, to a three-neck, 500 mL flask, 10.00 g (26.3 mmol) of Intermediate IM-48, 3.52 g (1.1 eq, 28.9 mmol) of phenylboronic acid, 10.89 g (3.0 eq, 78.8 mmol) of $K_2CO_3$, 1.52 g (0.05 eq, 1.3 mmol) of $Pd(PPh_3)_4$, and 184 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-49 (8.34 g, yield 84%). As measured by FAB-MS, mass number m/z=377 was observed as a molecular ion peak and Intermediate IM-49 was identified.

Synthesis of Compound F63

Under an argon atmosphere, to a three-neck, 300 mL flask, 5.00 g (13.2 mmol) of Intermediate IM-49, 7.62 g (1.1 eq, 14.6 mmol) of N-phenyl-N-(4-(4,4,5,5-tetramethyl-1,3,2-dioxaborolan-2-yl)phenyl)-[1,1':3',1"-terphenyl]-5'-amine, 5.49 g (3.0 eq, 39.7 mmol) of $K_2CO_3$, 0.76 g (0.05 eq, 0.7 mmol) of $Pd(PPh_3)_4$, and 93 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound F63 (8.31 g, yield 85%) as a white solid. As measured by FAB-MS, mass number m/z=738 was observed as a molecular ion peak and Compound F63 was identified.

Synthesis of Compound F82

Amine Compound F82 according to an embodiment of the present disclosure may be synthesized, for example, by Reaction 18:

Reaction 18

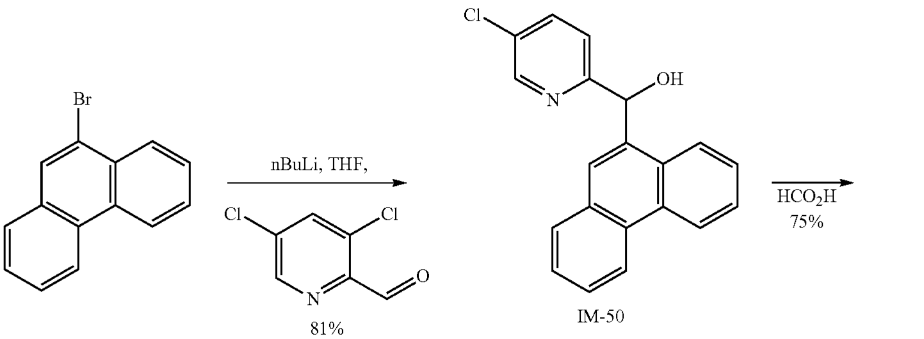

IM-50

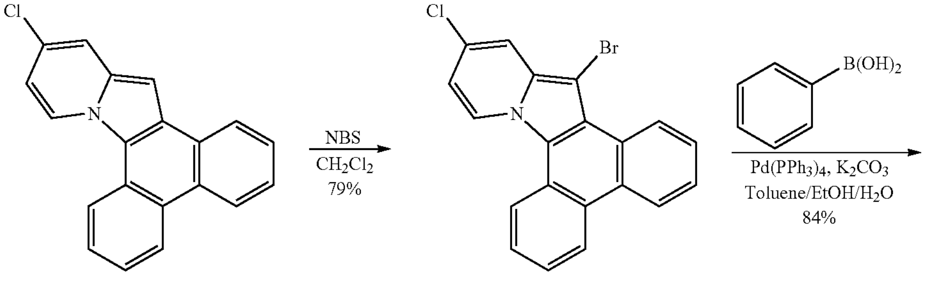

IM-51 IM-52

-continued

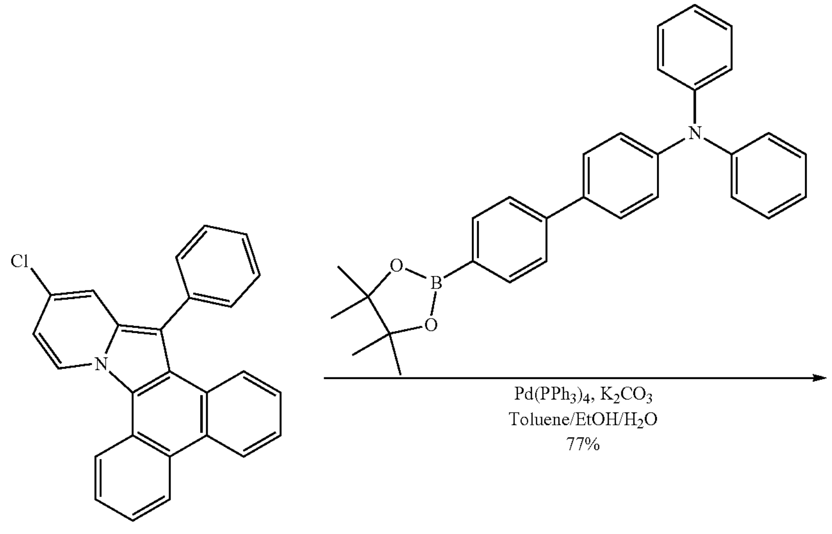

IM-53

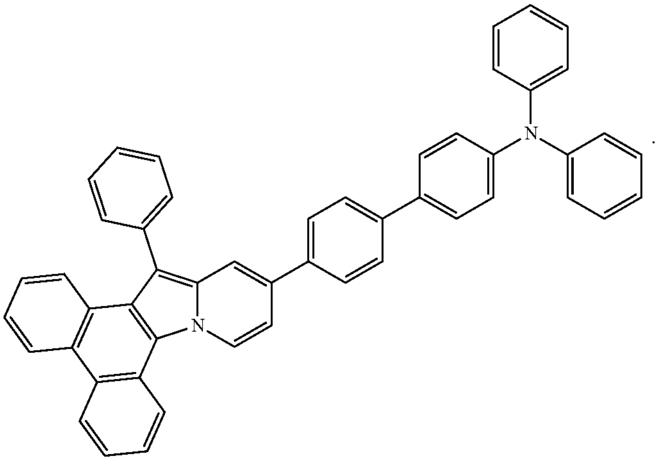

E82

Synthesis of Intermediate IM-50

Under an argon atmosphere, to a three-neck, 1,000 mL flask, 25.00 g (97.2 mmol) of 9-bromophenanthrene and 324 mL (0.3 M) of THF were added, and while stirring at about −78° C., 66.8 mL (1.1 eq) of a nBuLi/n-hexane solution of 1.6 mol/L was added dropwise thereto. After stirring for about 1 hour at the same temperature, a THF solution (27 mL, 1 mol/L) of 15.14 g (1.1 eq, 106.9 mmol) of 5-chloropicolinaldehyde was added dropwise thereto and stirred for about 30 minutes at the same temperature. Then, the temperature was increased to room temperature and additional stirring was performed. After securing the disappearance of raw materials, the reaction solution was cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-50 (25.18 g, yield 81%). As measured by FAB-MS, mass number m/z=319 was observed as a molecular ion peak and Intermediate IM-50 was identified.

Synthesis of Intermediate IM-51

Under an argon atmosphere, to a three-neck, 500 mL flask, 20.00 g (62.5 mmol) of Intermediate IM-50 and 208 mL (0.3 M) of formic acid were added, followed by stirring and heating at about 120° C. After cooling the reaction solution in the air to room temperature, the reaction solution was further cooled with water and extracted with toluene. The aqueous layer was removed, and the organic layer was washed with an aqueous sodium bicarbonate solution and a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-51 (14.15 g, yield 75%). As measured by FAB-MS, mass number m/z=301 was observed as a molecular ion peak and Intermediate IM-51 was identified.

Synthesis of Intermediate IM-52

Under an argon atmosphere, to a three-neck, 500 mL flask, 12.00 g (39.8 mmol) of Intermediate IM-51, 199 mL of $CH_2Cl_2$, and 8.49 g (1.2 eq, 47.7 mmol) of N-bromosuccinimide were added in order and stirred at room temperature. Water was added to the reaction solution, and extraction with $CHCl_3$ was performed. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-52 (11.96 g, yield 79%). As measured by FAB-MS, mass number m/z=380 was observed as a molecular ion peak and Intermediate IM-52 was identified.

Synthesis of Intermediate IM-53

Under an argon atmosphere, to a three-neck, 500 mL flask, 10.00 g (26.3 mmol) of Intermediate IM-52, 3.52 g (1.1 eq, 28.9 mmol) of phenylboronic acid, 10.89 g (3.0 eq, 78.8 mmol) of $K_2CO_3$, 1.52 g (0.05 eq, 1.3 mmol) of $Pd(PPh_3)_4$, and 184 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Intermediate IM-53 (8.34 g, yield 84%). As measured by FAB-MS, mass number m/z=377 was observed as a molecular ion peak and Intermediate IM-53 was identified.

Synthesis of Compound F82

Under an argon atmosphere, to a three-neck, 300 mL flask, 5.00 g (13.2 mmol) of Intermediate IM-53, 6.51 g (1.1 eq, 14.6 mmol) of N,N-diphenyl-4'-(4,4,5,5-tetramethyl-1,3,2-dioxaborolan-2-yl)-(1,1'-biphenyl)-4-amine, 5.49 g (3.0 eq, 39.7 mmol) of $K_2CO_3$, 0.76 g (0.05 eq, 0.7 mmol) of $Pd(PPh_3)_4$, and 93 mL of a mixture of toluene/ethanol (EtOH)/water (4/2/1) were added in order and stirred while heating at about 80° C. The reaction solution was air cooled to room temperature and extracted with toluene. The aqueous layer was removed, and the organic layer was washed with a saturated saline solution and dried over $MgSO_4$. $MgSO_4$ was filtered and the organic layer was concentrated, and the crude product thus obtained was separated by silica gel column chromatography (using a mixture of hexane and toluene as a developing solution) to obtain Compound F82 (6.74 g, yield 77%) as a white solid. As measured by FAB-MS, mass number m/z=662 was observed as a molecular ion peak and Compound F82 was identified.

2. Manufacture and Evaluation of Organic Electroluminescence Device Including Amine Compound Manufacture of Organic Electroluminescence Device Example organic electroluminescence devices including amine compounds according to embodiments of the present disclosure in their hole transport layers were manufactured by the method below. The organic electroluminescence devices of Examples 1 to 18 were manufactured using the amine compounds of Compound A1, Compound A28, Compound A57, Compound B36, Compound B46, Compound C47, Compound C87, Compound D47, Compound D60, Compound D74, Compound E6, Compound E25, Compound E55, Compound E73, Compound E89, Compound F21, Compound F63, and Compound F82, respectively, as materials for hole transport layers. The organic electroluminescence devices of Comparative Examples 1 to 6 were manufactured using Comparative Compounds R1 to R6, respectively, as materials for hole transport layers.

The compounds used in Examples 1 to 18 and Comparative Examples 1 to 6 are listed in Table 1:

TABLE 1

Compound A1

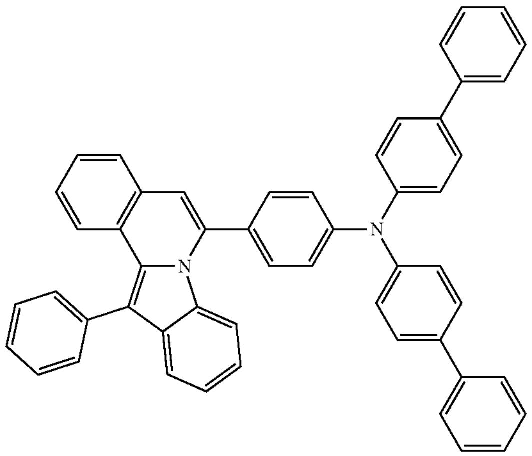

A1

TABLE 1-continued
Compound A28
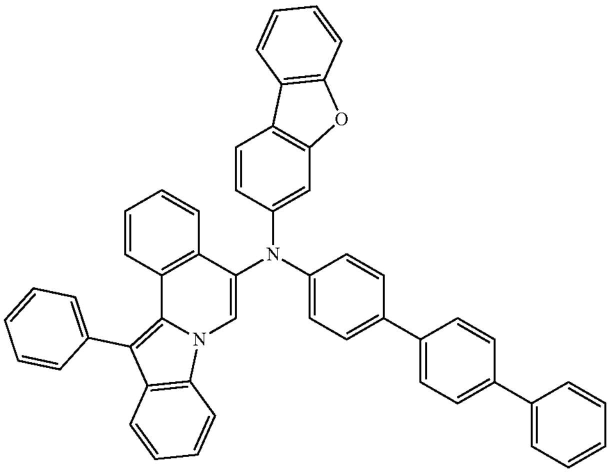
A28
Compound 57
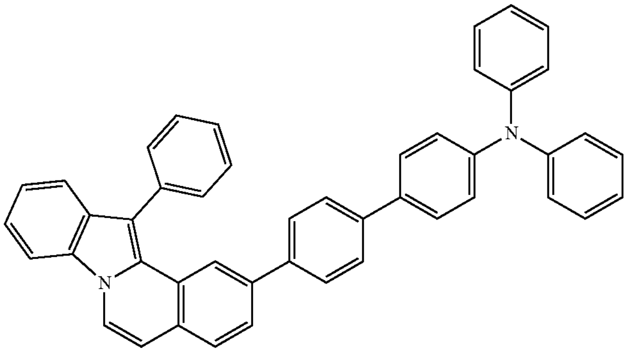
A57
Compound B36
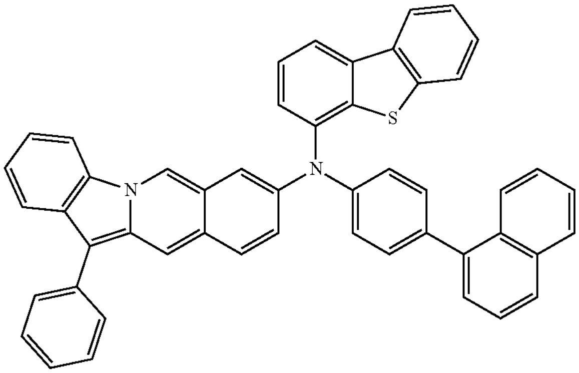
B36

TABLE 1-continued
Compound B46
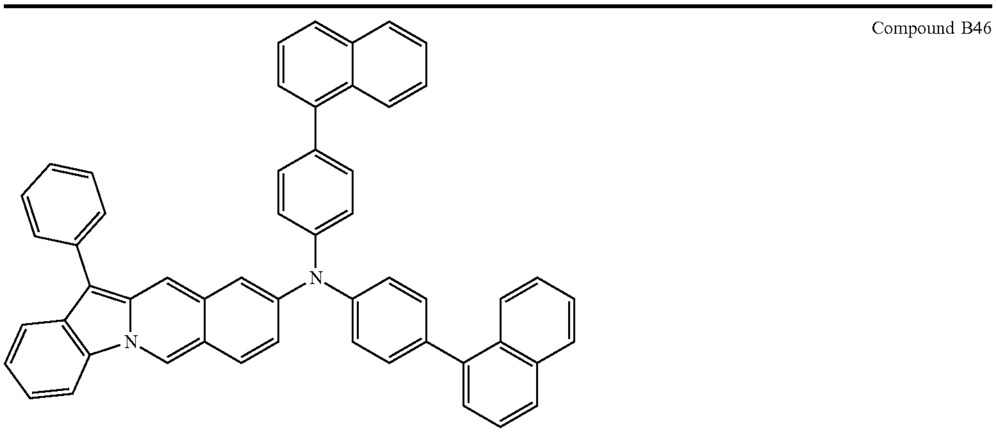
B46
Compound C47
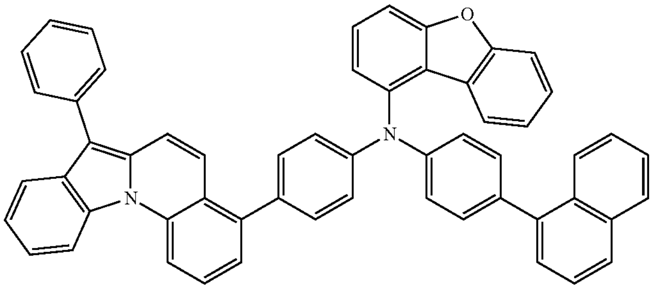
C47
Compound C87
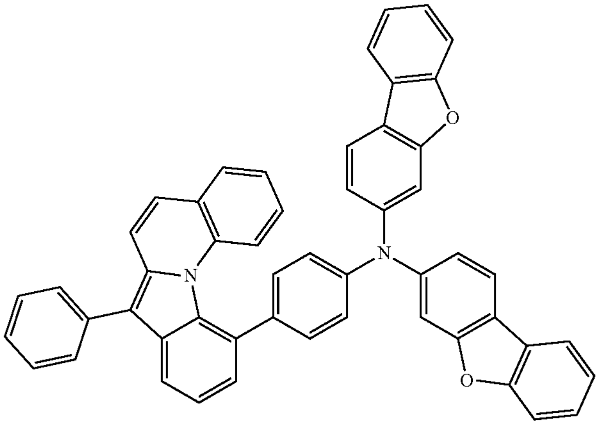
C87
Compound D47
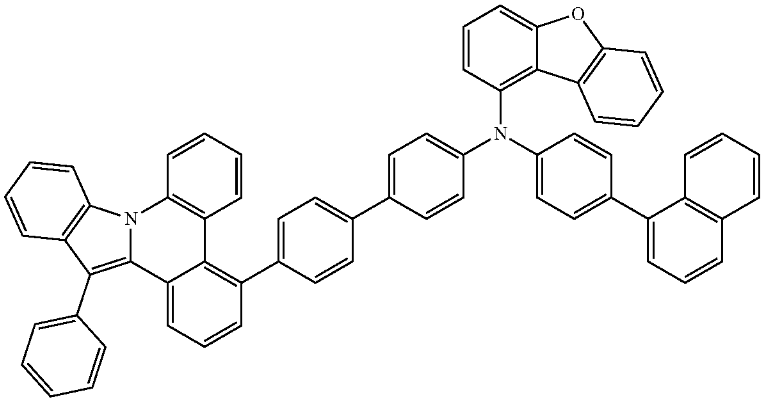
D47

TABLE 1-continued
Compound D60
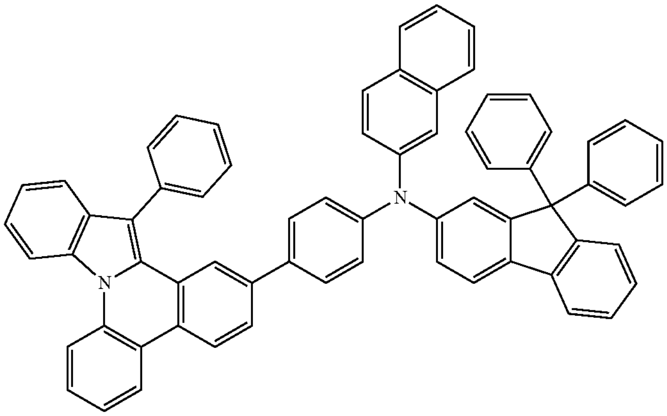
D60
Compound D74
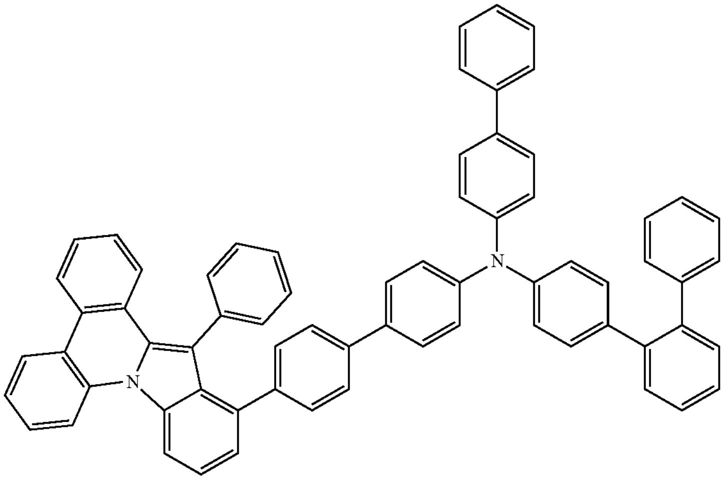
D74
Compound E6
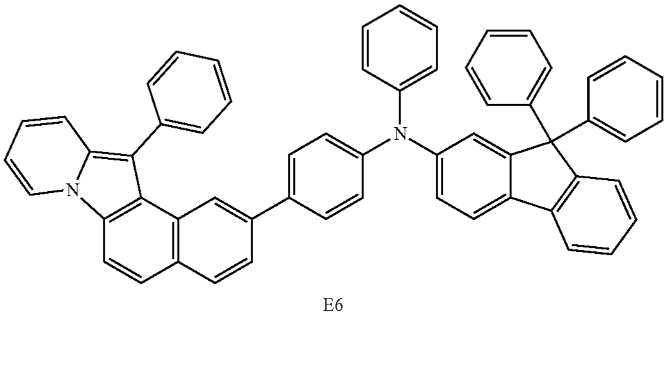 [SMILES: c1ccc(-c2c3c4cc(-c5ccc(N(c6ccccc6)c6ccc7c(c6)C(c6ccccc6)(c6ccccc6)c6ccccc6-7)cc5)ccc4ccc3n3ccccc23)cc1 ; "E6"]
E6

TABLE 1-continued
Compound E25
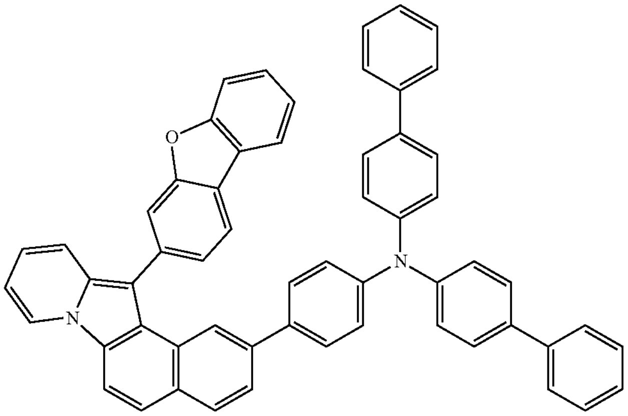
E25
Compound E55
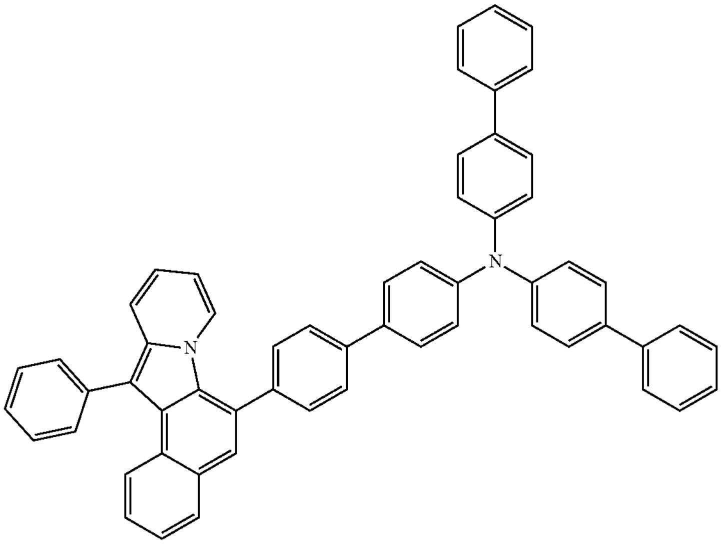
E55
Compound E73
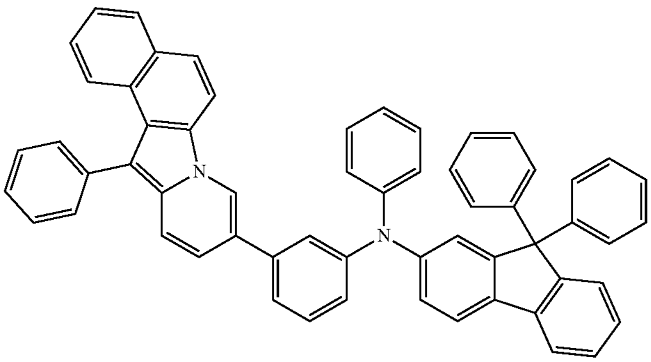
E73

TABLE 1-continued
Compound E89
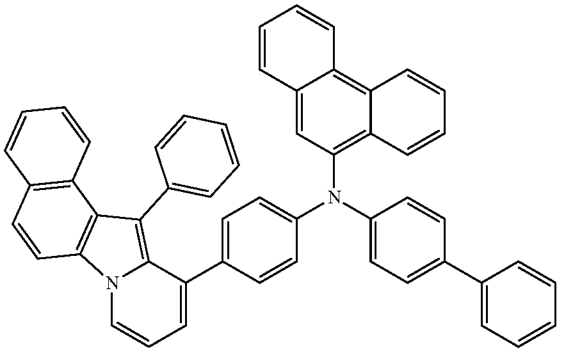
E89
Compound F21
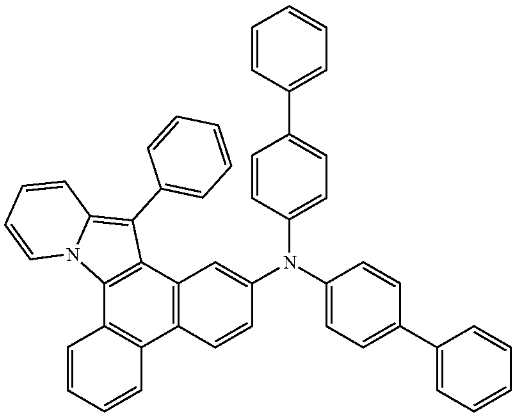
F21
Compound F63
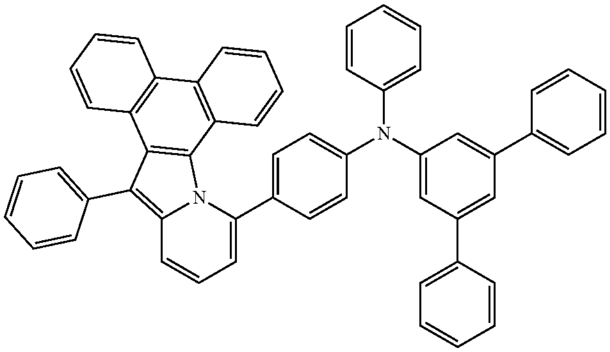
F63

TABLE 1-continued
Compound F82
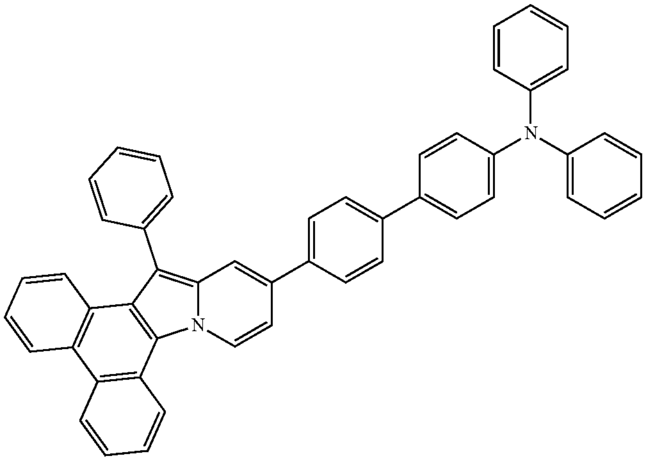
F82
Comparative Compound R1
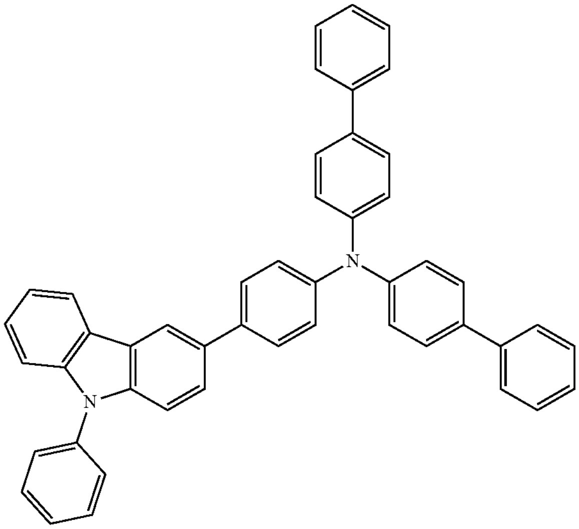
R1
Comparative Compound R2
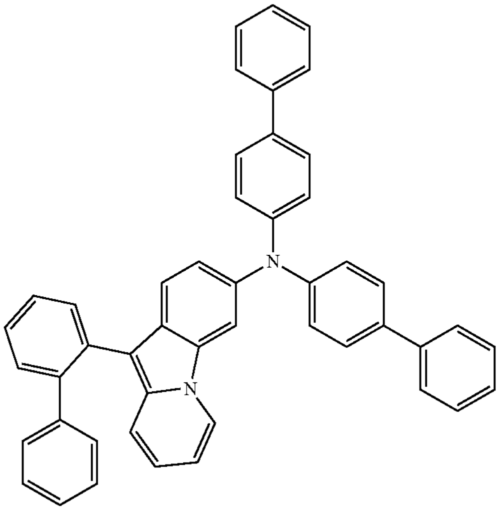
R2

TABLE 1-continued
Comparative Compound R3
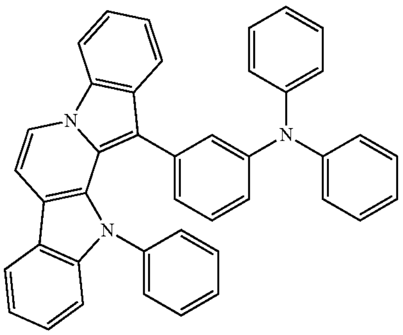
R3
Comparative Compound R4
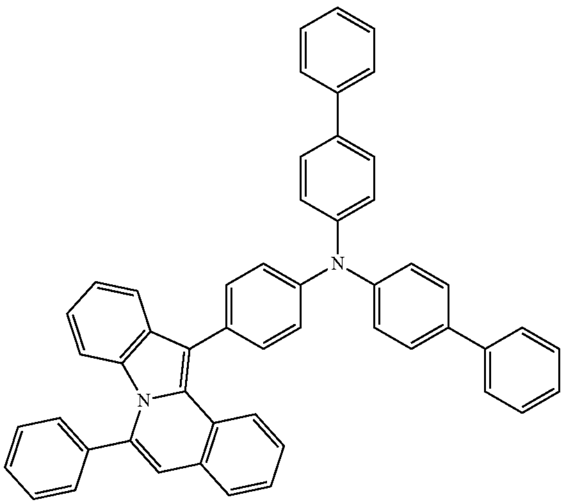
R4
Comparative Compound R5
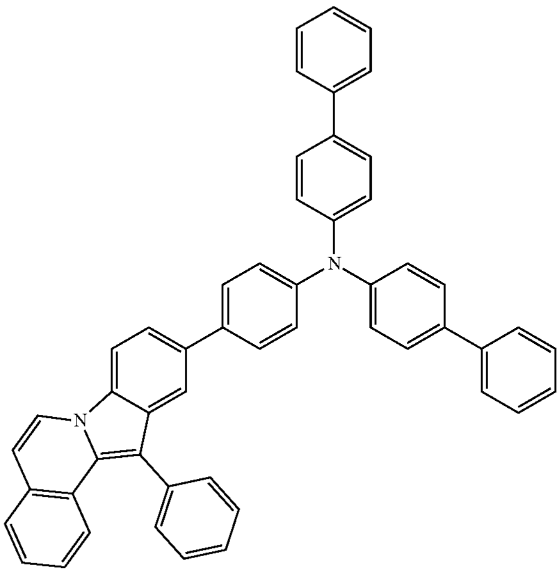
R5

TABLE 1-continued

Comparative Compound R6

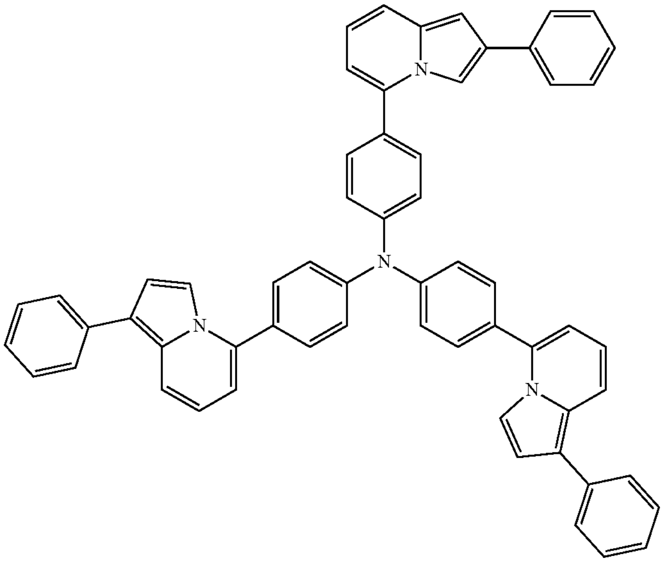

R6

On a glass substrate, ITO was patterned to a thickness of about 1,500 Å, washed with ultra-pure water, and subjected to UV ozone treatment for about 10 minutes. Then, a hole injection layer was formed by depositing 2-TNATA to a thickness of about 600 Å. Then, a hole transport layer was formed by depositing the Example Compound or the Comparative Compound to a thickness of about 300 Å.

After that, an emission layer was formed using ADN doped with 3% TBP to a thickness of about 250 Å. Then, an electron transport layer was formed by depositing $Alq_3$ to a thickness of about 250 Å and an electron injection layer was formed by depositing LiF to a thickness of about 10 Å.

Then, a second electrode was formed by depositing Al to a thickness of about 1,000 Å.

The hole injection layer, the hole transport layer, the emission layer, the electron transport layer, the electron injection layer and the second electrode were each formed using a vacuum deposition apparatus.

Evaluation of Properties of Organic Electroluminescence Device

The evaluation results of the organic electroluminescence devices according to Example 1 to Example 18 and Comparative Example 1 to Comparative Example 6 are shown in Table 2. In Table 2, the driving voltage, the emission efficiency, and the device life of the organic electroluminescence devices thus manufactured are compared and shown. In the evaluation results of the properties of the Examples and the Comparative Examples in Table 2, the emission efficiency is the efficiency value at a current density of 10 $mA/cm^2$, and the device life is the half-life at a current density of 1.0 $mA/cm^2$.

The current density, voltage, and emission efficiency of the organic electroluminescence devices of the Examples and the Comparative Examples were measured using a 2400 series Source Meter (Keithley Instrument Co.), a luminous brightness measurement apparatus, CS-200 (Konica Minolta Co.), and PC Program LabVIEW 2.0 (National Instrument Co., Japan).

TABLE 2

| Device manufacturing example | Hole transport layer material | Voltage (V) | Emission efficiency (cd/A) | Device life [LT50] (hrs) |
|---|---|---|---|---|
| Example 1 | Compound A1 | 5.4 | 7.8 | 2050 |
| Example 2 | Compound A28 | 5.5 | 7.8 | 2000 |
| Example 3 | Compound A57 | 5.6 | 7.6 | 2000 |
| Example 4 | Compound B36 | 5.7 | 7.9 | 2050 |
| Example 5 | Compound B46 | 5.6 | 8.0 | 1950 |
| Example 6 | Compound C47 | 5.9 | 8.0 | 1900 |
| Example 7 | Compound C87 | 5.6 | 7.7 | 2050 |
| Example 8 | Compound D47 | 5.9 | 7.9 | 2050 |
| Example 9 | Compound D60 | 5.8 | 7.8 | 2100 |
| Example 10 | Compound D74 | 5.7 | 7.8 | 2100 |
| Example 11 | Compound E6 | 5.6 | 7.7 | 2050 |
| Example 12 | Compound E25 | 5.6 | 7.7 | 2000 |
| Example 13 | Compound E55 | 5.8 | 7.6 | 2000 |
| Example 14 | Compound E73 | 5.7 | 7.8 | 2050 |
| Example 15 | Compound E89 | 5.8 | 7.8 | 2000 |
| Example 16 | Compound F21 | 5.6 | 7.6 | 2100 |
| Example 17 | Compound F63 | 5.8 | 7.8 | 2050 |
| Example 18 | Compound F82 | 5.6 | 7.6 | 2000 |
| Comparative Example 1 | Comparative Compound R1 | 6.3 | 6.4 | 1600 |
| Comparative Example 2 | Comparative Compound R2 | 6.2 | 6.4 | 1650 |
| Comparative Example 3 | Comparative Compound R3 | 6.5 | 6.0 | 1650 |
| Comparative Example 4 | Comparative Compound R4 | 6.0 | 7.0 | 1800 |
| Comparative Example 5 | Comparative Compound R5 | 6.0 | 7.0 | 1850 |
| Comparative Example 6 | Comparative Compound R6 | 6.7 | 5.8 | 1550 |

Referring to the results of Table 2, it may be found that the example organic electroluminescence devices using the amine compounds according to embodiments of the present disclosure as hole transport materials showed a low driving voltage, excellent device efficiency, and good life characteristics.

It may be found that each of Example 1 to Example 18 showed a lower driving voltage, higher emission efficiency, and improved half-life compared to each of Comparative Example 1 to Comparative Example 6.

In Example 1 to Example 10, the amine compounds in Compound Group 1 were used as hole transport layer materials. In Example 11 to Example 18, the amine compounds in Compound Group 2 were used as the hole transport layer materials. For example, in Example 1 to Example 10, amine compounds according to embodiments of the present disclosure, in which an aromatic hydrocarbon ring was condensed with the pyridine ring of a pyridoindole moiety were used as hole transport layer materials, and in Example 11 to Example 18, amine compounds according to embodiments of the present disclosure in which an aromatic hydrocarbon ring was condensed with the indole ring of a pyridoindole moiety were used as hole transport layer materials. Referring to the results of Table 2, it was found that all devices including the amine compounds of Compound Group 1 and Compound Group 2 showed better emission efficiency and improved life characteristics than the devices of the Comparative Examples. In addition, referring to the results of Example 1 to Example 7, excellent emission efficiency and life characteristics were shown regardless of the particular position of a hexagonal hydrocarbon ring.

In addition, in Example 8 to Example 10 and Example 16 to Example 18, amine compounds including two hexagonal hydrocarbon rings condensed with a pyridoindole moiety were used as hole transport layer materials. In this case, it was found that emission life characteristics were somewhat improved when compared with the other Examples. Without being bound by the correctness of any particular explanation or theory, it is thought that the highest occupied molecular orbital (HOMO) of a substituent including an arylamine moiety is expanded to the condensed rings in the pyridoindole moiety, and the greater delocalization enables improved stability of a radical state.

Comparative Example 1 corresponds to a case in which an amine compound having a carbazole group instead of a pyridoindole moiety is used. Comparative Example 2 corresponds to a case in which an amine compound includes a pyridoindole moiety but without a condensed hexagonal ring. Both cases showed inferior device life and emission efficiency when compared with the Examples. Without being bound by the correctness of any particular explanation or theory, it is thought that the delocalization of the HOMO over the arylamine moiety is decreased in these Comparative Examples compared to the Example Compounds, and as such, stability of a radical state is decreased.

Comparative Example 3 includes a pyridoindole moiety, but differs in that an additional indole ring is condensed with the pyridoindole (e.g., at the pyridine ring). In the structure of Comparative Example 3, it was found that carrier balance was collapsed, and both device efficiency and device life were degraded (e.g., simultaneously) compared to the Examples.

Each of Comparative Example 4 and Comparative Example 5 include a similar pyridoindole moiety and arylamine moiety as the amine compounds of the Examples, but device life was decreased when compared with the Examples. Without being bound by the correctness of any particular explanation or theory, it is thought that the pyridoindole moiety is combined with the arylamine moiety at a position having particularly high reactivity, such that the stability of a radical state is degraded. For example, the arylamine moiety in Comparative Example 4 is combined with "HT" at position $R_1$ as denoted in Formula 2. The arylamine moiety in Comparative Example 5 is combined with "HT" at position $R_8$ as denoted in Formula 2. In each of the Example Compounds of the present disclosure, the $R_1$ and $R_8$ positions as denoted in Formula 2 are not combined with an arylamine moiety.

Formula 2

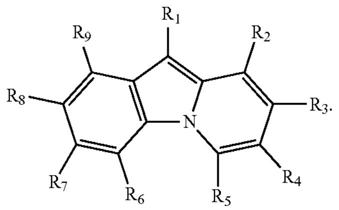

Comparative Example 6 includes a material having three nitrogen-containing heterocycles, and molecular symmetry was excessively high (e.g., three-fold symmetric around the nitrogen atom). Without being bound by the correctness of any particular explanation or theory, it is believed that molecular stacking was induced, and the amorphous properties of the compound were degraded. Accordingly, both device efficiency and device life were low (e.g., simultaneously) compared to the Examples.

Accordingly, referring to the results of Example 1 to Example 18 and Comparative Example 1 to Comparative Example 6, the amine compound according to an embodiment of the present disclosure included both (e.g., simultaneously) a pyridoindole moiety condensed with an aromatic hexagonal ring and an arylamine moiety, and by selecting a suitable combination position of the arylamine moiety and the pyridoindole moiety, both emission efficiency and device life may be improved (e.g., simultaneously).

For example, the amine compound according to an embodiment of the present disclosure may be used in a hole transport region and may improve the emission efficiency of an organic electroluminescence device.

The amine compound according to an embodiment of the present disclosure includes a pyridoindole moiety with which at least one hexagonal hydrocarbon ring is condensed, and an arylamine moiety that is combined with the pyridoindole moiety, such that the hole transport capacity of the compound may be increased, and tolerance to high heat and charge tolerance may be increased. Accordingly, the emission efficiency and device life of the organic electroluminescence device according to an embodiment of the present disclosure may be improved.

The amine compound according to an embodiment of the present disclosure may improve the emission efficiency and device life of an organic electroluminescence device.

The organic electroluminescence device according to an embodiment of the present disclosure includes the amine compound according to an embodiment of the present disclosure in a hole transport region and may achieve high efficiency.

As used herein, the terms "use", "using", and "used" may be considered synonymous with the terms "utilize", "utilizing", and "utilized", respectively. Further, the use of "may" when describing embodiments of the present disclosure refers to "one or more embodiments of the present disclosure".

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although example embodiments of the present disclosure have been described herein, it is understood that the present disclosure should not be limited to these example embodiments, and that various changes and modifications can be made by one ordinary skilled in the art within the spirit and scope of the present disclosure, as defined by the following claims and equivalents thereof.

What is claimed is:

1. An organic electroluminescence device, comprising:

a first electrode;

a second electrode on the first electrode; and a plurality of organic layers between the first electrode and the second electrode, wherein at least one organic layer of the plurality of organic layers comprises an amine compound represented by Formula 1:

Formula 1

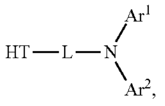

wherein, in Formula 1, $Ar_1$ and $Ar_2$ are each independently a substituted or unsubstituted aryl group having 6 to 40 ring-forming carbon atoms, or a substituted or unsubstituted heteroaryl group having 2 to 40 ring-forming carbon atoms, L is a direct linkage, a substituted or unsubstituted arylene group having 6 to 30 ring-forming carbon atoms, or a substituted or unsubstituted heteroarylene group having 2 to 30 ring-forming carbon atoms, and HT is represented by Formula 2:

Formula 2

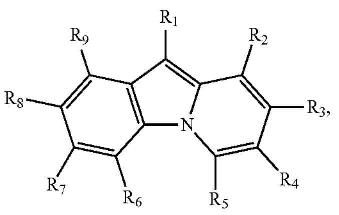

wherein, in Formula 2, $R_1$ to $R_9$ are each independently a hydrogen atom, a deuterium atom, a halogen atom, a cyano group, a nitro group, an amino group, a substituted or unsubstituted aryl group having 6 to 40 ring-forming carbon atoms, a substituted or unsubstituted heteroaryl group having 2 to 40 ring-forming carbon atoms, or a substituted or unsubstituted alkyl group of 1 to 20 carbon atoms, at least one pair selected from $R_2$ and $R_3$, $R_3$ and $R_4$, $R_4$ and $R_5$, $R_6$ and $R_7$, $R_7$ and $R_8$, and $R_8$ and $R_9$ is combined with each other to form a hexagonal hydrocarbon ring, and when at least one pair of $R_2$ and $R_3$, $R_3$ and $R_4$, and $R_4$ and $R_5$ forms a hexagonal hydrocarbon ring, $R_8$ is a hydrogen atom, and wherein the $R_1$ and $R_8$ positions as denoted in Formula 2 are not combined with the L in Formula 1.

2. The organic electroluminescence device of claim 1, wherein the plurality of organic layers comprises:

an emission layer; and a hole transport region between the first electrode and the emission layer, wherein the hole transport region comprises the amine compound represented by Formula 1.

3. The organic electroluminescence device of claim 2, wherein the emission layer is to emit blue light and/or green light.

4. The organic electroluminescence device of claim 1, wherein the plurality of organic layers comprises:

an emission layer;

a hole injection layer between the first electrode and the emission layer; and a hole transport layer between the hole injection layer and the emission layer, wherein the hole transport layer comprises the amine compound represented by Formula 1.

5. The organic electroluminescence device of claim 1, wherein one or two pairs selected from $R_2$ and $R_3$, $R_3$ and $R_4$, and $R_4$ and $R_5$ each form the hexagonal hydrocarbon ring.

6. The organic electroluminescence device of claim 1, wherein one or two pairs selected from $R_6$ and $R_7$, $R_7$ and $R_8$, and $R_8$ and $R_9$ each form the hexagonal hydrocarbon ring.

7. The organic electroluminescence device of claim 1, wherein the hexagonal hydrocarbon ring is represented by Formula 3:

Formula 3

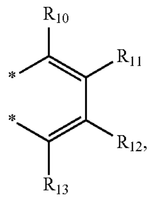

wherein, in Formula 3, $R_{10}$ to $R_{13}$ are each independently a hydrogen atom, a deuterium atom, a halogen atom, a cyano group, a nitro group, an amino group, a substituted or unsubstituted aryl group having 6 to 40 ring forming carbon atoms, a substituted or unsubstituted heteroaryl group having 2 to 40 ring-forming carbon atoms, or a substituted or unsubstituted alkyl group of 1 to 20 carbon atoms, and

* is a combining part with Formula 2.

8. The organic electroluminescence device of claim 7, wherein any one of $R_2$ to $R_9$ that is not a combining part with the hexagonal hydrocarbon ring or any one of $R_{10}$ to $R_{13}$ is combined with L in Formula 1.

9. The organic electroluminescence device of claim 7, wherein HT is represented by one selected from Formula 2-1a to Formula 2-1d:

Formula 2-1a

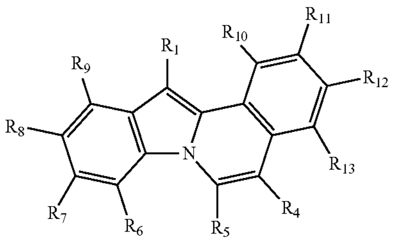

Formula 2-1b

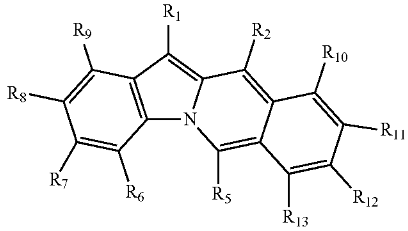

Formula 2-1c

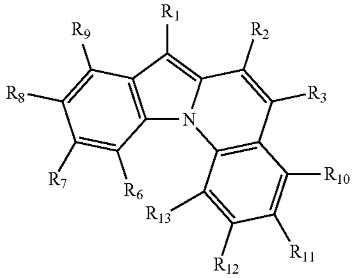

Formula 2-1d

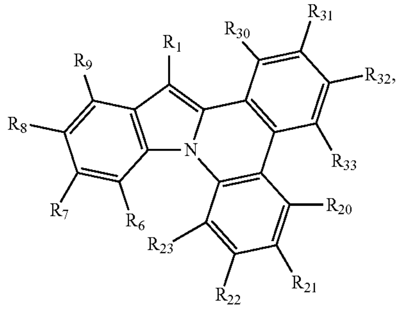

wherein, in Formula 2-1d, $R_{20}$ to $R_{23}$ and $R_{30}$ to $R_{33}$ are each independently a hydrogen atom, a deuterium atom, a halogen atom, a cyano group, a nitro group, an amino group, a substituted or unsubstituted aryl group having 6 to 40 ring-forming carbon atoms, a substituted or unsubstituted heteroaryl group having 2 to 40 ring-forming carbon atoms, or a substituted or unsubstituted alkyl group of 1 to 20 carbon atoms, wherein, in Formula 2-1a to Formula 2-1d, $R_1$ to $R_9$ are the same as defined in Formula 2, and $R_{10}$ to $R_{13}$ are the same as defined in Formula 3.

10. The organic electroluminescence device of claim 7, wherein HT is represented by one selected from Formula 2-2a to Formula 2-2d:

Formula 2-2a

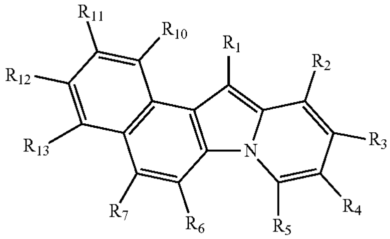

Formula 2-2b

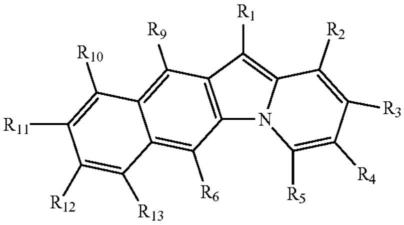

Formula 2-2c

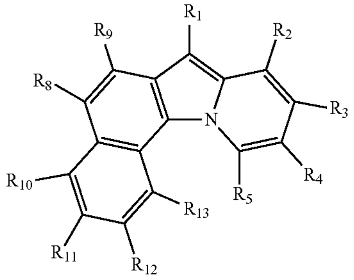

Formula 2-2d

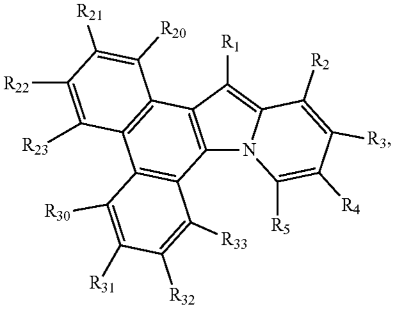

wherein, in Formula 2-2d, $R_{20}$ to $R_{23}$ and $R_{30}$ to $R_{33}$ are each independently a hydrogen atom, a deuterium atom, a halogen atom, a cyano group, a nitro group, an amino group, a substituted or unsubstituted aryl group having 6 to 40 ring-forming carbon atoms, a substituted or unsubstituted heteroaryl group having 2 to 40 ring-forming carbon atoms, or a substituted or unsubstituted alkyl group of 1 to 20 carbon atoms, wherein, in Formula 2-2a to Formula 2-2d, $R_1$ to $R_9$ are the same as defined in Formula 2, and $R_{10}$ to $R_{13}$ are the same as defined in Formula 3.

11. The organic electroluminescence device of claim 1, wherein $R_1$ is an unsubstituted phenyl group, an unsubstituted naphthyl group, an unsubstituted biphenyl group, an unsubstituted dibenzofuranyl group, or an unsubstituted dibenzothiophene group.

12. The organic electroluminescence device of claim 1, wherein L is a direct linkage, a substituted or unsubstituted phenylene group, a substituted or unsubstituted divalent biphenyl group, a substituted or unsubstituted divalent terphenyl group, a substituted or unsubstituted divalent phenanthrene group, a substituted or unsubstituted naphthylene group, or a substituted or unsubstituted divalent dibenzofuran group.

13. The organic electroluminescence device of claim 1, wherein the amine compound represented by Formula 1 is represented by at least one selected from Compound Group 1 and Compound Group 2:

Compound Group 1

A1

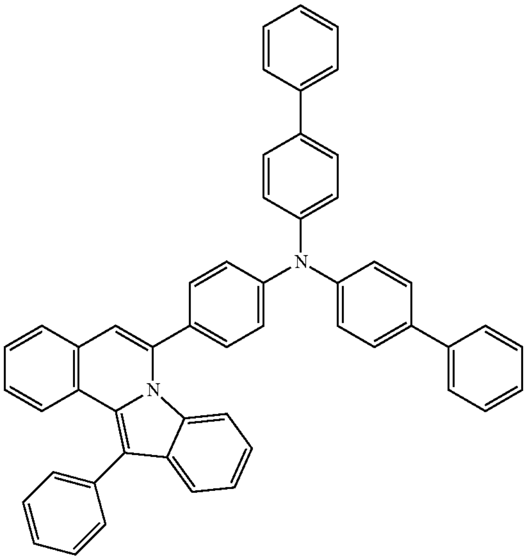

A2

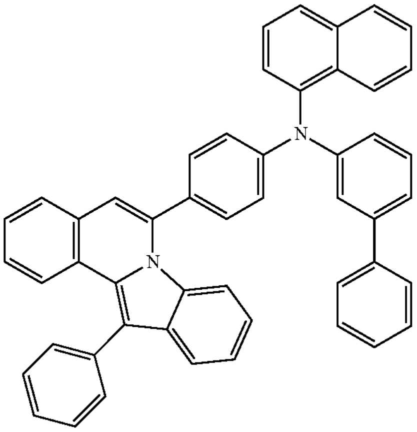

A3

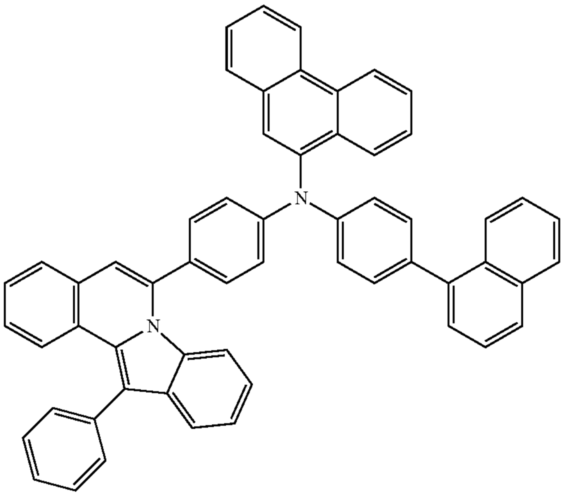

A4

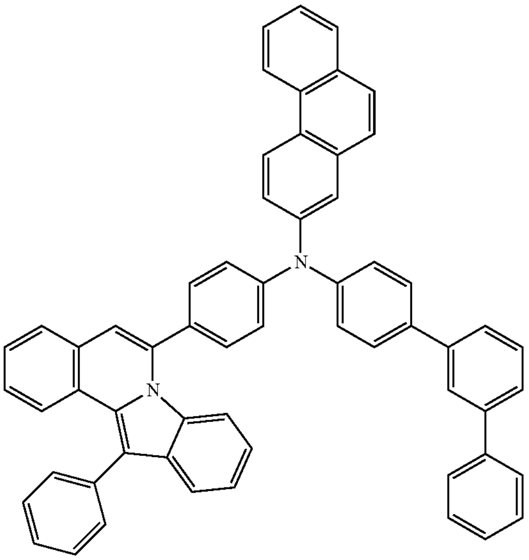

-continued
A5
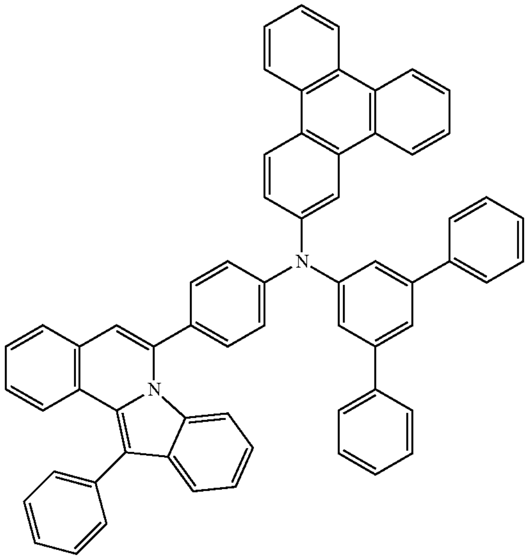
A6
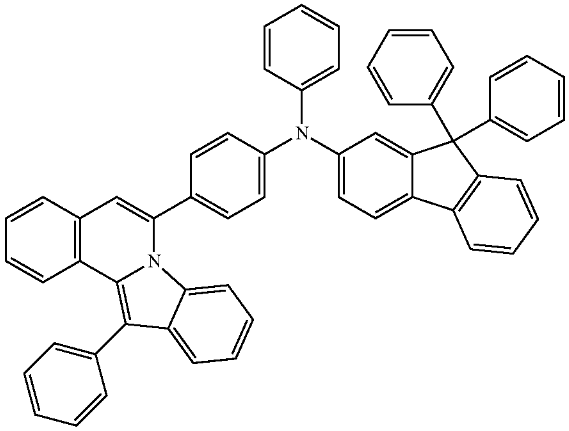
A7
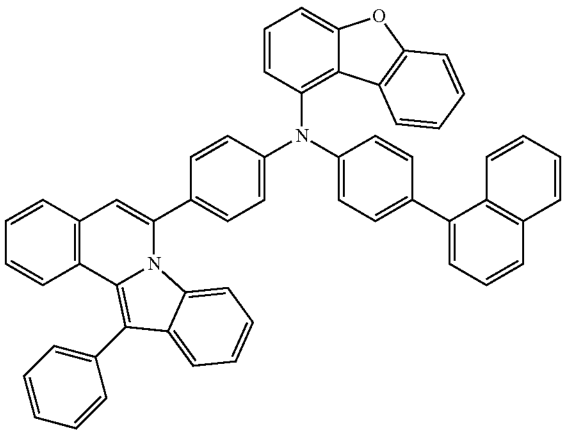
A8
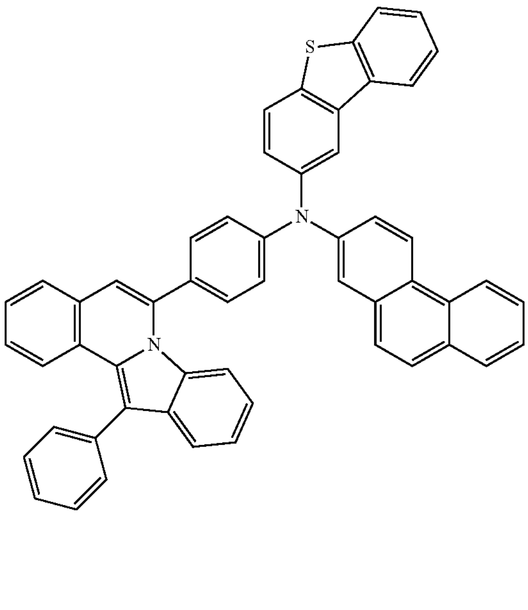

-continued
A9
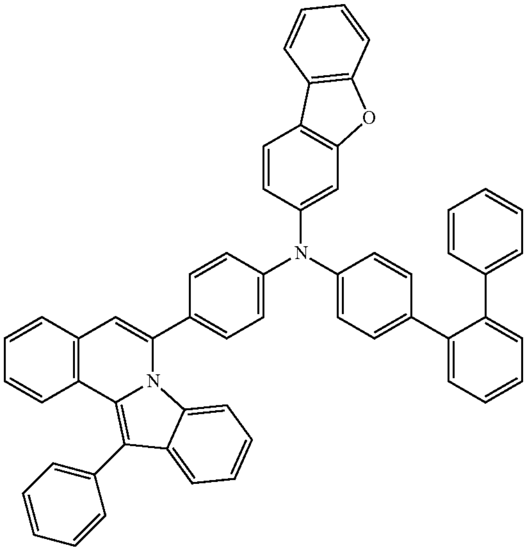
A10
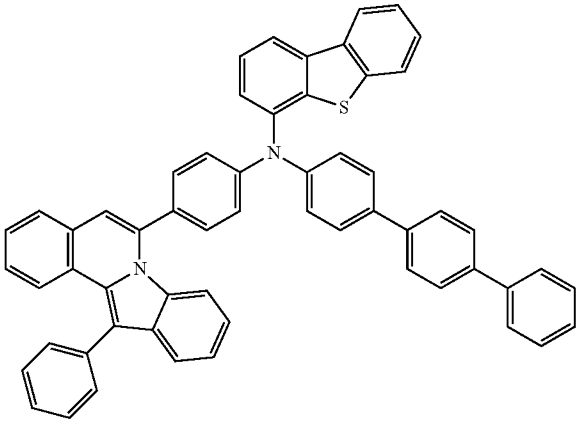
A11
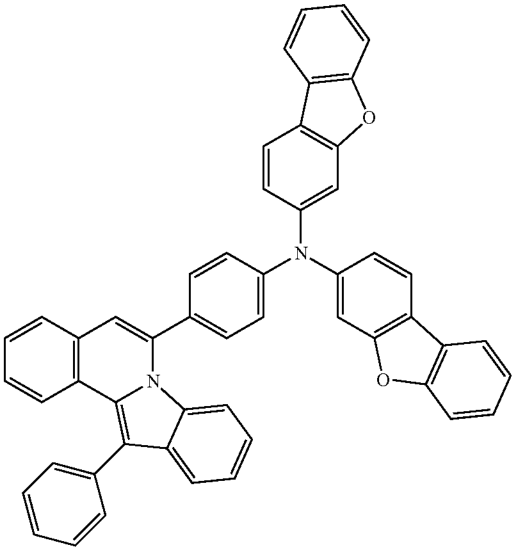
A12
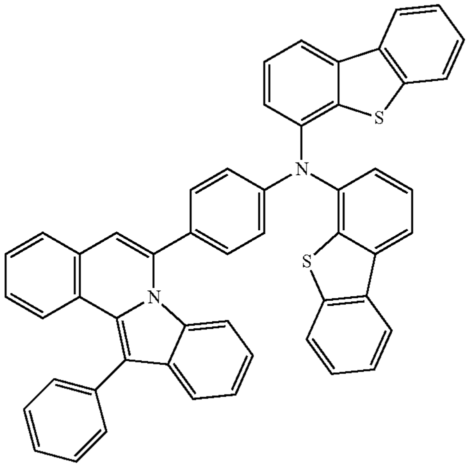
A13
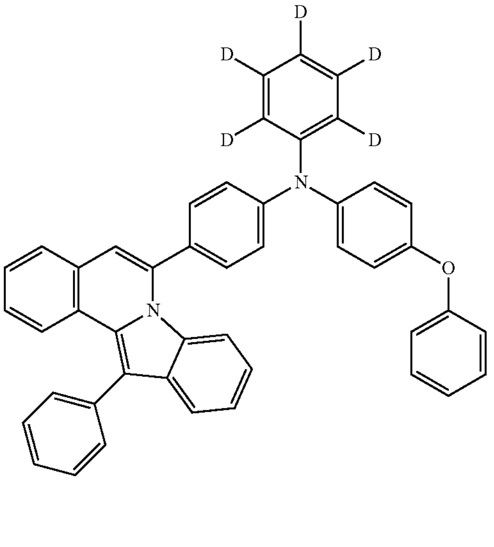
A14
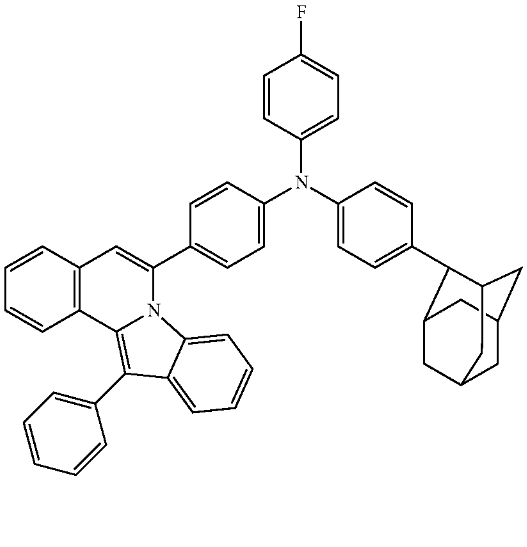

-continued
A15
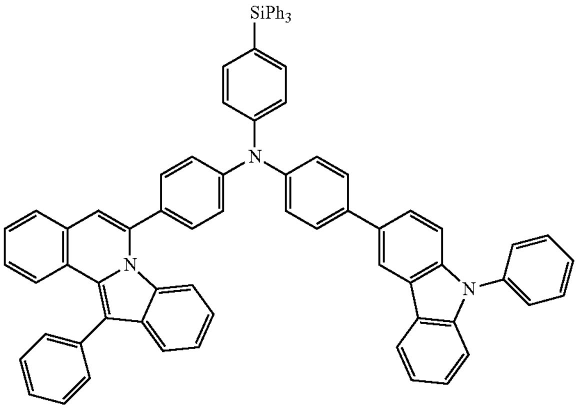
A16
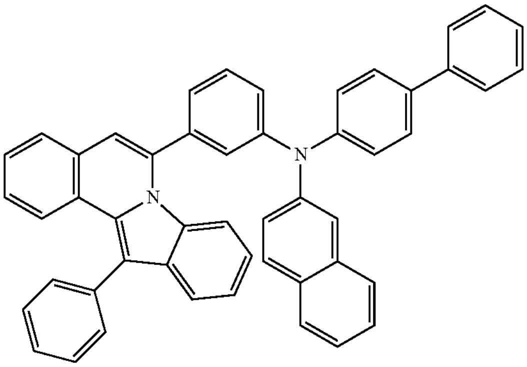
A17
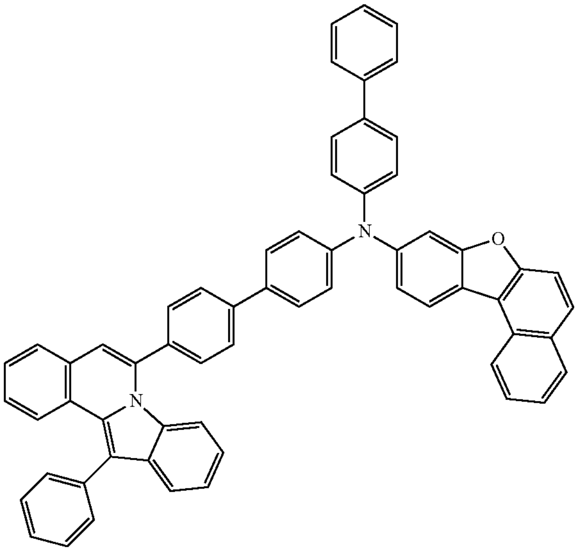
A18
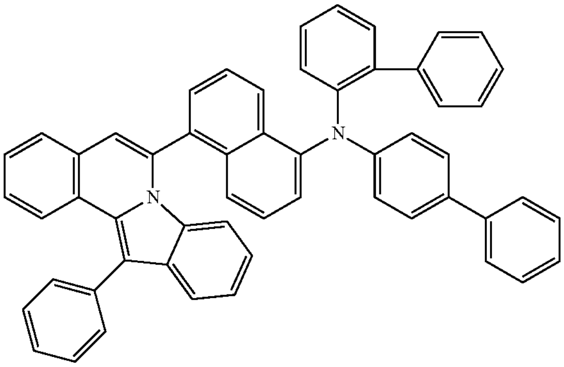
A19
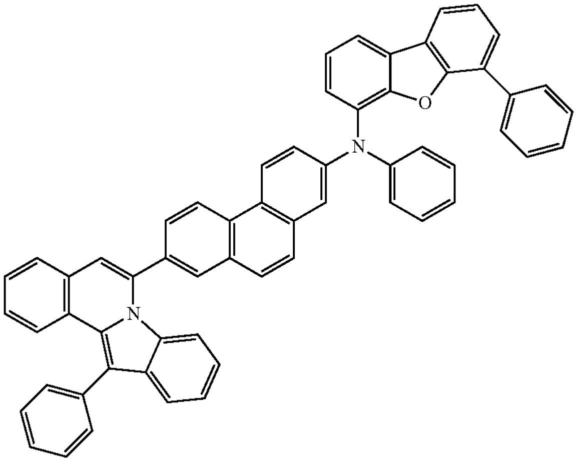
A20
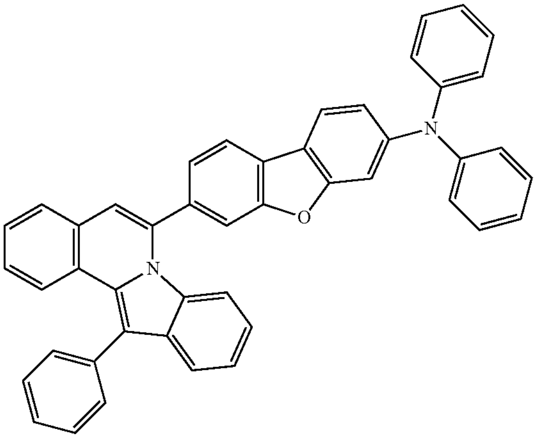

-continued
A21
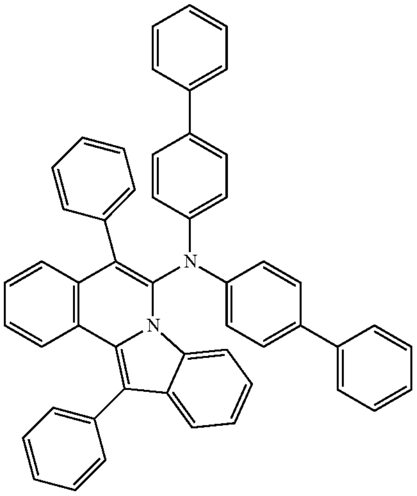
A22
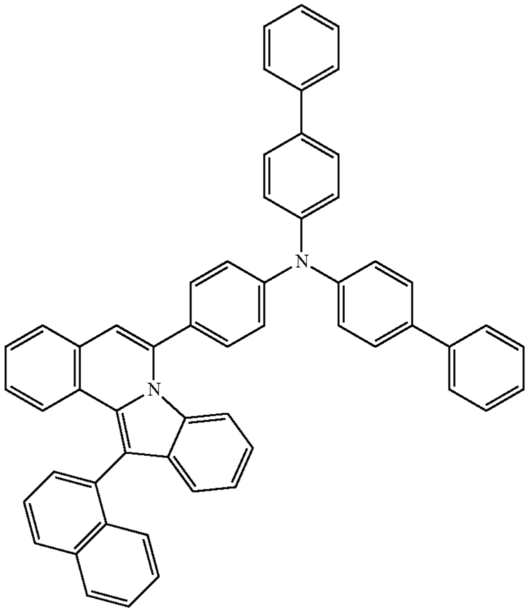
A23
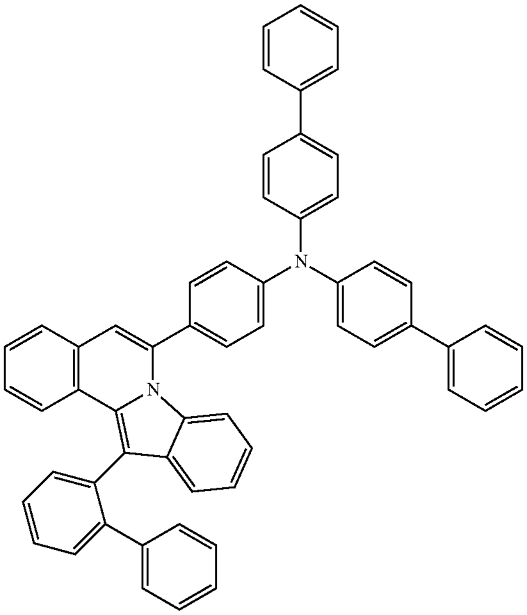
A24
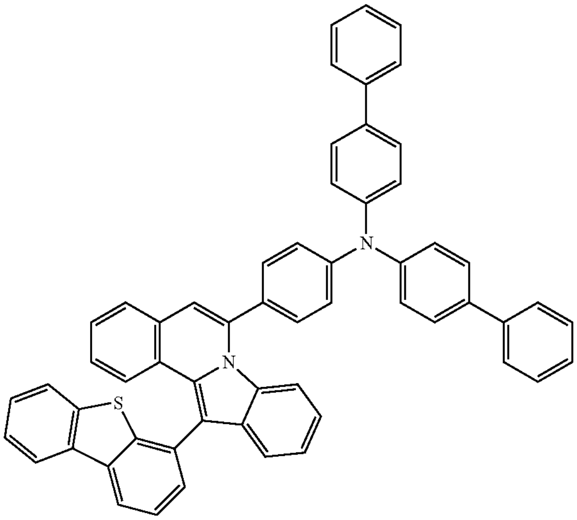

-continued
A25
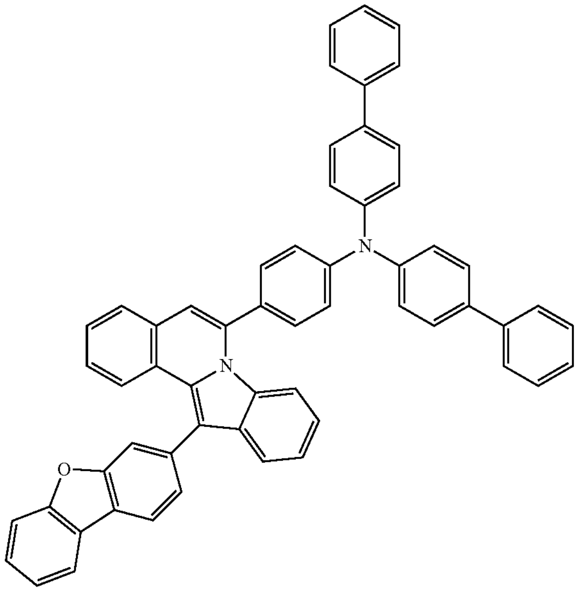
A26
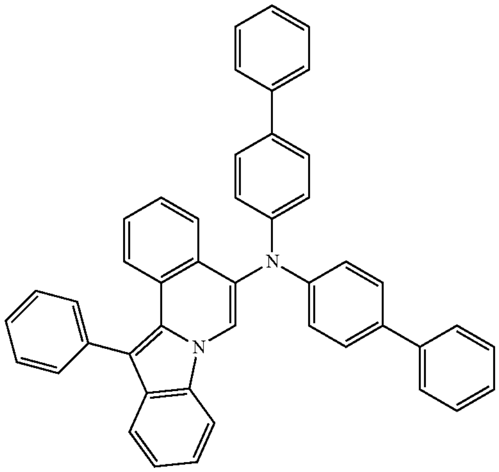
A27
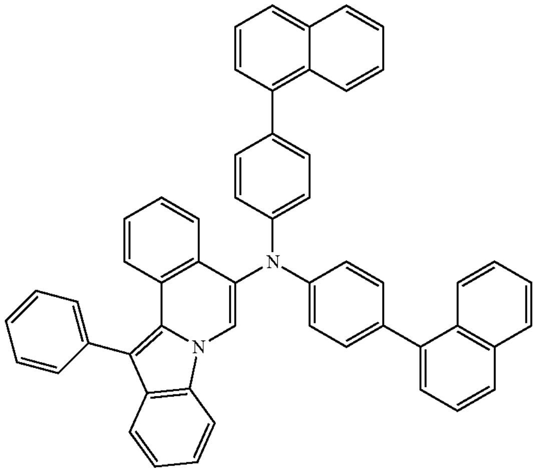
A28
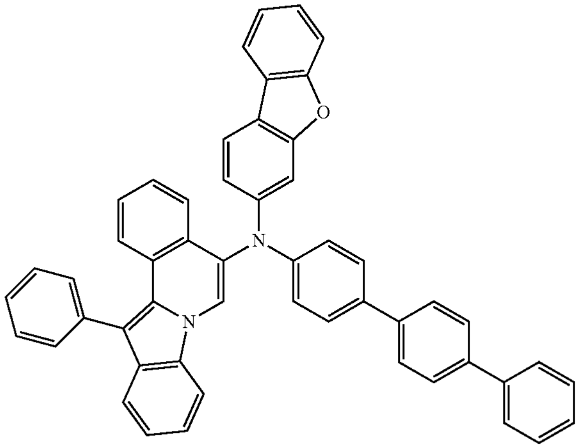
A29
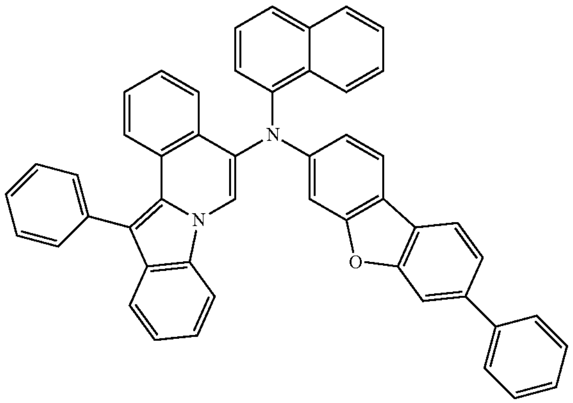
A30
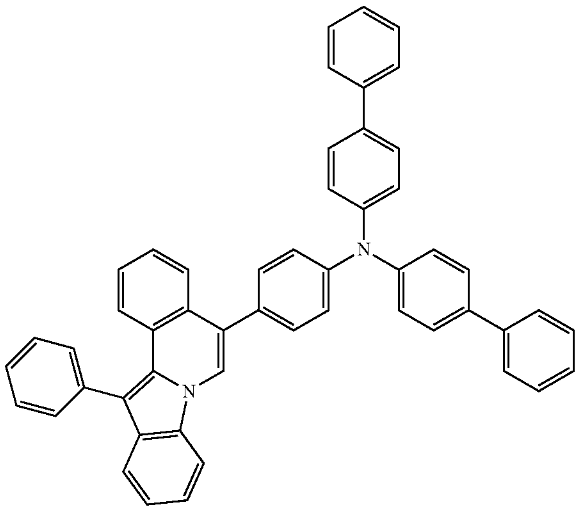

-continued
A31
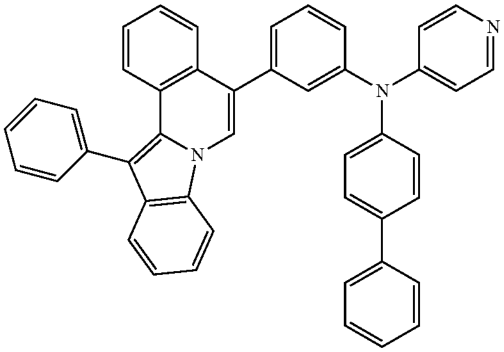
A32
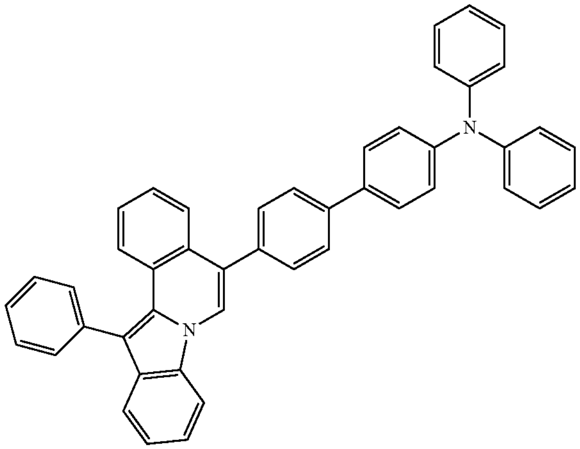
A33
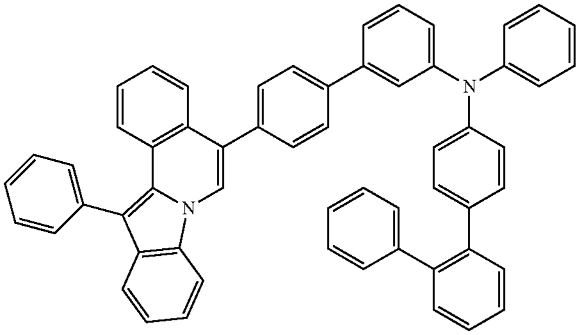
A34
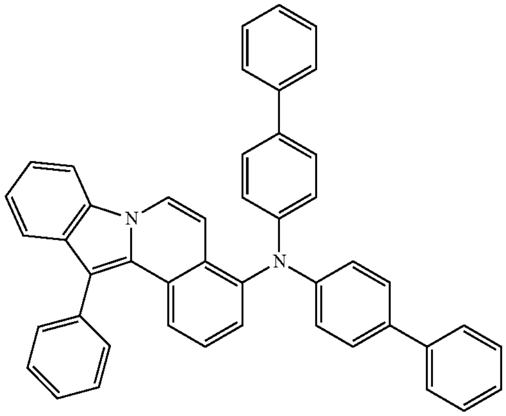
A35
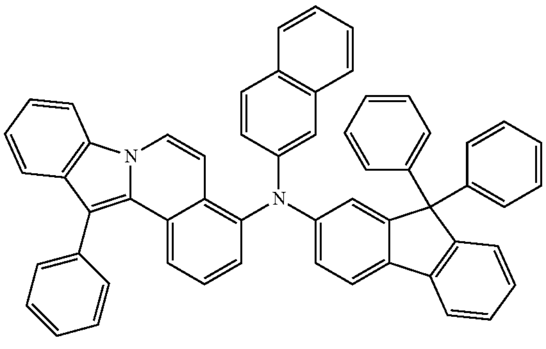
A36
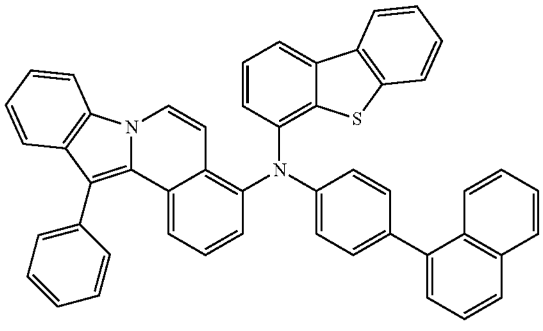

-continued
A37
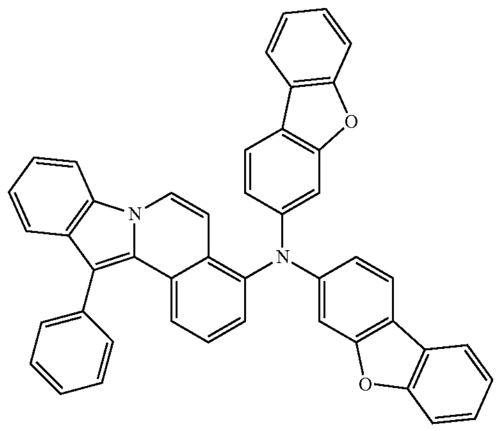
A38
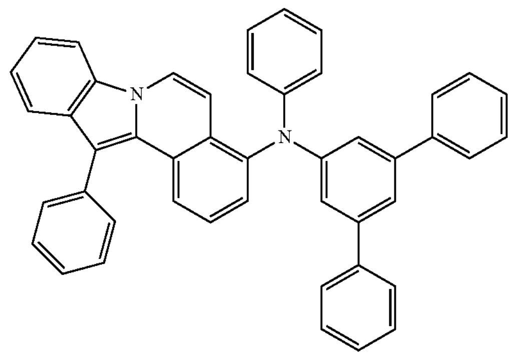
A39
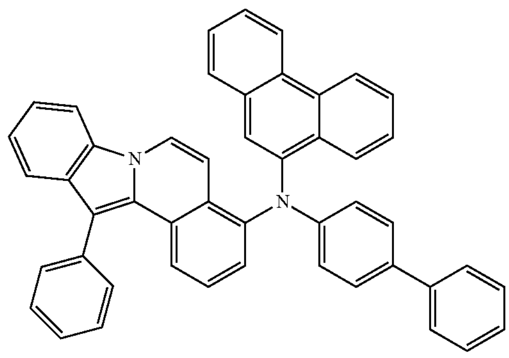
A40
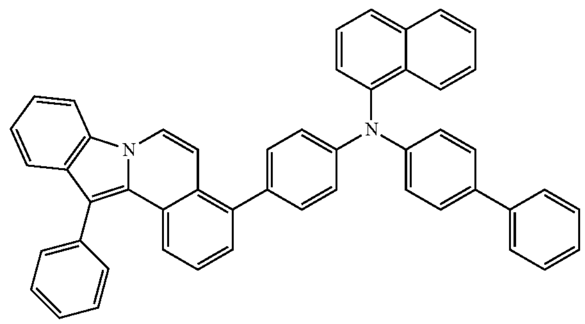
A41
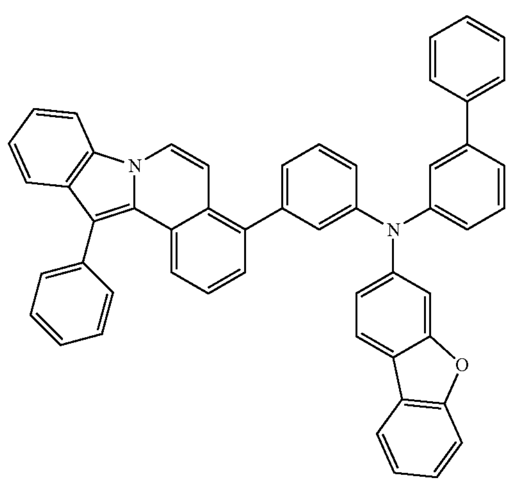
A42
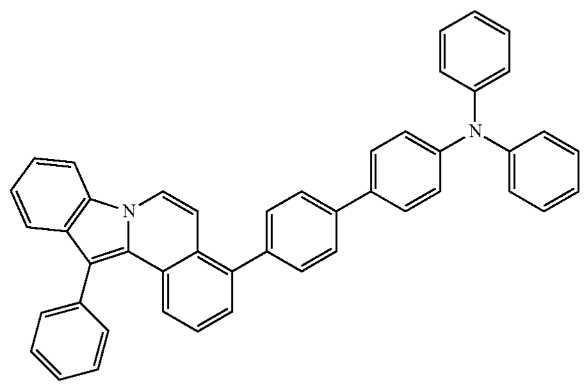

-continued
A43
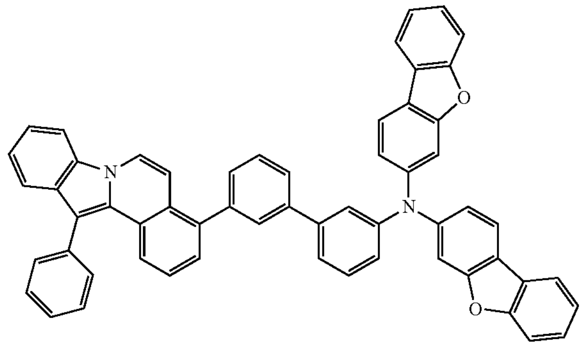
A44
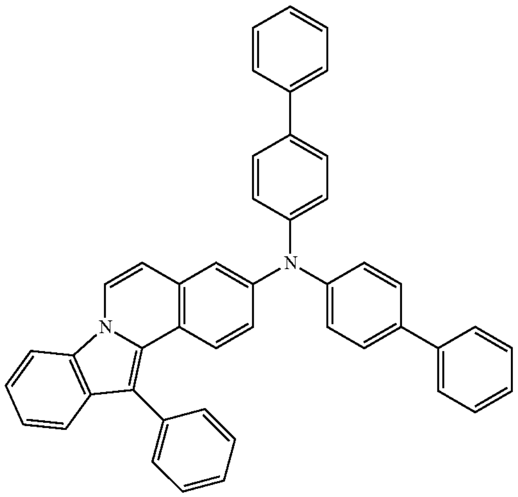
A45
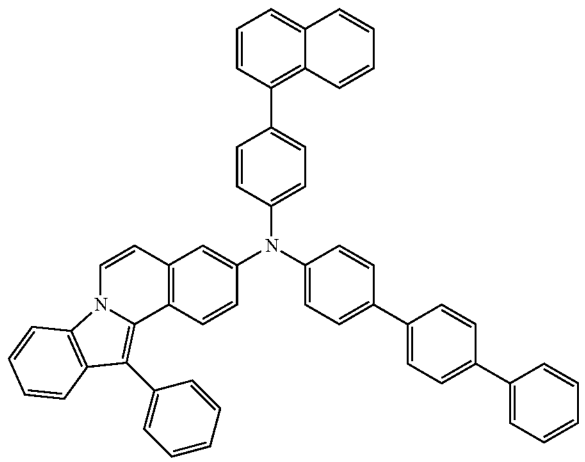
A46
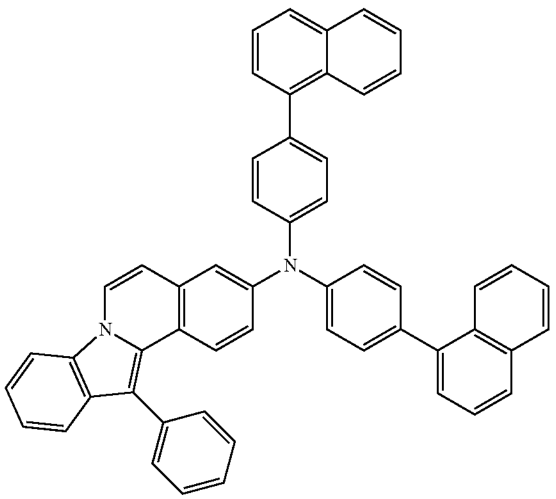
A47
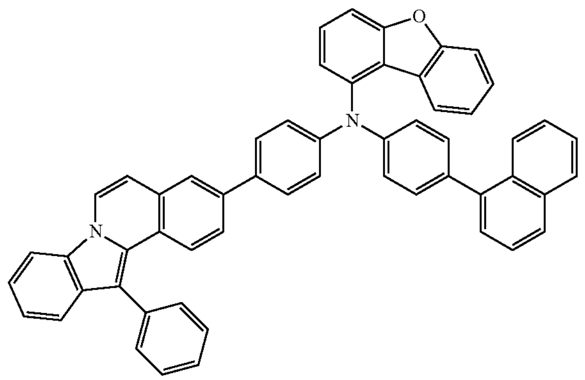
A48
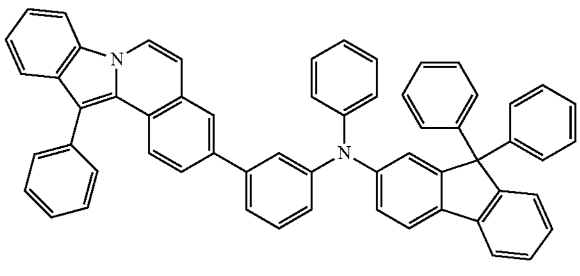

-continued
A49
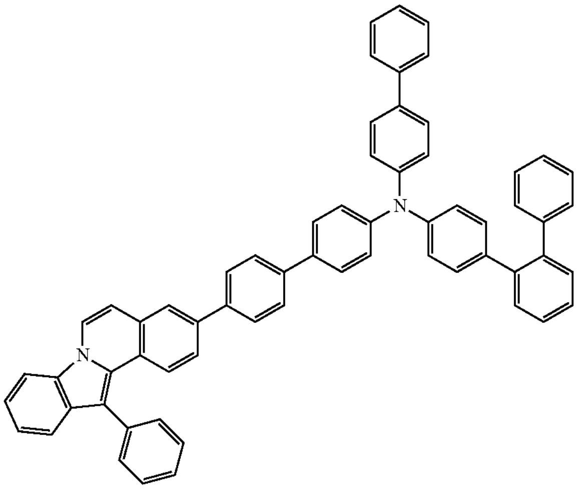
A50
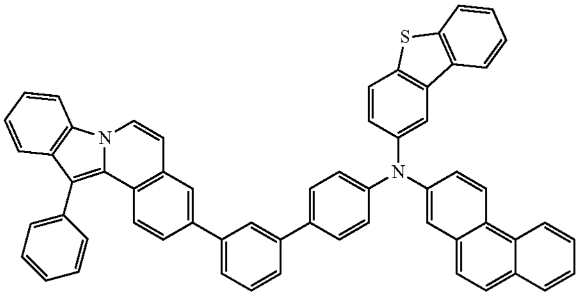
A51
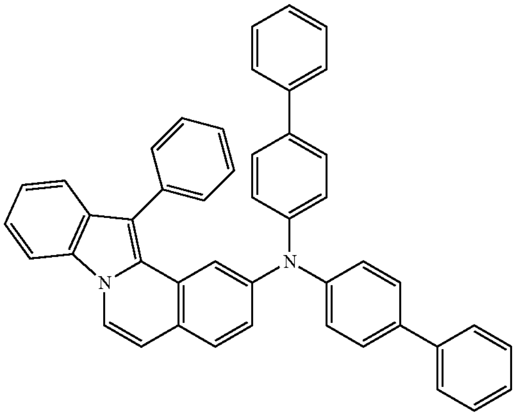
A52
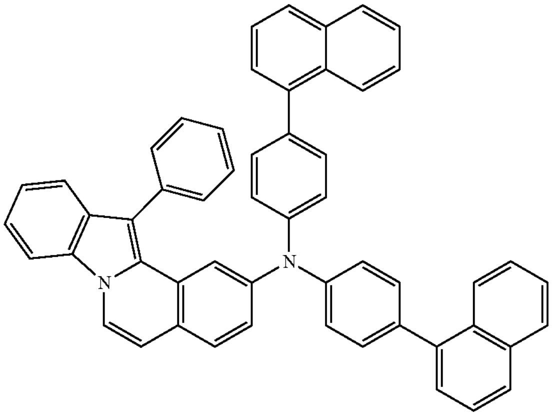
A53
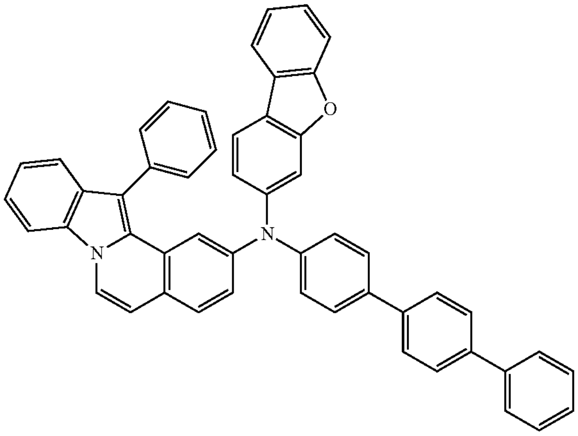
A54
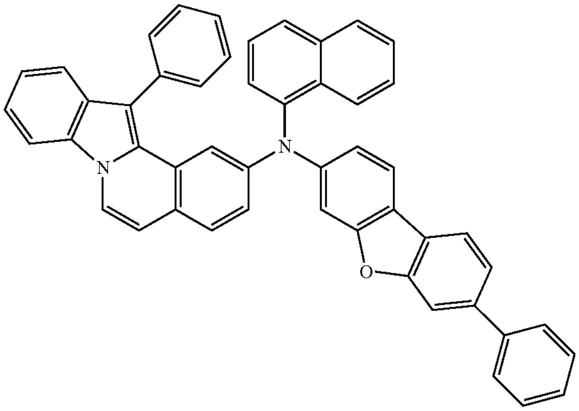

-continued
A55
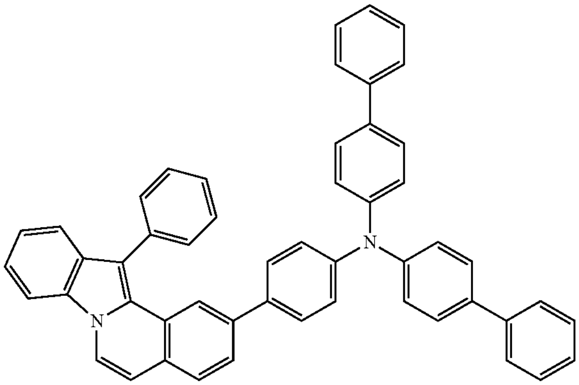
A56
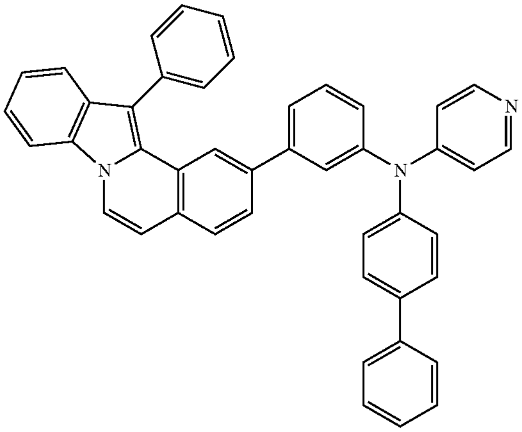
A57
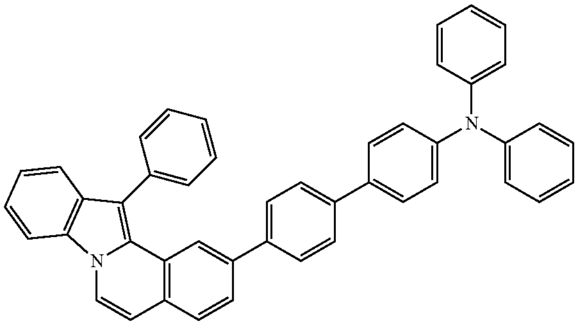
A58
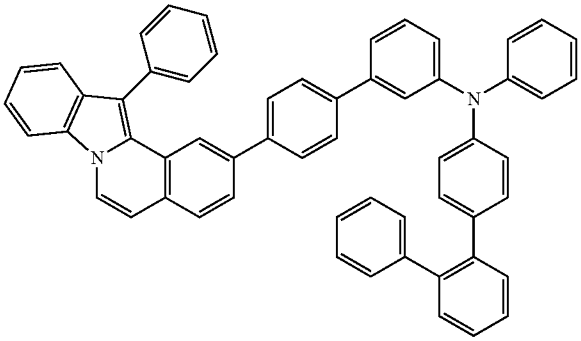
A59
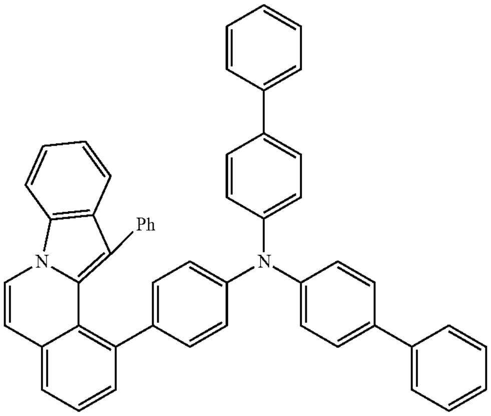
A60
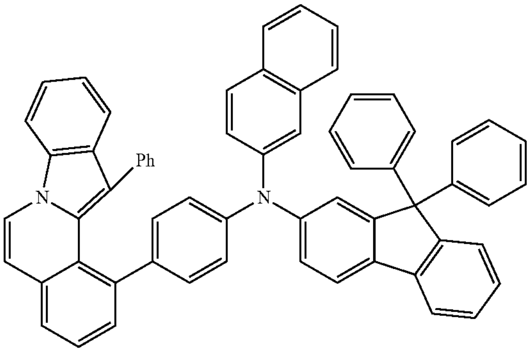

-continued
A61
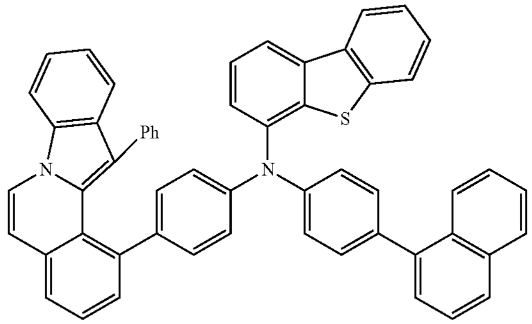
A62
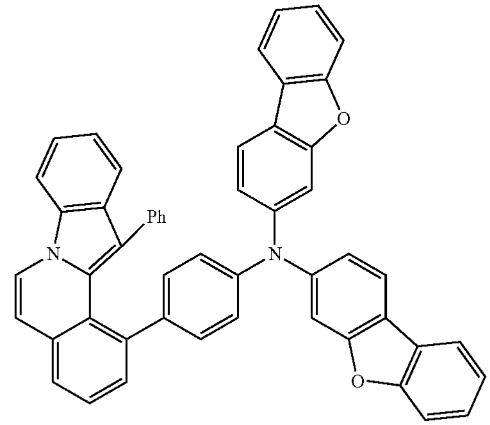
A63
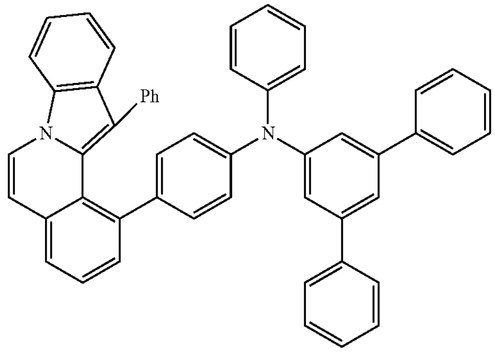
A64
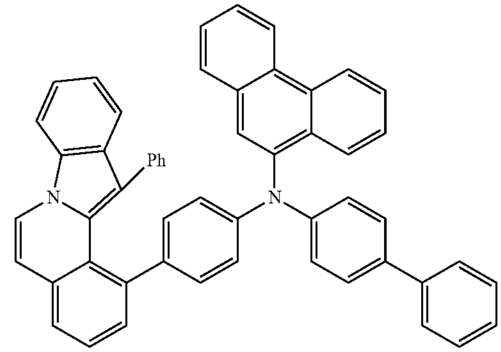
A65
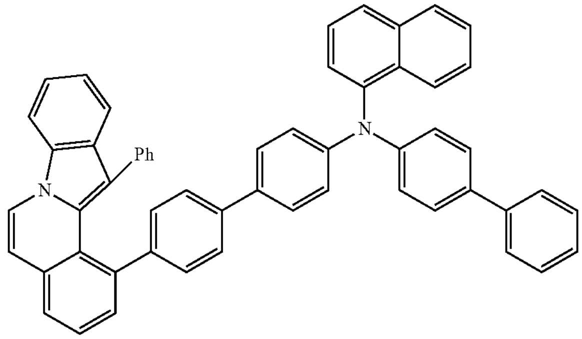
A66
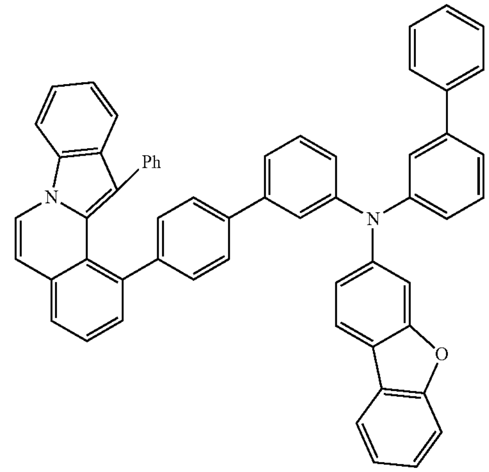
A67
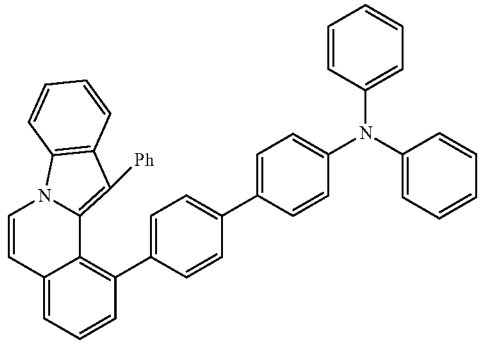
A68
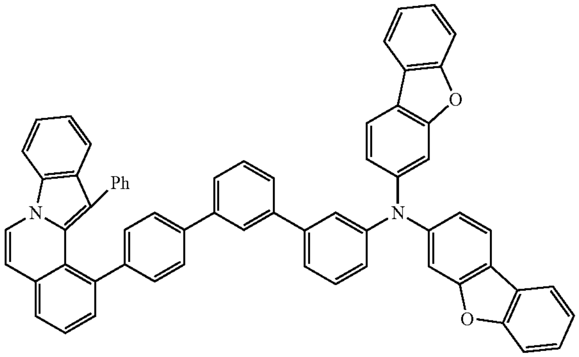

-continued
A69
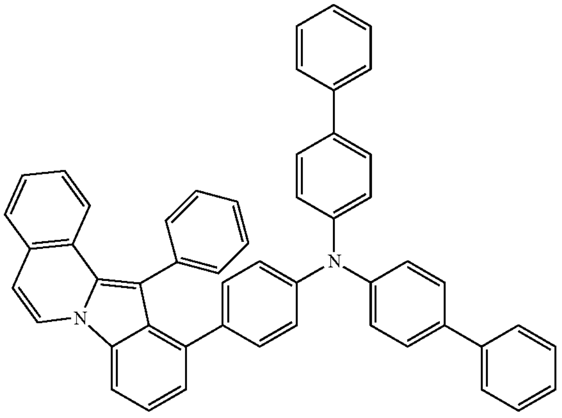
A70
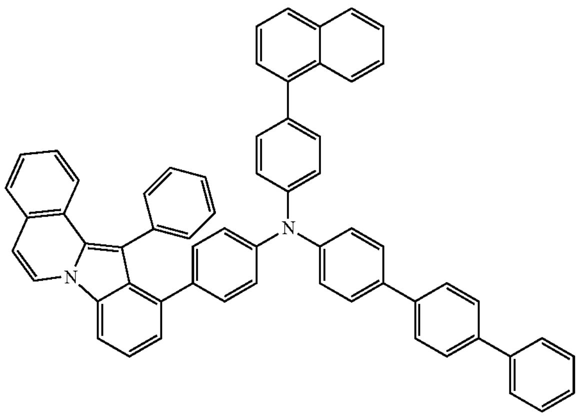
A71
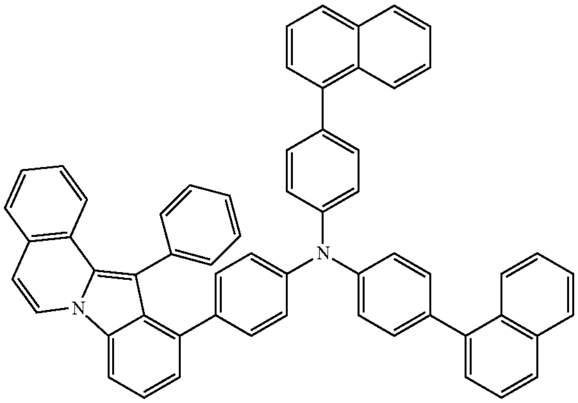
A72
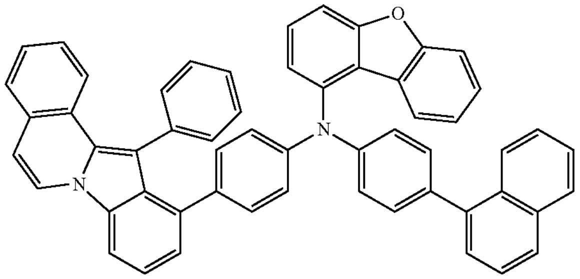
A73
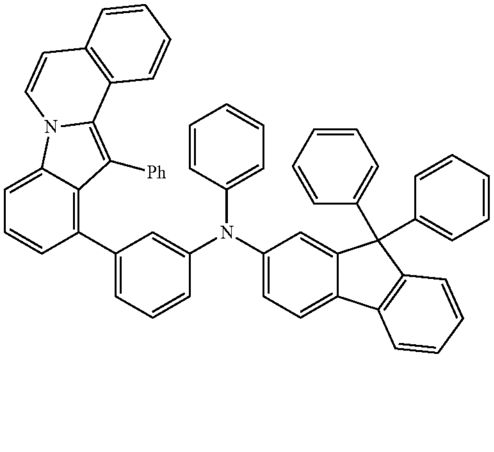
A74
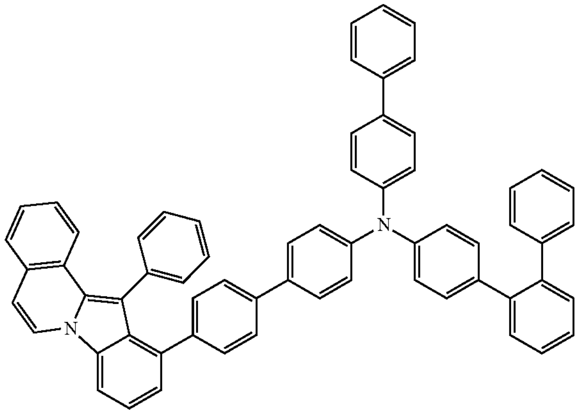

-continued
A75
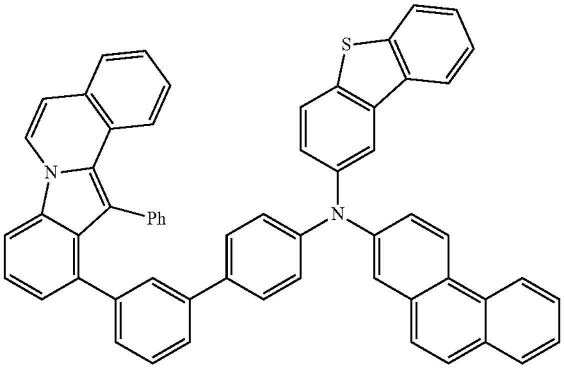
A76
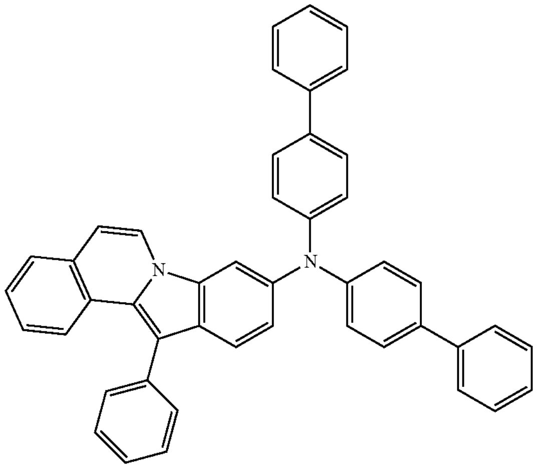
A77
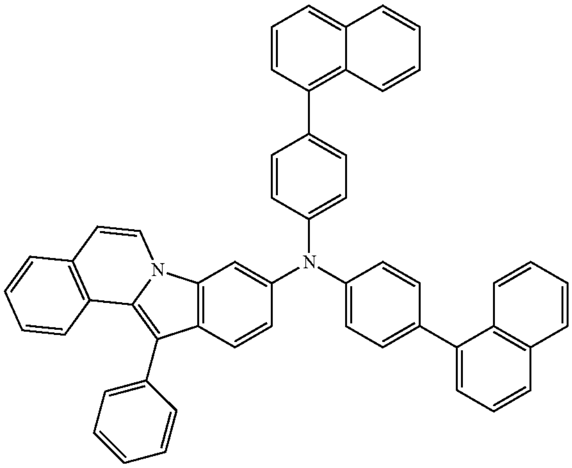
A78
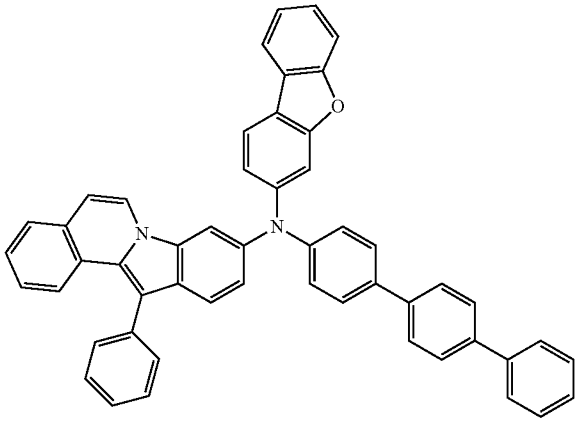
A79
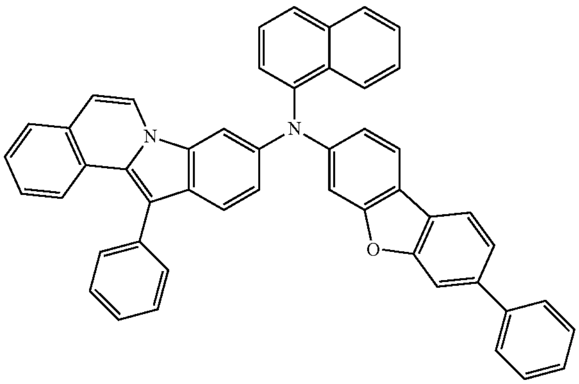
A80
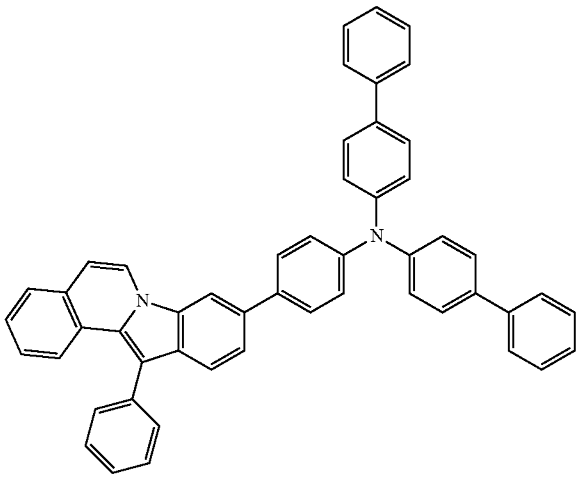

-continued
A81
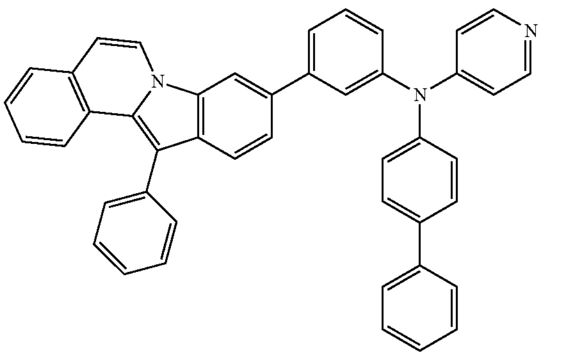
A82
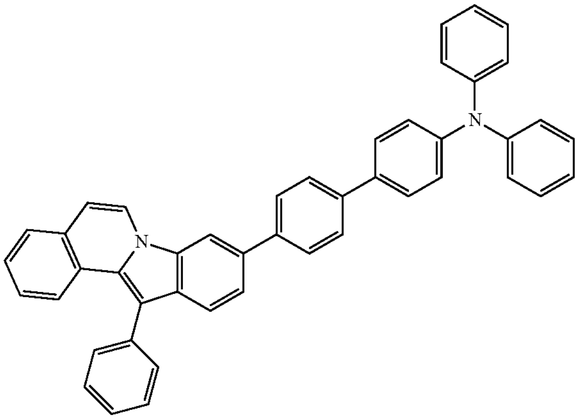
A83
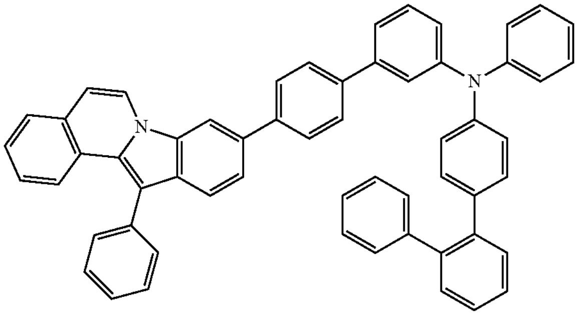
A84
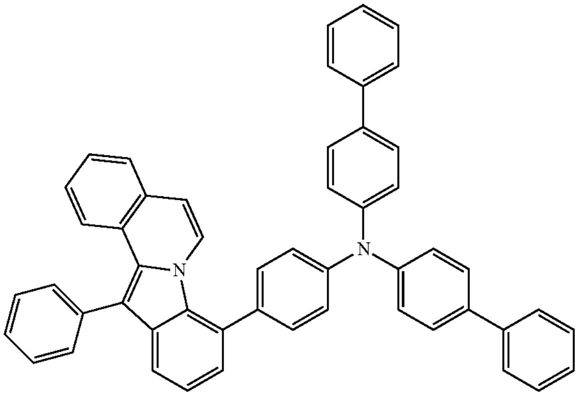
A85
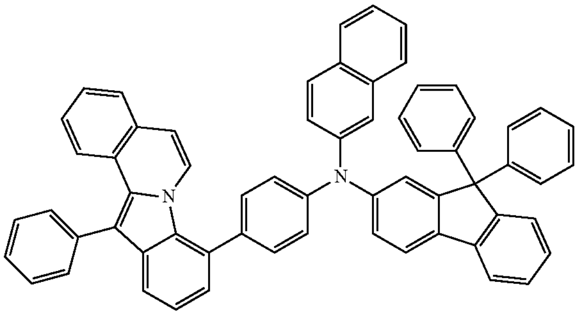
A86
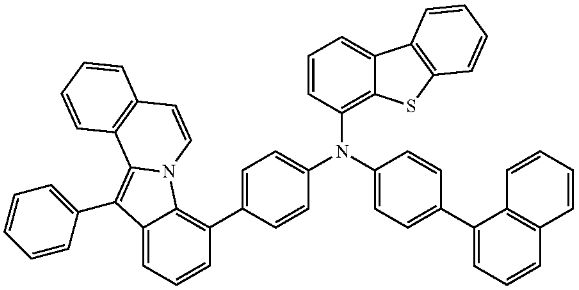
A87
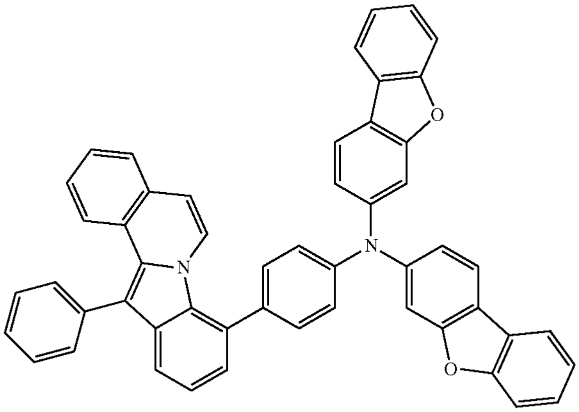
A88
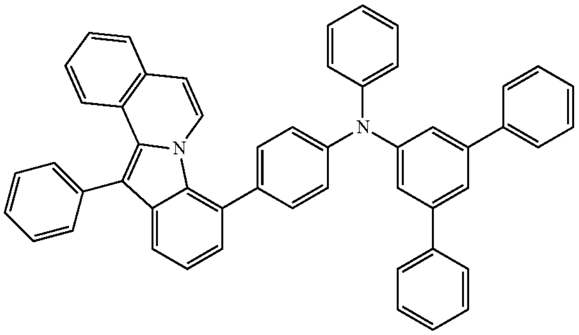

-continued
A89
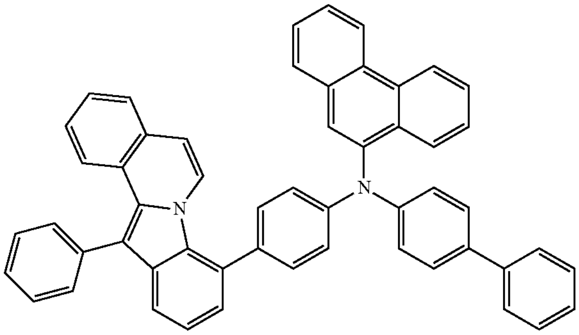
A90
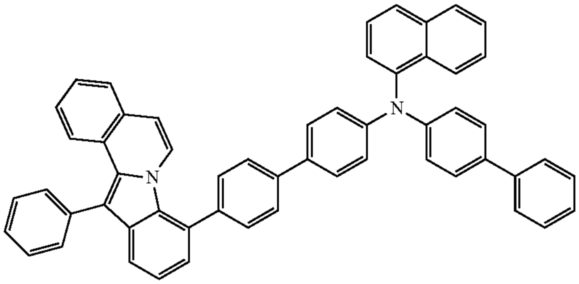
A91
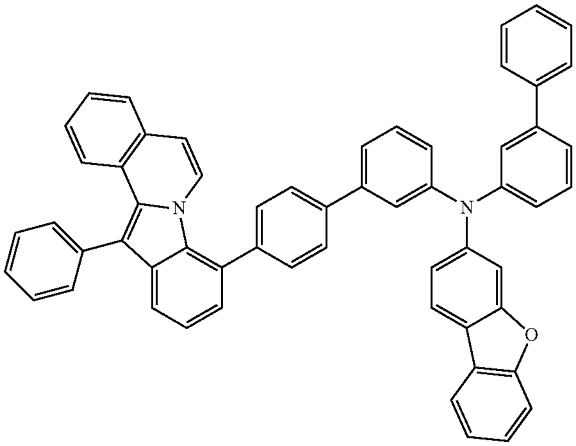
A92
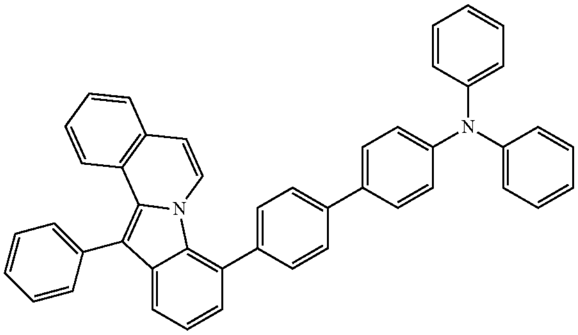
A93
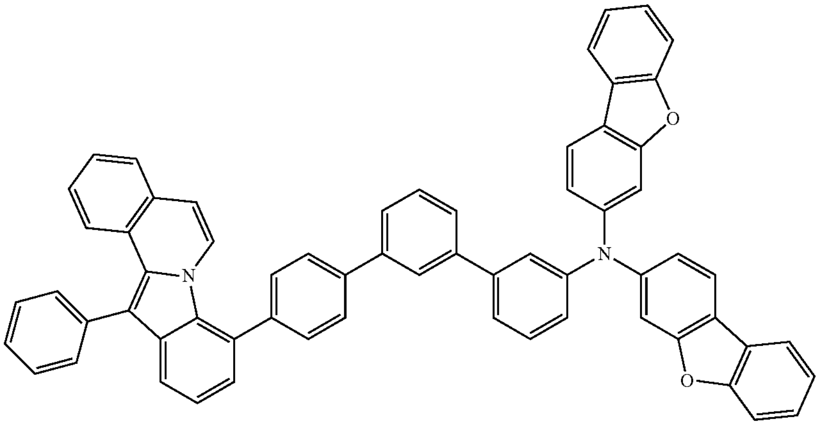

-continued
A94
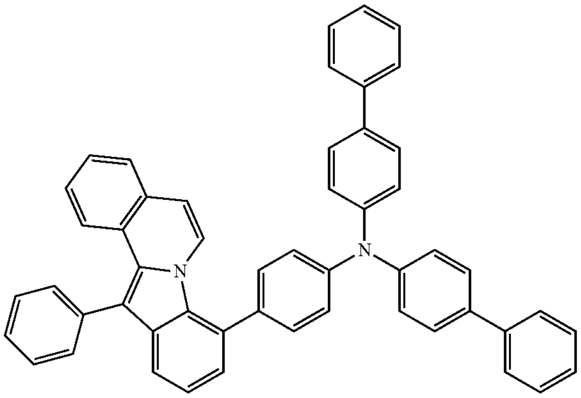
A95
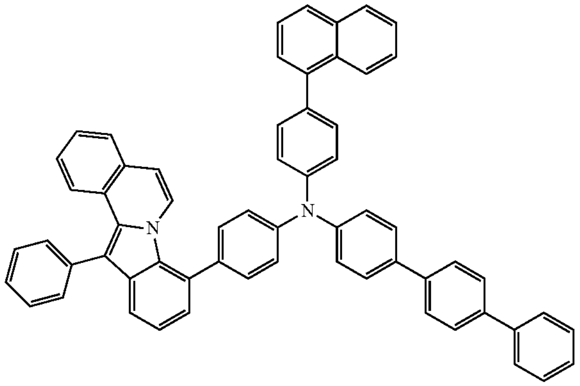
A96
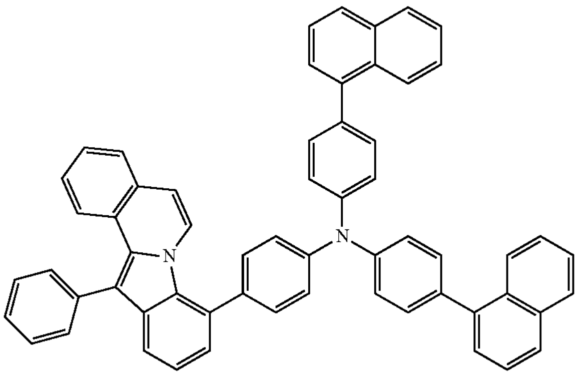
A97
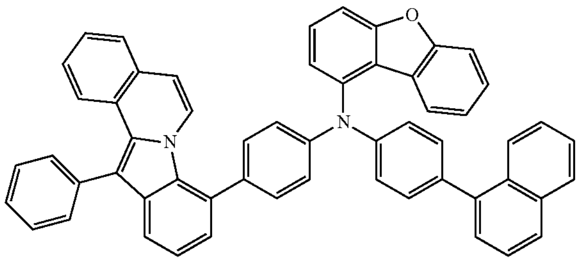
B1
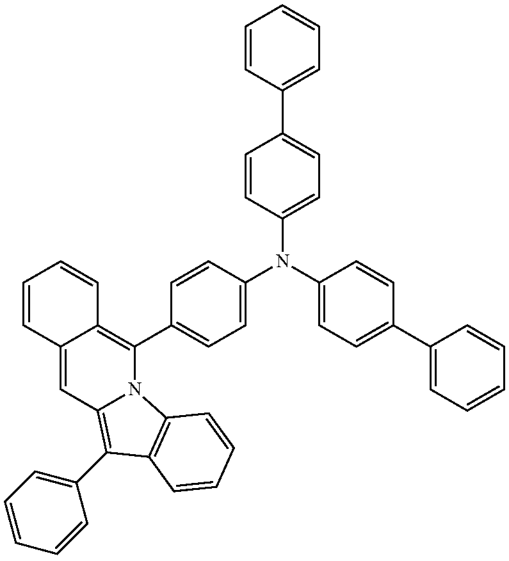
B2
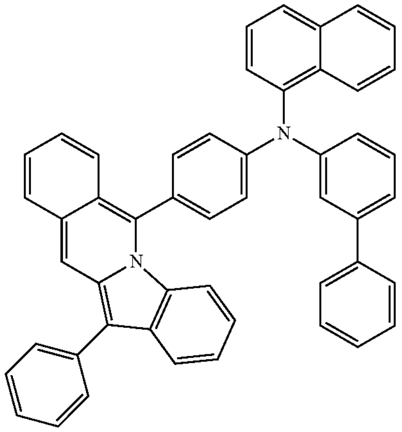

-continued
B3
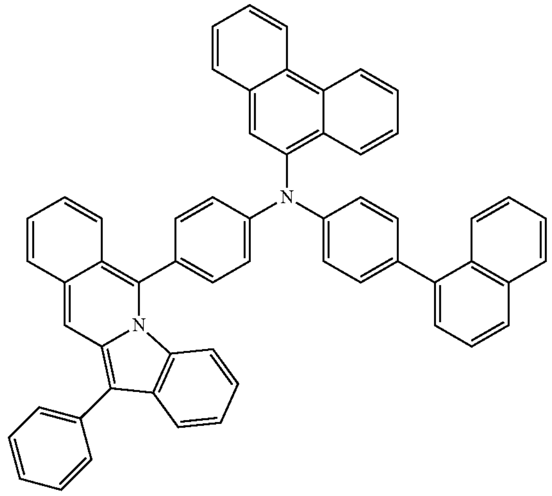
B4
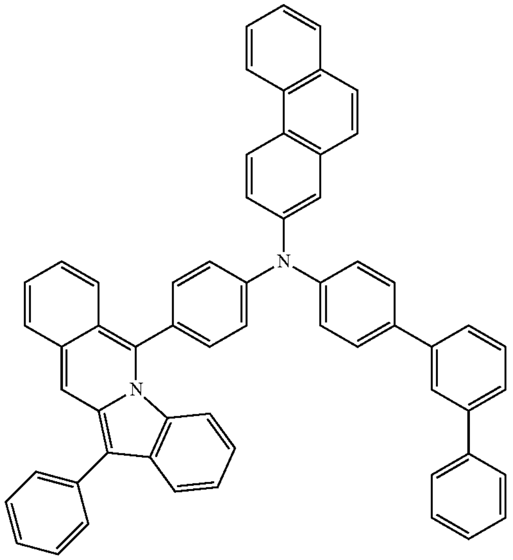
B5
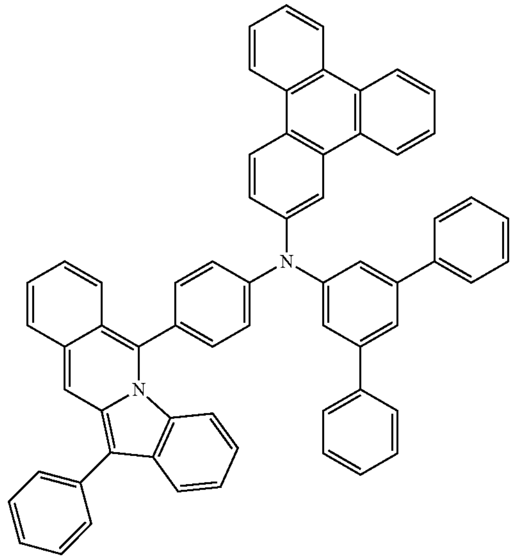
B6
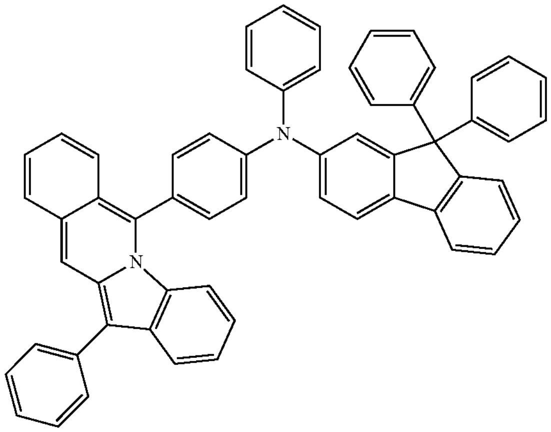
B7
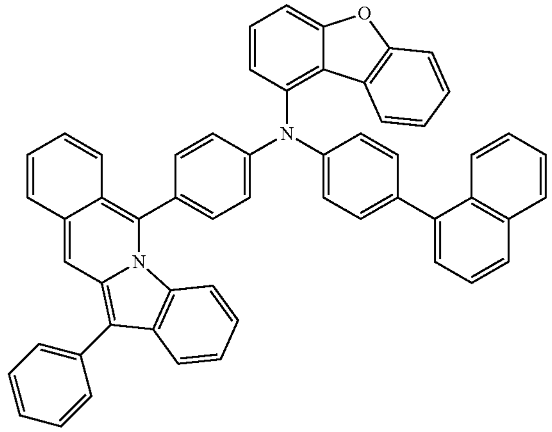
B8
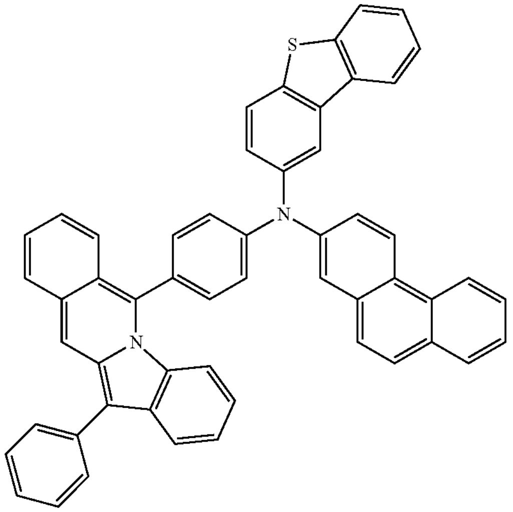

-continued
B9
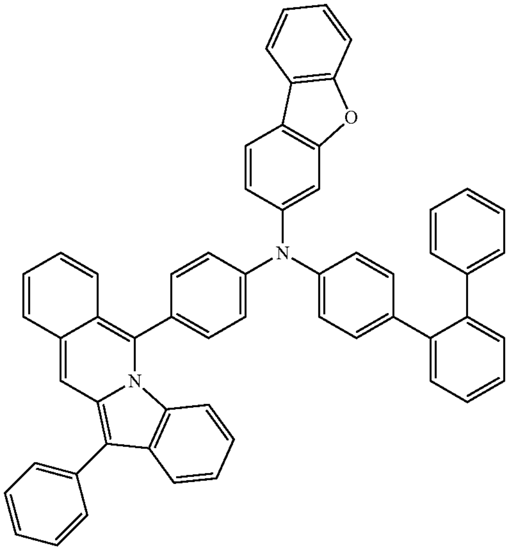
B10
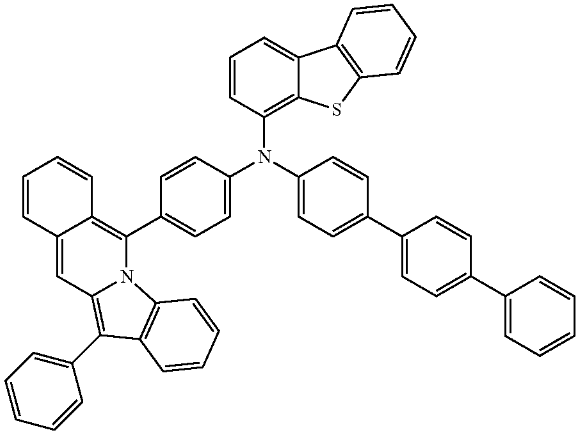
B11
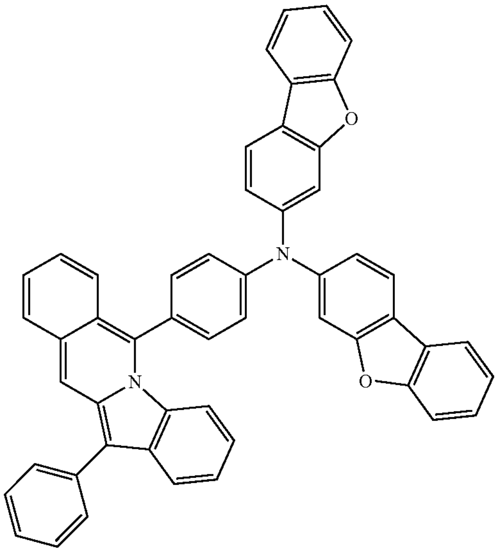
B12
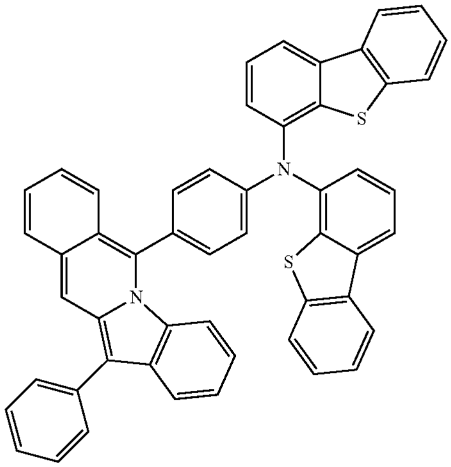
B13
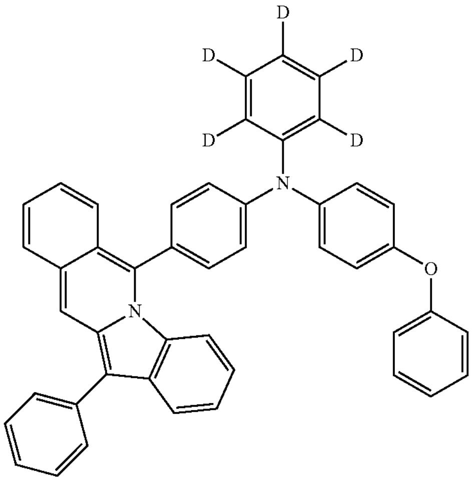
B14
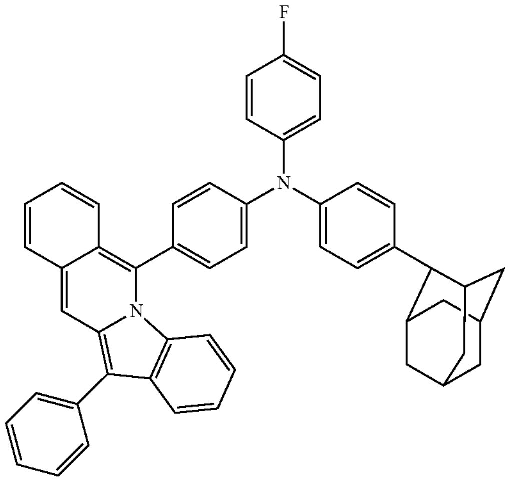

-continued
B15
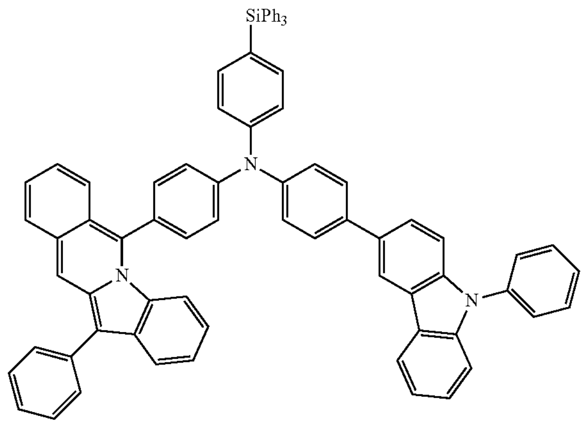
B16
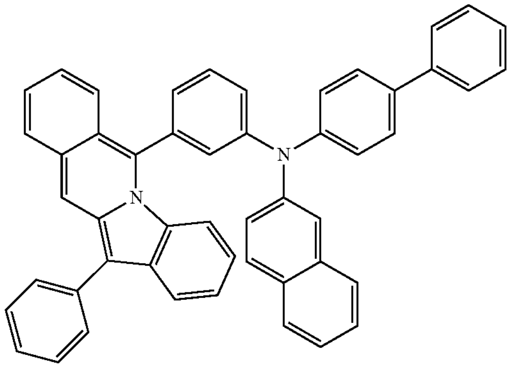
B17
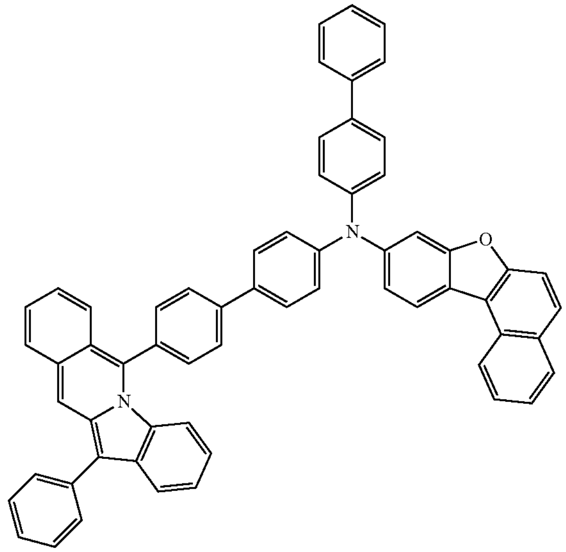
B18
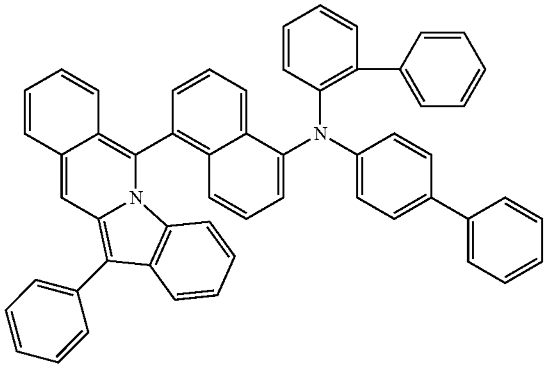
B19
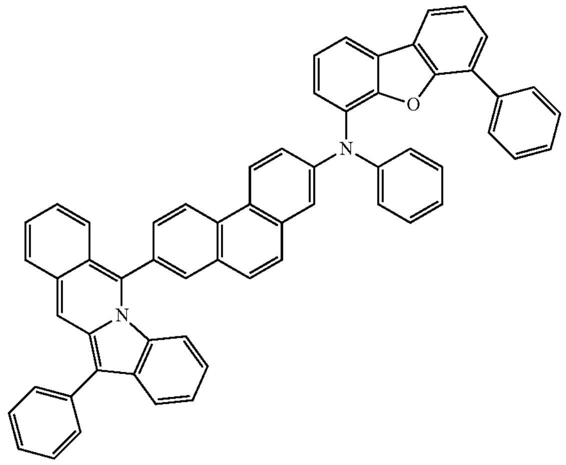
B20
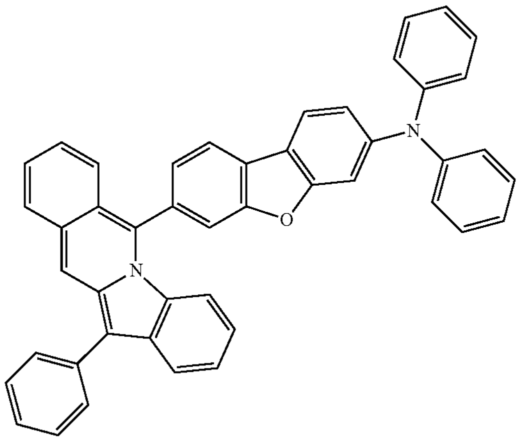

-continued
B21
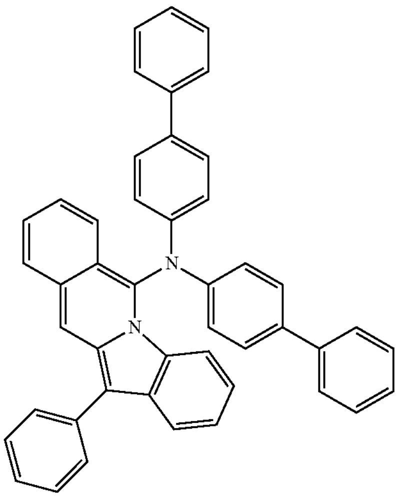
B22
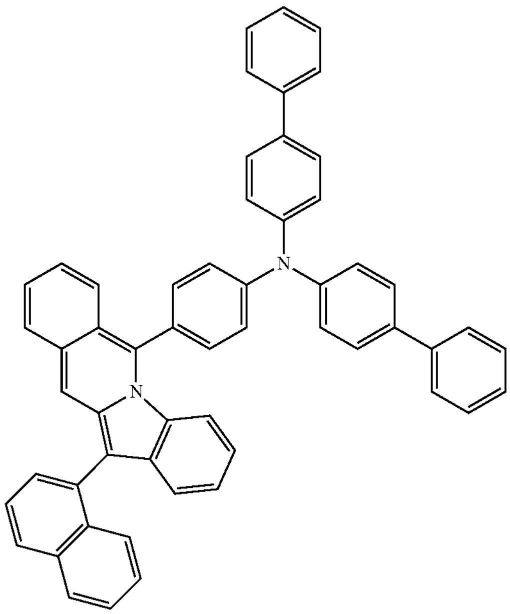
B23
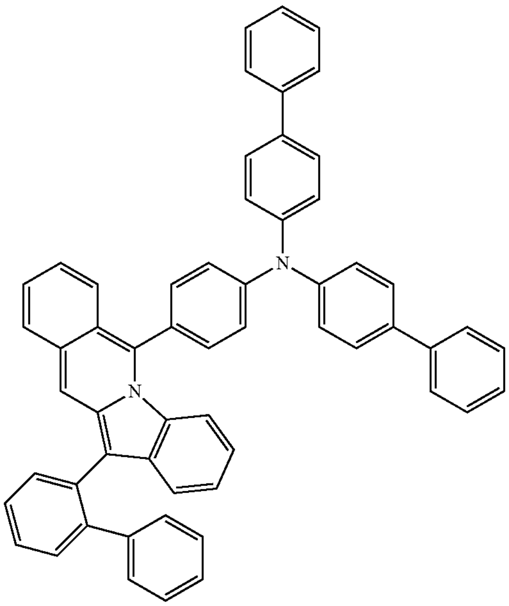
B24
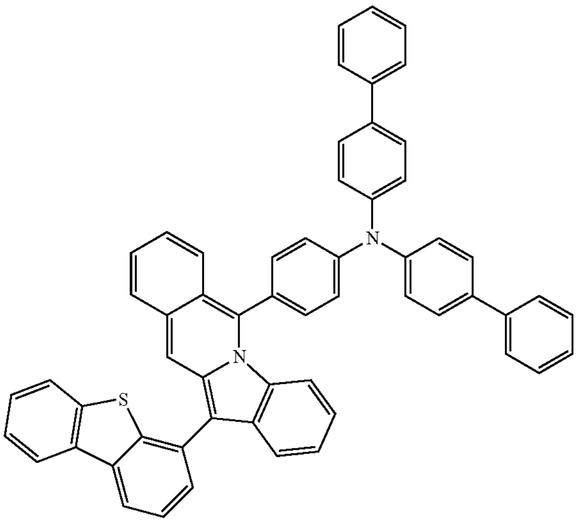

-continued
B25
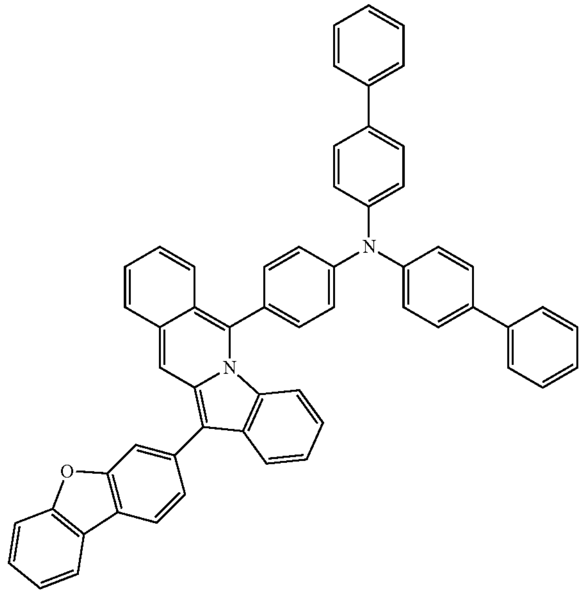
B26
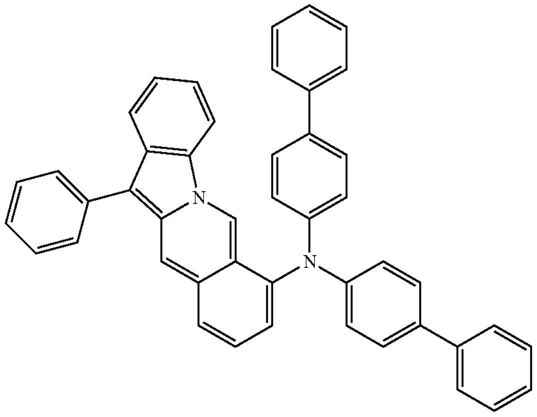
B27
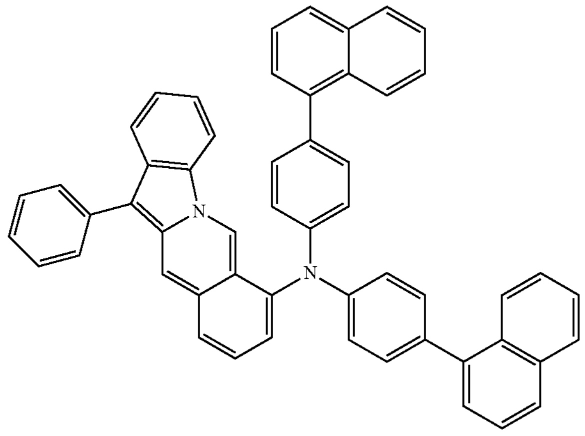
B28
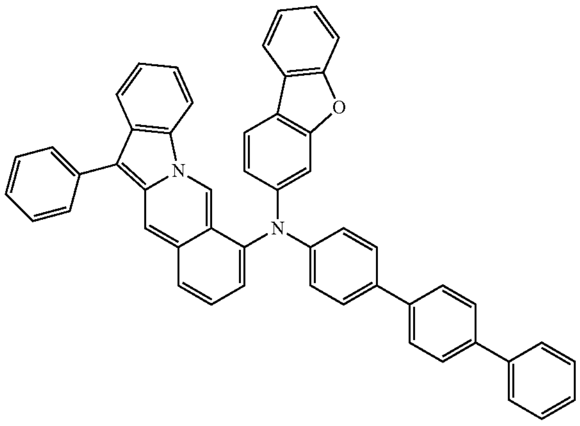
B29
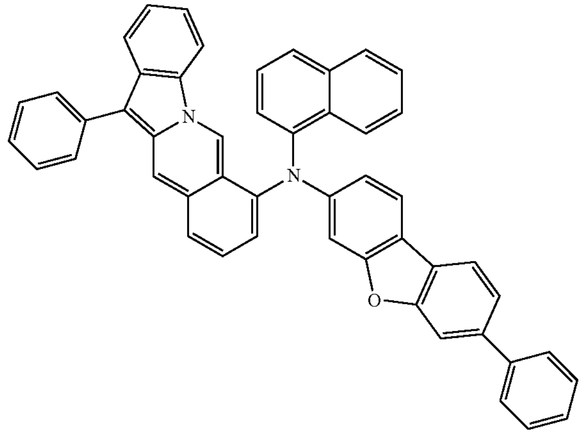
B30
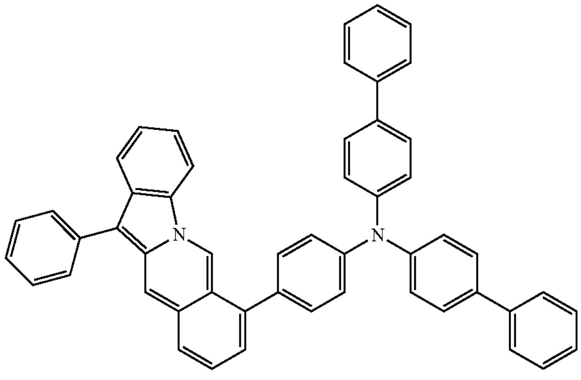

-continued
B31
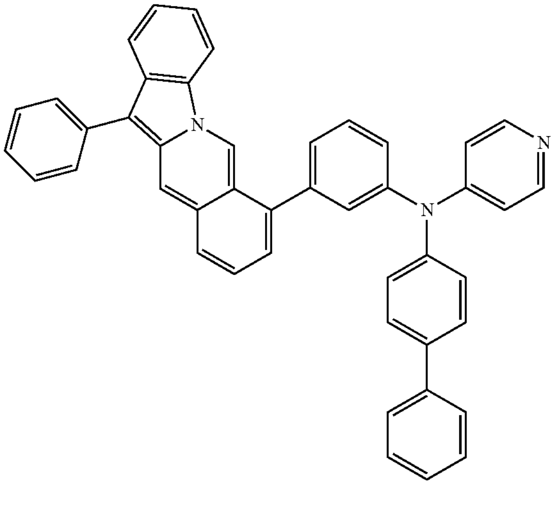
B32
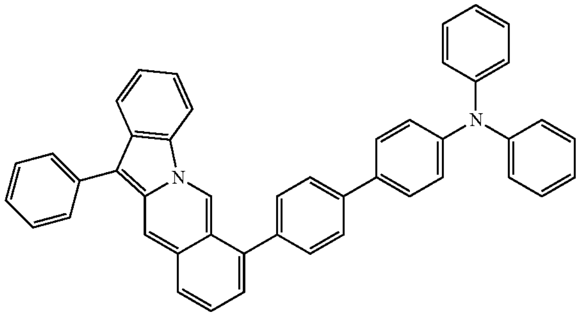
B33
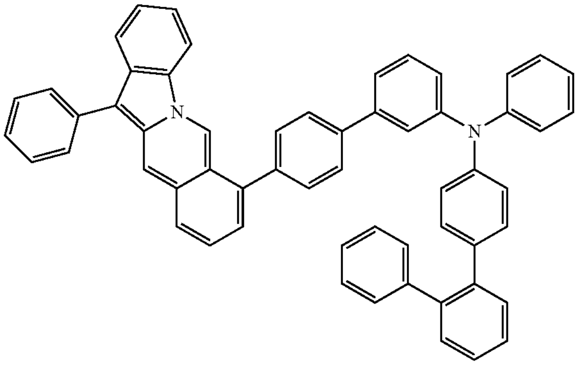
B34
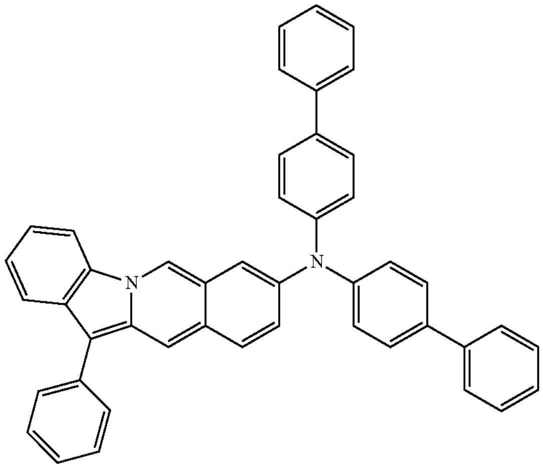
B35
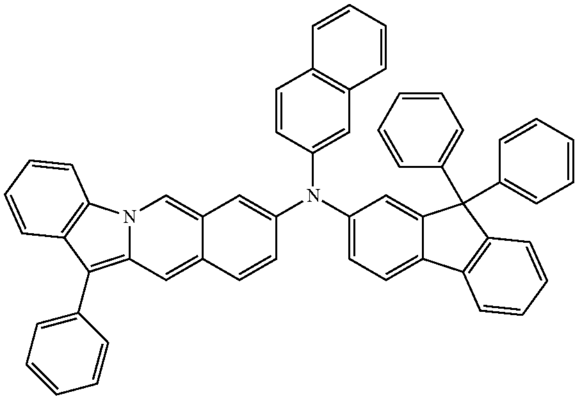
B36
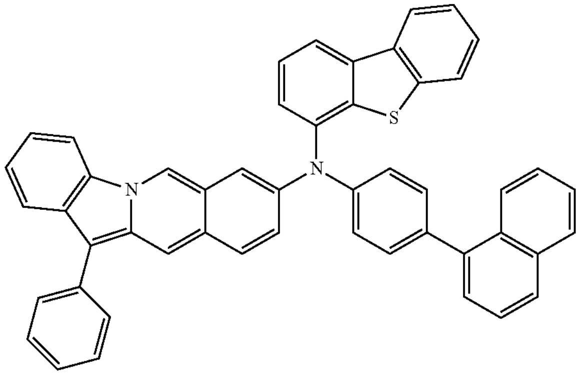

-continued
B37
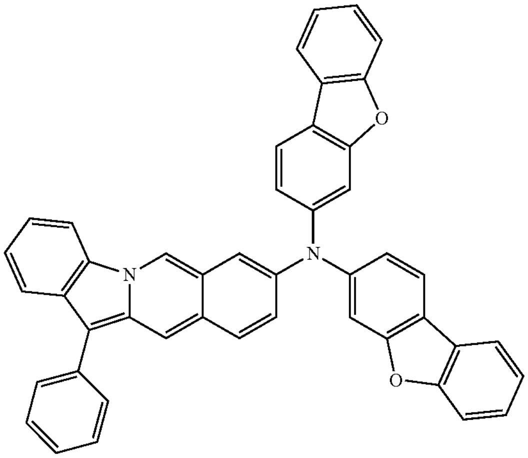
B38
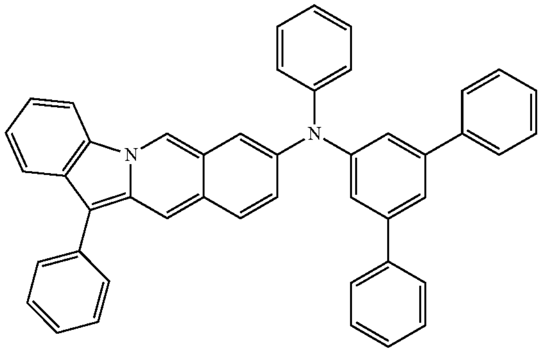
B39
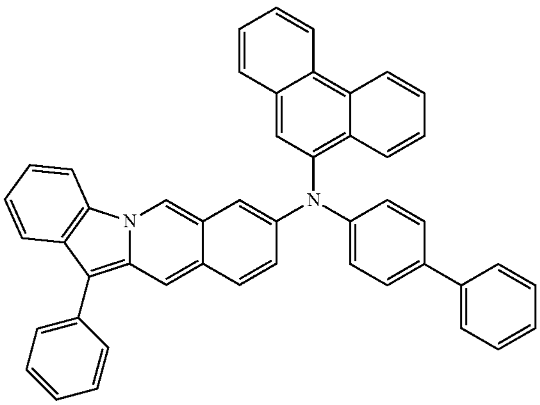
B40
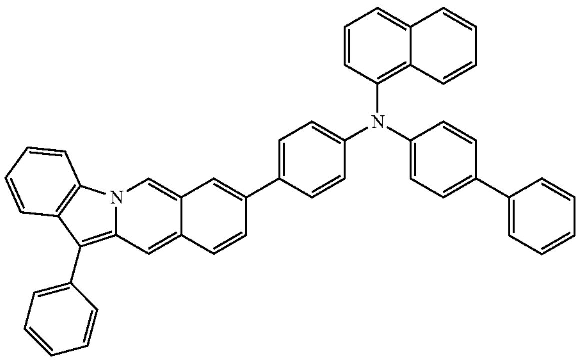
B41
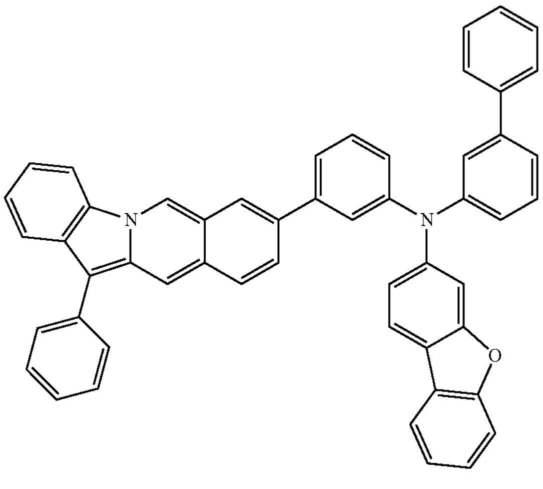
B42
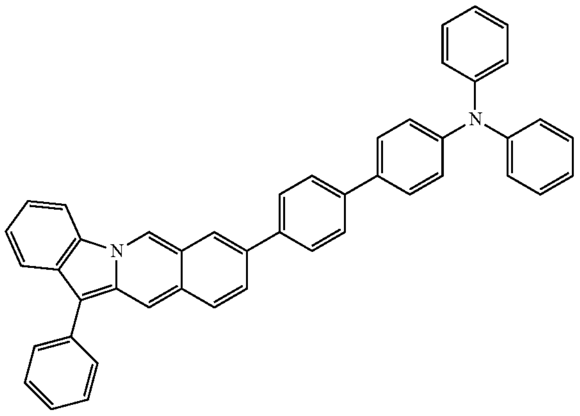

-continued
B43
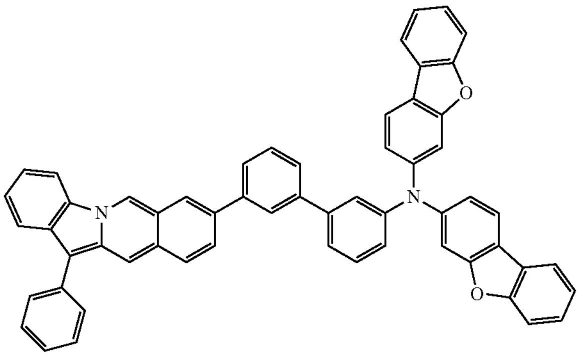
B44
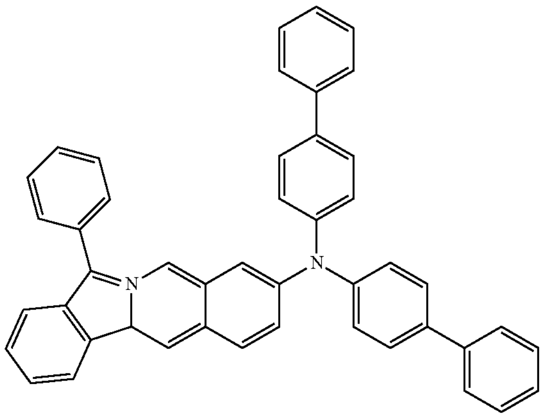
B45
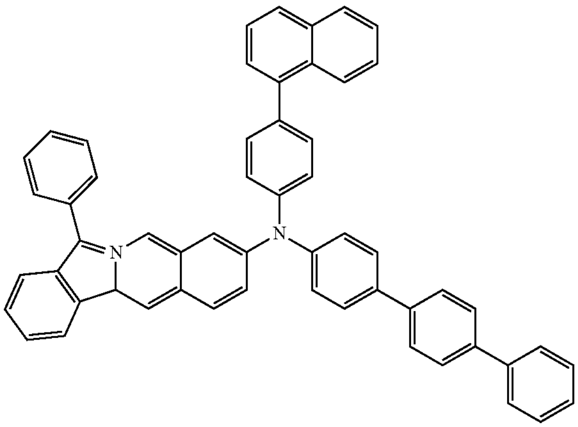
B46
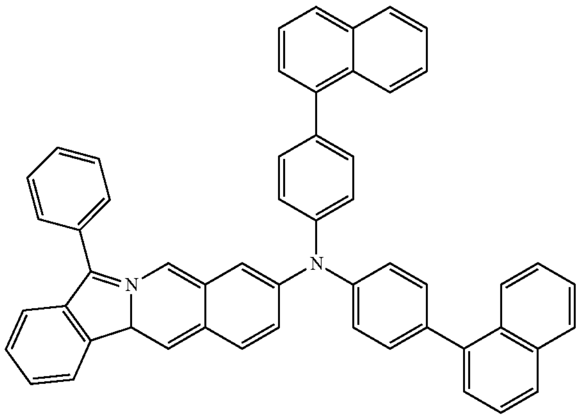
B47
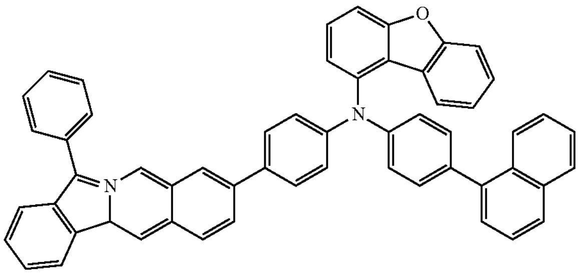
B48
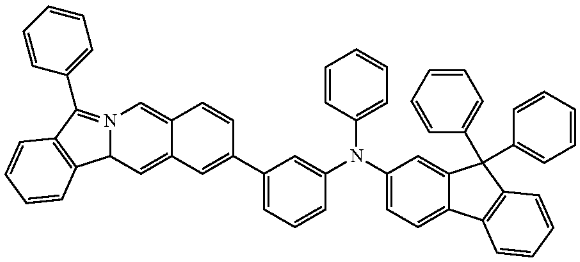
B49
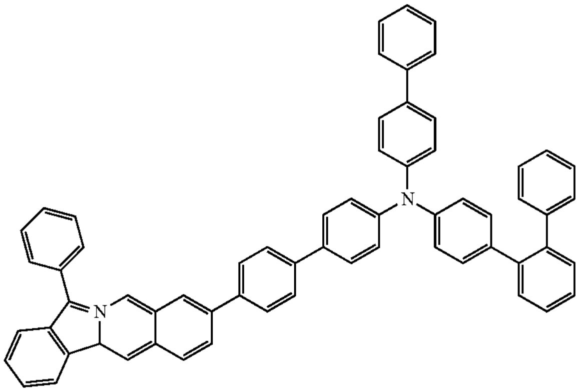
B50
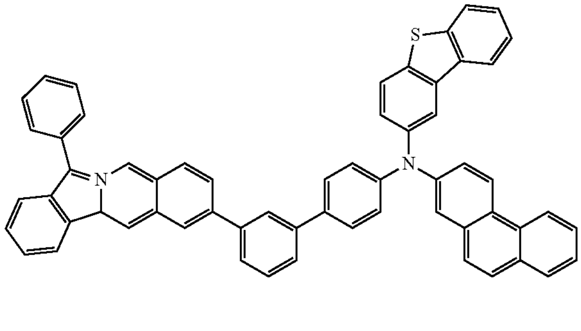

-continued
B51
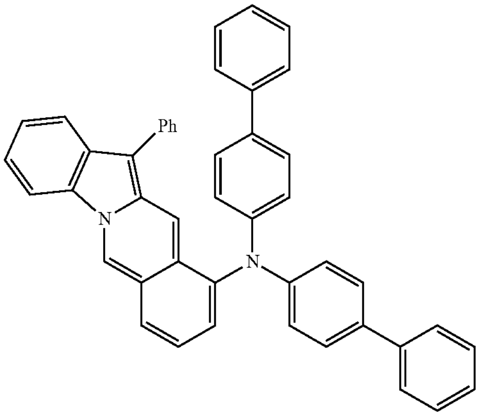
B52
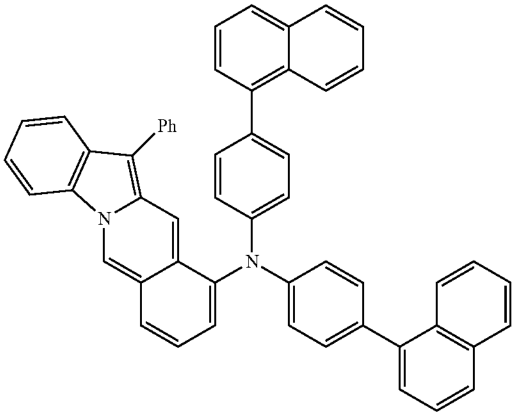
B53
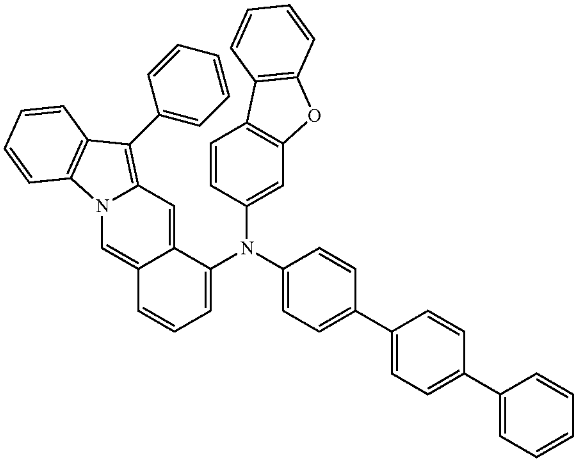
B54
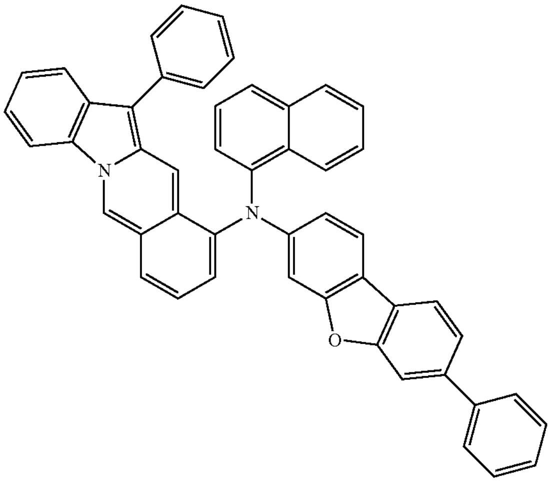
B55
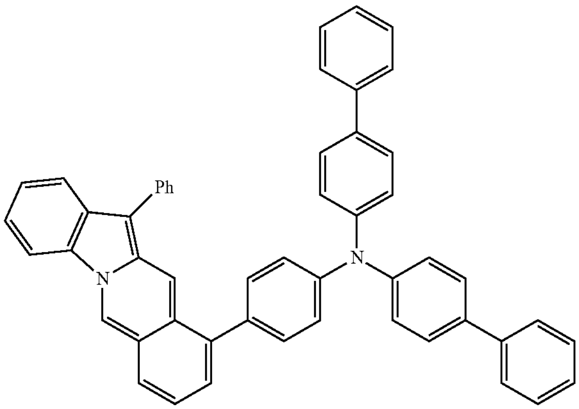
B56
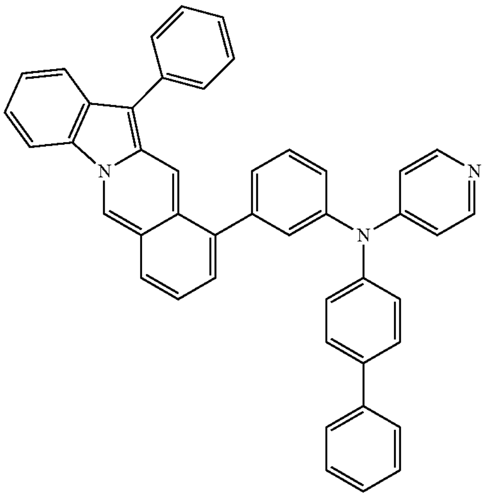

-continued
B57
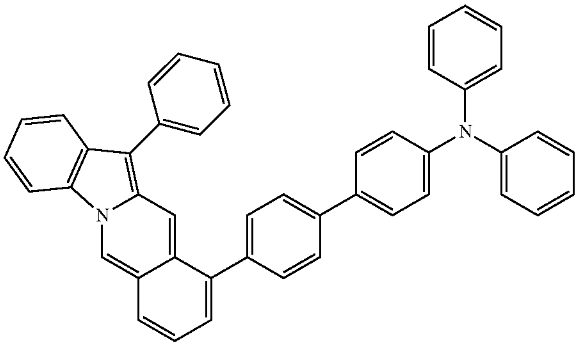
B58
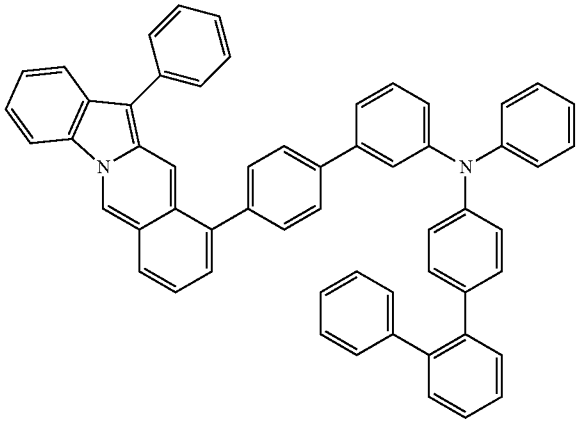
B59
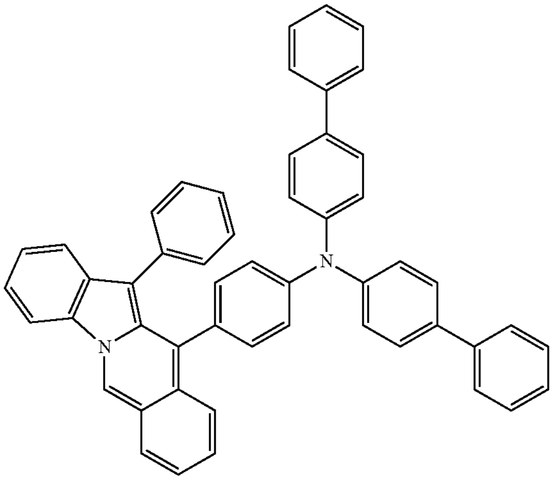
B60
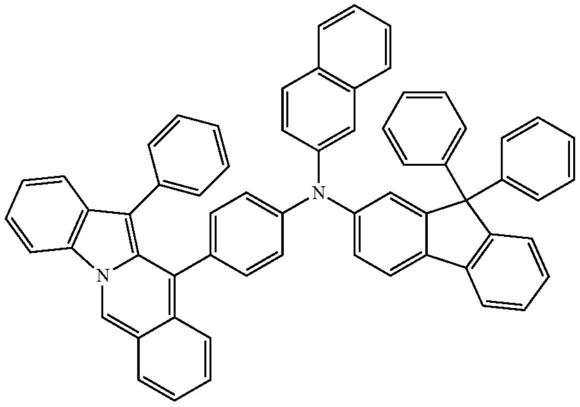
B61
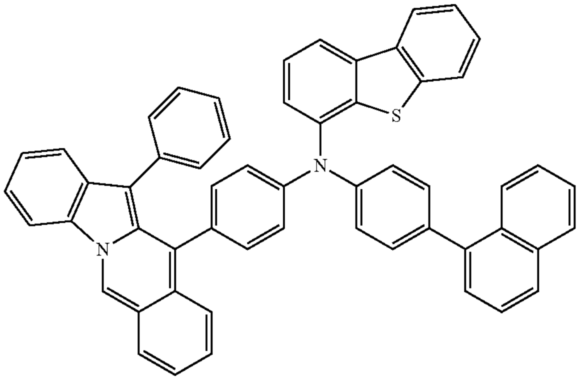
B62
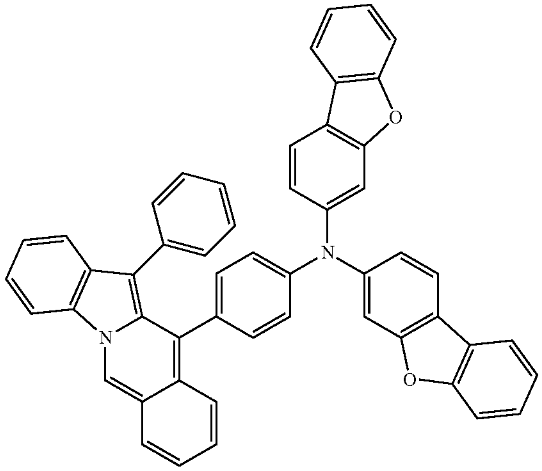

-continued
B63
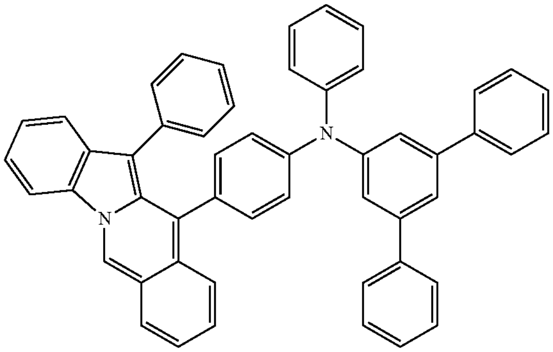
B64
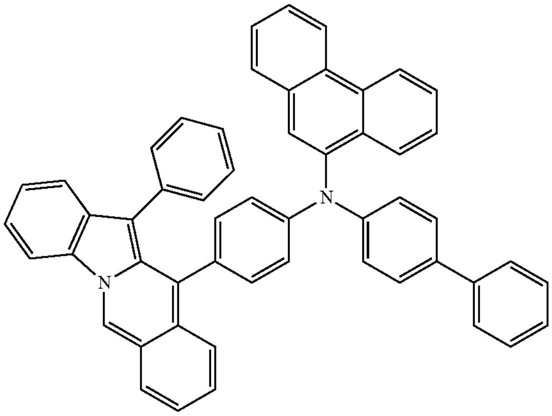
B65
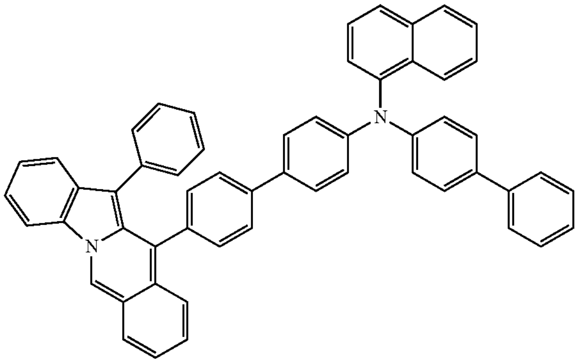
B66
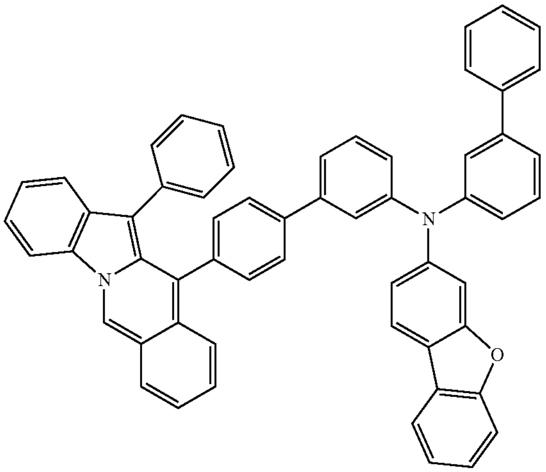
B67
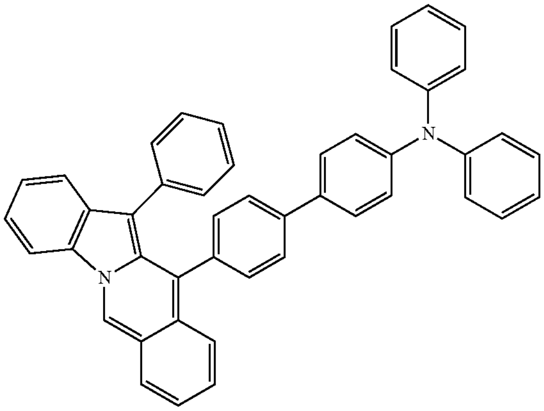
B68
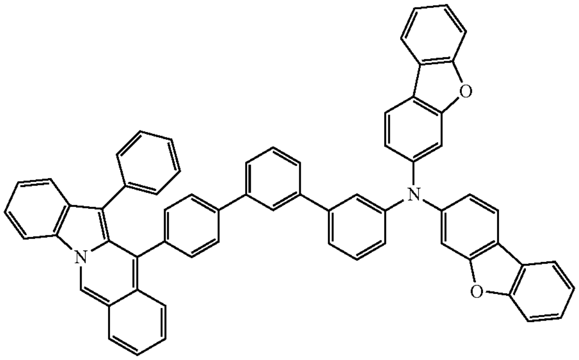

-continued
B69
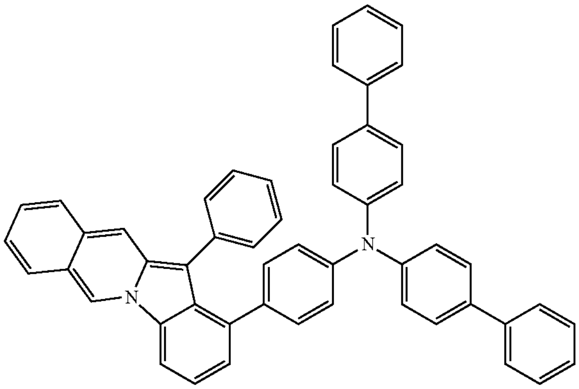
B70
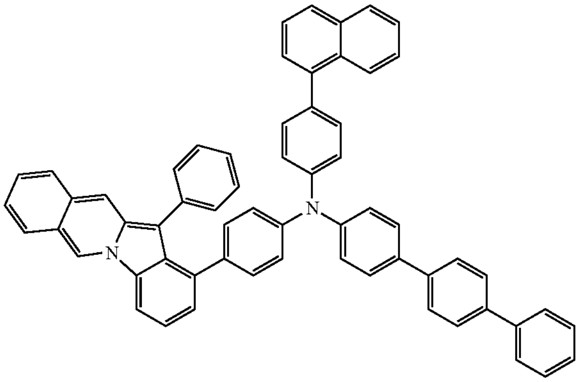
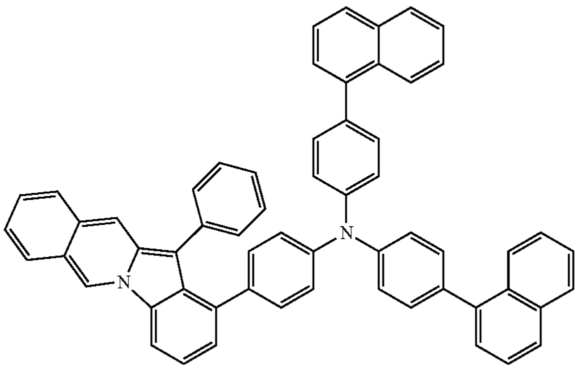
B72
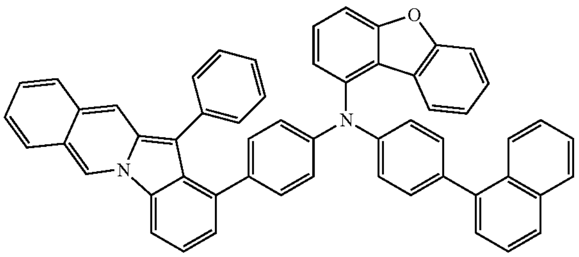
B73
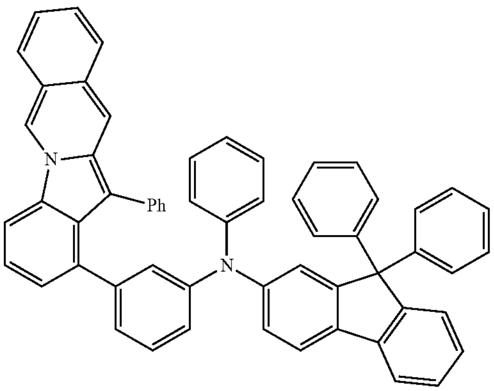
B74
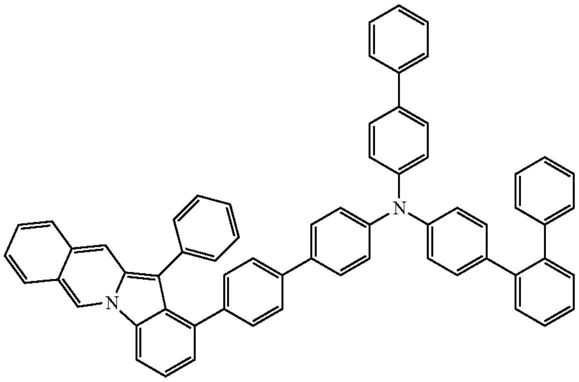

-continued
B75
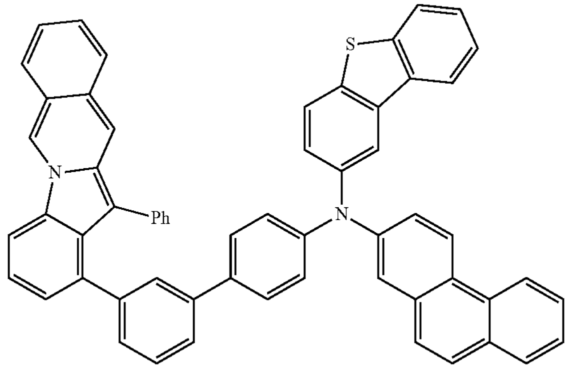
B76
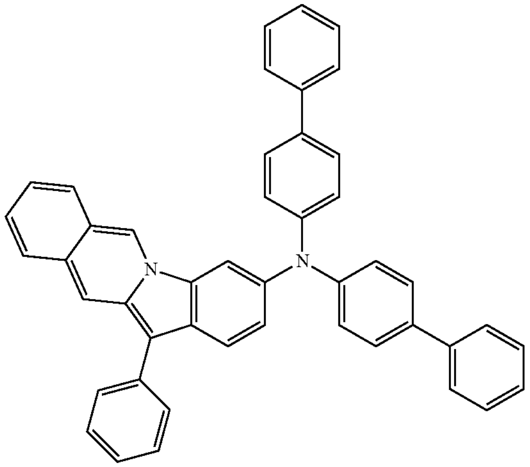
B77
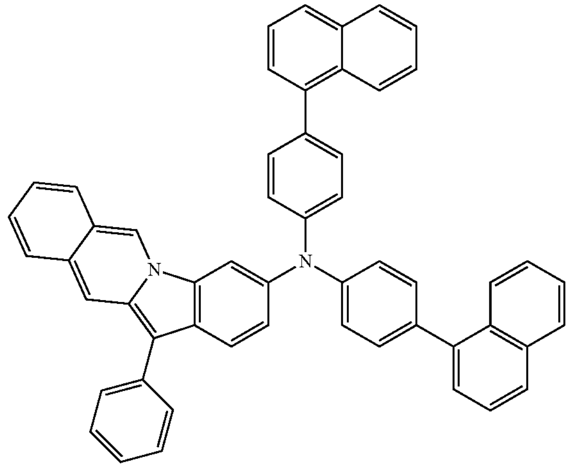
B78
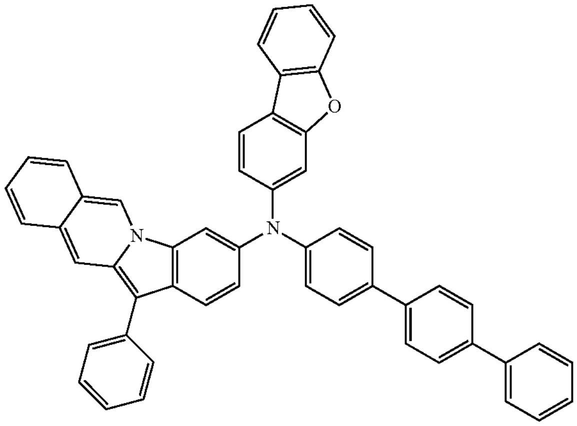
B79
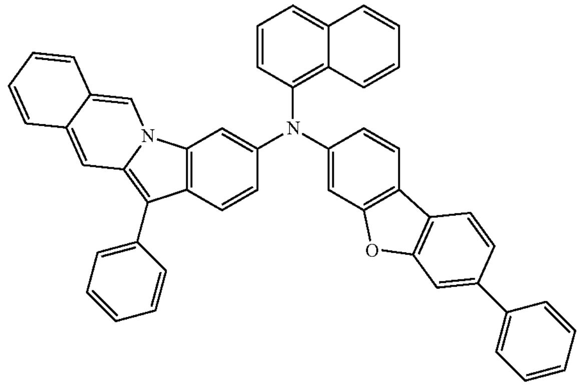
B80
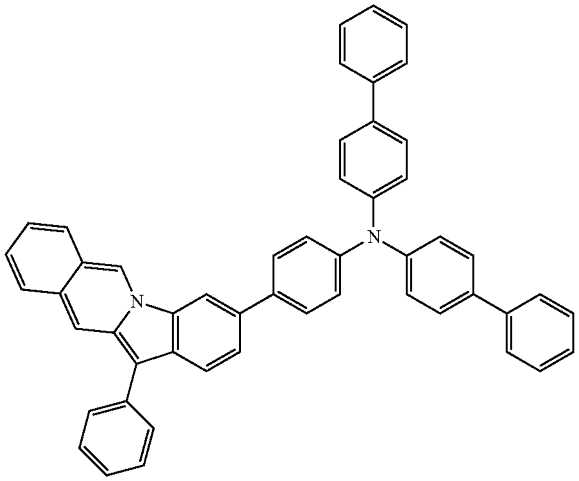

-continued
B81
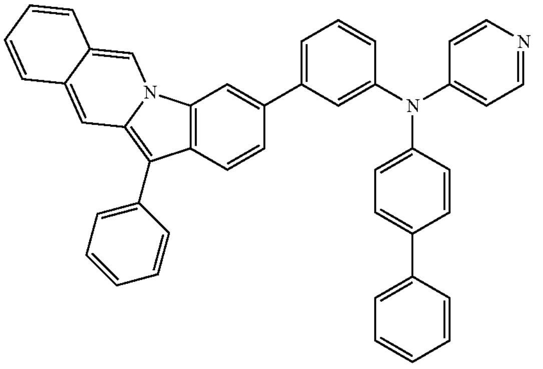
B82
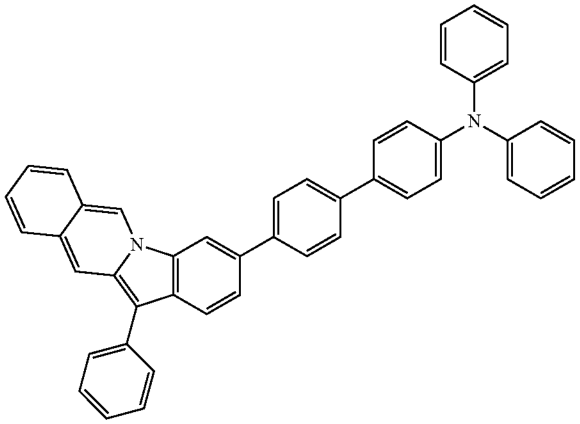
B83
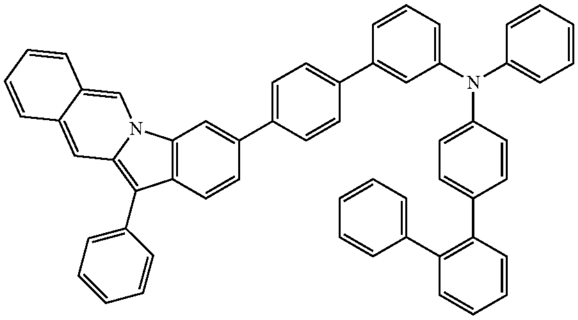
B84
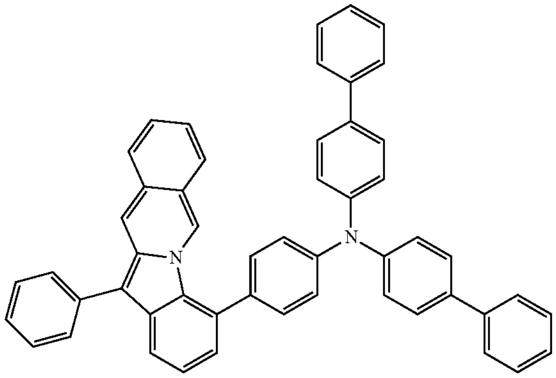
B85
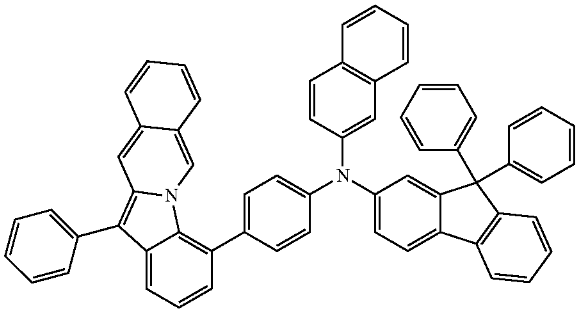
B86
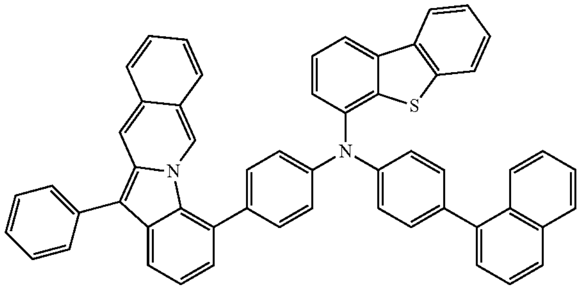
B87
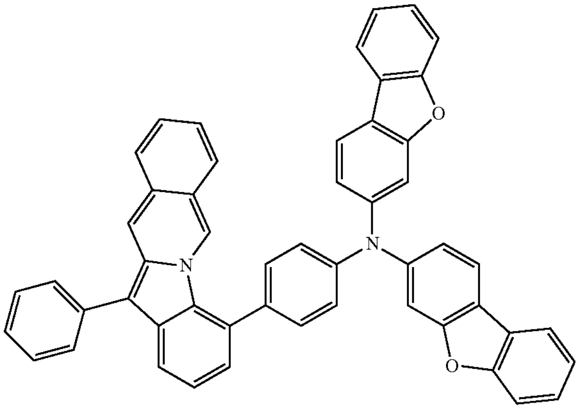
B88
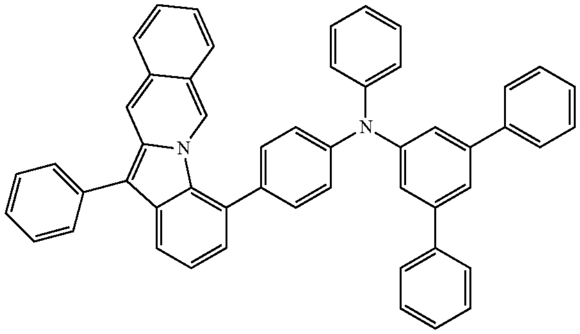

-continued
B89
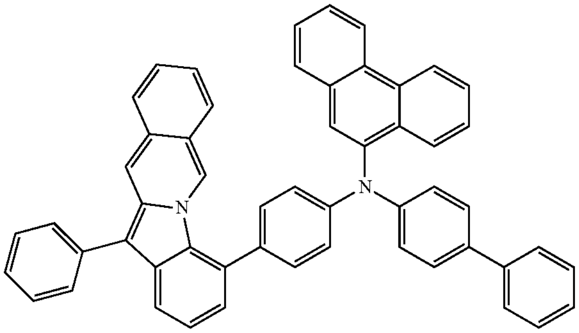
B90
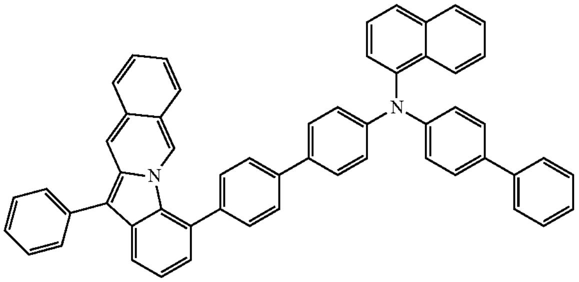
B91
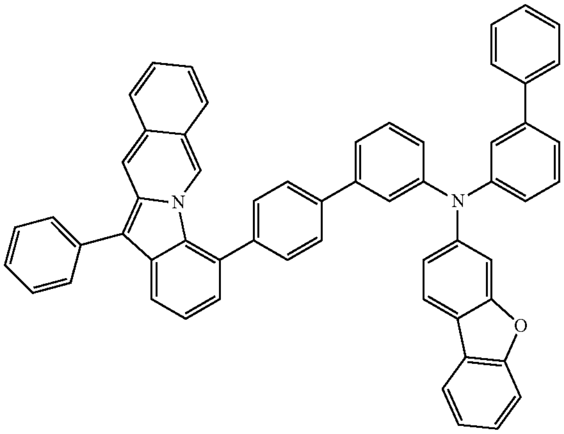
B92
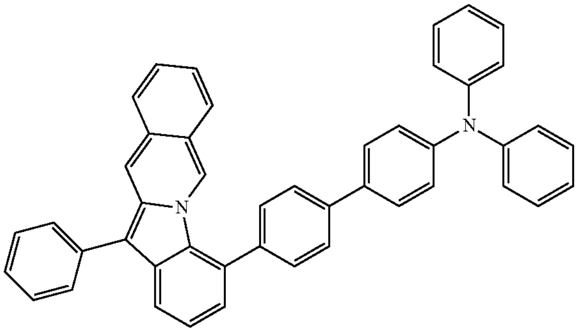
B93
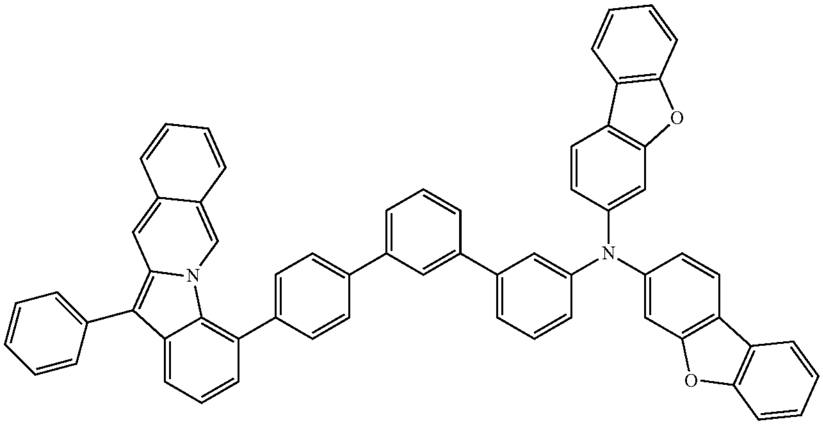
B94
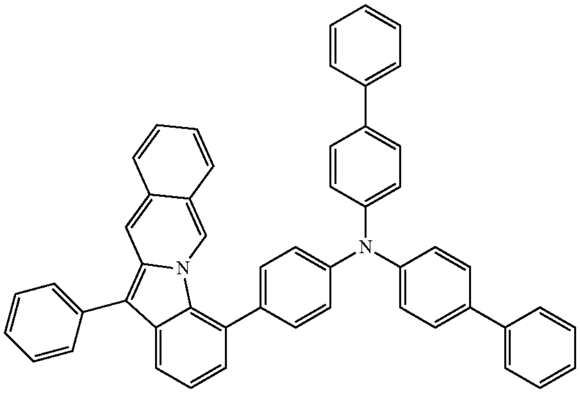
B95
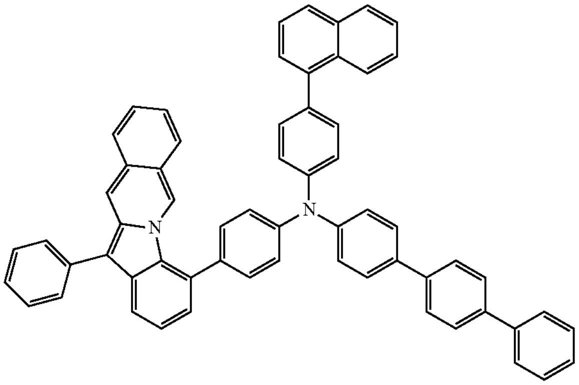

-continued
B96
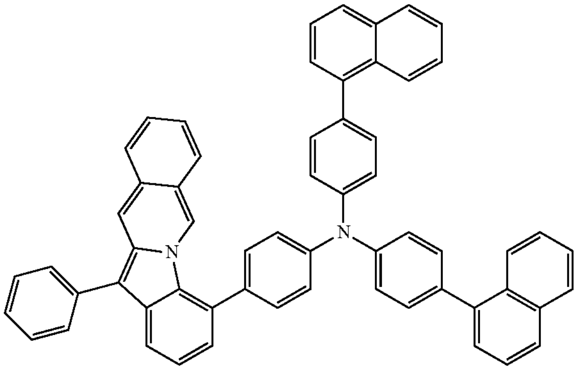
B97
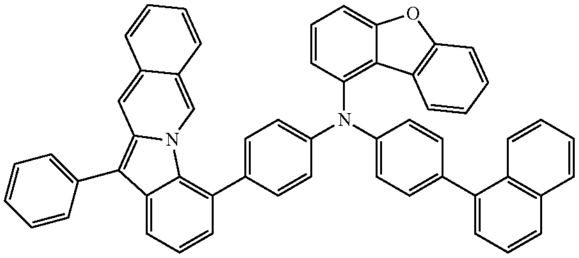
C1
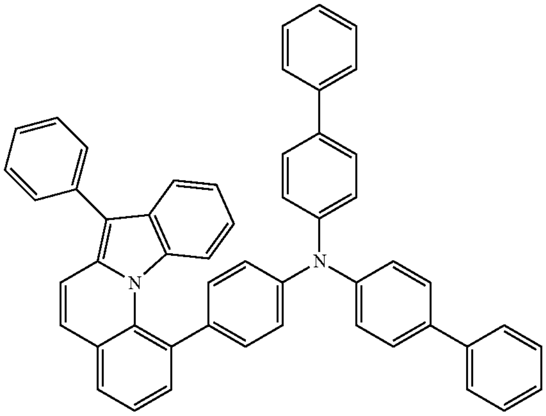
C2
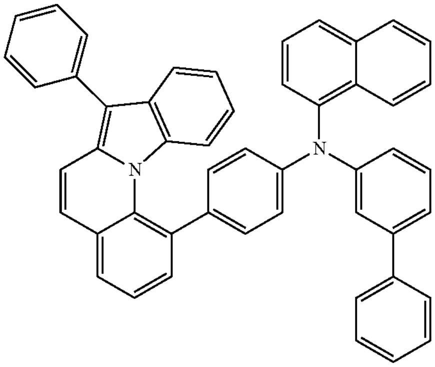
C3
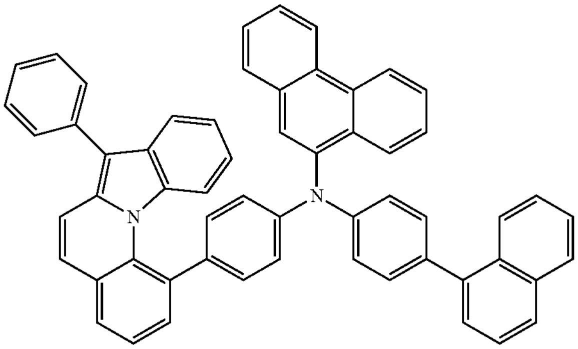
C4
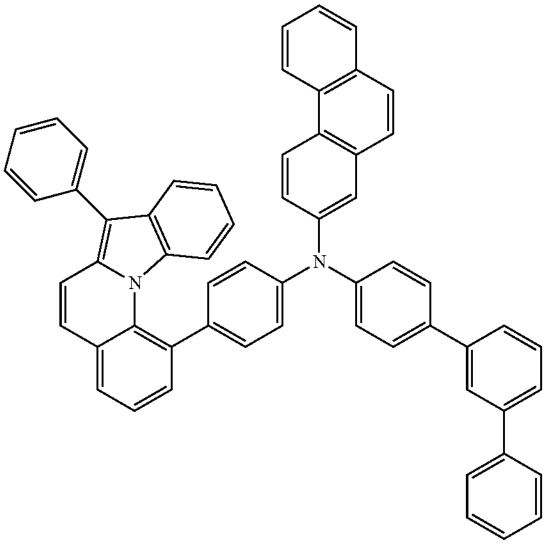

-continued
C5
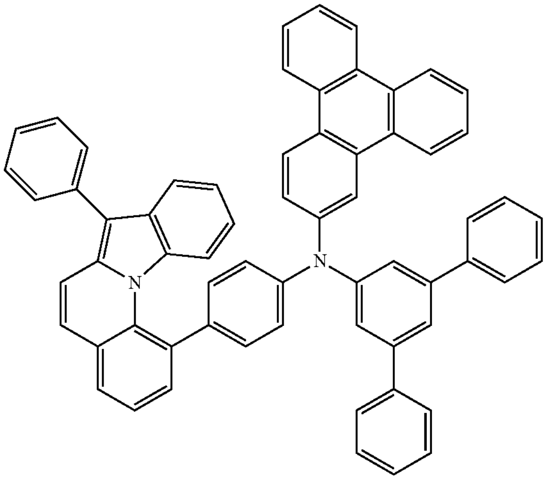
C6
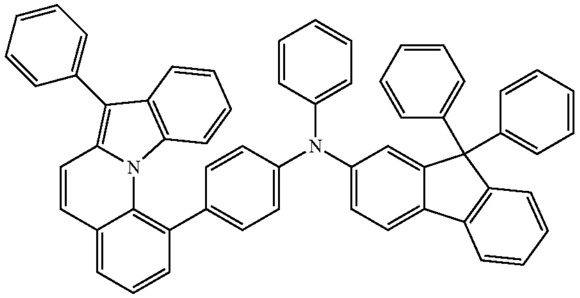
C7
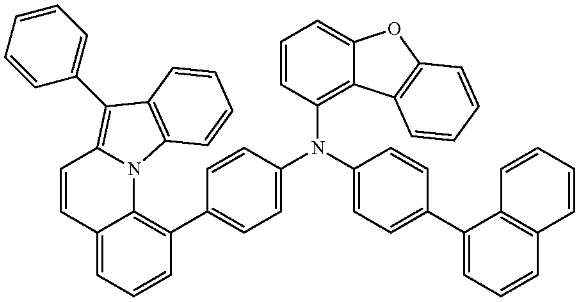
C8
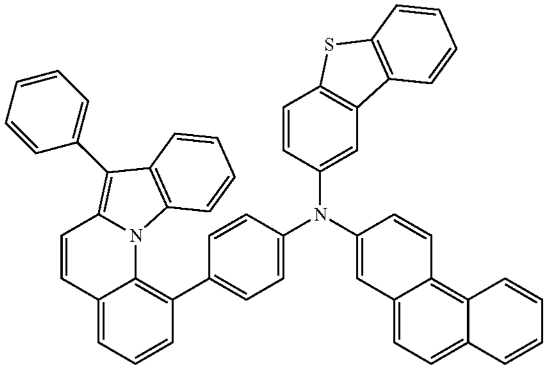
C9
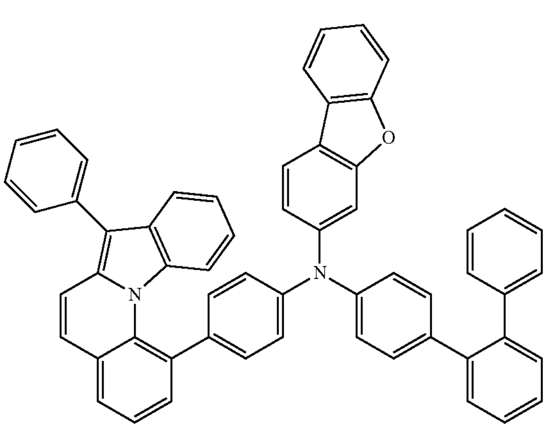
C10
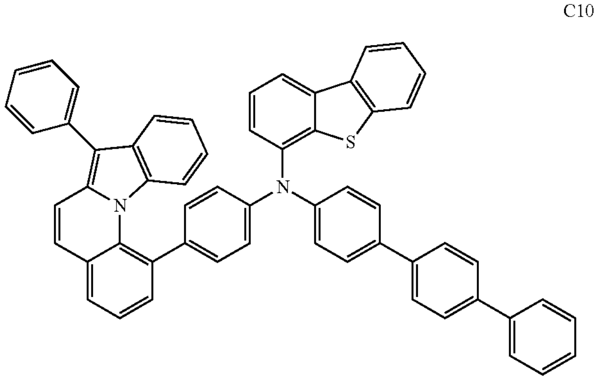

-continued
C11
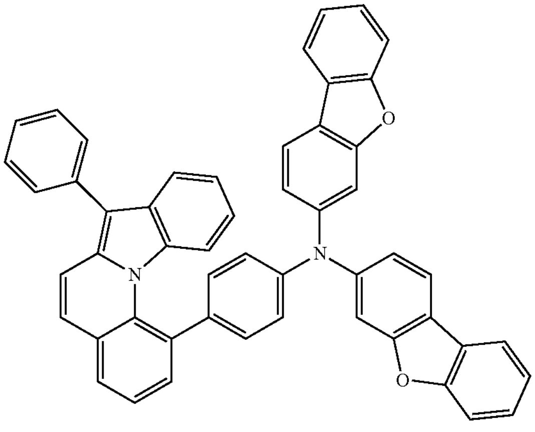
C12
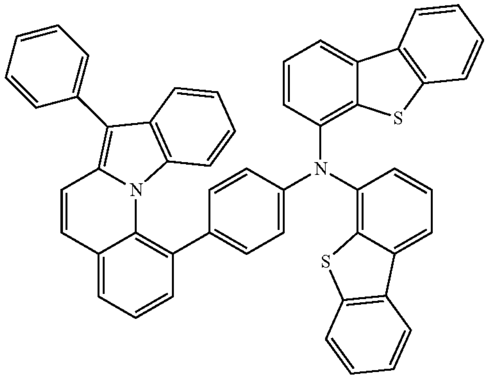
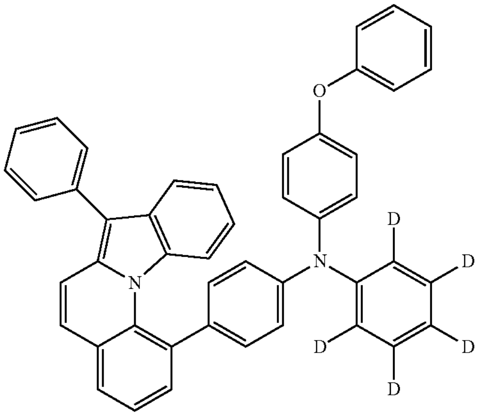
C14
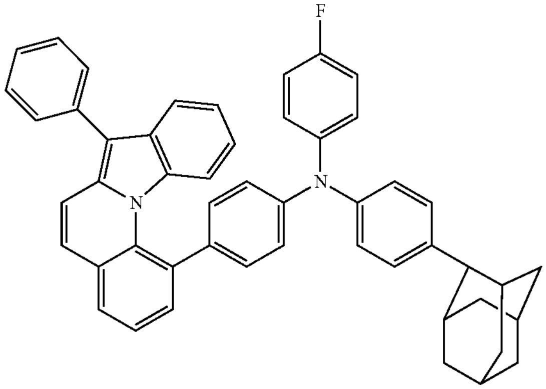
C15
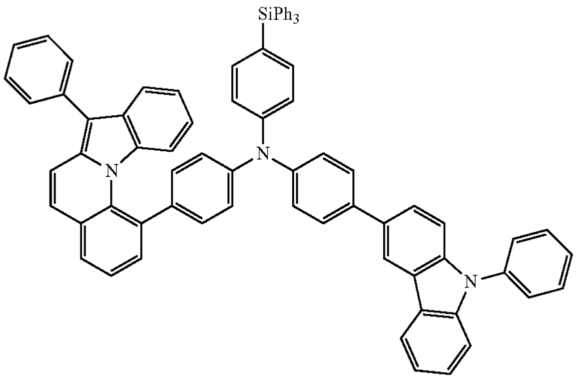
C16
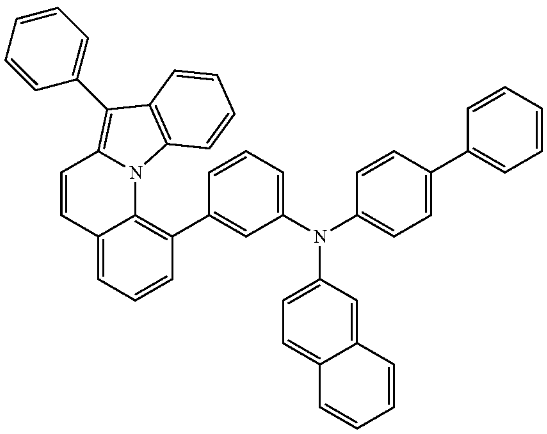

-continued
C17
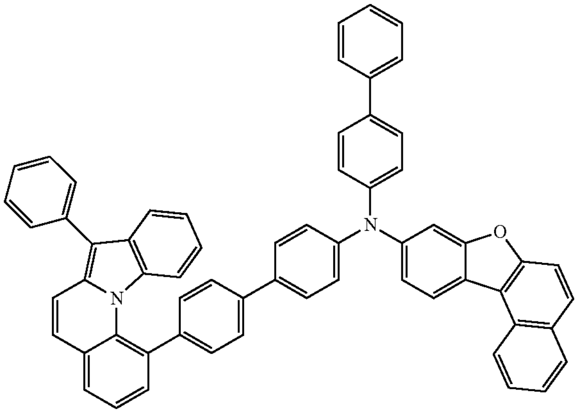
C18
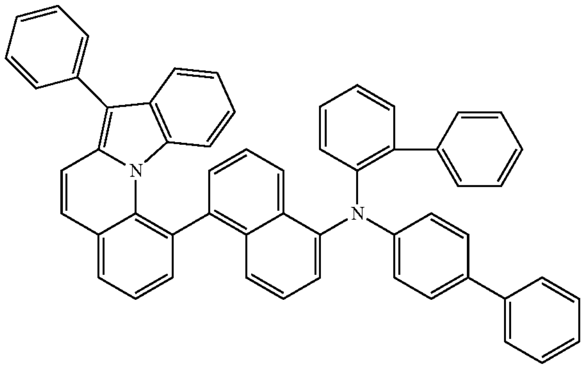
C19
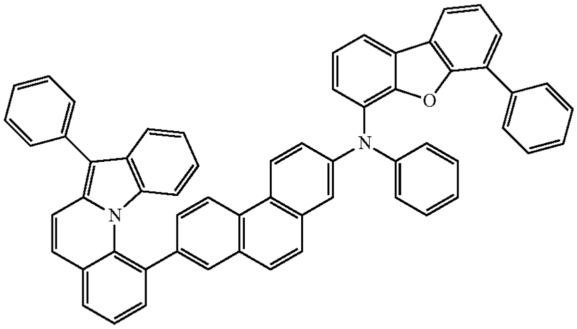
C20
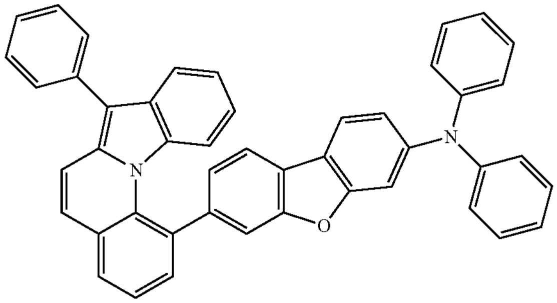
C21
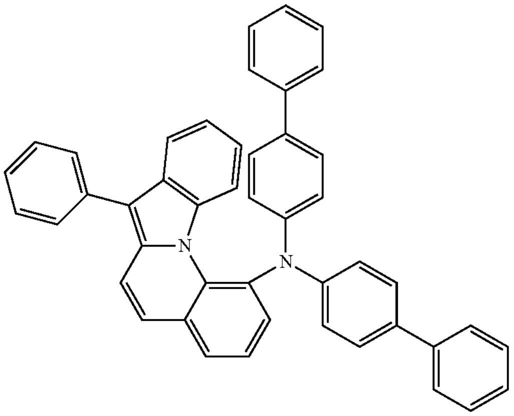
C22
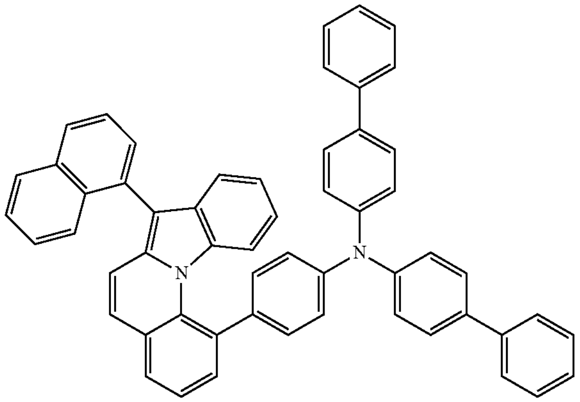
C23
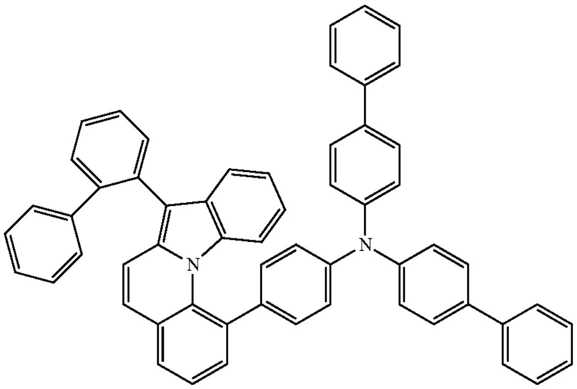
C24
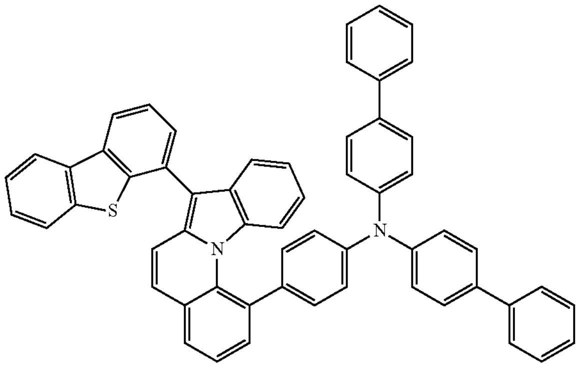

-continued
C25
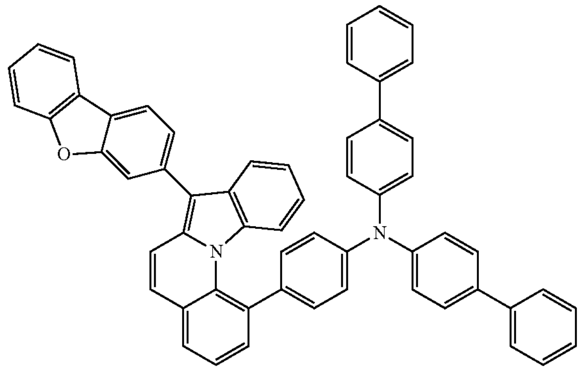
C26
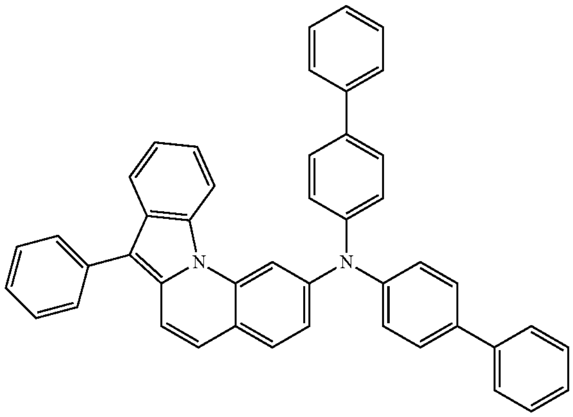
C27
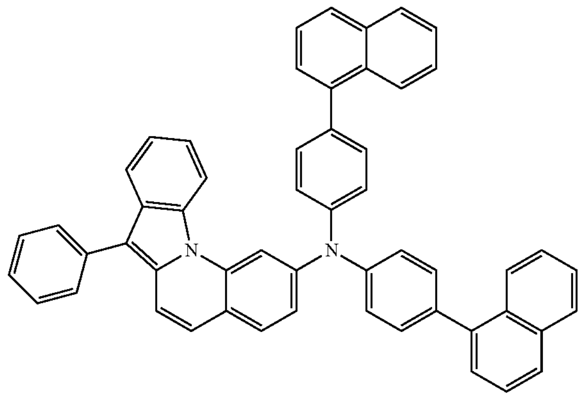
C28
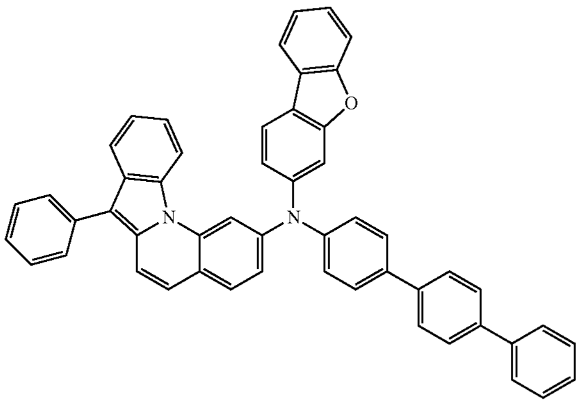
C29
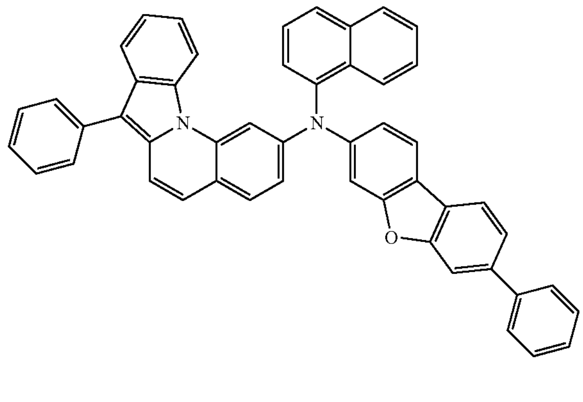
C30
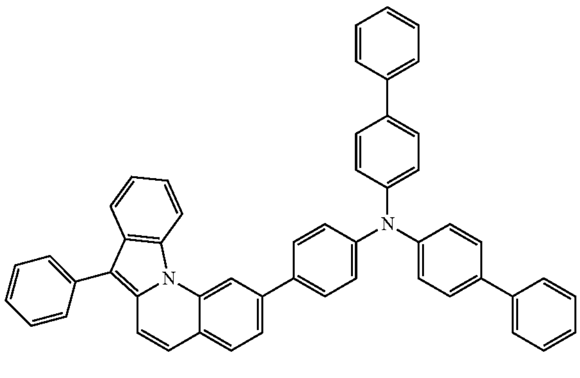

-continued
C31
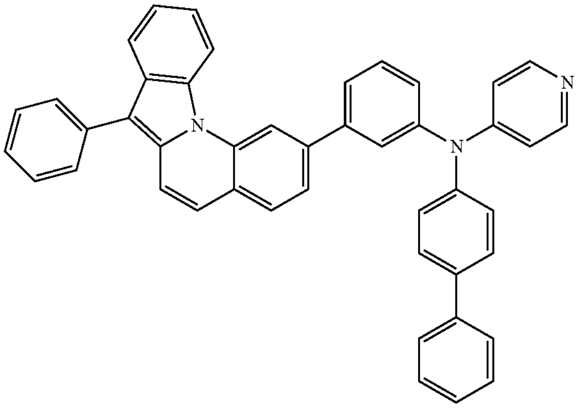
C32
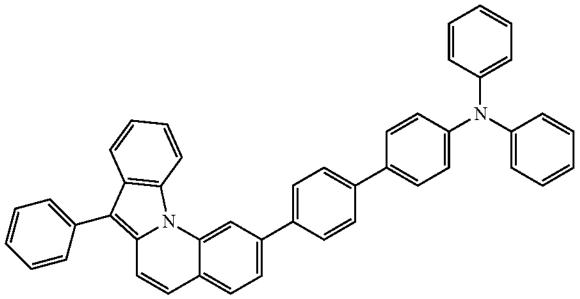
C33
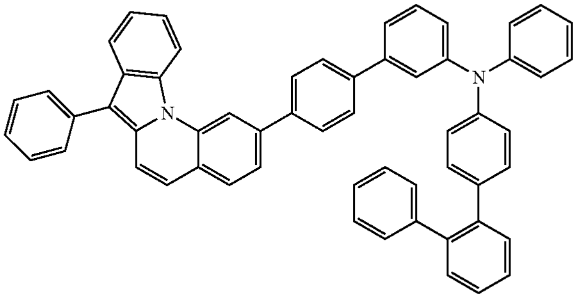
C34
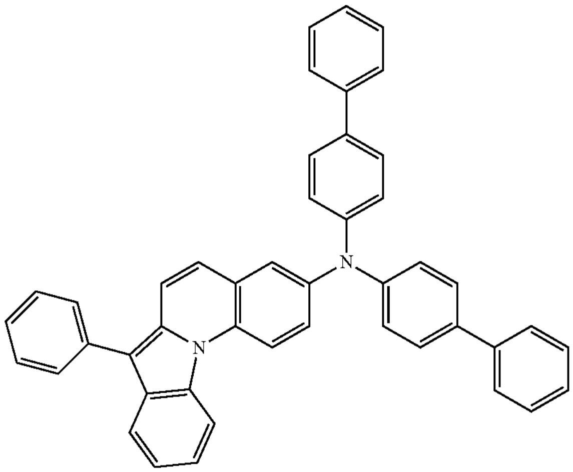
C35
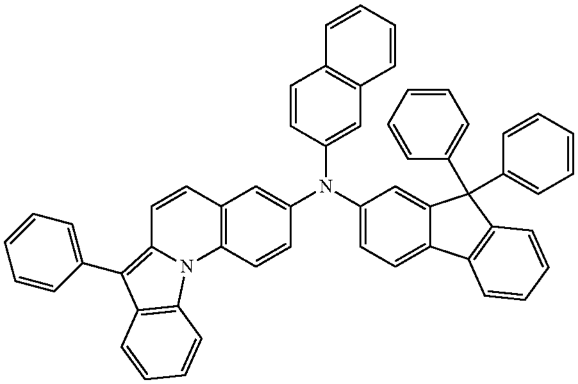
C36
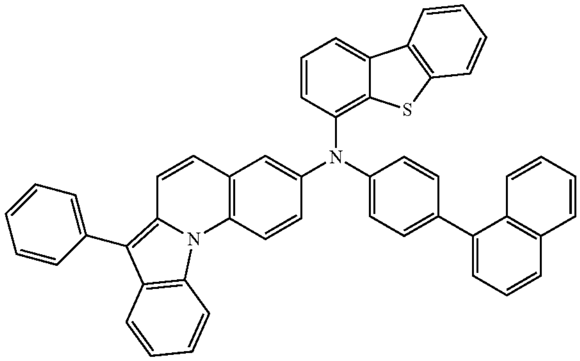

-continued
C37
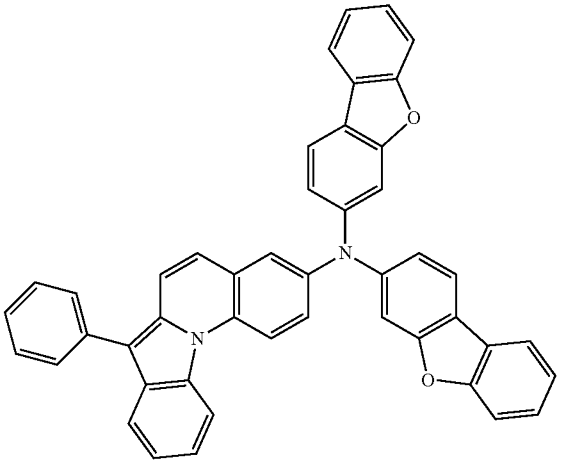
C38
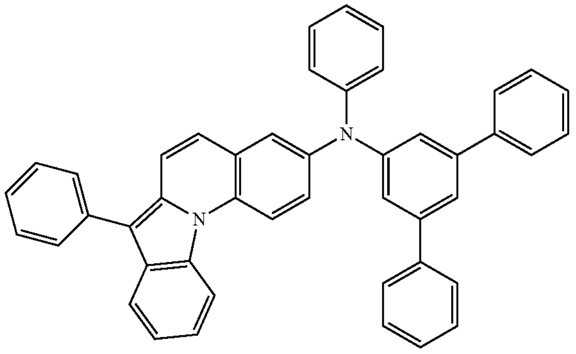
C39
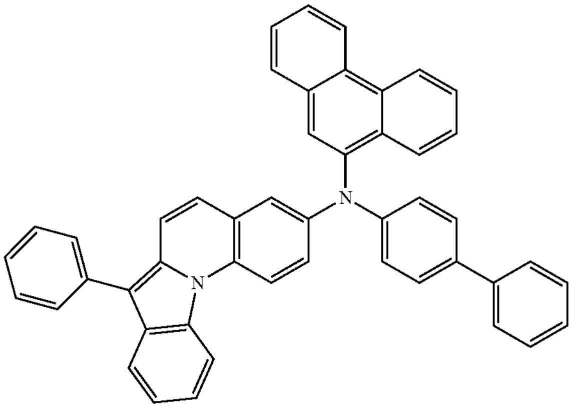
C40
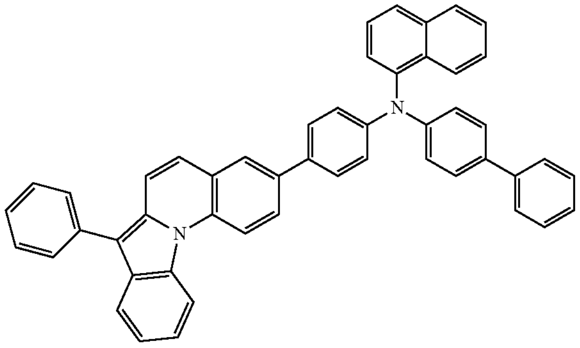
C41
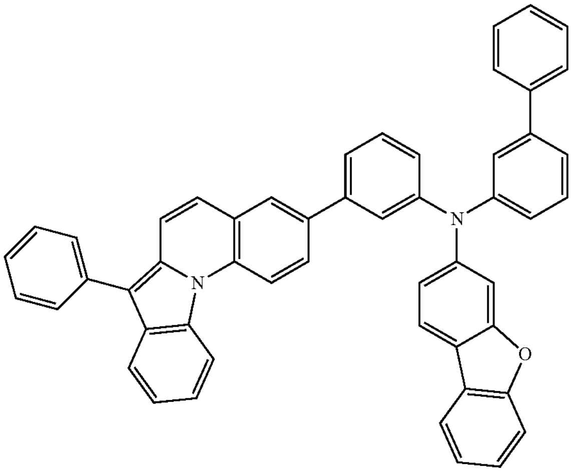
C42
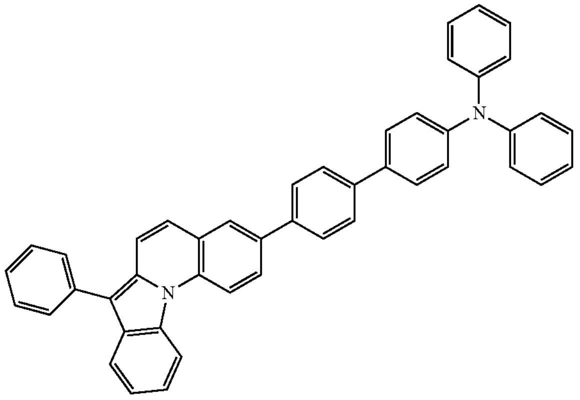

-continued
C43
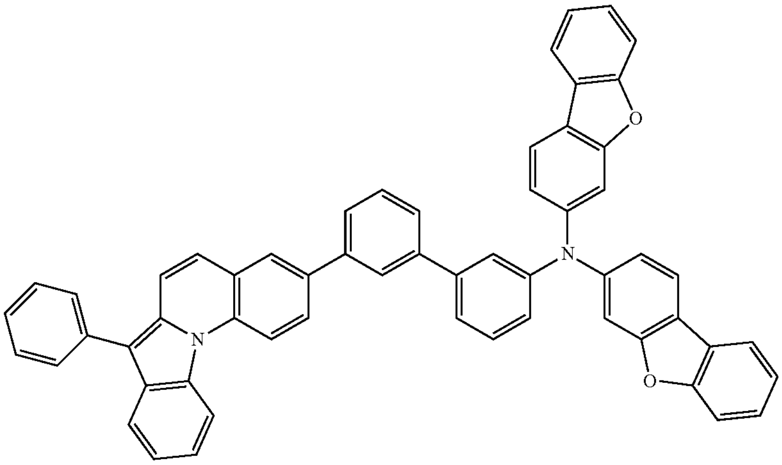
C44
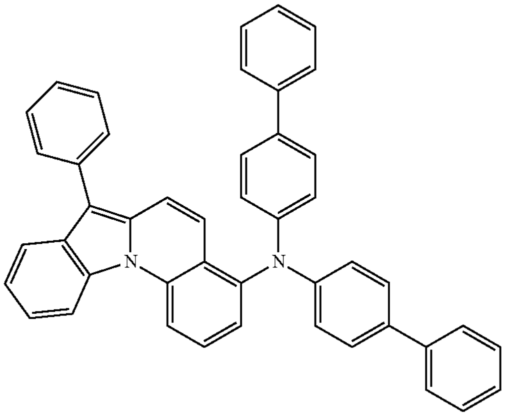
C45
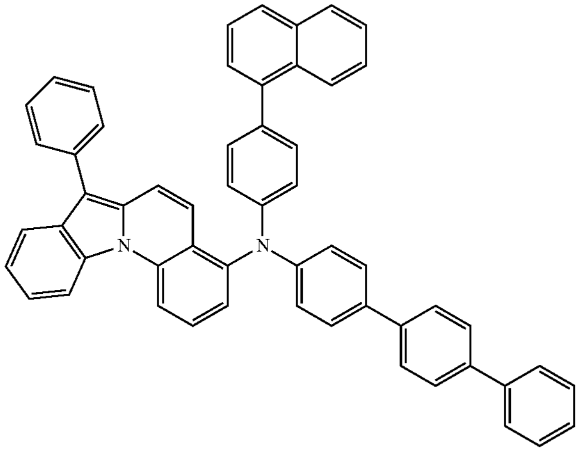
C46
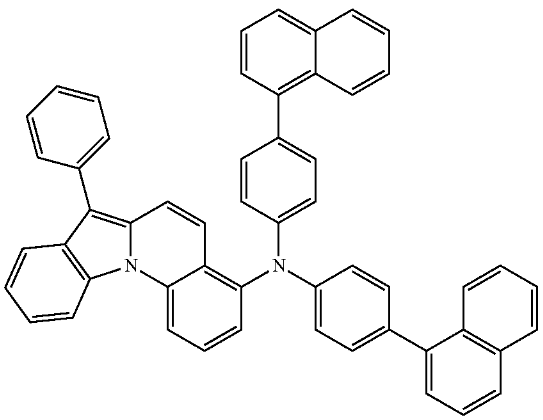
C47
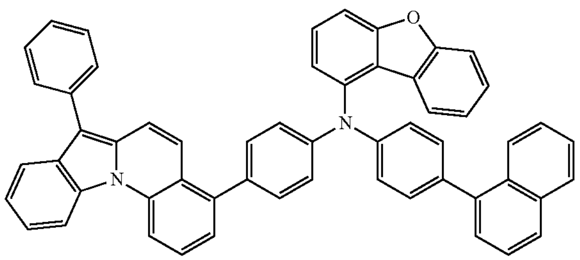

-continued
C48
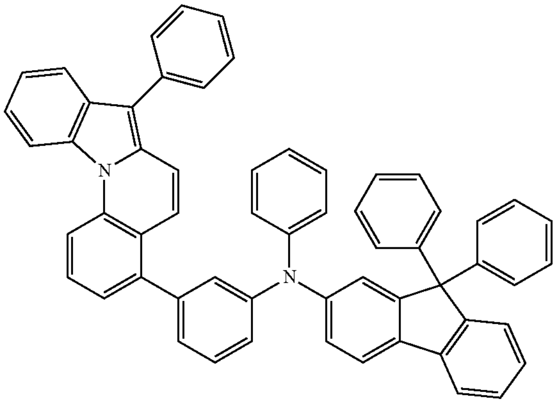
C49
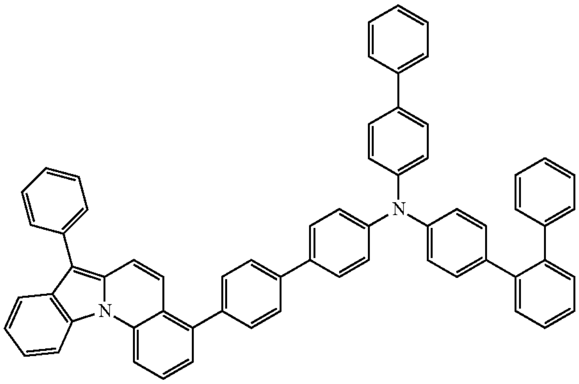
C50
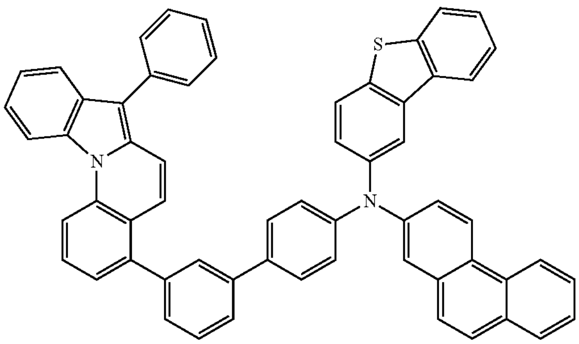
C51
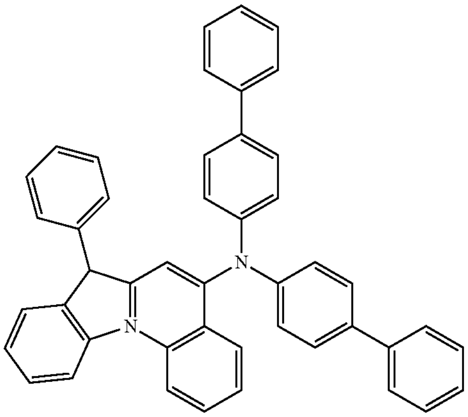
C52
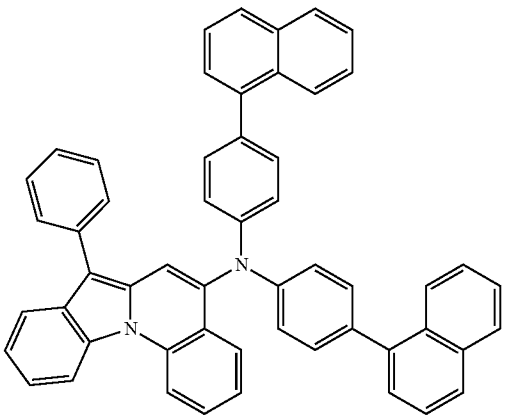
C53
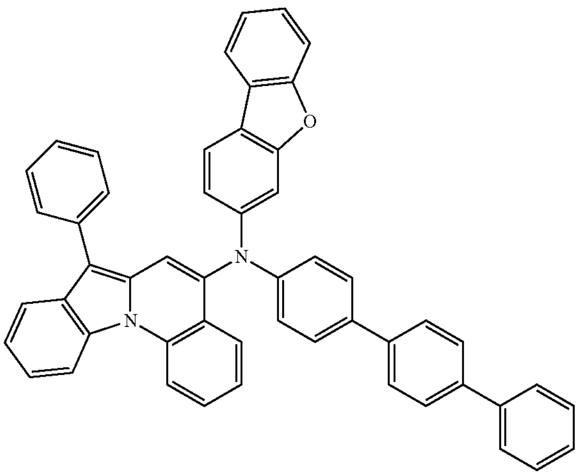

-continued
C54
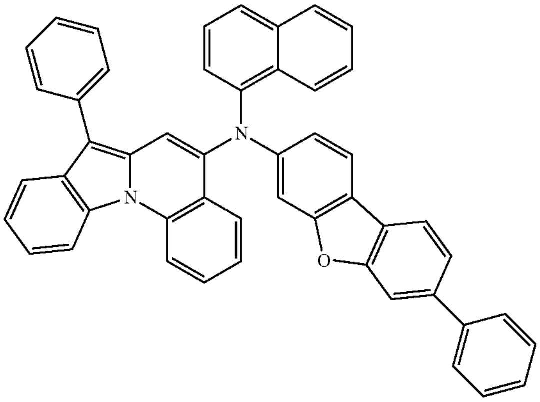
C55
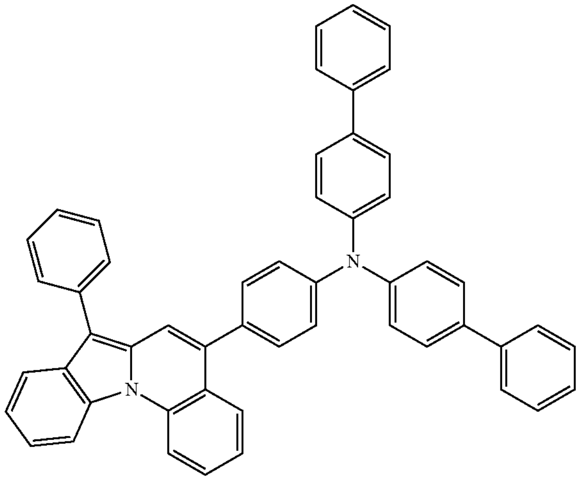
C56
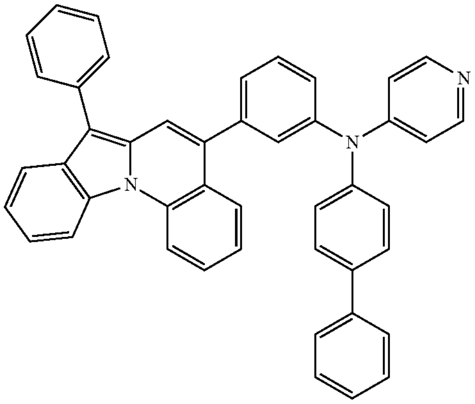
C57
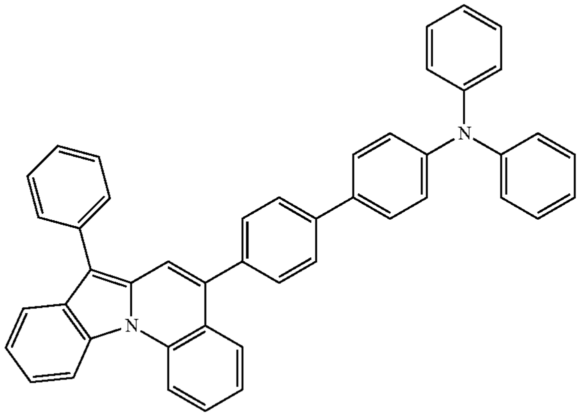
C58
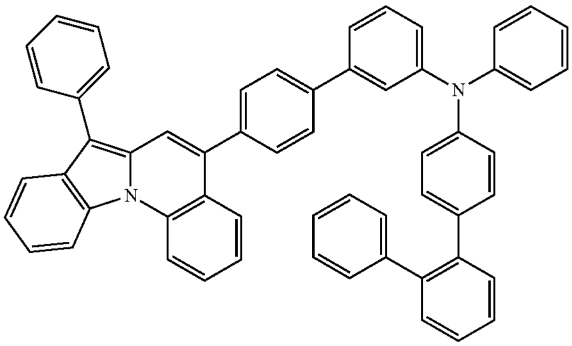
C59
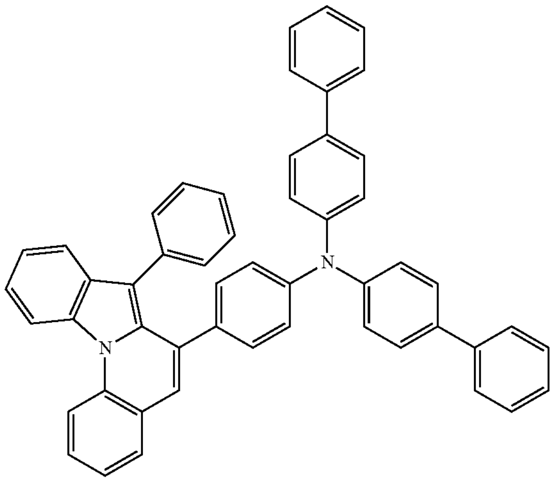

-continued
C60
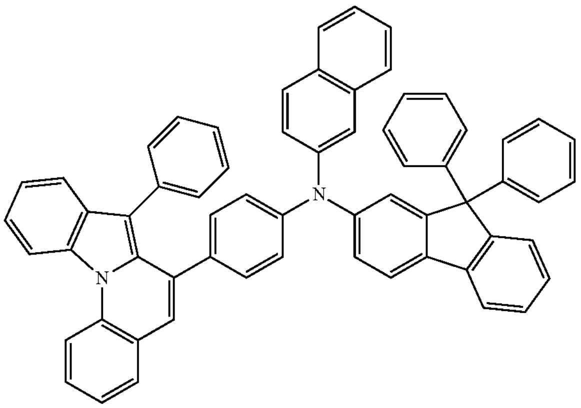
C61
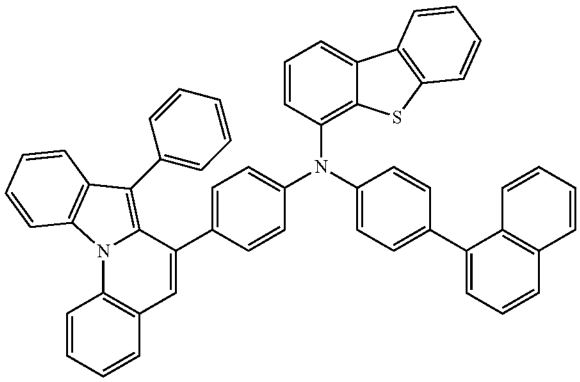
C62
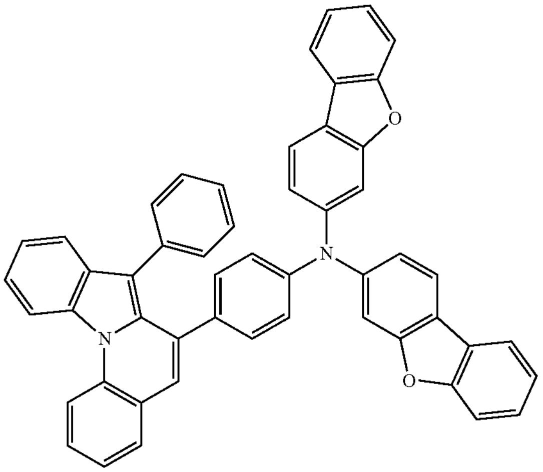
C63
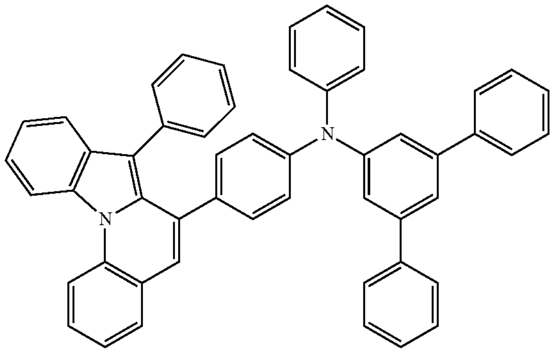
C64
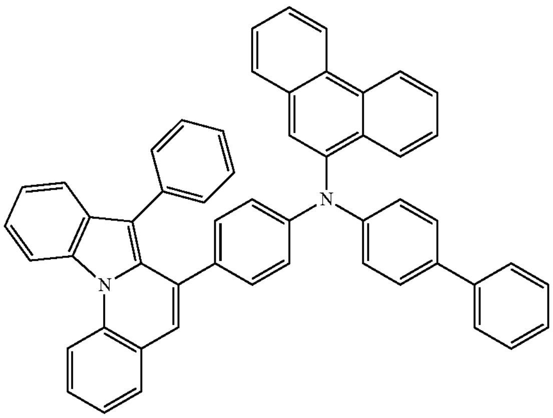
C65
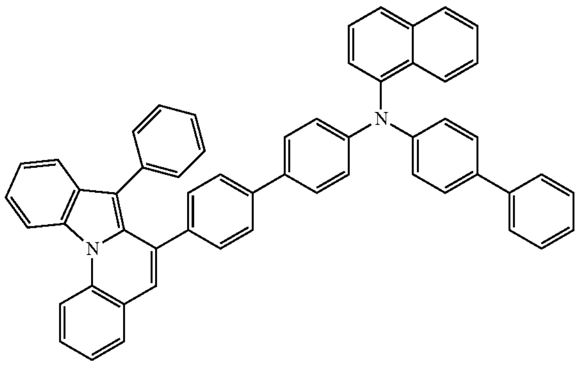

-continued
C66
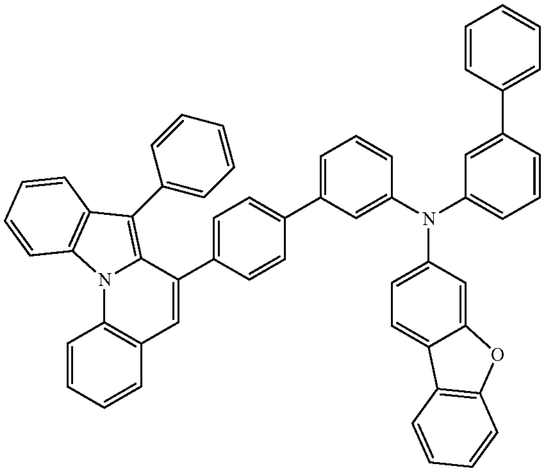
C67
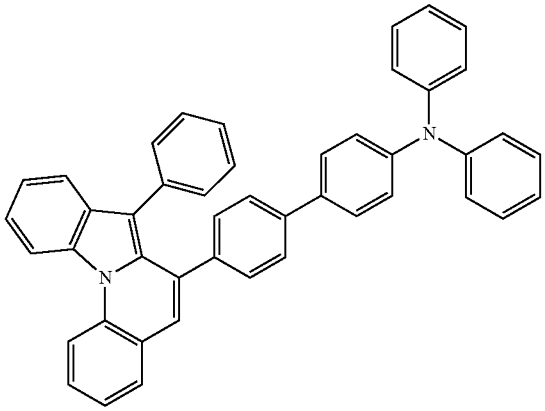
C68
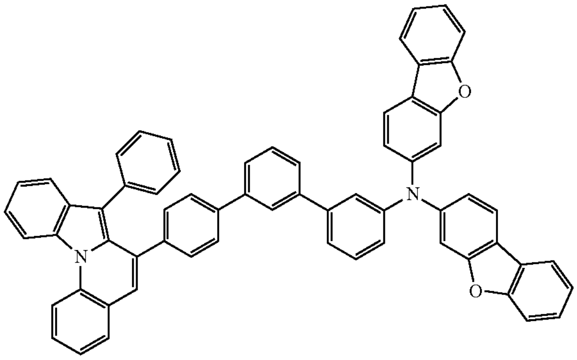
C69
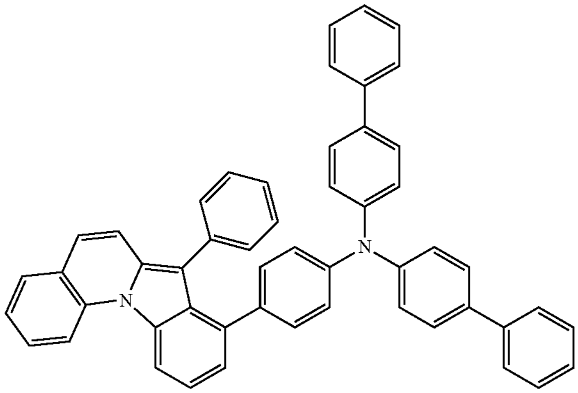
C70
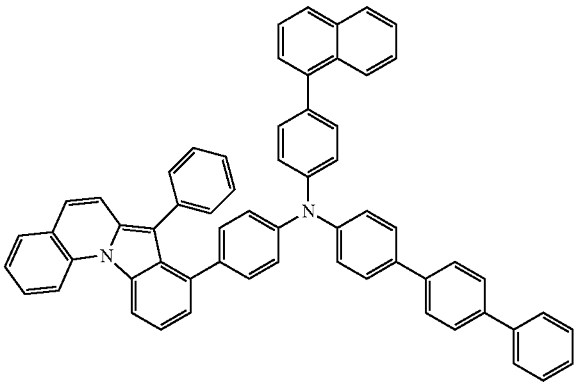
C71
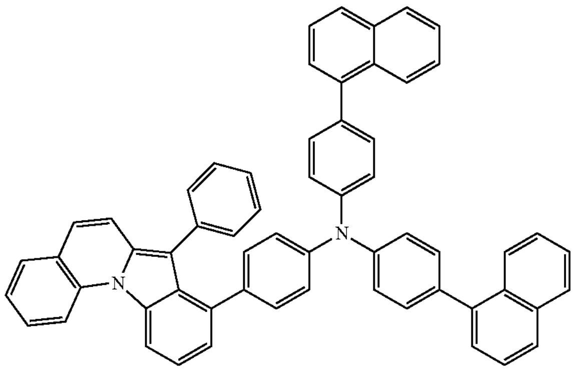

-continued
C72
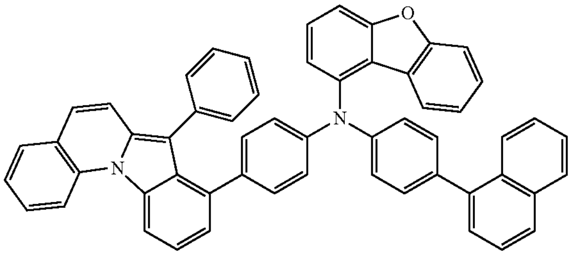
C73
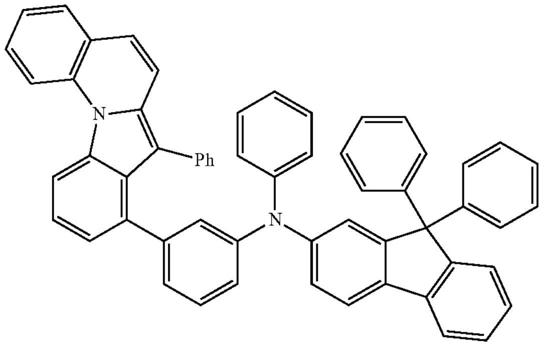
C74
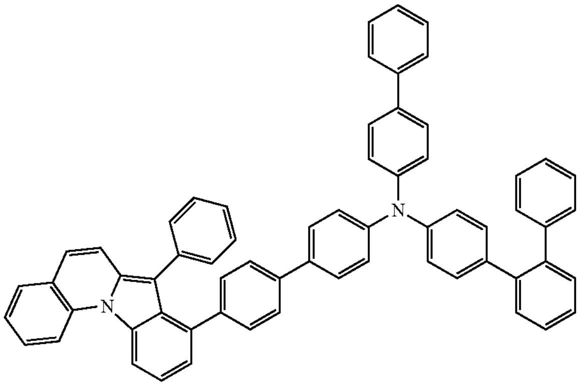
C75
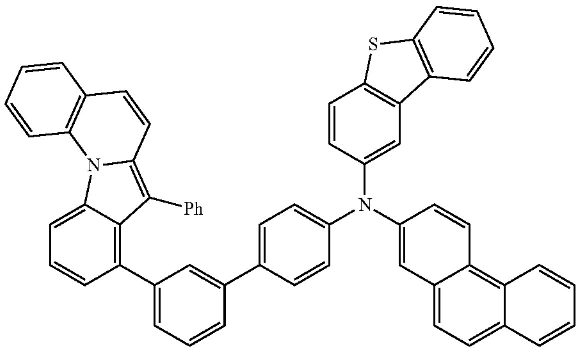
C76
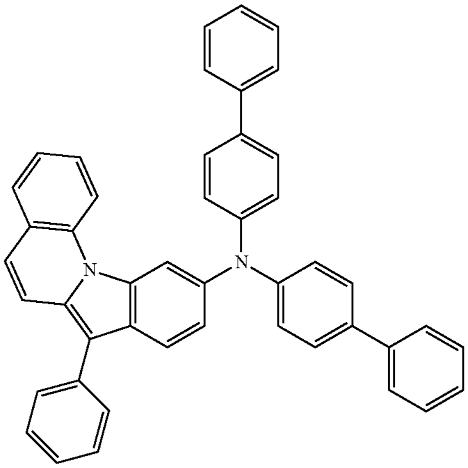
C77
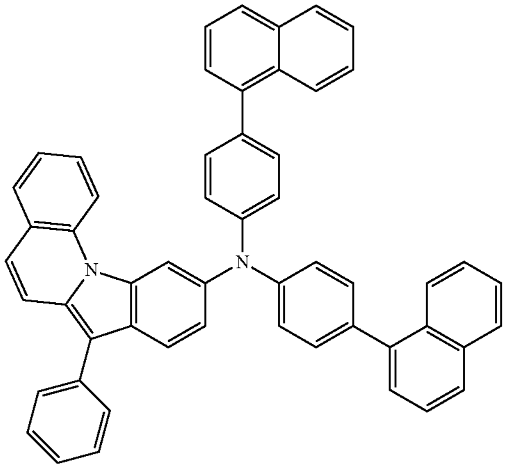

-continued
C78
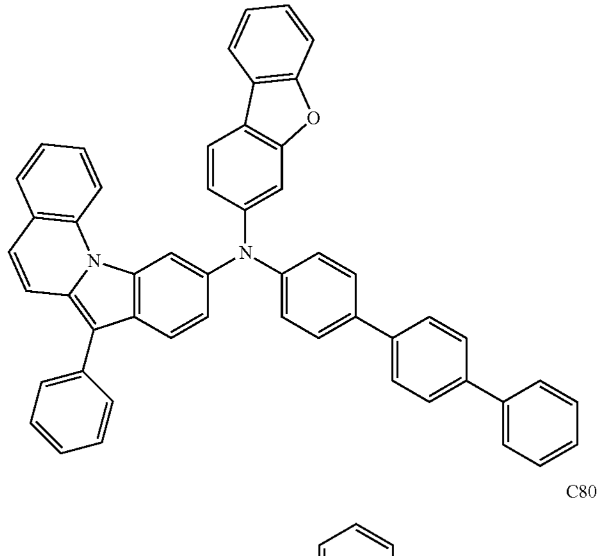
C79
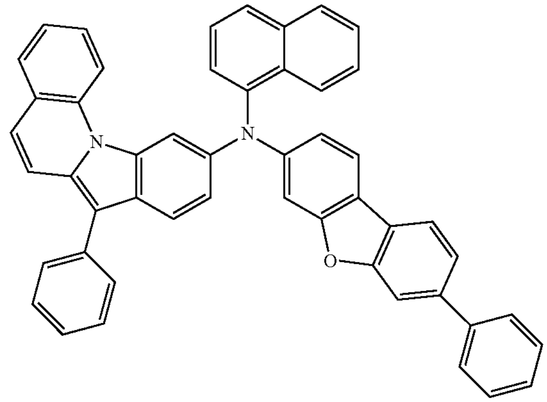
C80
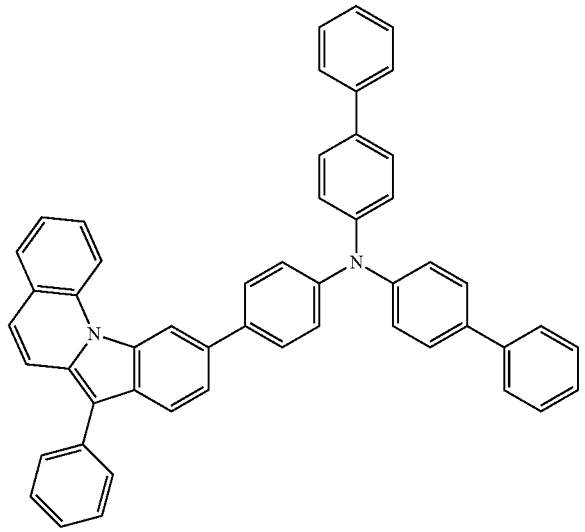
C81
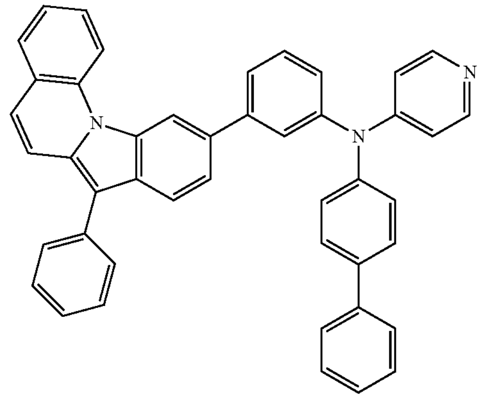
C82
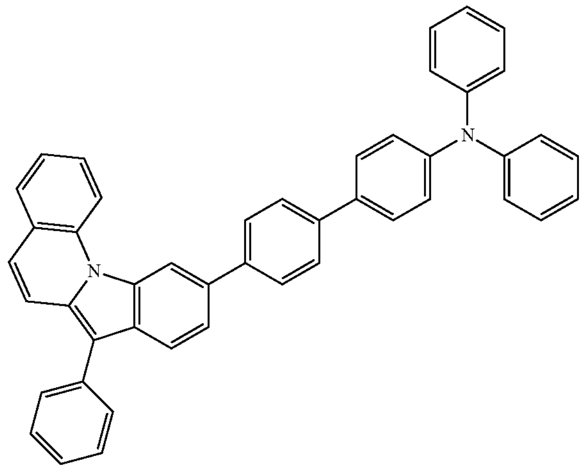
C83
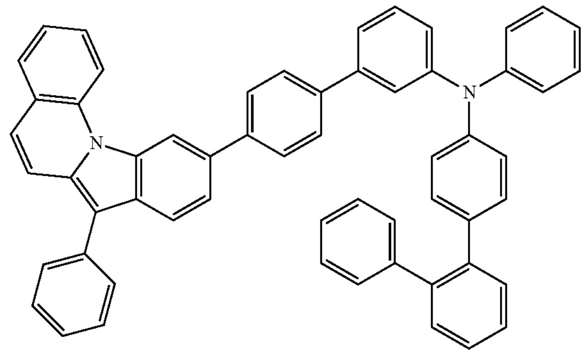

-continued
C84
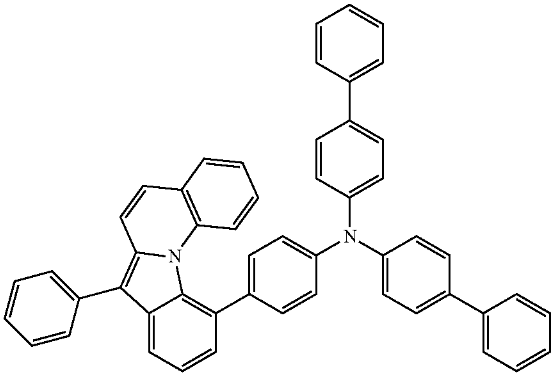
C85
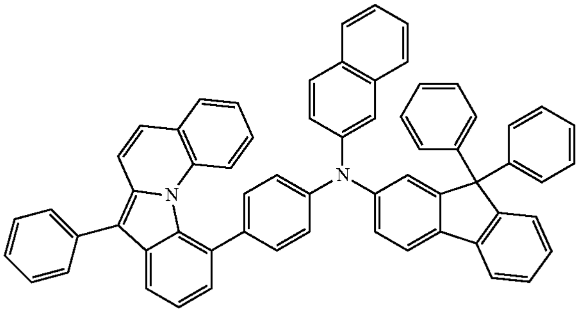
C86
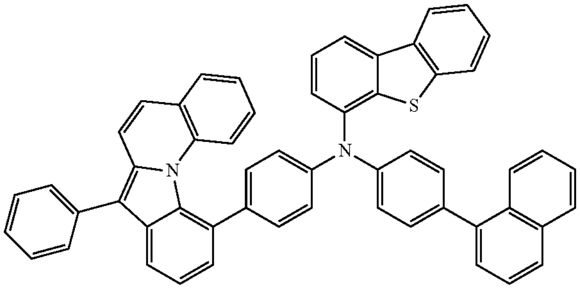
C87
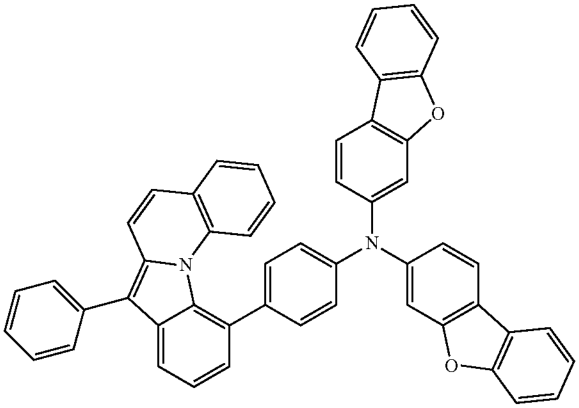
C88
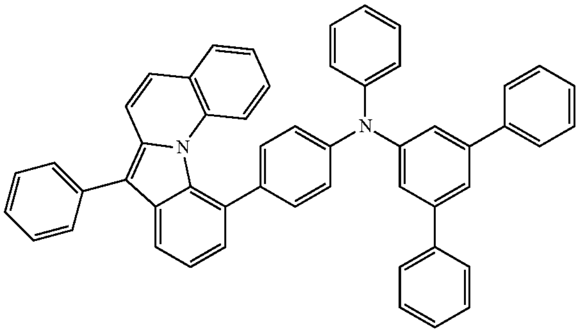
C89
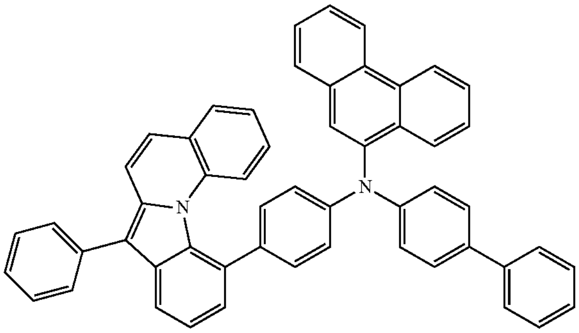
C90
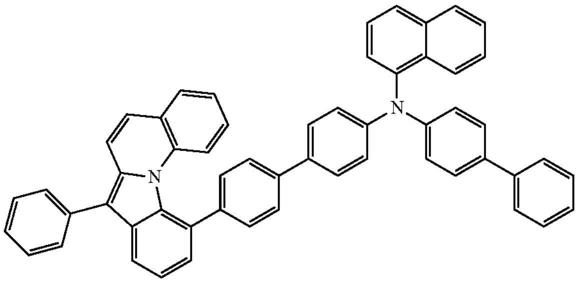
C91
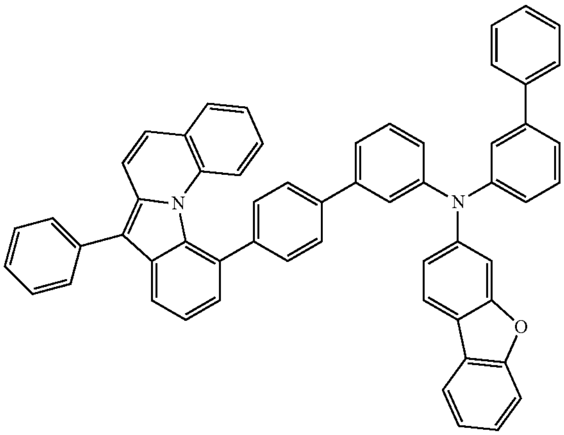

-continued
C92
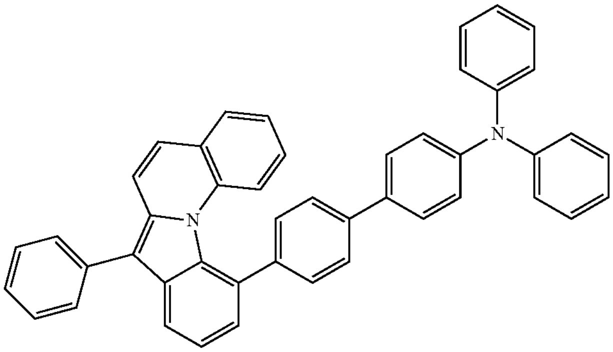
C93
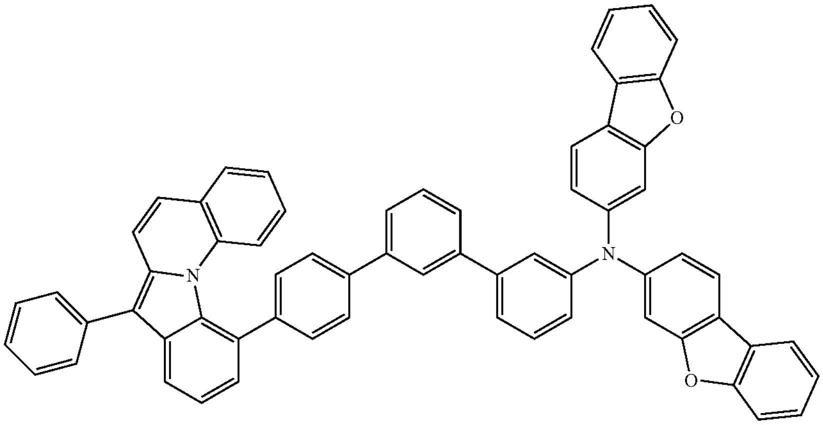
C94
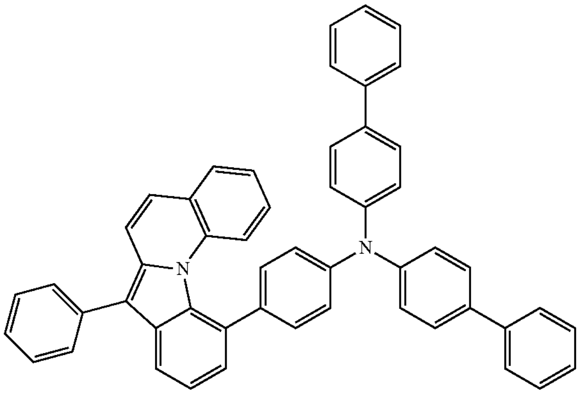
C95
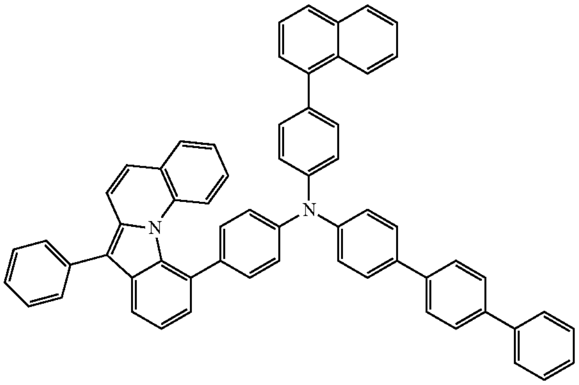
C96
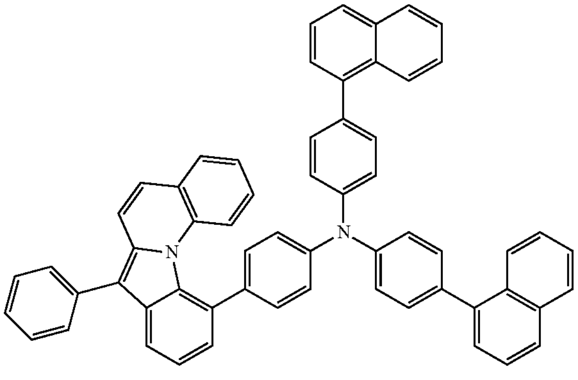
C97
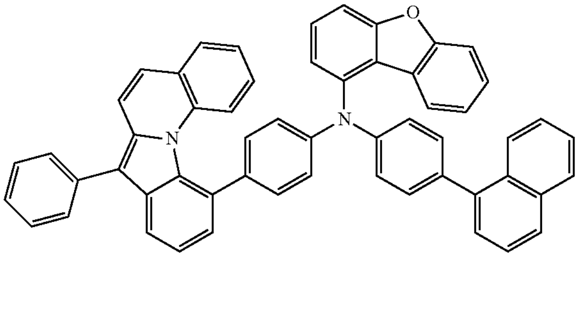

D1
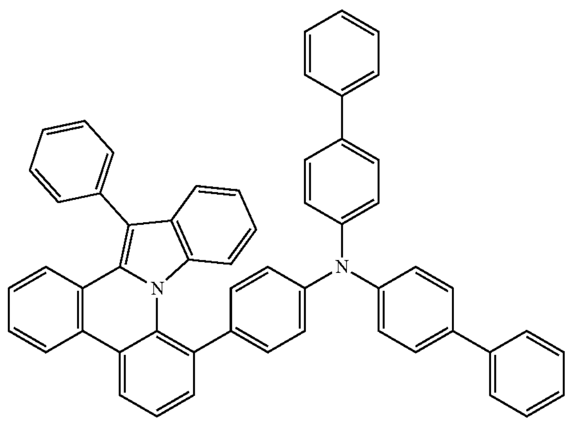
D2
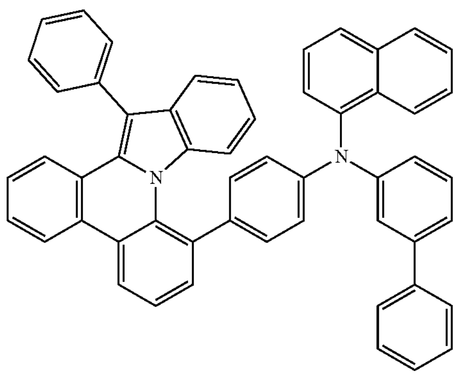
D3
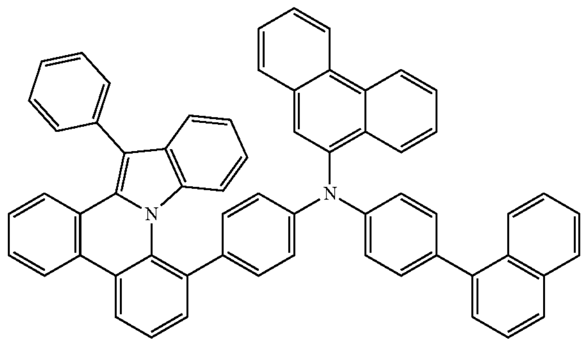
D4
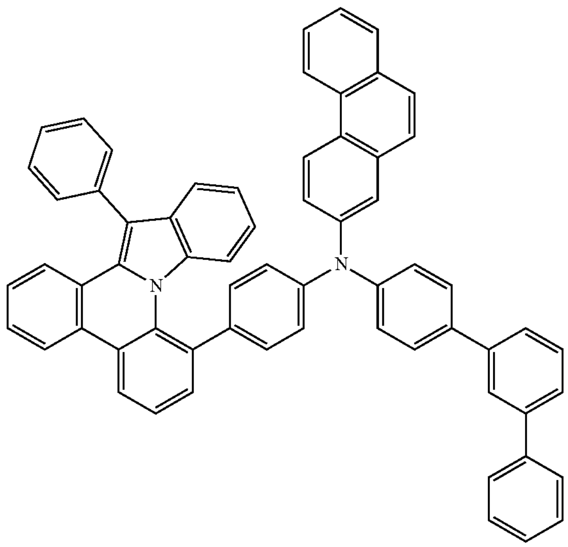
D5
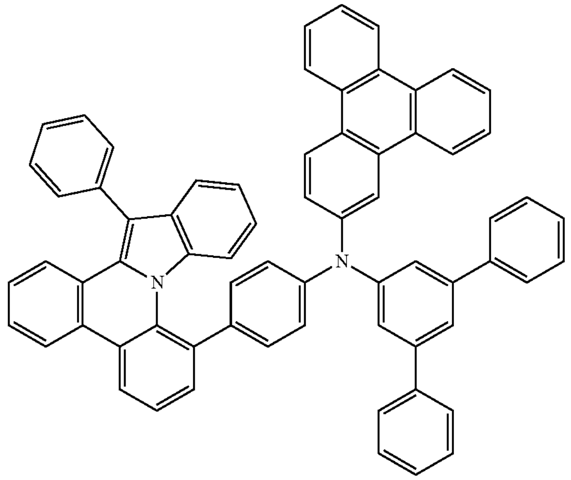
D6
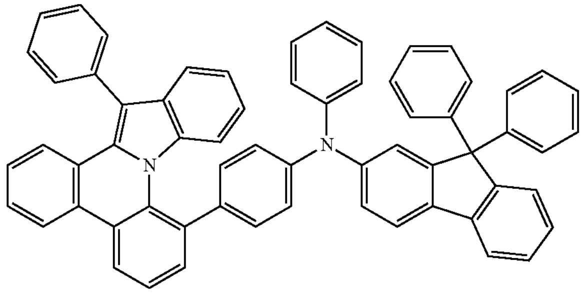

-continued
D7
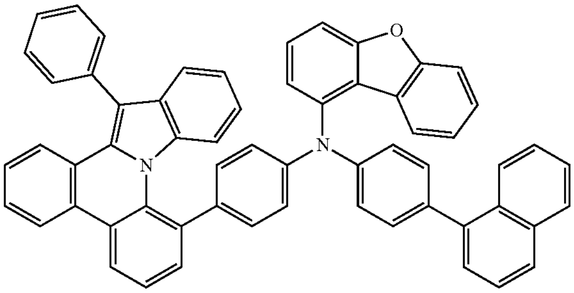
D8
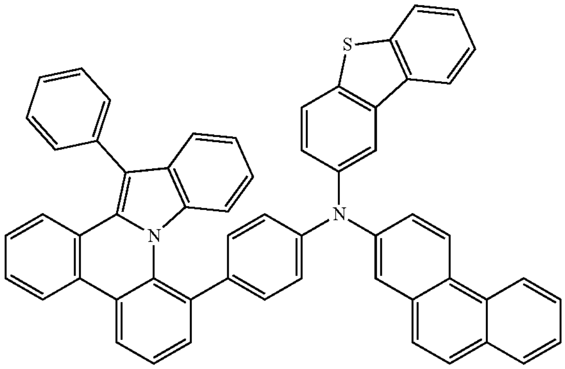
D9
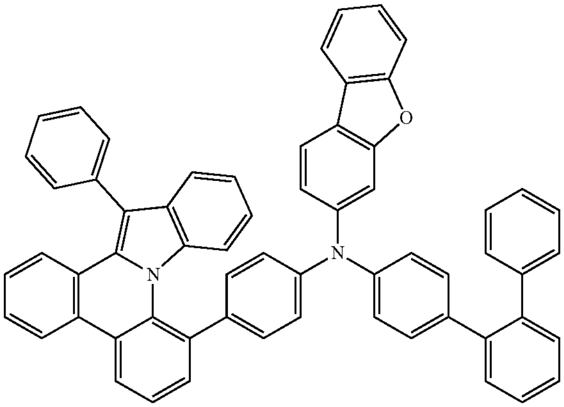
D10
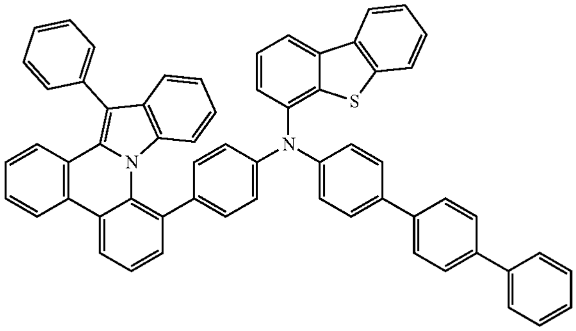
D11
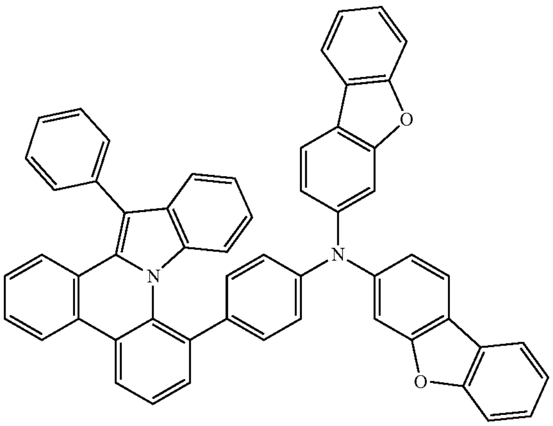
D12
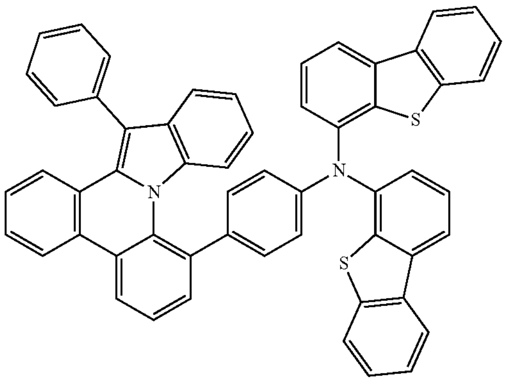

-continued
D14
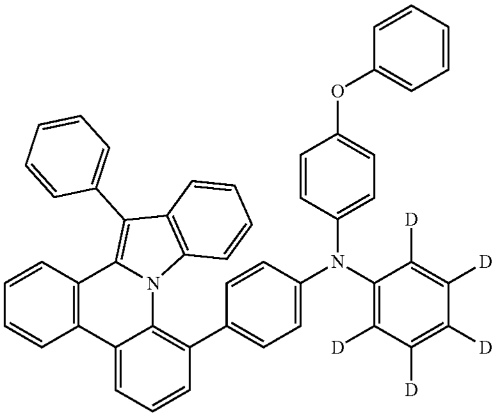
D13
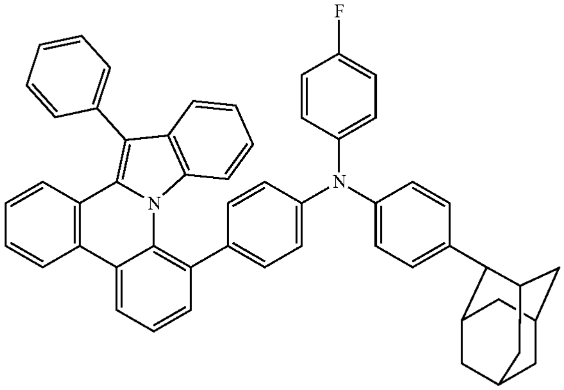
D15
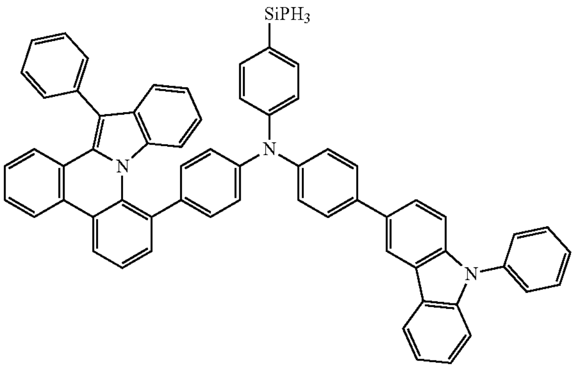
D16
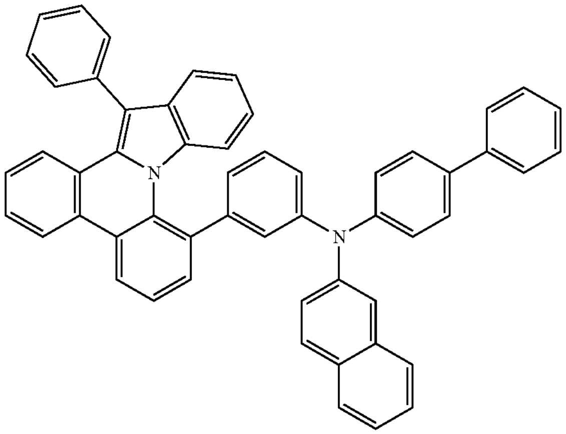
D17
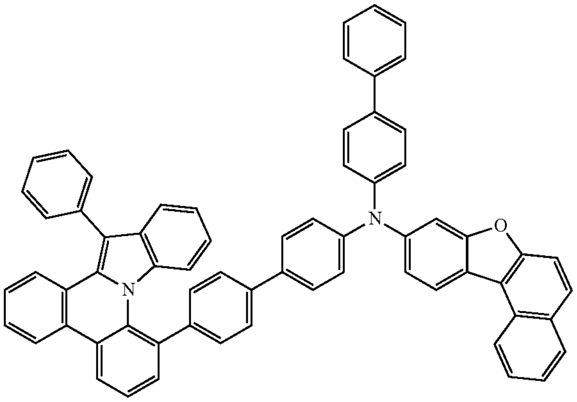
D18
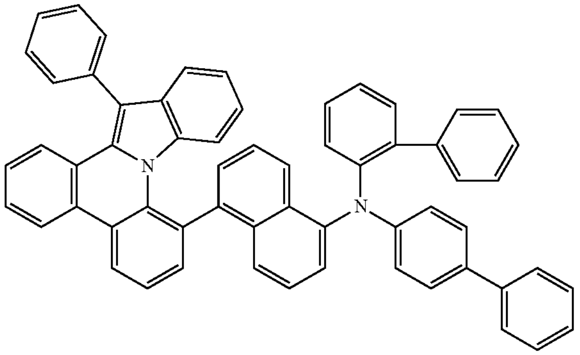

-continued
D19
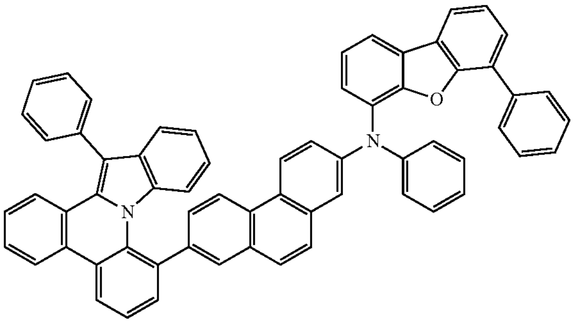
D20
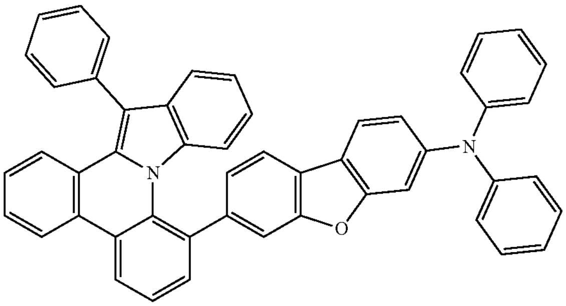
D21
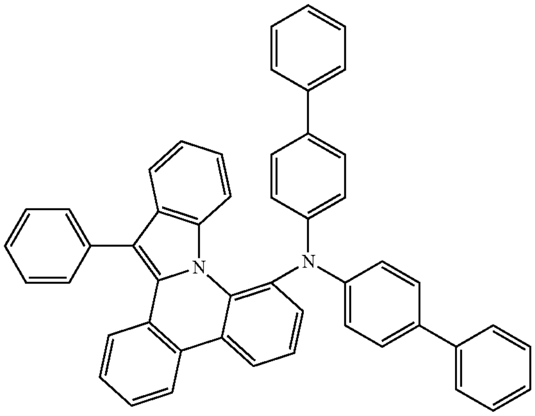
D22
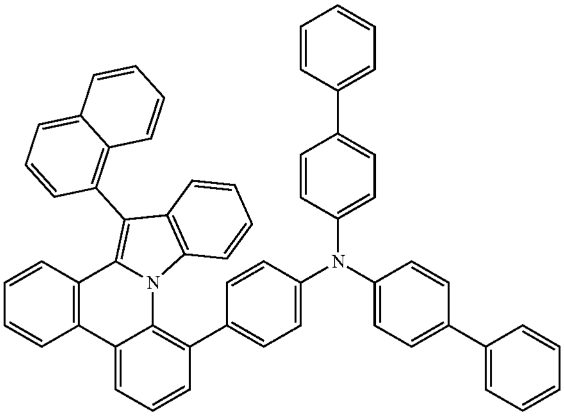
D23
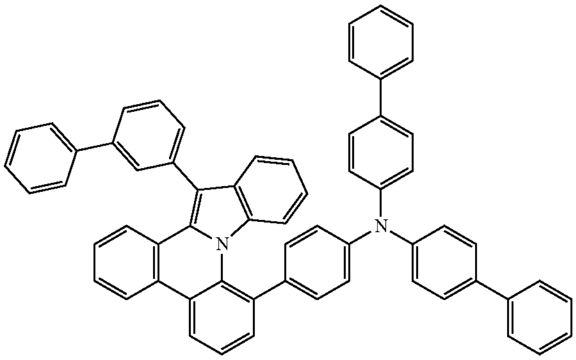
D24
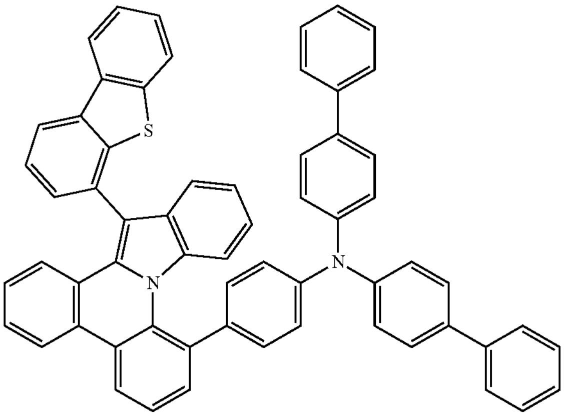
D25
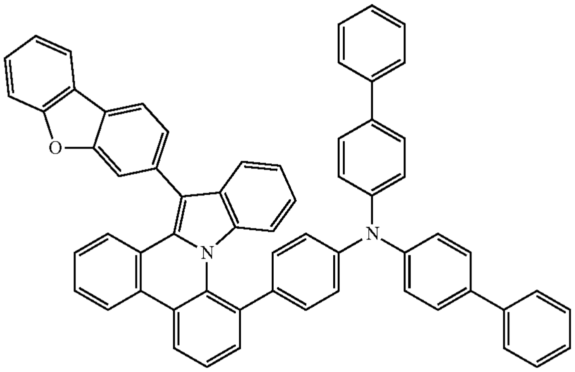
D26
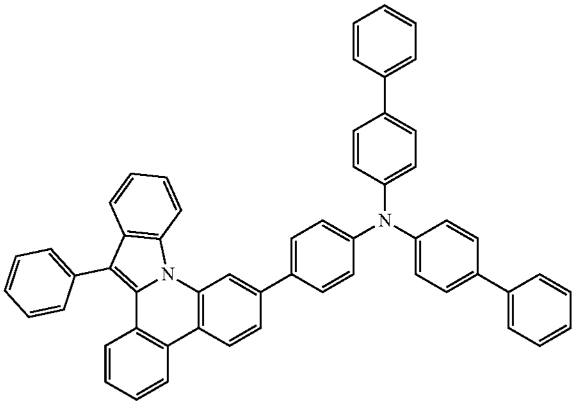

-continued
D27
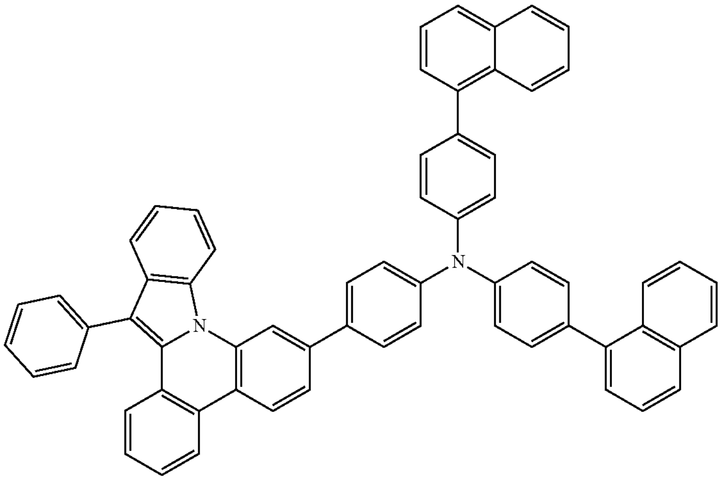
D28
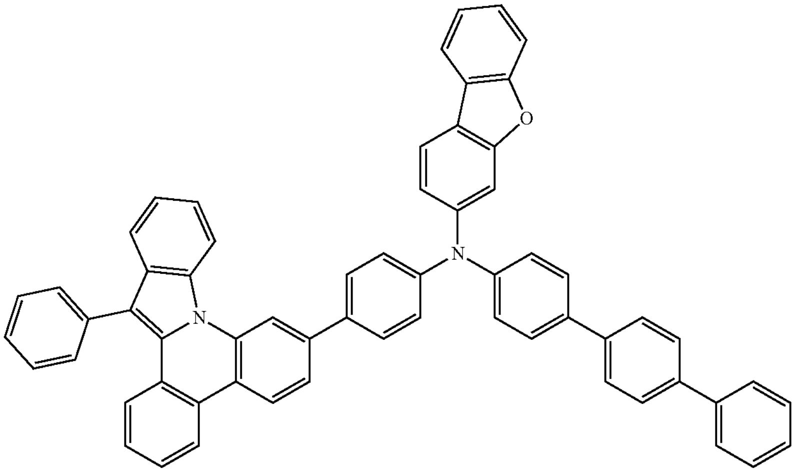
D29
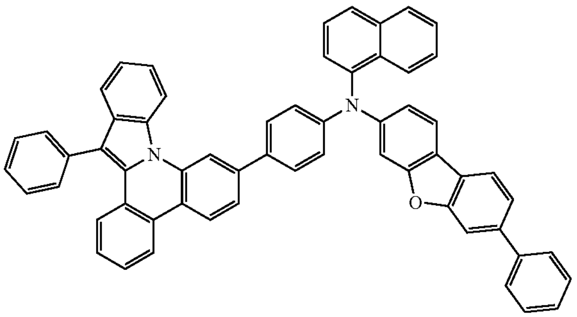
D30
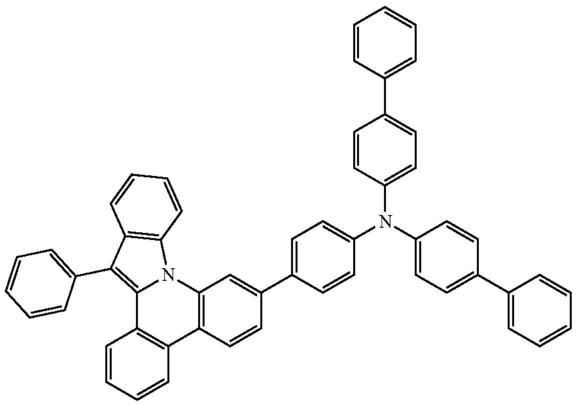

-continued
D31
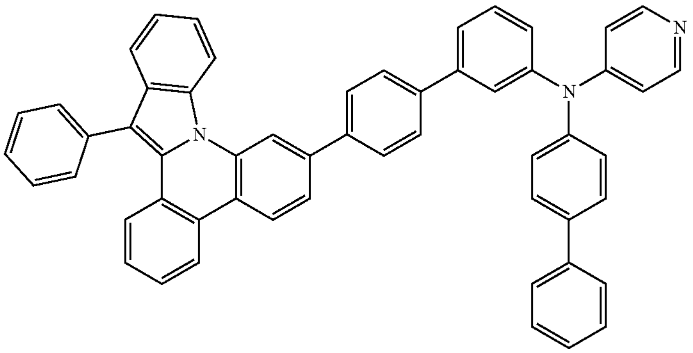
D32
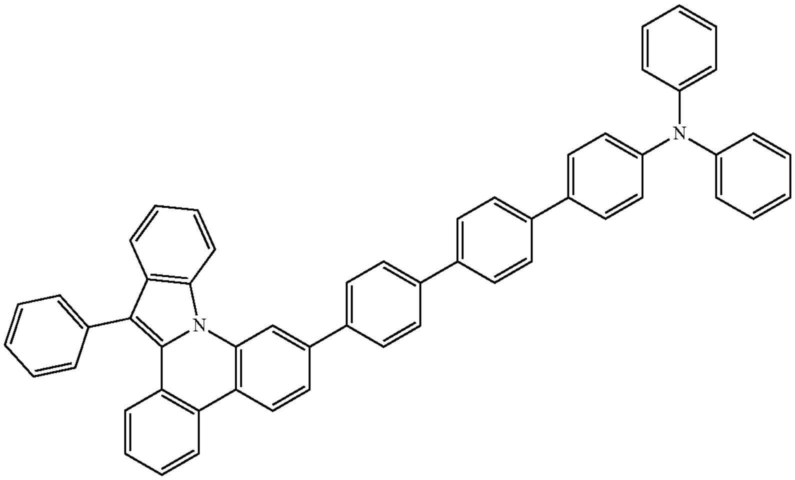
D33
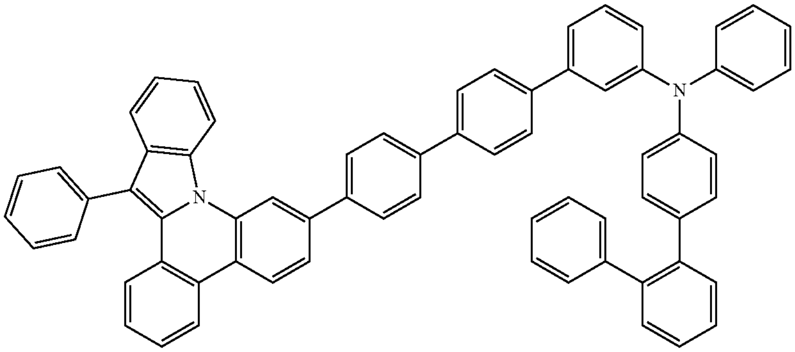
D34
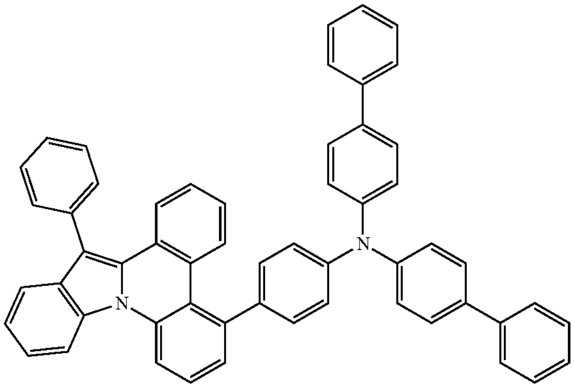
D35
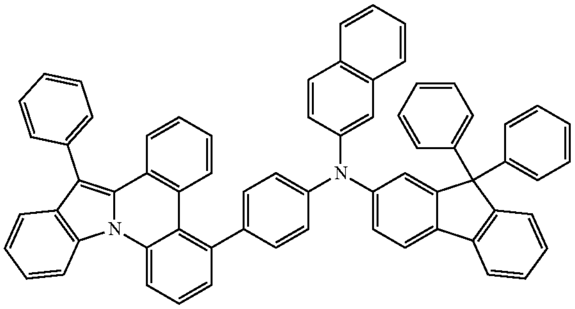

-continued
D36
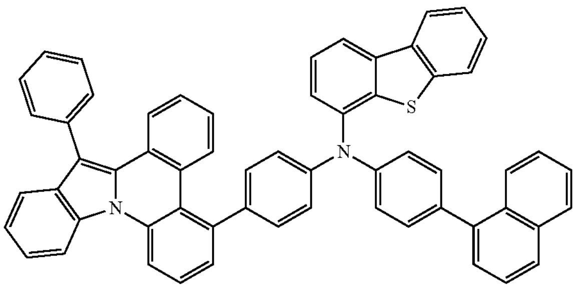
D37
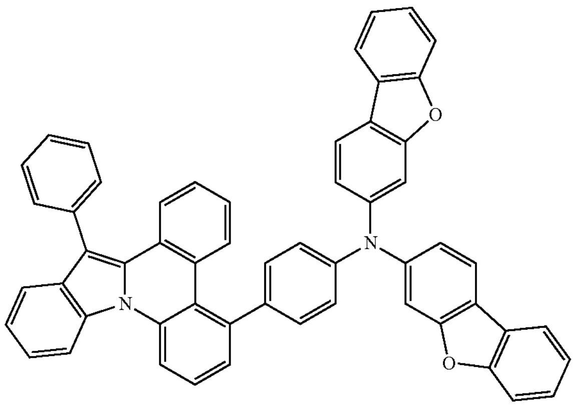
D38
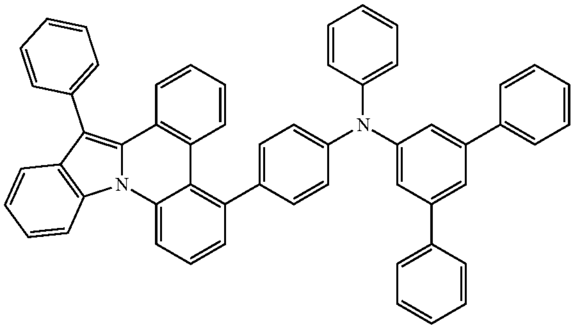
D39
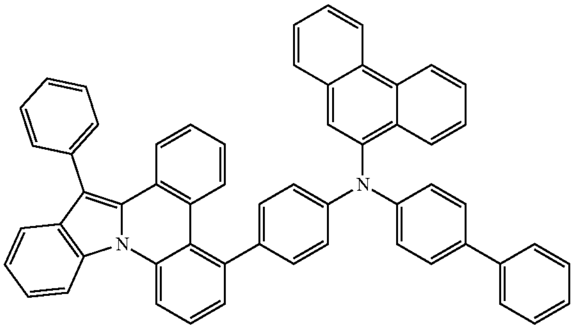
D40
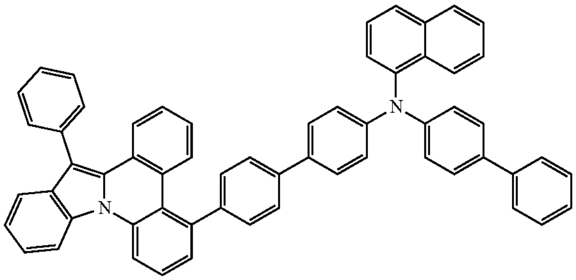
D41
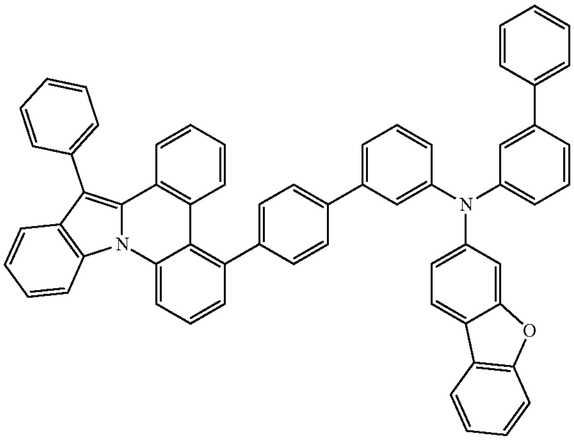
D42
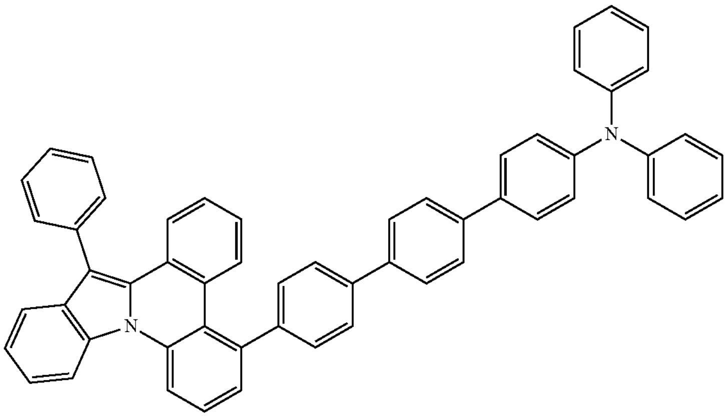

-continued
D43
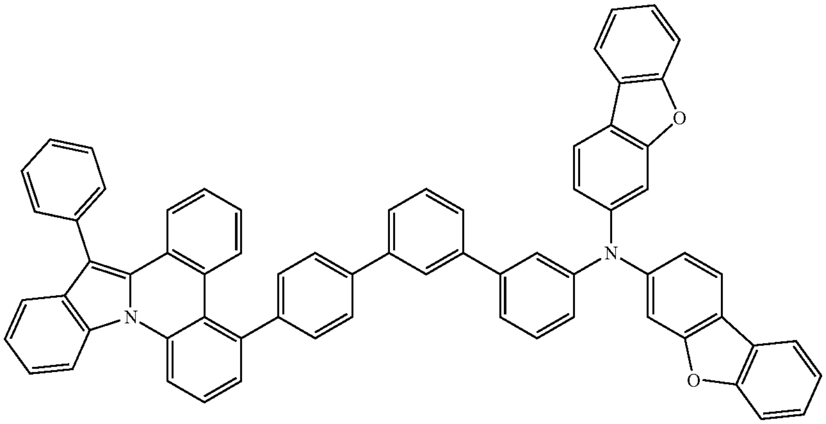
D44
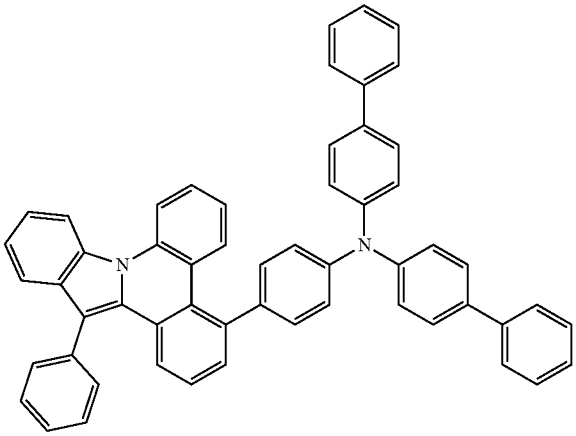
D45
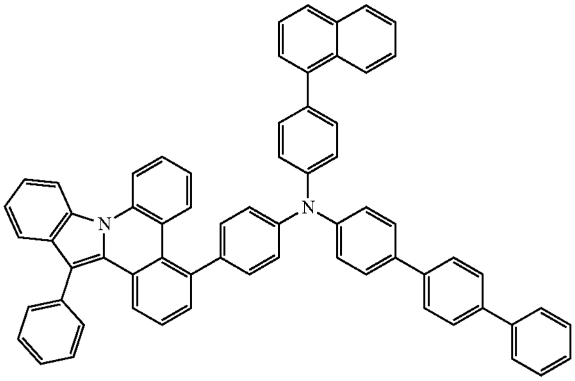
D46
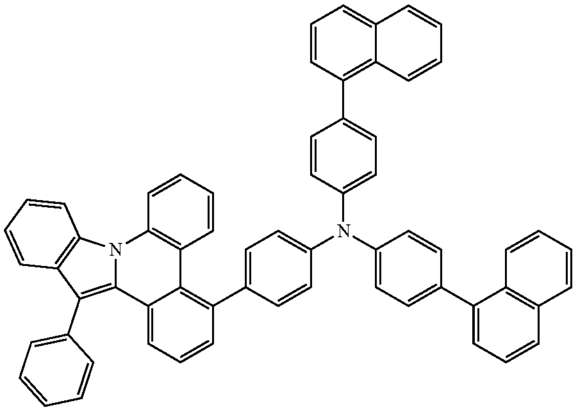
D47
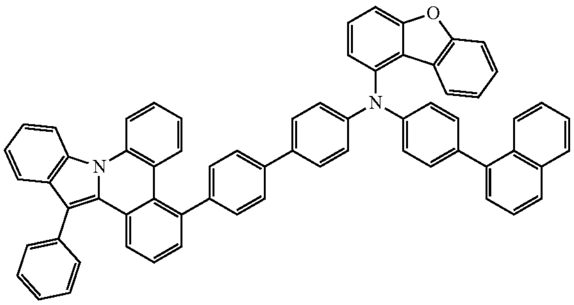

-continued
D48
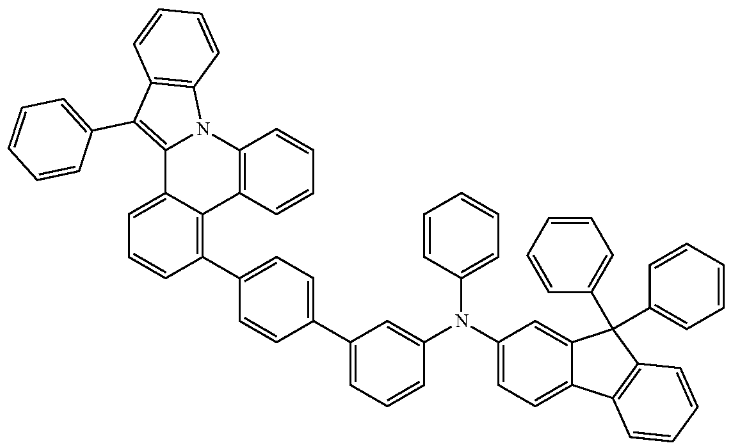
D49
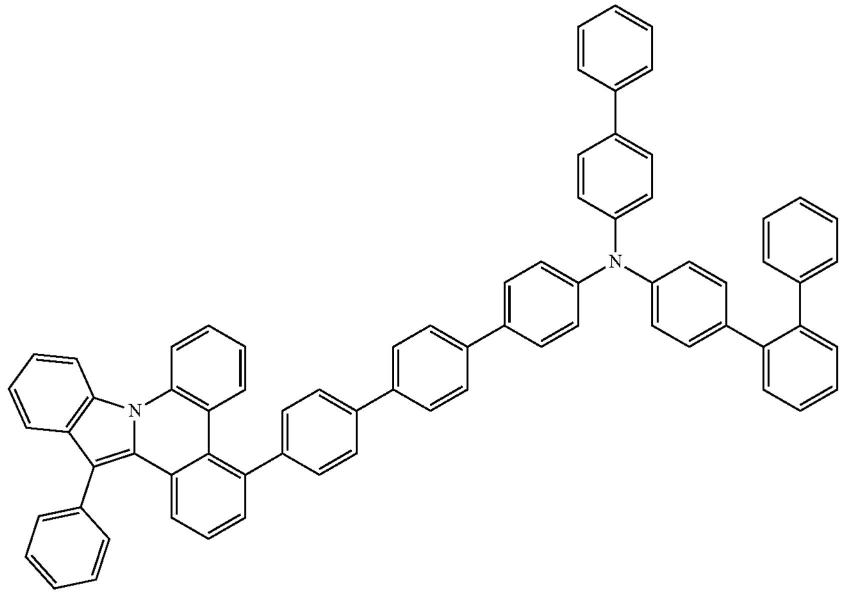
D50
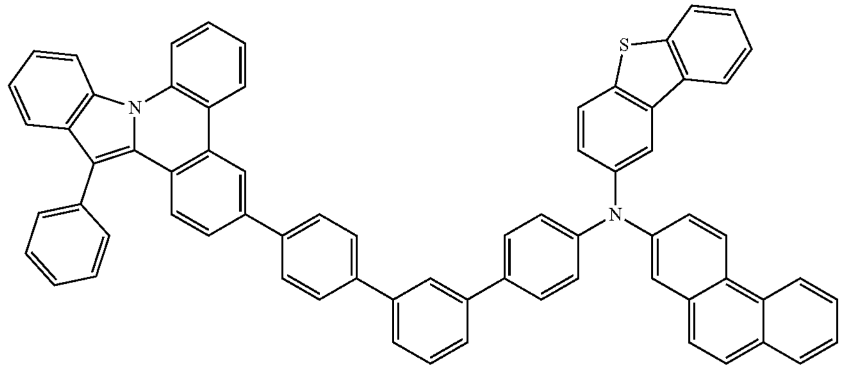

-continued
D51
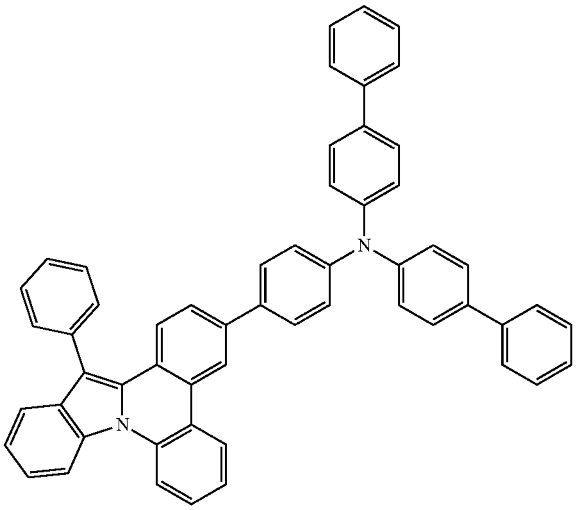
D52
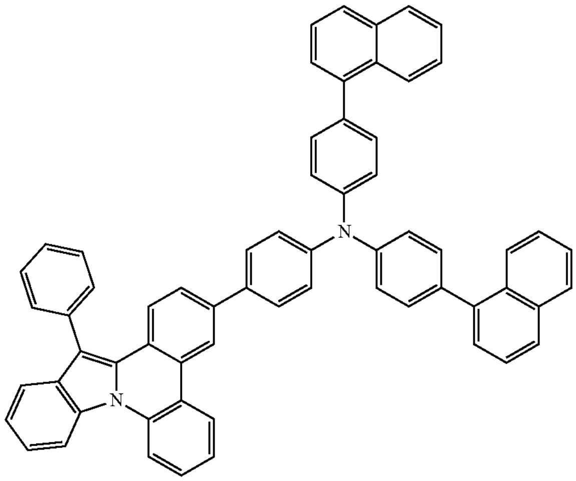
D53
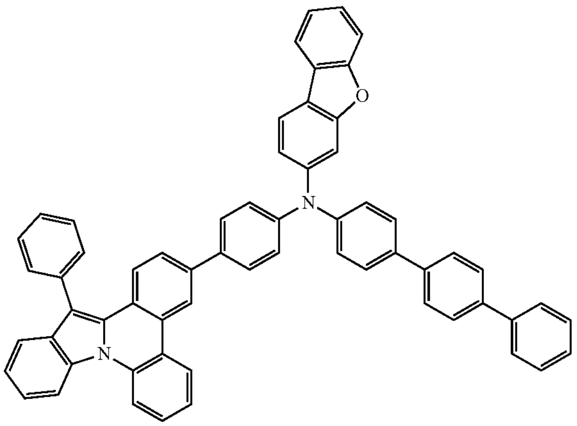
D54
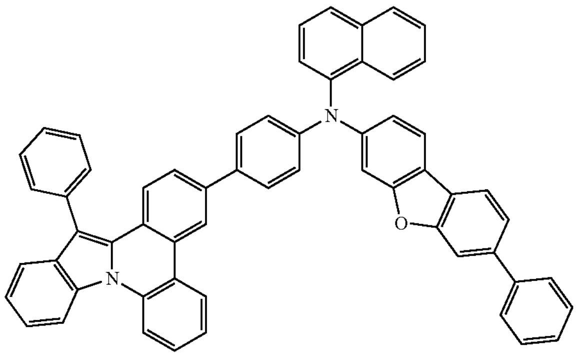
D55
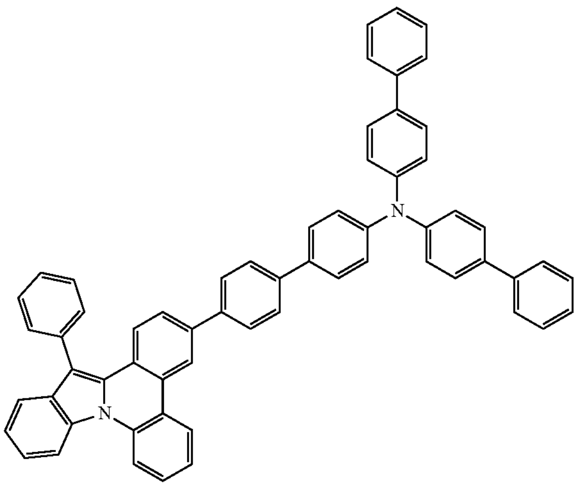
D56
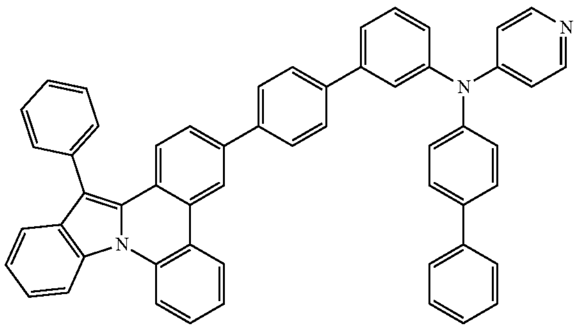

-continued
D57
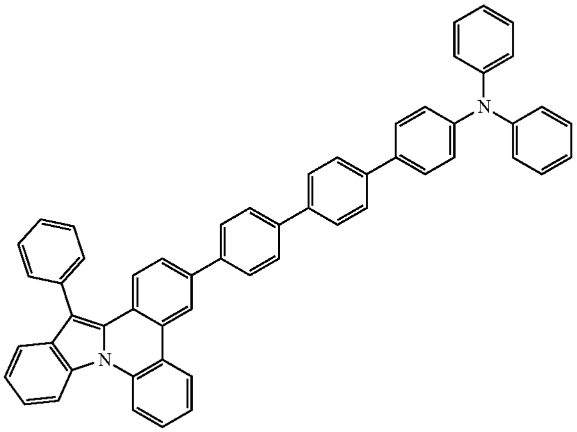
D58
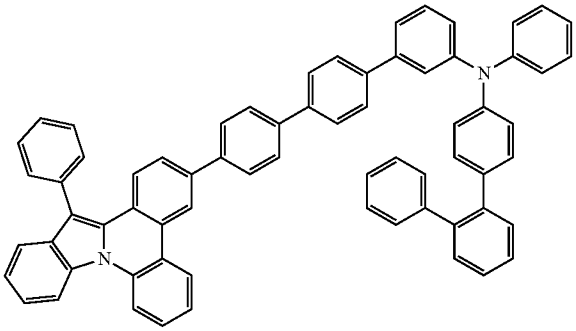
D59
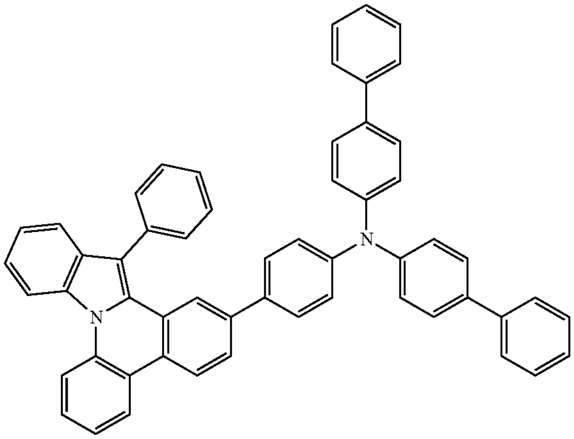
D60
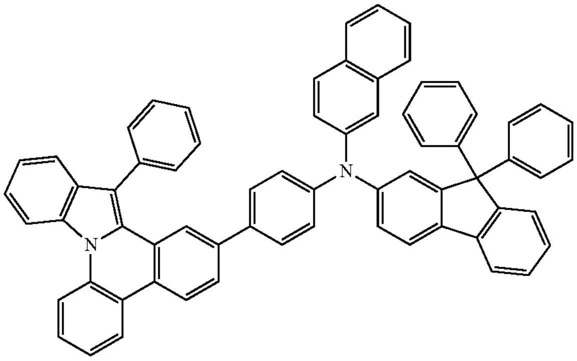
D61
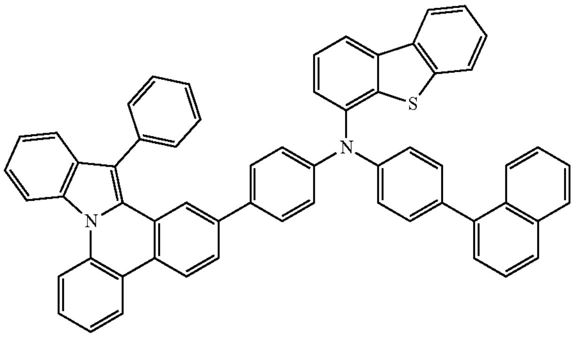
D62
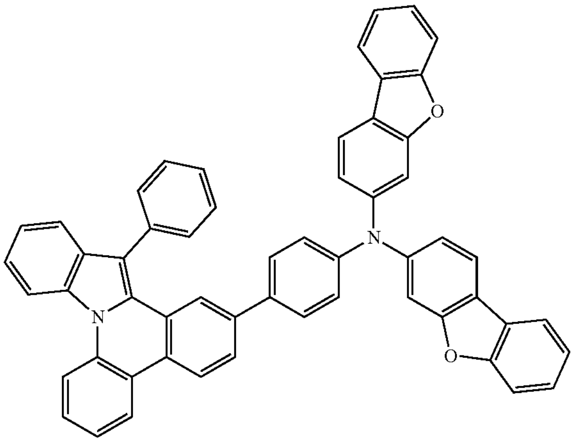

-continued
D63
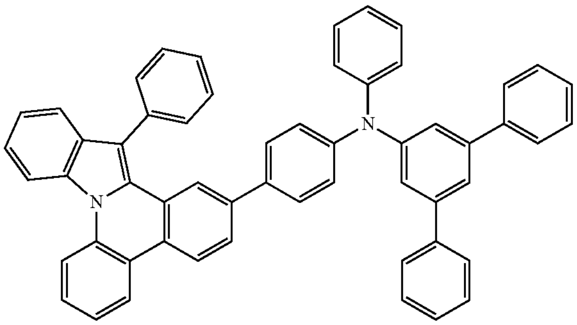
D64
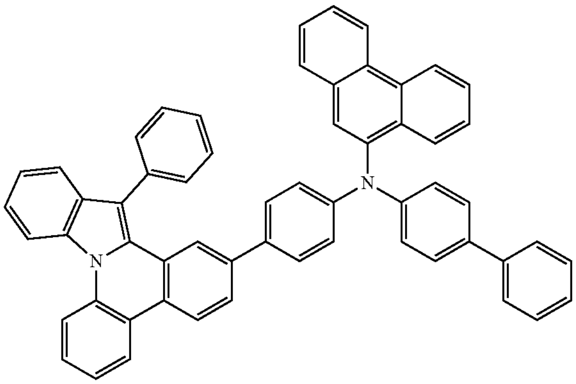
D65
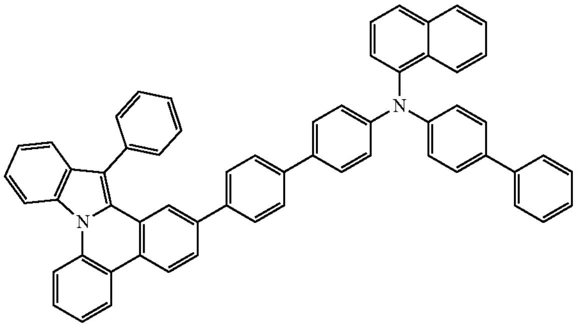
D66
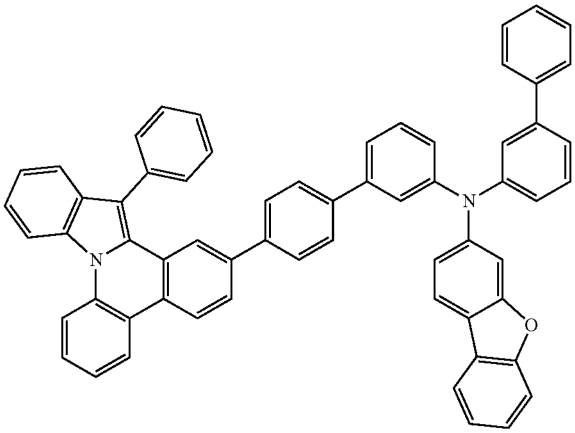
D67
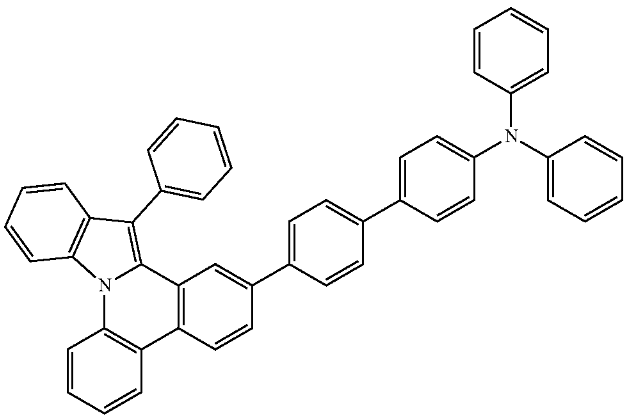

-continued
D68
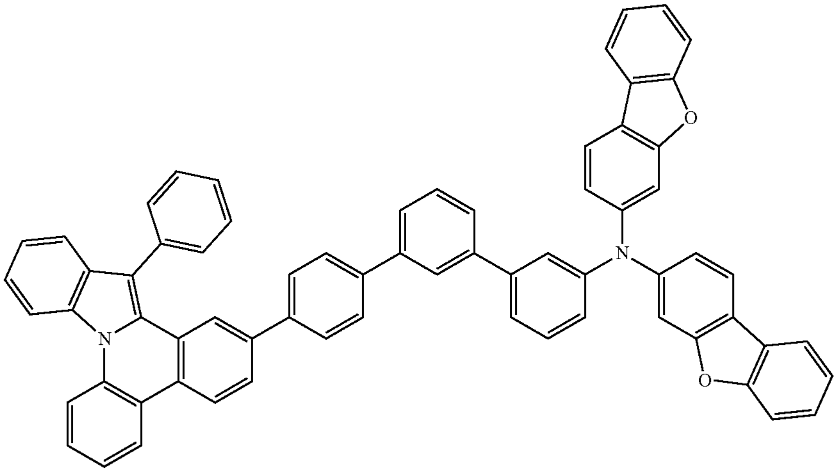
D69
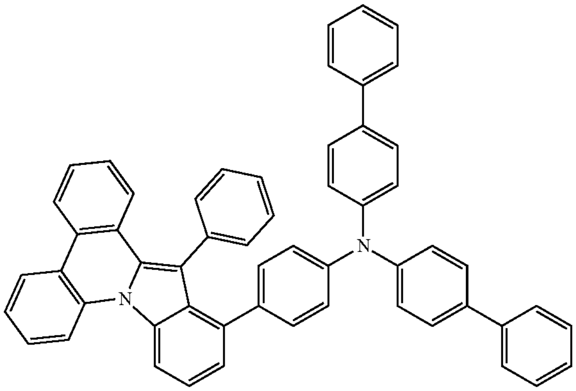
D70
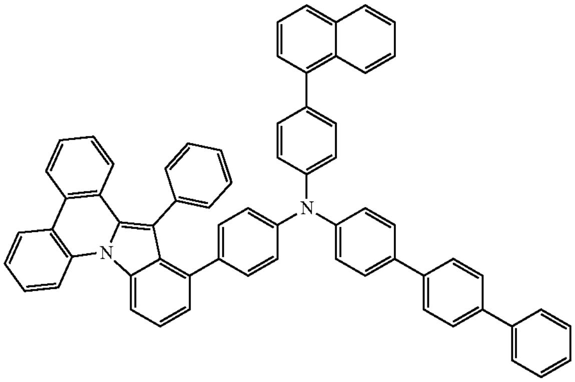
D71
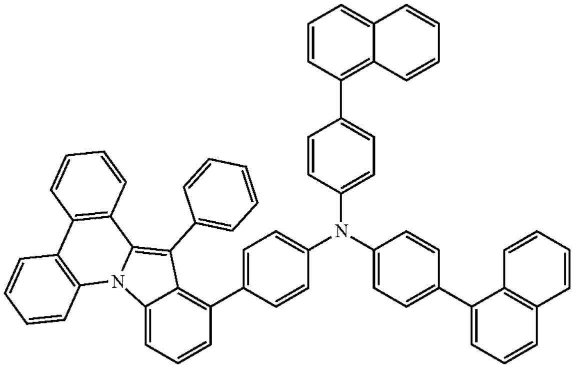
D72
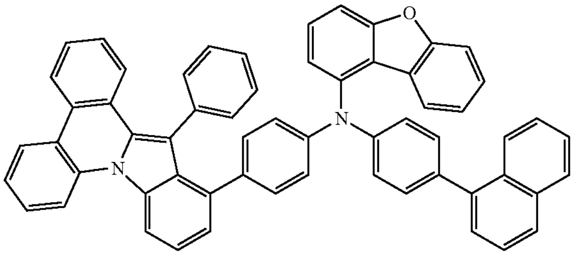

-continued
D73
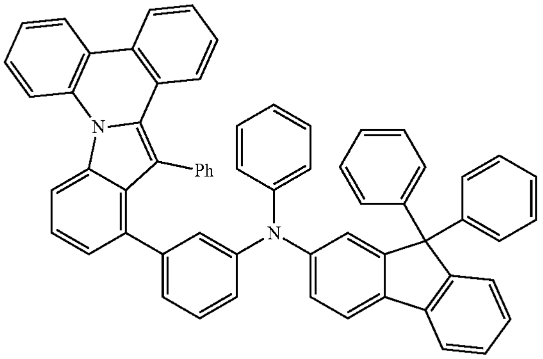
D74
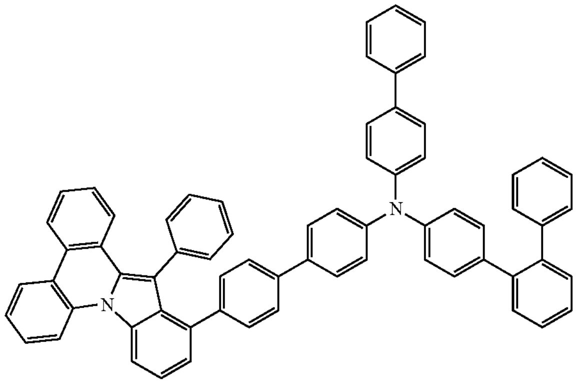
D75
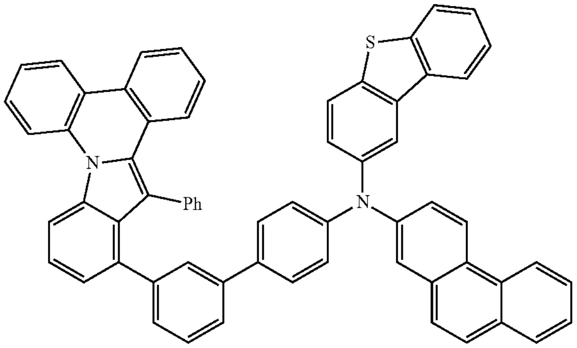
D76
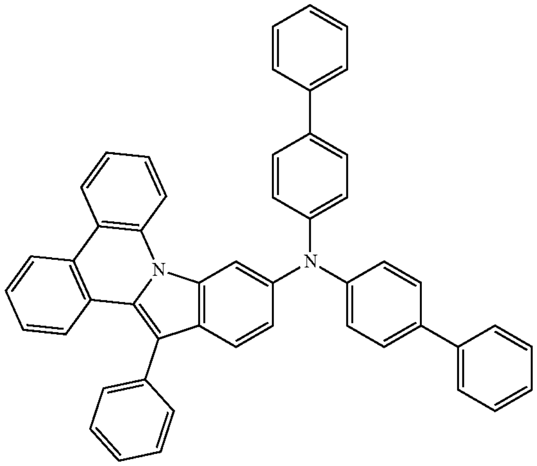
D77
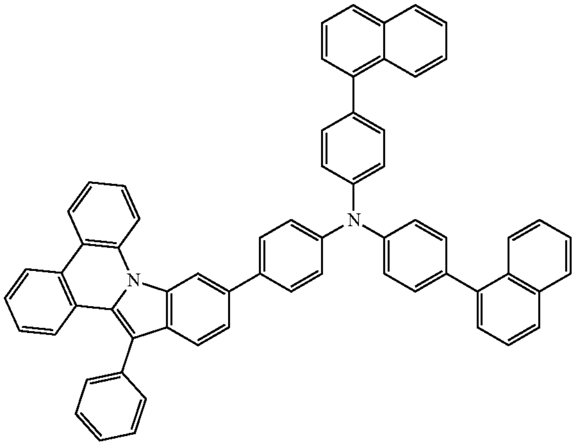
D78
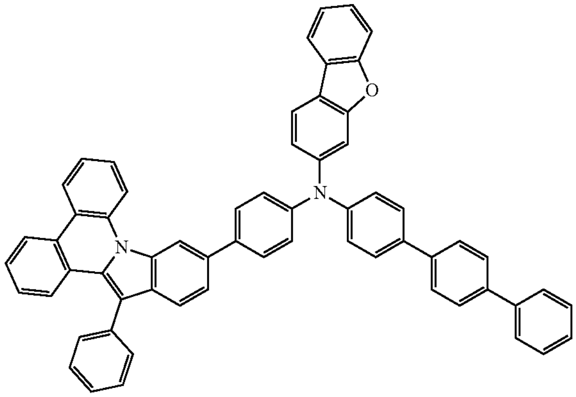

-continued
D79
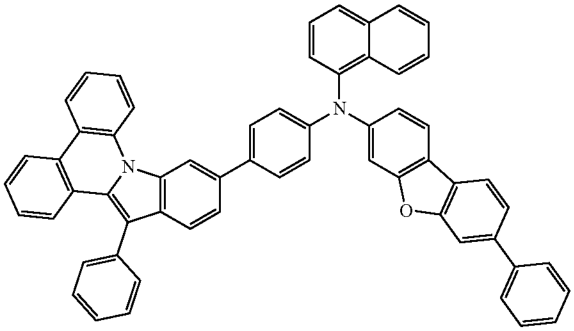
D80
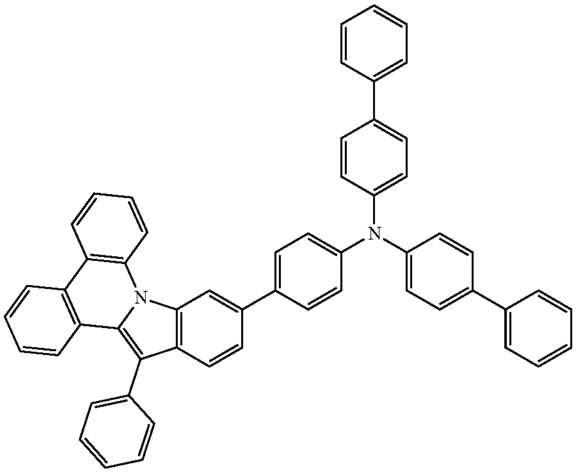
D81
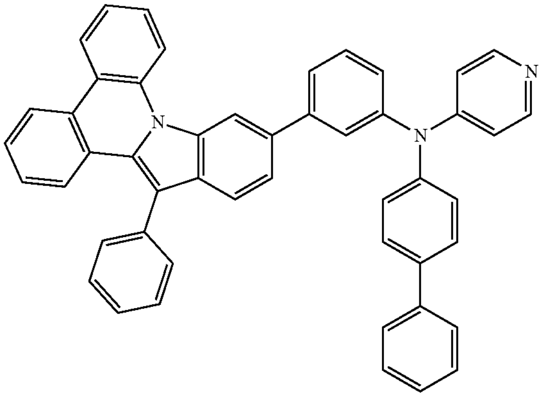
D82
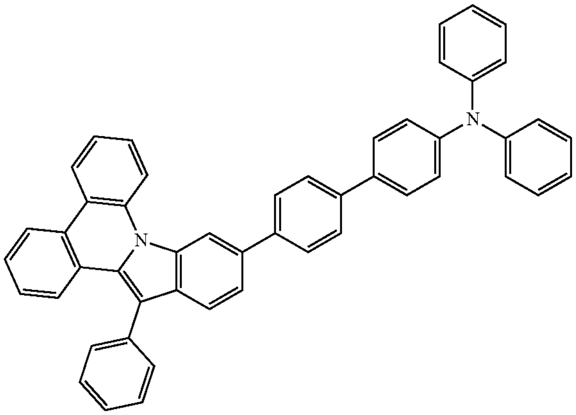
D83
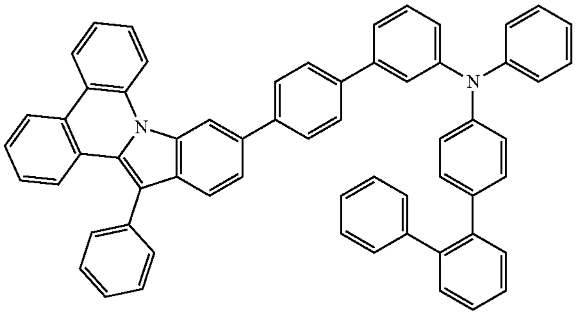
D84
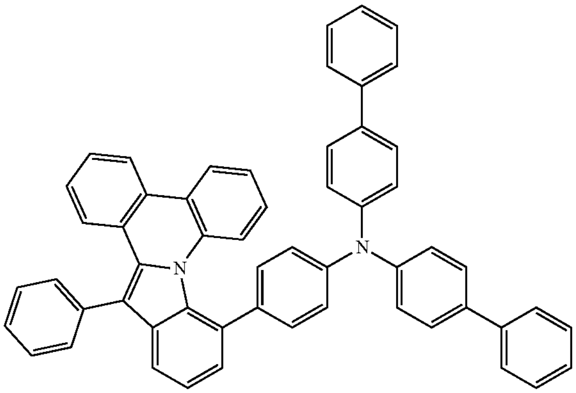

-continued
D85
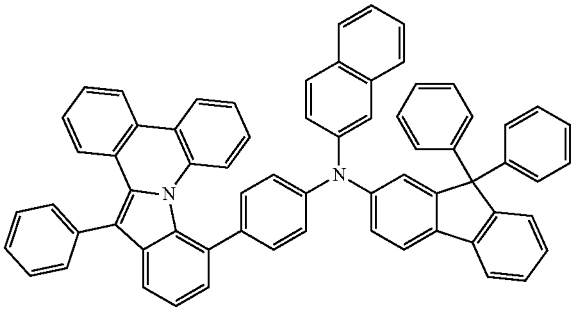
D86
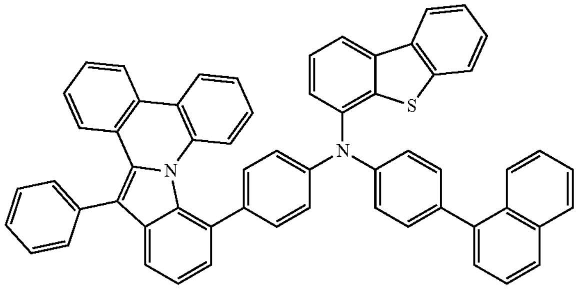
D87
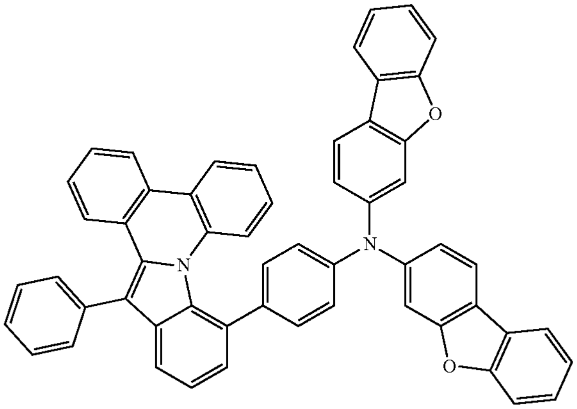
D88
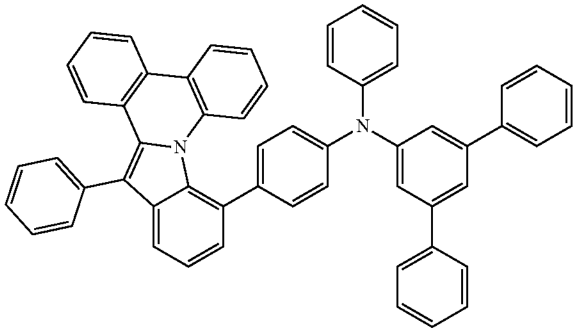
D89
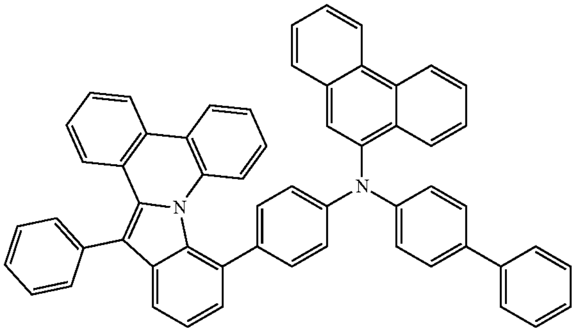
D90
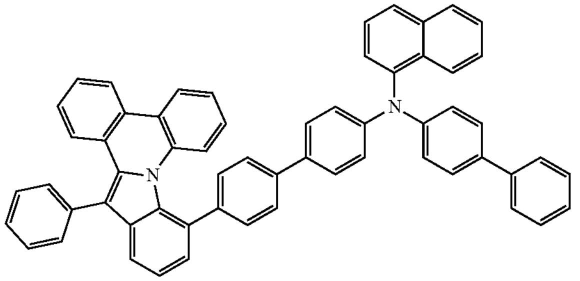
D91
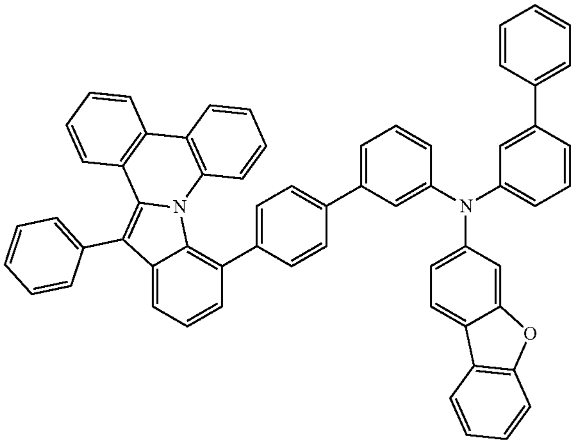
D92
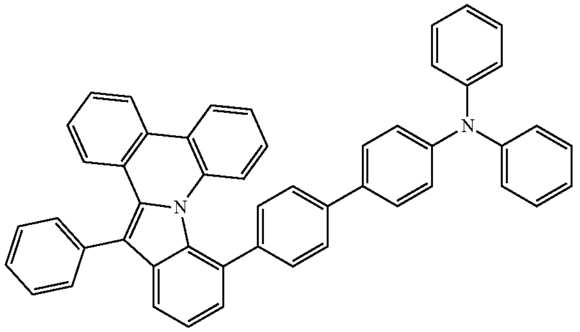

-continued
D93
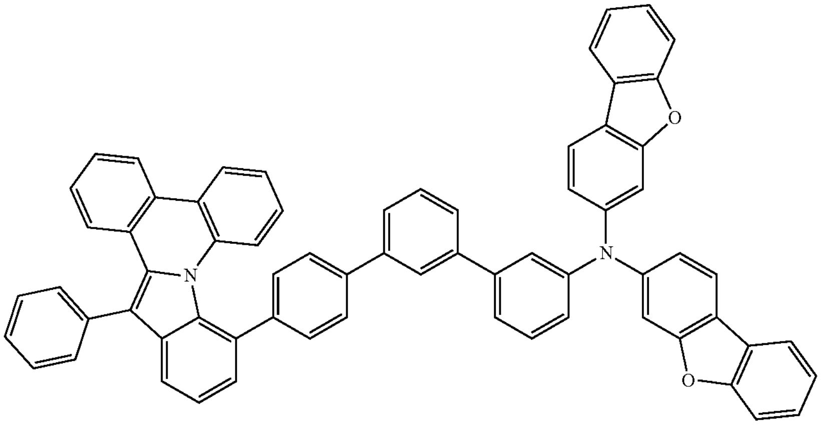
D94
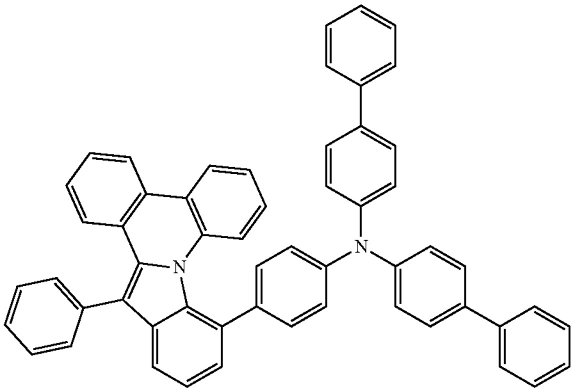
D95
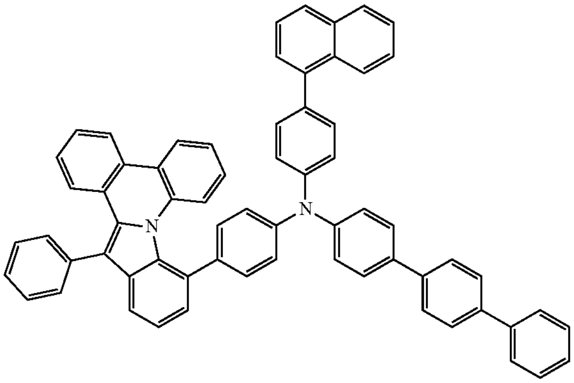
D96
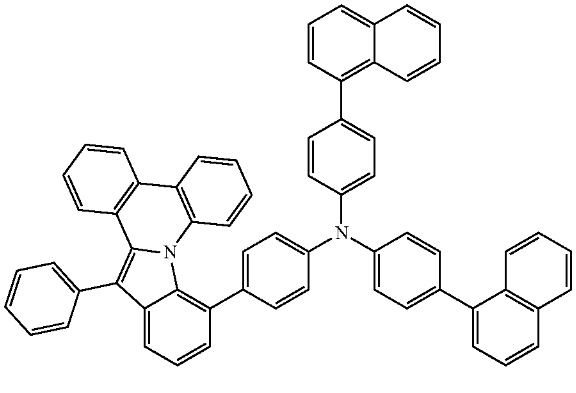
D97
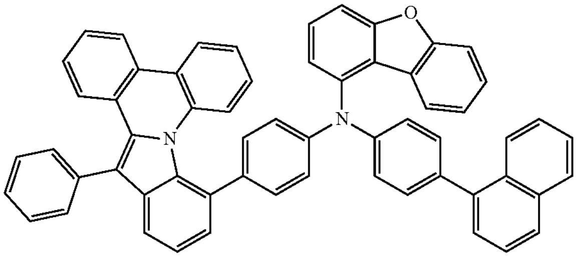

-continued
D98
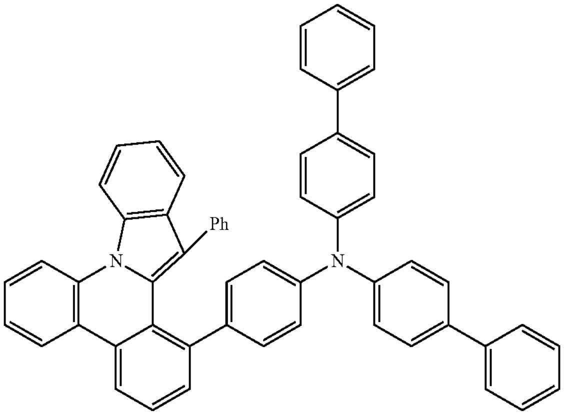
D99
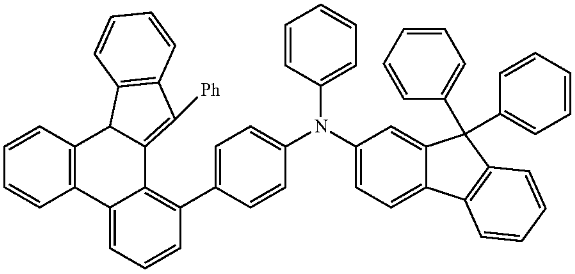
D100
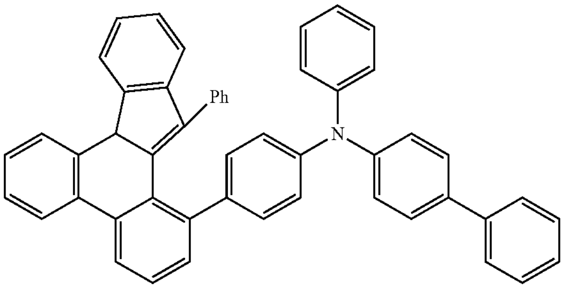
Compound Group 2
E1
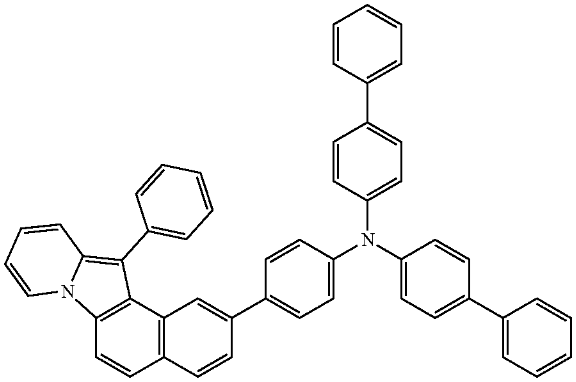
E2
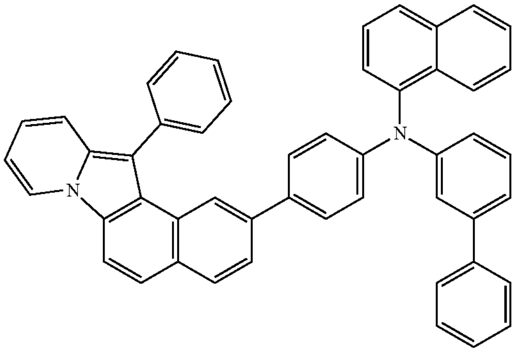

-continued
E3
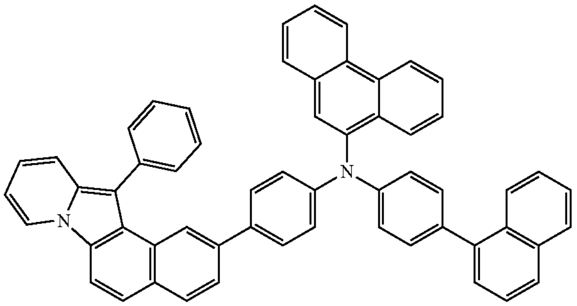
E4
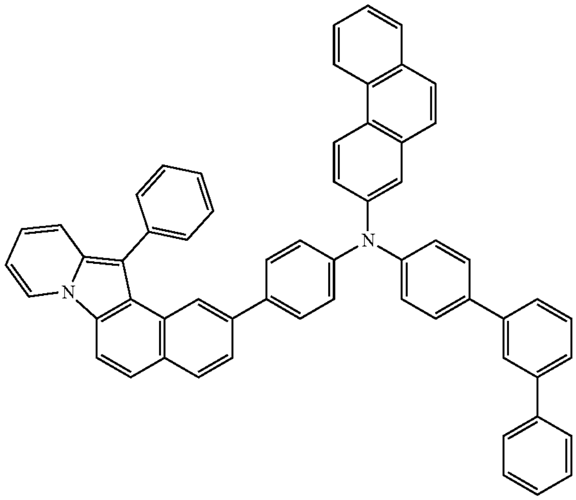
E5
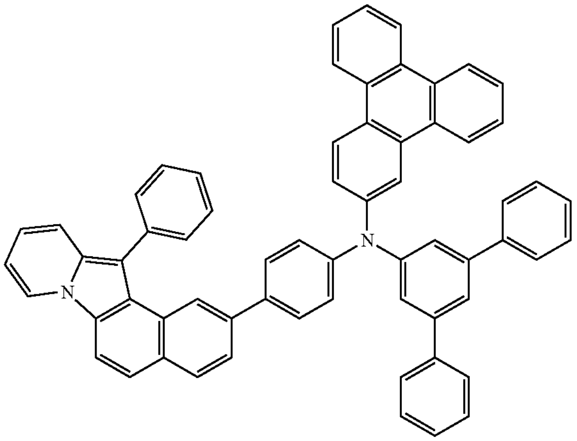
E6
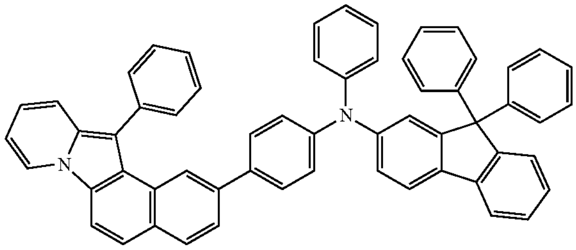
E7
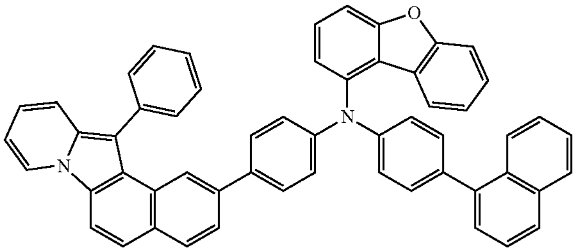
E8
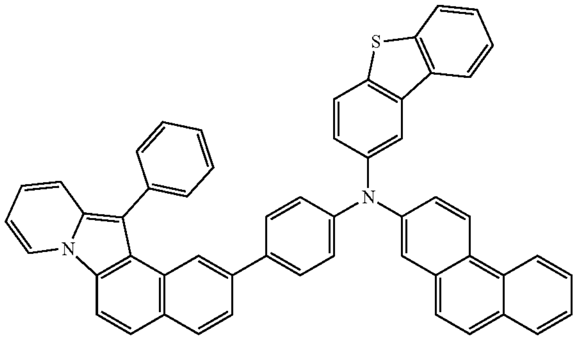

-continued
E9
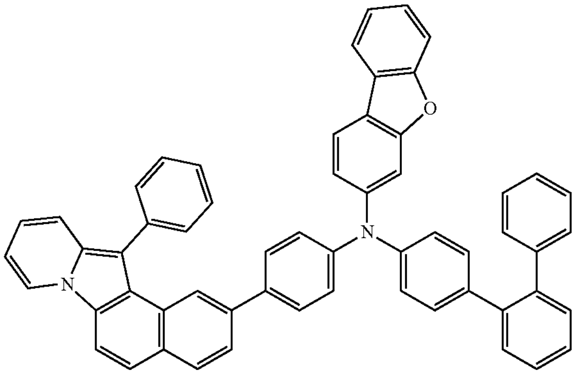
E10
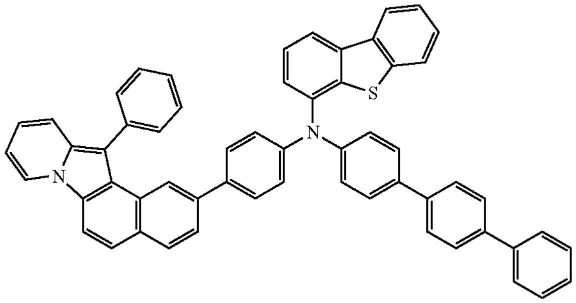
E11
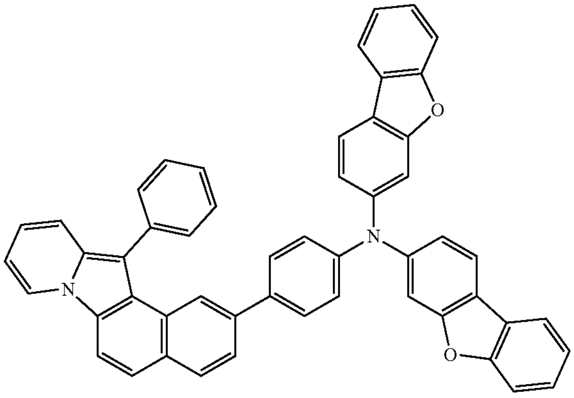
E12
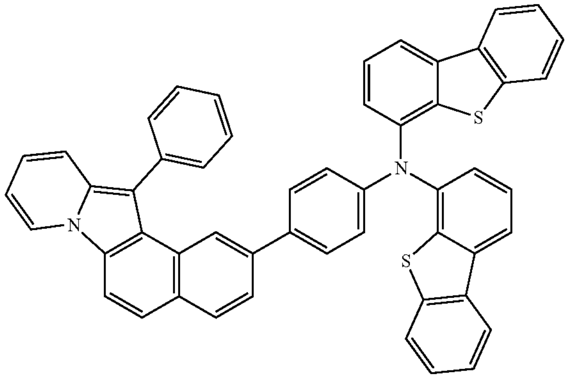
E13
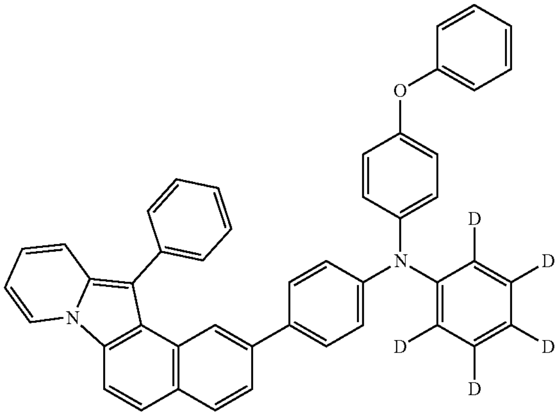
E14
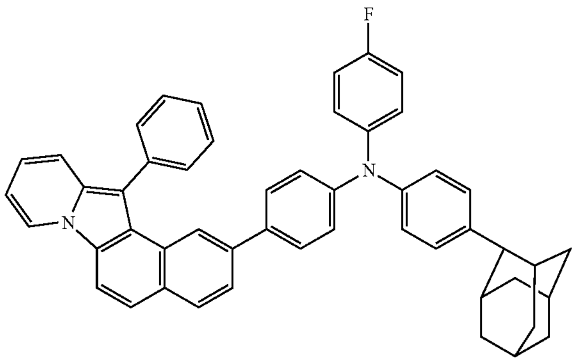

-continued
E15
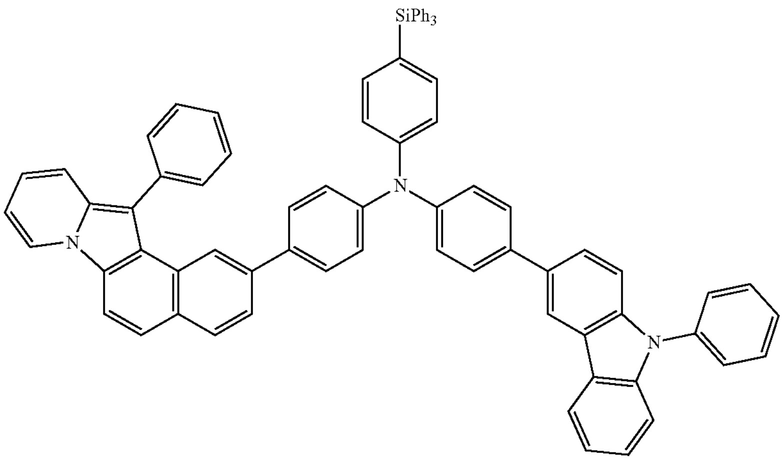
E16
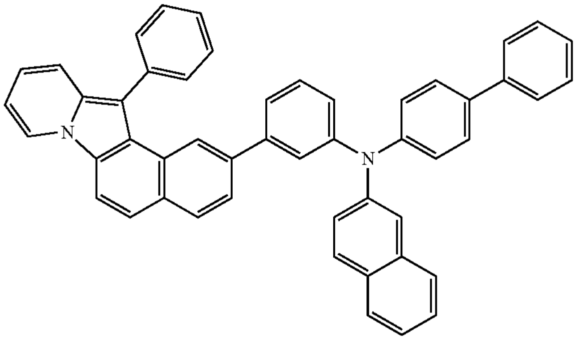
E17
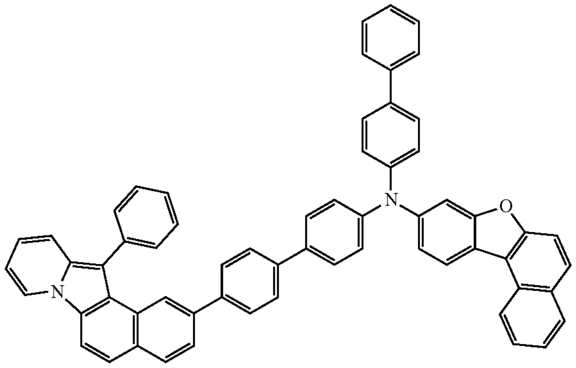
E18
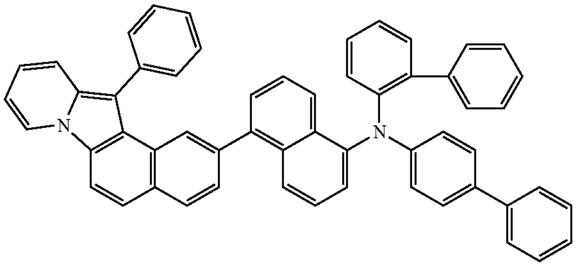
E19
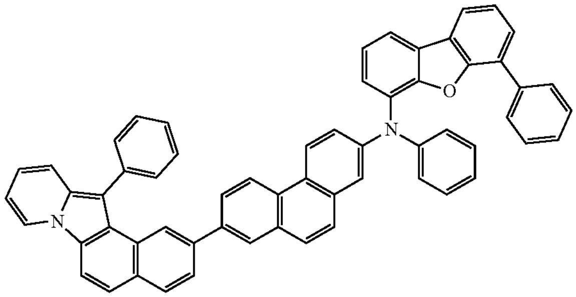
E20
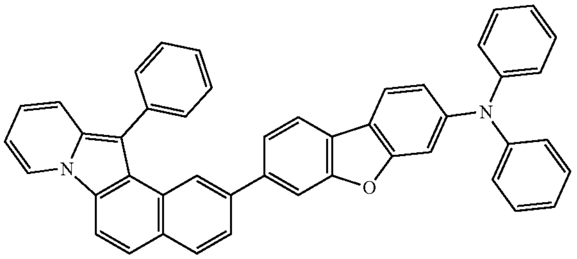
E21
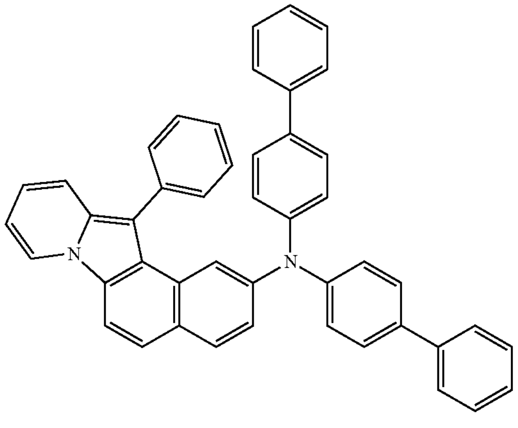

-continued
E22
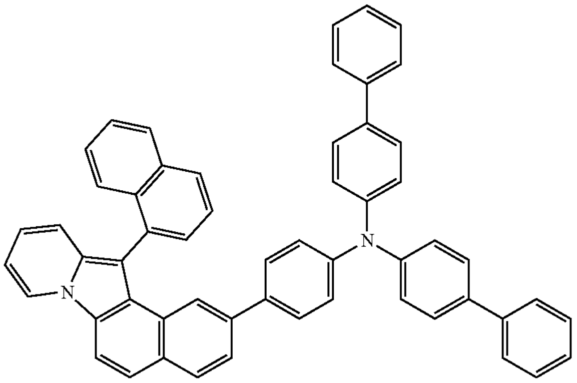
E23
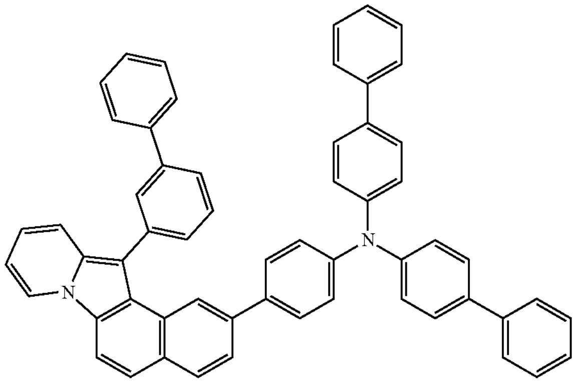
E24
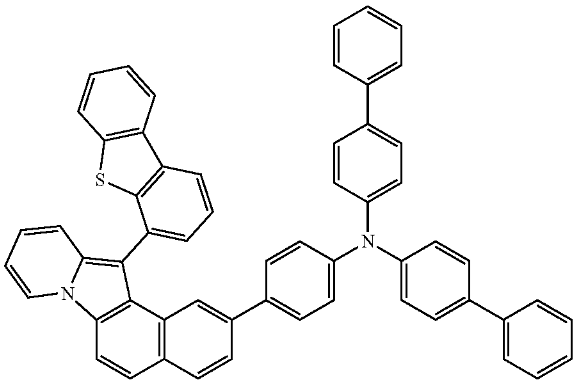
E25
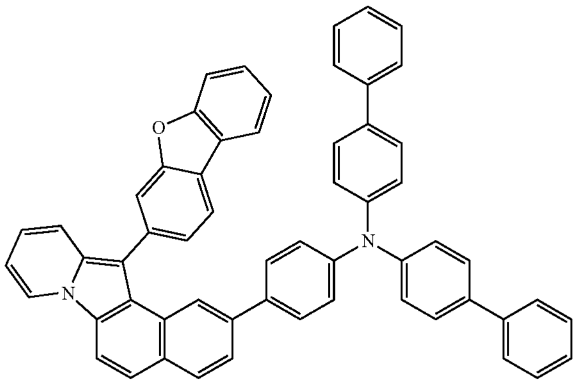
E26
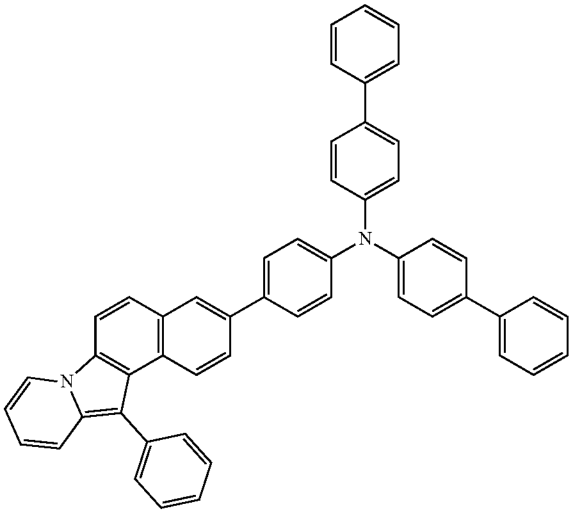
E27
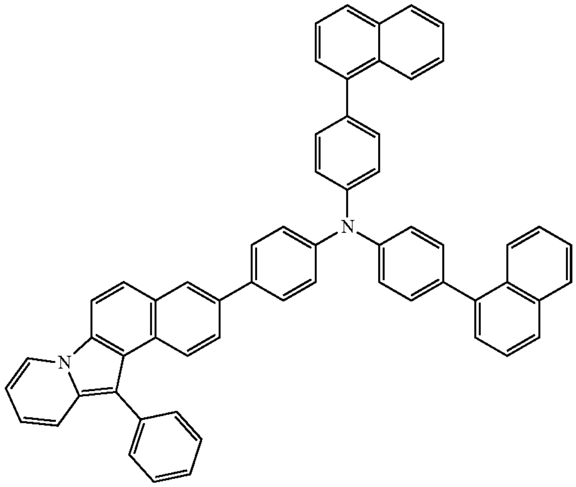

-continued
E28
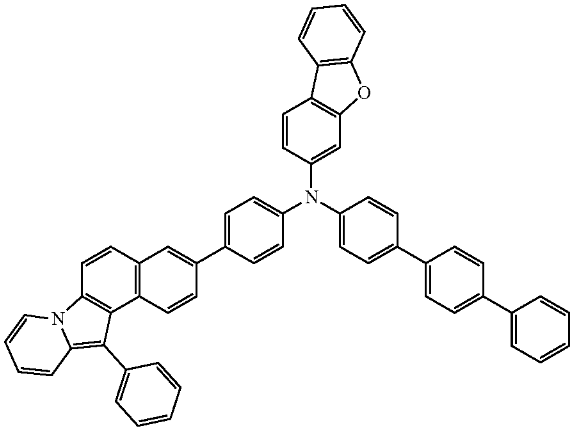
E29
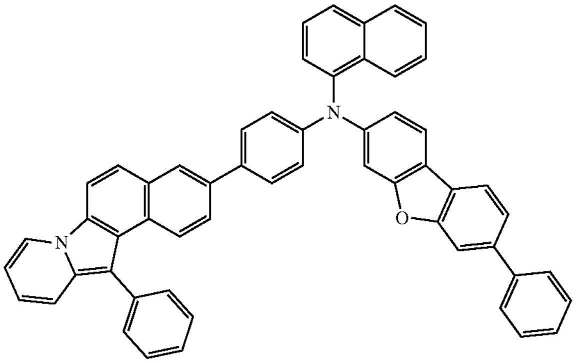
E30
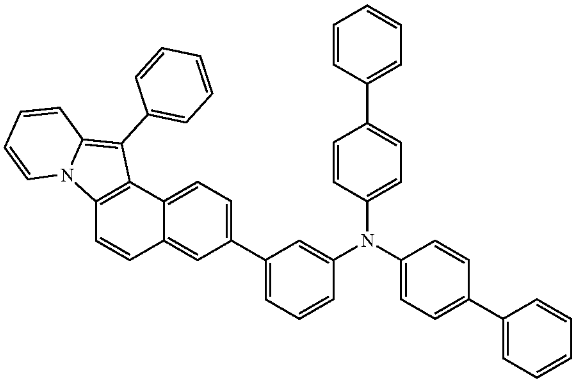
E31
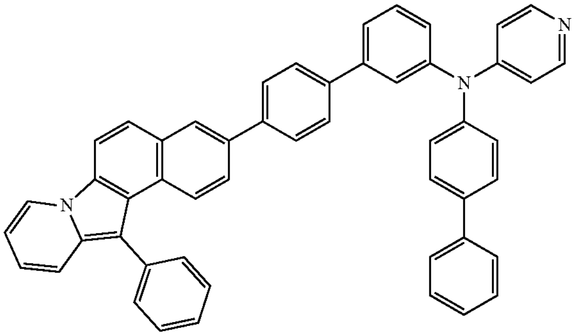
E32
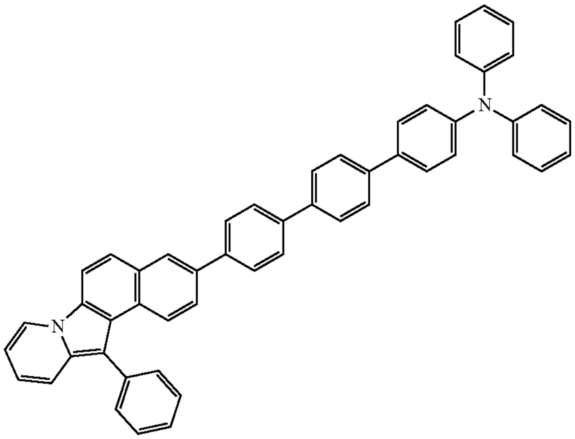
E33
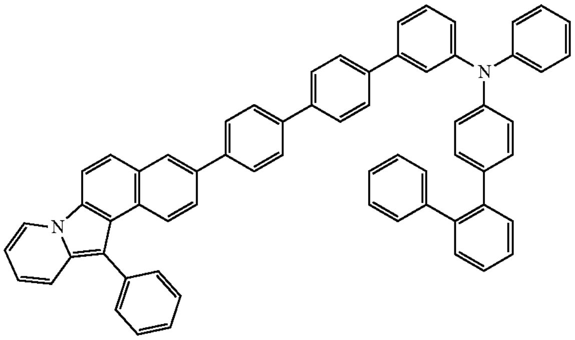

-continued
E34
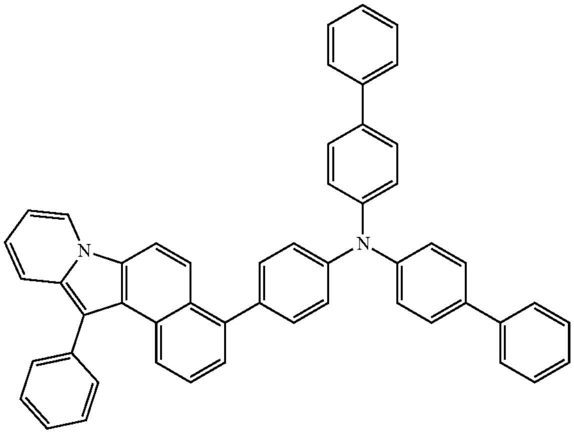
E35
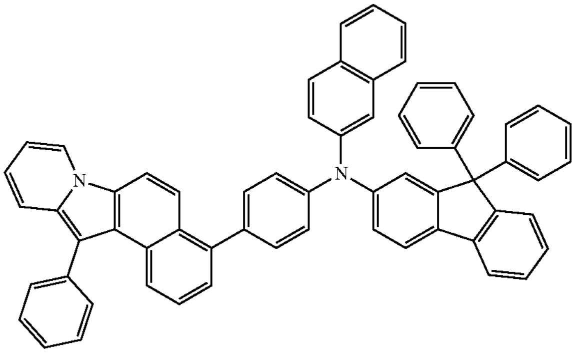
E36
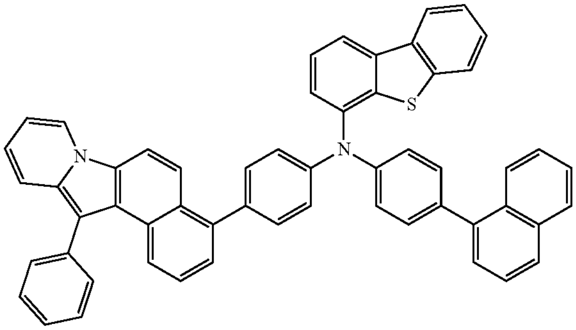
E37
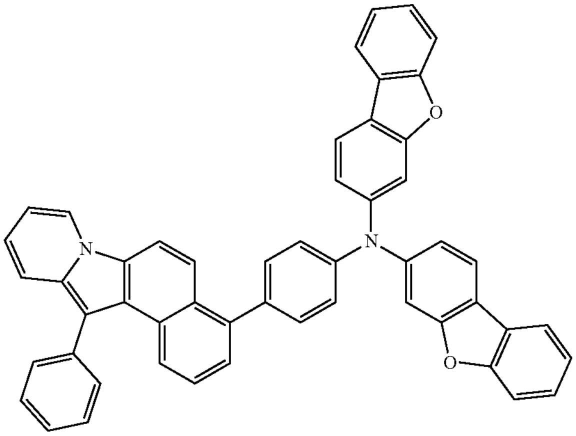
E38
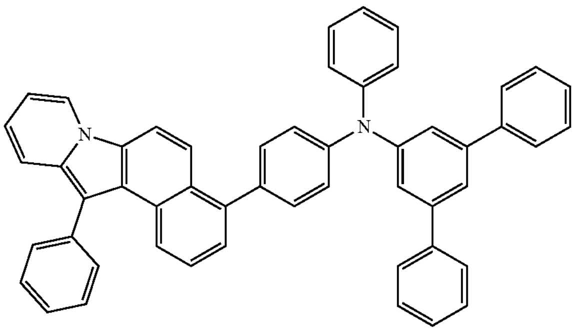
E39
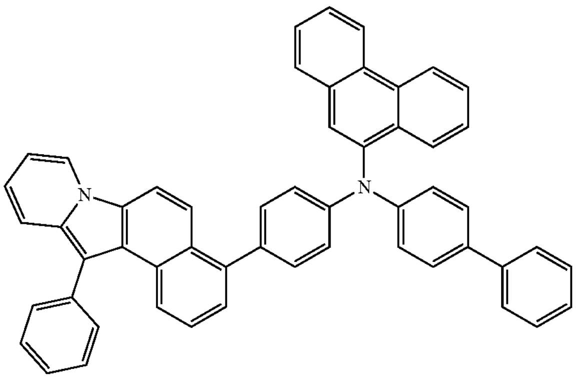

-continued
E40
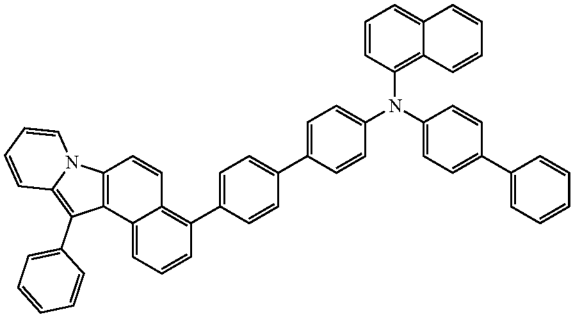
E41
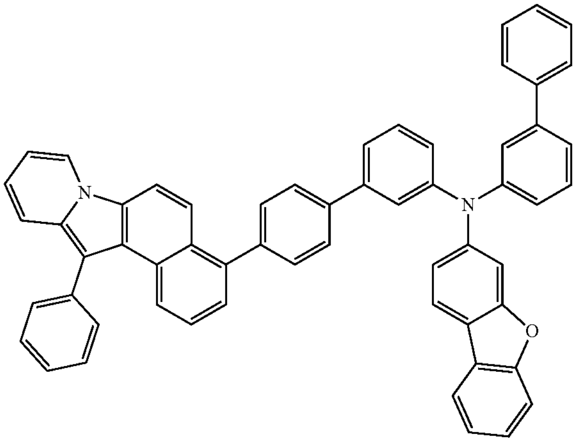
E42
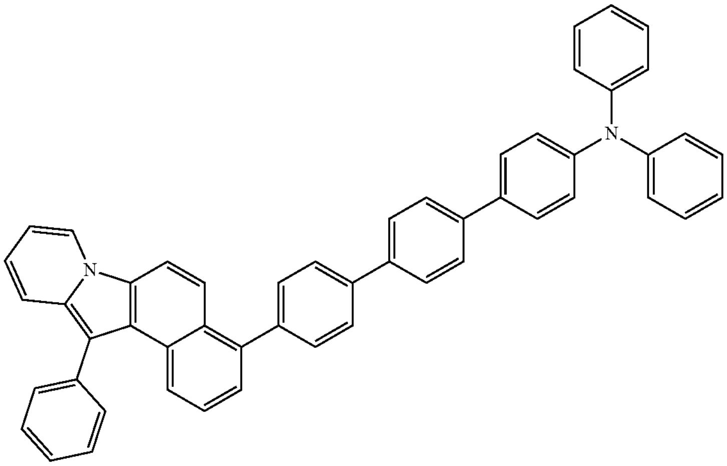
E43
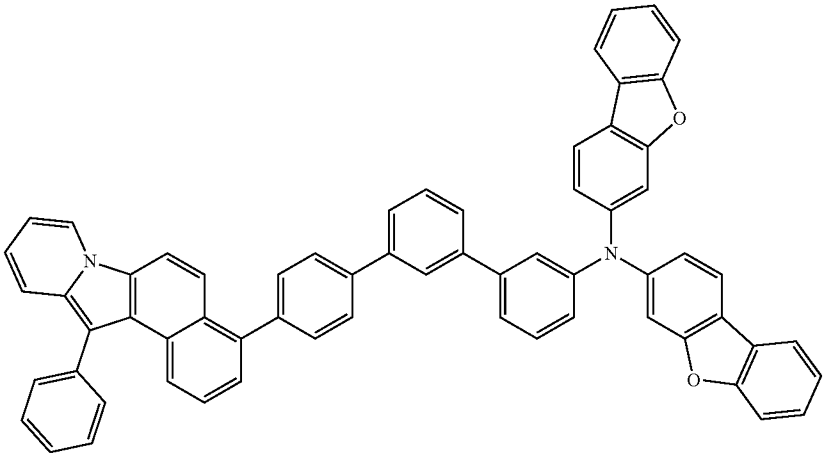

-continued
E44
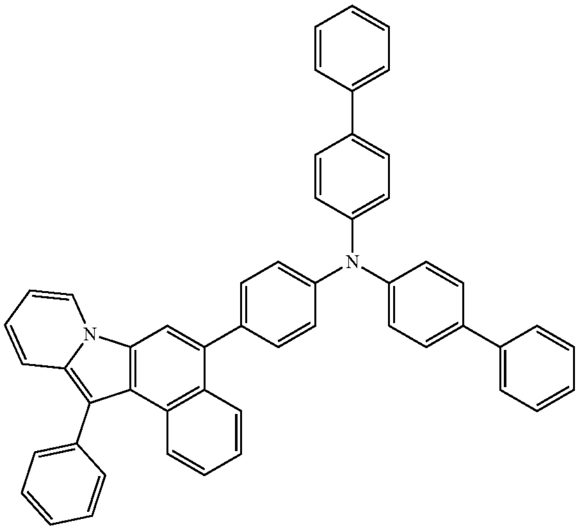
E45
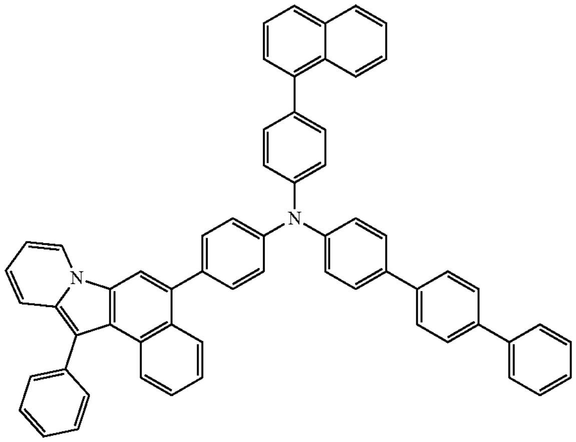
E46
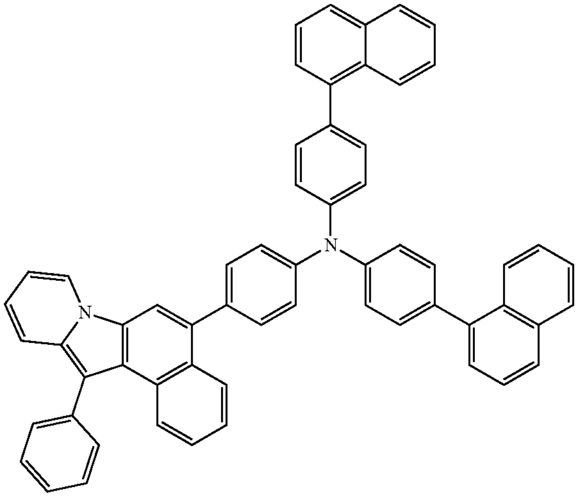
E47
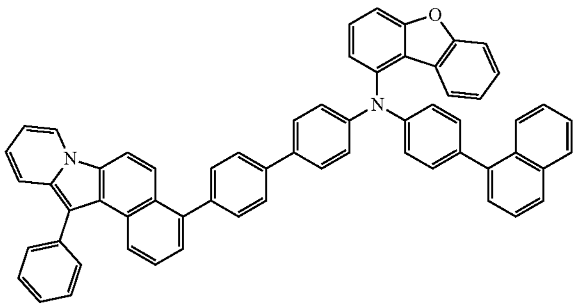
E48
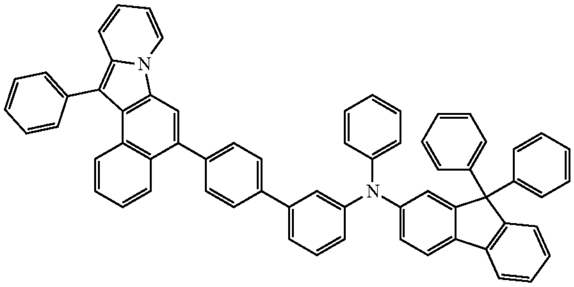

-continued
E49
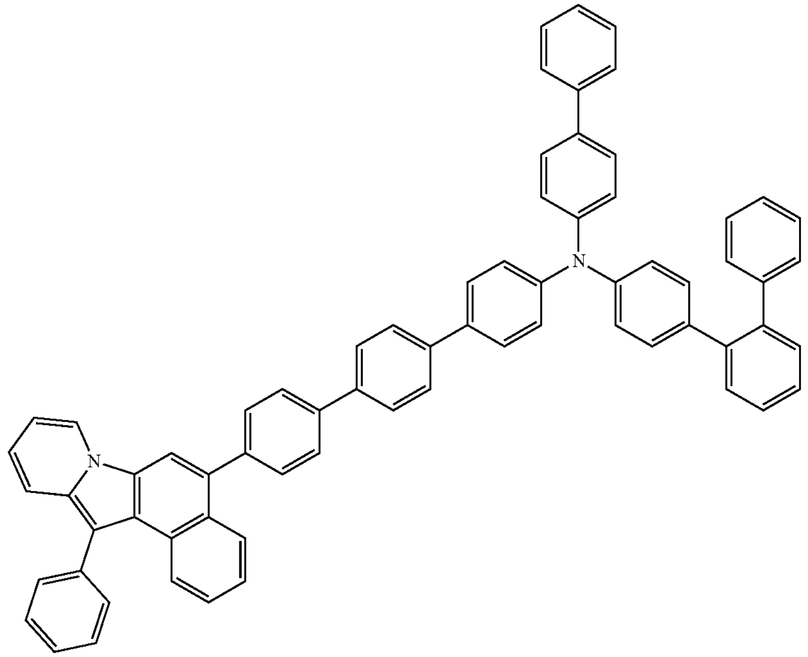
E50
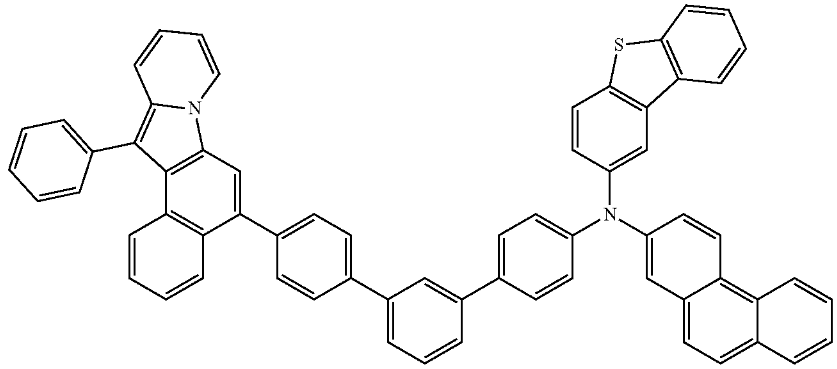
E51
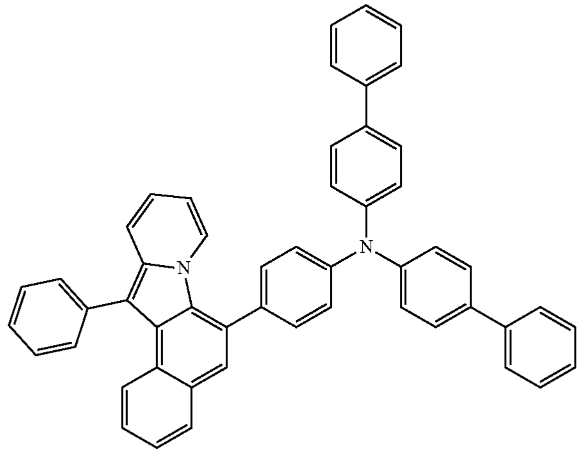
E52
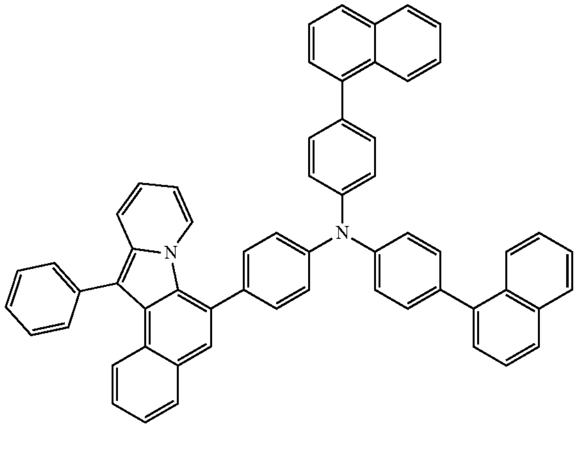

-continued
E53
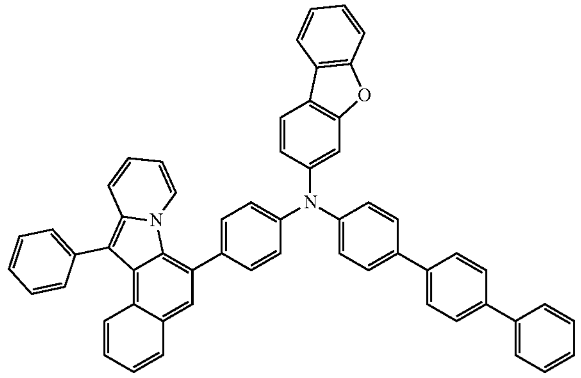
E54
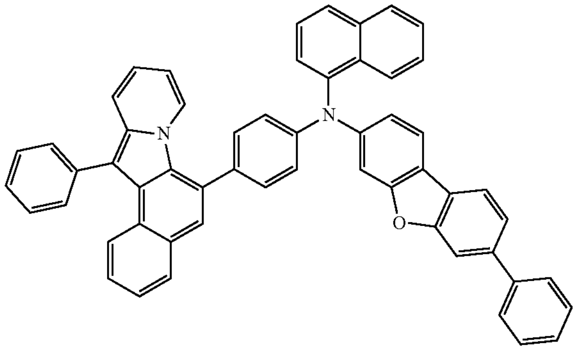
E55
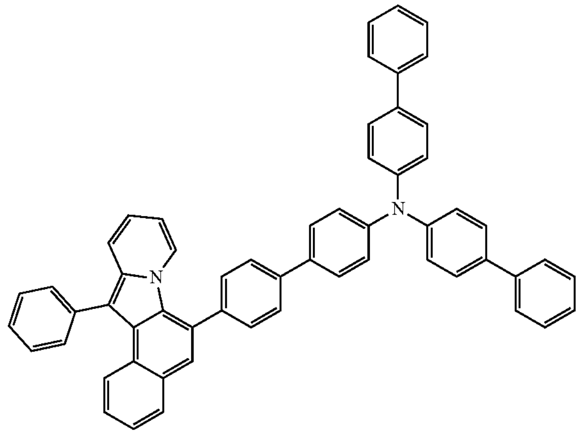
E56
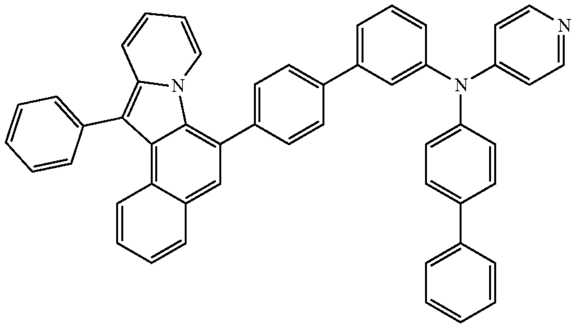
E57
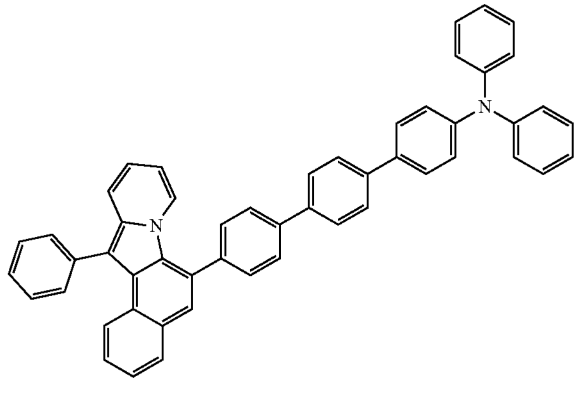
E58
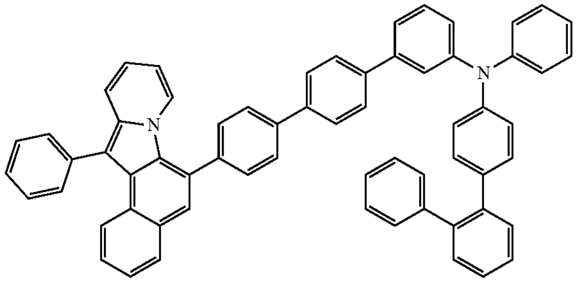

-continued
E59
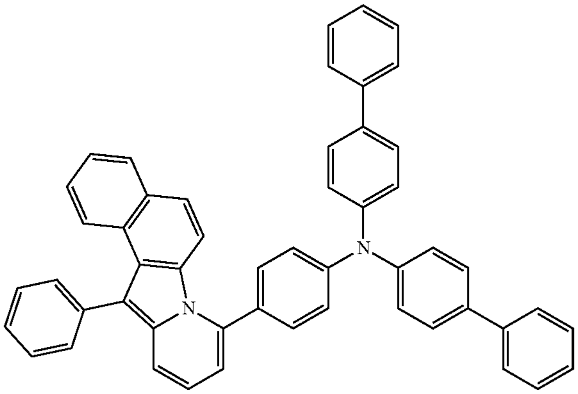
E60
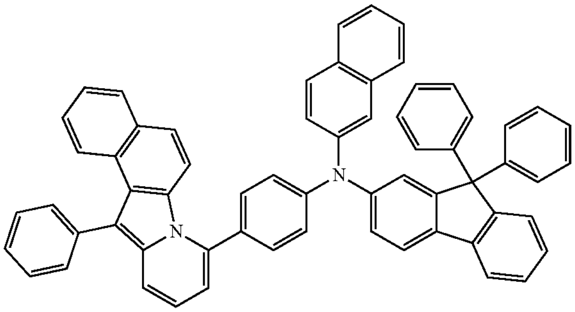
E61
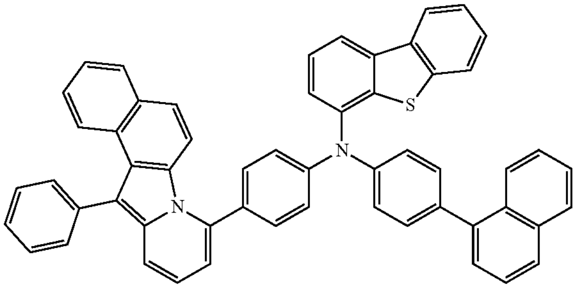
E62
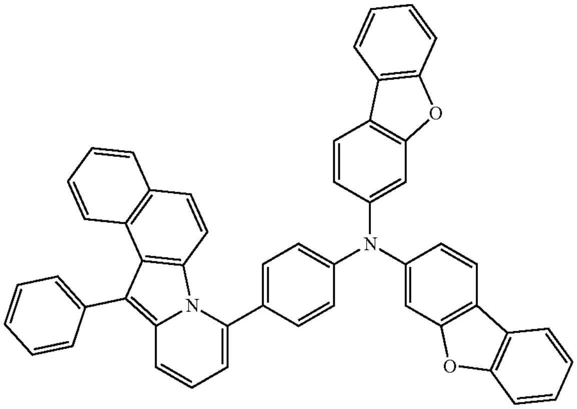
E63
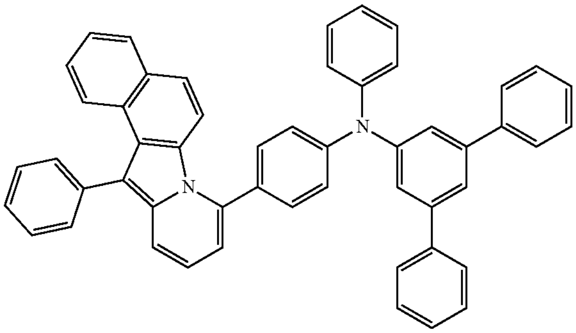
E64
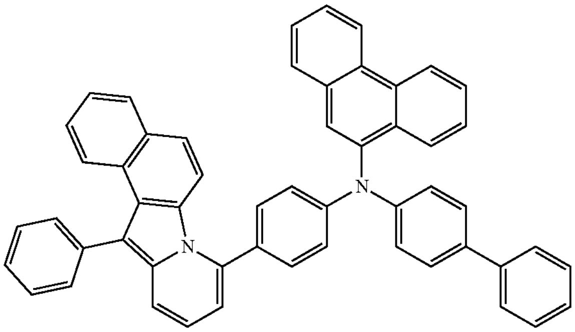

-continued
E65
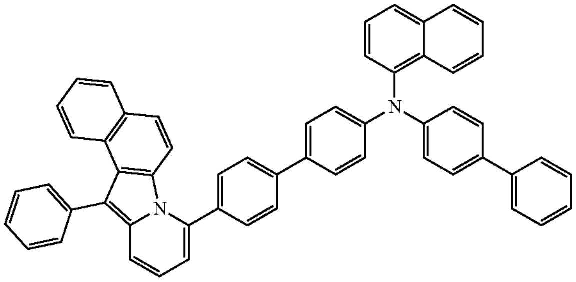
E66
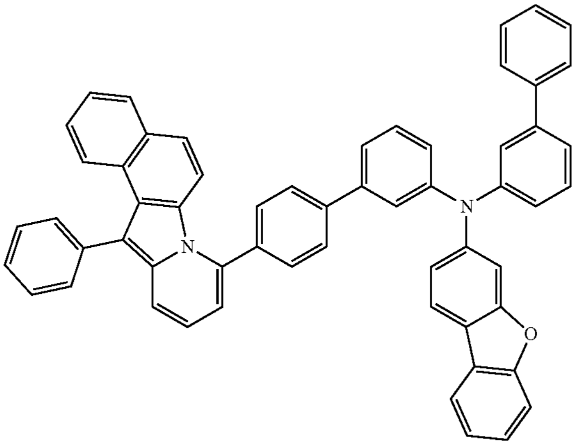
E67
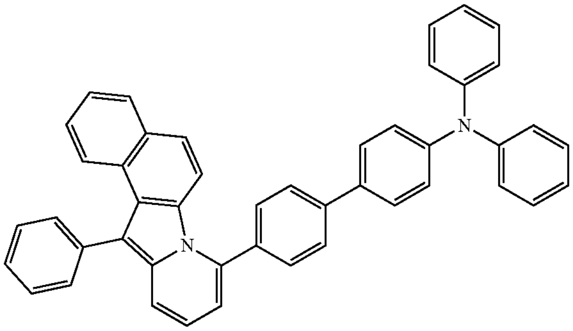
E68
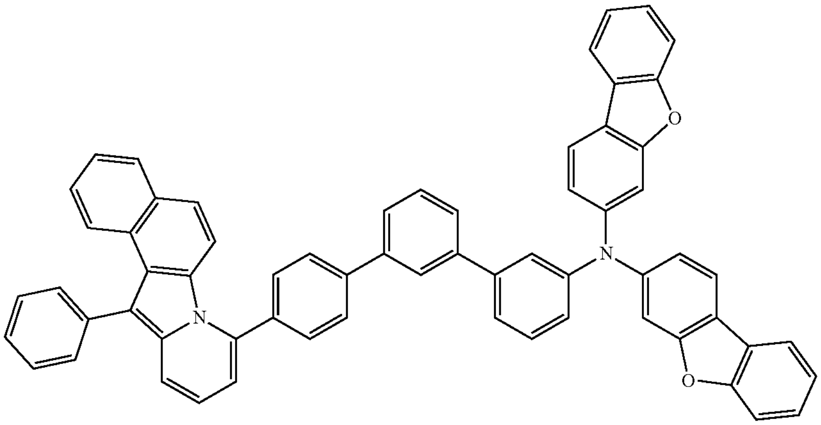

-continued
E69
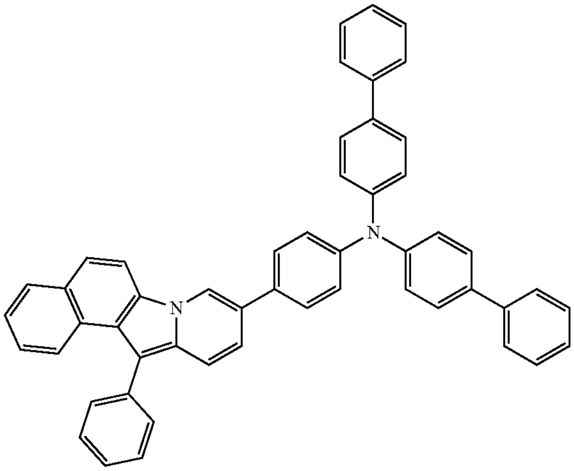
E70
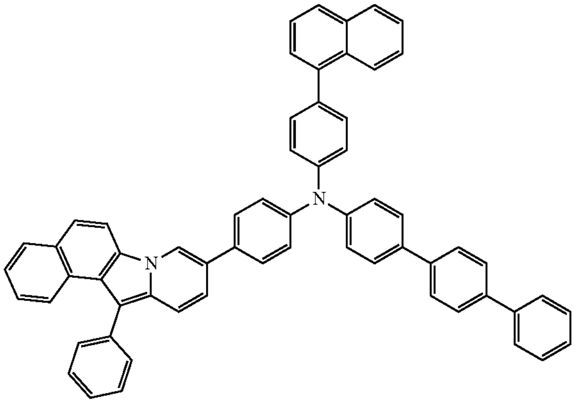
E71
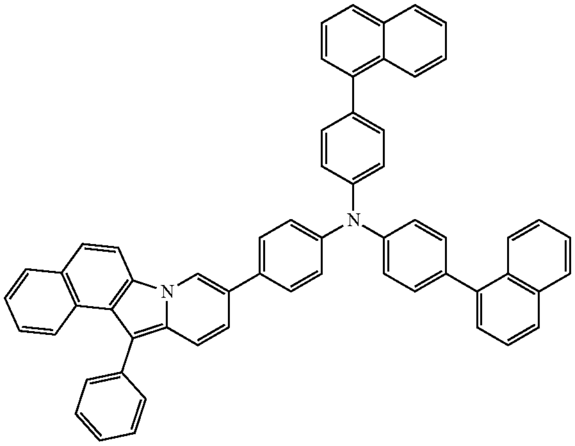
E72
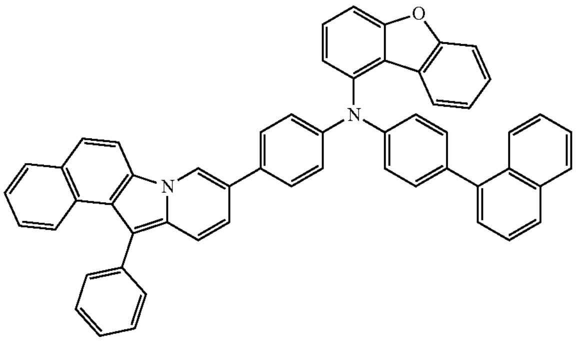
E73
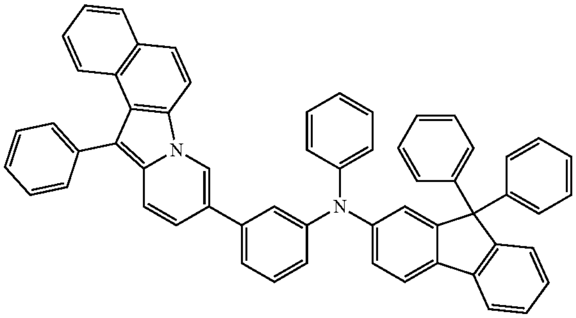
E74
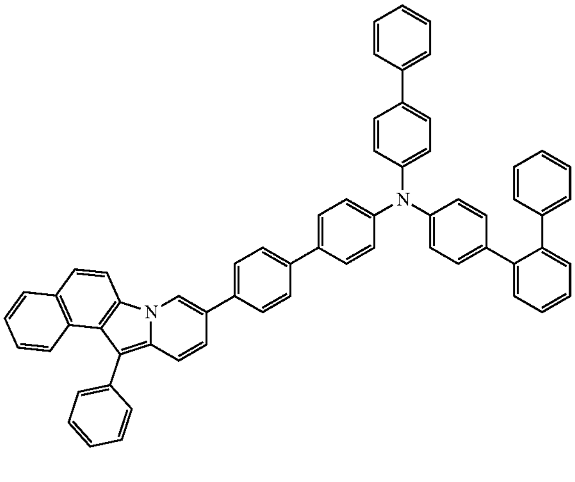

-continued
E75
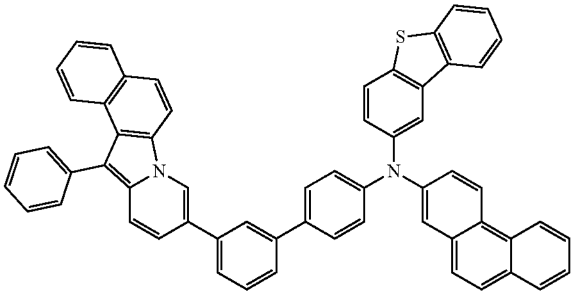
E76
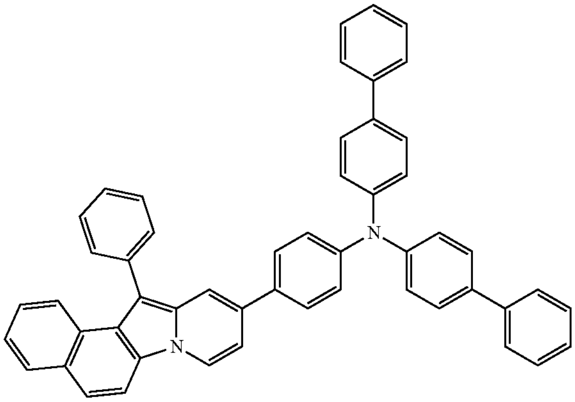
E77
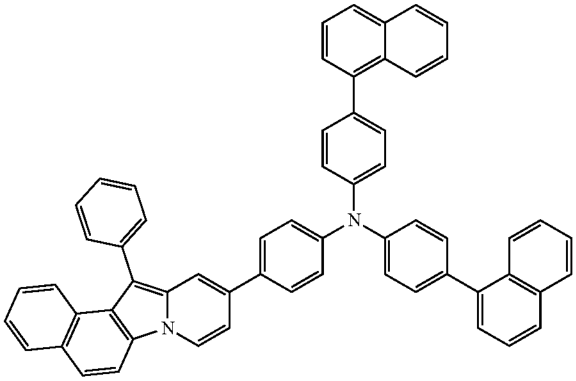
E78
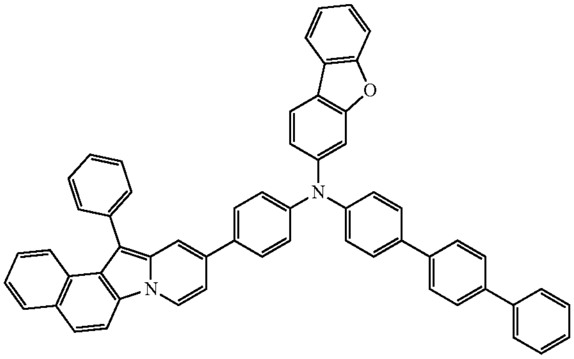
E79
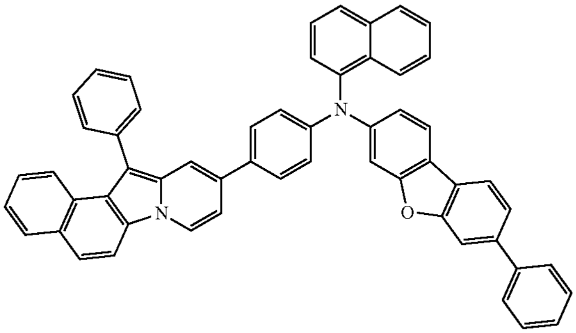
E80
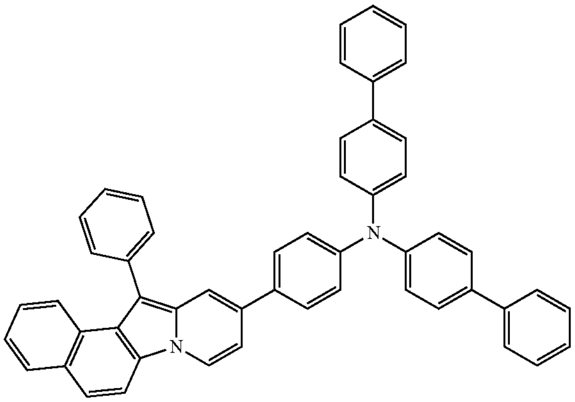

-continued
E81
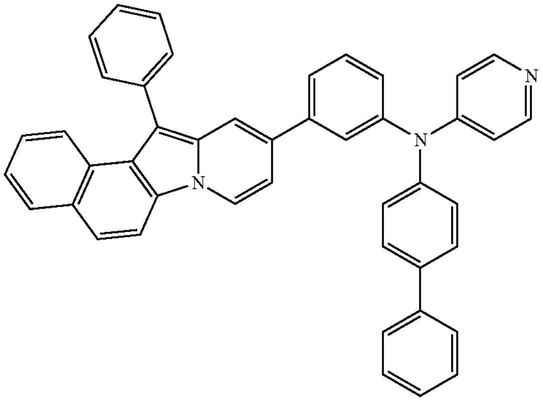
E82
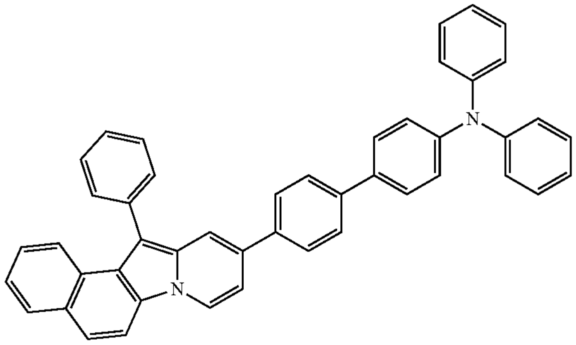
E83
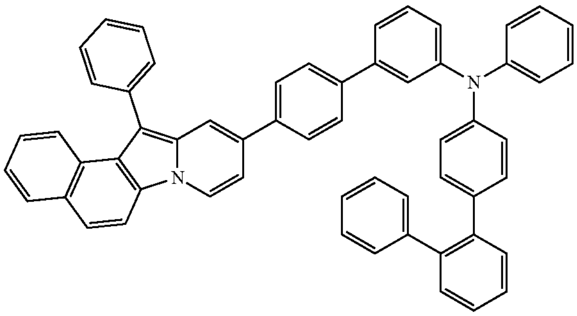
E84
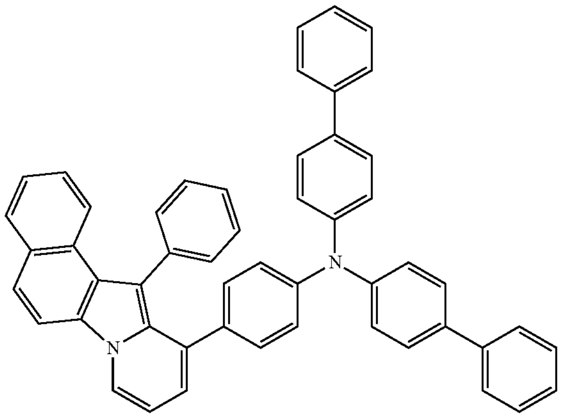
E85
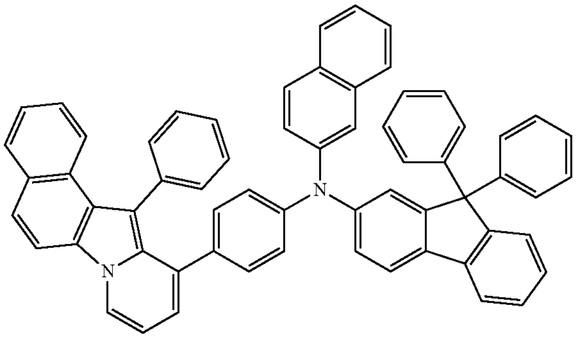
E86
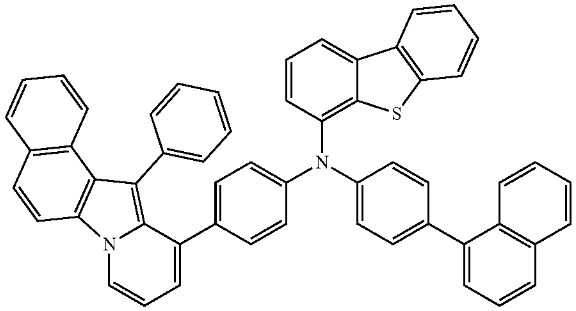

-continued
E87
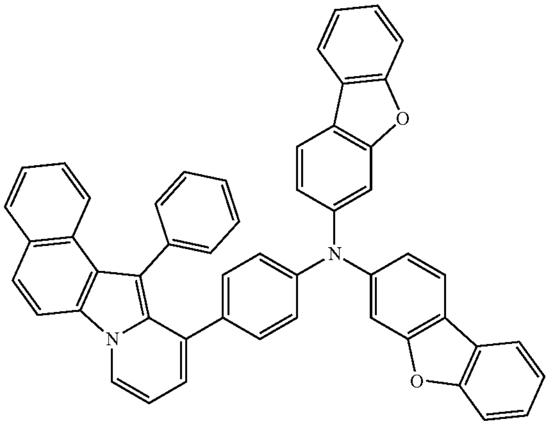
E88
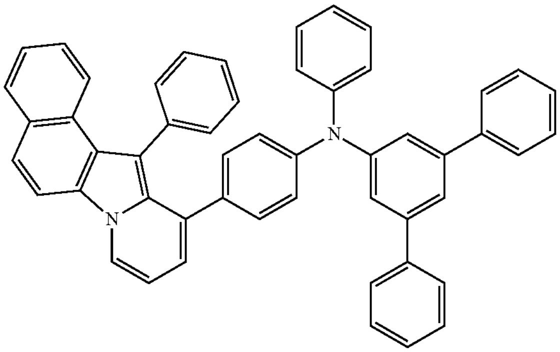
E89
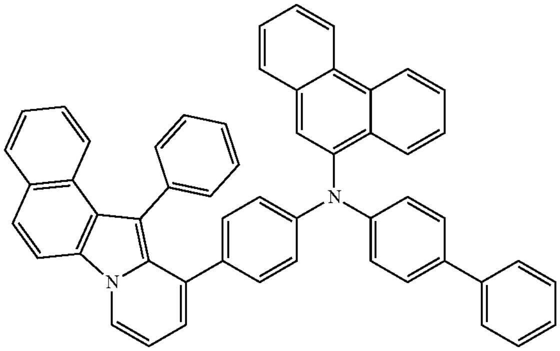
E90
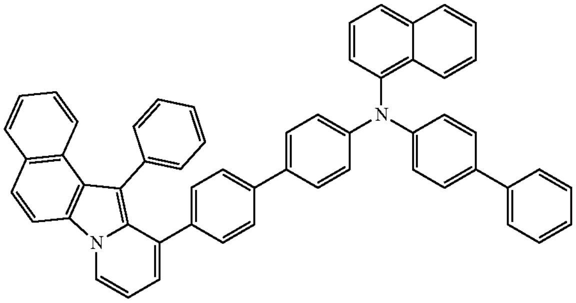
E91
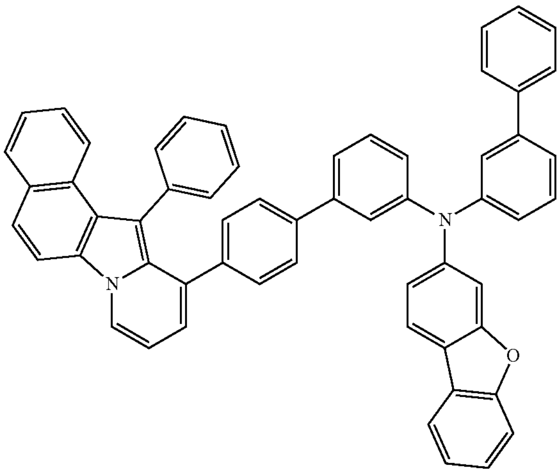
E92
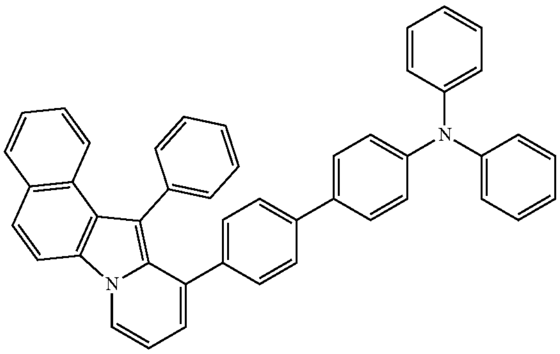

-continued
E93
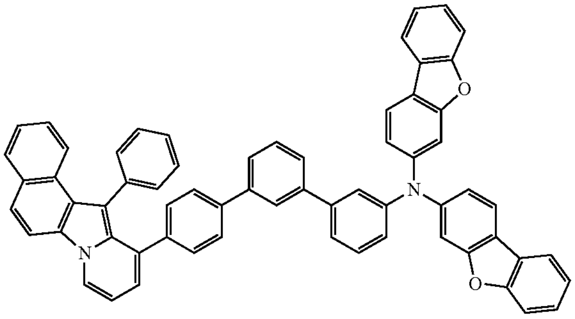
E94
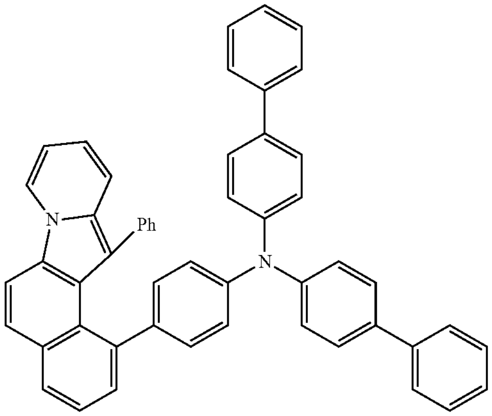
E95
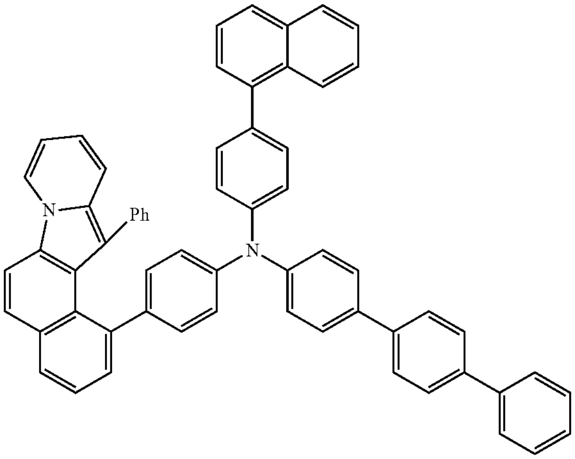
E96
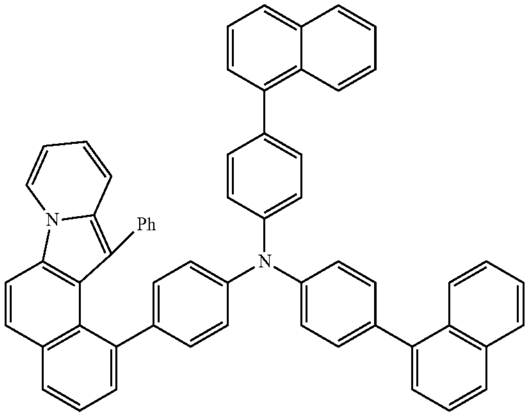
E97
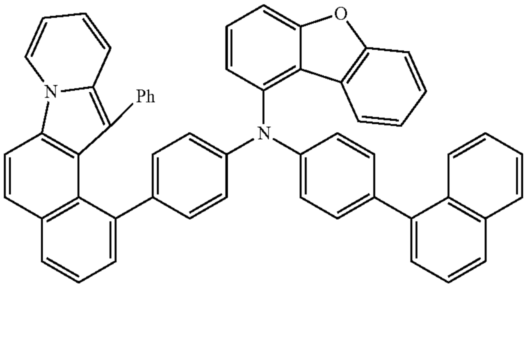
E98
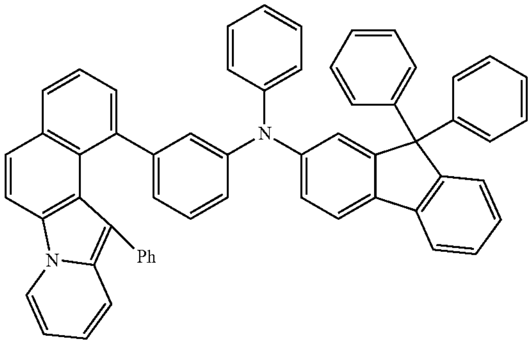

-continued
E99
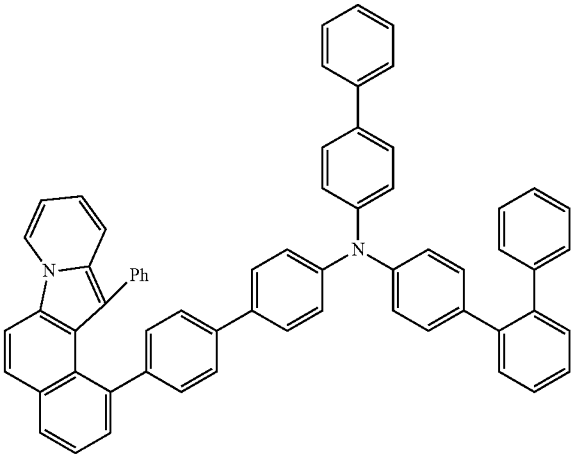
E100
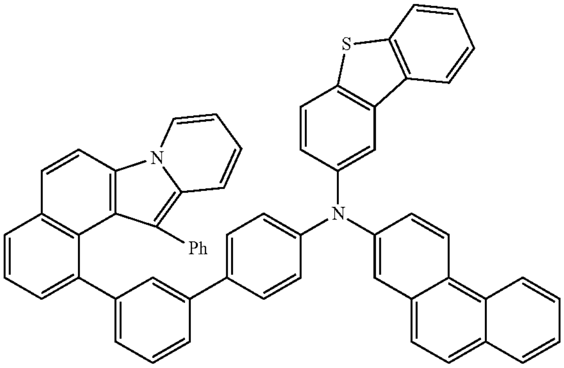
F1
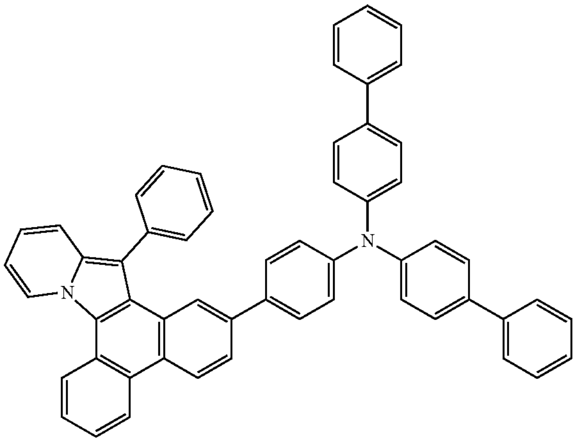
F2
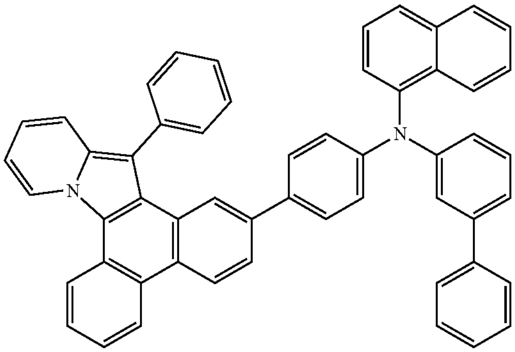
F3
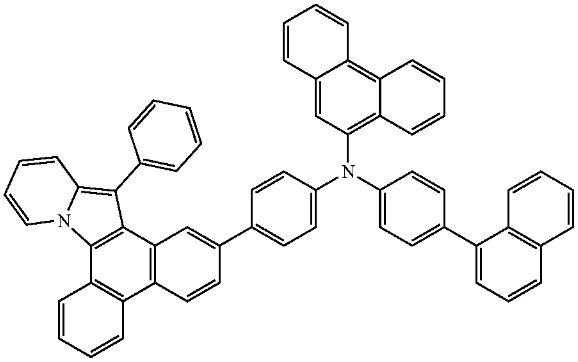
F4
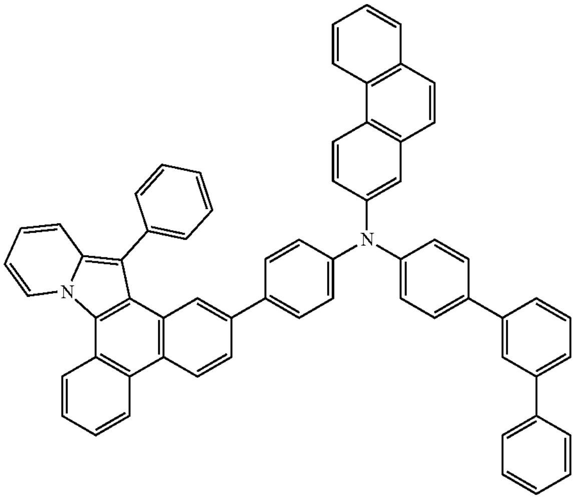

-continued
F5
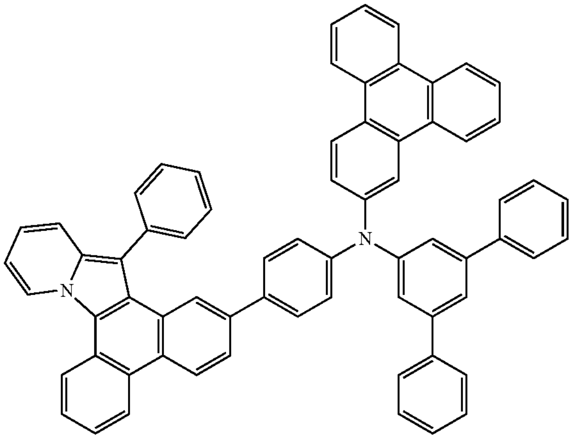
F6
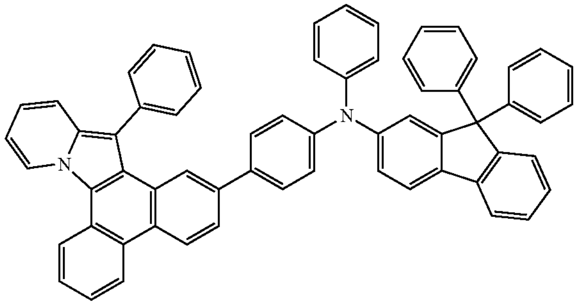
F7
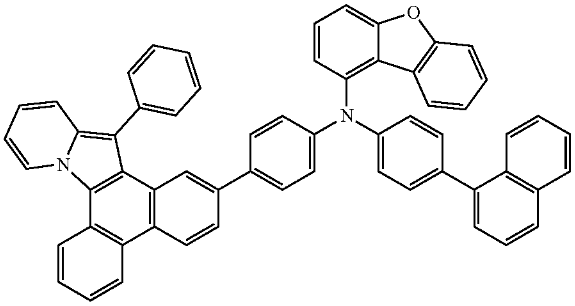
F8
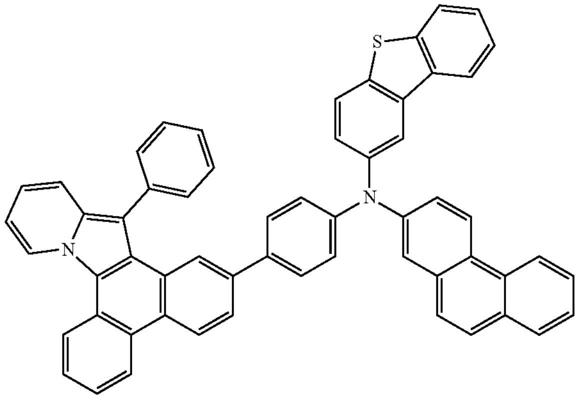
F9
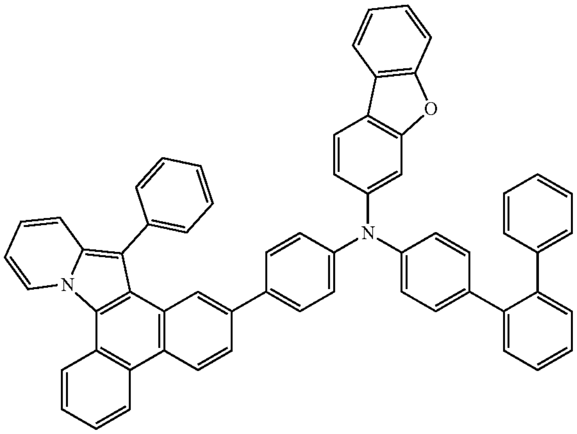
F10
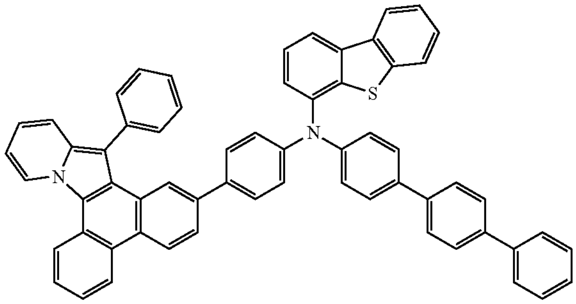

-continued
F11
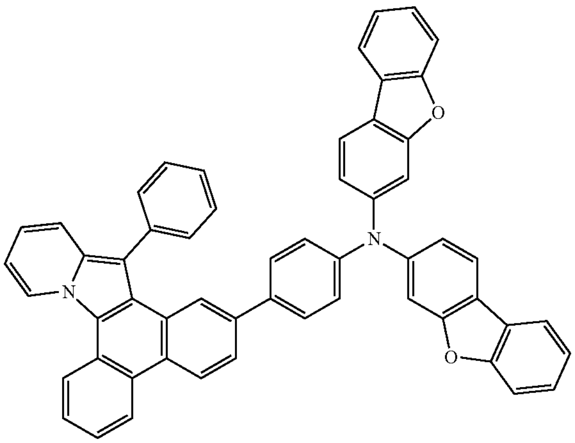
F12
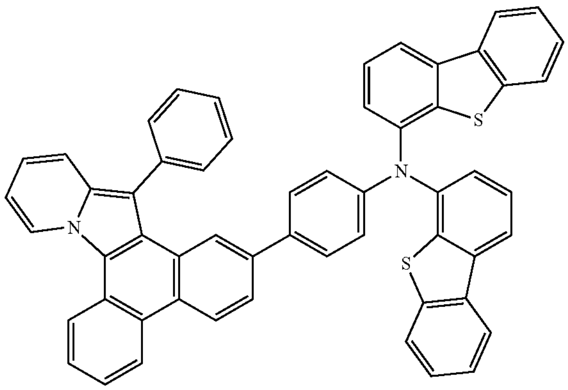
F13
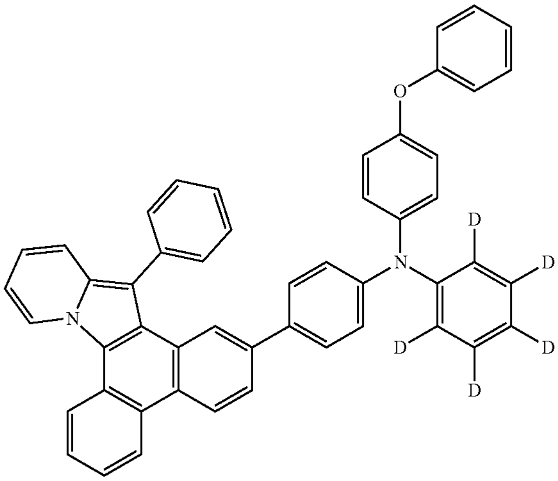
F14
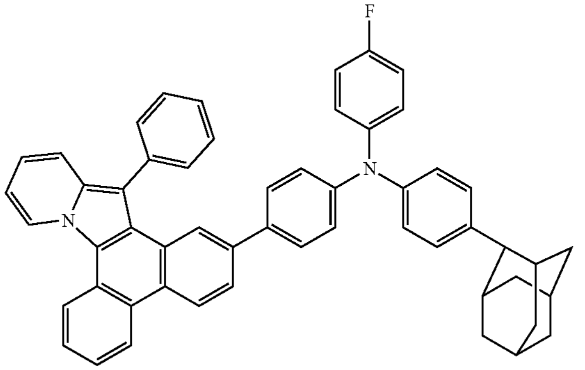
F15
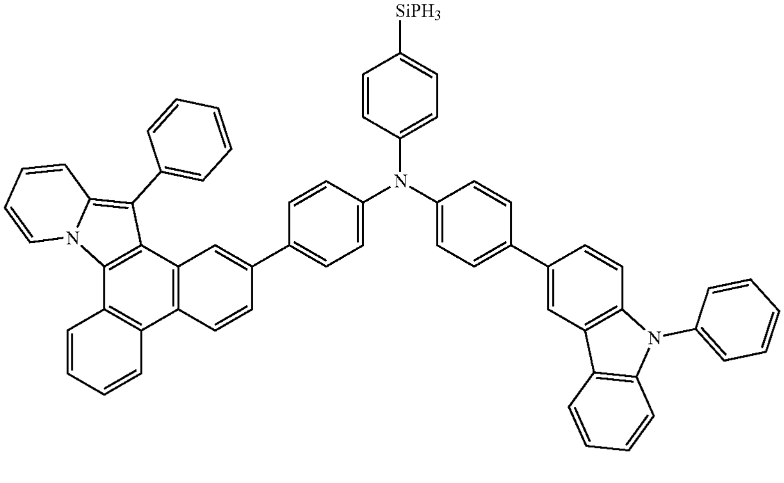

-continued
F16
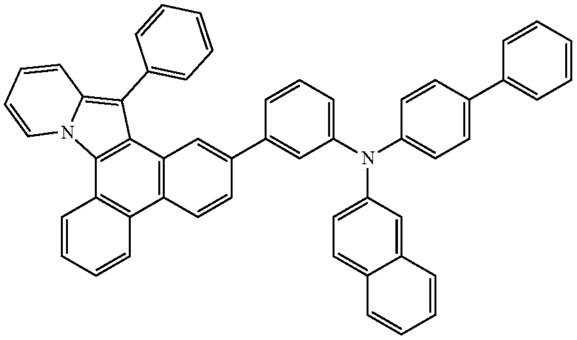
F17
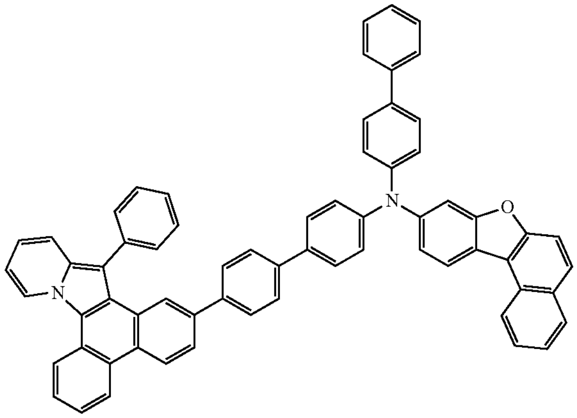
F18
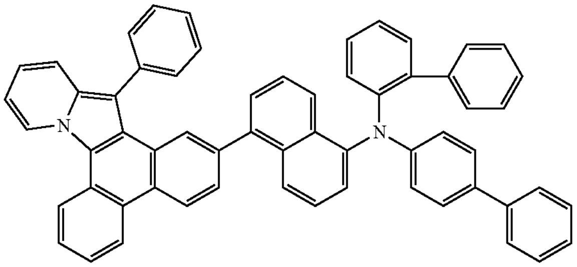
F19
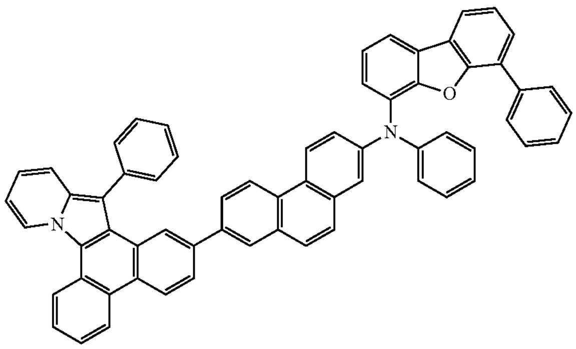
F20
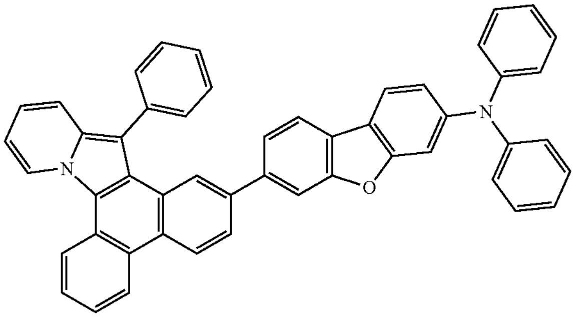
F21
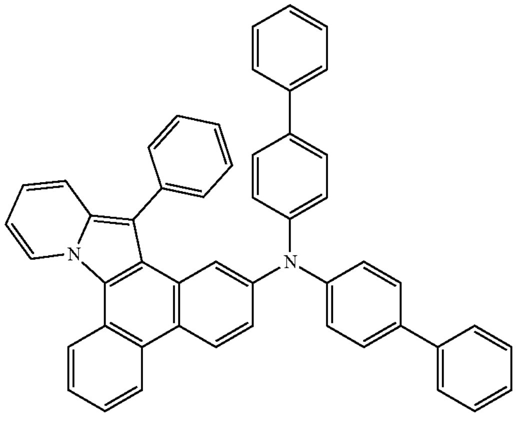

-continued
F22
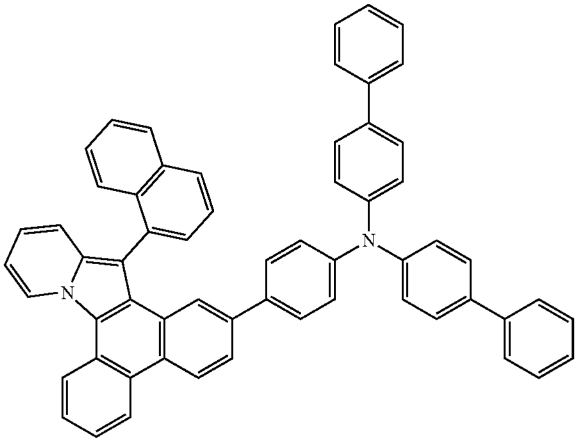
F23
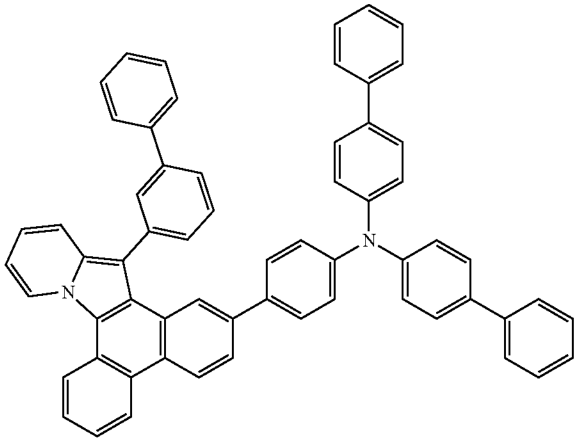
F24
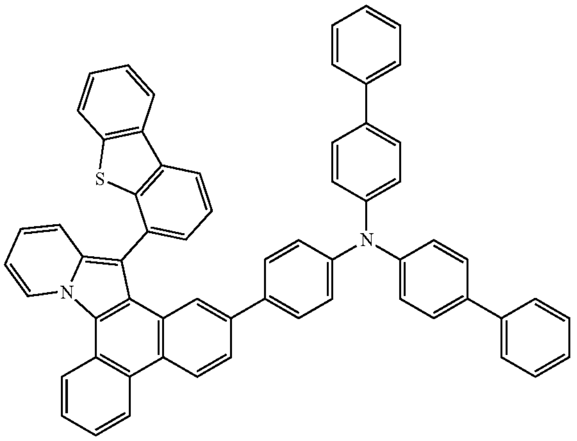
F25
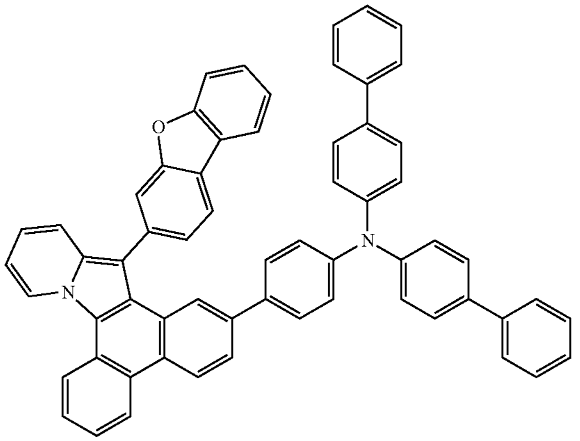
F26
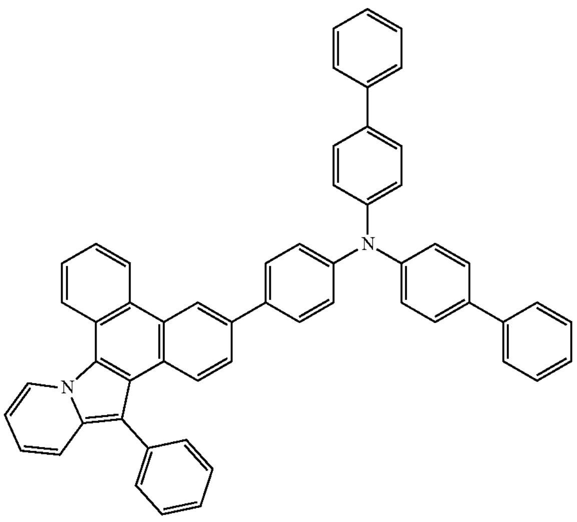
F27
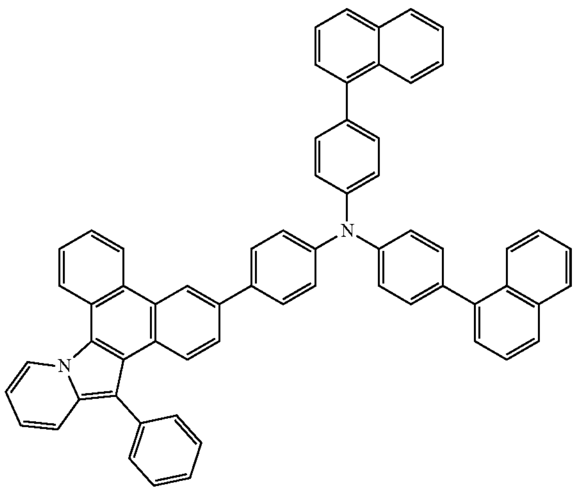

-continued
F28
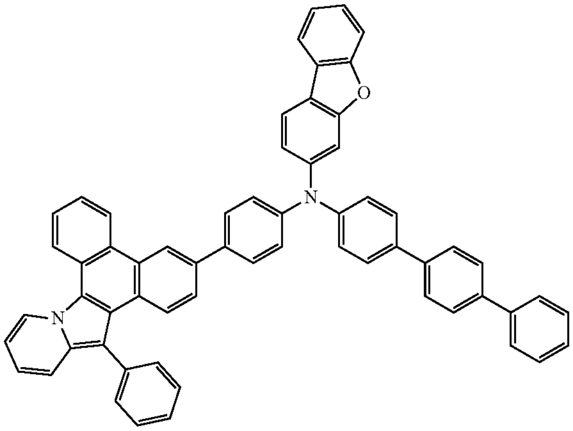
F29
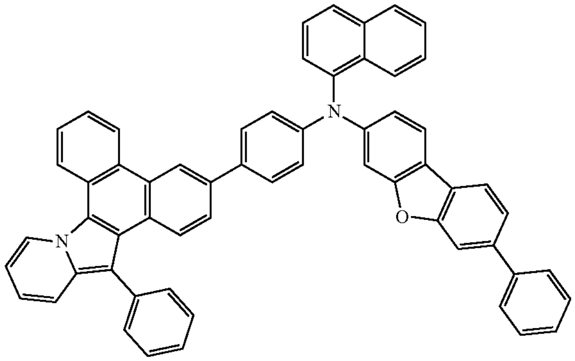
F30
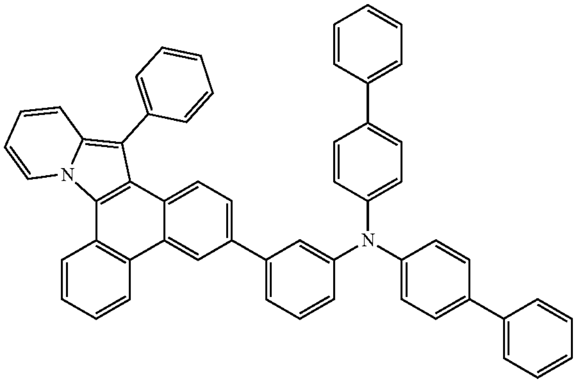
F31
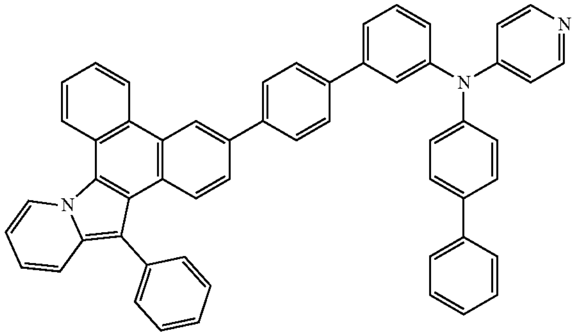
F32
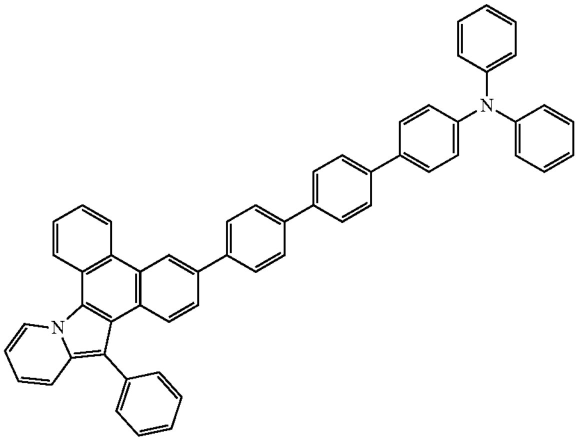
F33
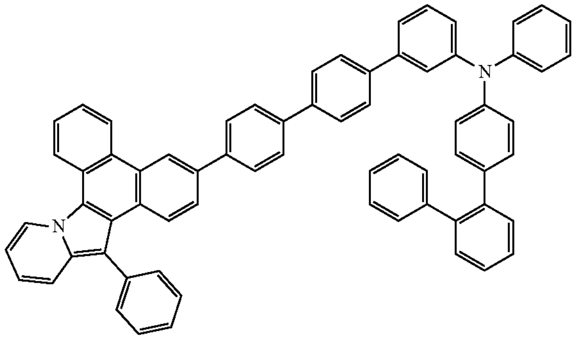

-continued
F34
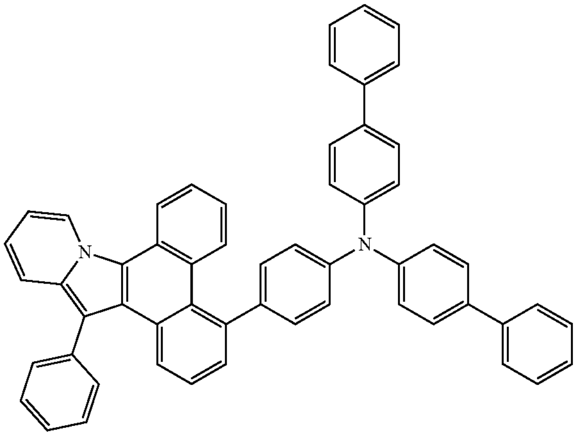
F35
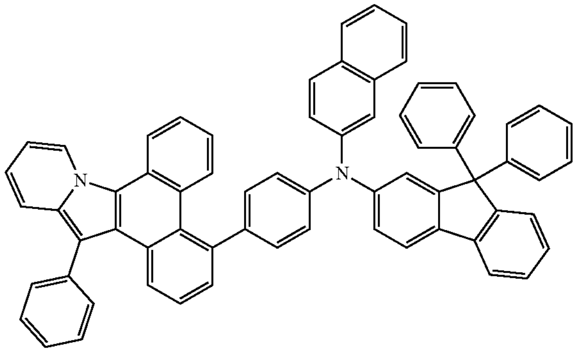
F36
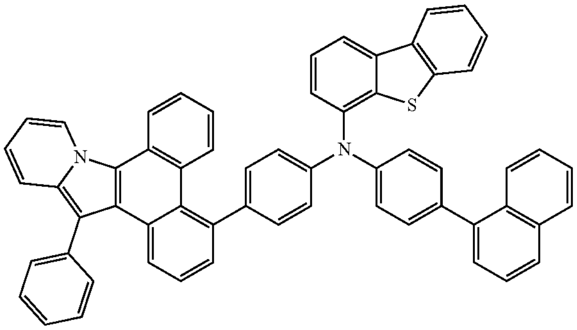
F37
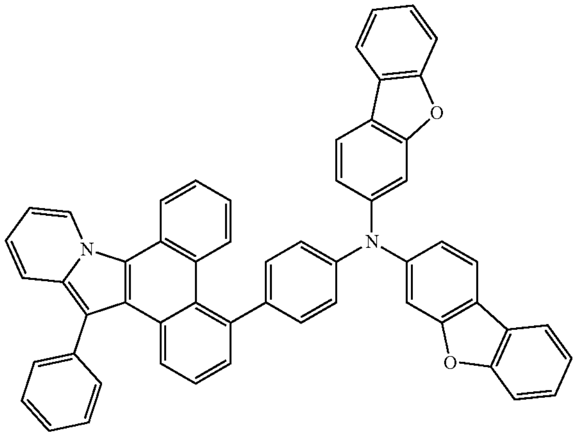
F38
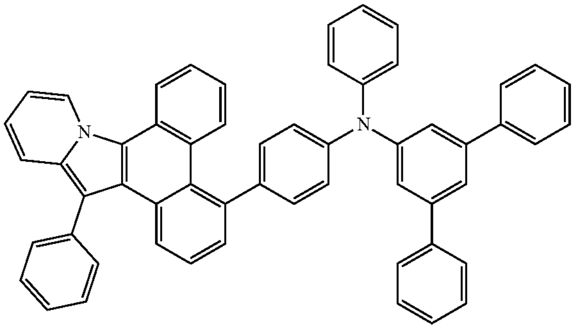
F39
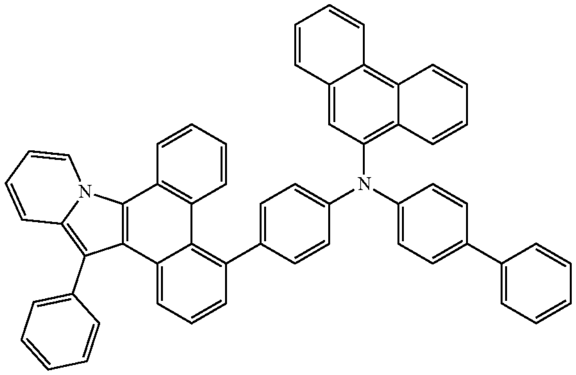

-continued
F40
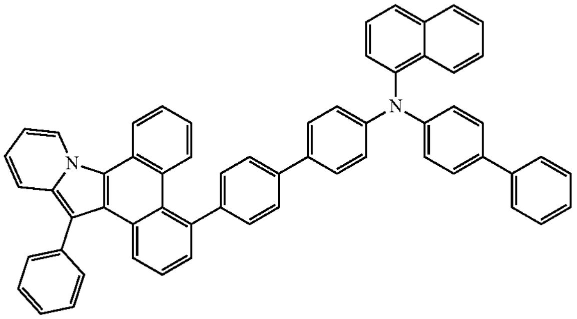
F41
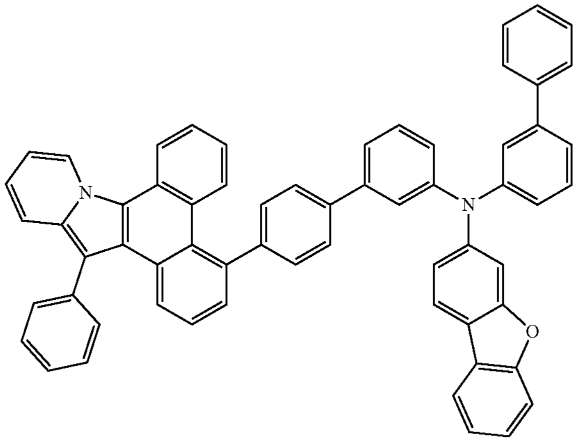
F42
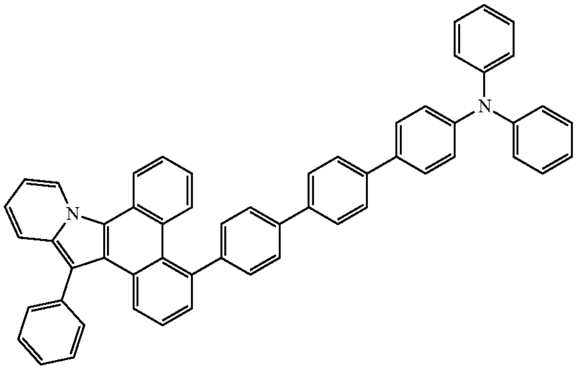
F43
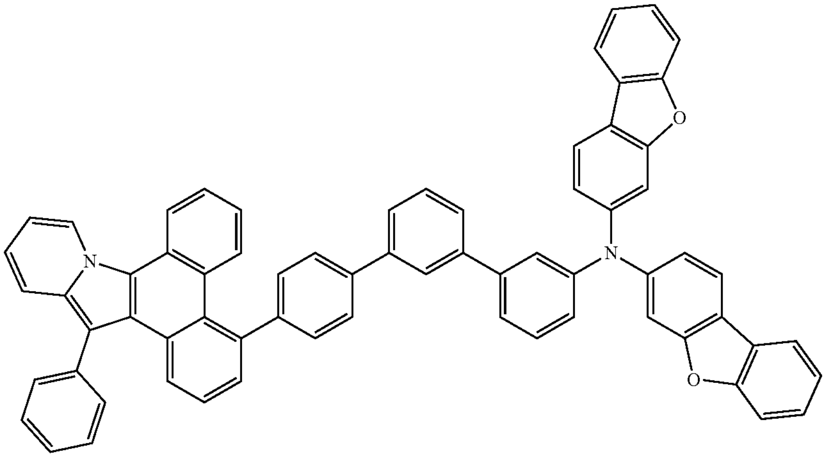

-continued
F44
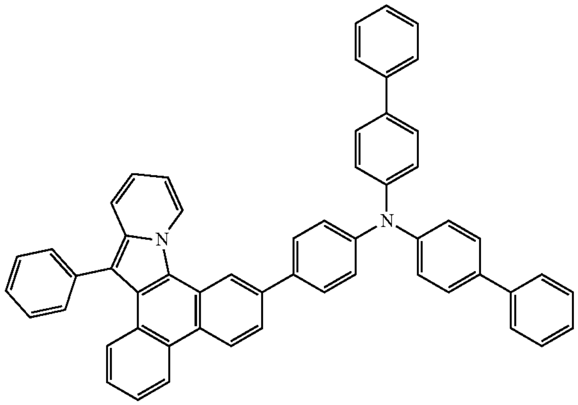
F45
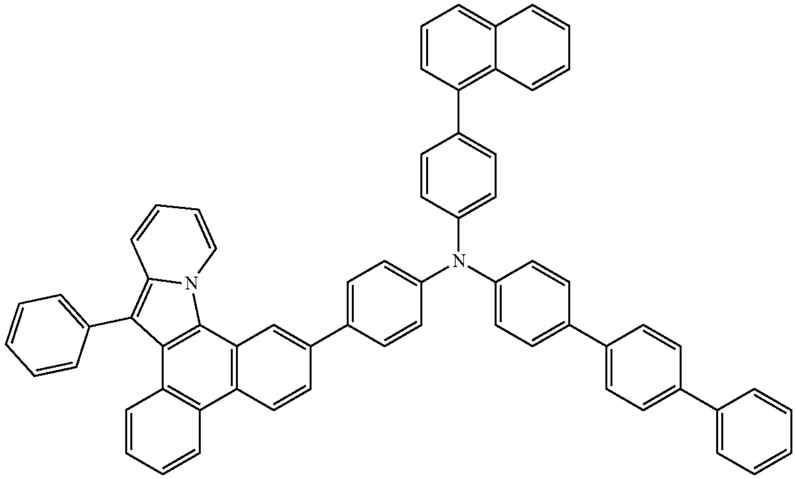
F46
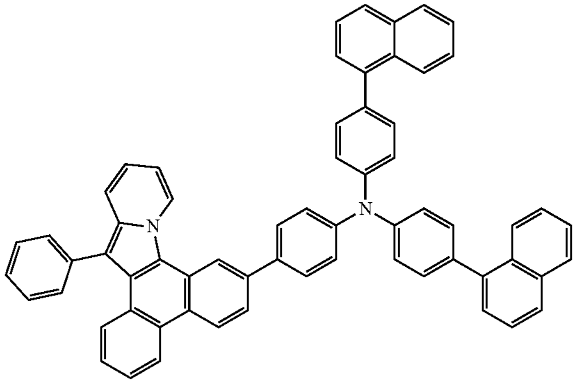

-continued
F47
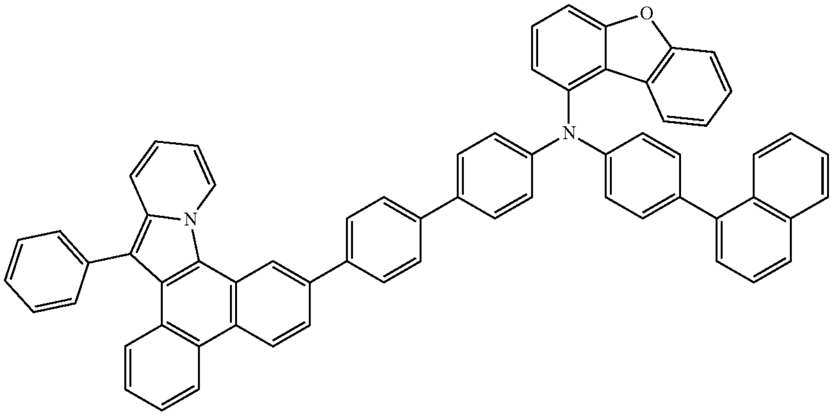
F48
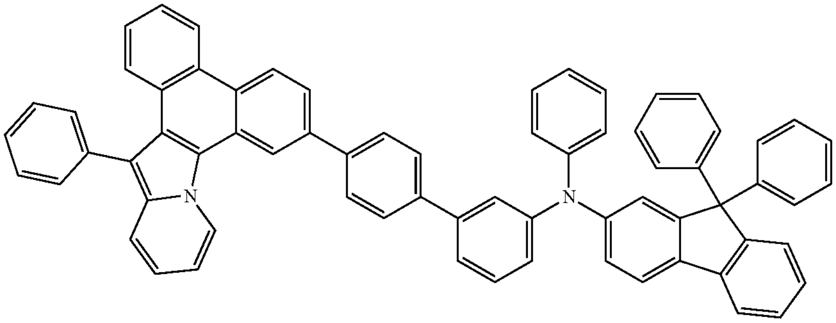
F49
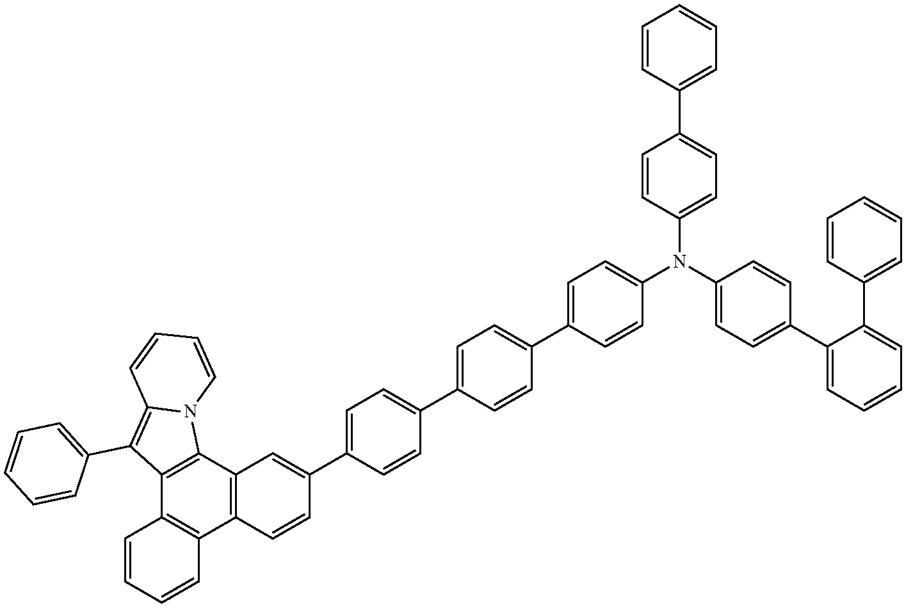

-continued
F50
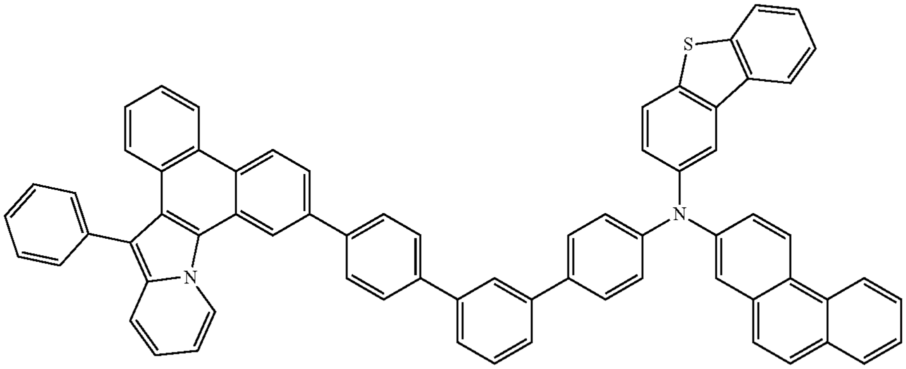
F51
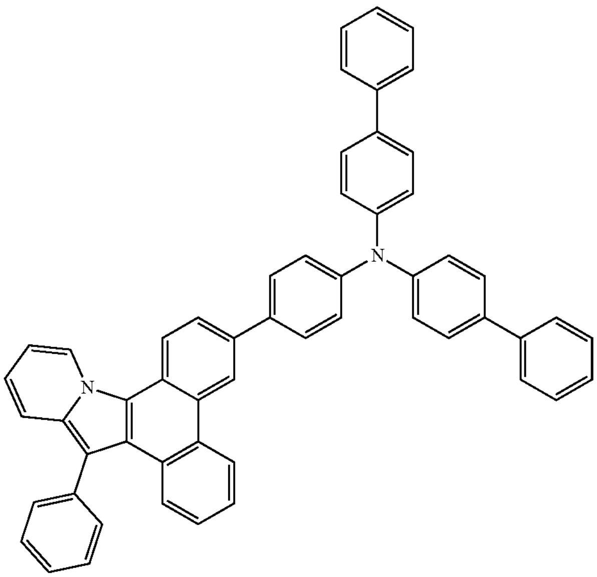
F52
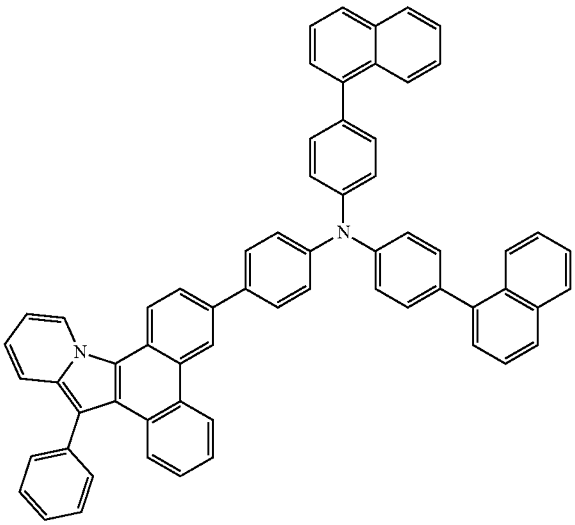
F53
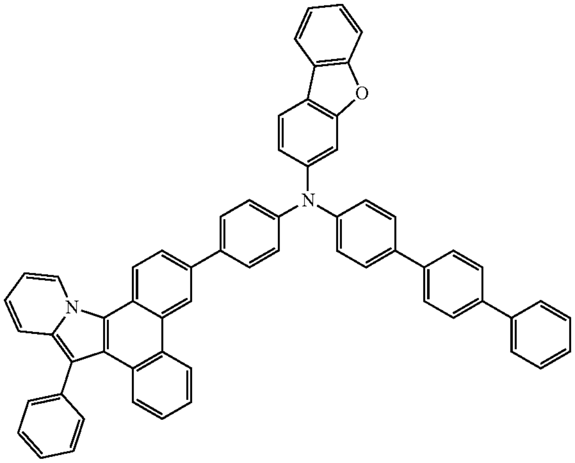
F54
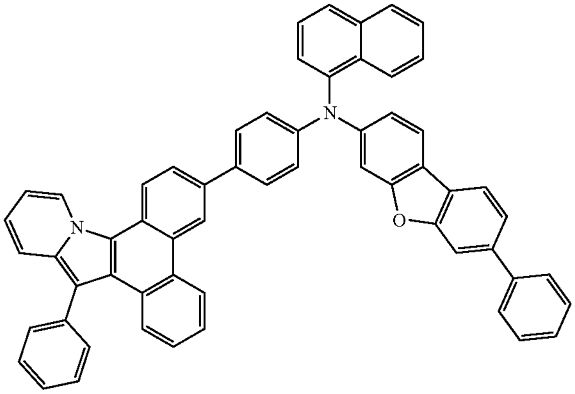

-continued
F55
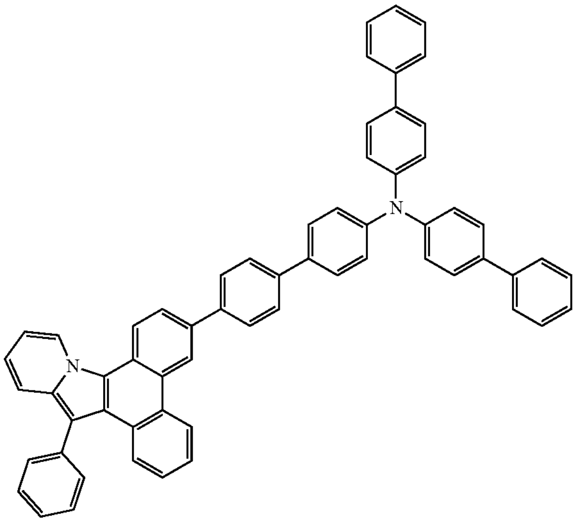
F56
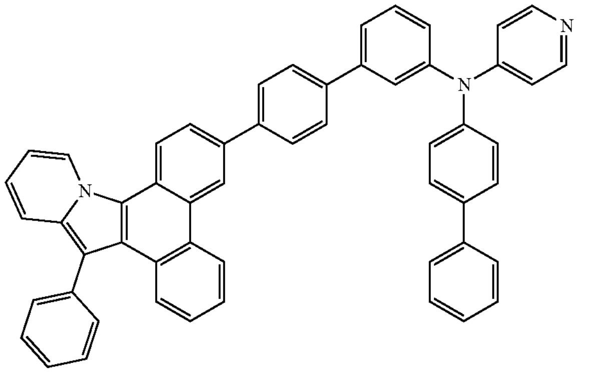
F57
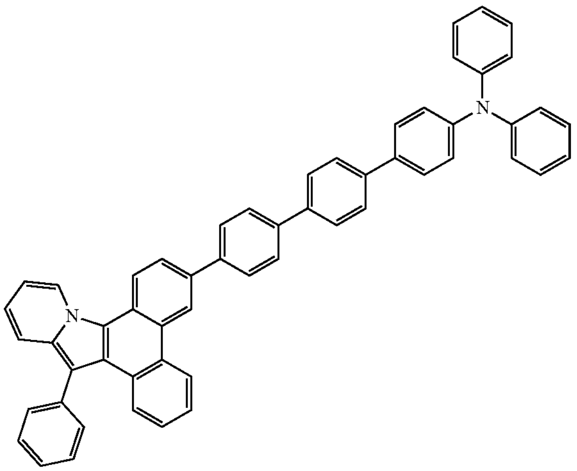
F58
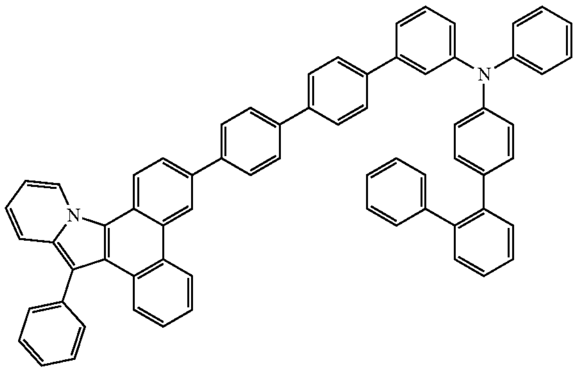
F59
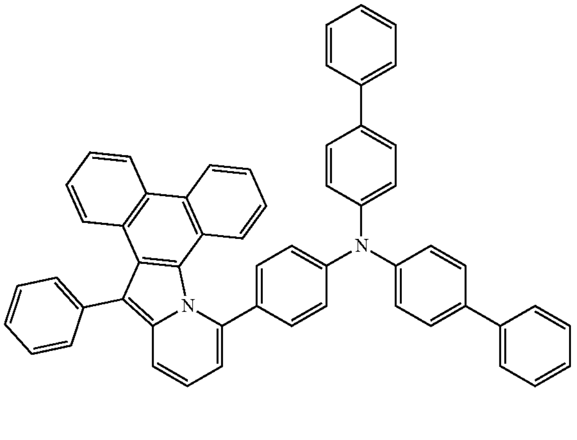
F60
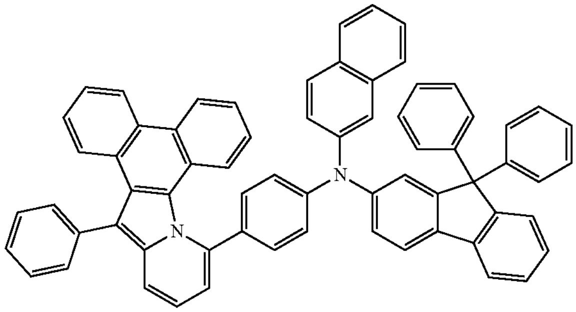

-continued
F61
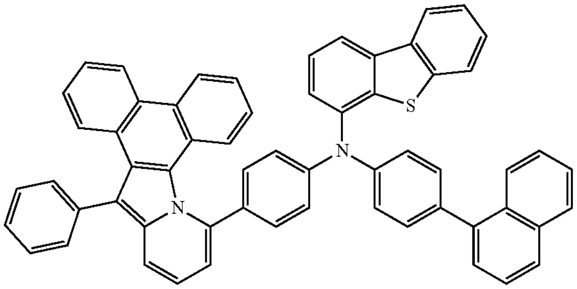
F62
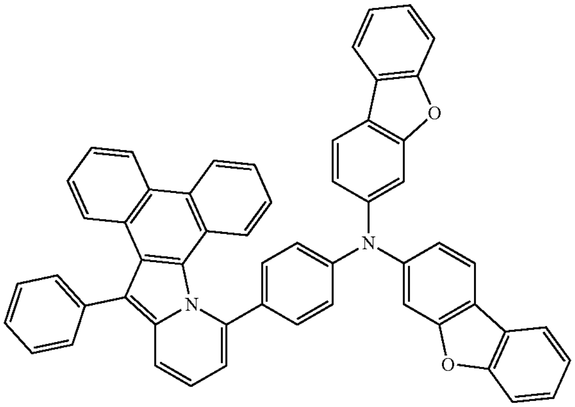
F63
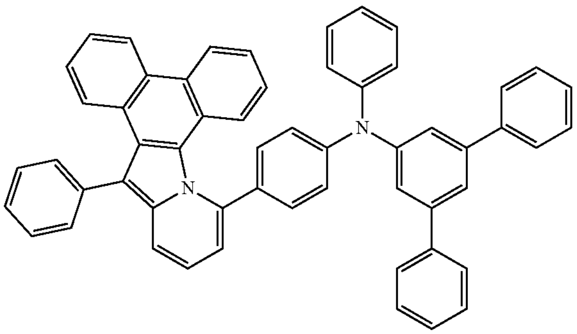
F64
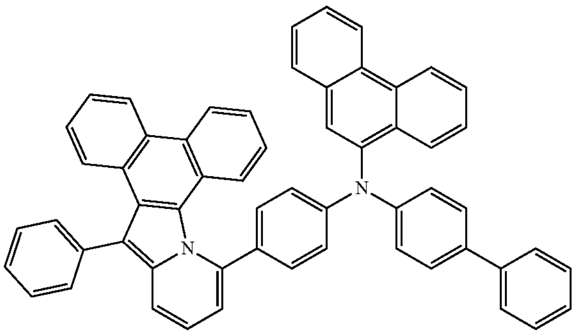
F65
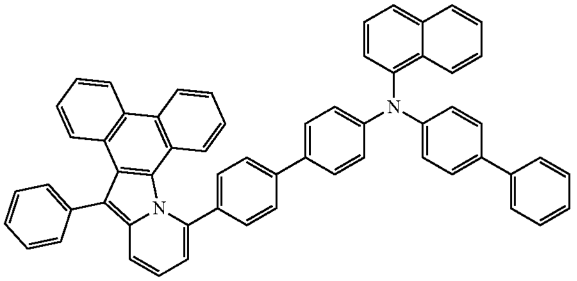
F66
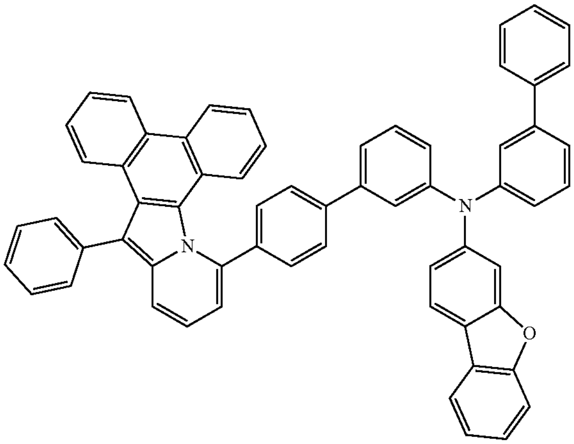
F67
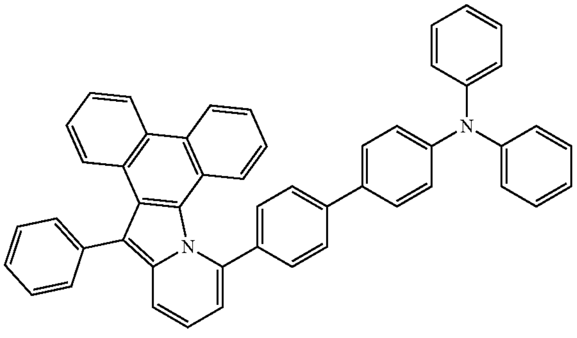

-continued
F68
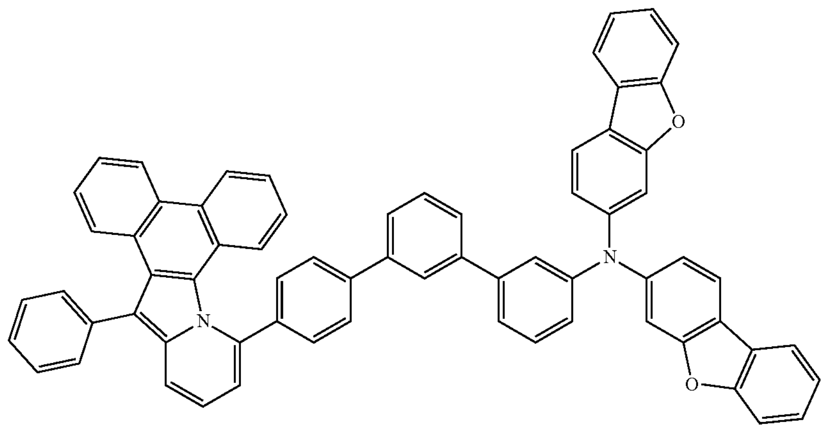
F69
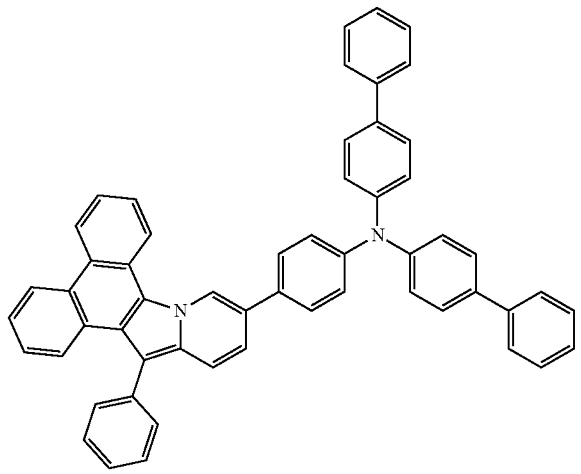
F70
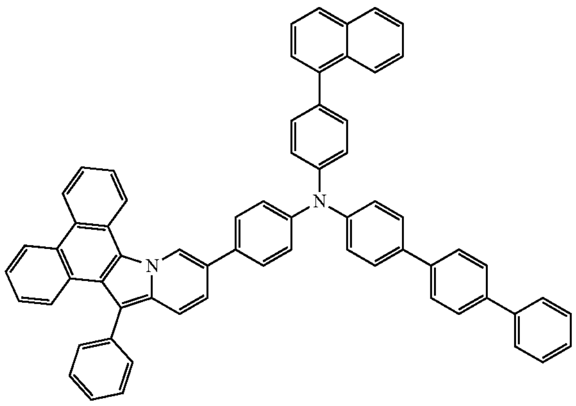
F71
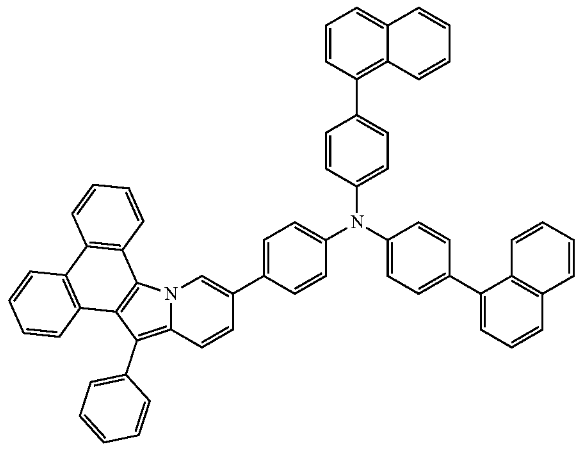
F72
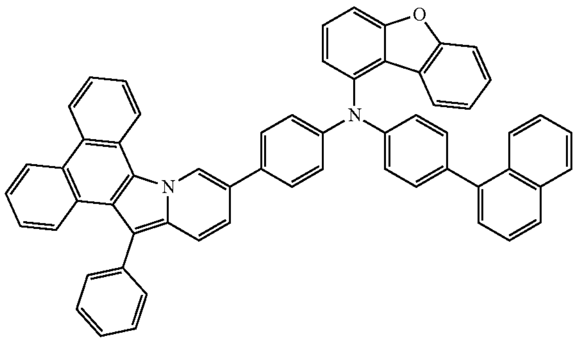

-continued
F73
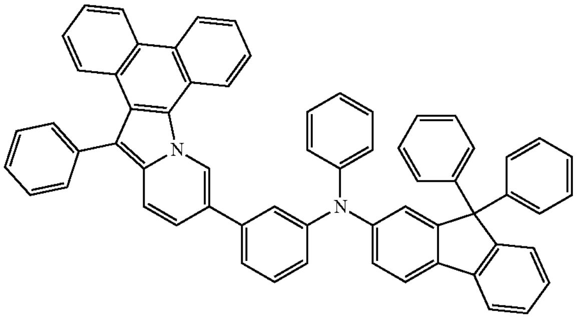
F74
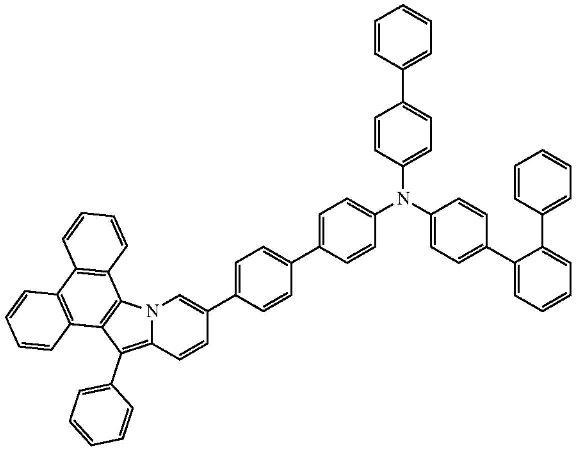
F75
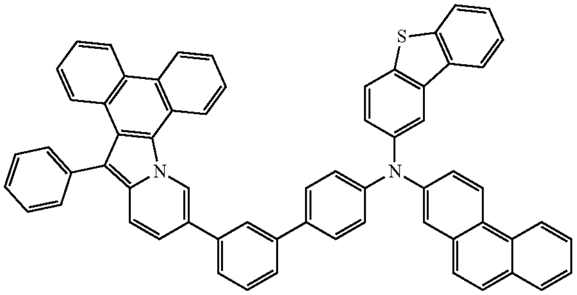
F76
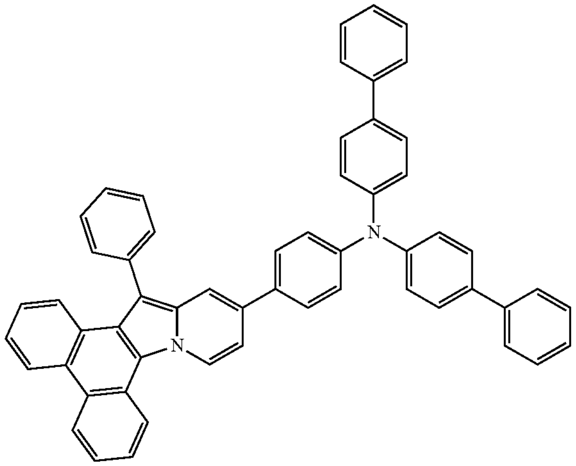
F77
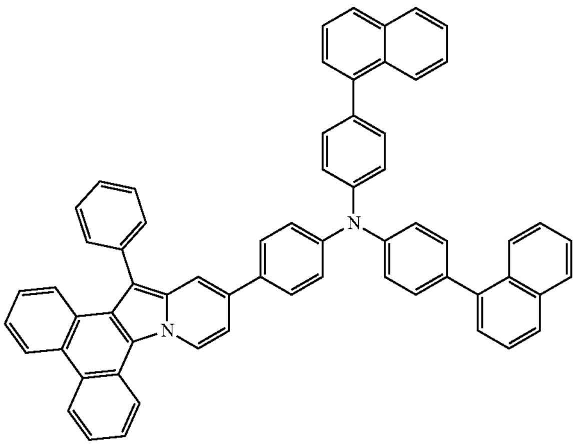
F78
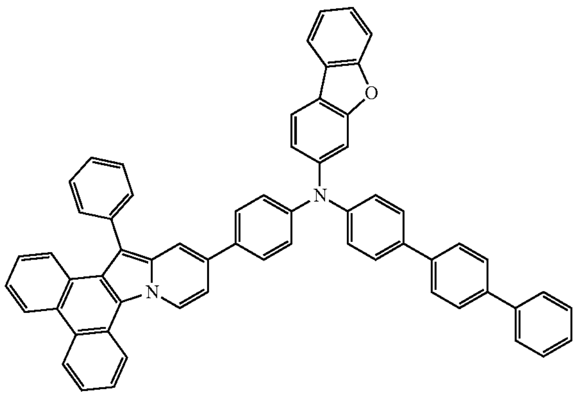

-continued
F79
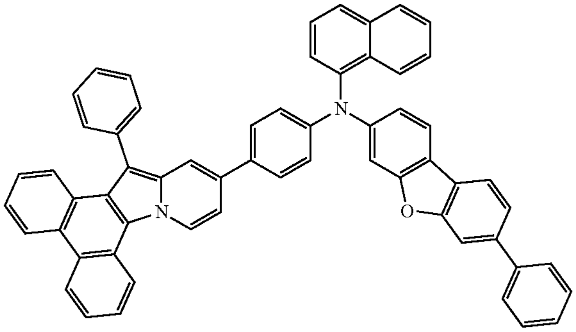
F80
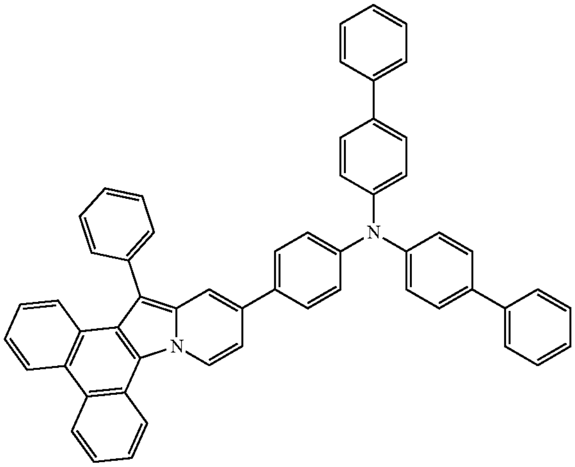
F81
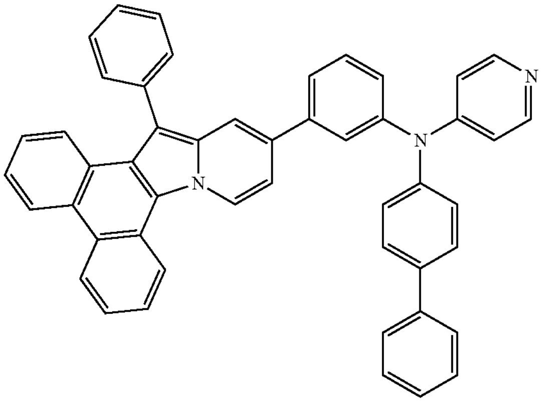
F82
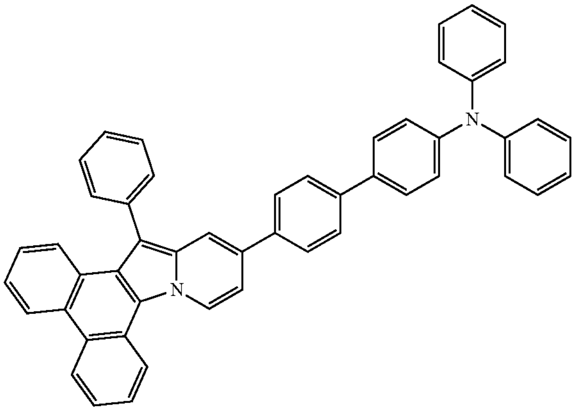
F83
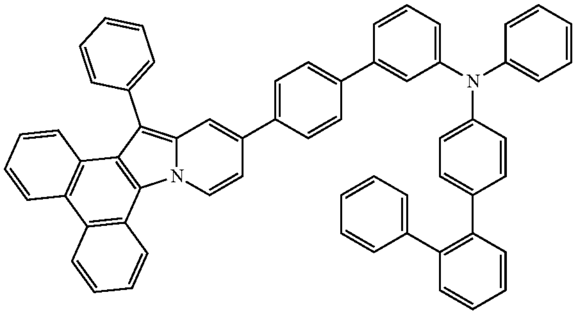
F84
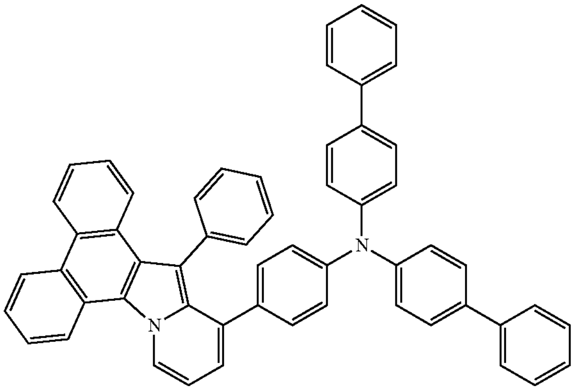

-continued
F85
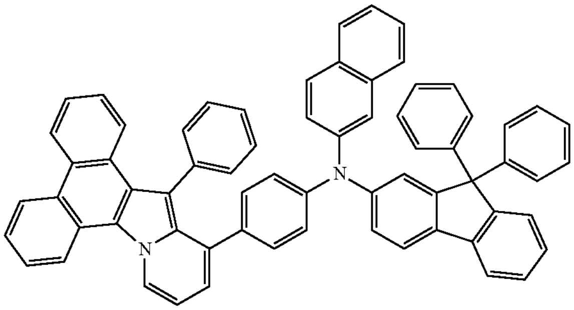
F86
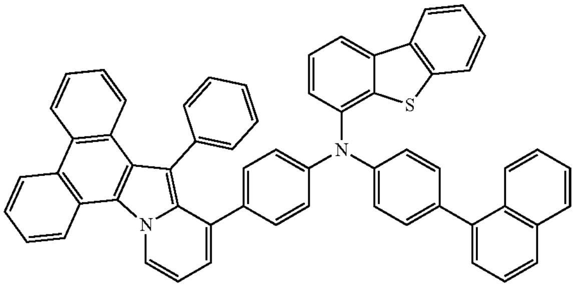
F87
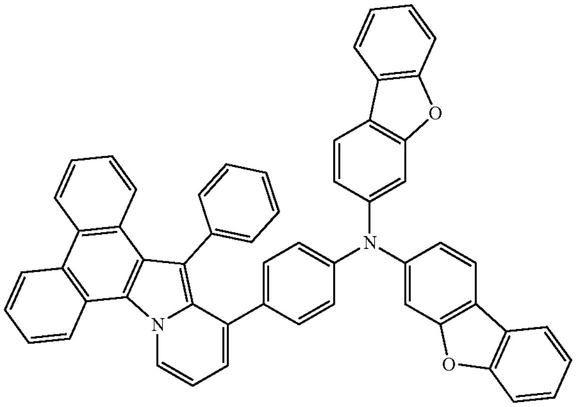
F88
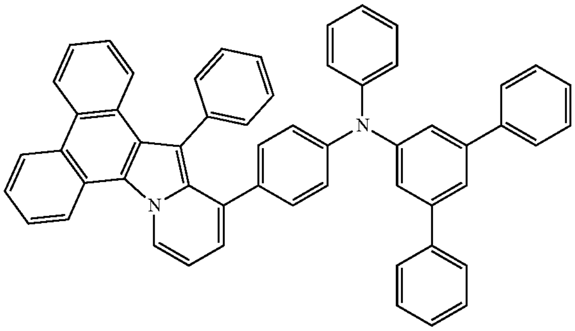
F89
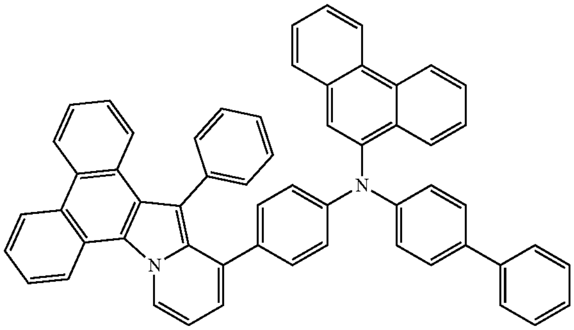
F90
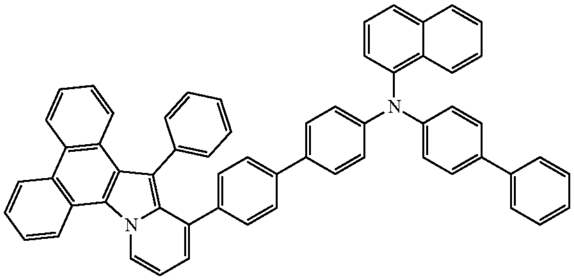
F91
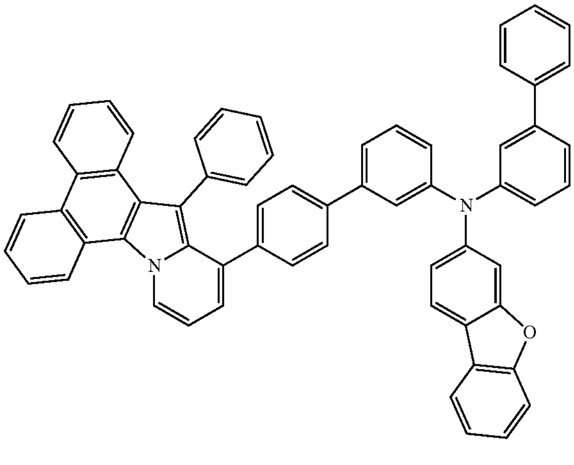
F92
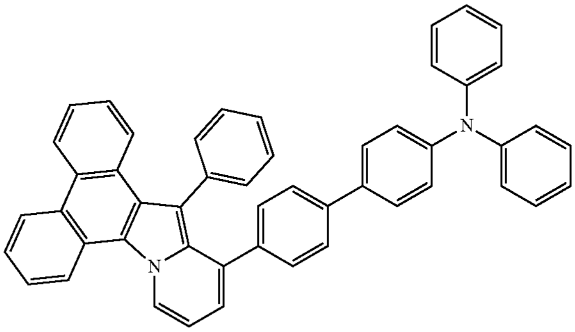

-continued
F93
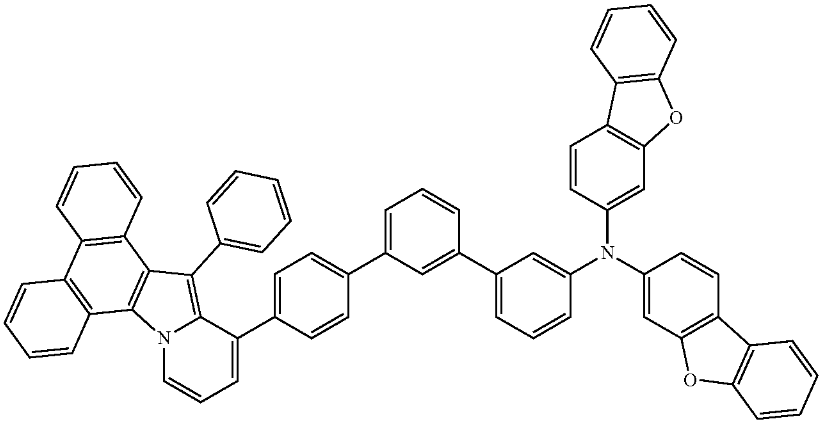
F94
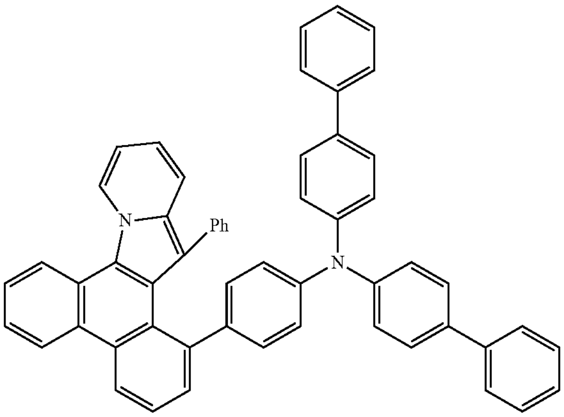
F95
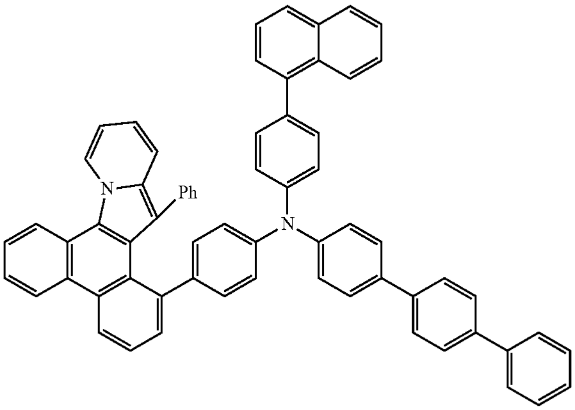
F96
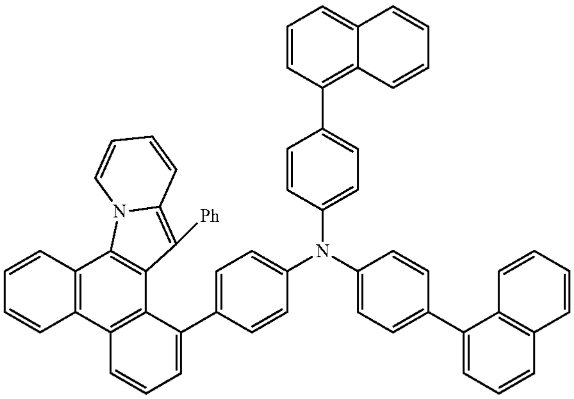
F97
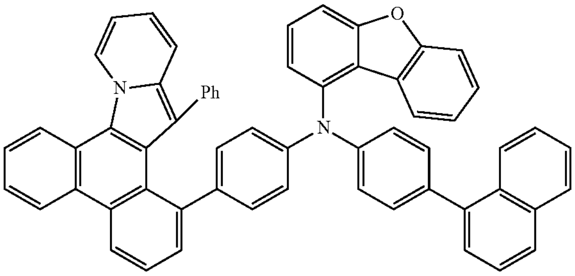

-continued

F98

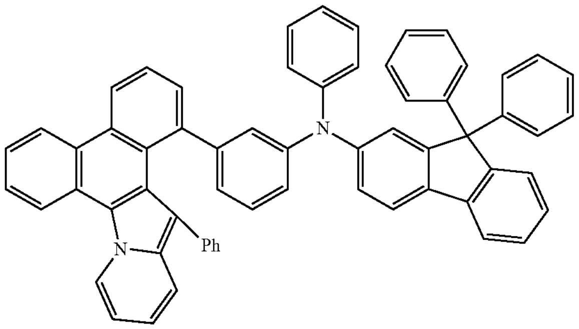

F99

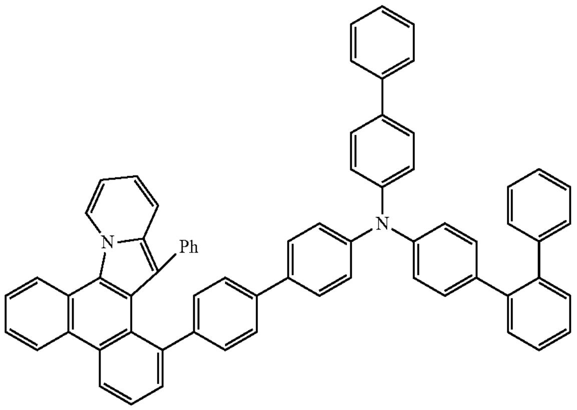

F100

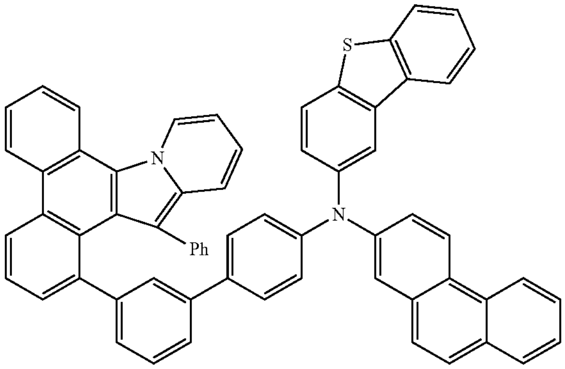

14. An amine compound represented by Formula 1:

Formula 1

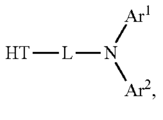

wherein, in Formula 1, $Ar_1$ and $Ar_2$ are each independently a substituted or unsubstituted aryl group having 6 to 40 ring-forming carbon atoms, or a substituted or unsubstituted heteroaryl group having 2 to 40 ring-forming carbon atoms, L is a direct linkage, a substituted or unsubstituted arylene group having 6 to 30 ring-forming carbon atoms, or a substituted or unsubstituted heteroarylene group having 2 to 30 ring-forming carbon atoms, and HT is represented by Formula 2:

Formula 2

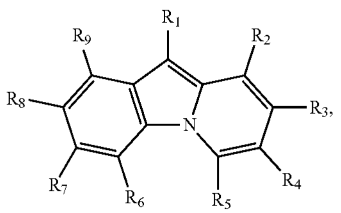

wherein, in Formula 2, $R_1$ to $R_9$ are each independently a hydrogen atom, a deuterium atom, a halogen atom, a cyano group, a nitro group, an amino group, a substituted or unsubstituted aryl group having 6 to 40 ring-forming carbon atoms, a substituted or unsubstituted heteroaryl group having 2 to 40 ring-forming carbon atoms, or a substituted or unsubstituted alkyl group of 1 to 20 carbon atoms, at least one pair selected from $R_2$ and $R_3$, $R_3$ and $R_4$, $R_4$ and $R_5$, $R_6$ and $R_7$, $R_7$ and $R_8$, and $R_8$ and $R_9$ is combined with each other to form a hexagonal hydrocarbon ring, and when at least one pair selected from $R_2$ and $R_3$, $R_3$ and $R_4$, and $R_4$ and $R_5$ forms a hexagonal hydrocarbon ring, $R_8$ is a hydrogen atom, and wherein the $R_1$ and $R_8$ positions as denoted in Formula 2 are not combined with the L in Formula 1.

15. The amine compound of claim 14, wherein one or two pairs selected from $R_2$ and $R_3$, $R_3$ and $R_4$, and $R_4$ and $R_5$ each form the hexagonal hydrocarbon ring.

16. The amine compound of claim 14, wherein one or two pairs selected from $R_6$ and $R_7$, $R_7$ and $R_8$, and $R_5$ and $R_9$ each form the hexagonal hydrocarbon ring.

17. The amine compound of claim 14, wherein the hexagonal hydrocarbon ring is represented by Formula 3:

Formula 3

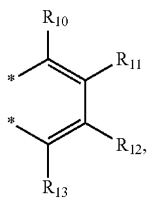

wherein, in Formula 3, $R_{10}$ to $R_{13}$ are each independently a hydrogen atom, a deuterium atom, a halogen atom, a cyano group, a nitro group, an amino group, a substituted on unsubstituted aryl group having 6 to 40 ring forming carbon atoms, a substituted or unsubstituted heteroaryl group having 2 to 40 ring-forming carbon atoms, or a substituted or unsubstituted alkyl group of 1 to 20 carbon atoms, and

* is a combining part with Formula 2.

18. The amine compound of claim 17, wherein one of $R_2$ to $R_9$ that is not a combining part with the hexagonal hydrocarbon ring or any one of $R_{10}$ to $R_{13}$ is combined with L in Formula 1.

19. The amine compound of claim 17, wherein HT is represented by one selected from Formula 2-1a to Formula 2-1d:

Formula 2-1a

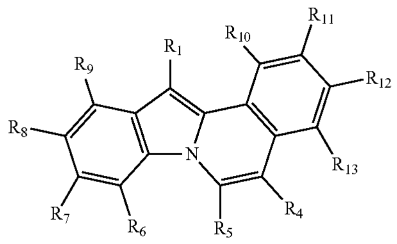

-continued

Formula 2-1b

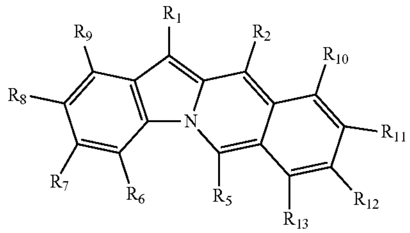

Formula 2-1c

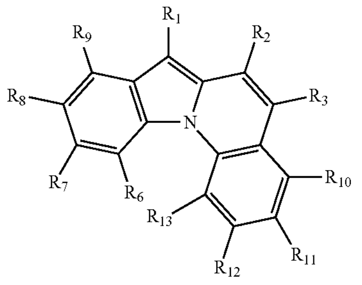

Formula 2-1d

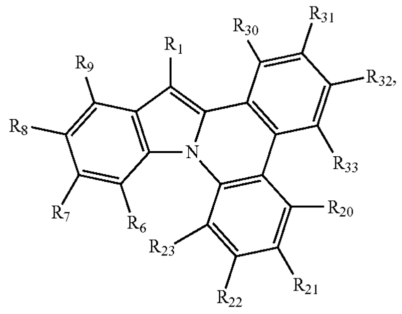

wherein, in Formula 2-1d, $R_{20}$ to $R_{23}$ and $R_{30}$ to $R_{33}$ are each independently a hydrogen atom, a deuterium atom, a halogen atom, a cyano group, a nitro group, an amino group, a substituted or unsubstituted aryl group having 6 to 40 ring-forming carbon atoms, a substituted or unsubstituted heteroaryl group having 2 to 40 ring-forming carbon atoms, or a substituted or unsubstituted alkyl group of 1 to 20 carbon atoms, wherein, in Formula 2-1a to Formula 2-1d, $R_1$ to $R_9$ are the same as defined in Formula 2, and $R_{10}$ to $R_{13}$ are the same as defined in Formula 3.

20. The amine compound of claim 17, wherein HT is represented by one selected from Formula 2-2a to Formula 2-2d:

Formula 2-2a

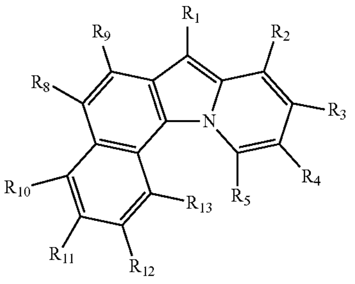

-continued

Formula 2-2b

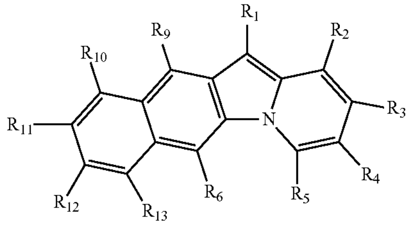

Formula 2-2c

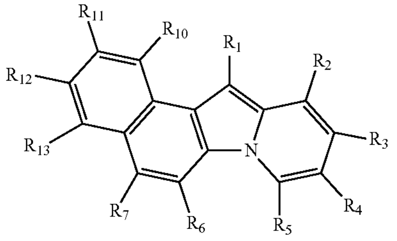

Formula 2-2d

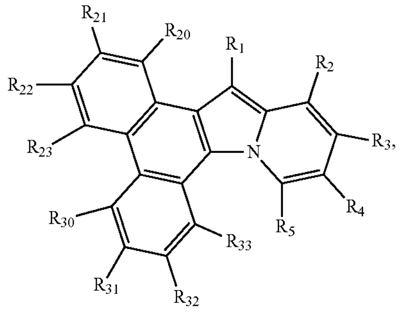

wherein, in Formula 2-2d, $R_{20}$ to $R_{23}$ and $R_{30}$ to $R_{33}$ are each independently a hydrogen atom, a deuterium atom, a halogen atom, a cyano group, a nitro group, an amino group, a substituted or unsubstituted aryl group having 6 to 40 ring-forming carbon atoms, a substituted or unsubstituted heteroaryl group having 2 to 40 ring-forming carbon atoms, or a substituted or unsubstituted alkyl group of 1 to 20 carbon atoms, wherein, in Formula 2-2a to Formula 2-2d, $R_1$ to $R_9$ are the same as defined in Formula 2, and $R_{10}$ to $R_{13}$ are the same as defined in Formula 3.

21. The amine compound of claim 14, wherein $R_1$ is an unsubstituted phenyl group, an unsubstituted naphthyl group, an unsubstituted biphenyl group, an unsubstituted dibenzofuranyl group, or an unsubstituted dibenzothiophene group.

22. The amine compound of claim 14, wherein L is a direct linkage, a substituted or unsubstituted phenylene group, a substituted or unsubstituted divalent biphenyl group, a substituted or unsubstituted divalent terphenyl group, a substituted or unsubstituted divalent phenanthrene group, a substituted or unsubstituted naphthylene group, or a substituted or unsubstituted divalent dibenzofuran group.

23. The amine compound of claim 14, wherein $Ar_1$ and $Ar_2$ are each independently a substituted or unsubstituted phenyl group, a substituted or unsubstituted biphenyl group, a substituted or unsubstituted terphenyl group, a substituted or unsubstituted phenanthrene group, a substituted or unsubstituted triphenylene group, a substituted or unsubstituted naphthyl group, a substituted or unsubstituted fluorenyl group, a substituted or unsubstituted adamantyl group, a substituted or unsubstituted dibenzofuran group, a substituted or unsubstituted dibenzothiophene group, or a substituted or unsubstituted pyridinyl group.

24. The amine compound of claim 14, wherein $Ar_1$ and $Ar_2$ are each independently:

an aryl group having 6 to 40 ring-forming carbon atoms, which is unsubstituted or substituted with at least one substituent selected from a halogen atom, a cyano group, an alkyl group of 1 to 20 carbon atoms, an alkoxy group of 1 to 10 carbon atoms, an aryloxy group of 1 to 20 carbon atoms, an aryl group of 6 to 30 carbon atoms, a triarylsilyl group of 18 to 50 carbon atoms, and an adamantyl group, or a heteroaryl group having 2 to 40 ring forming carbon atoms, which is unsubstituted or substituted with at least one substituent selected from a halogen atom, a cyano group, an alkyl group of 1 to 20 carbon atoms, an alkoxy group of 1 to 10 carbon atoms, an aryloxy group of 1 to 20 carbon atoms, an aryl group of 6 to 30 carbon atoms, a triarylsilyl group of 18 to 50 carbon atoms, and an adamantyl group.

25. An amine compound selected from Compound Group 1 and Compound Group 2:

Compound Group 1

A1

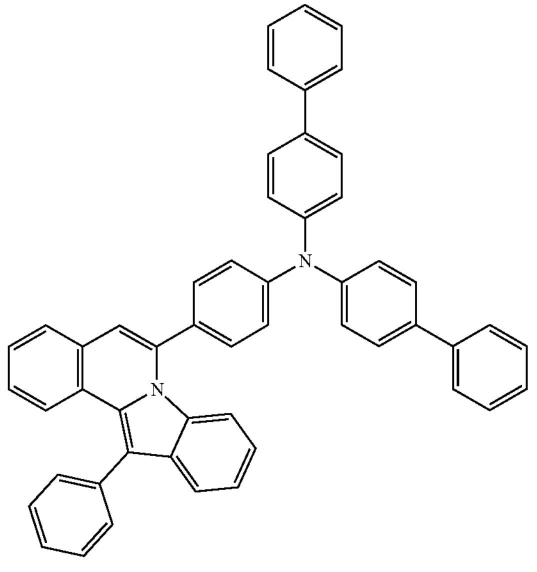

A2

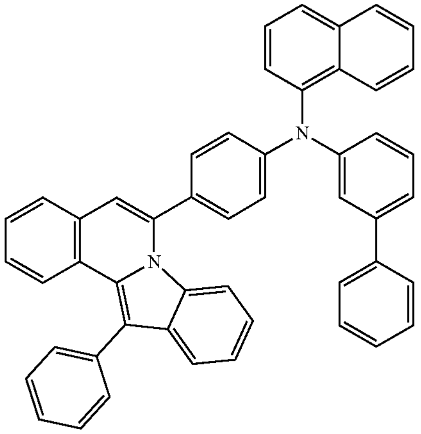

-continued
A3
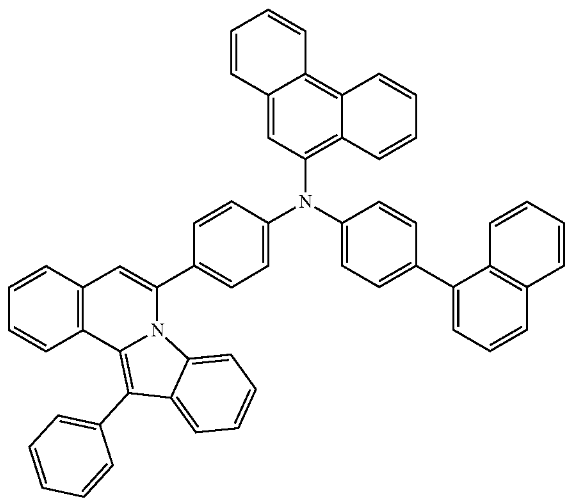
A4
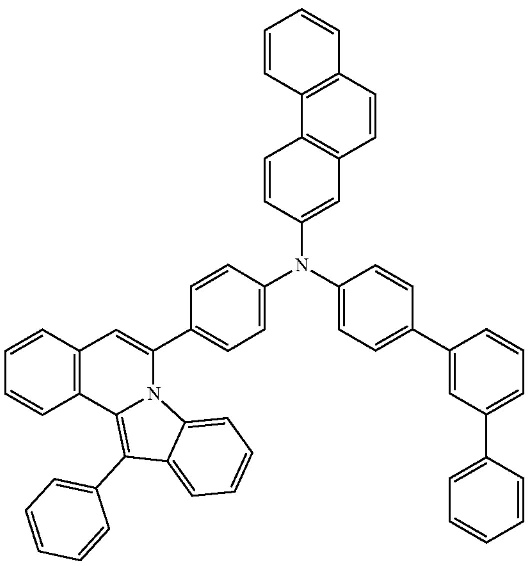
A5
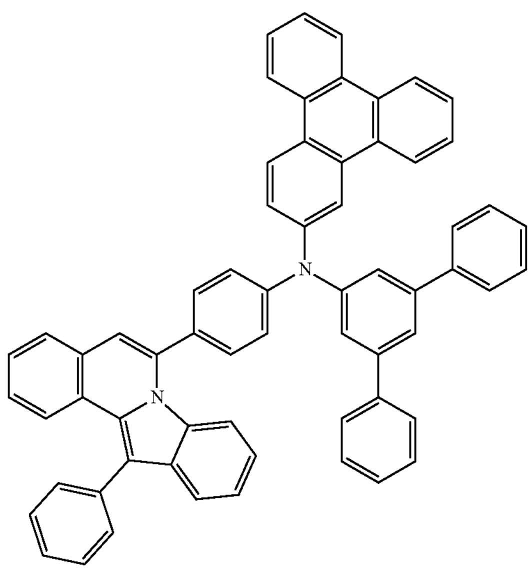
A6
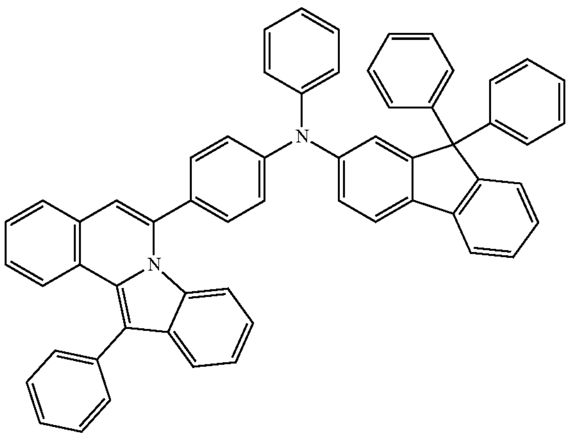

-continued
A7
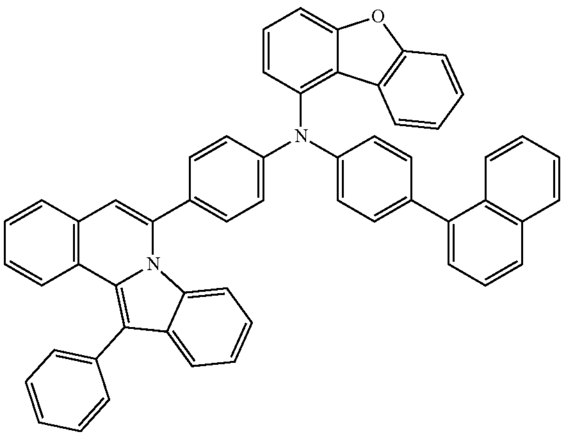
A8
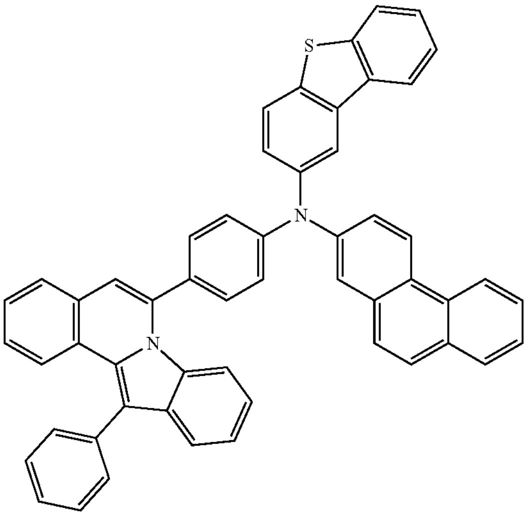
A9
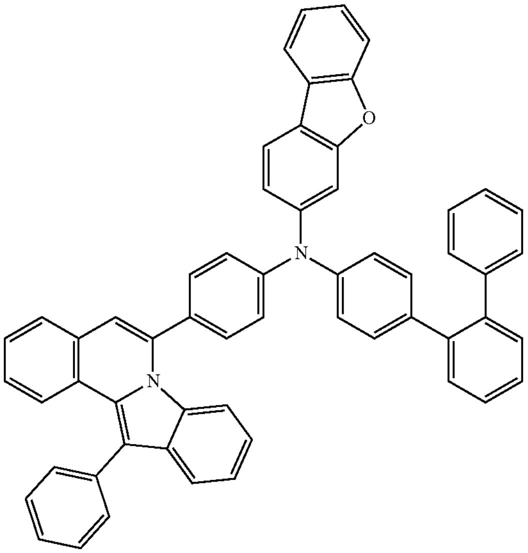
A10
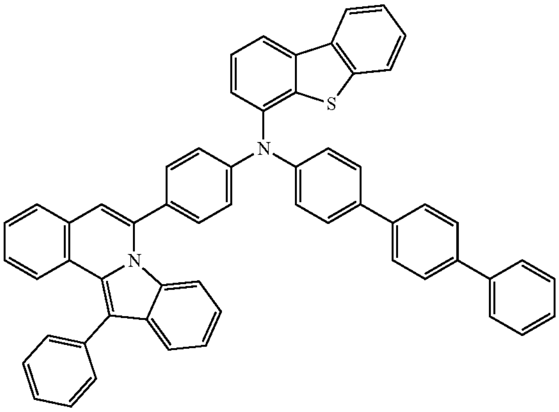
A11
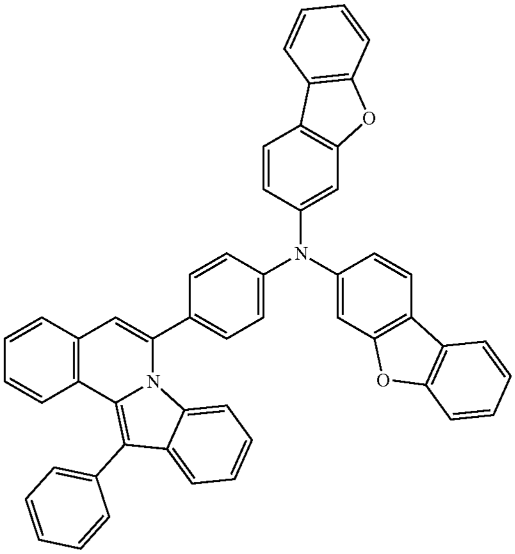
A12
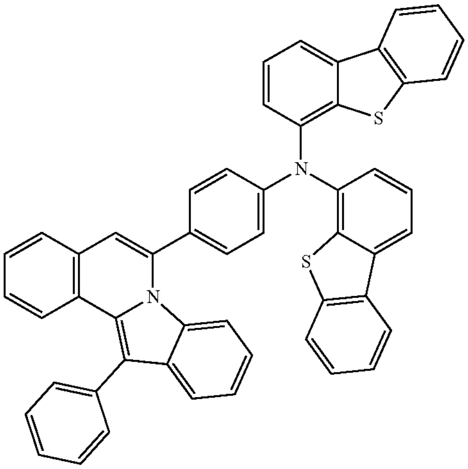

-continued
A13
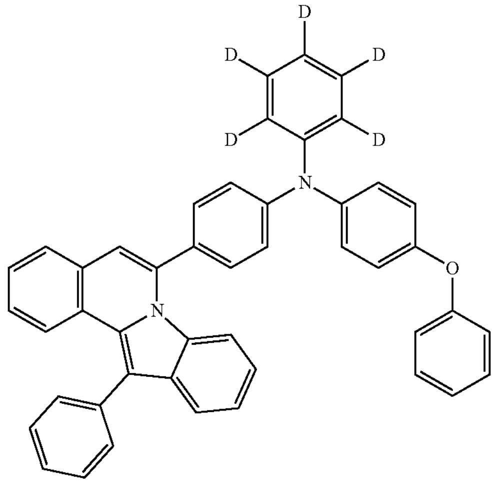
A14
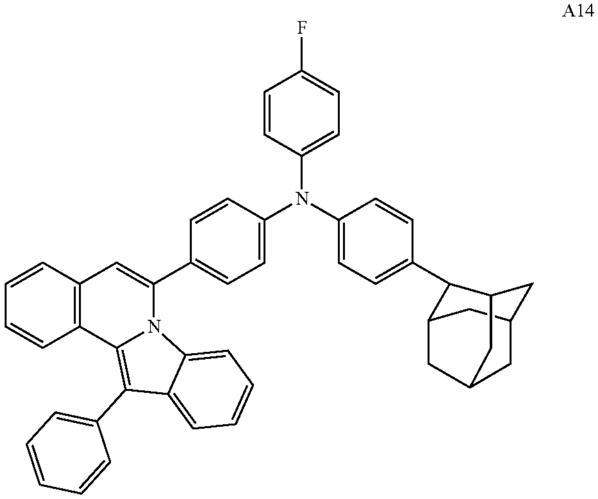
A15
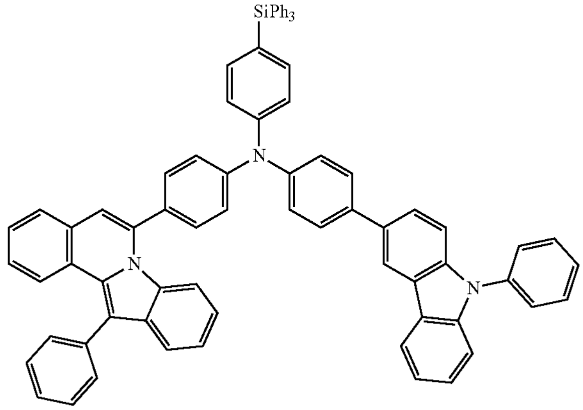
A16
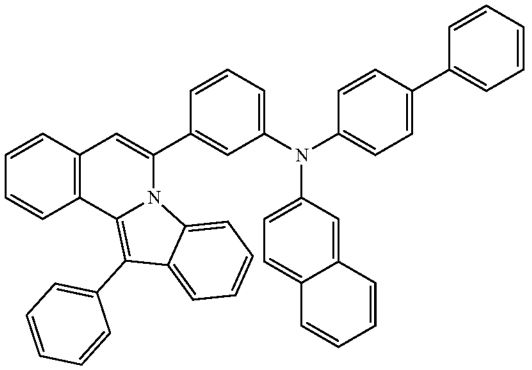
A17
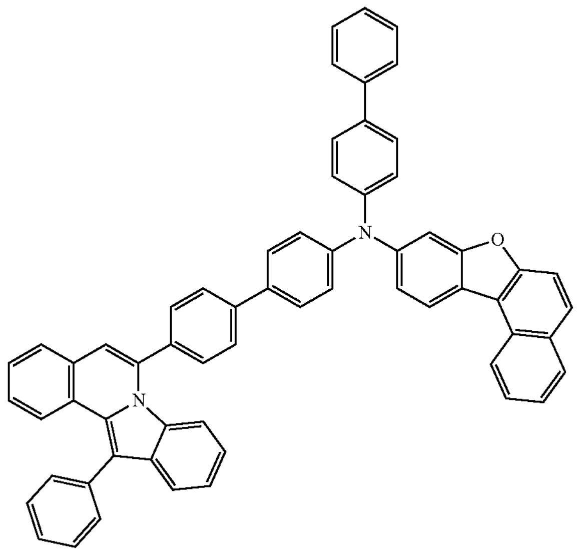
A18
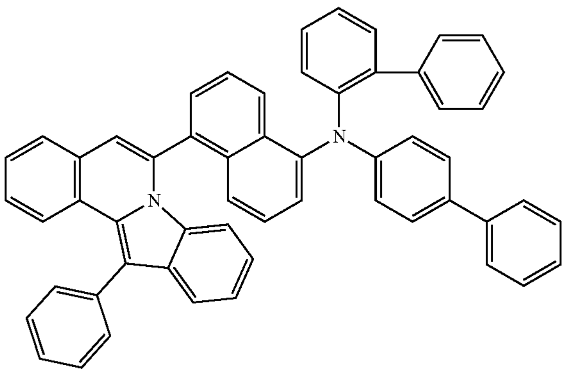

-continued
A19
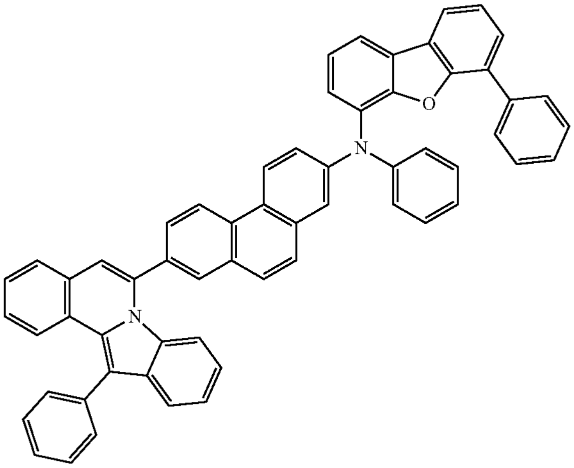
A20
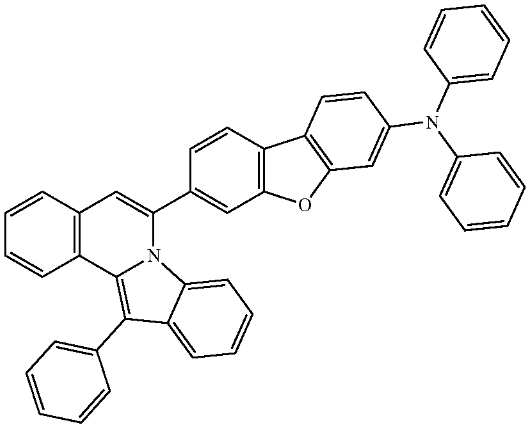
A21
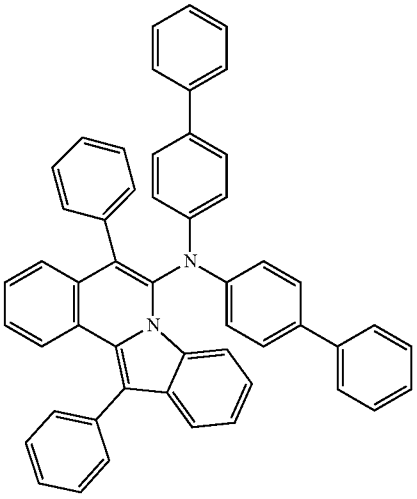
A22
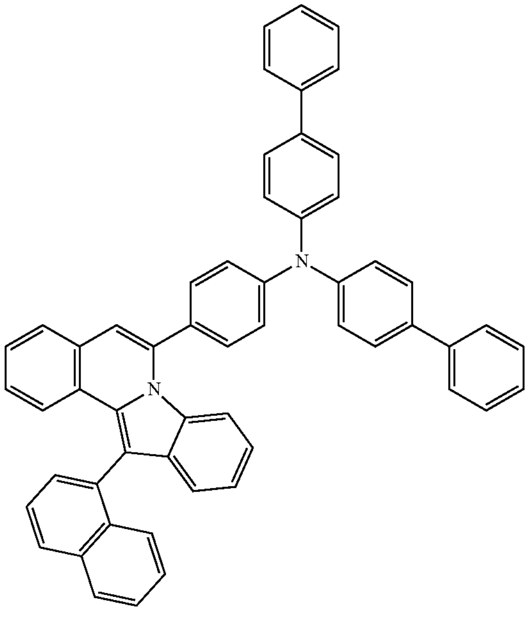

-continued
A23
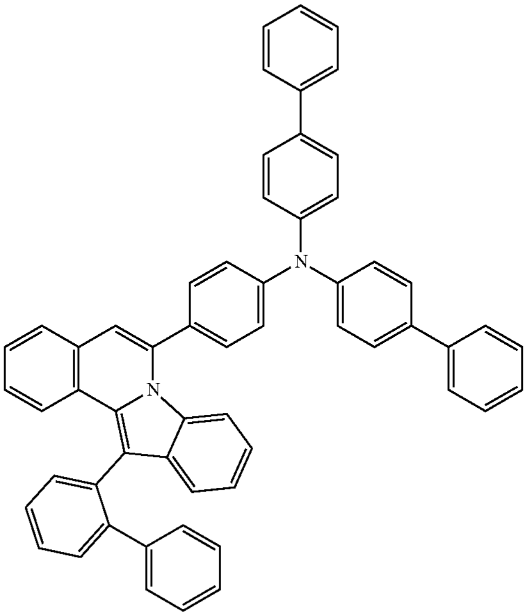
A24
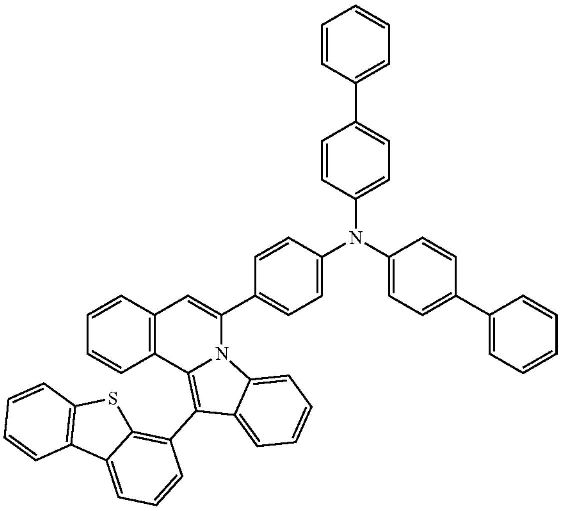
A25
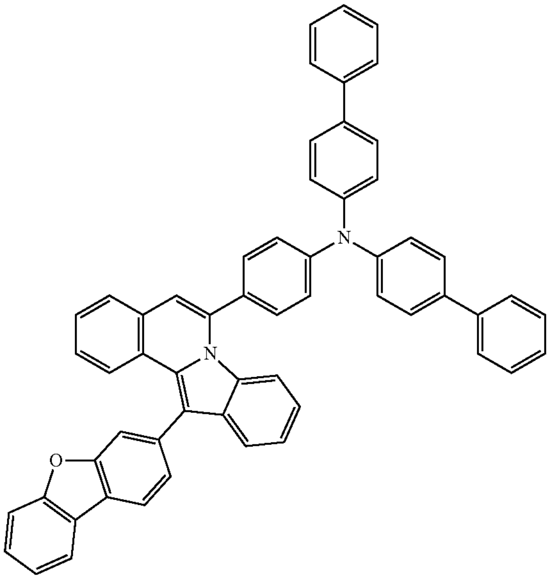
A26
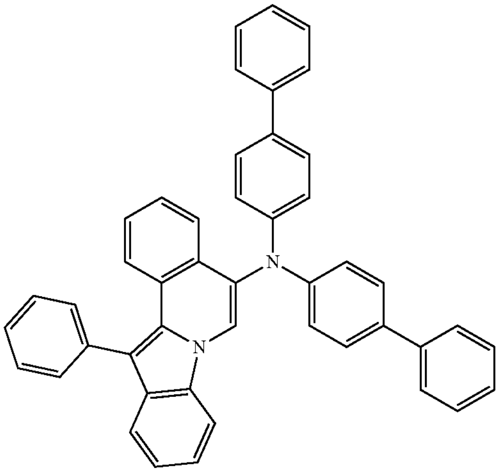

-continued
A27
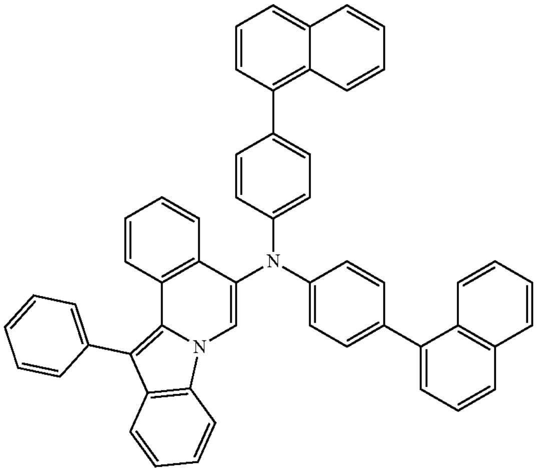
A28
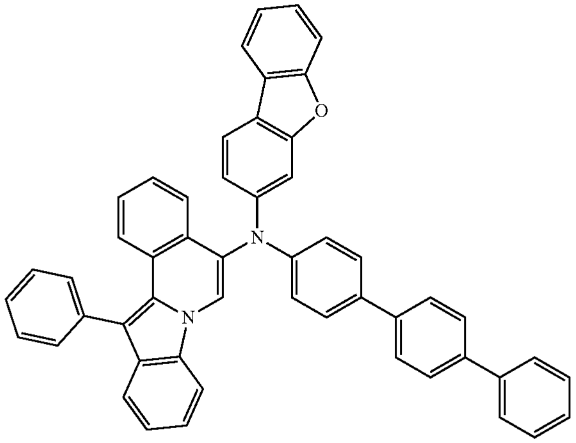
A29
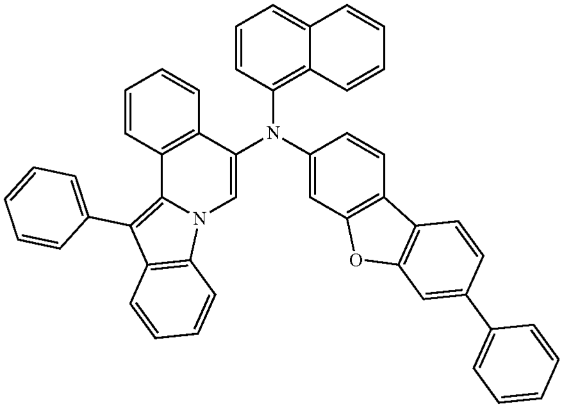
A30
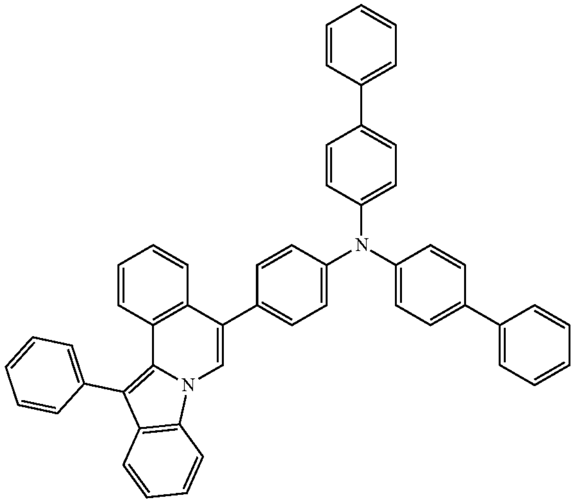
A31
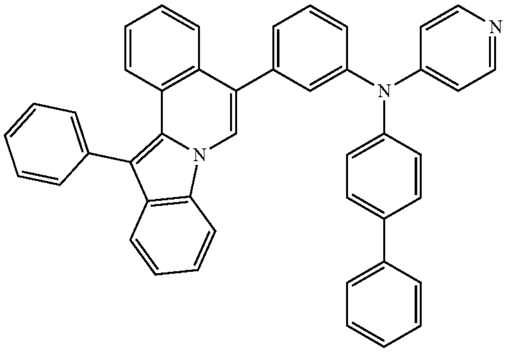
A32
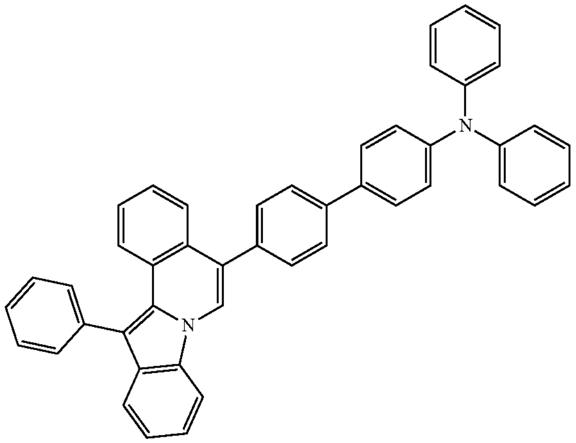

-continued
A33
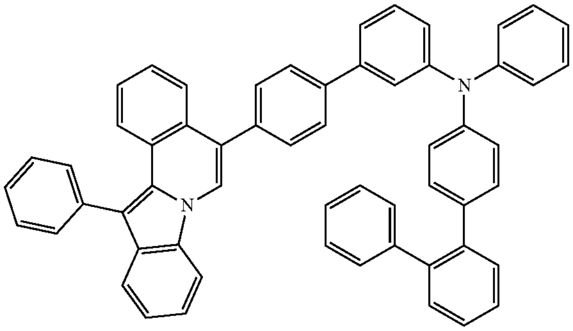
A34
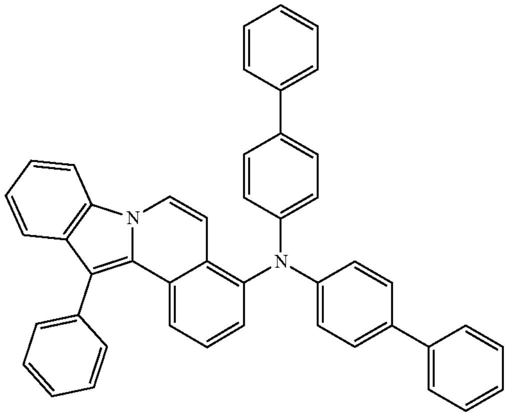
A35
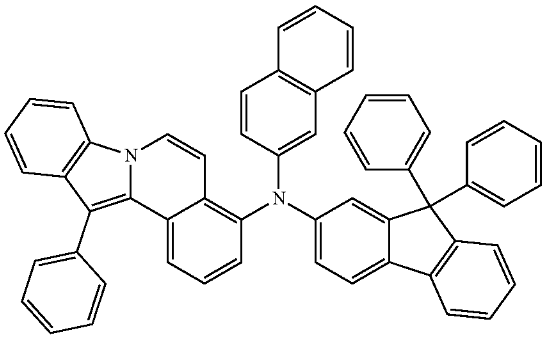
A36
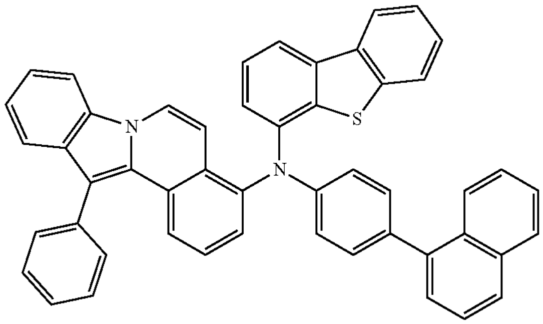
A37
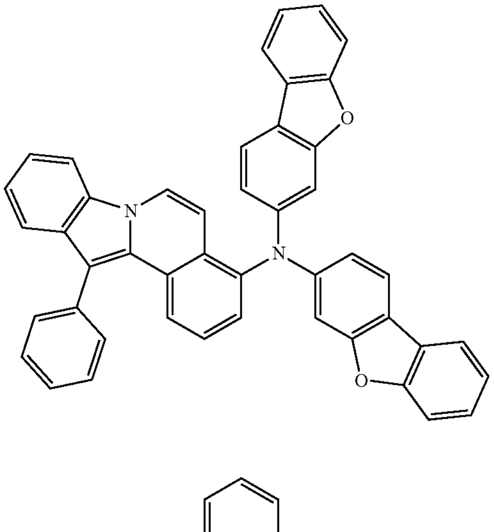
A38
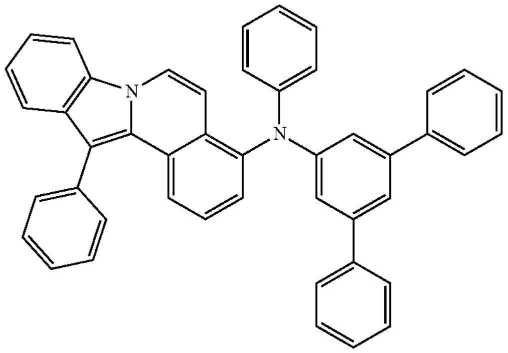
A39
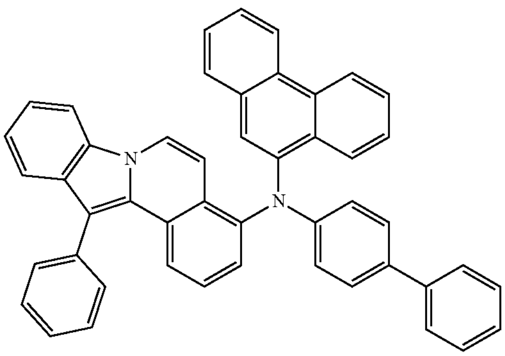
A40
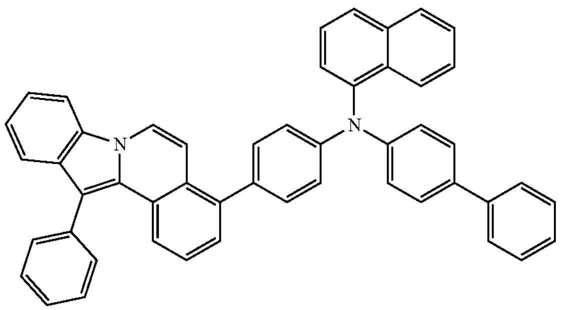

-continued
A41
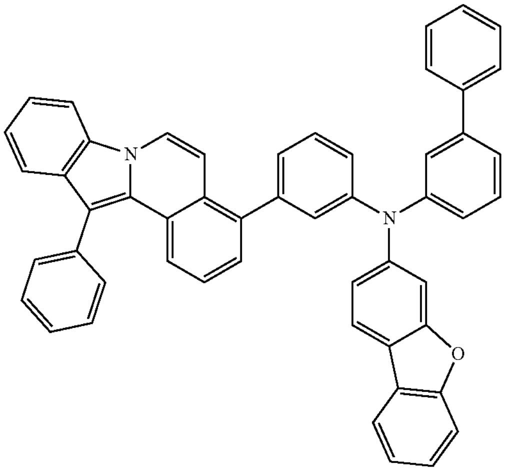
A42
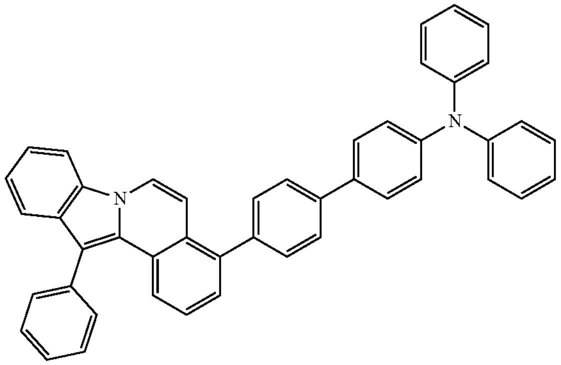
A43
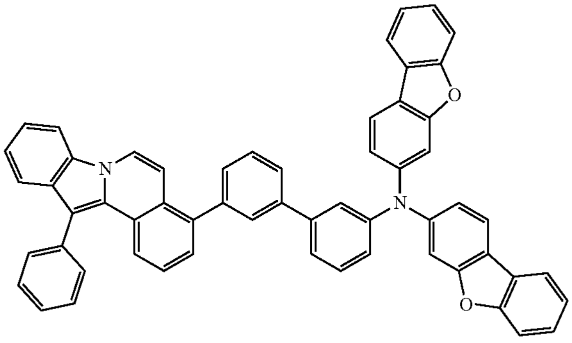
A44
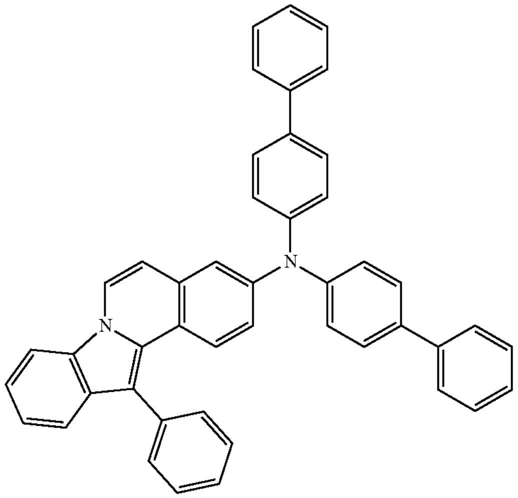
A45
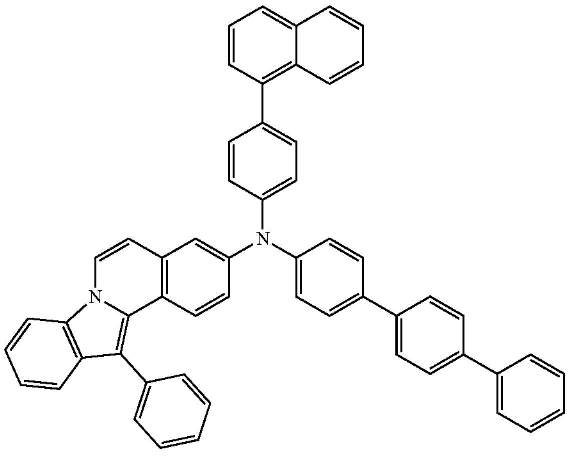
A46
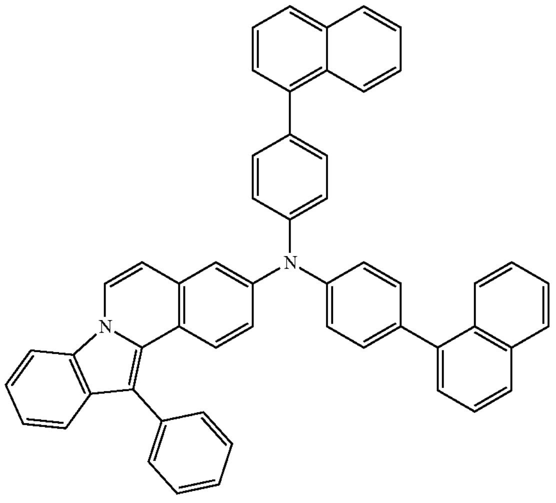

-continued
A47
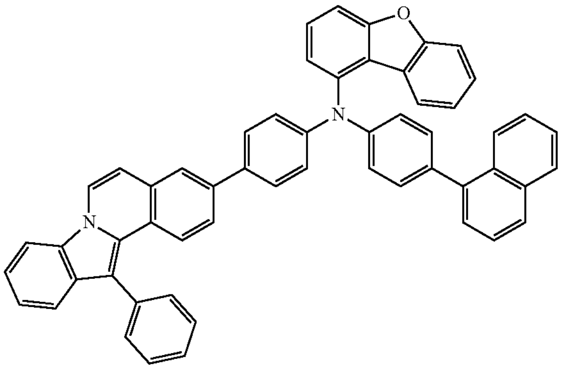
A48
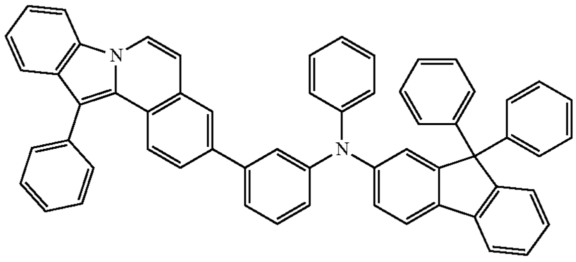
A49
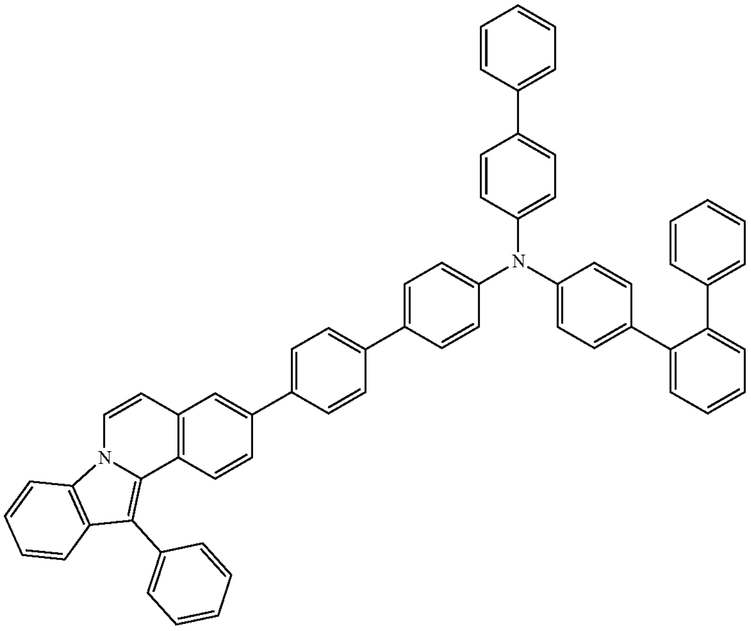
A50
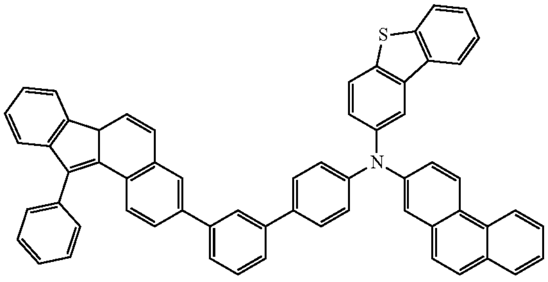
A51
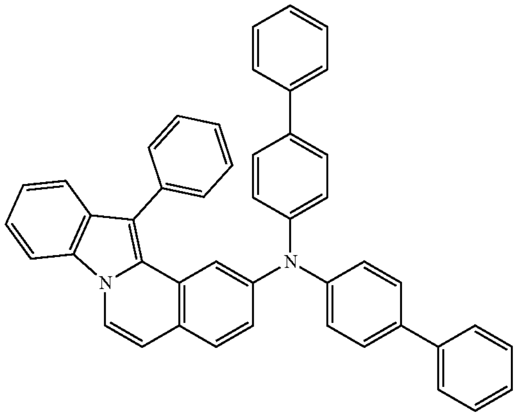

-continued
A52
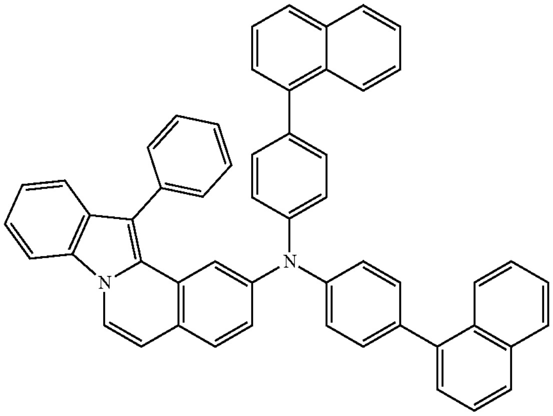
A53
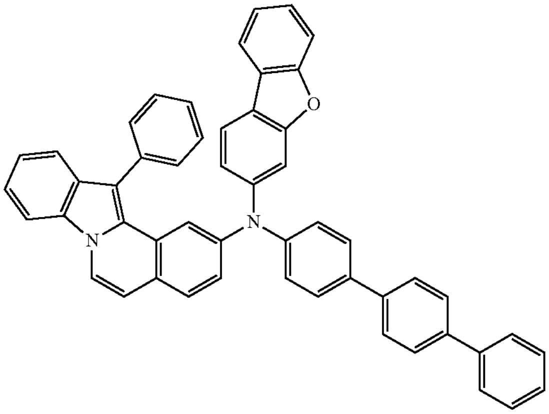
A54
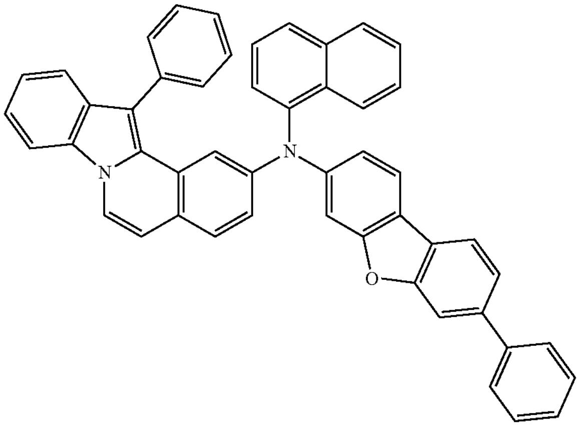
A55
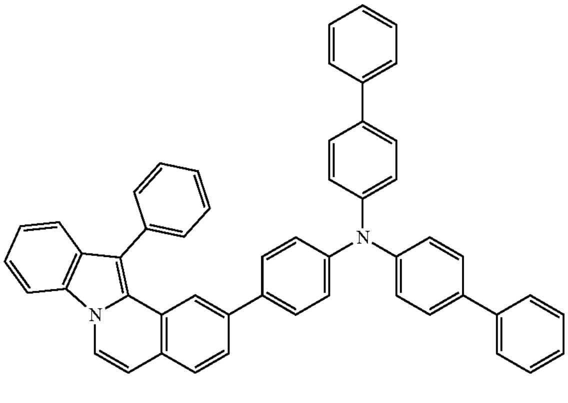
A56
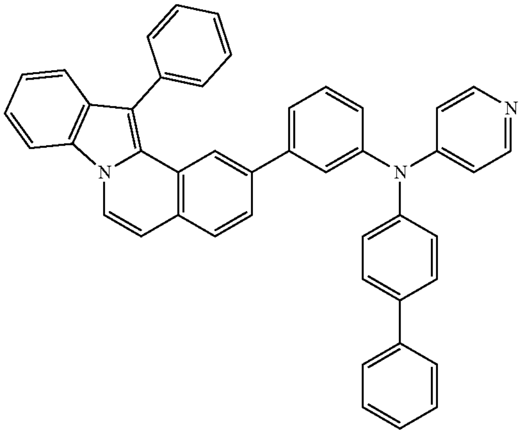
A57
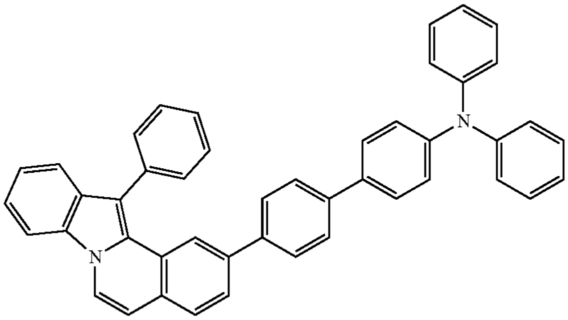

-continued
A58
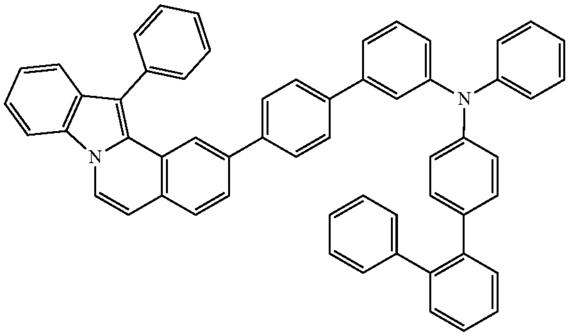
A59
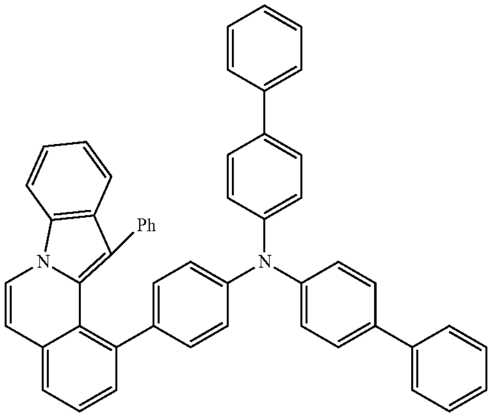
A60
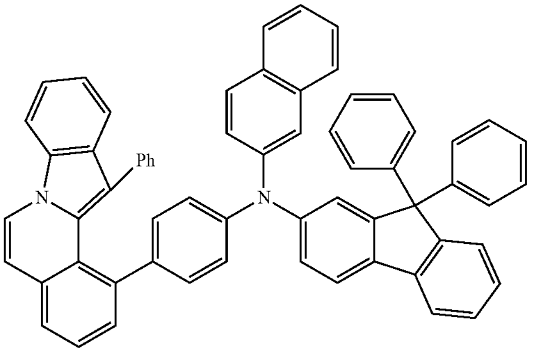
A61
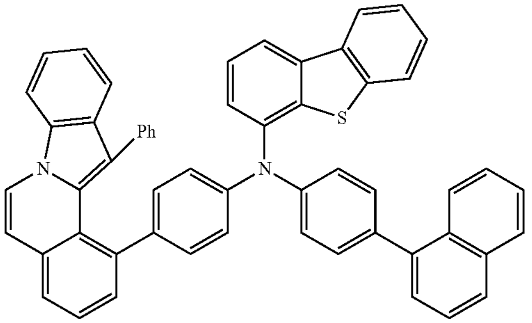
A62
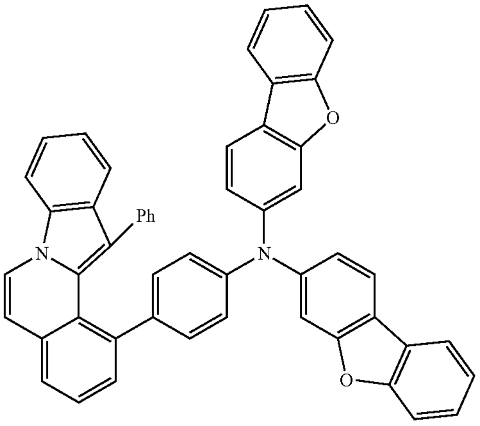
A63
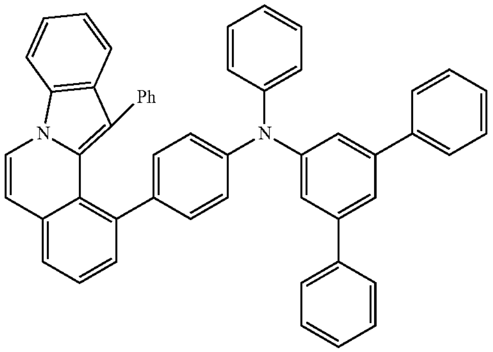
A64
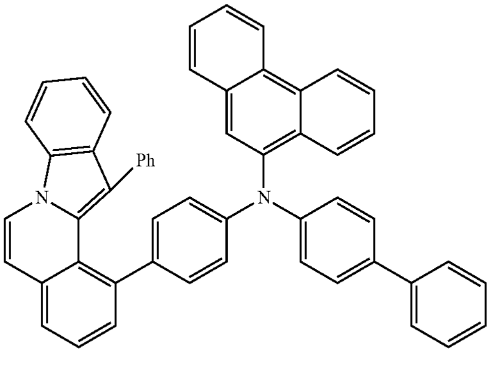
A65
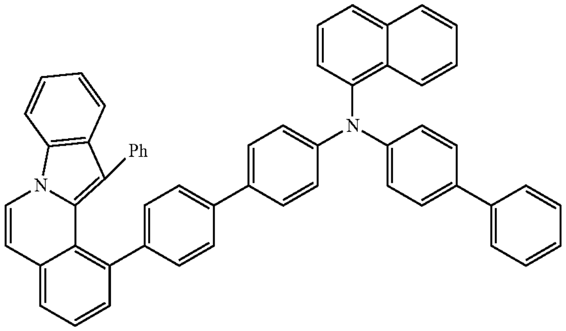

-continued
A66
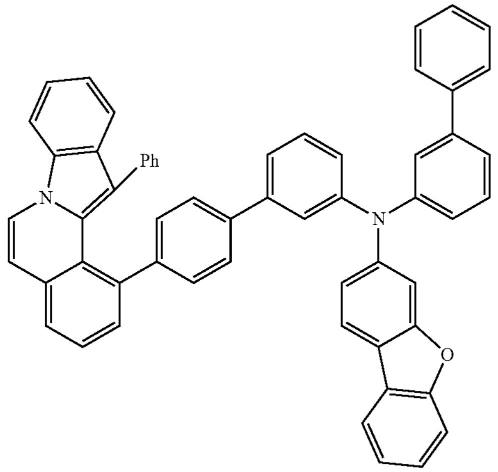
A67
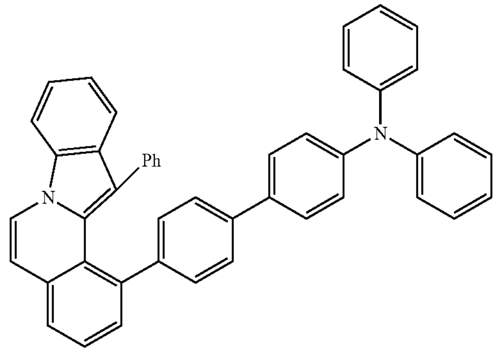
A68
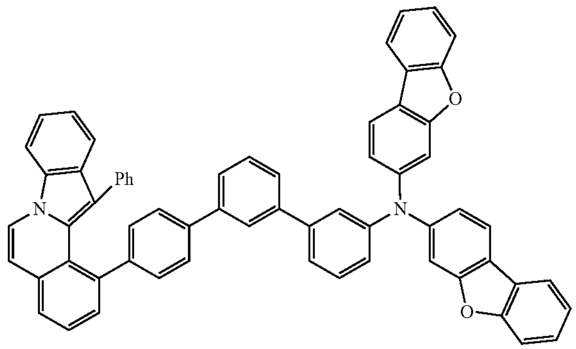
A69
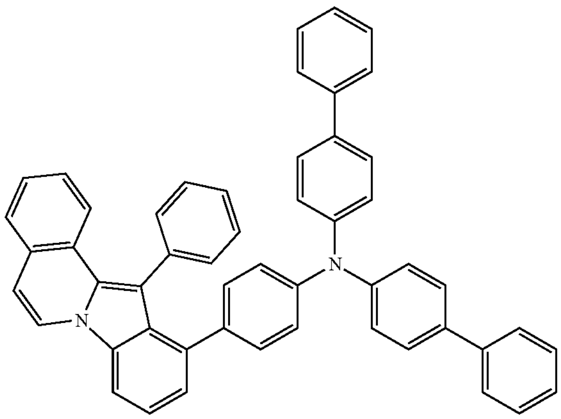
A70
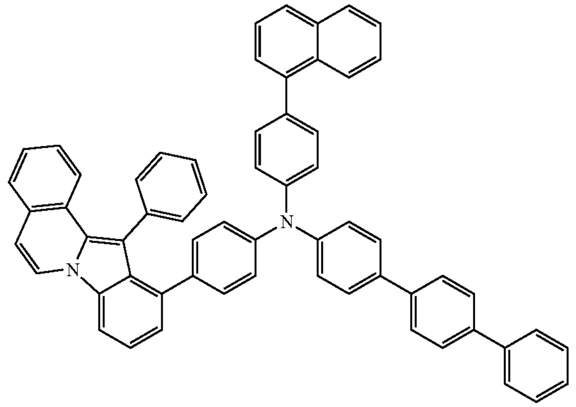
A71
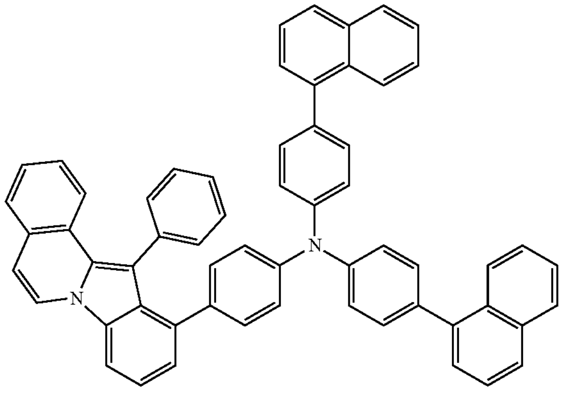

-continued
A72
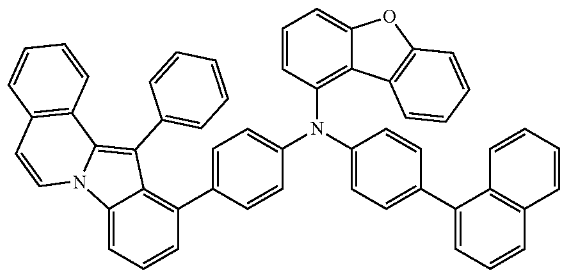
A73
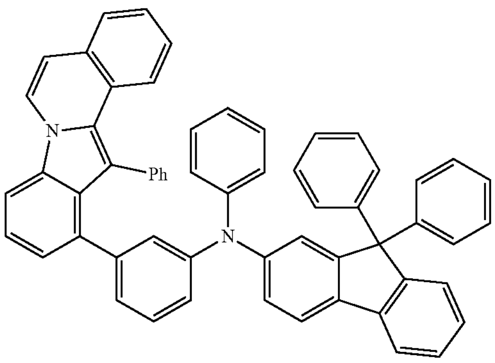
A74
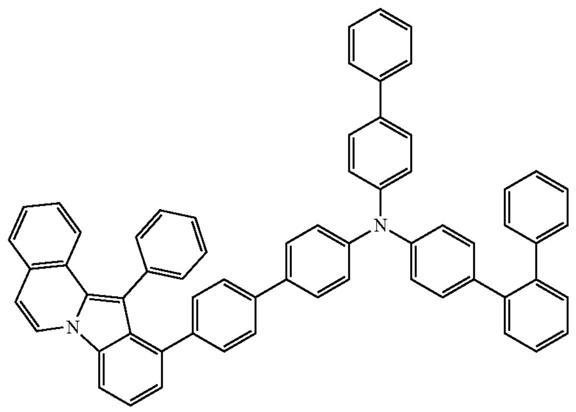
A75
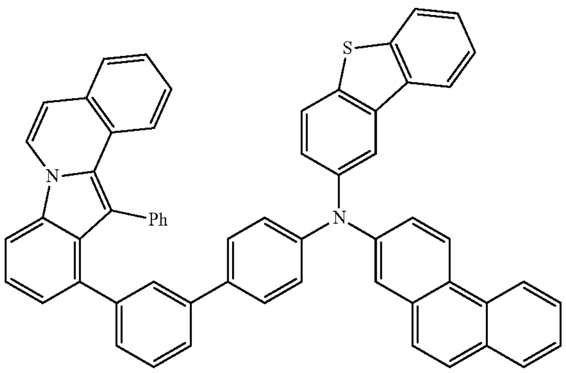
A76
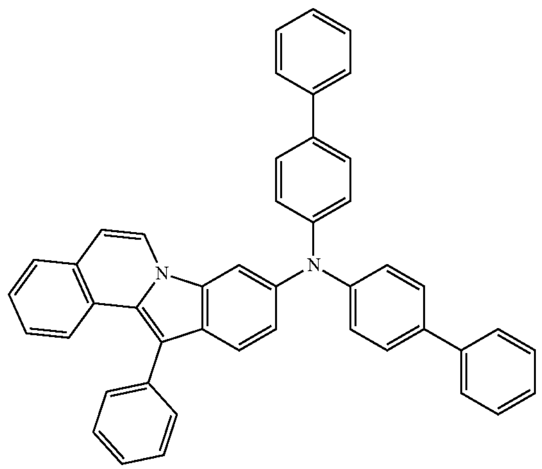
A77
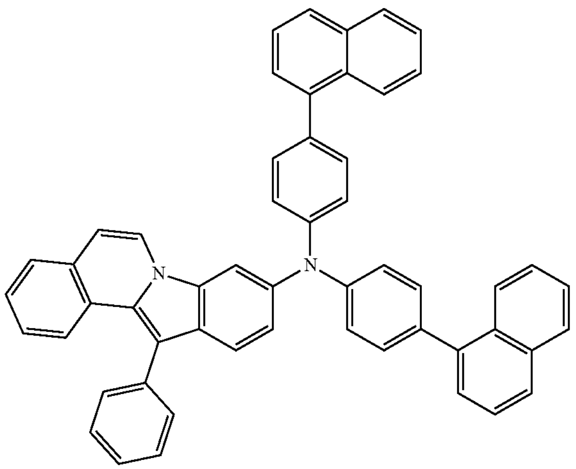

-continued
A78
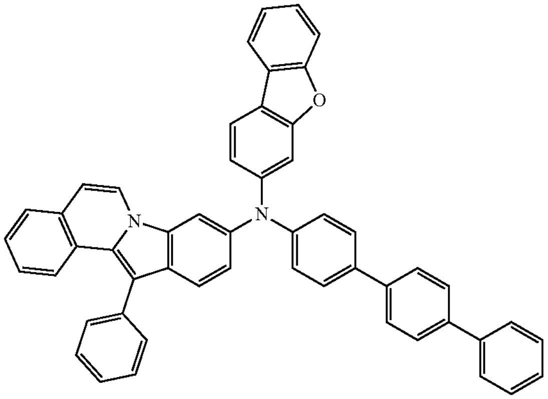
A79
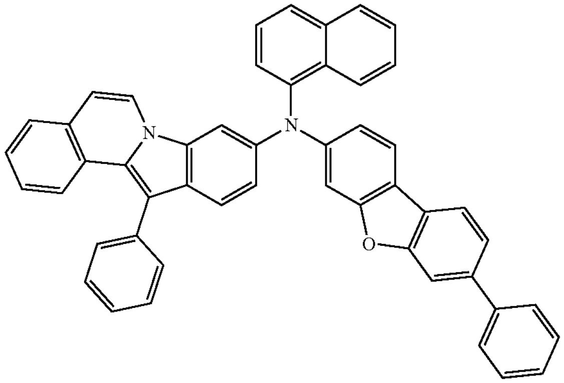
A80
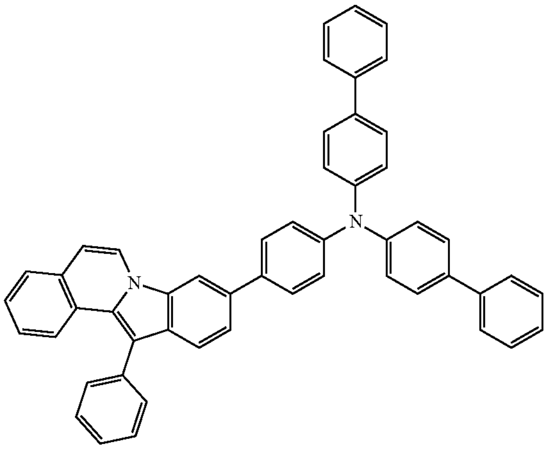
A81
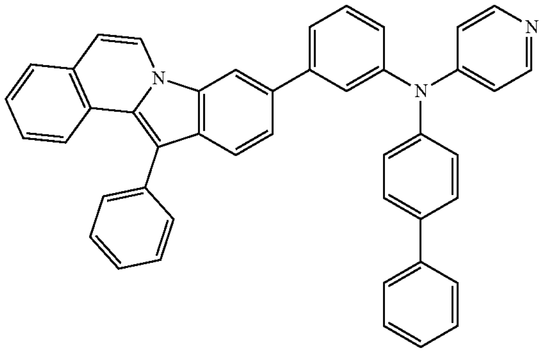
A82
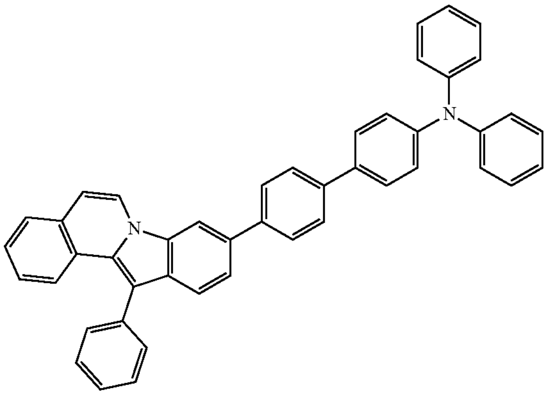
A83
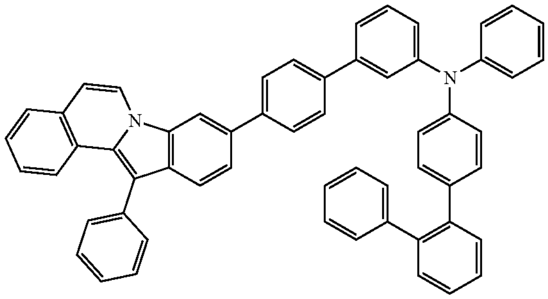

-continued
A84
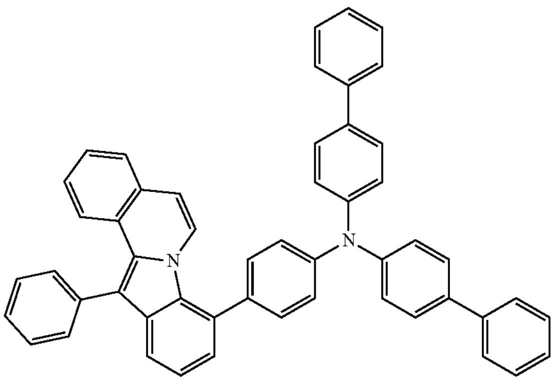
A85
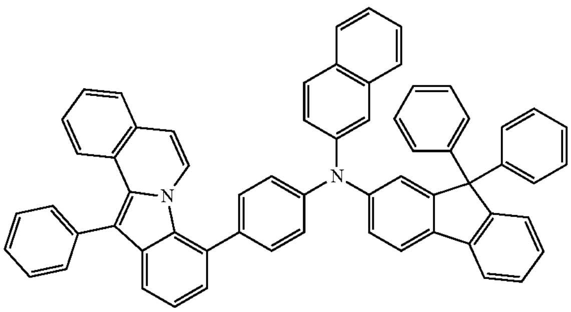
A86
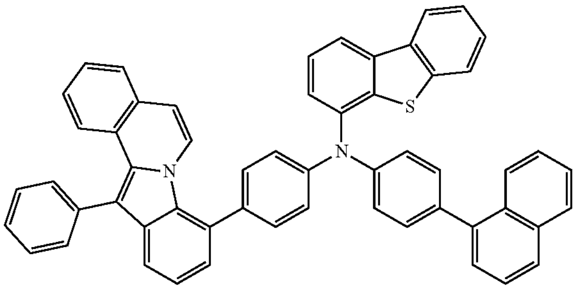
A87
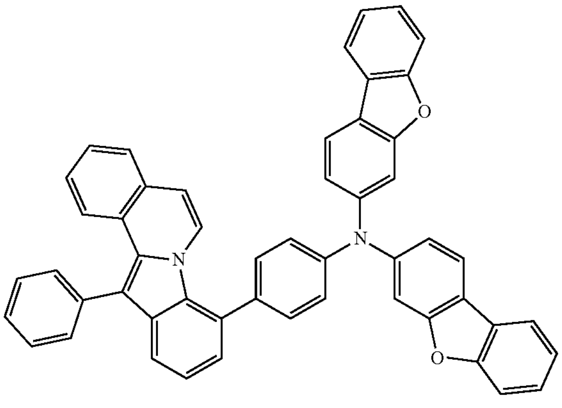
A88
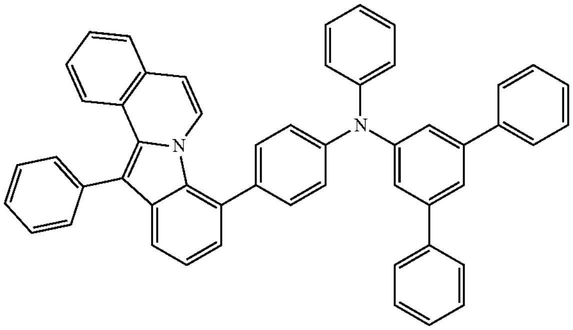
A89
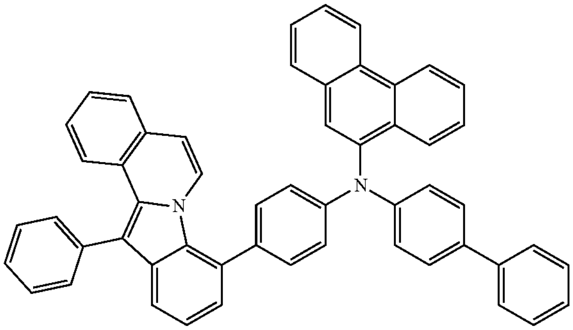
A90
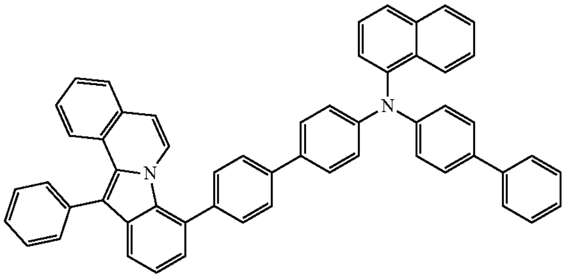
A91
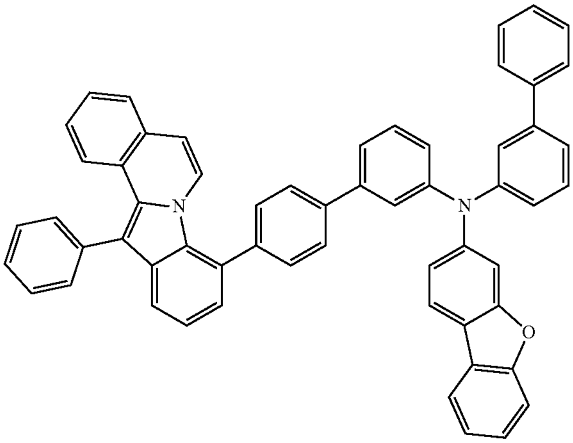

-continued
A92
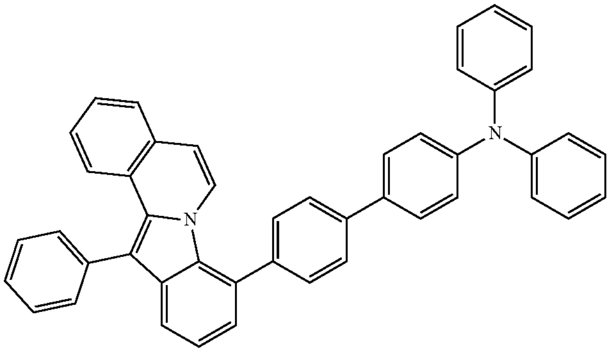
A93
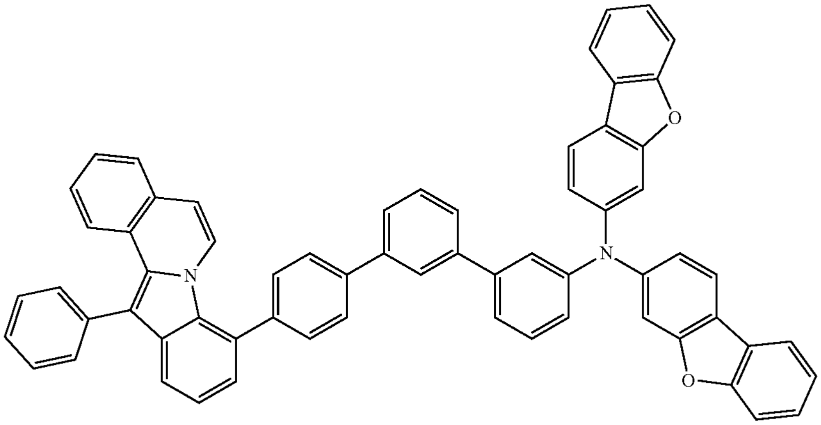
A94
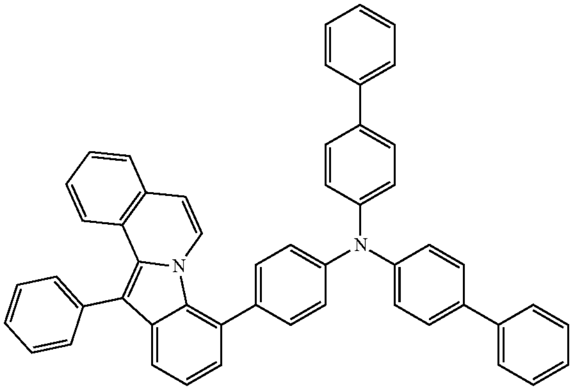
A95
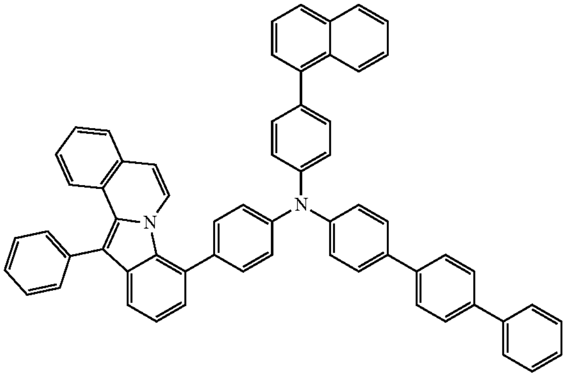

-continued
A96
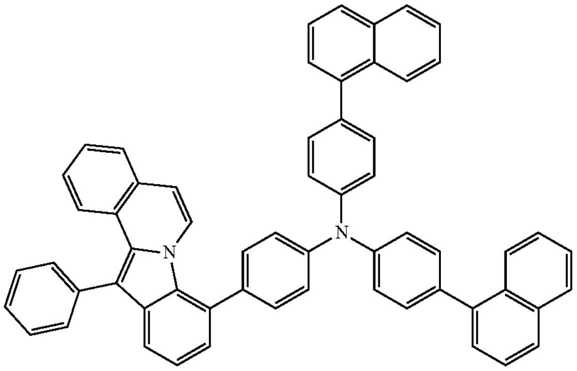
A97
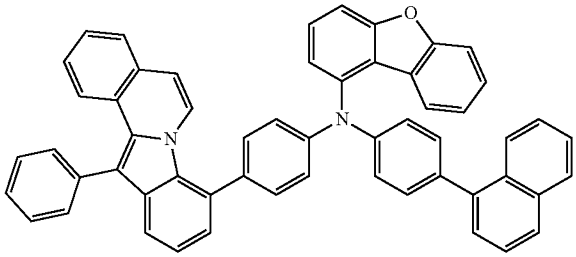
B1
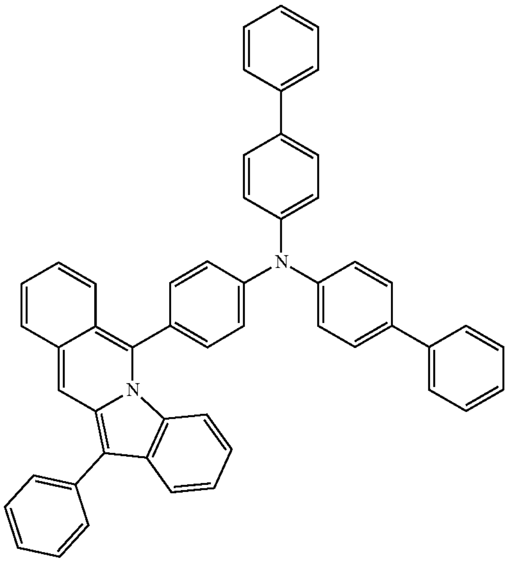
B2
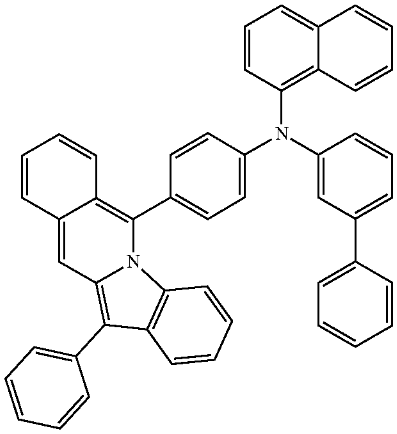
B3
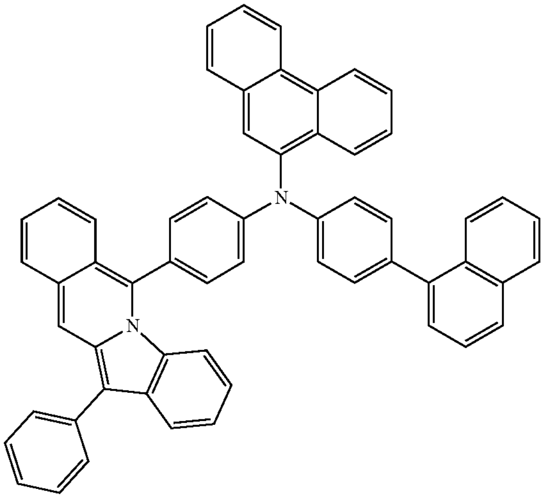
B4
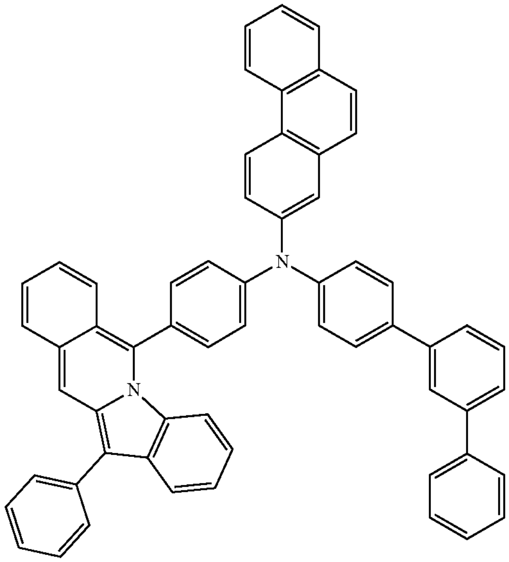

-continued
B5
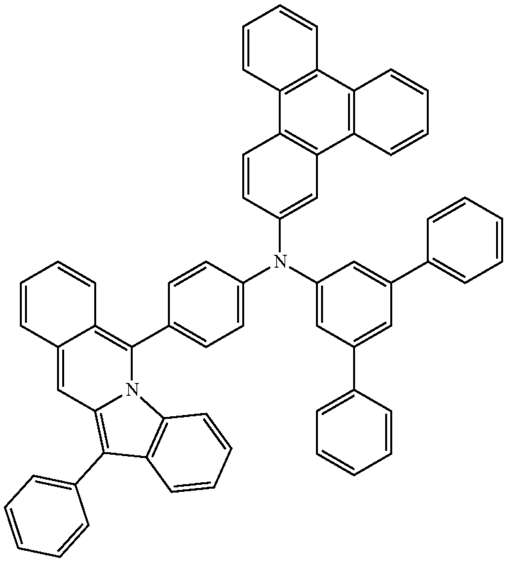
B6
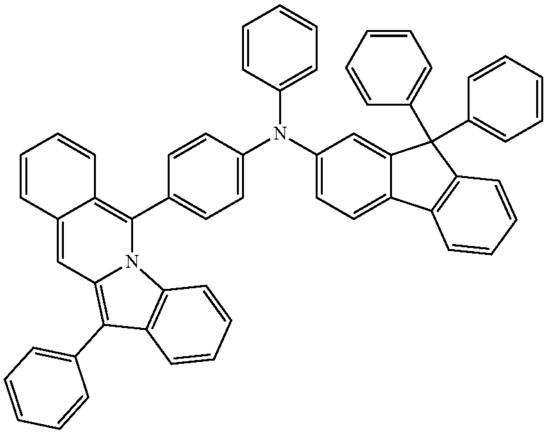
B7
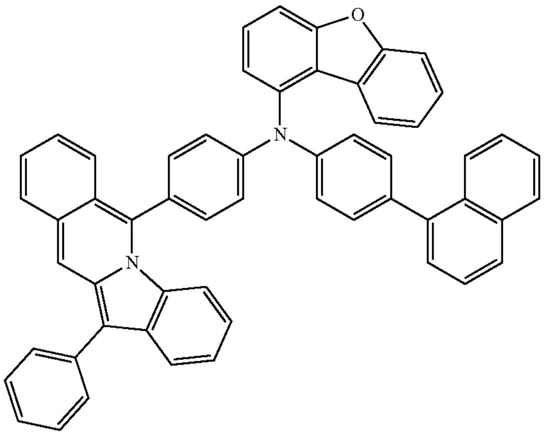
B8
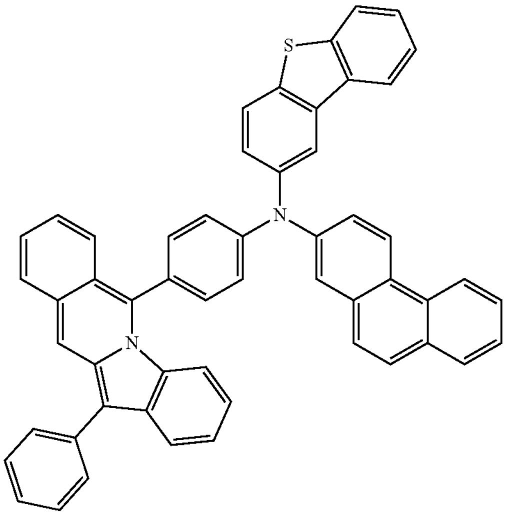
B9
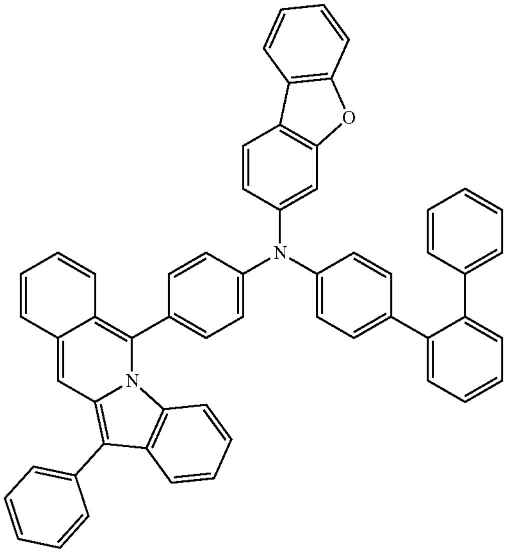
B10
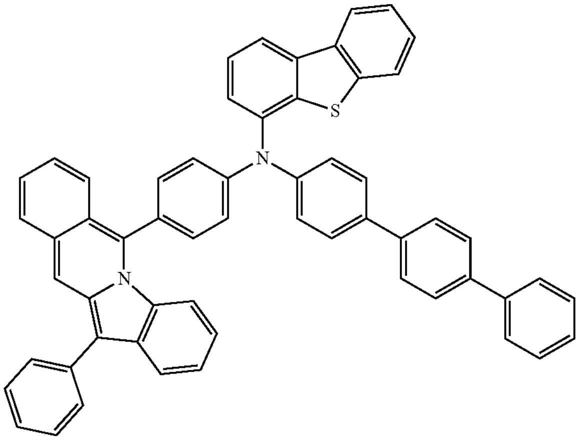

-continued
B11
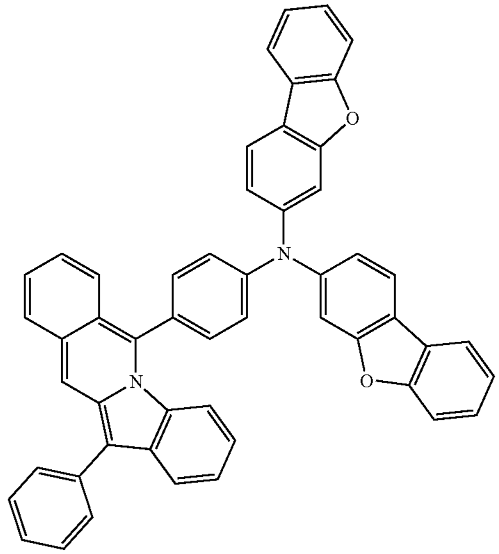
B12
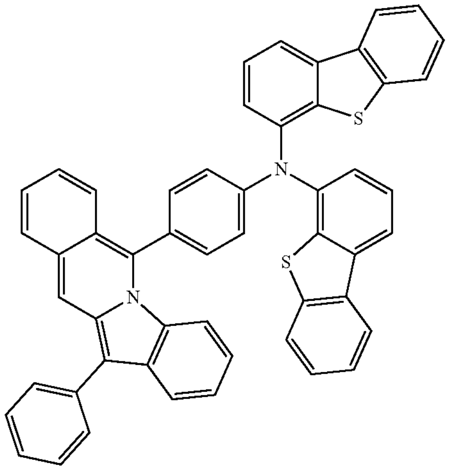
B13
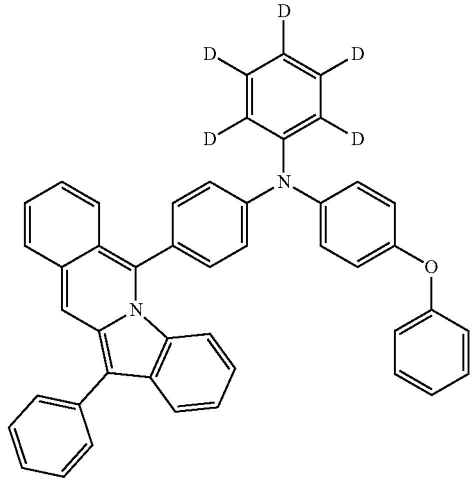
B14
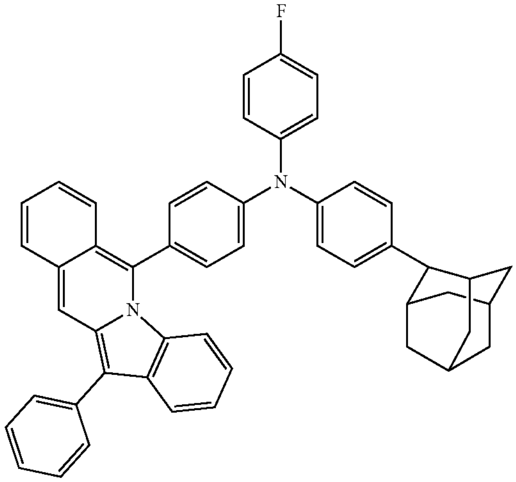
B15
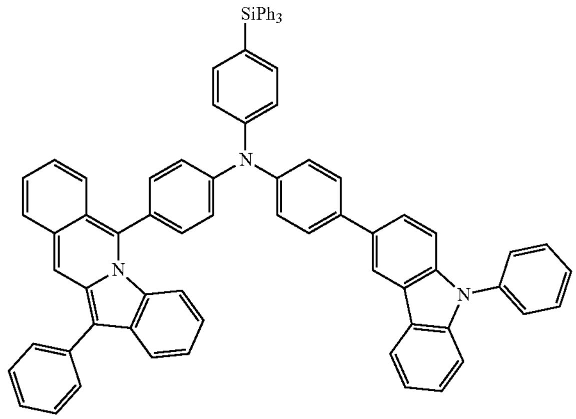
B16
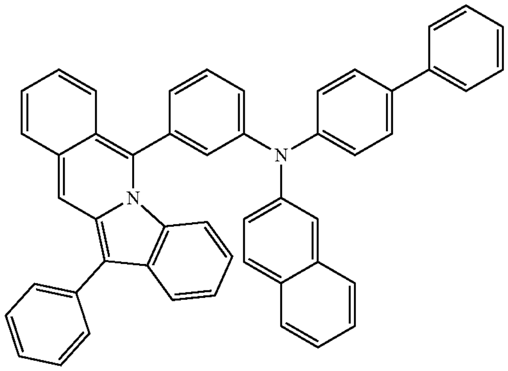

-continued
B17
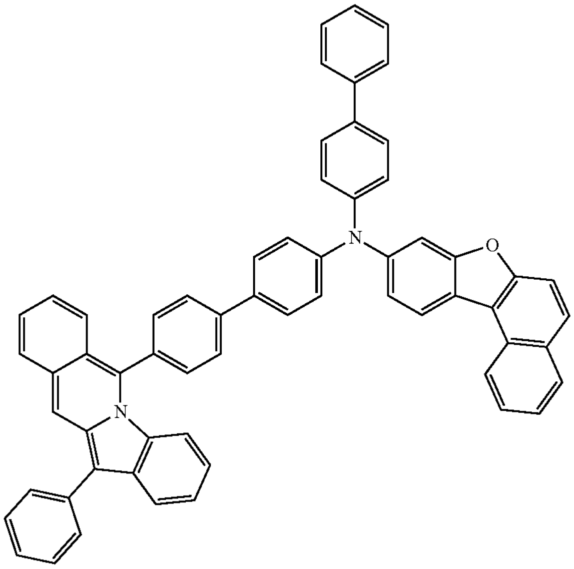
B18
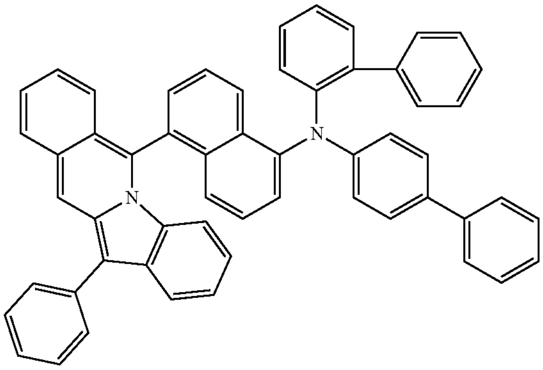
B19
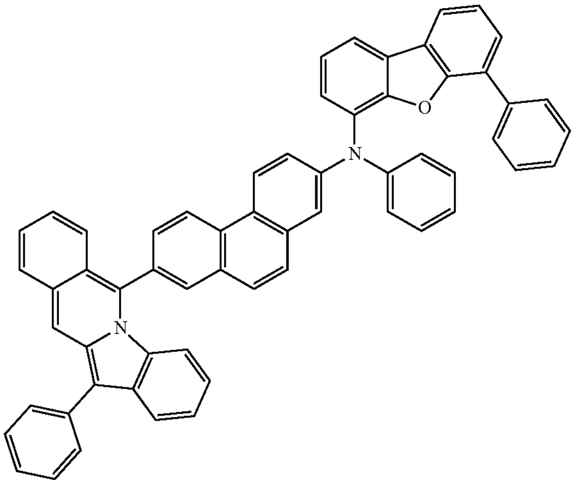
B20
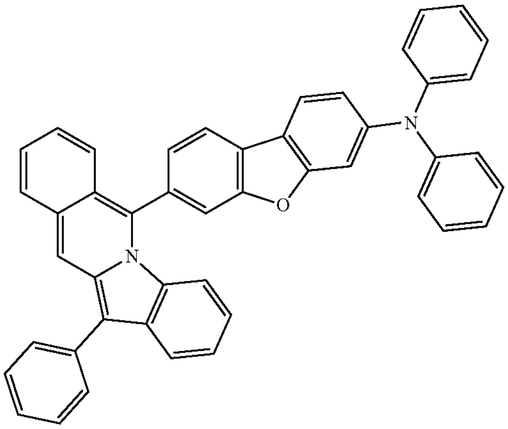

-continued
B21
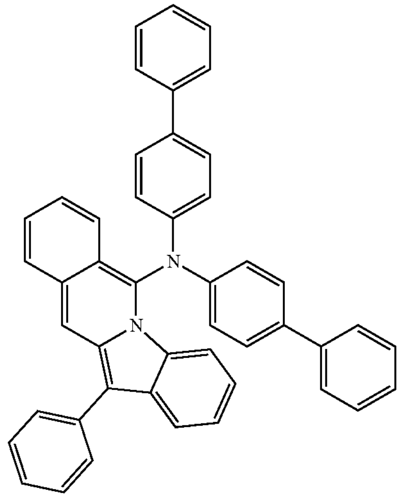
B22
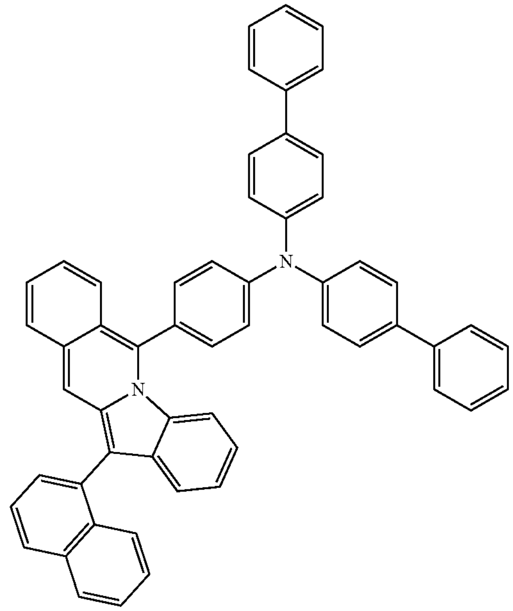
B23
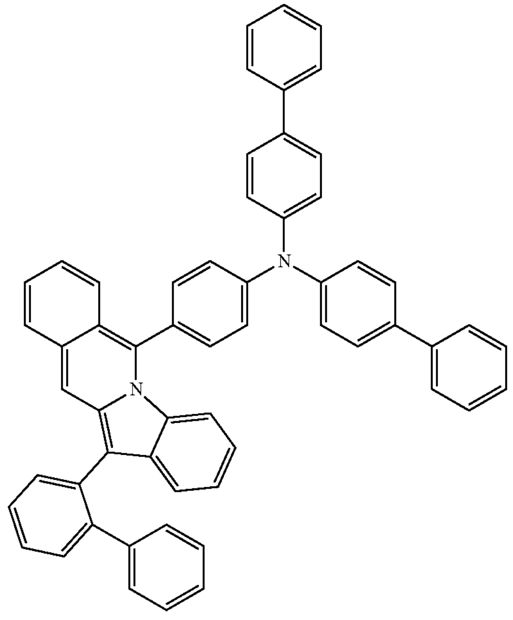
B24
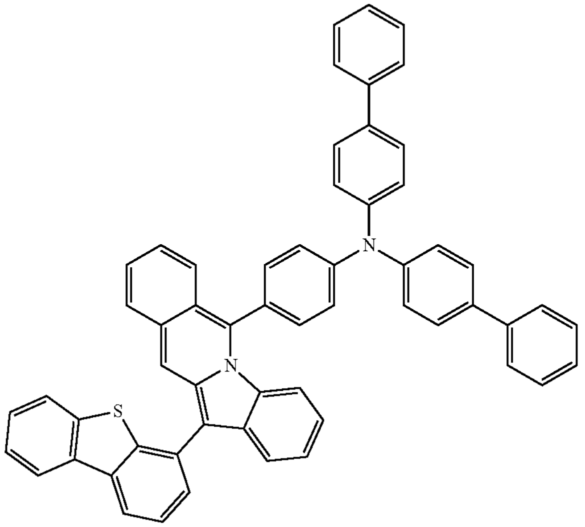

-continued
B25
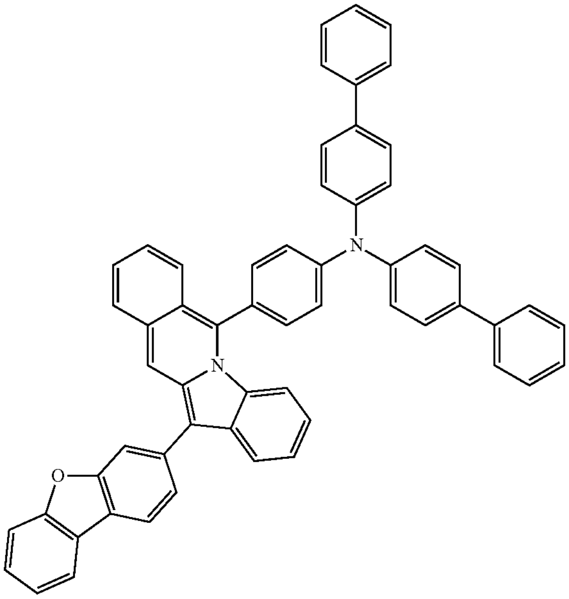
B26
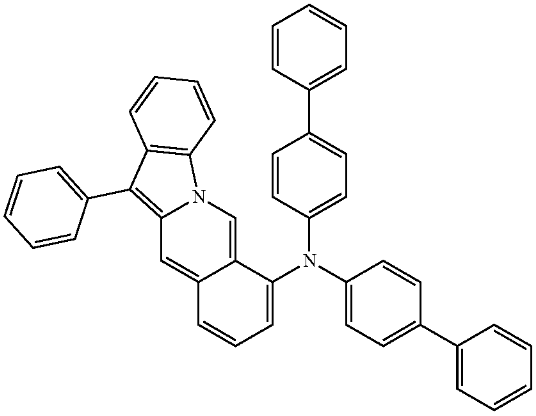
B27
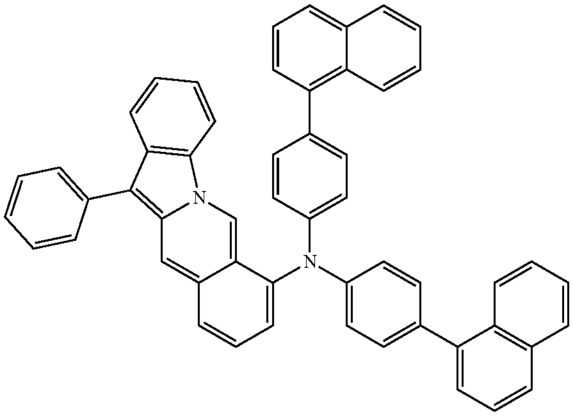
B28
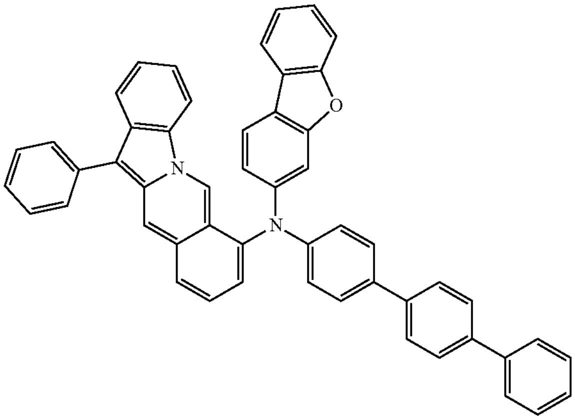
B29
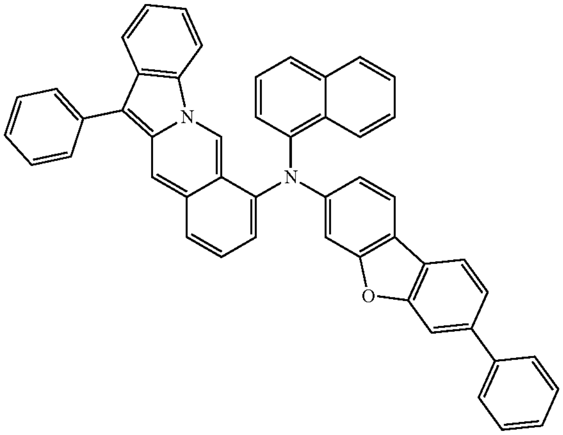
B30
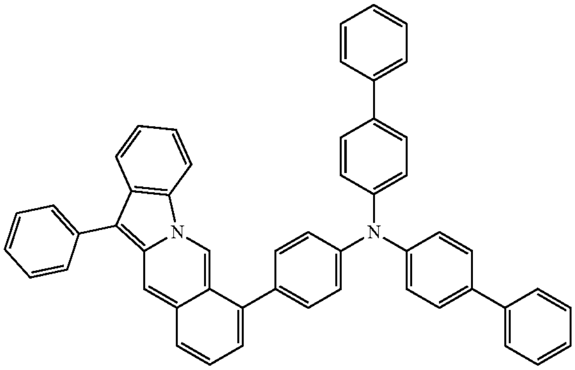

-continued
B31
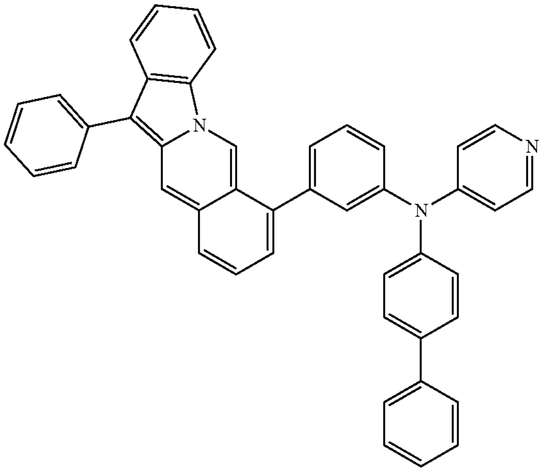
B32
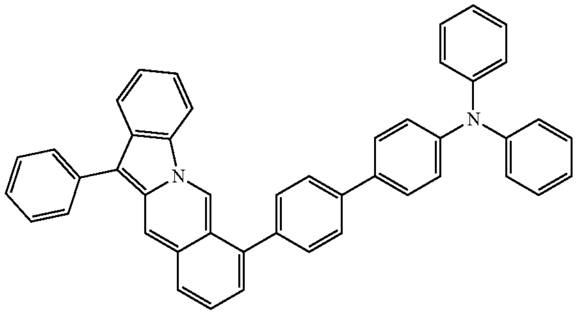
B33
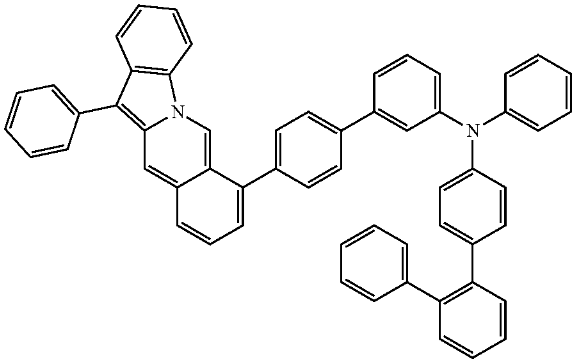
B34
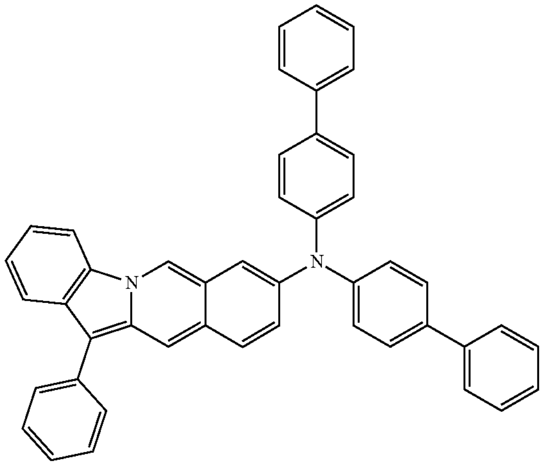
B35
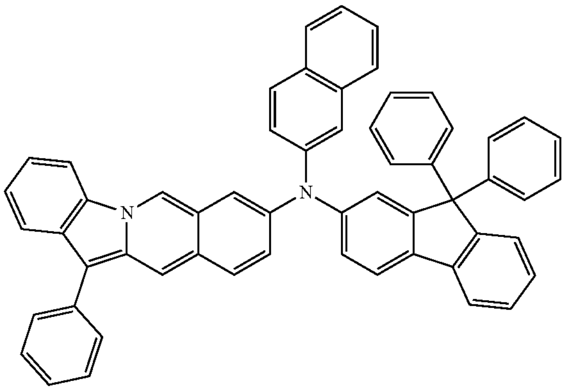
B36
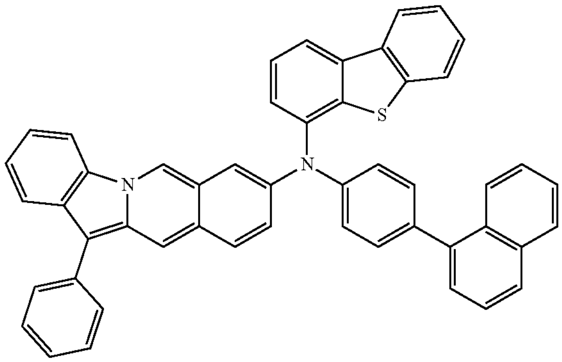

-continued
B37
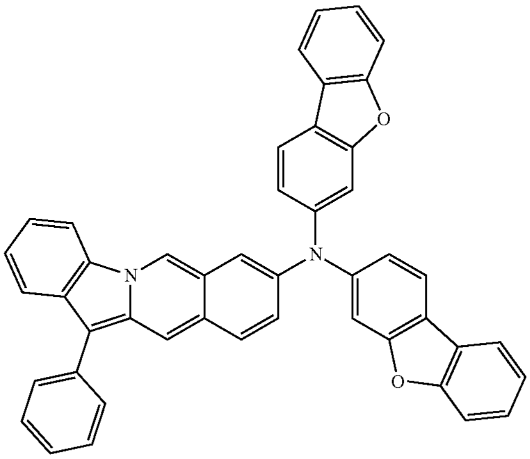
B38
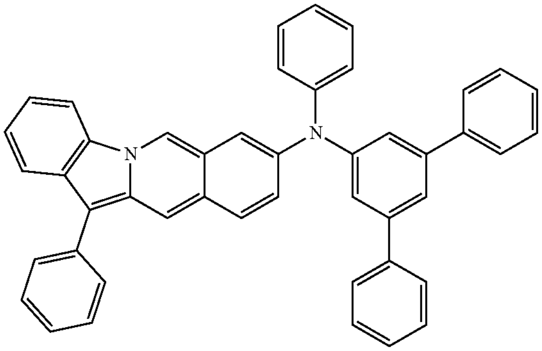
B39
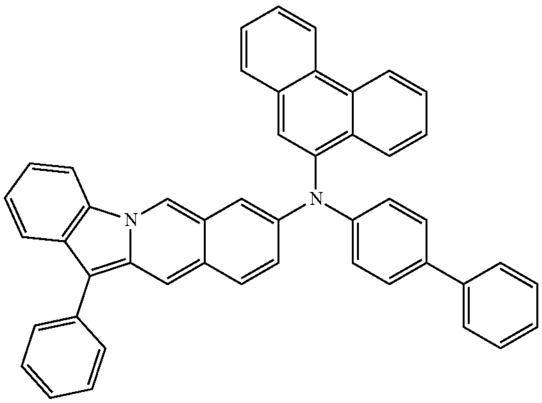
B40
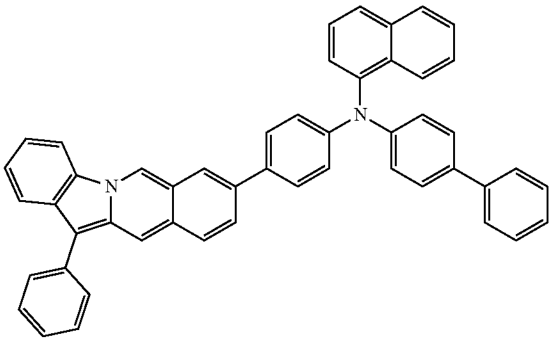
B41
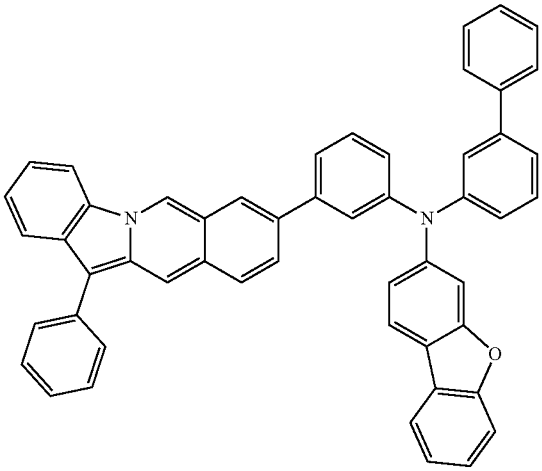
B42
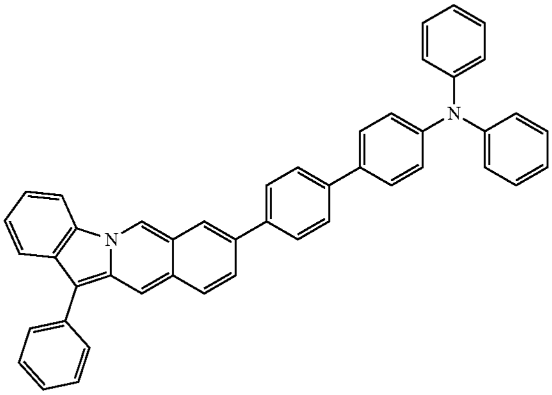

-continued
B43
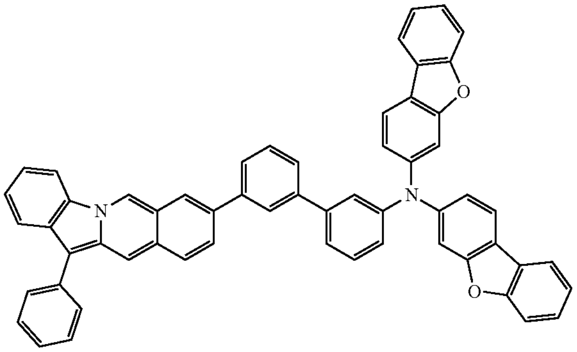
B44
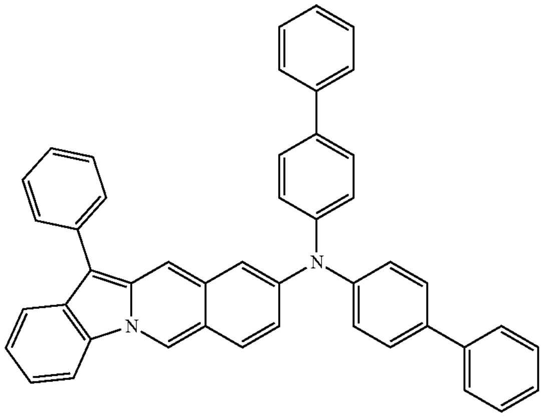
B45
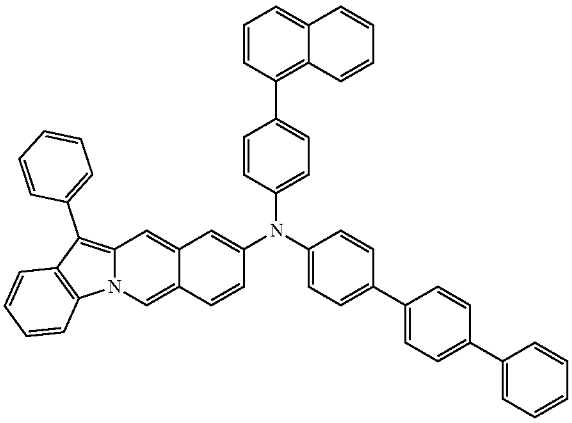
B46
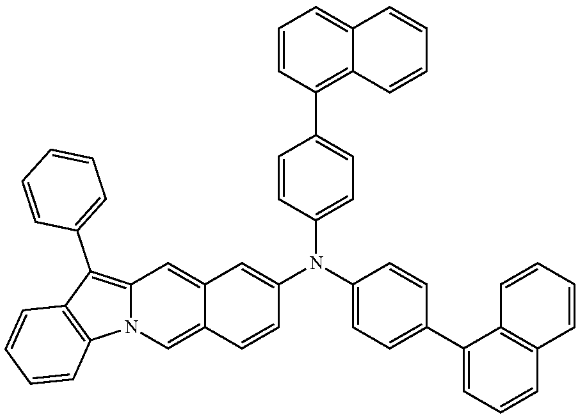
B47
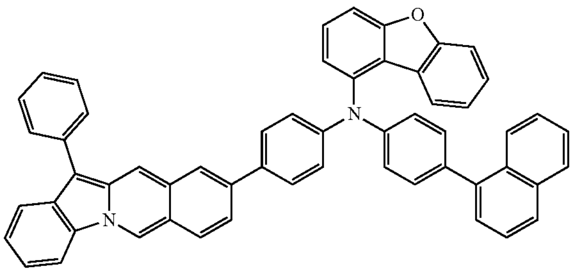
B48
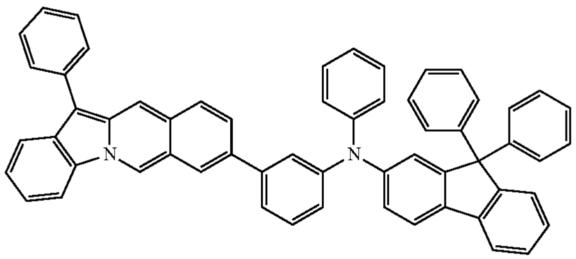
B49
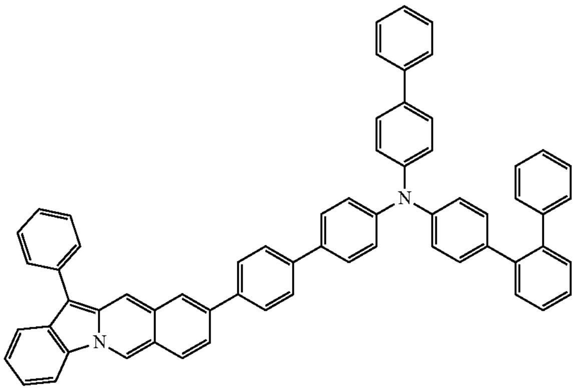
B50
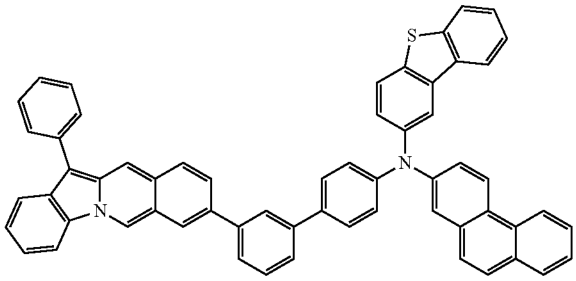

-continued
B51
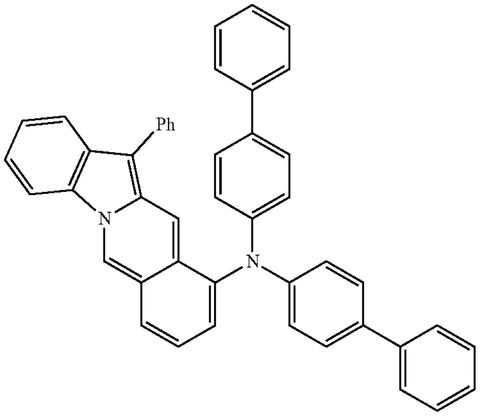
B52
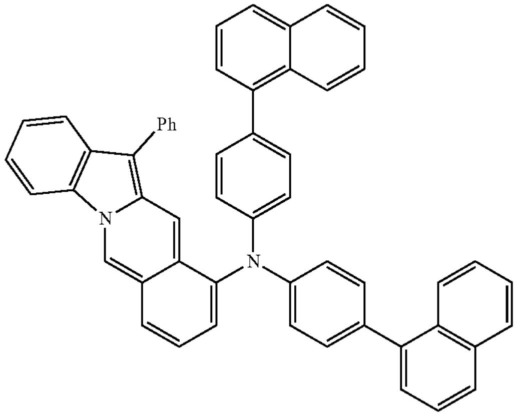
B53
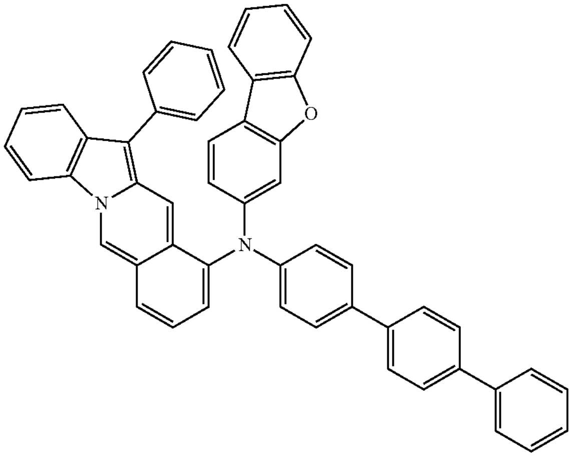
B54
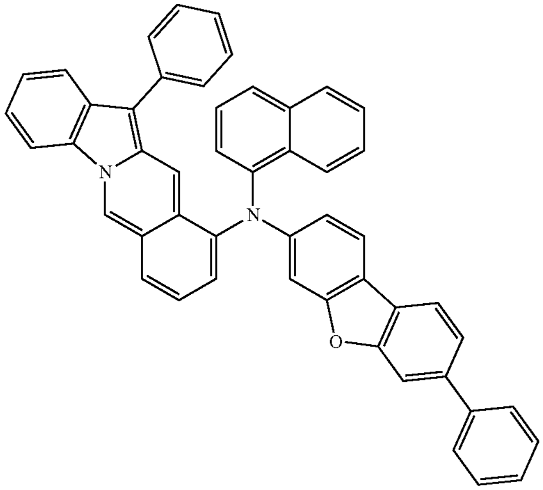
B55
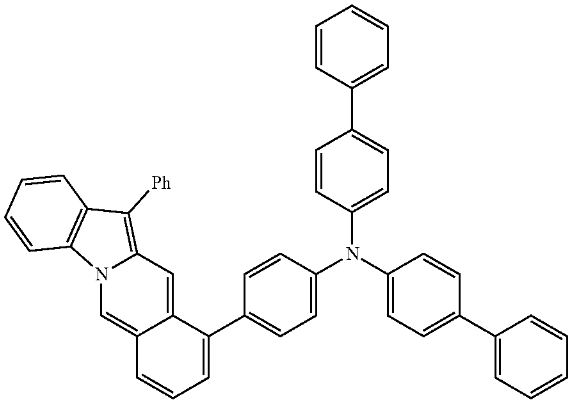
B56
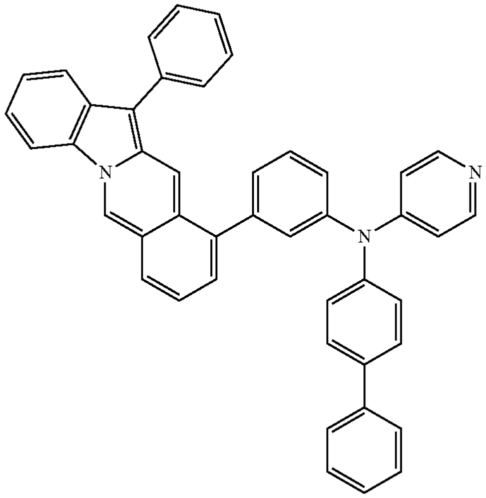

-continued
B57
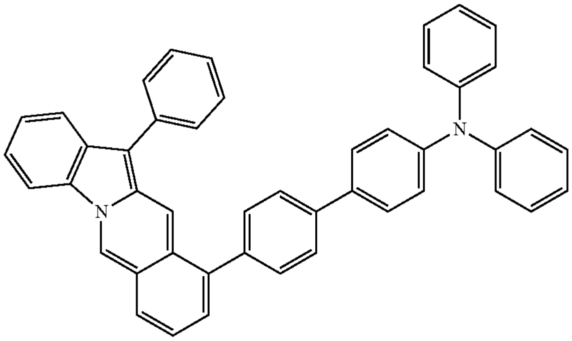
B58
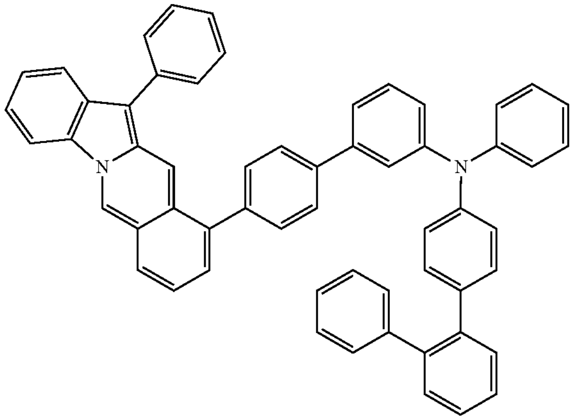
B59
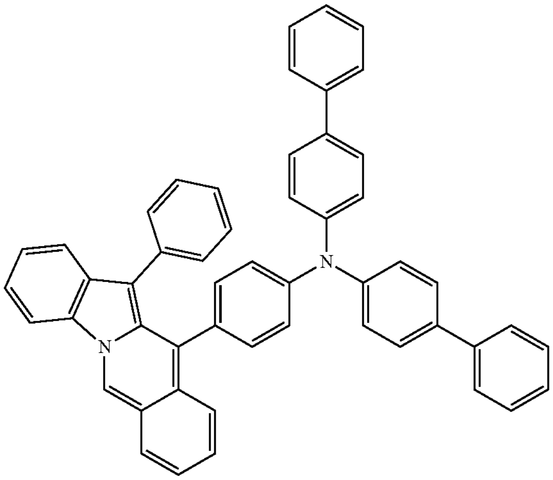
B60
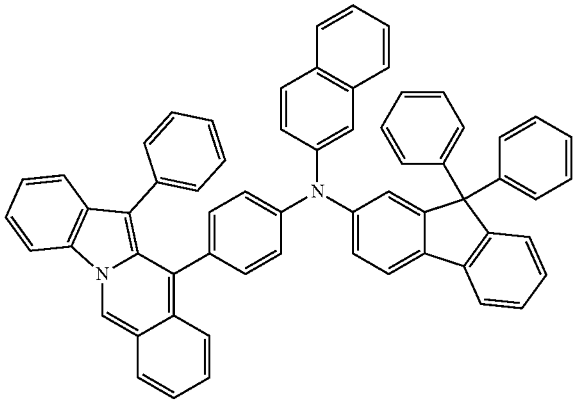
B61
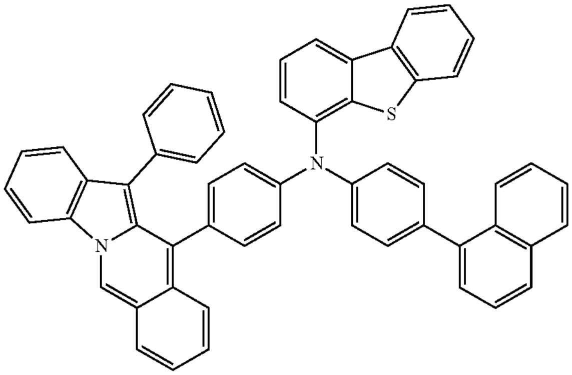
B62
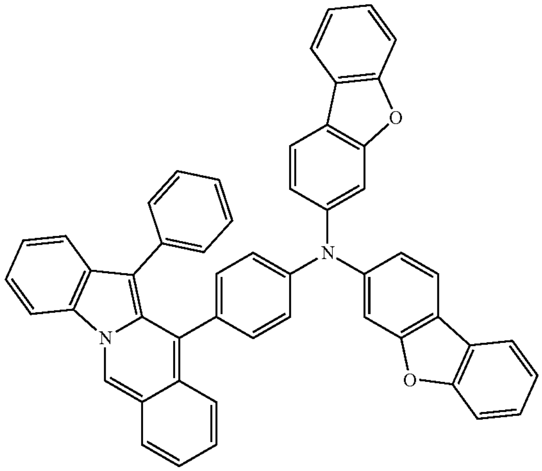

-continued
B63
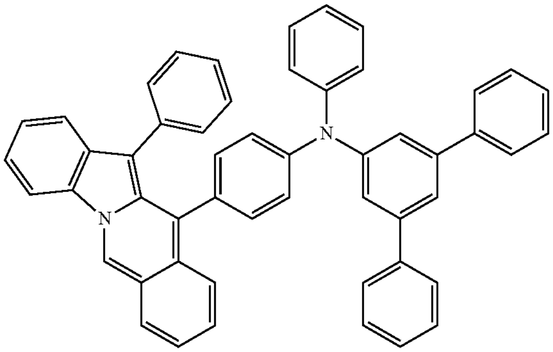
B64
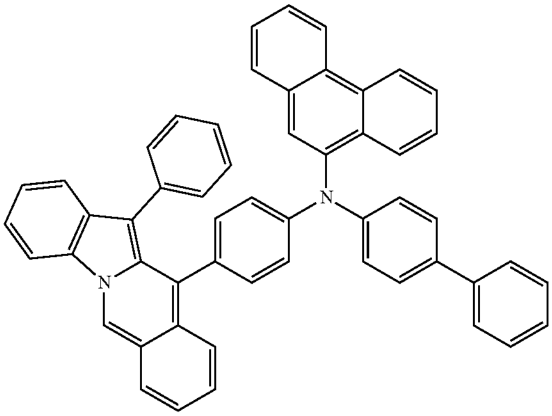
B65
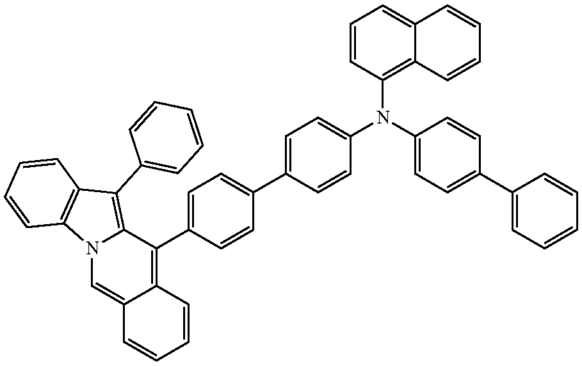
B66
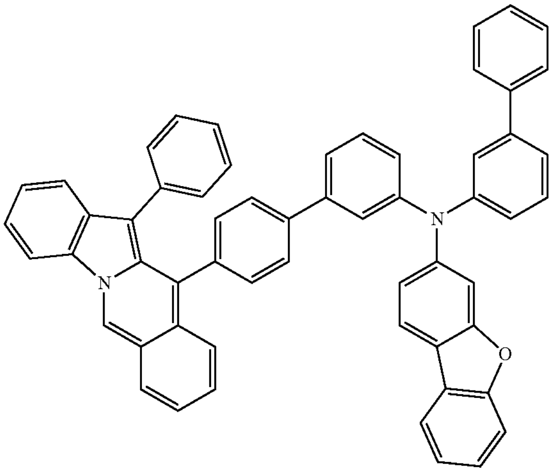
B67
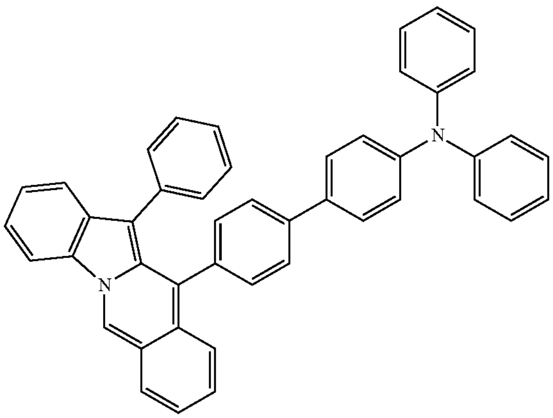
B68
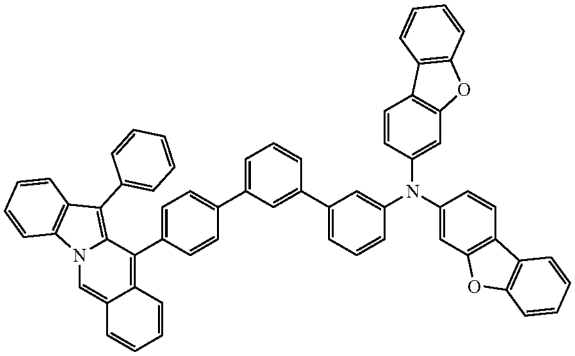

-continued
B69
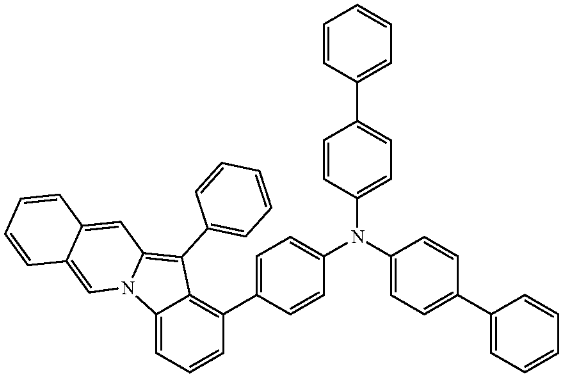
B70
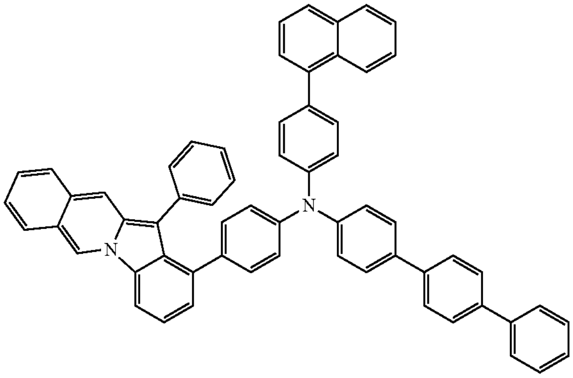
B71
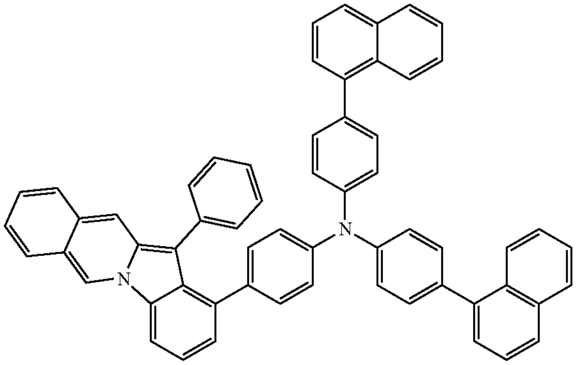
B72
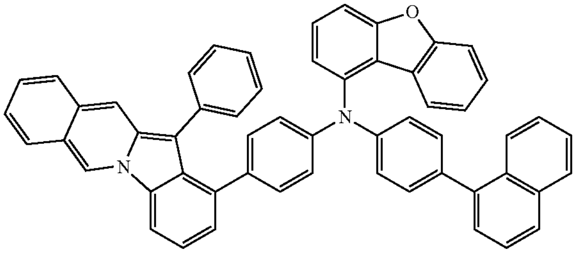
B73
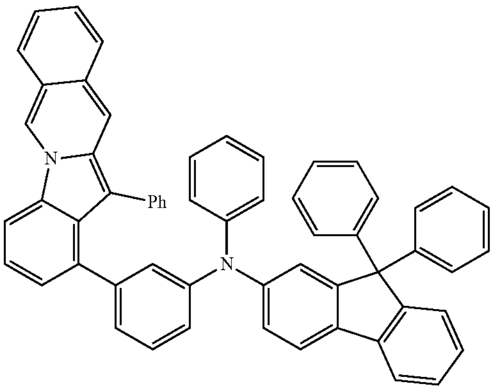
B74
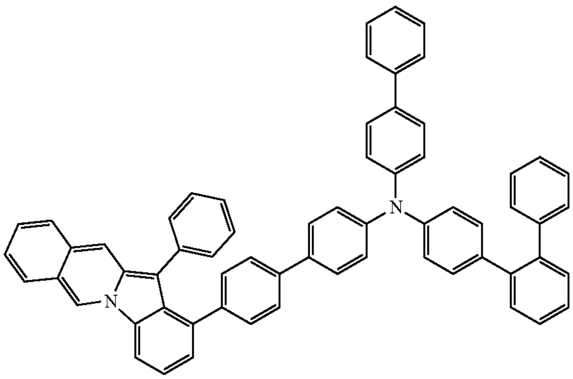

-continued
B75
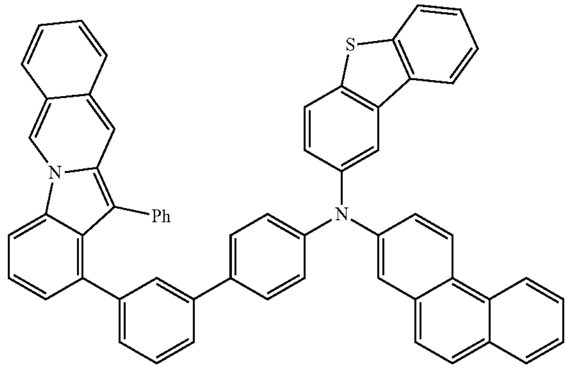
B76
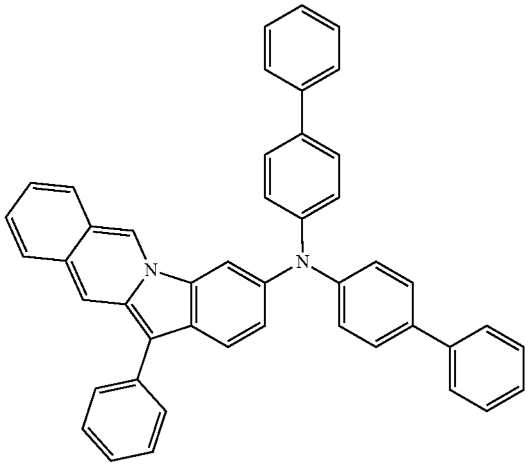
B77
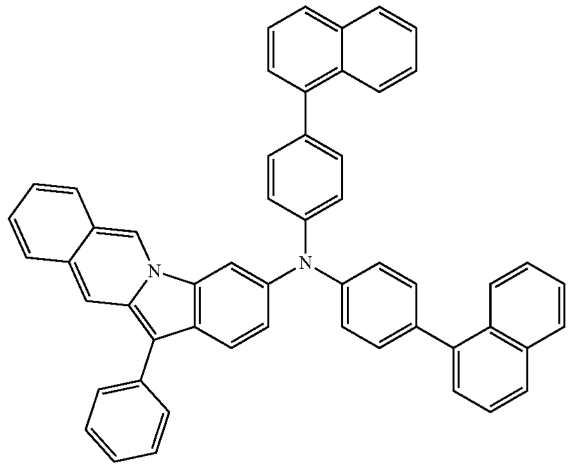
B78
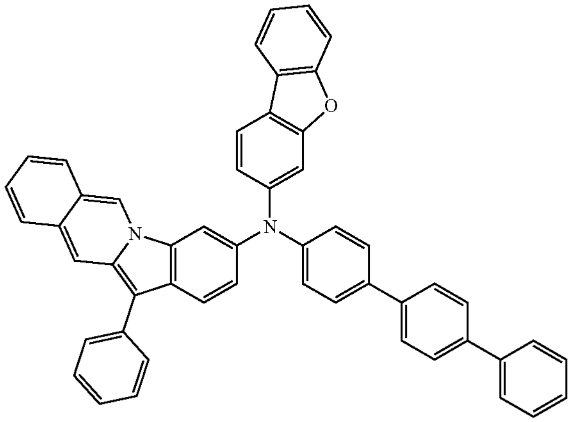
B79
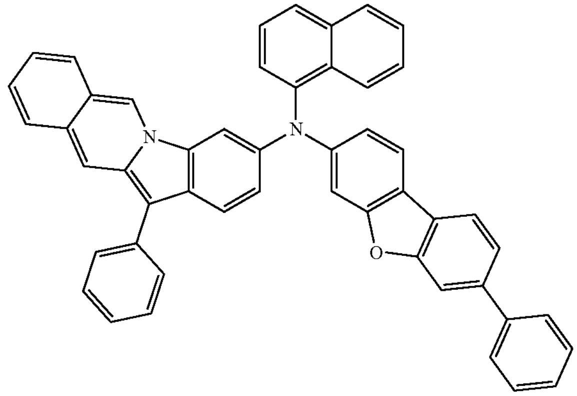
B80
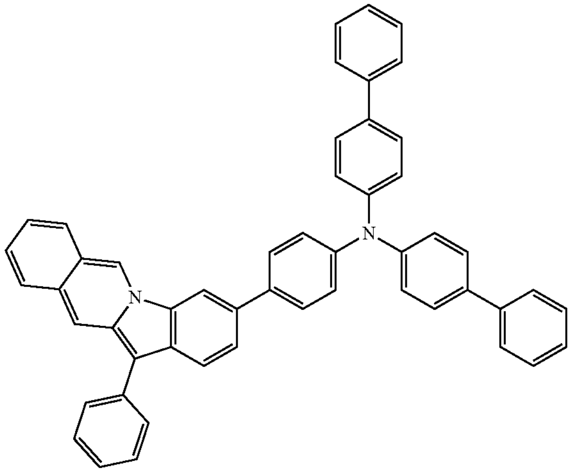

-continued
B81
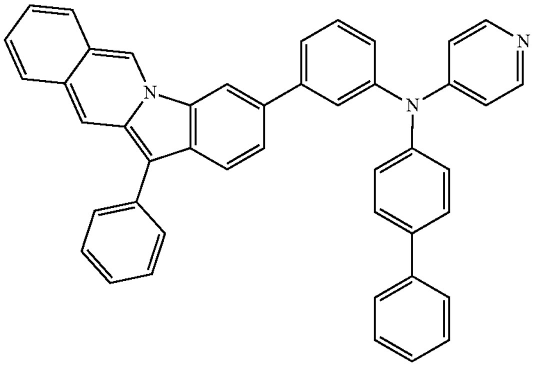
B82
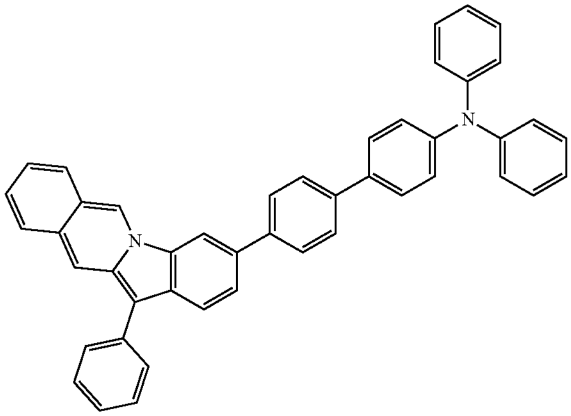
B83
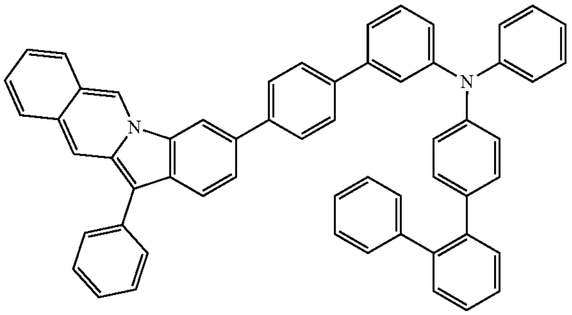
B84
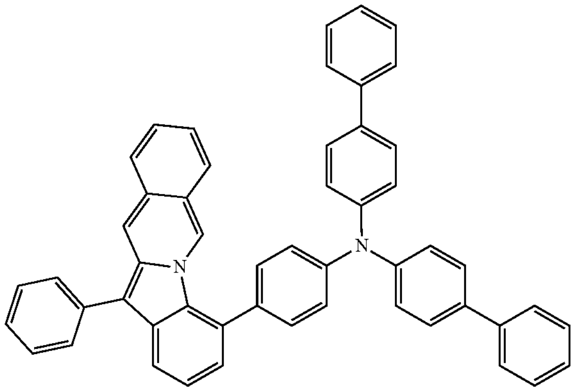
B85
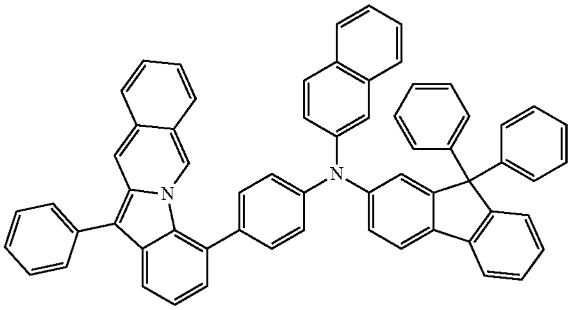
B86
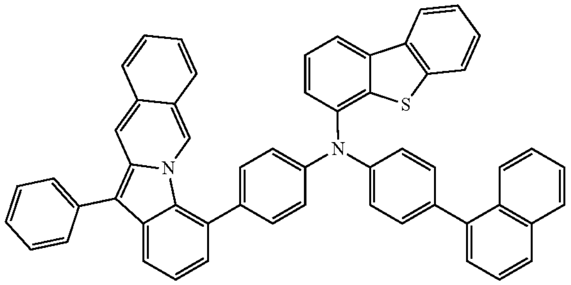
B87
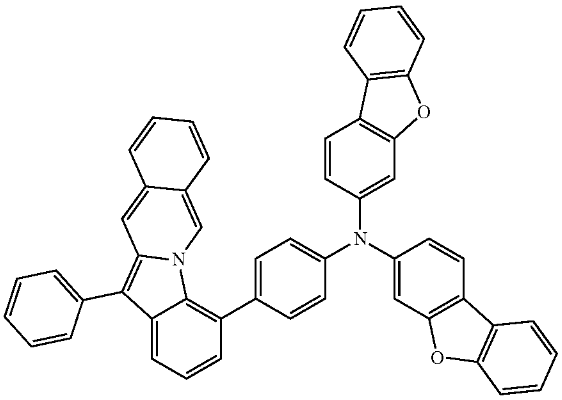
B88
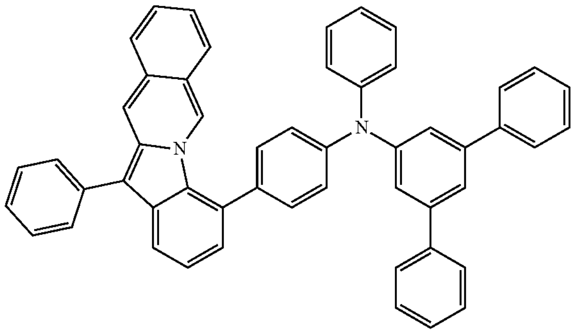

-continued
B89
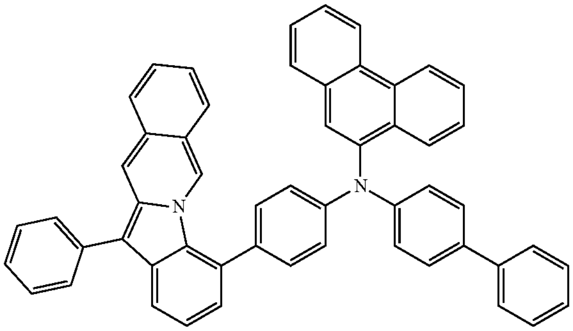
B90
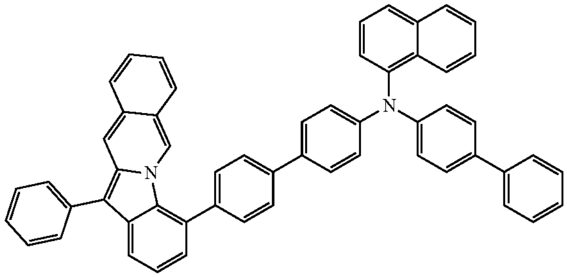
B91
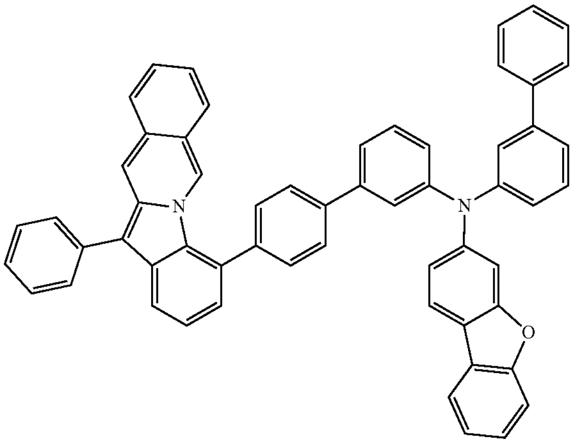
B92
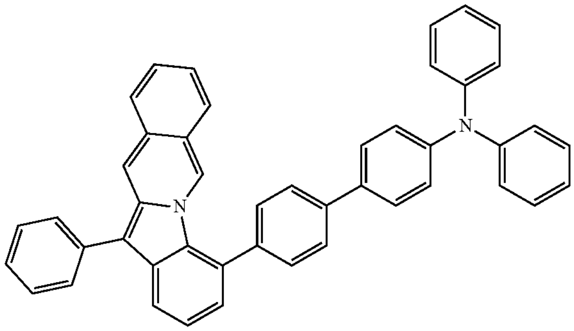
B93
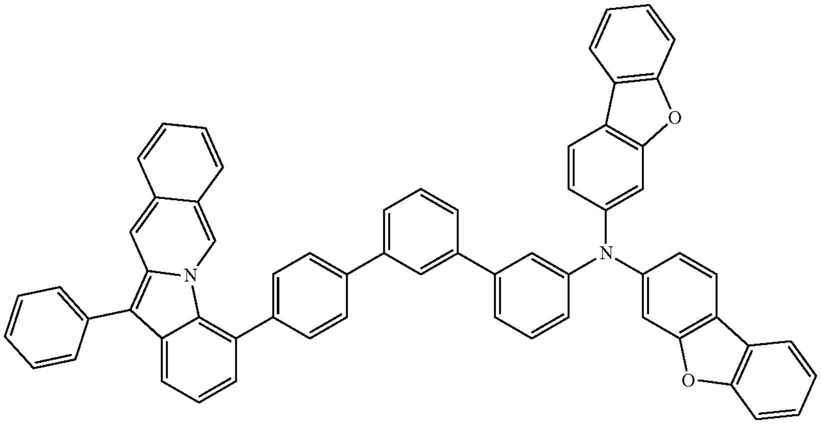
B94
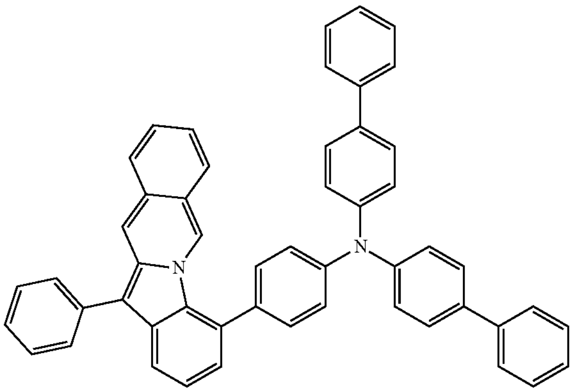
B95
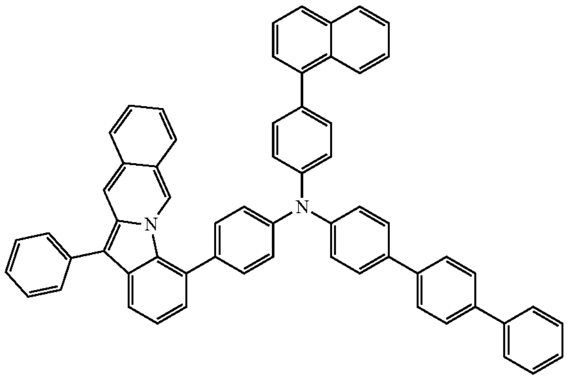

-continued
B96
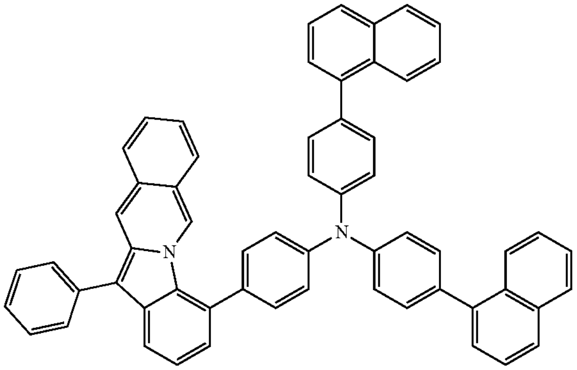
B97
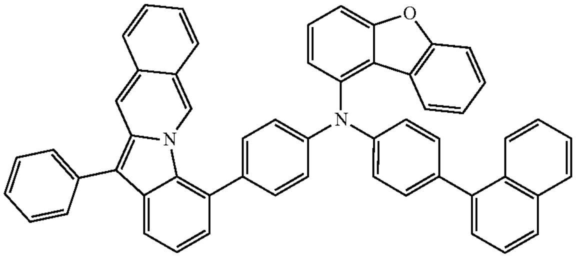
C1
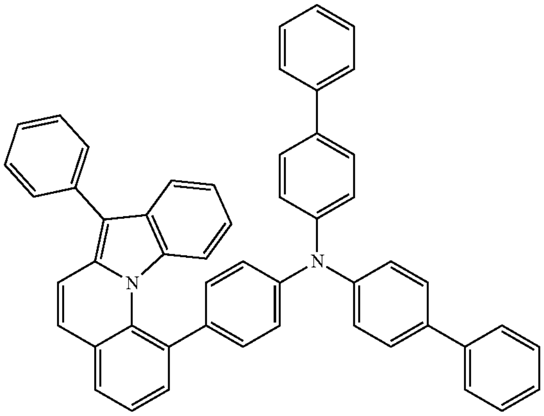
C2
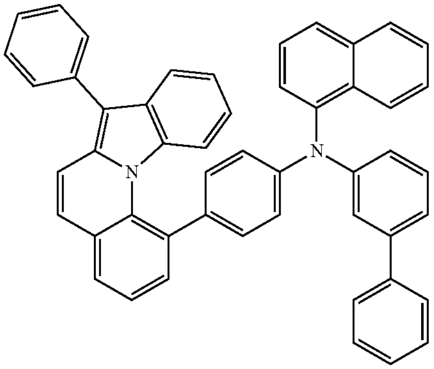
C3
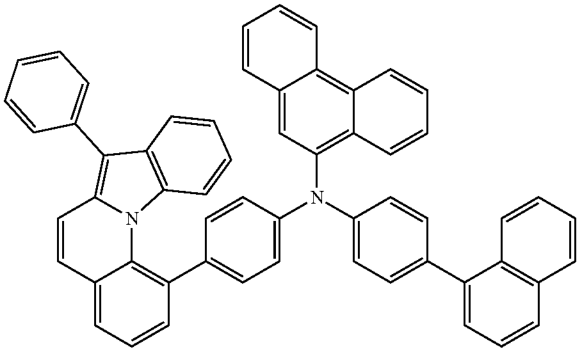
C4
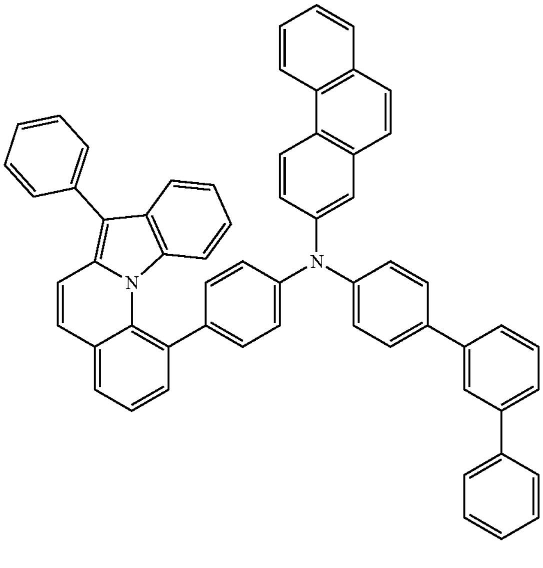

-continued
C5
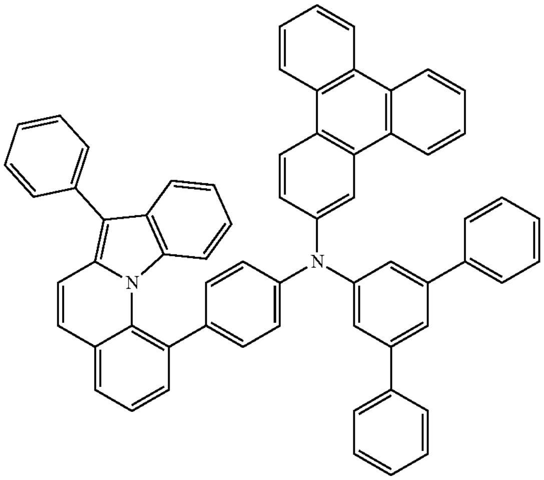
C6
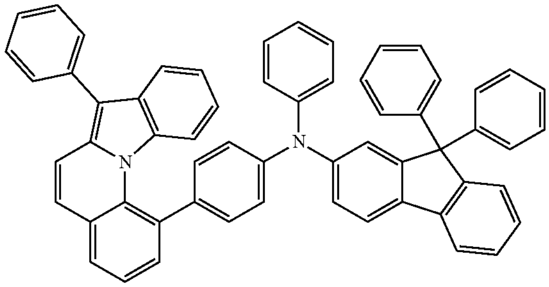
C7
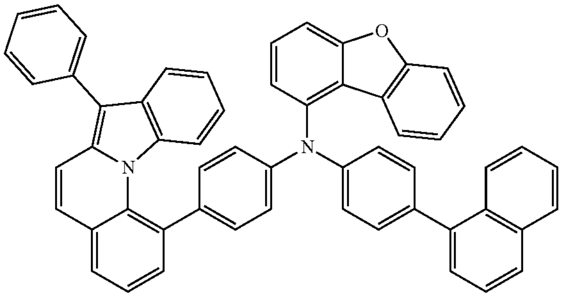
C8
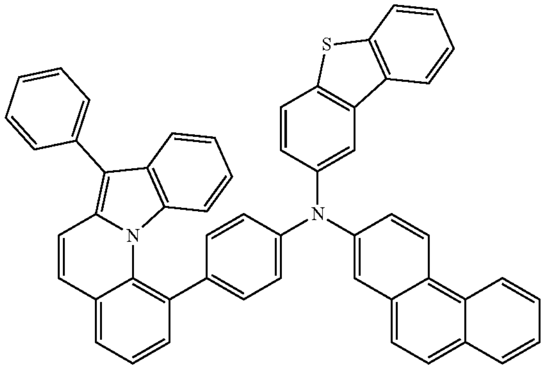
C9
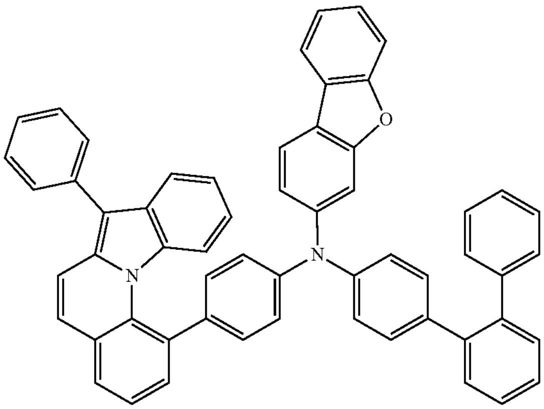
C10
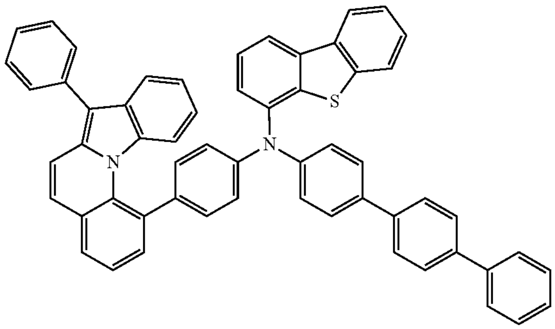

-continued
C11
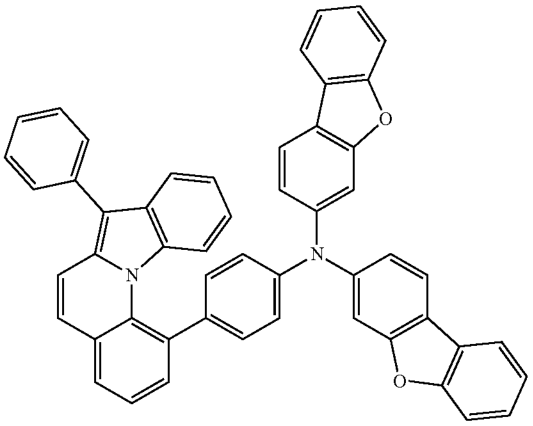
C12
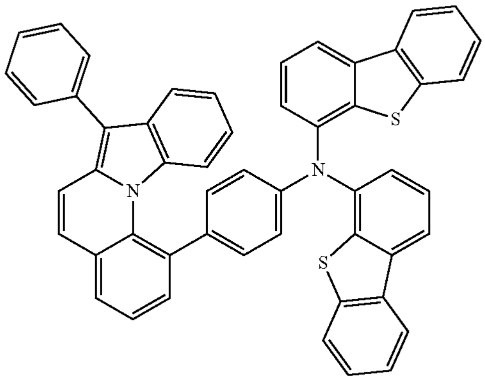
C13
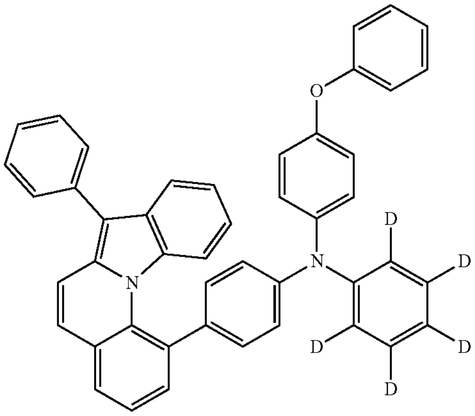
C14
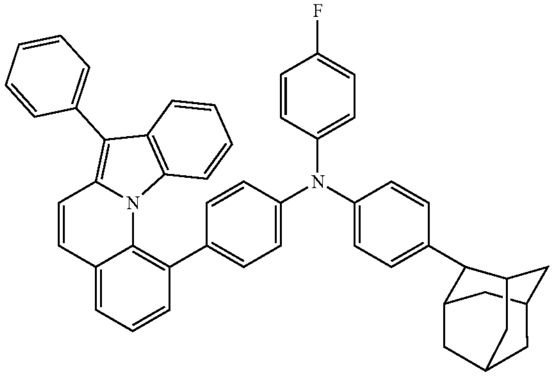
C15
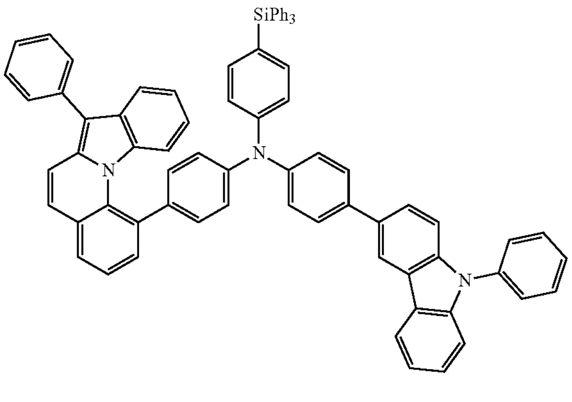
C16
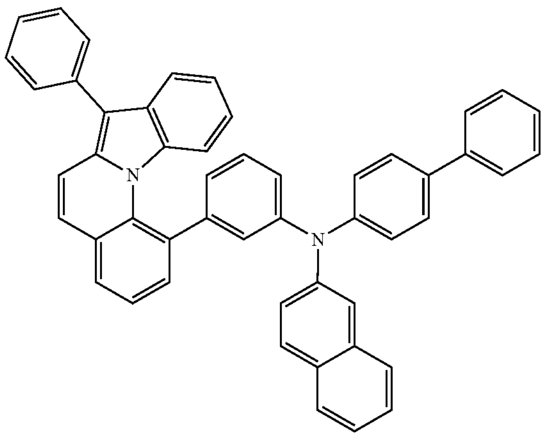

-continued
C17
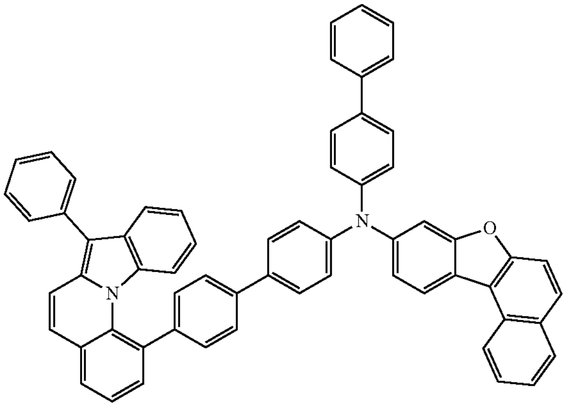
C18
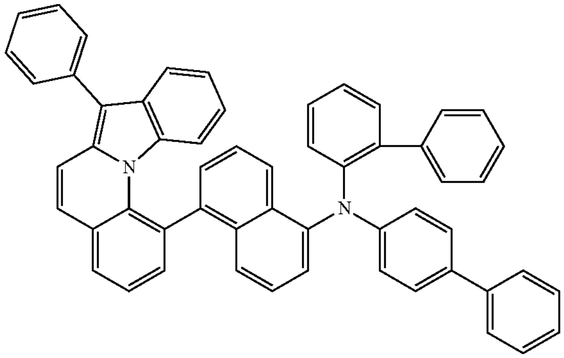
C19
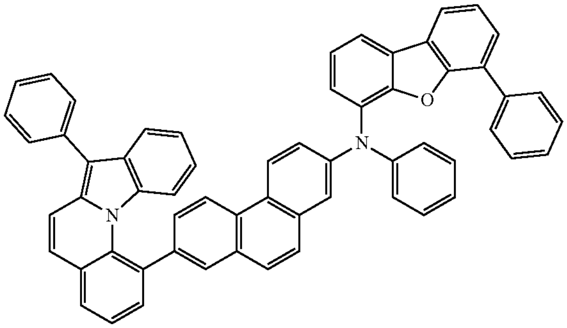
C20
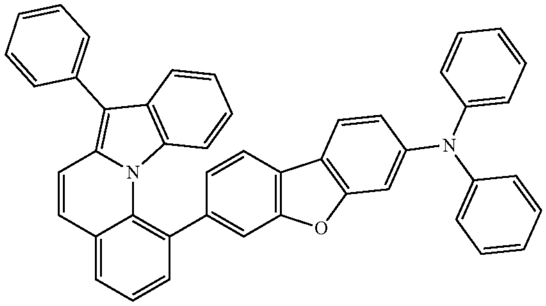
C21
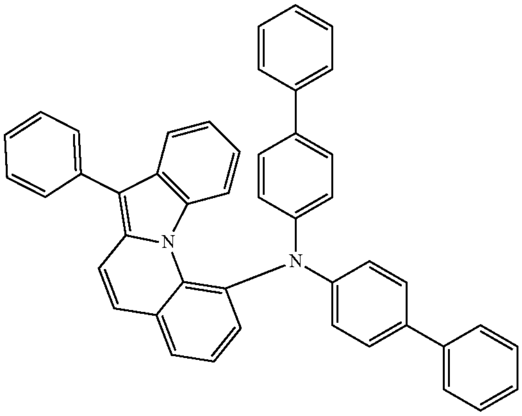
C22
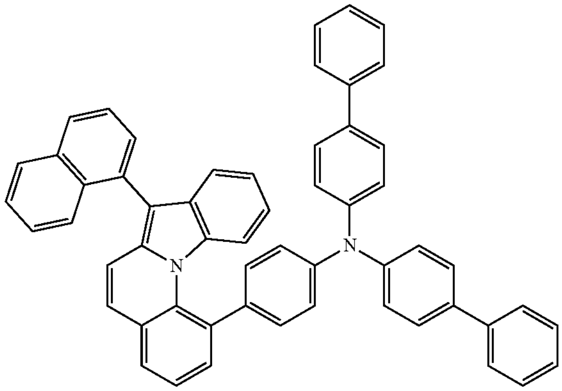
C23
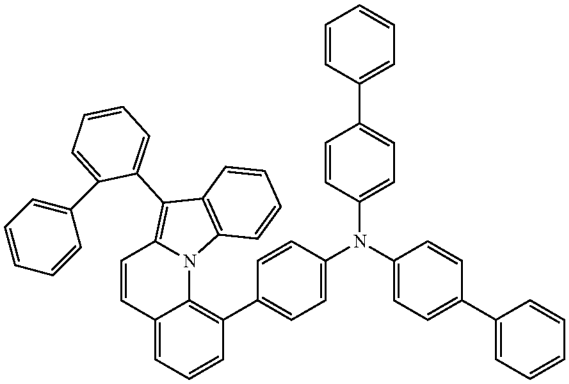
C24
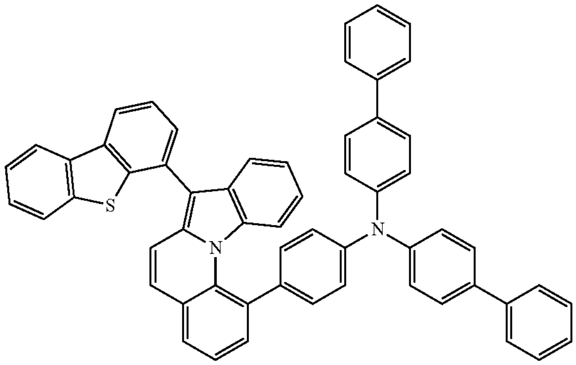

-continued
C25
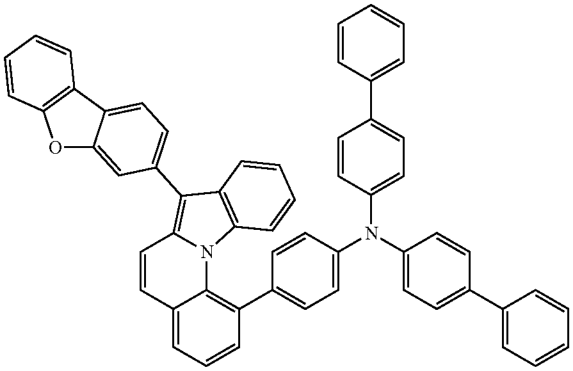
C26
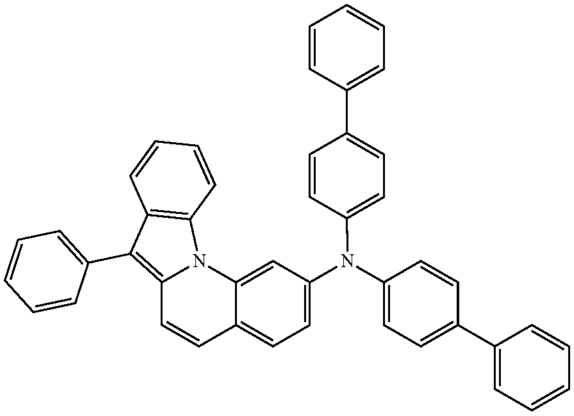
C27
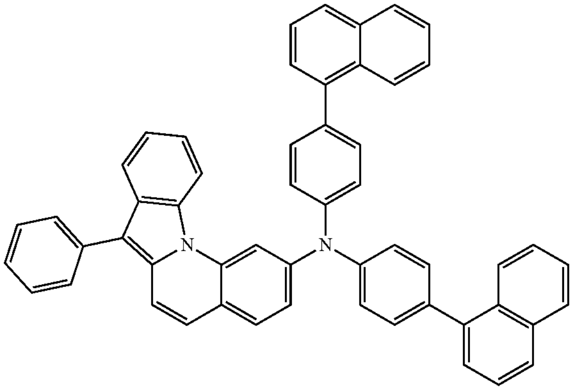
C28
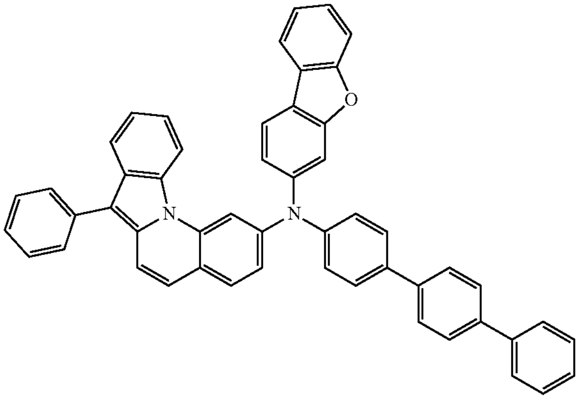
C29
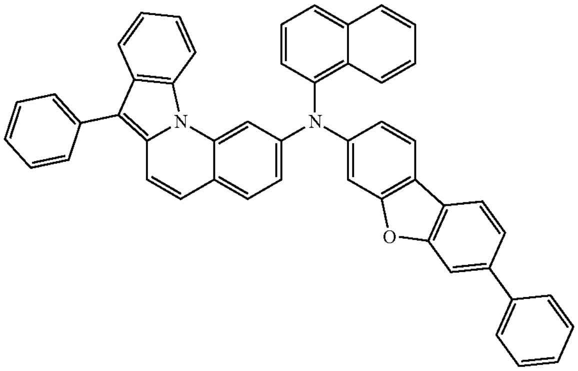
C30
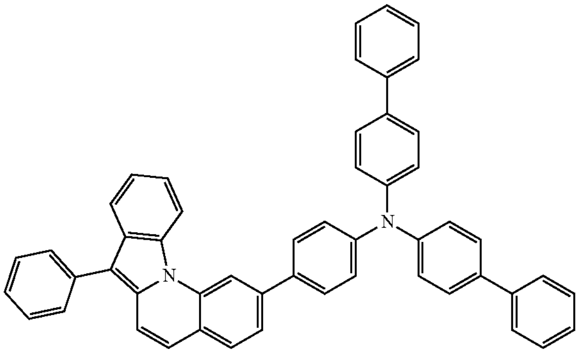

-continued
C31
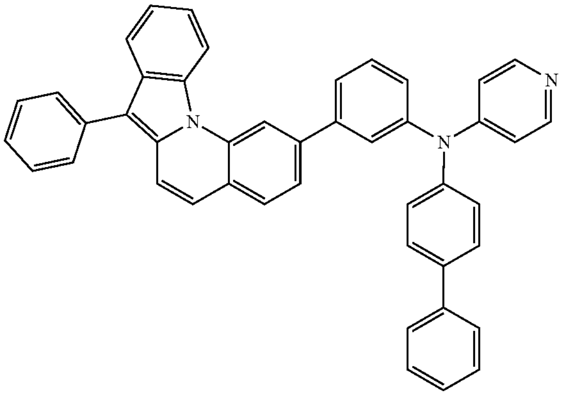
C32
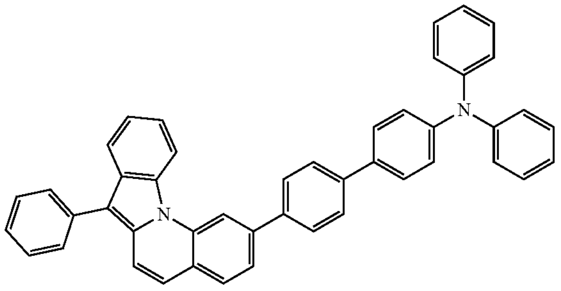
C33
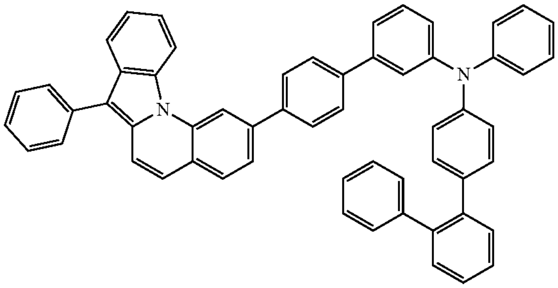
C34
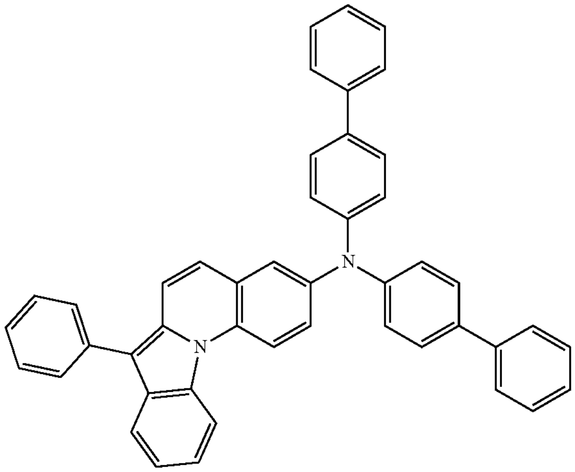
C35
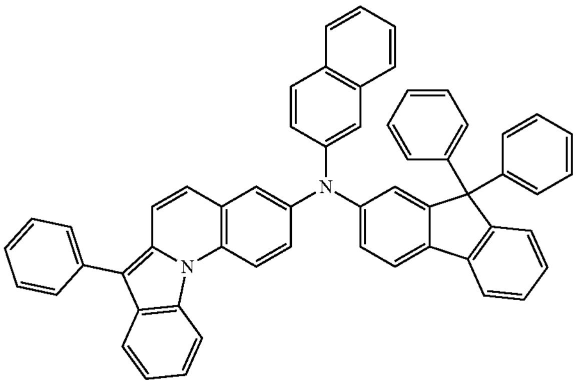
C36
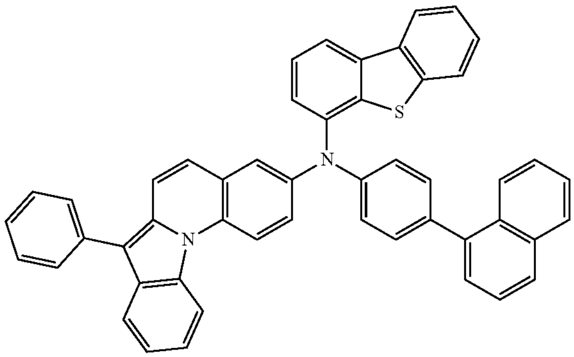

-continued
C37
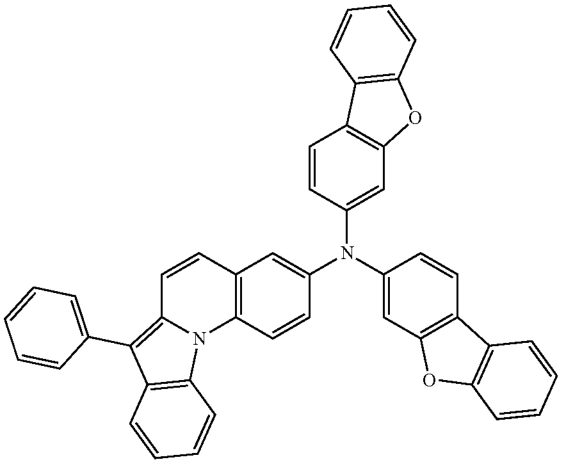
C38
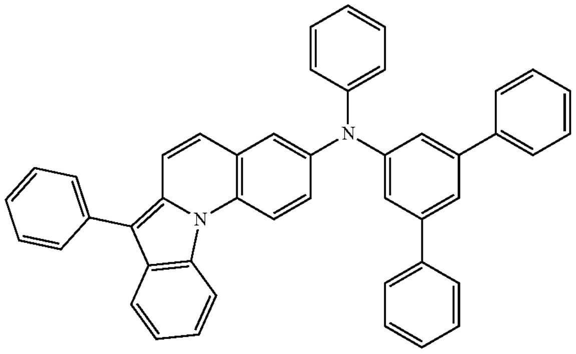
C39
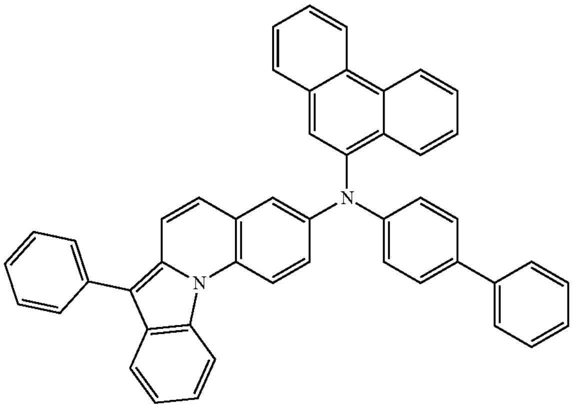
C40
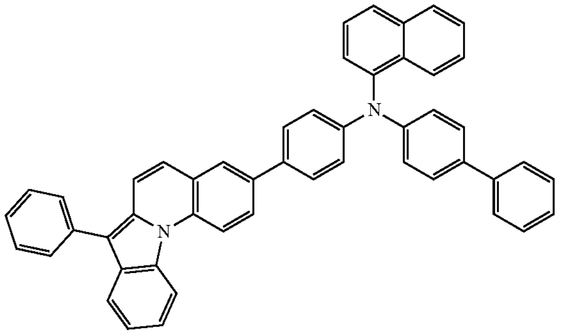
C41
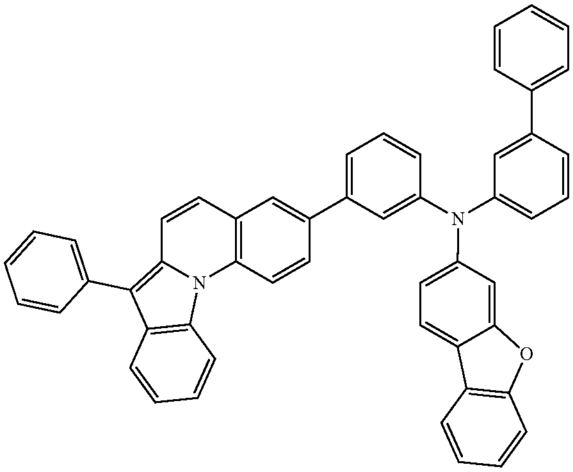
C42
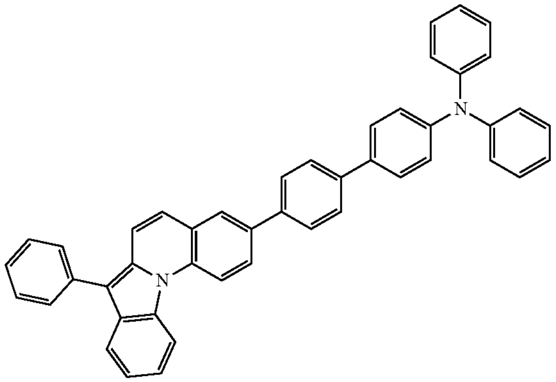

-continued
C43
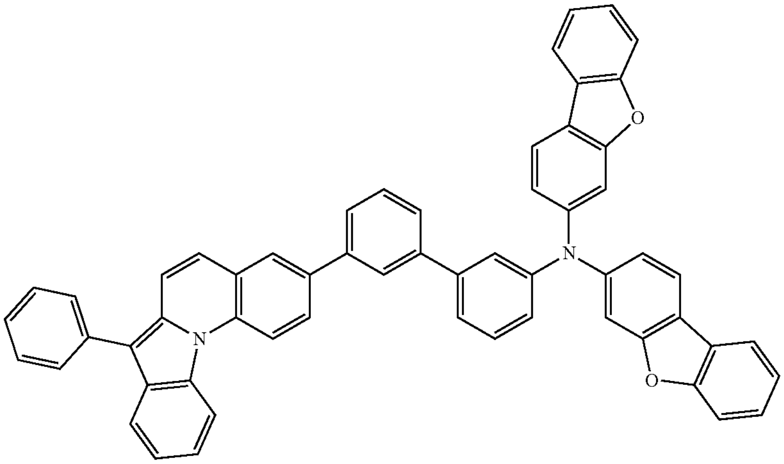
C44
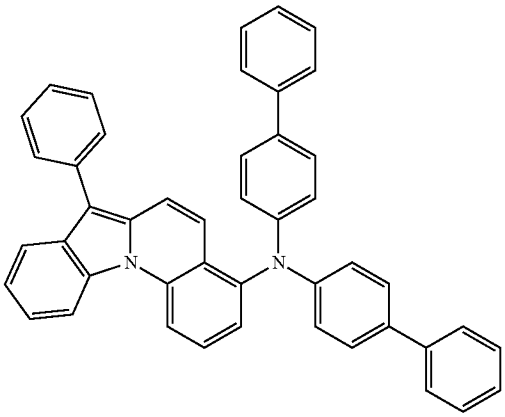
C45
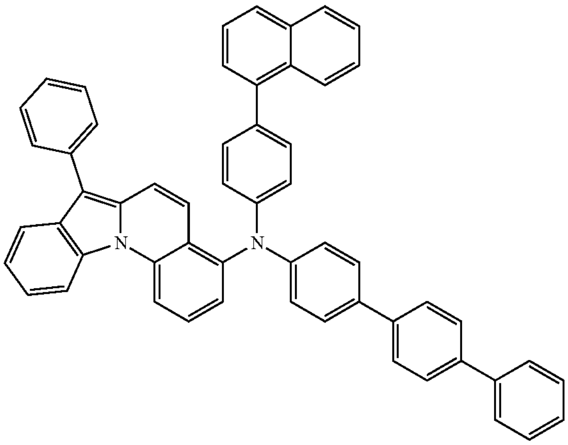
C46
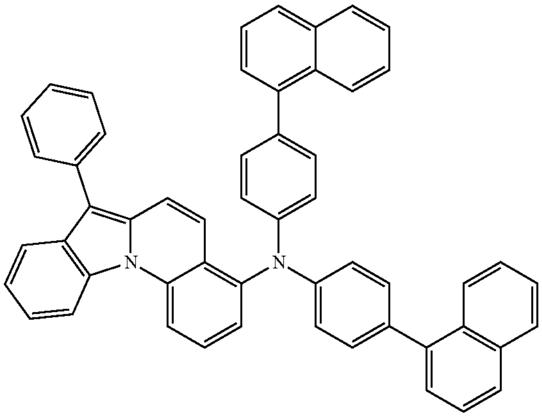
C47
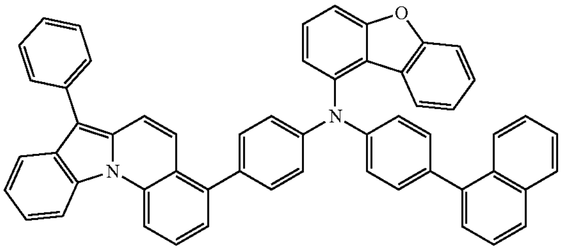

-continued
C48
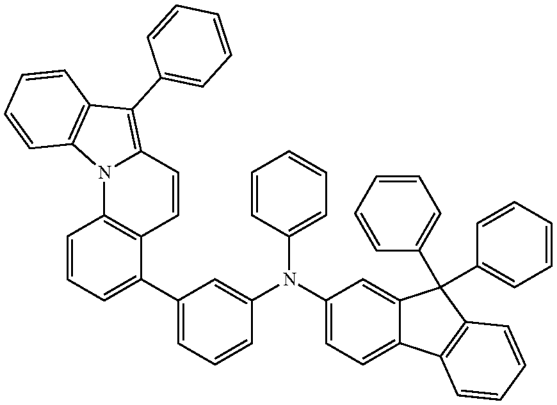
C49
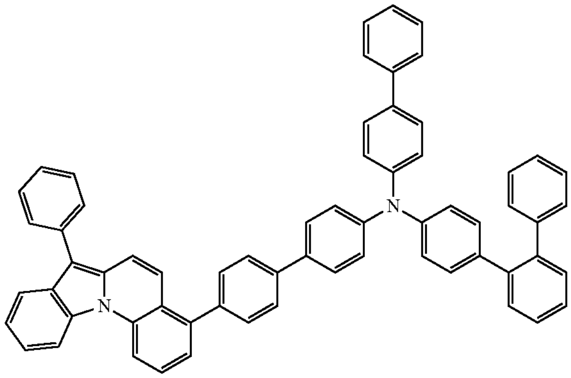
C50
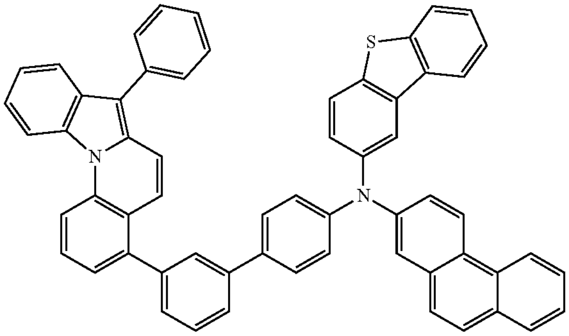
C51
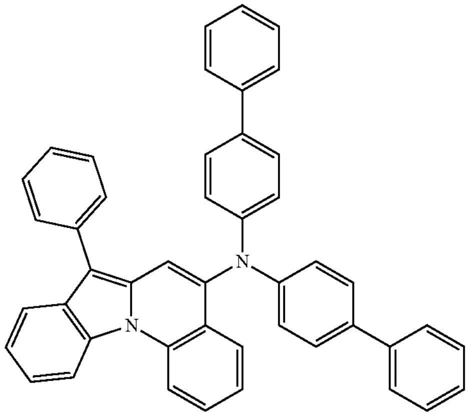
C52
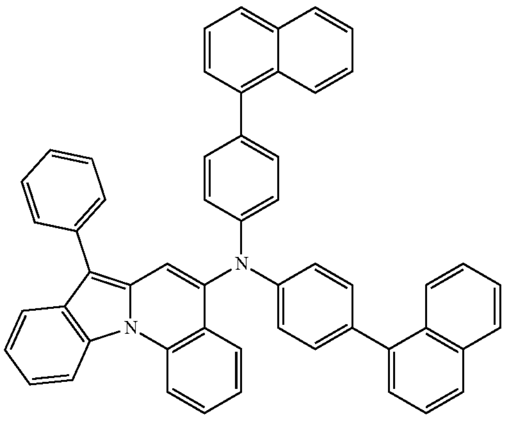
C53
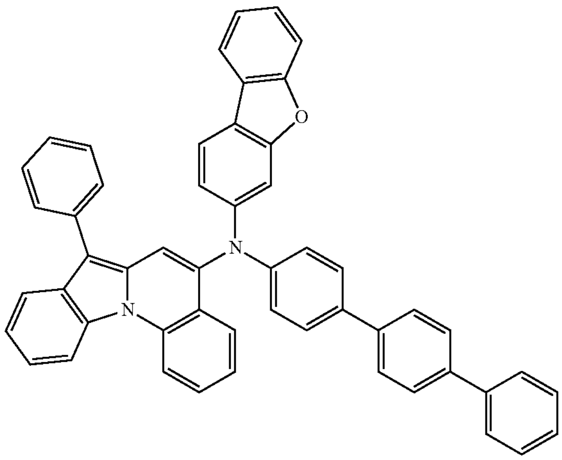

-continued
C54
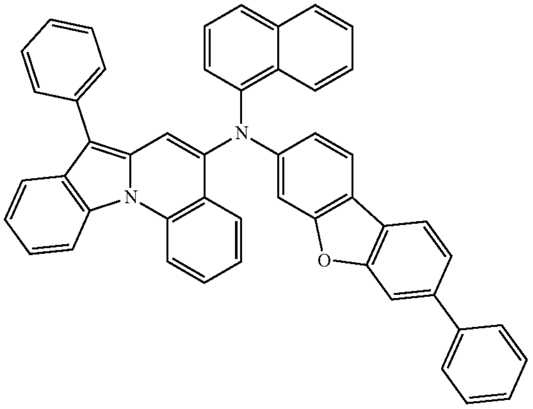
C55
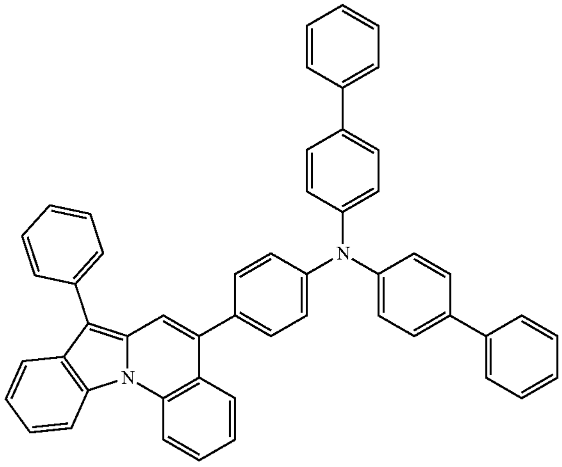
C56
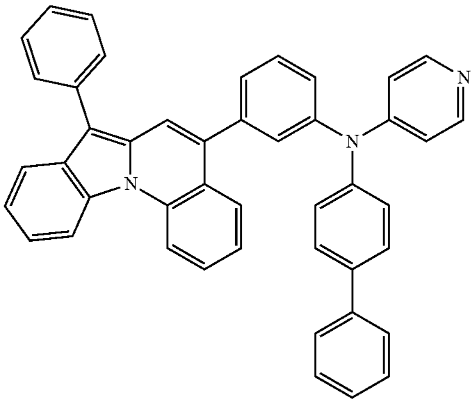
C57
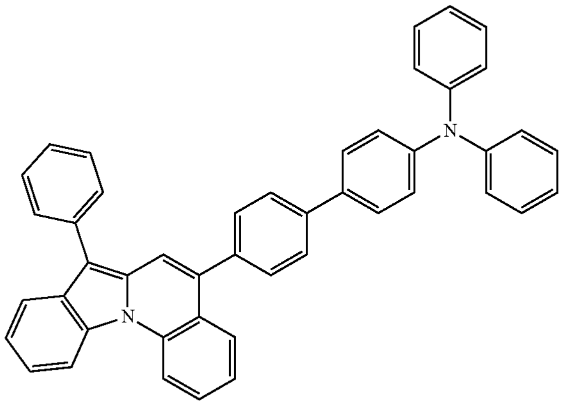
C58
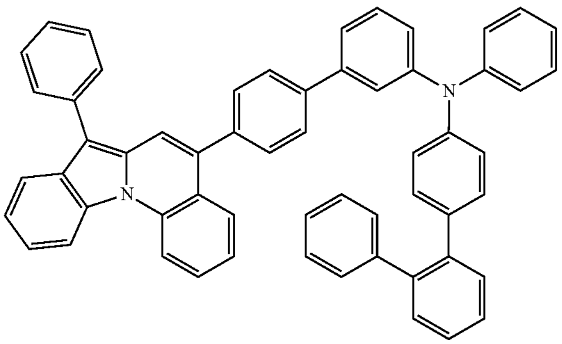
C59
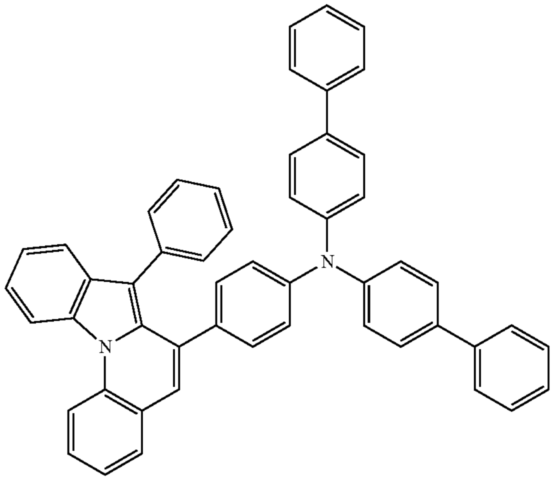

-continued
C60
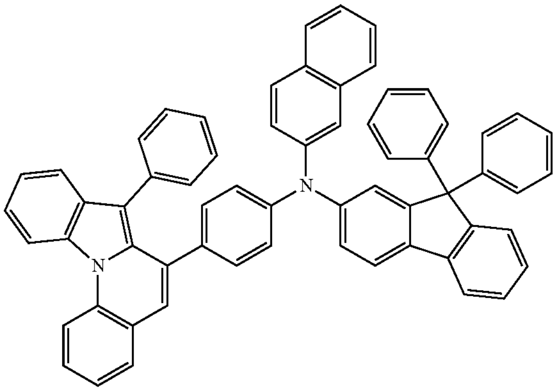
C61
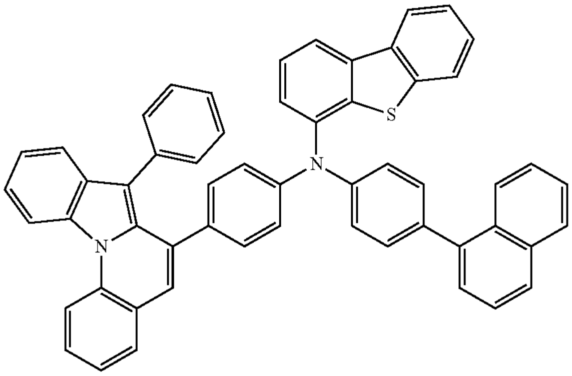
C62
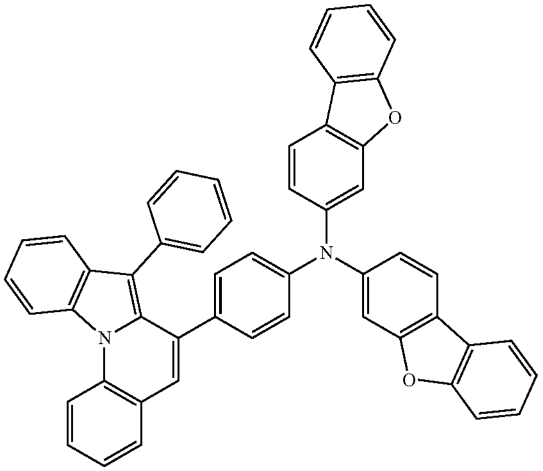
C63
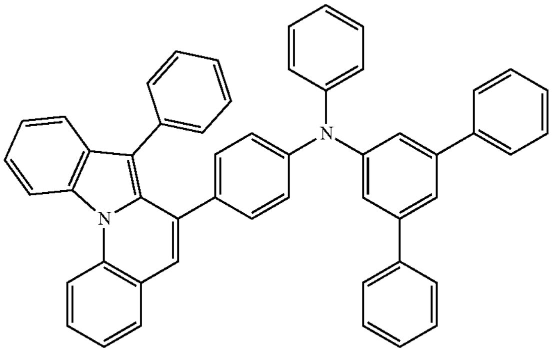
C64
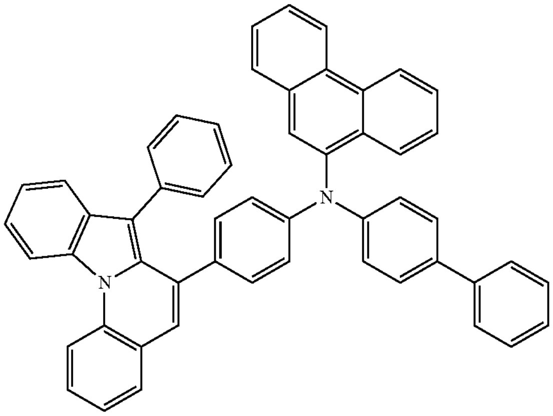
C65
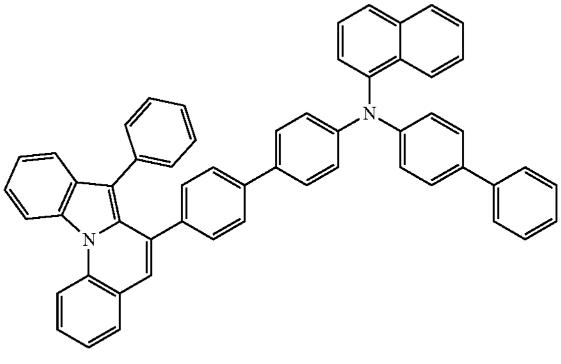

-continued
C66
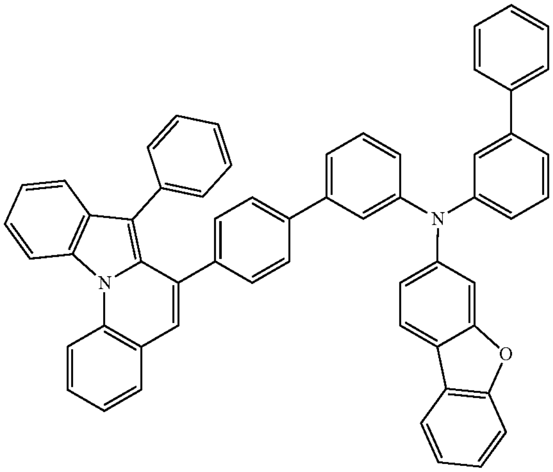
C67
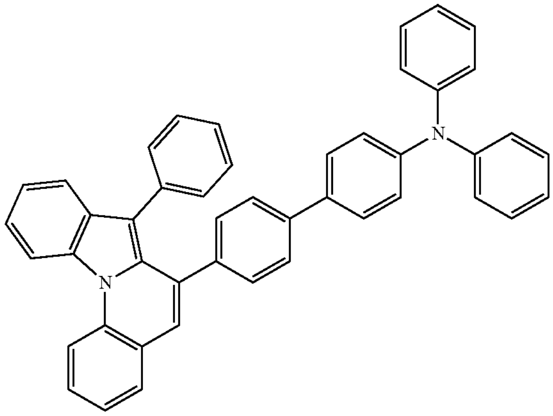
C68
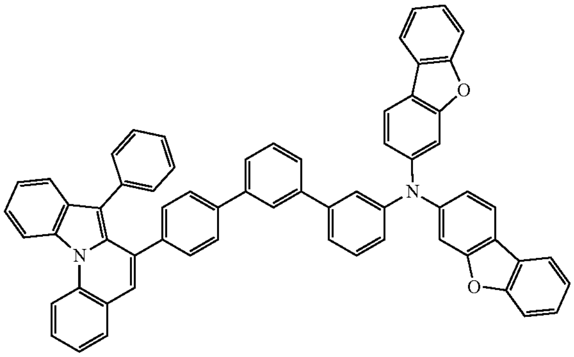
C69
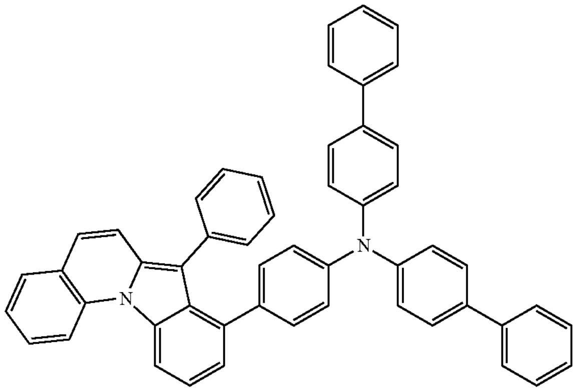
C70
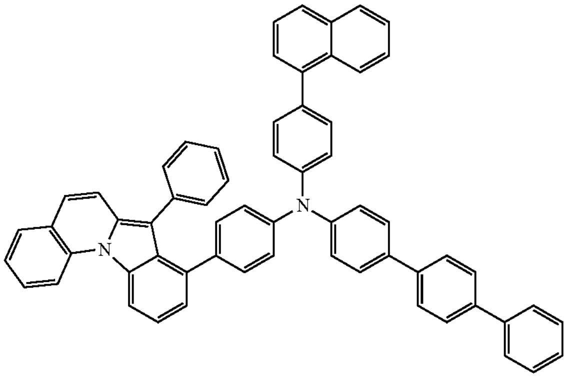
C71
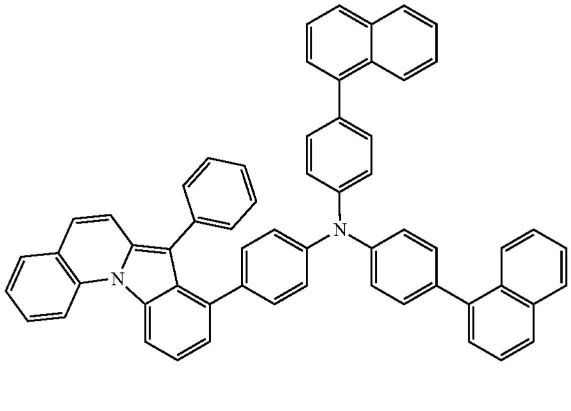

-continued
C72
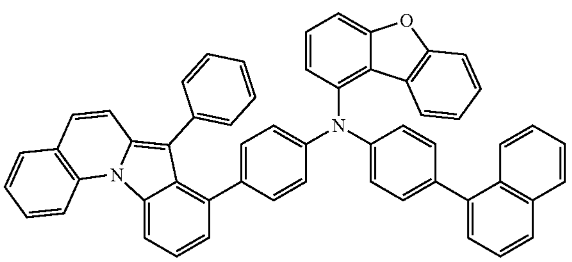
C73
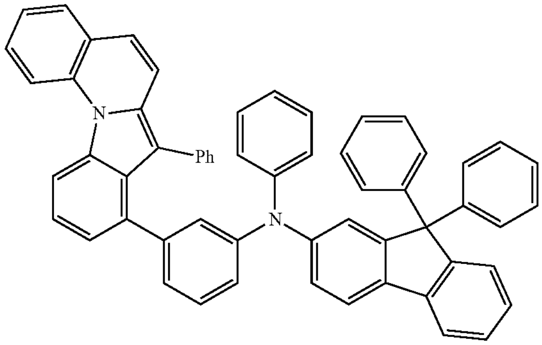
C74
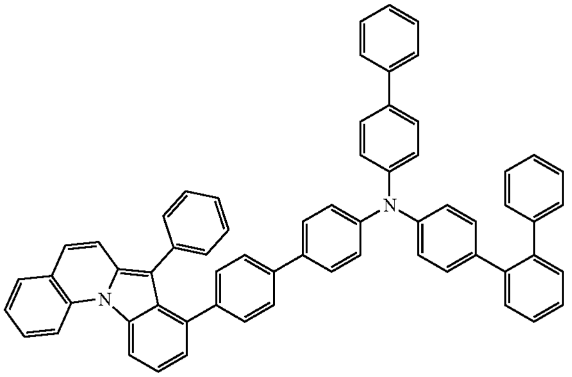
C75
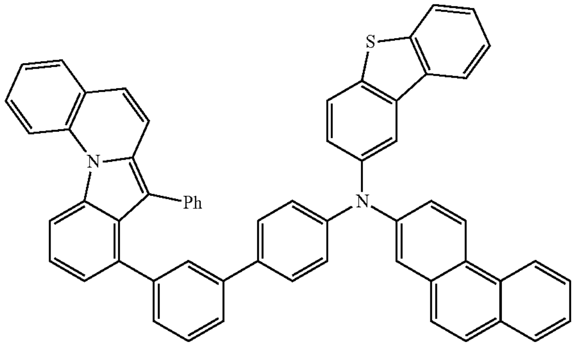
C76
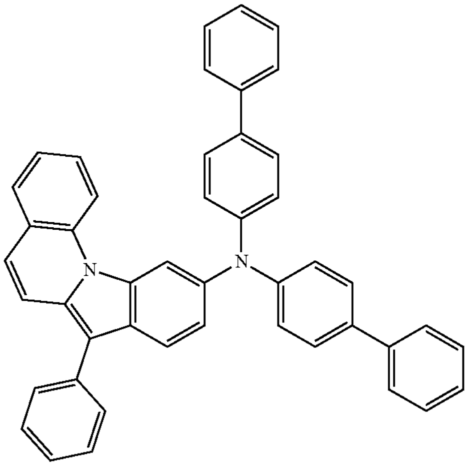
C77
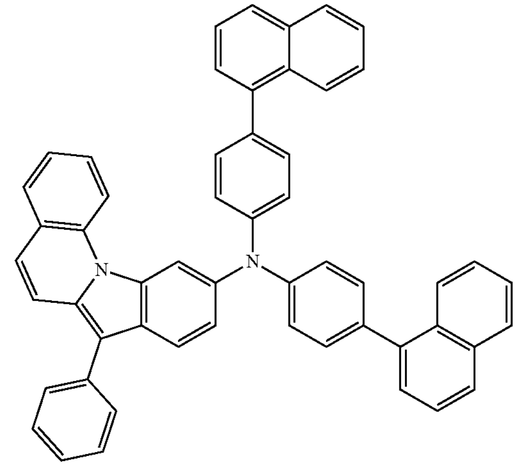

-continued
C78
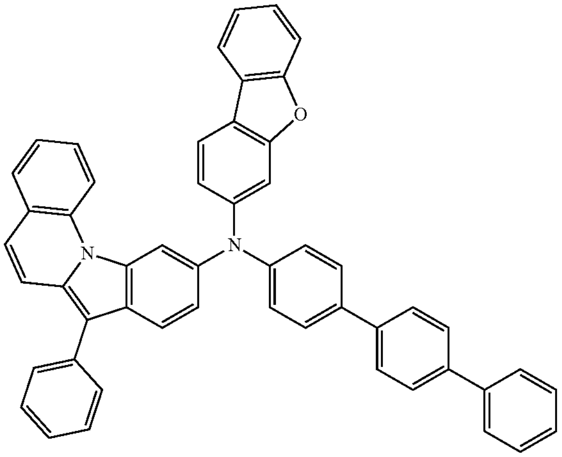
C79
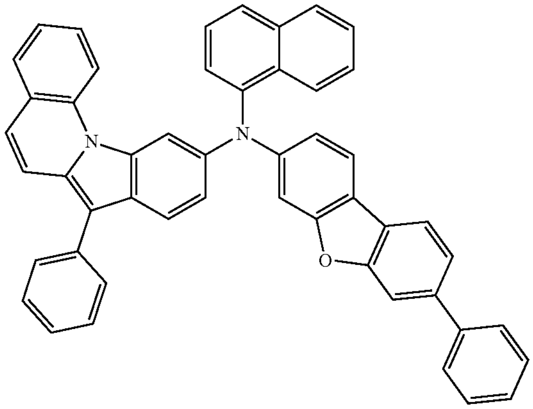
C80
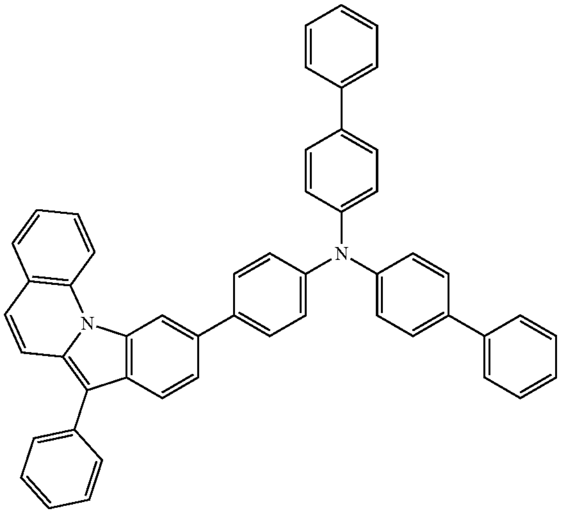
C81
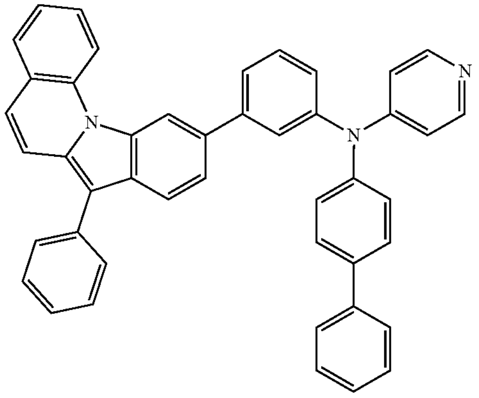
C82
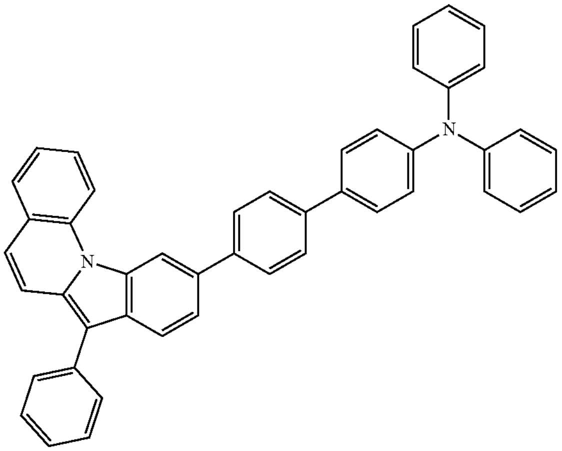
C83
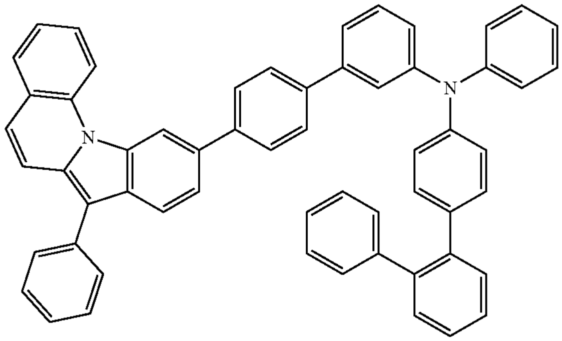

-continued
C84
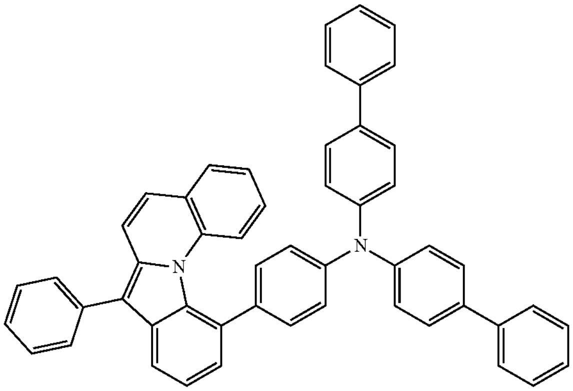
C85
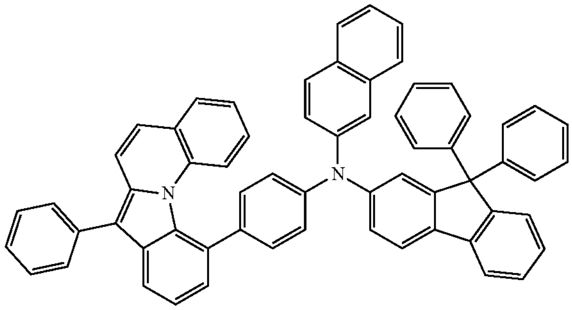
C86
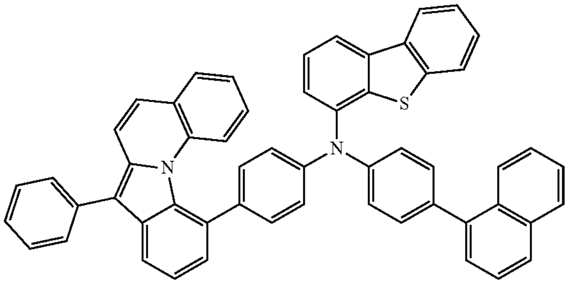
C87
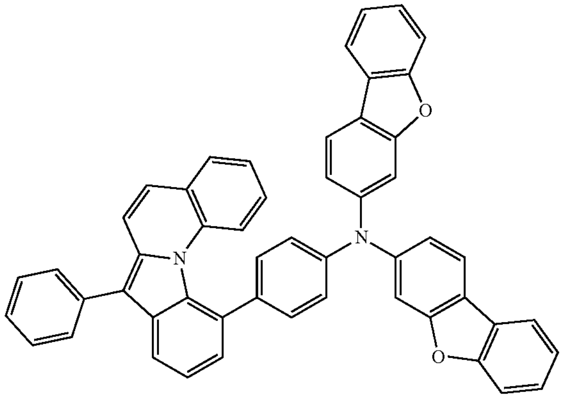
C88
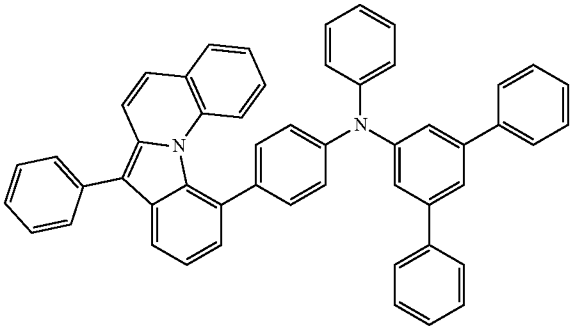
C89
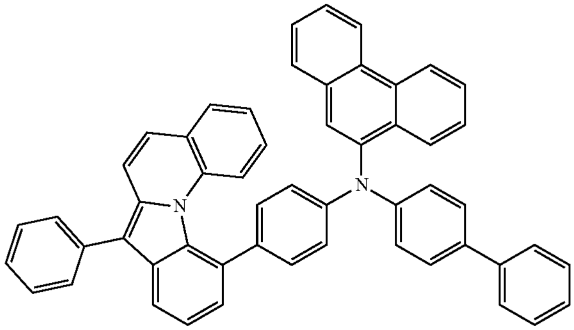
C90
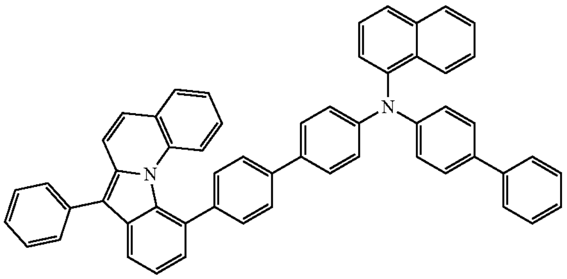
C91
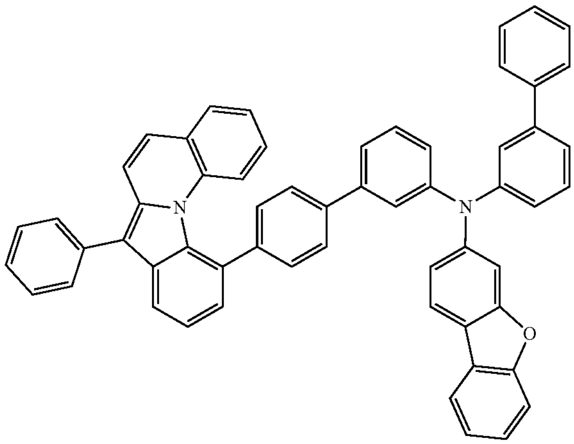

-continued
C92
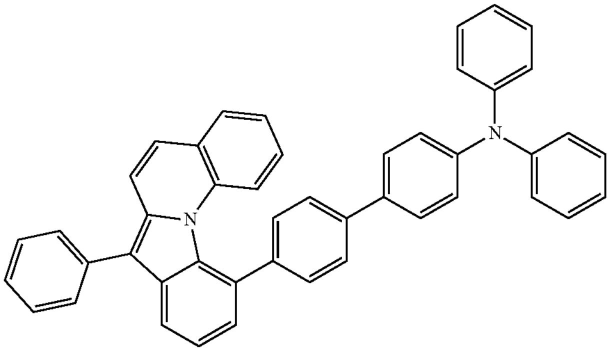
C93
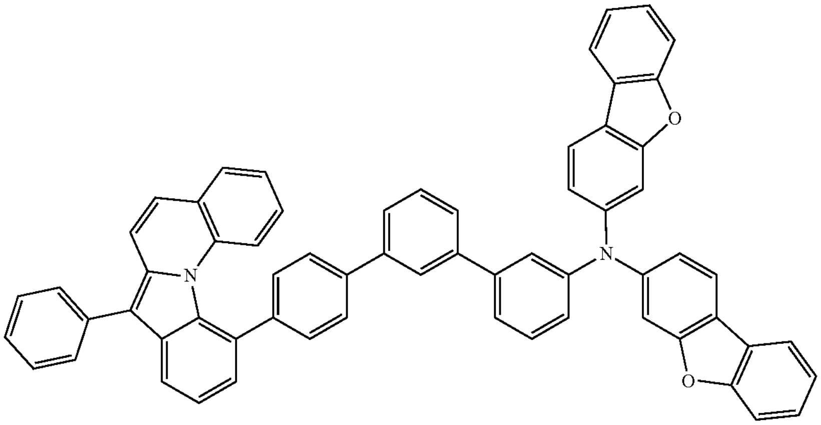
C94
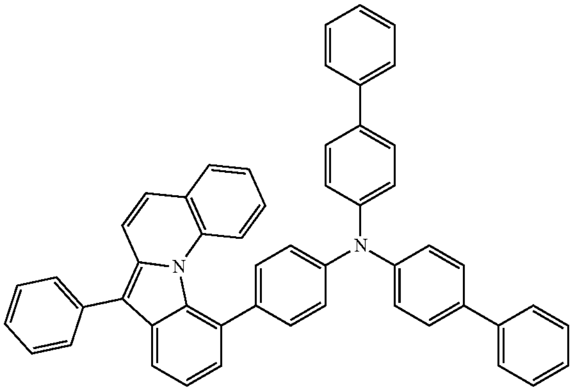
C95
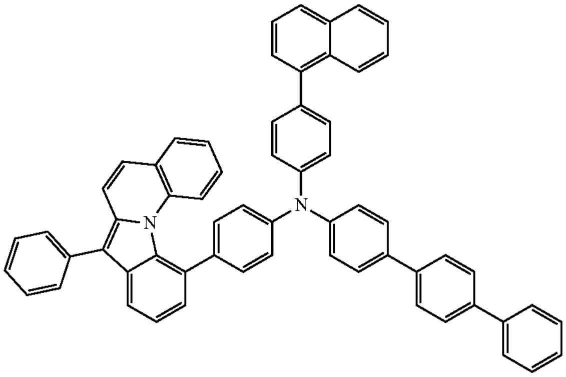
C96
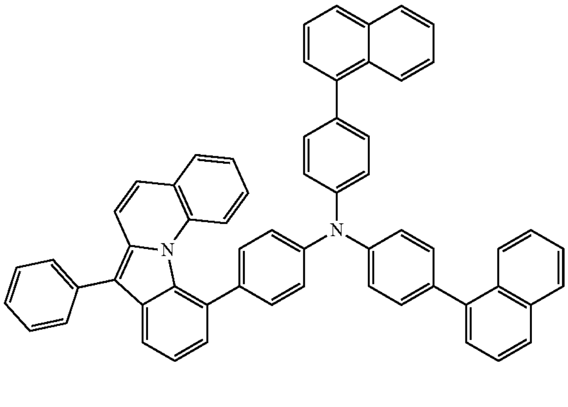
C97
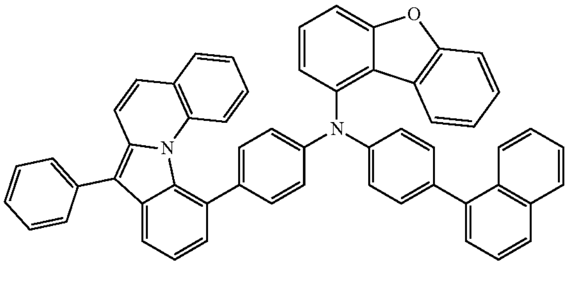

D1
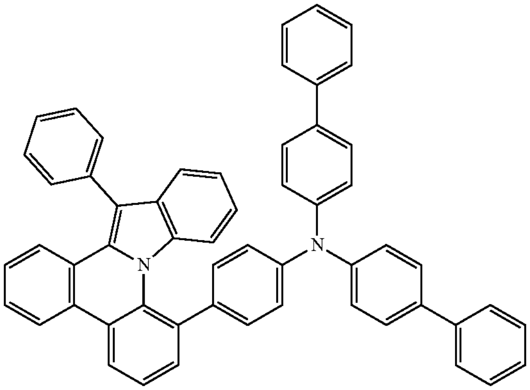
D2
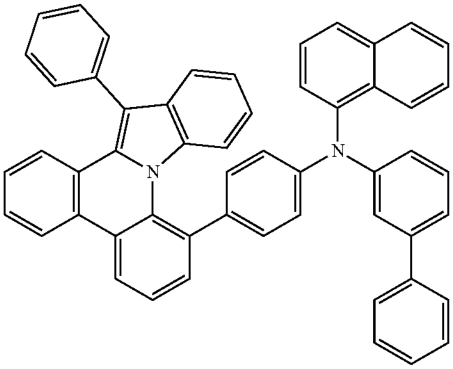
D3
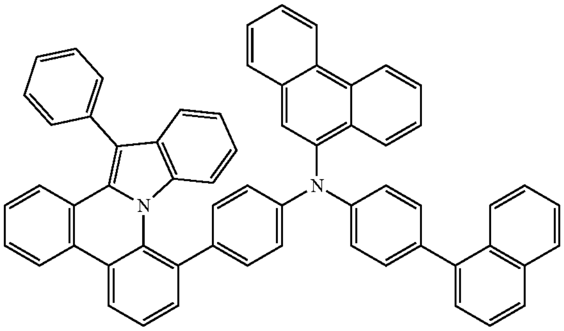
D4
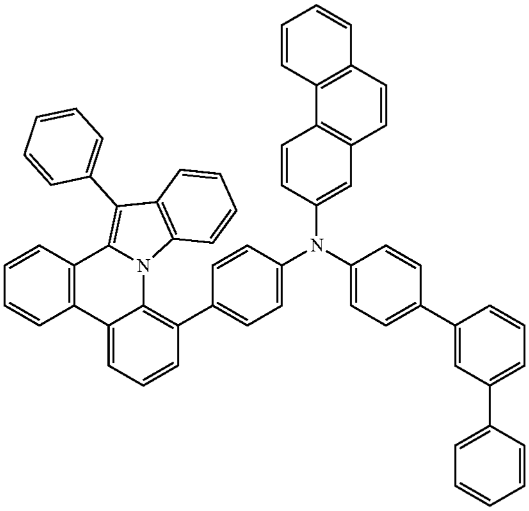
D5
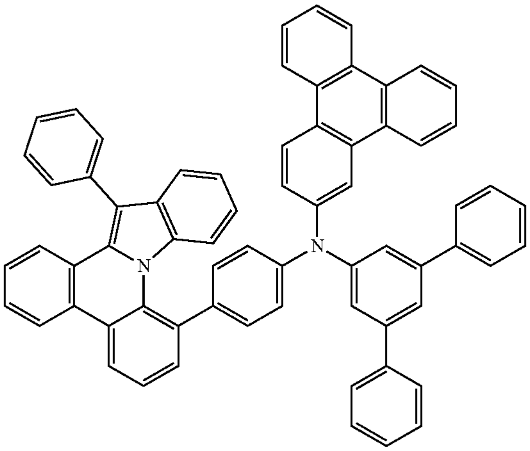
D6
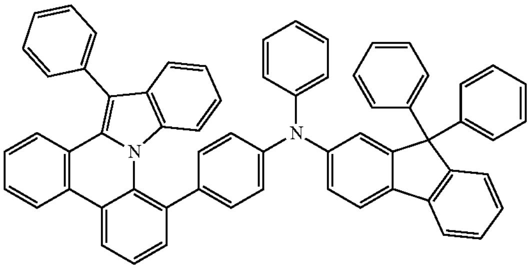

-continued
D7
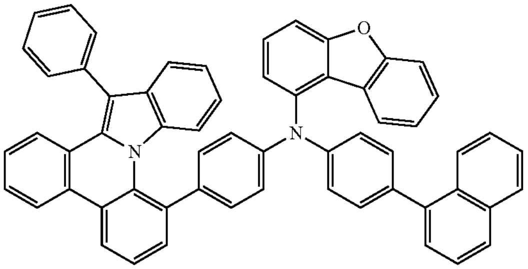
D8
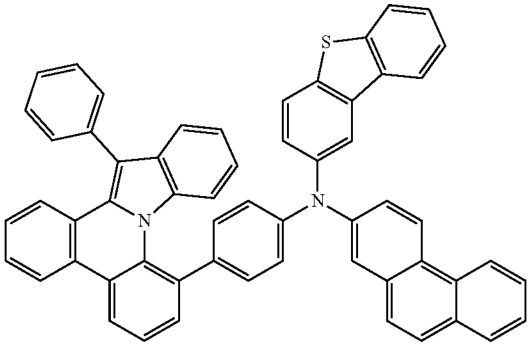
D9
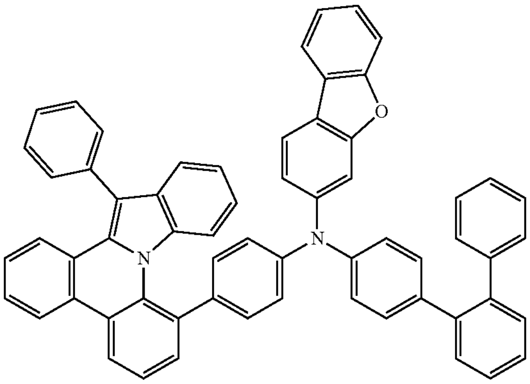
D10
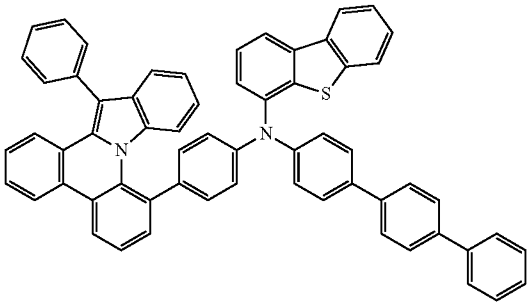
D11
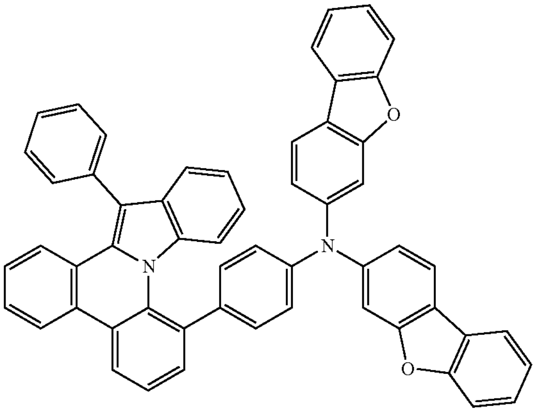
D12
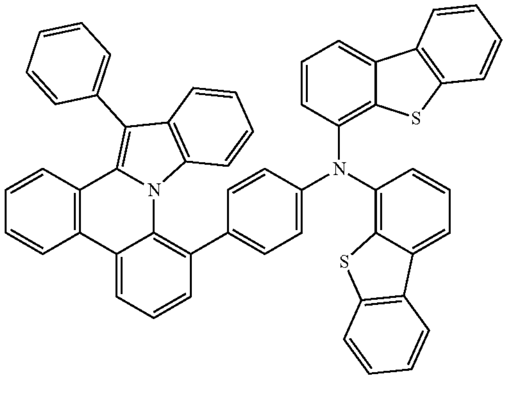
D13
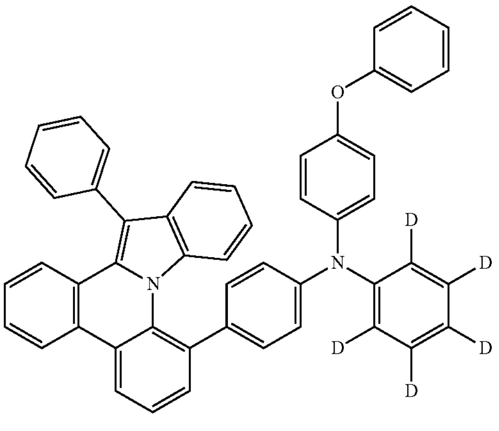
D14
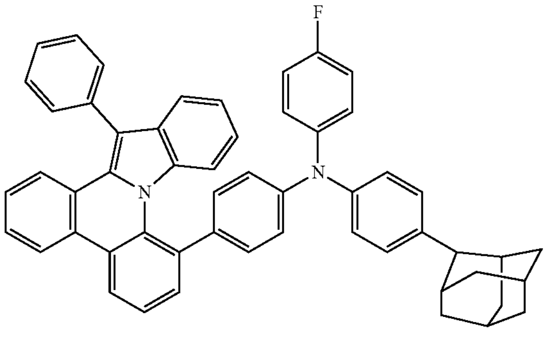

-continued
D15
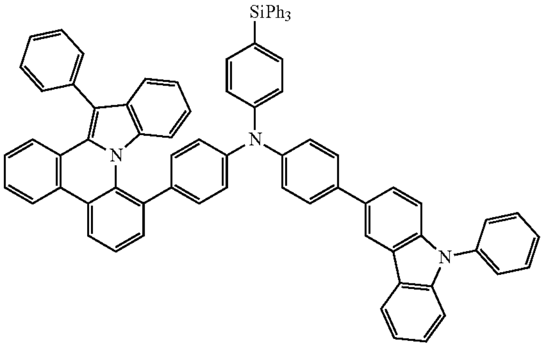
D16
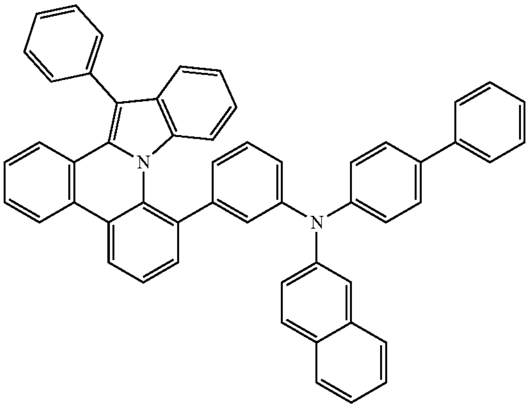
D17
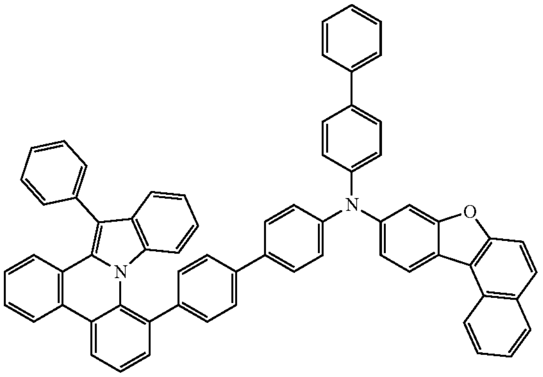
D18
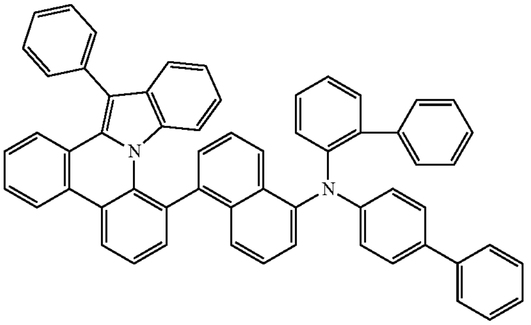
D19
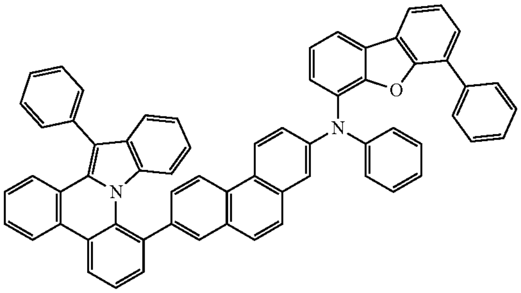
D20
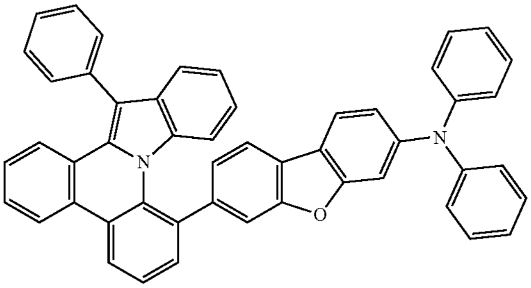
D21
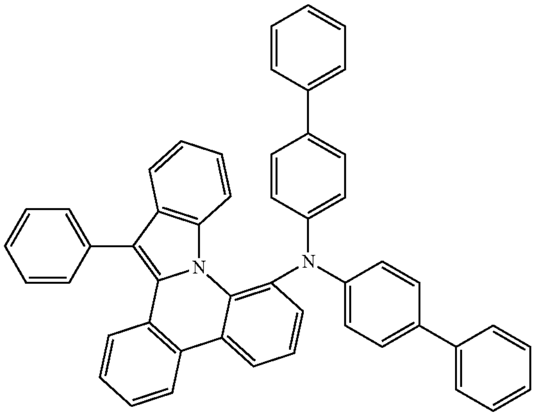
D22
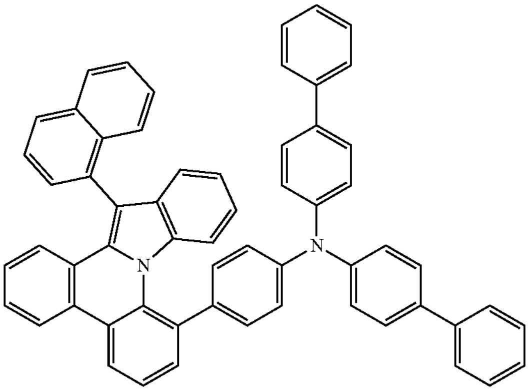

-continued
D23
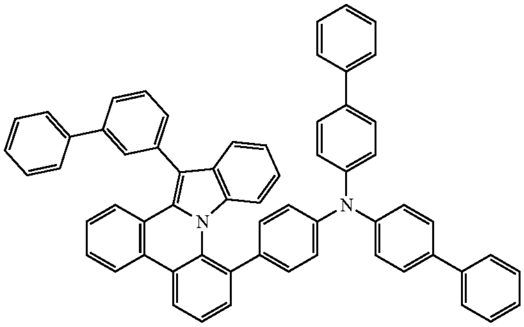
D24
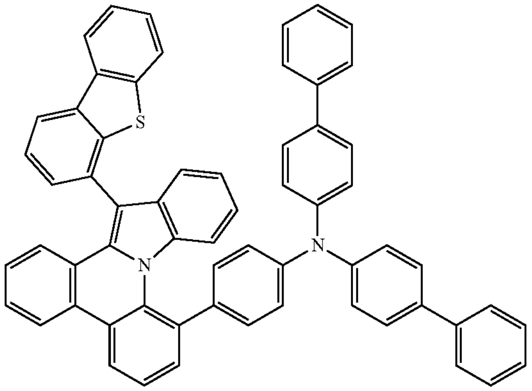
D25
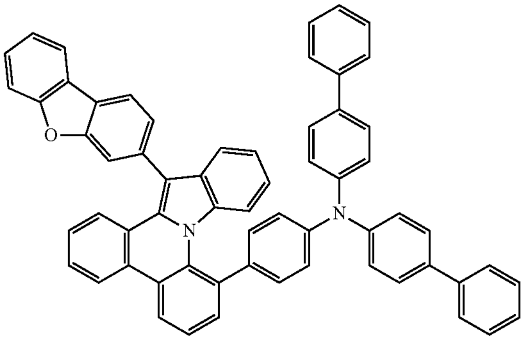
D26
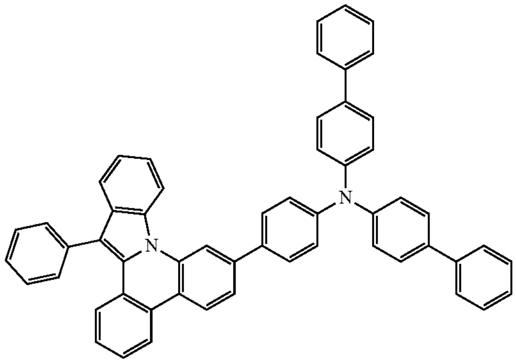
D27
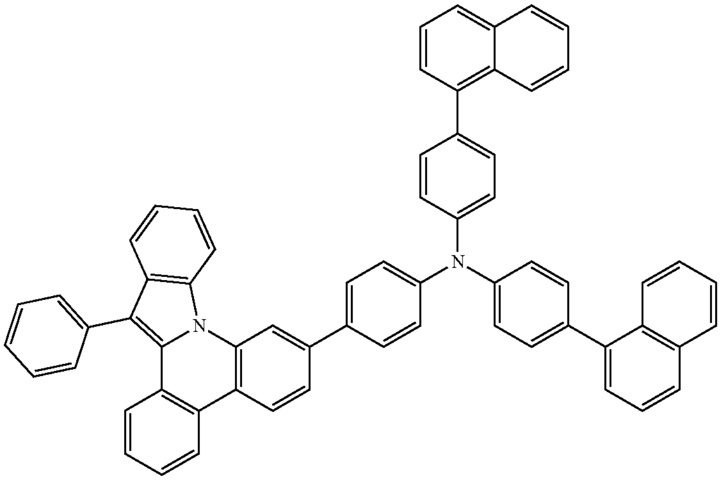

-continued
D28
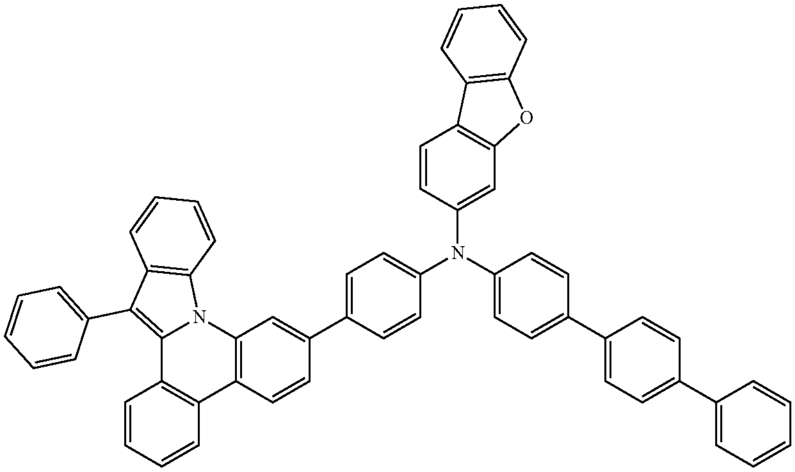
D29
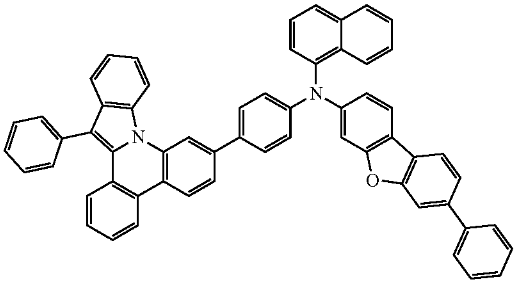
D30
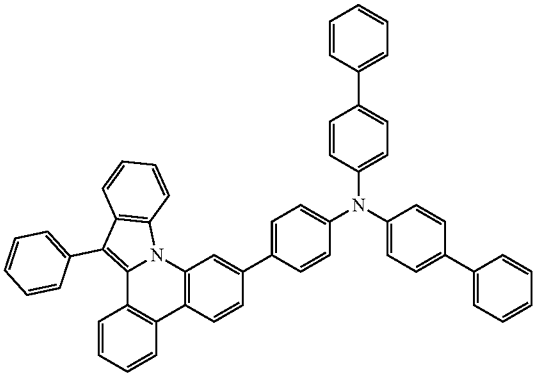
D31
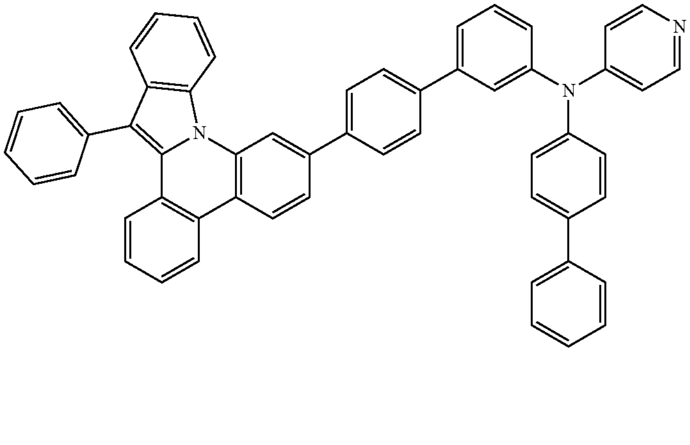

-continued
D32
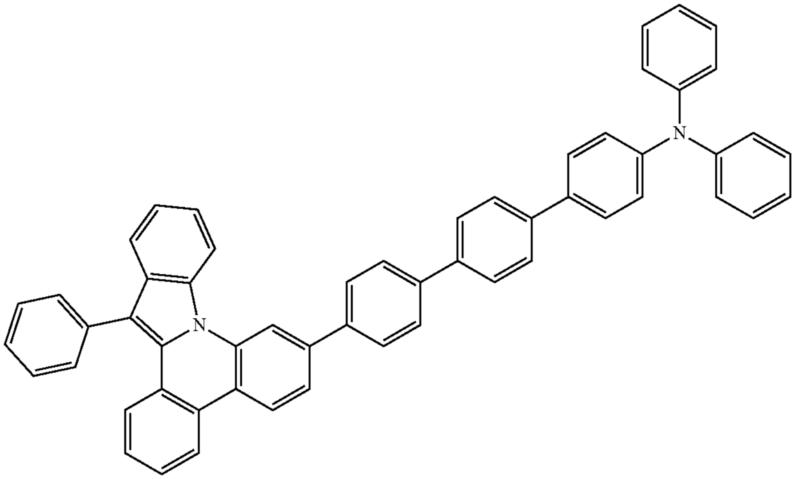
D33
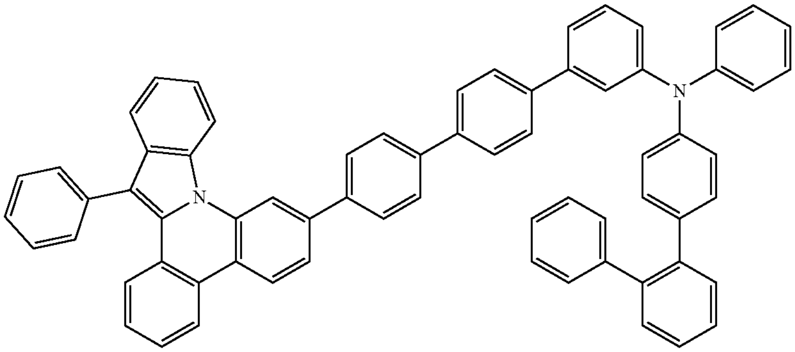
D34
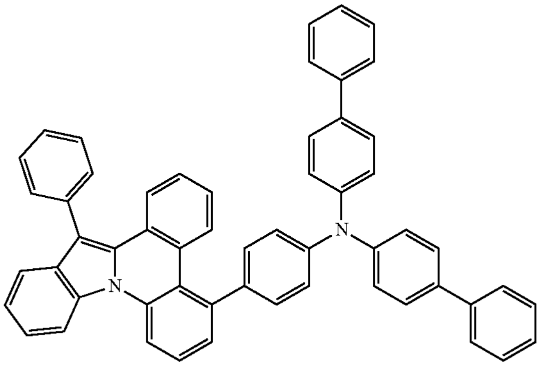
D35
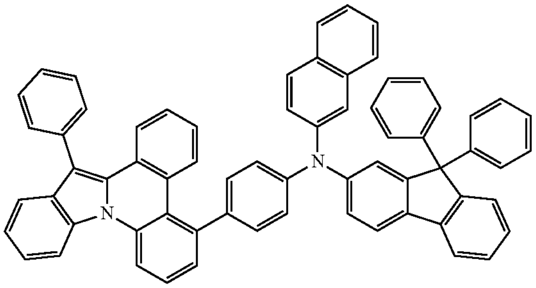
D36
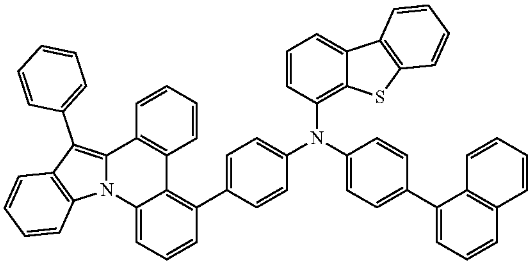
D37
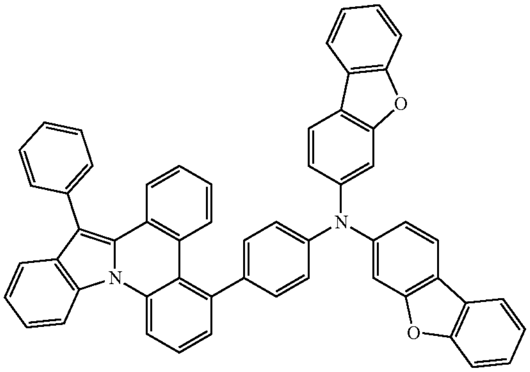

-continued
D38
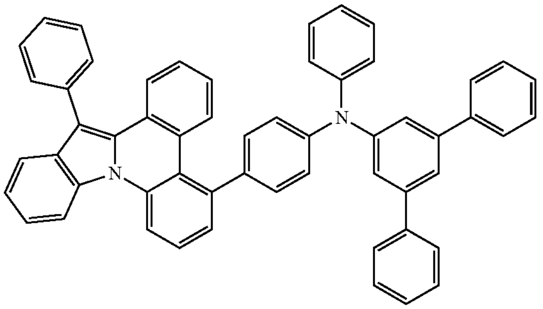
D39
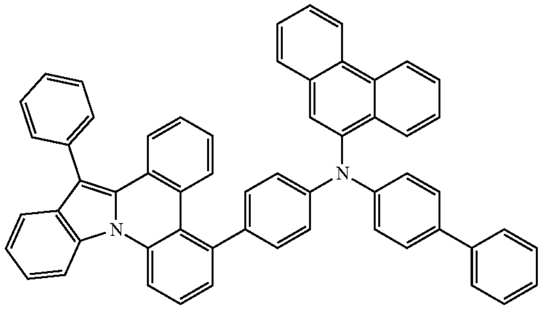
D40
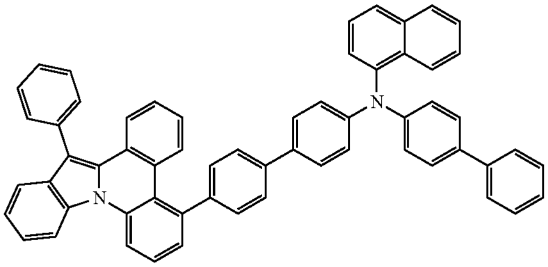
D41
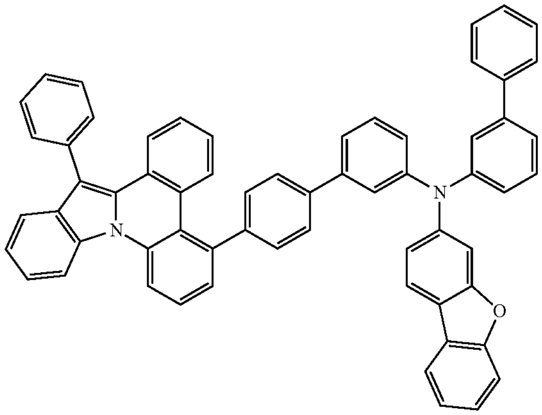
D42
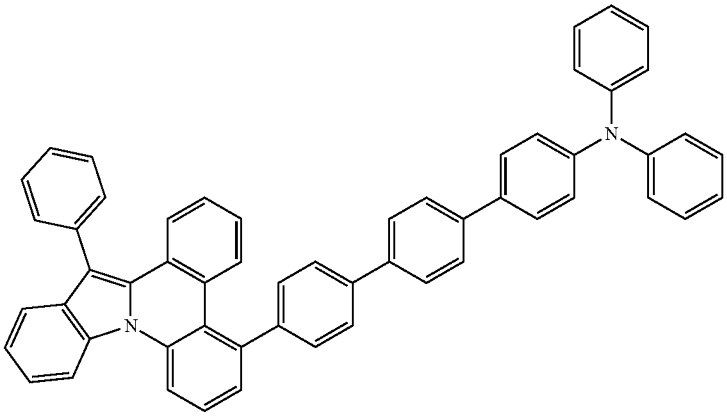
D43
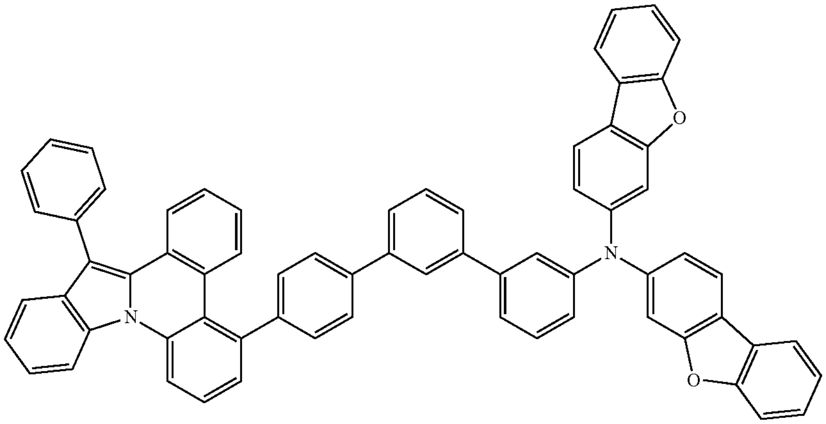

-continued
D44
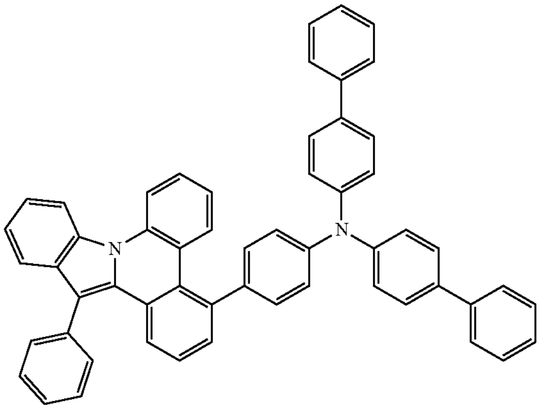
D45
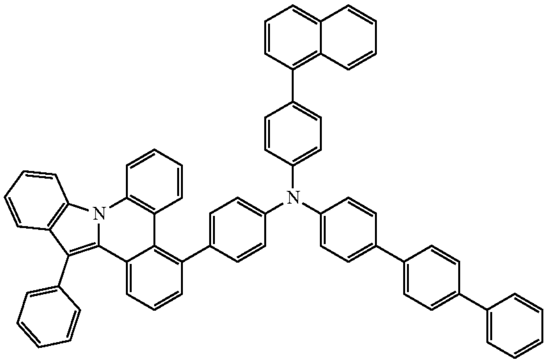
D46
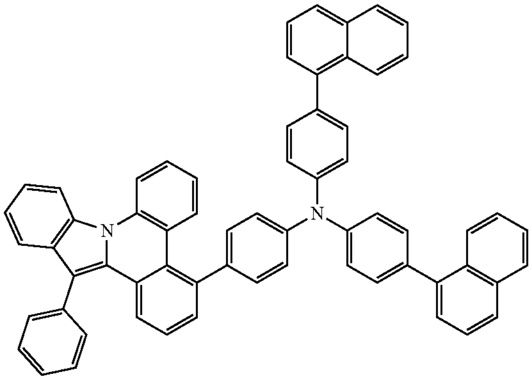
D47
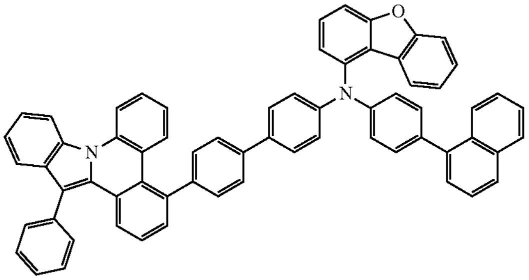
D48
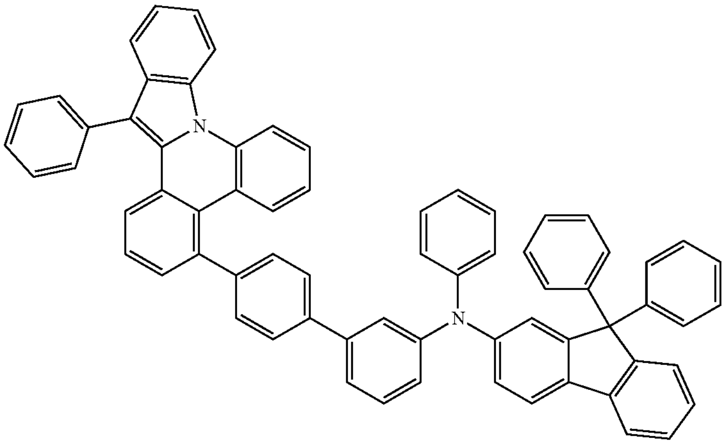

-continued
D49
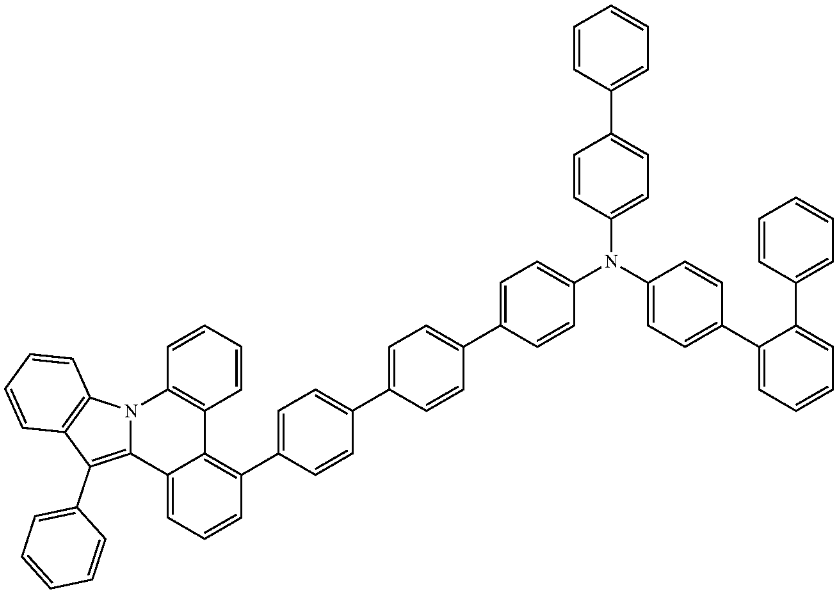
D50
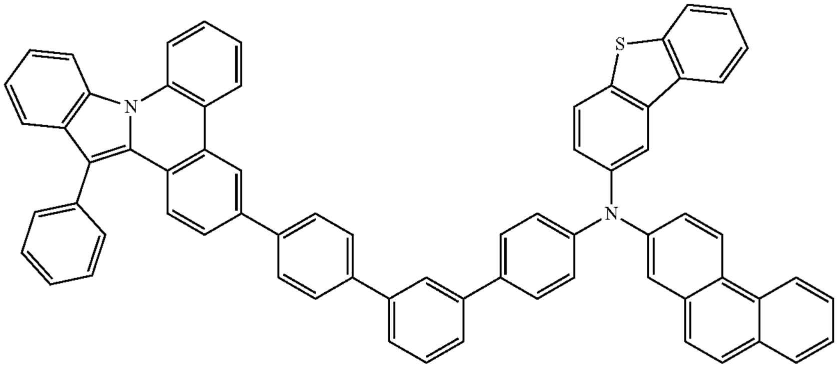
D51
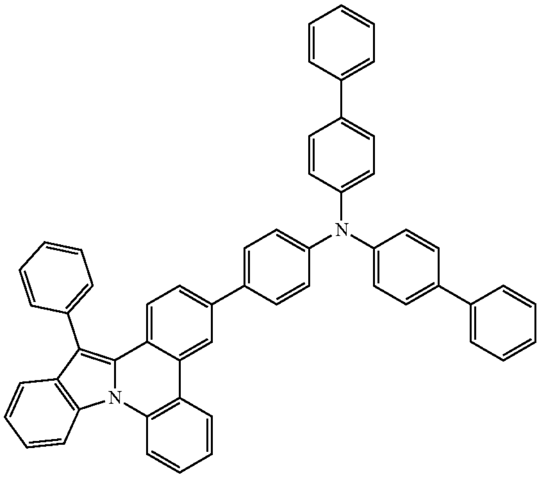
D52
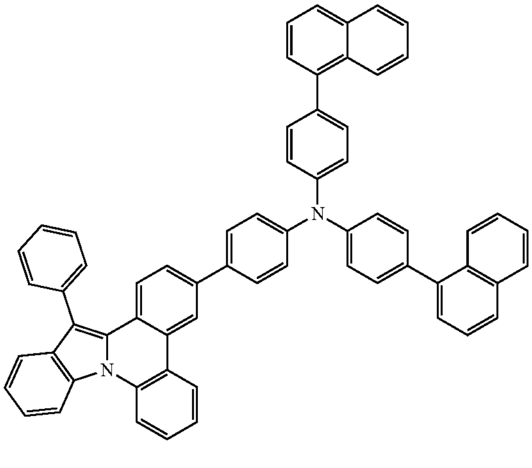

-continued
E53
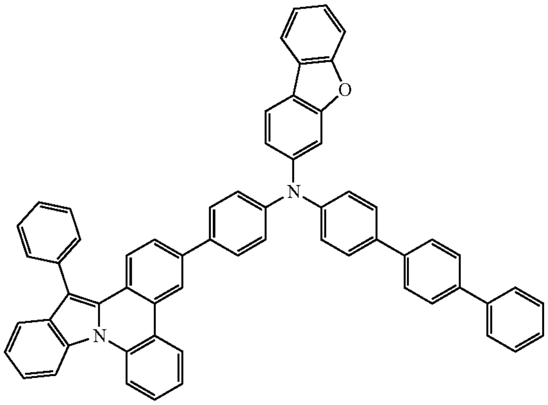
D54
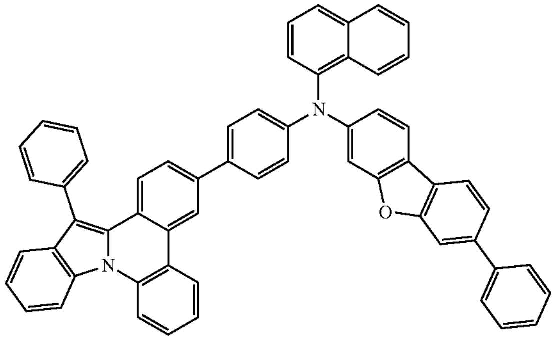
D55
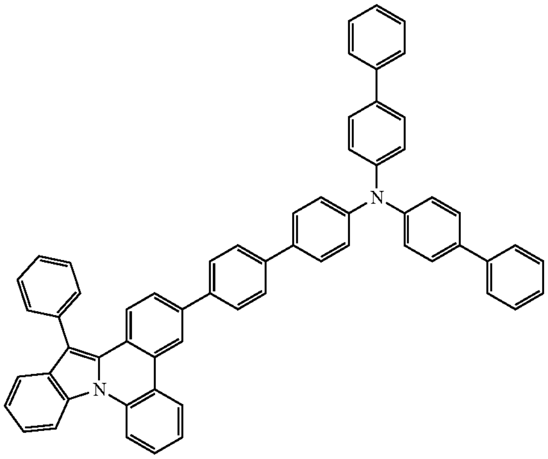
D56
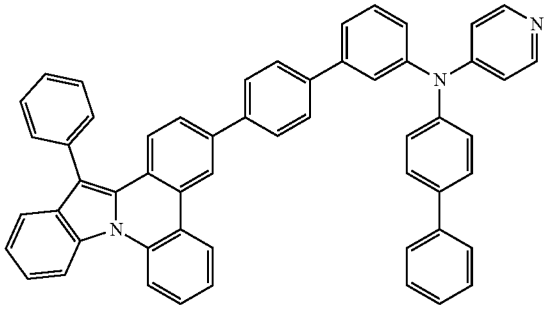
D57
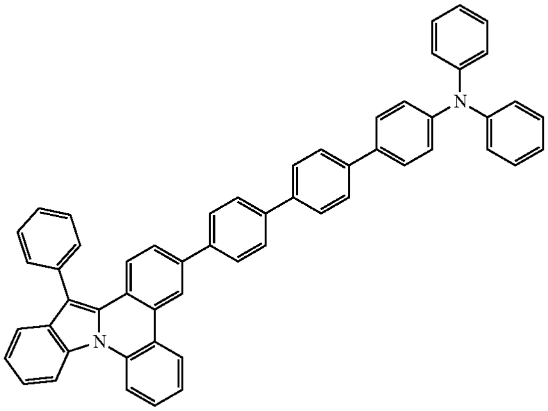
D58
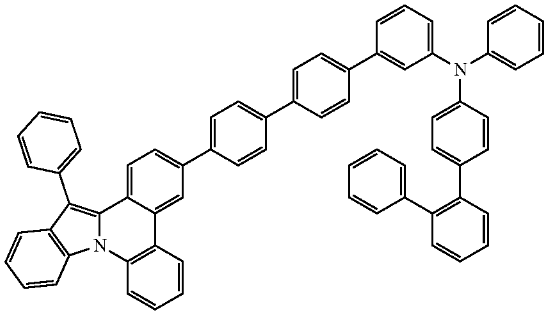

-continued
D59
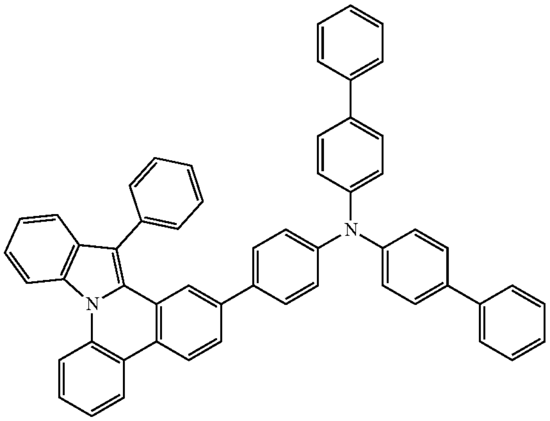
D60
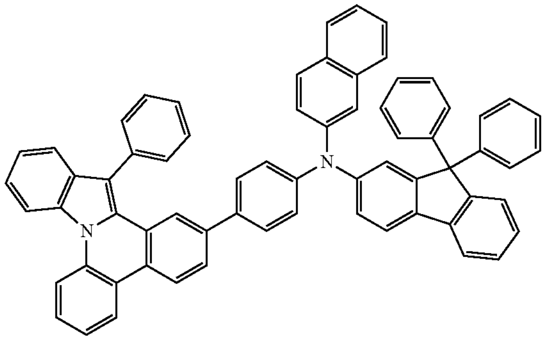
D61
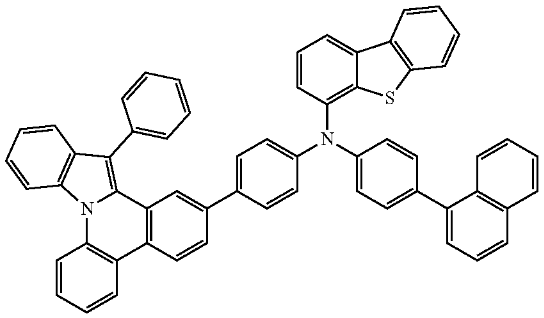
D62
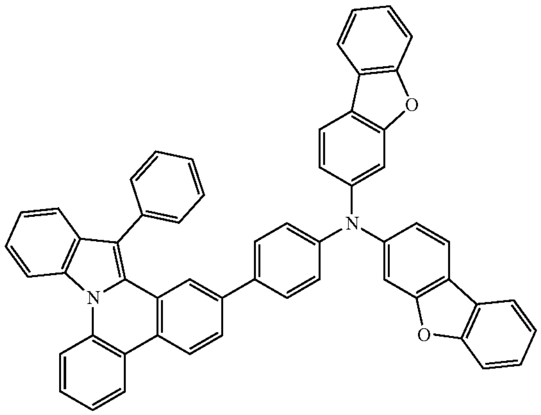
D63
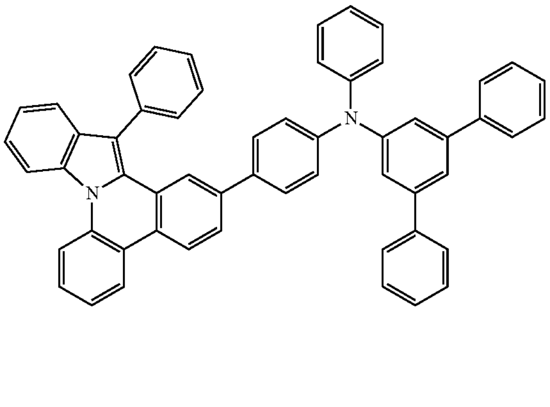
D64
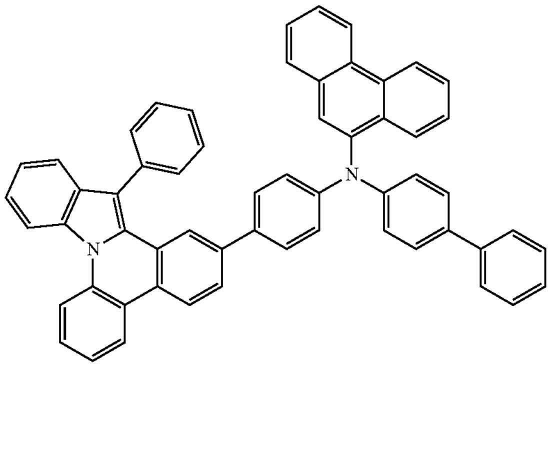

-continued
D65
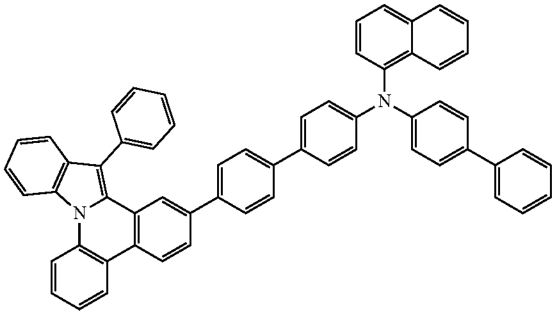
D66
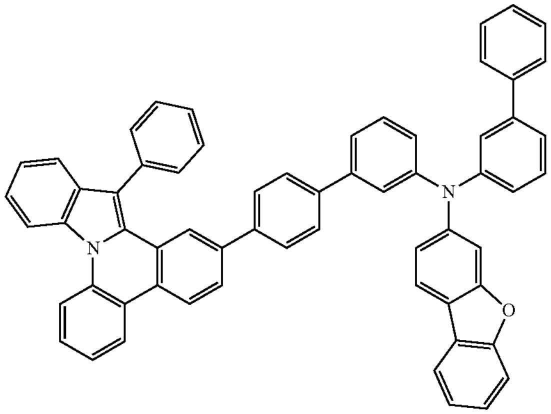
D67
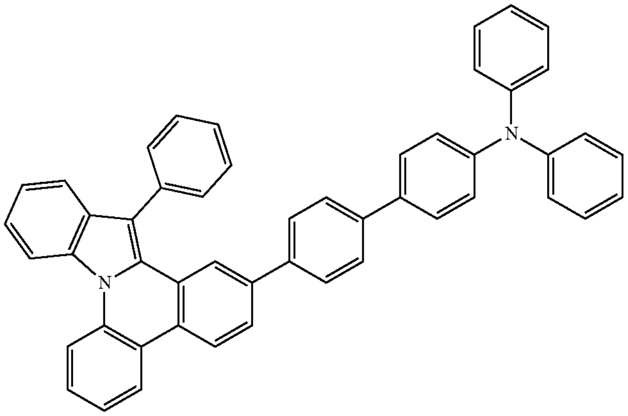
D68
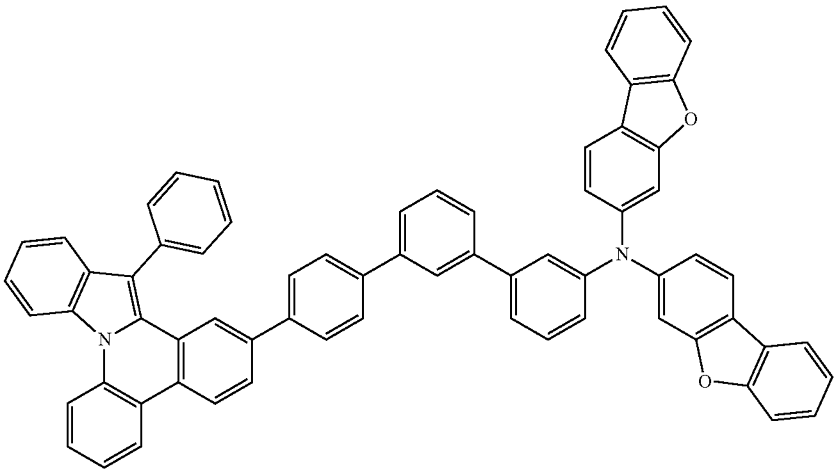

-continued
D69
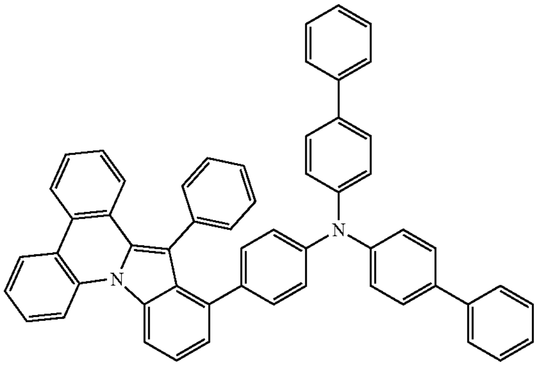
D70
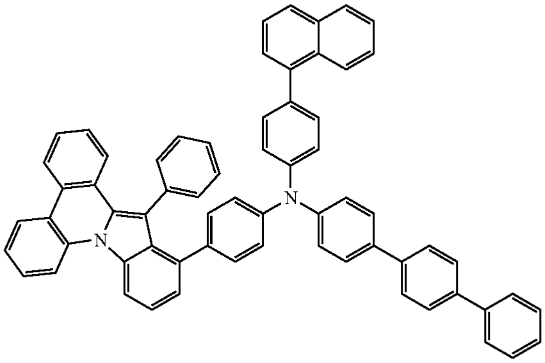
D71
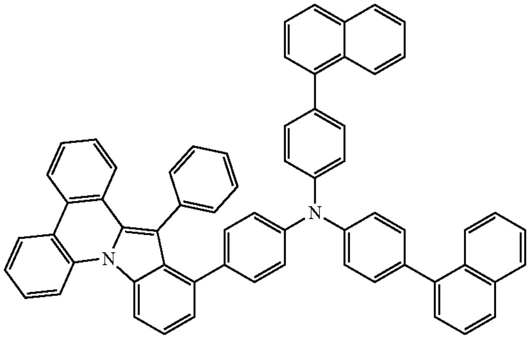
D72
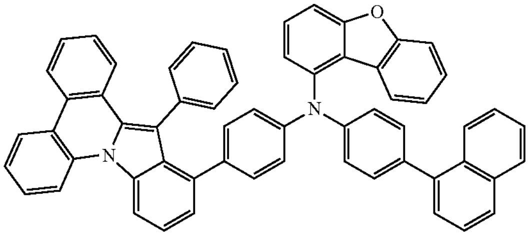
D73
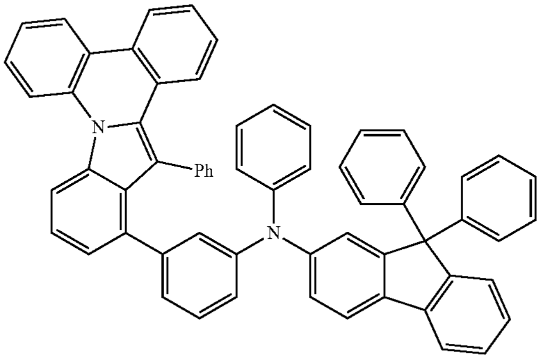
D74
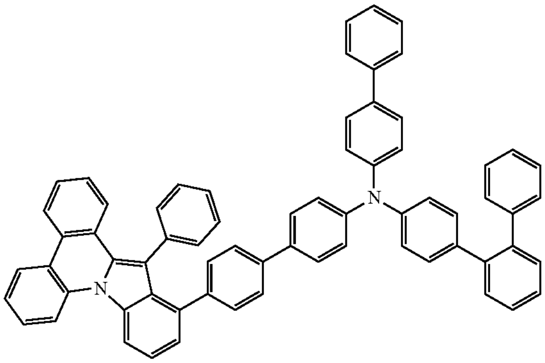
D75
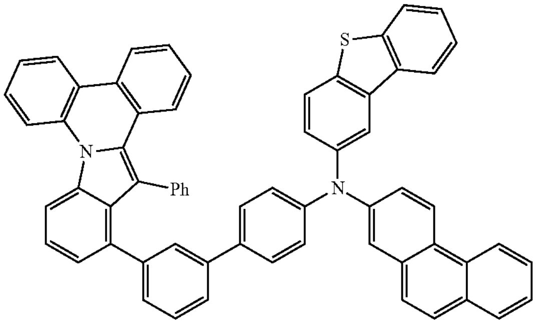
D76
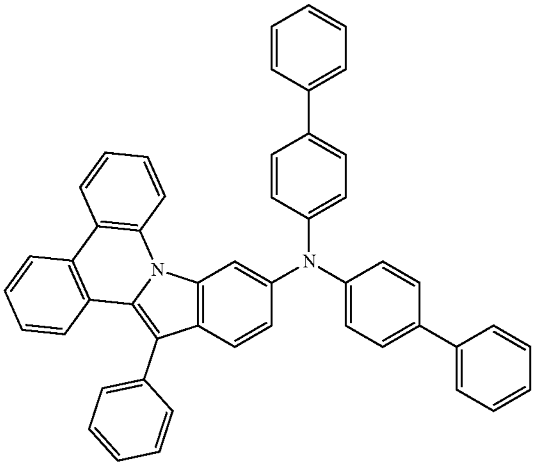

-continued
D77
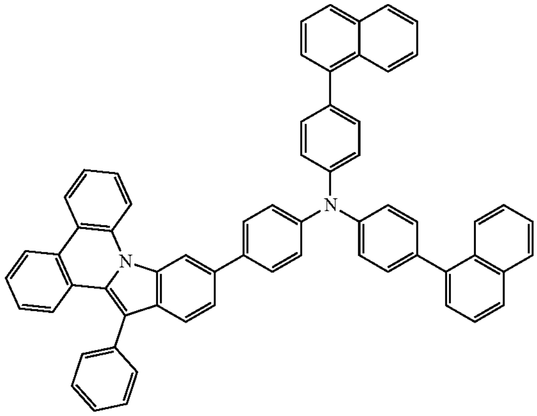
D78
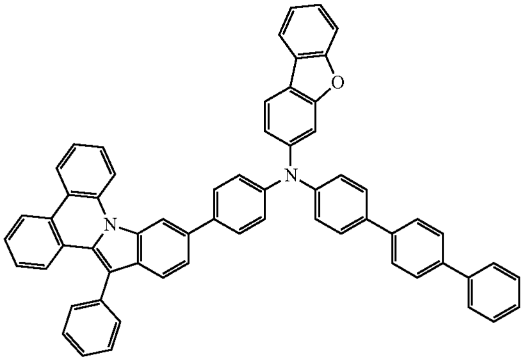
D79
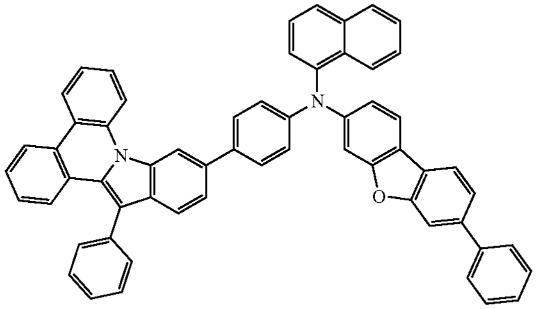
D80
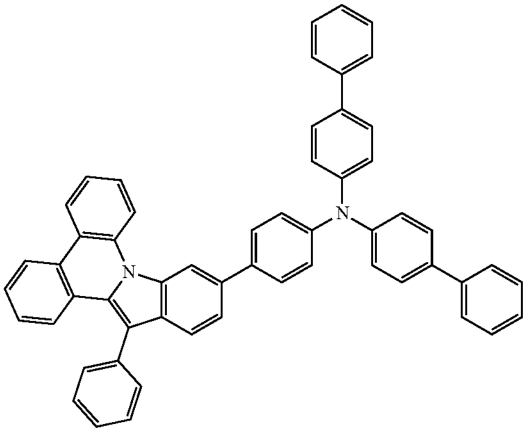
D81
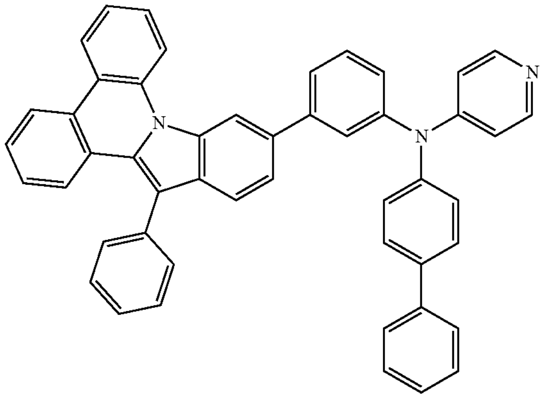
D82
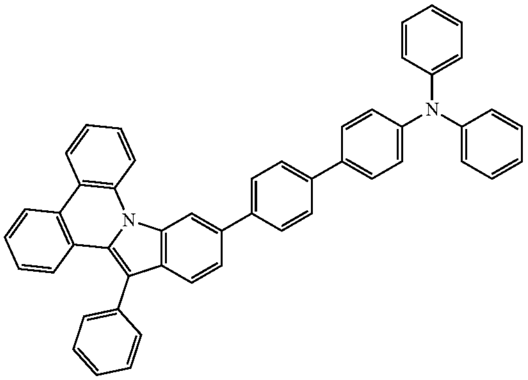
D83
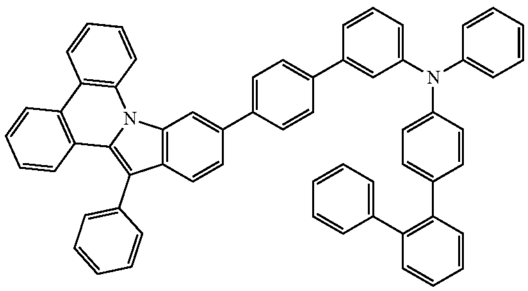
D84
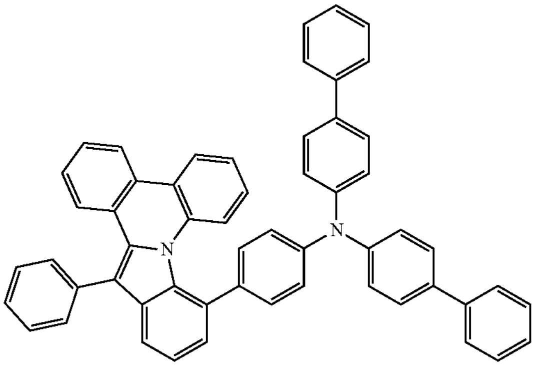

-continued
D85
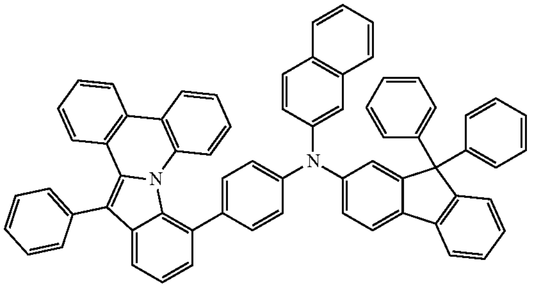
D86
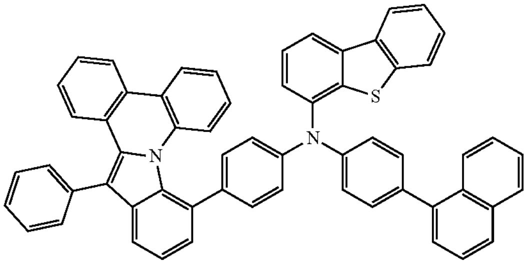
D87
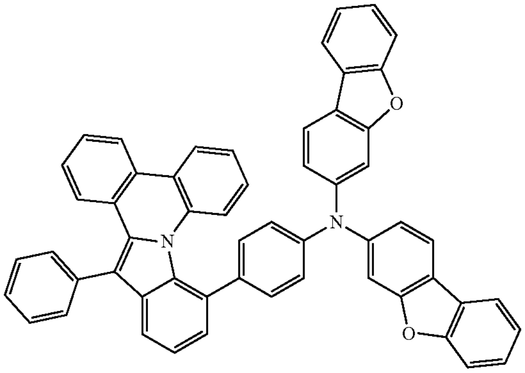
D88
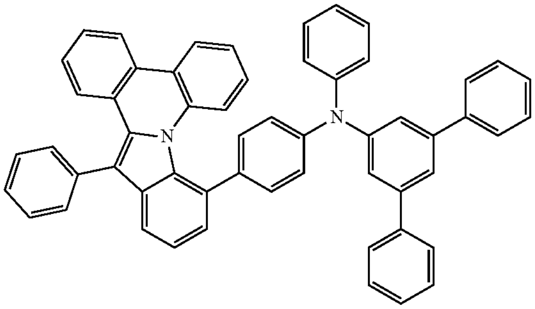
D89
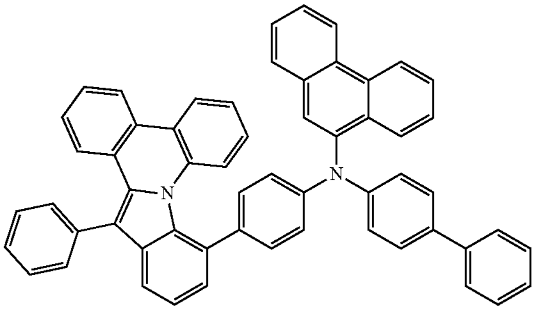
D90
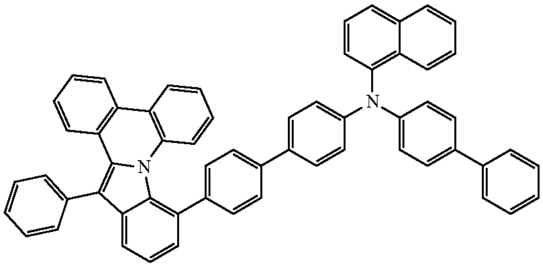
D91
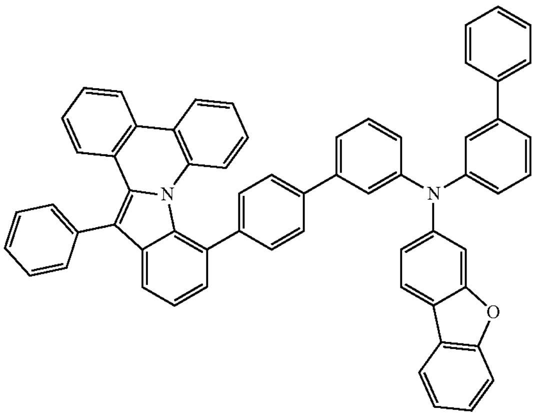
D92
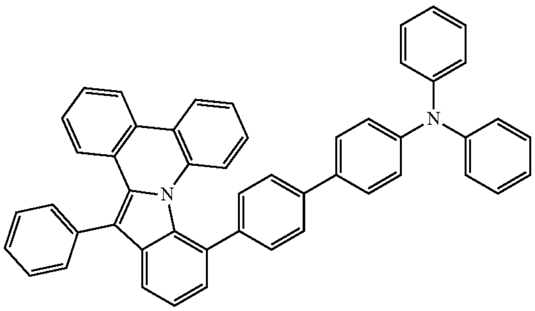

-continued
D93
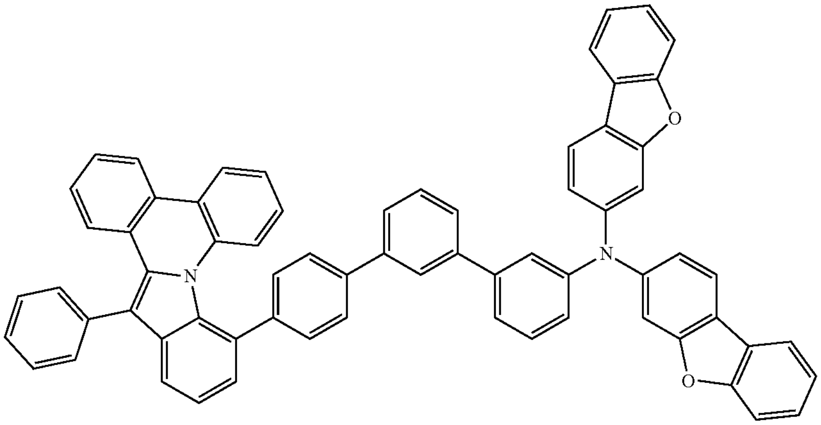
D94
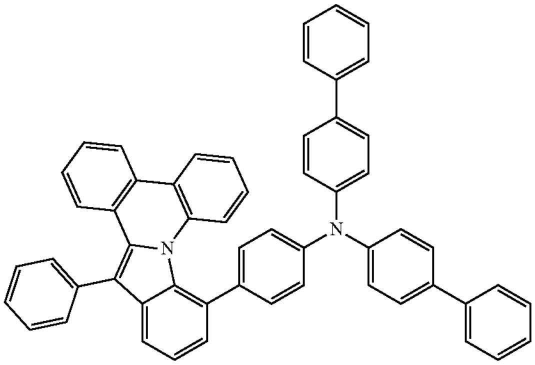
D95
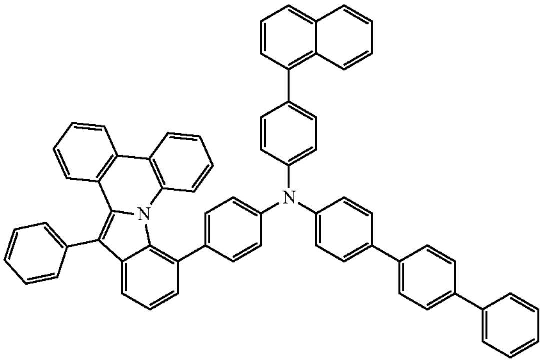
D96
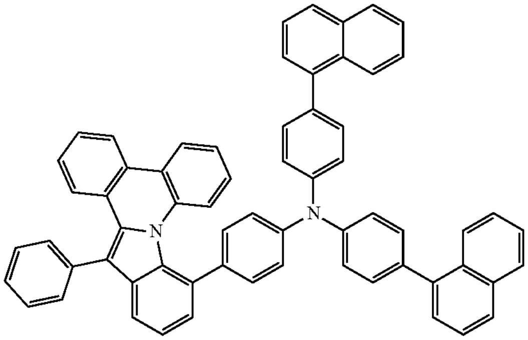
D97
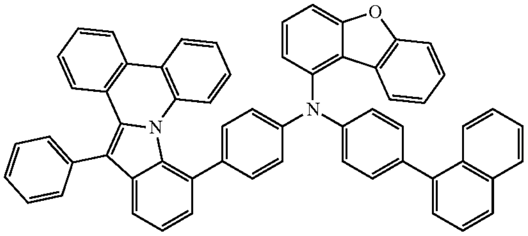
D98
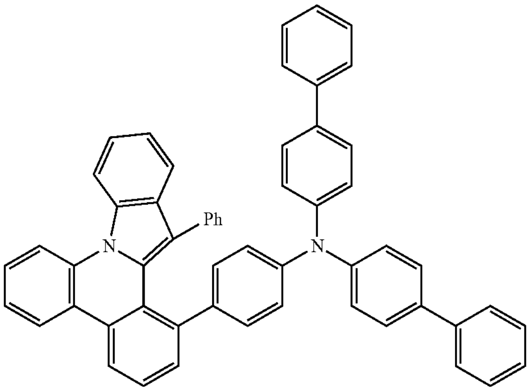
D99
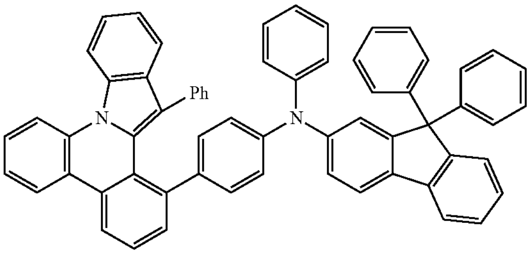

-continued
D100
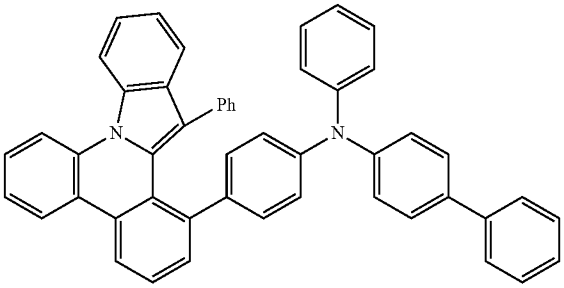
Compound Group 2
E1
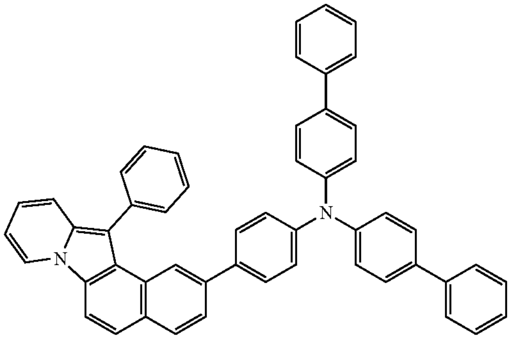
E2
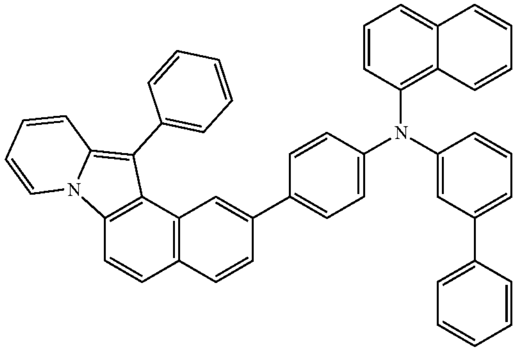
E3
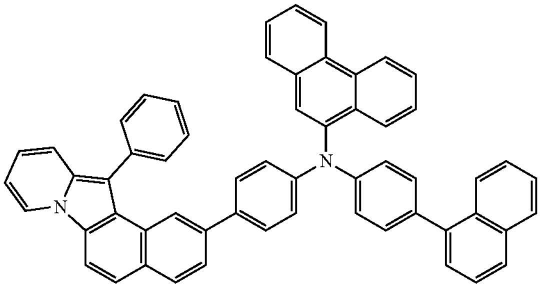
E4
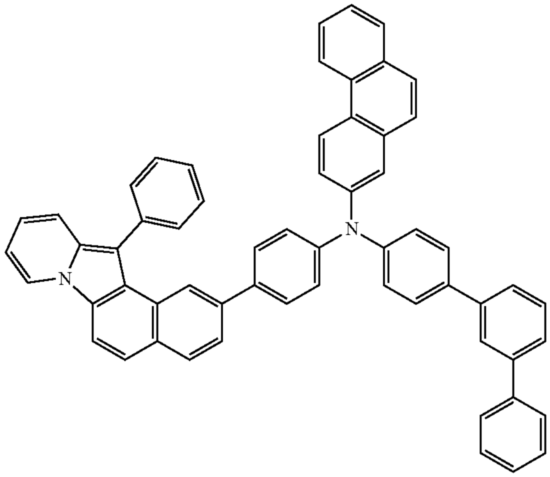
E5
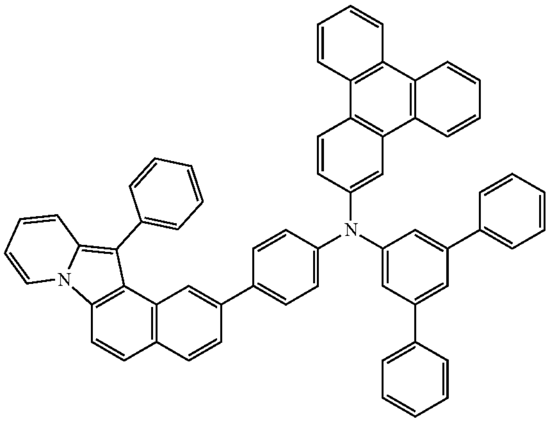
E6
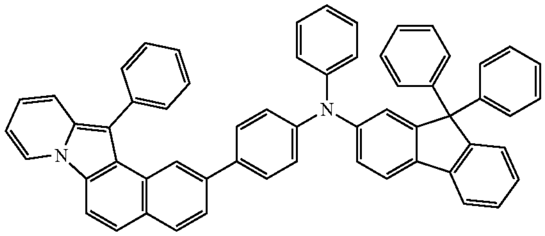

-continued
E7
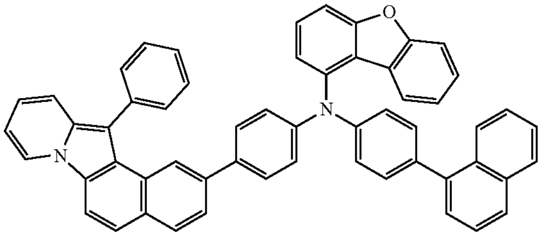
E8
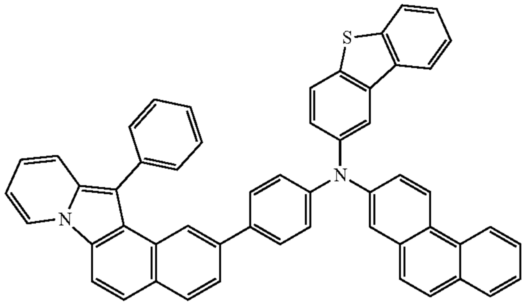
E9
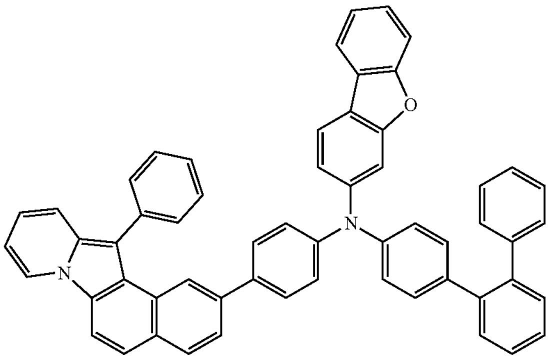
E10
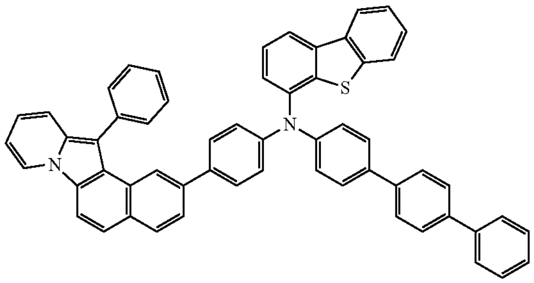
E11
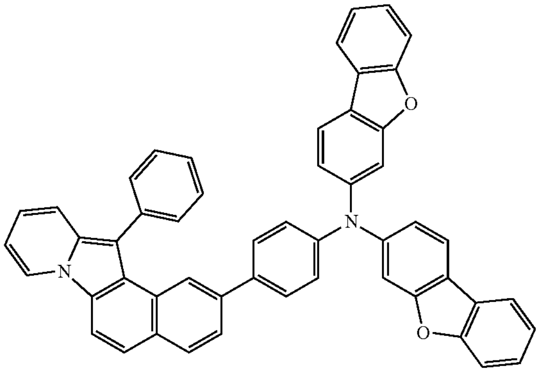
E12
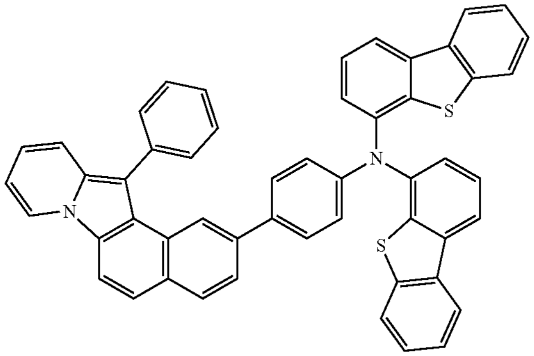
E13
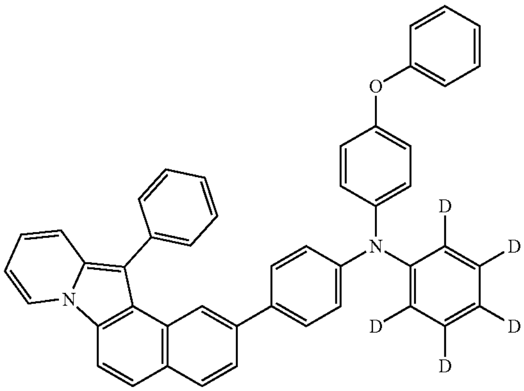
E14
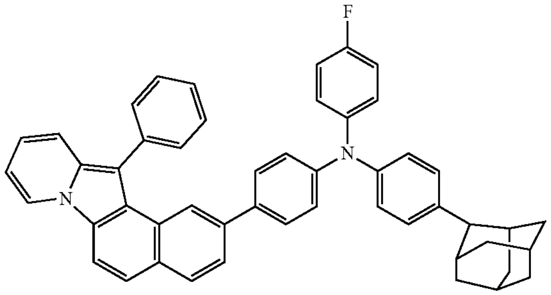

-continued
E15
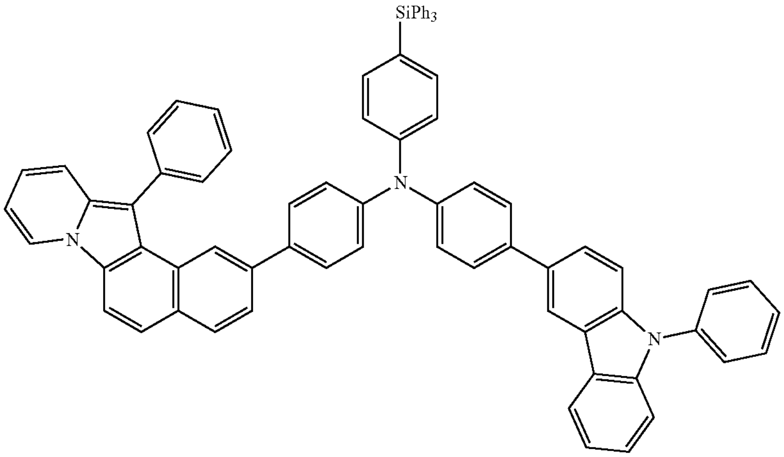
E16
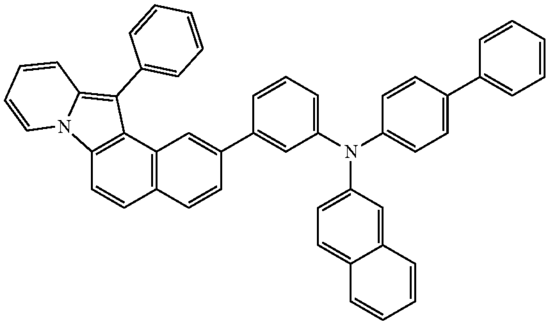
E17
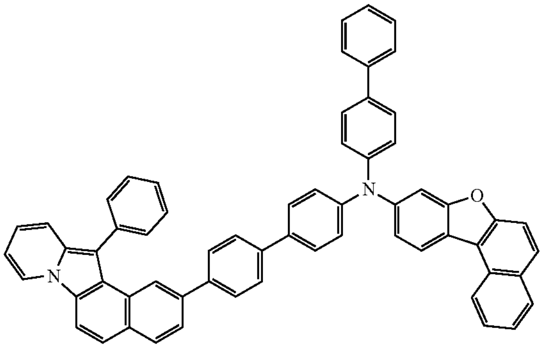
E18
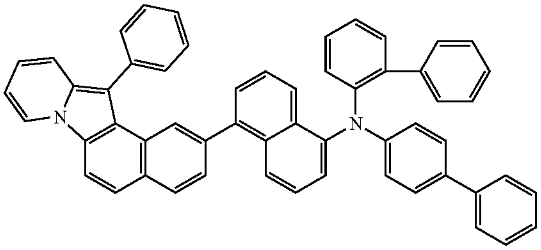
E19
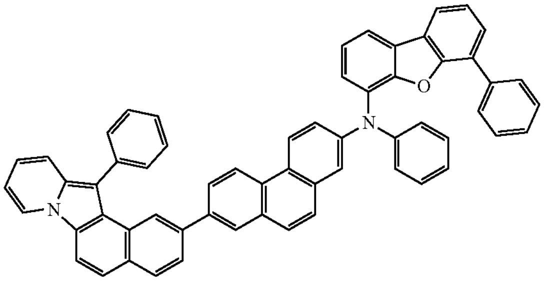
E20
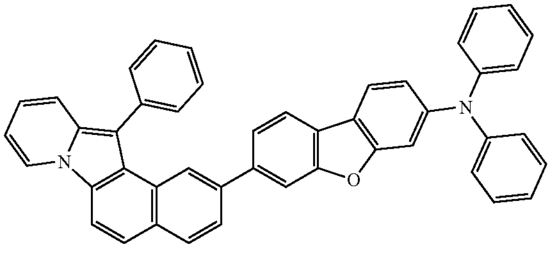
E21
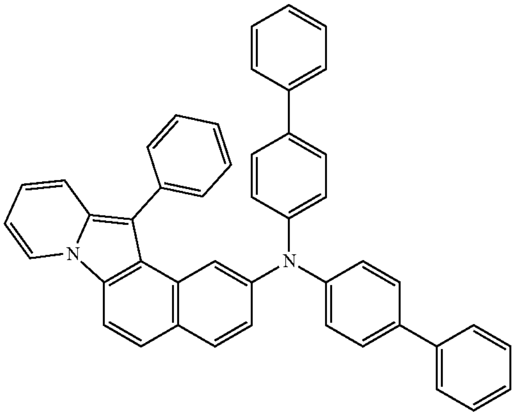

-continued
E22
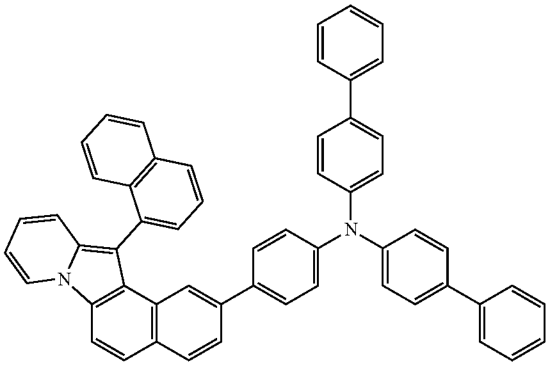
E23
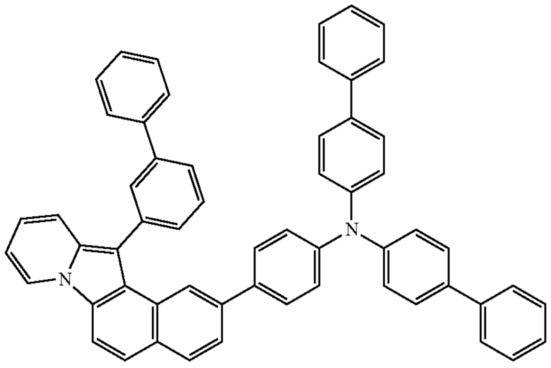
E24
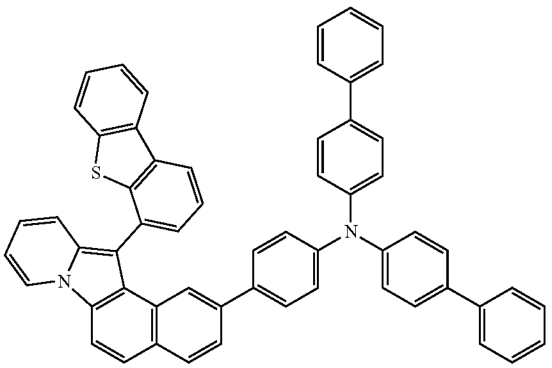
E25
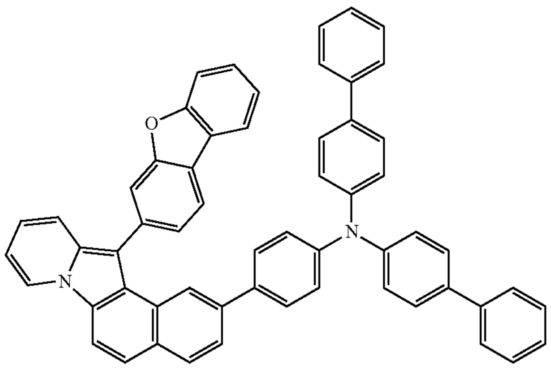
E26
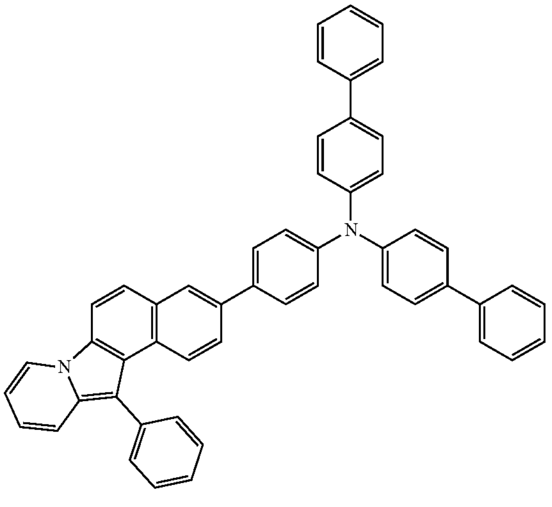
E27
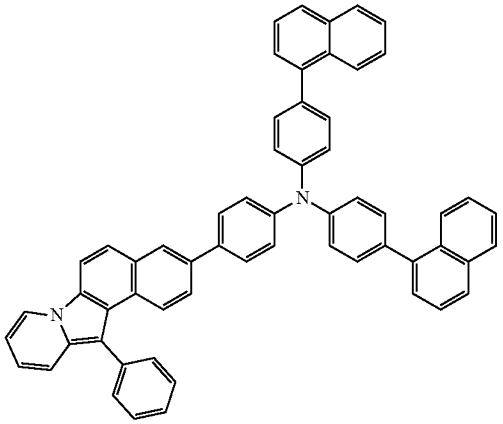

-continued
E28
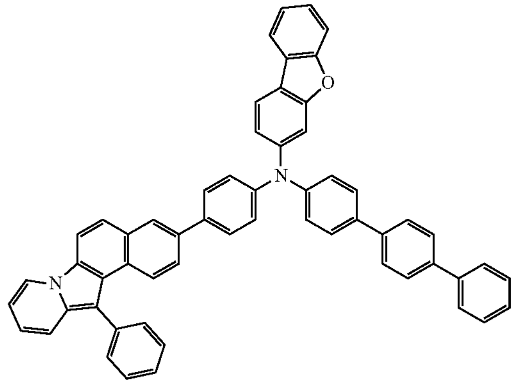
E29
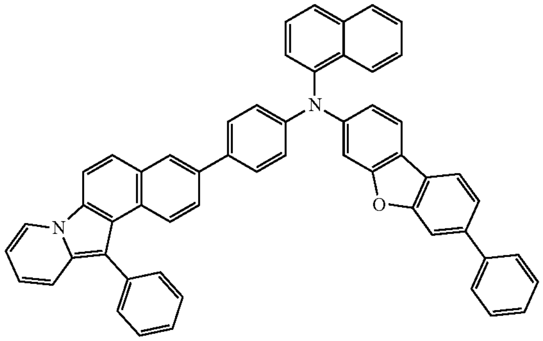
E30
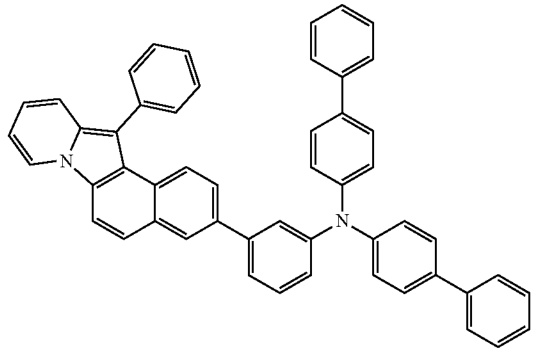
E31
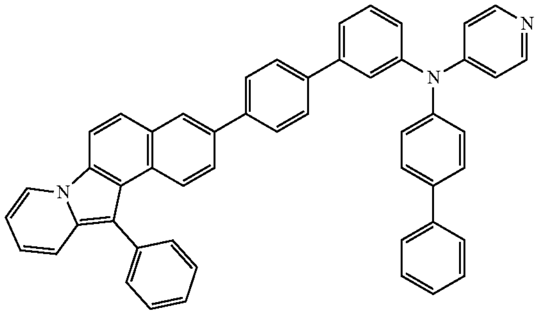
E32
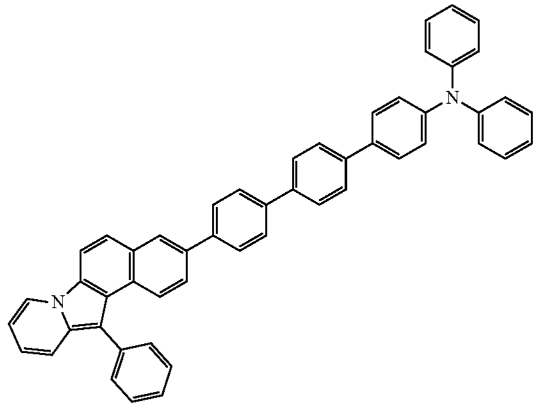
E33
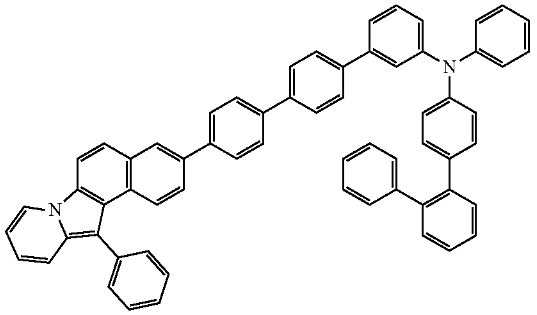
E34
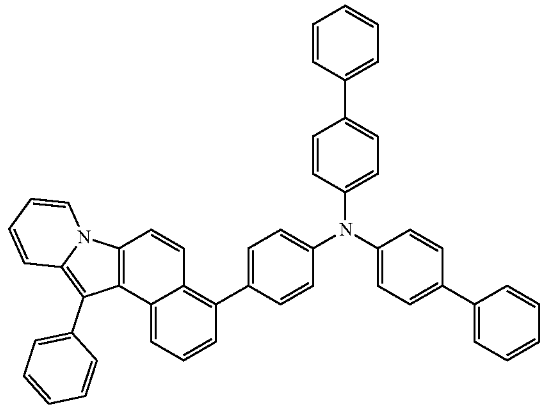
E35
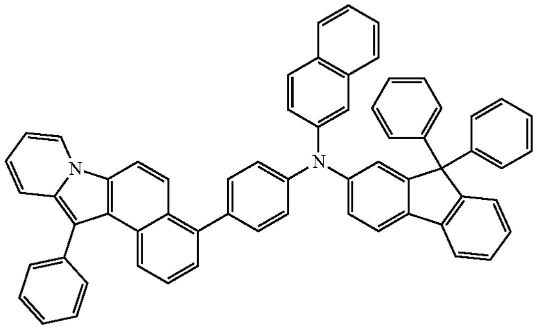

-continued
E36
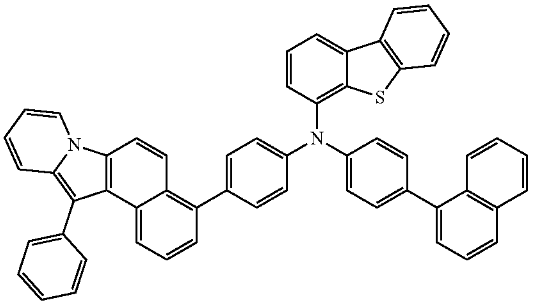
E37
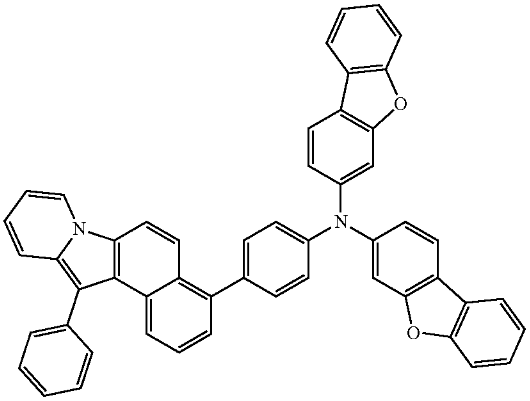
E38
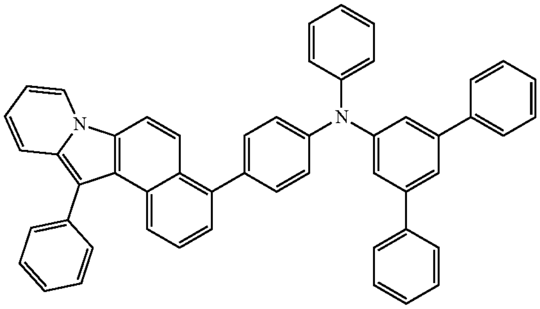
E39
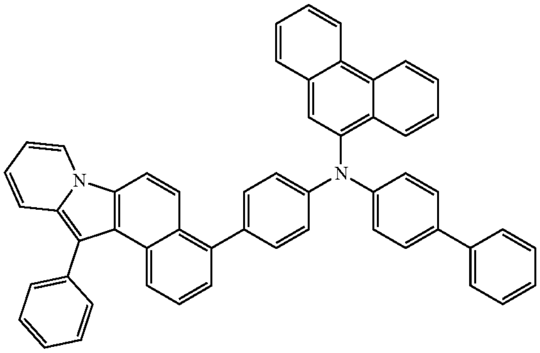
E40
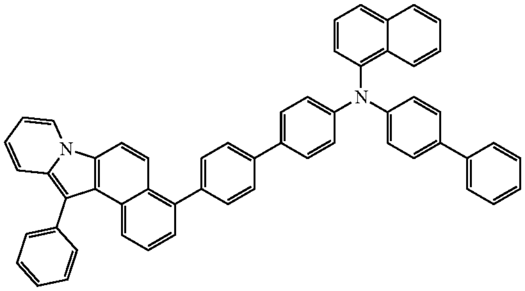
E41
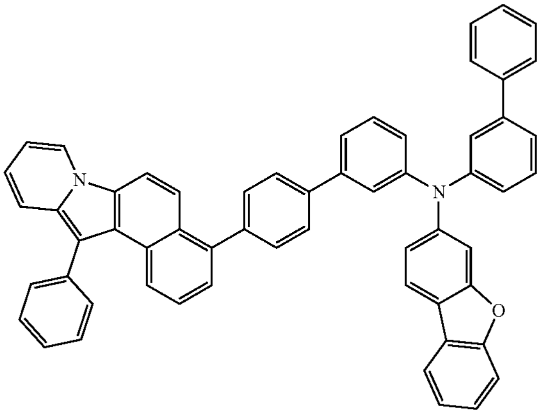
E42
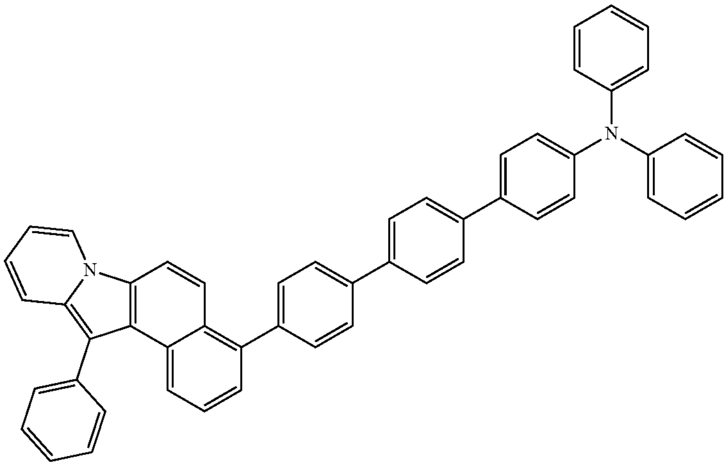

-continued
E43
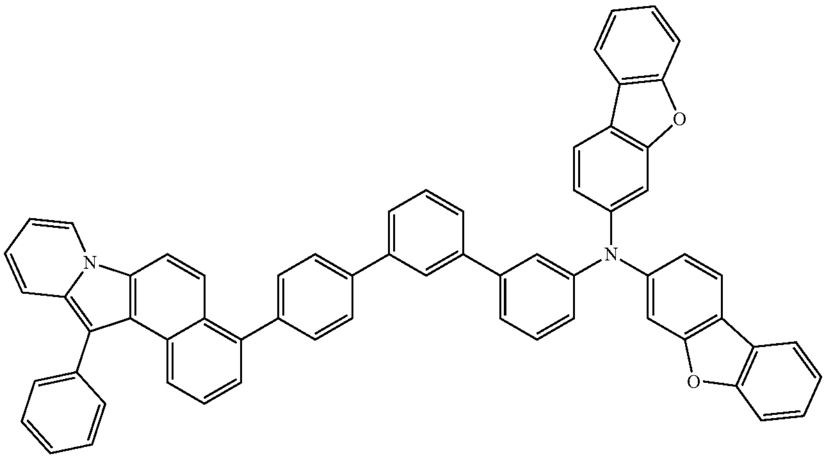
E44
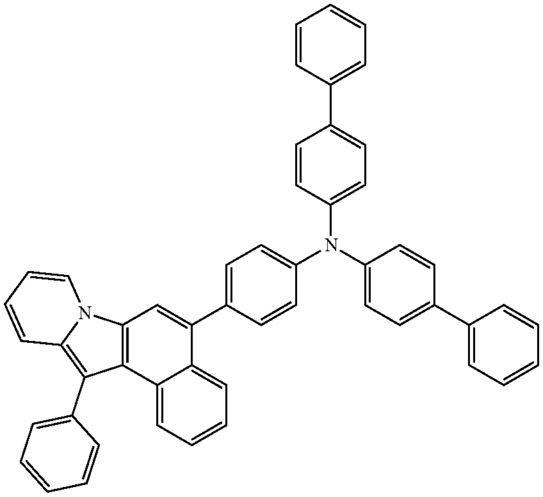
E45
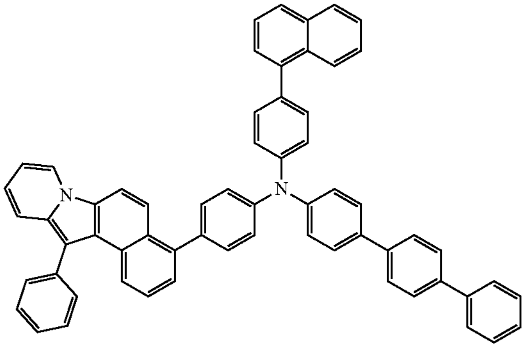
E46
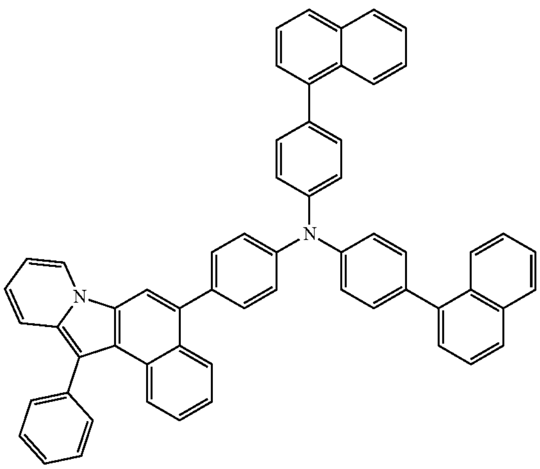
E47
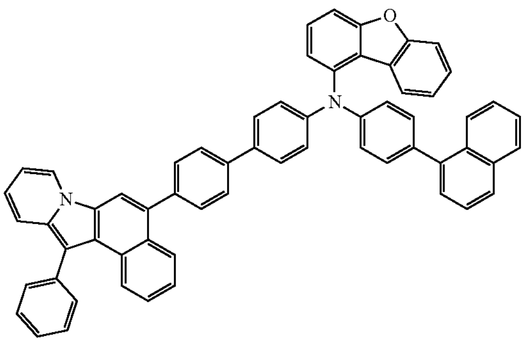

-continued
E48
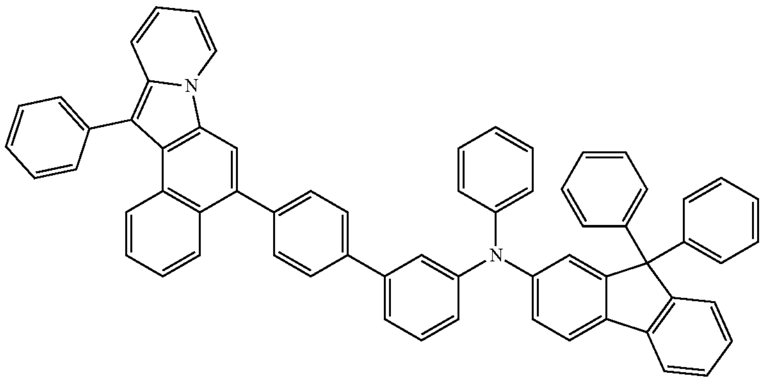
E49
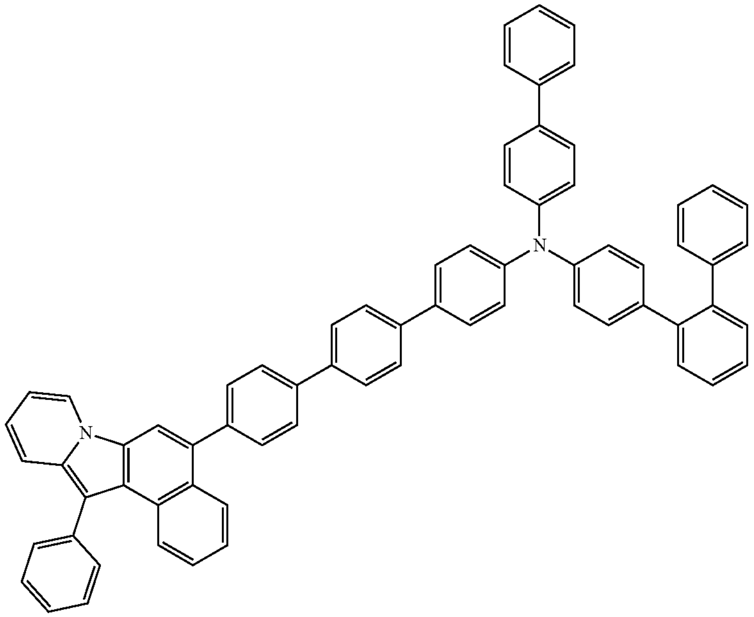
E50
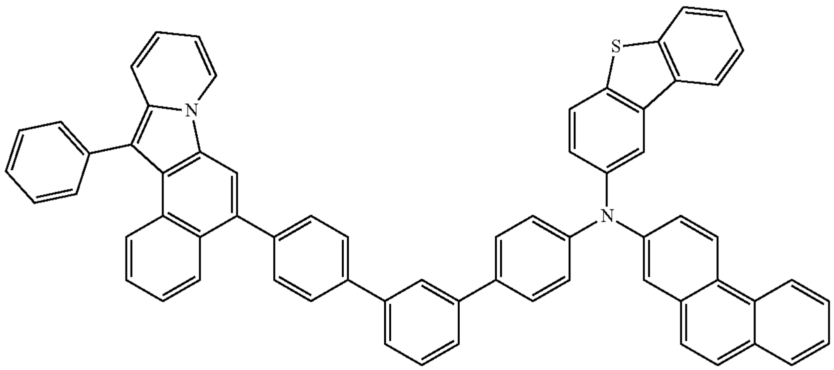

-continued
E51
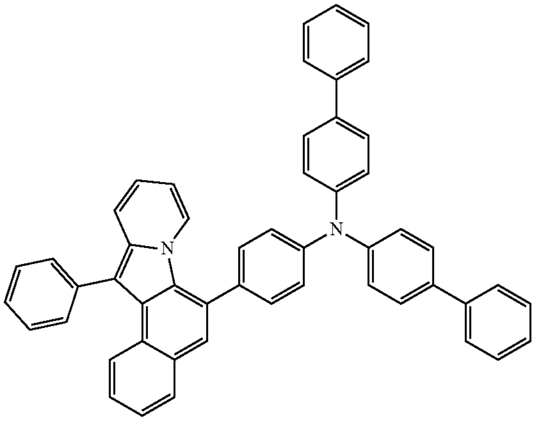
E52
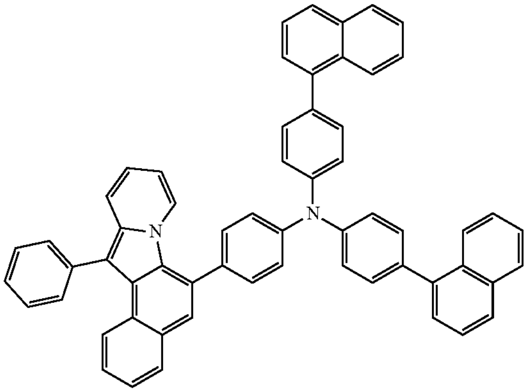
E53
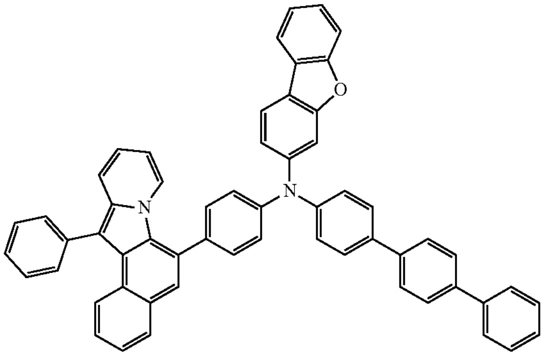
E54
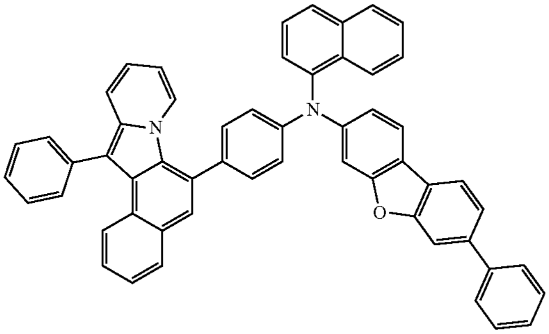
E55
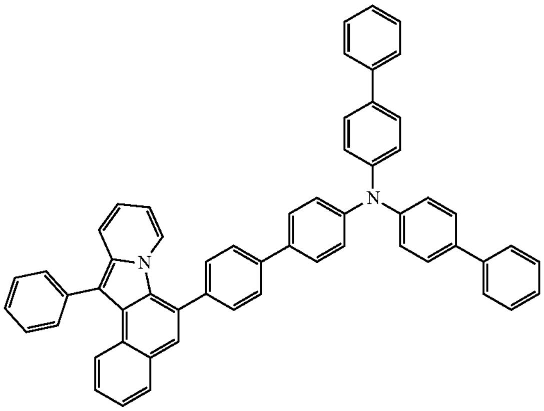
E56
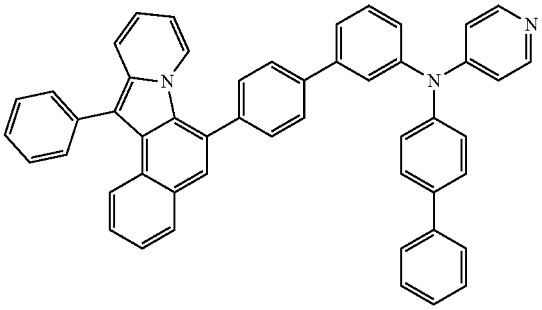
E57
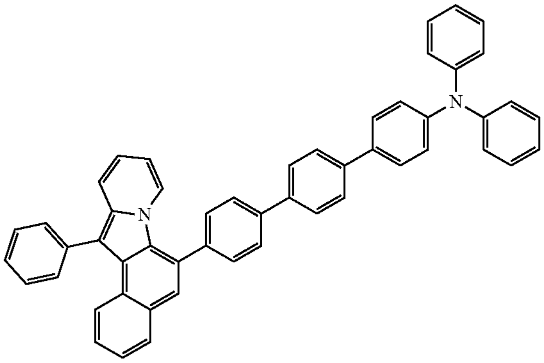
E58
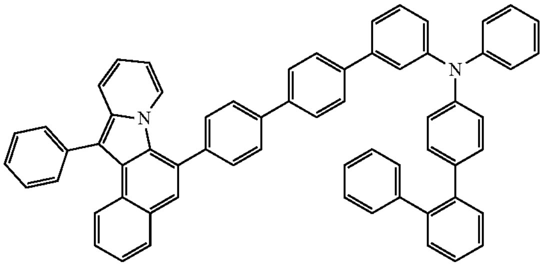

-continued
E59
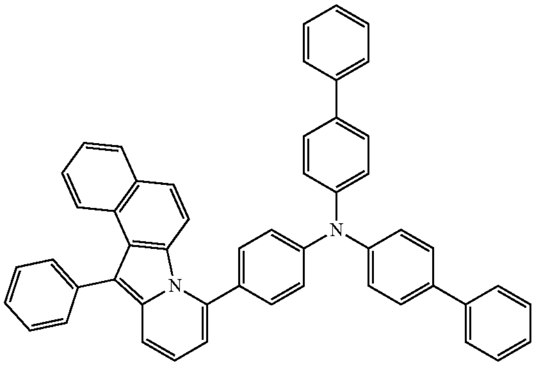
E60
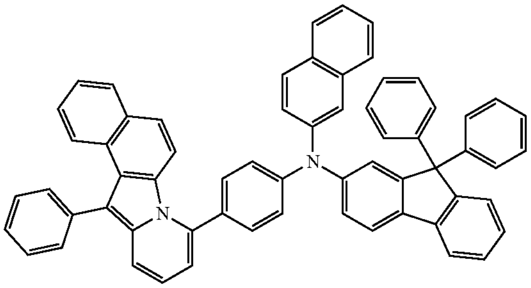
E61
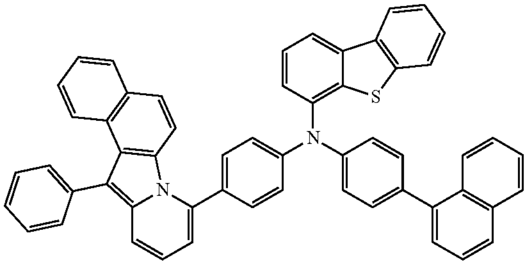
E62
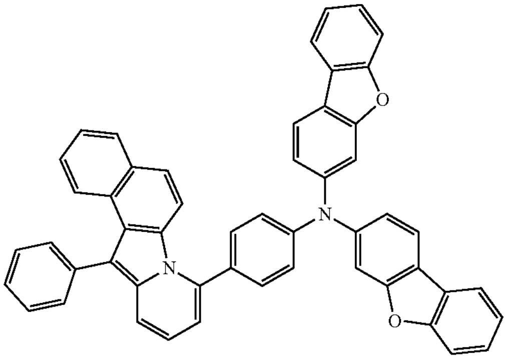
E63
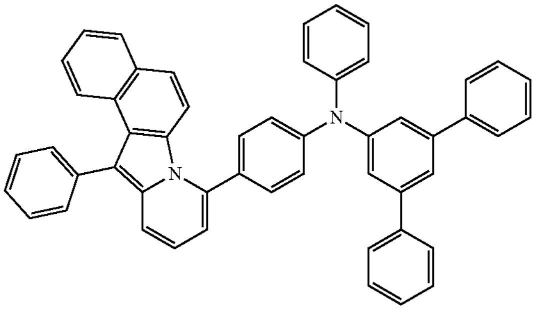
E64
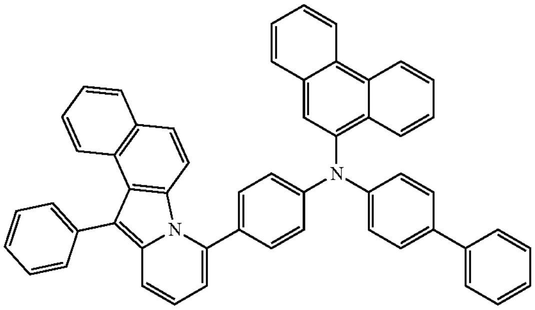
E65
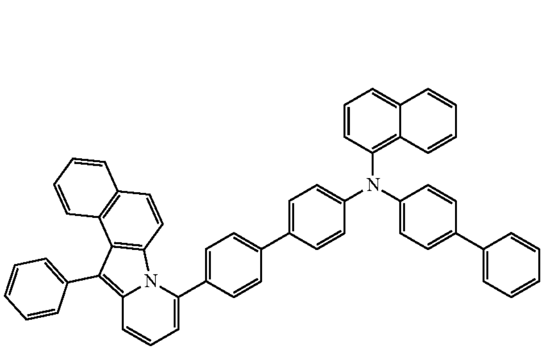
E66
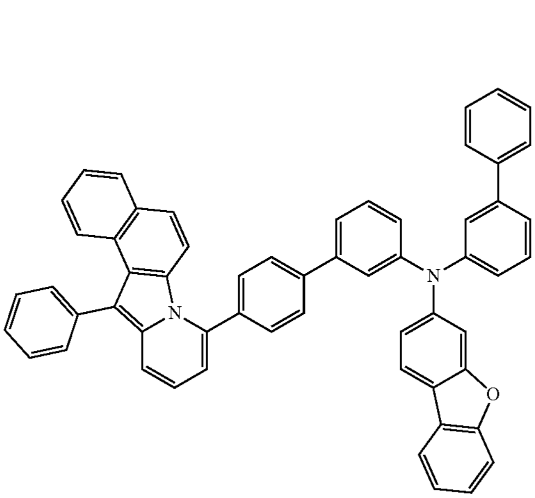

-continued
E67
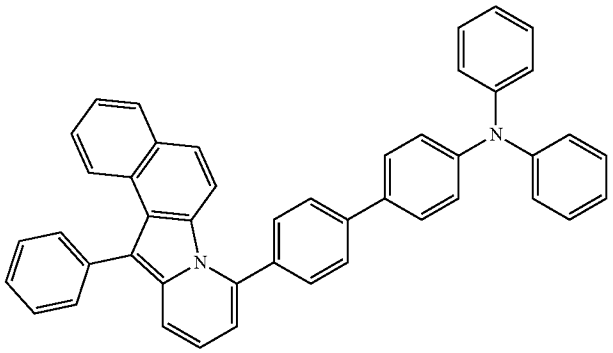
E68
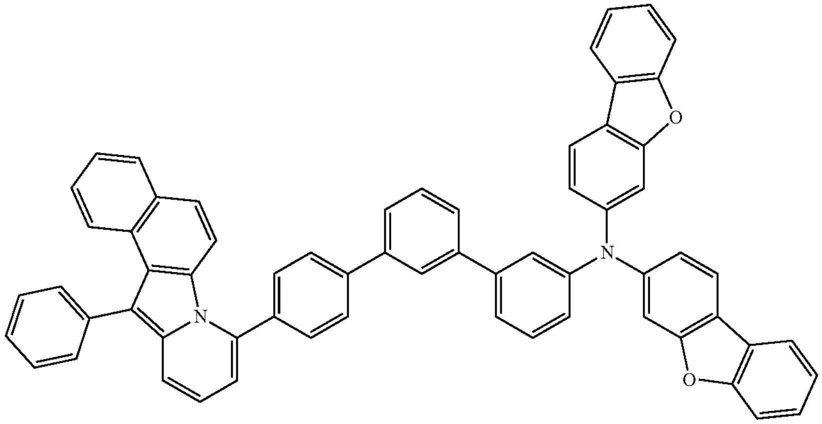
E69
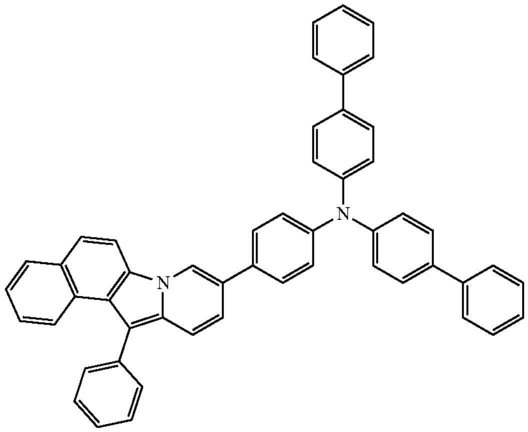
E70
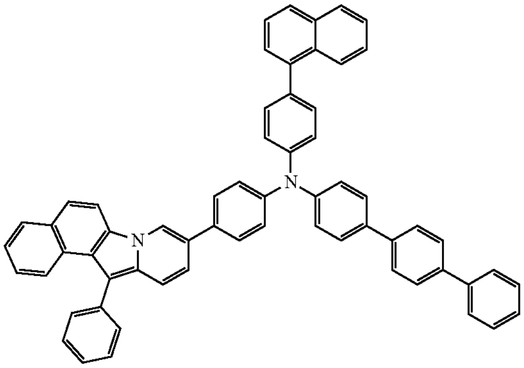
E71
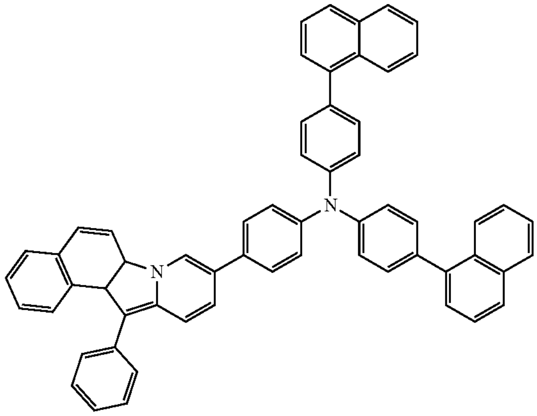
E72
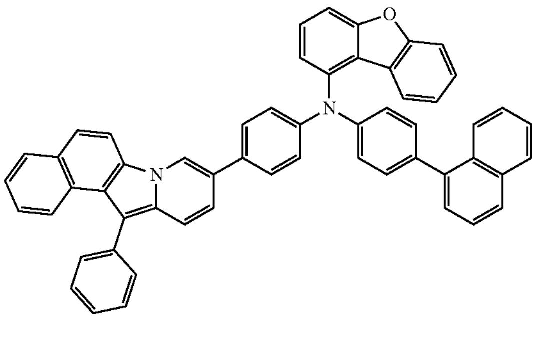

-continued
E73
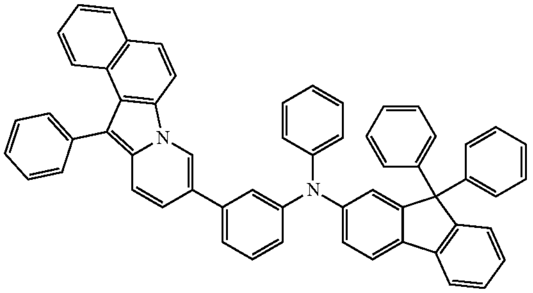
E74
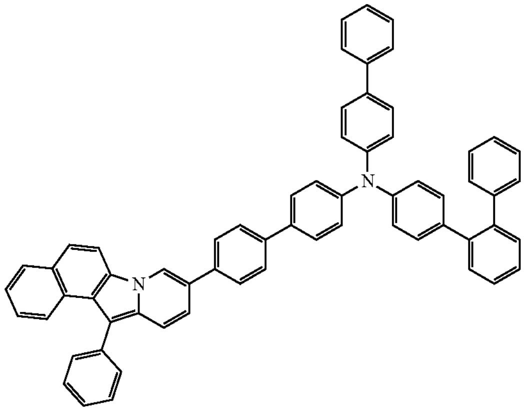
E75
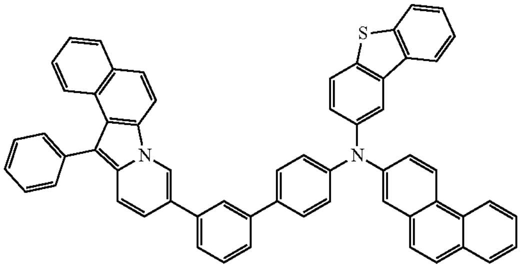
E76
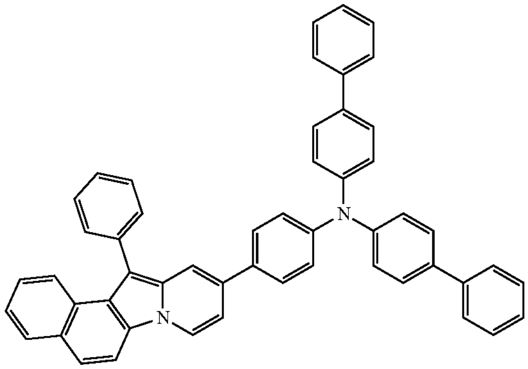
E77
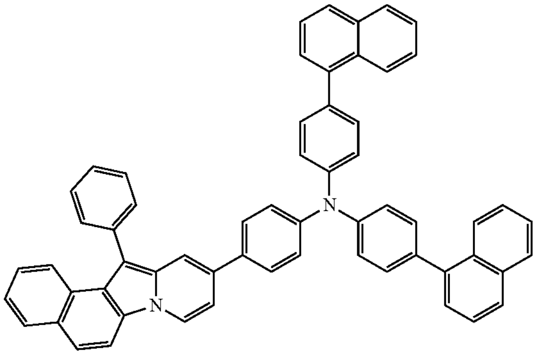
E78
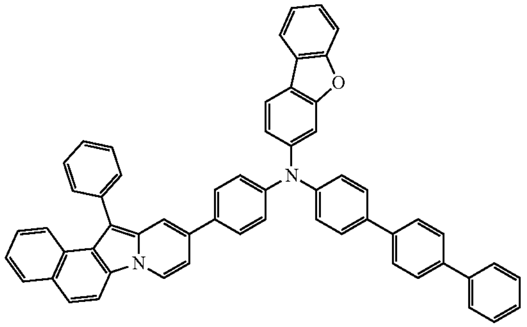
E79
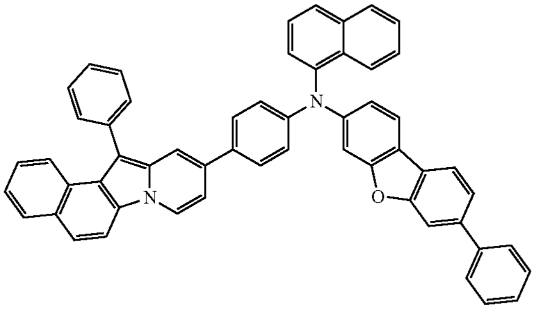
E80
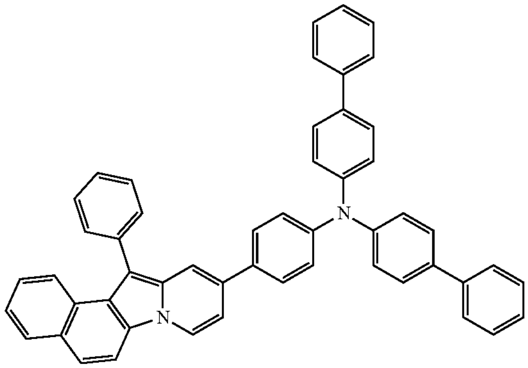

-continued
E81
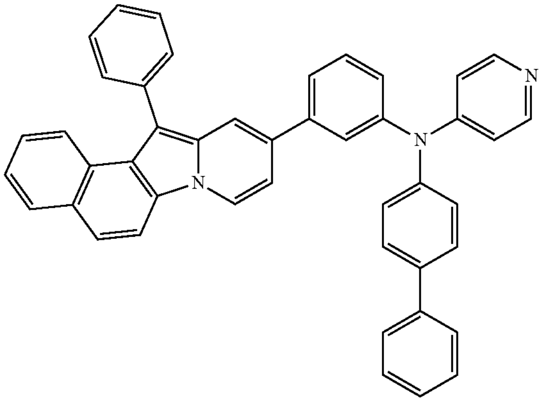
E82
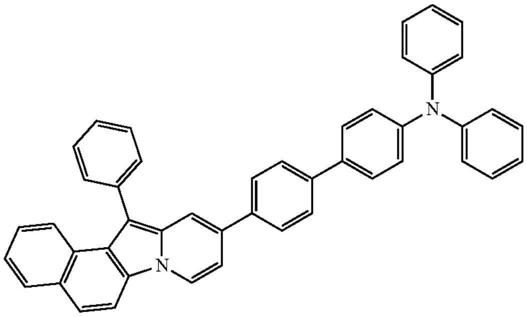
E83
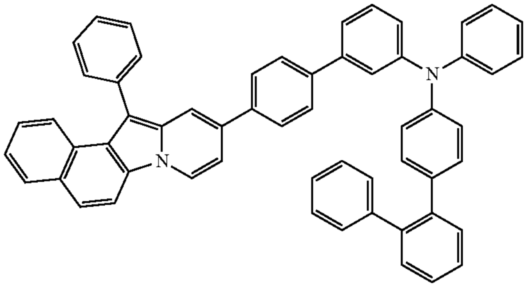
E84
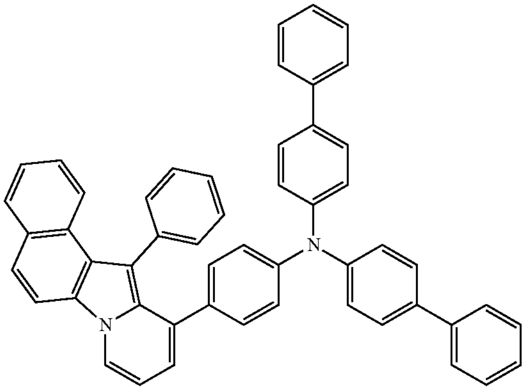
E85
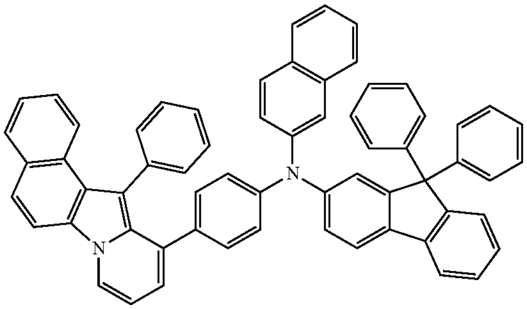
E86
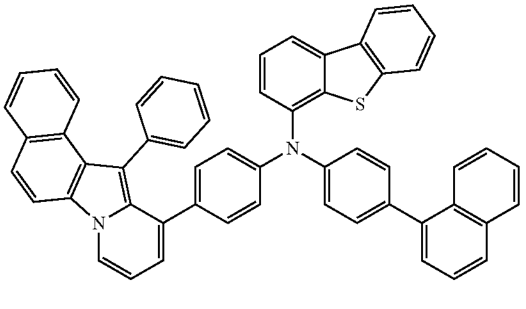
E87
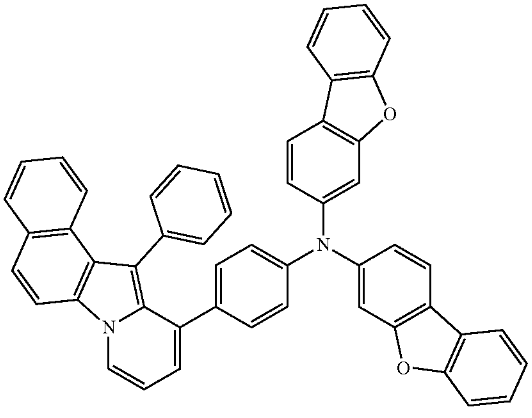
E88
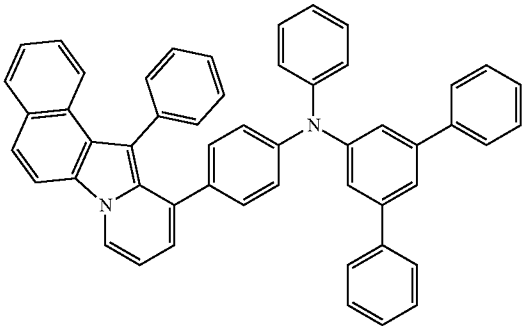

-continued
E89
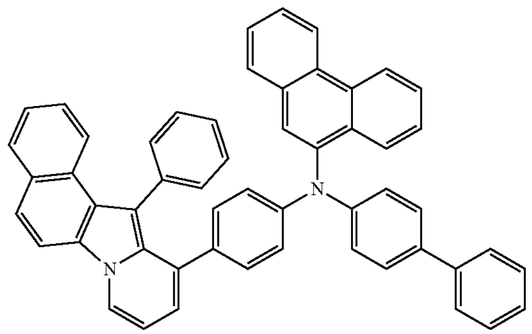
E90
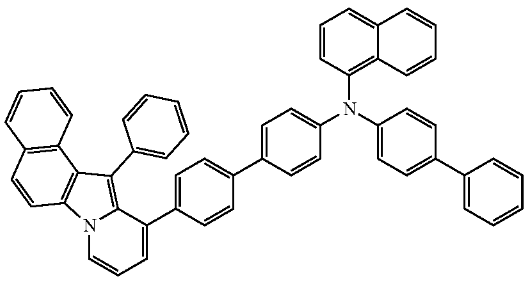
E91
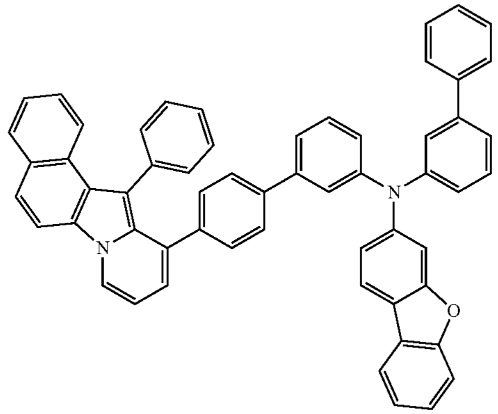
E92
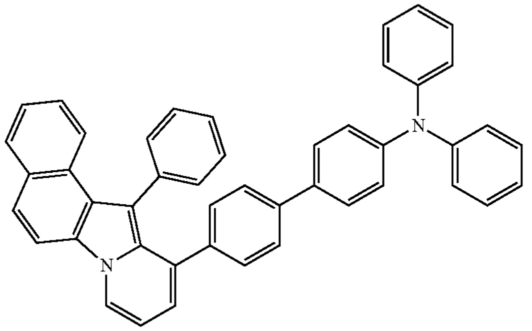
E93
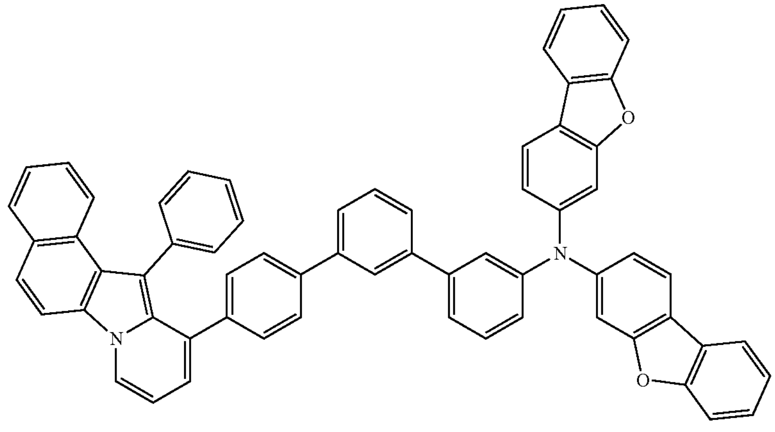
E94
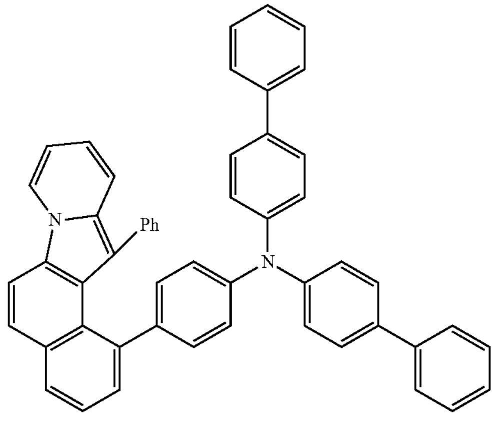
E95
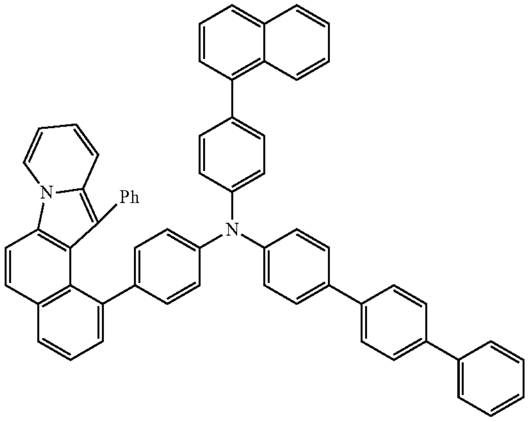

-continued
E96
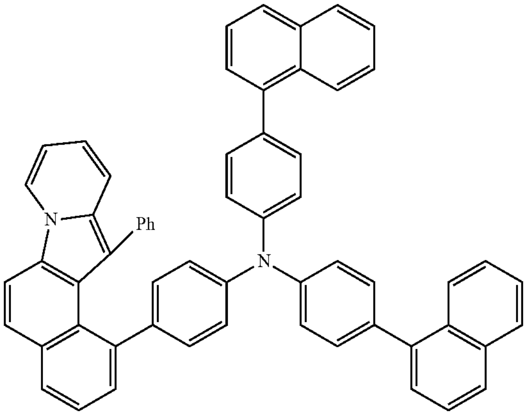
E97
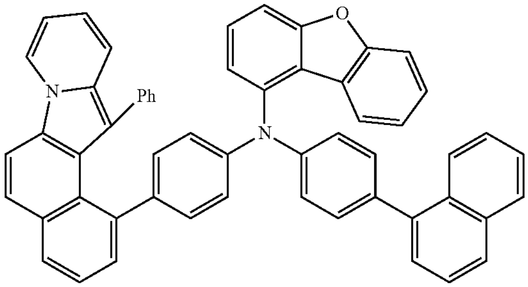
E98
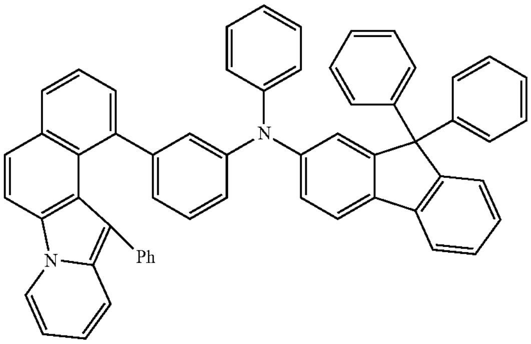
E99
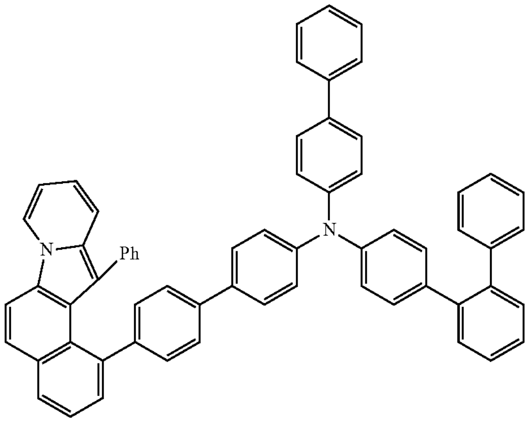
E100
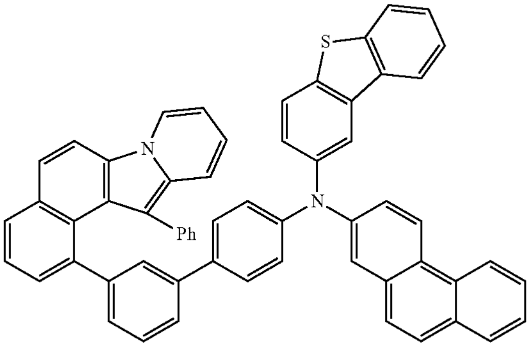
F1
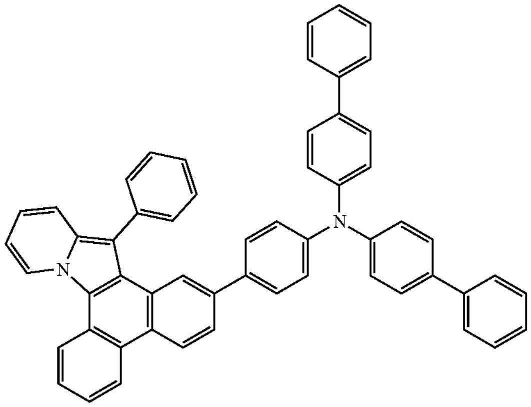
F2
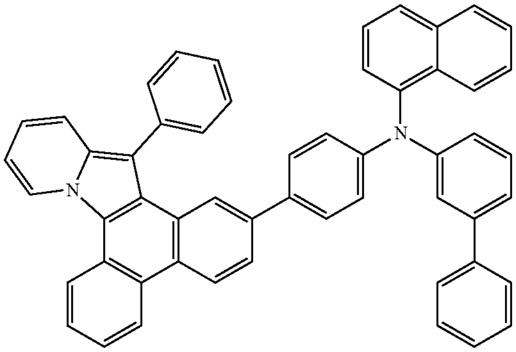
F3
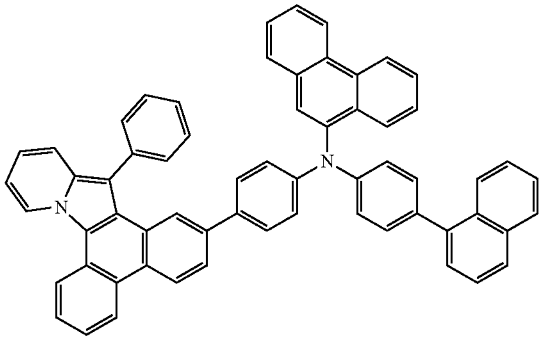

-continued
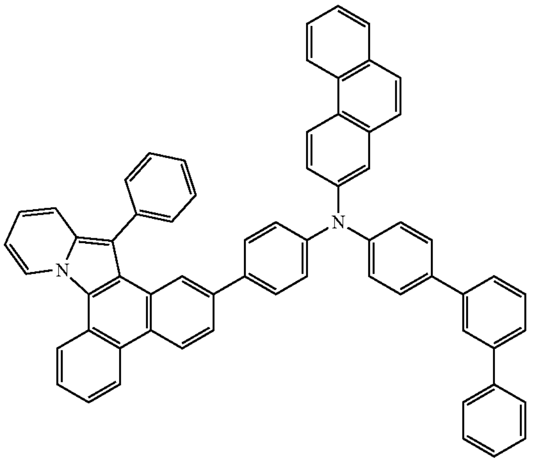
F4
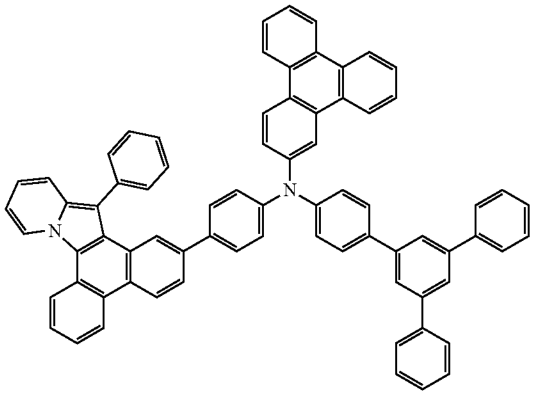
F5
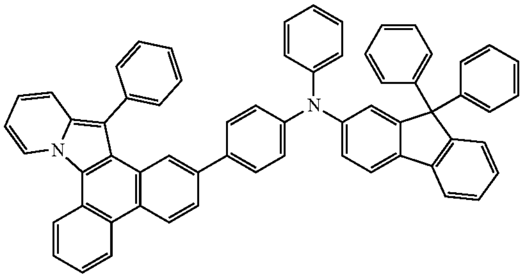
F6
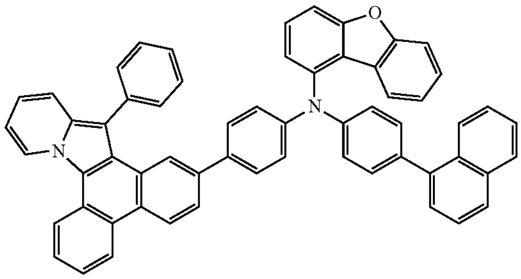
F7
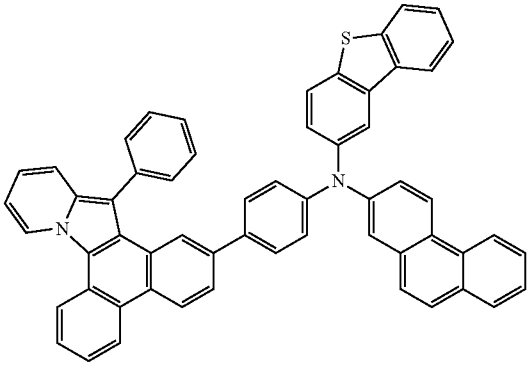
F8
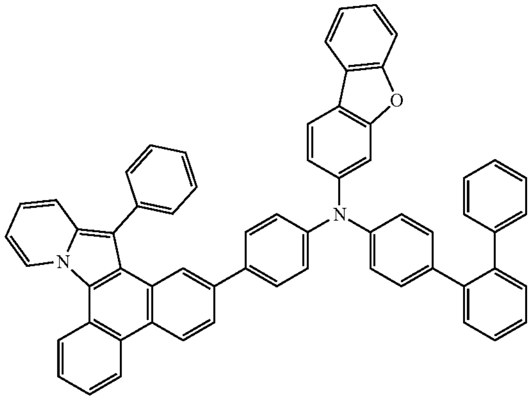
F9
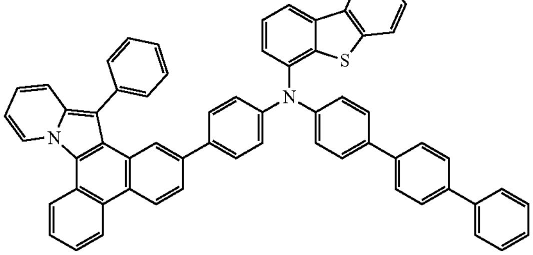
F10
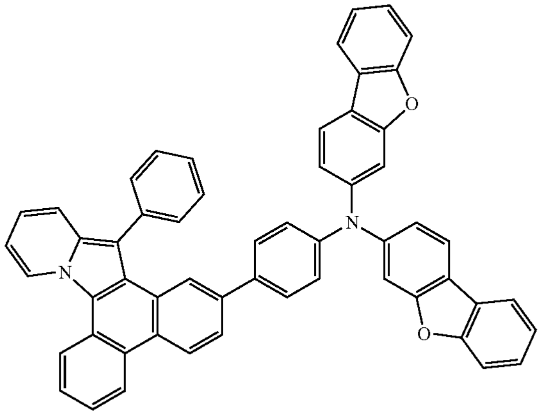
F11

-continued
F12
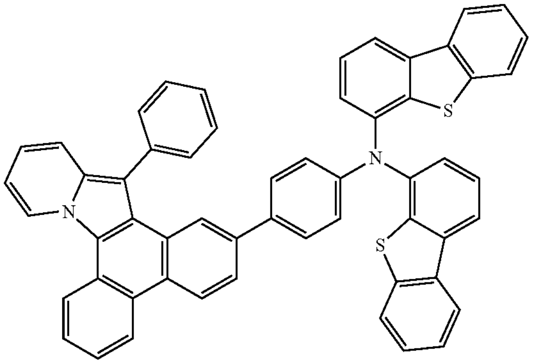
F13
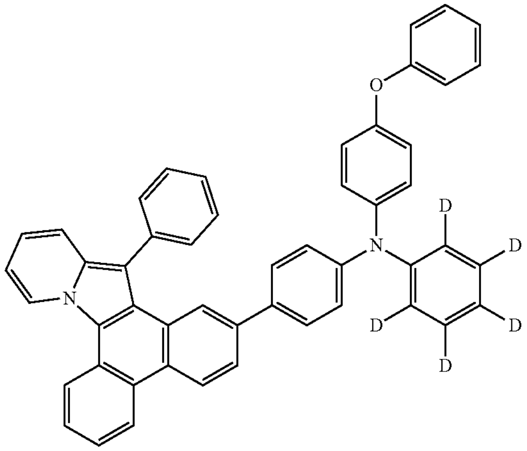
F14
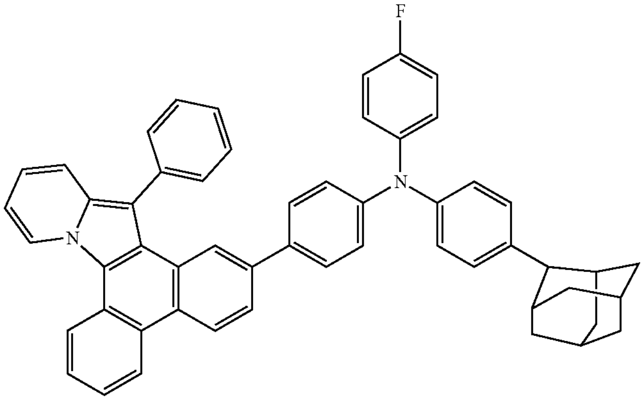
F15
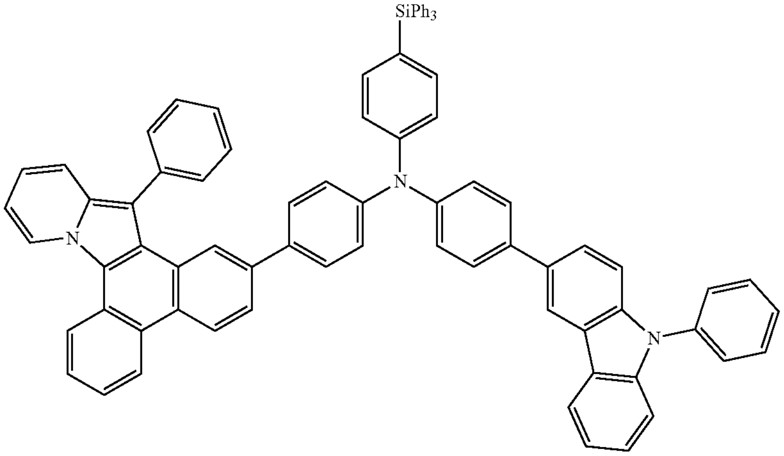

-continued
F16
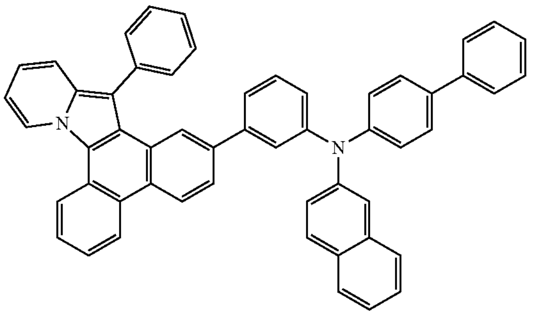
F17
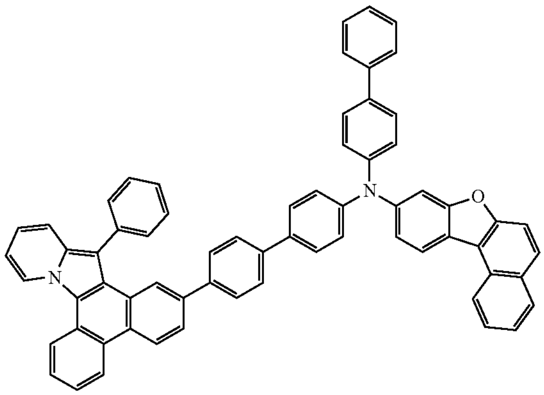
F18
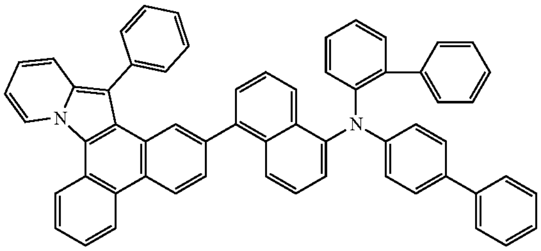
F19
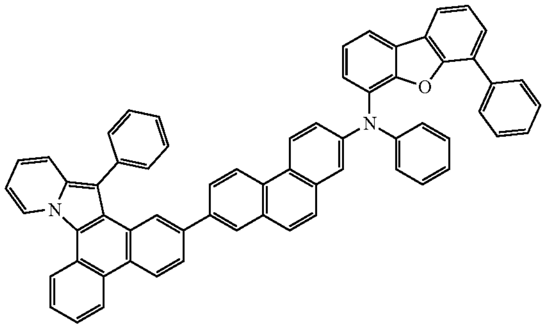
F20
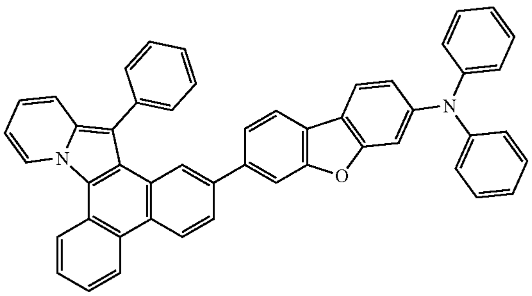
F21
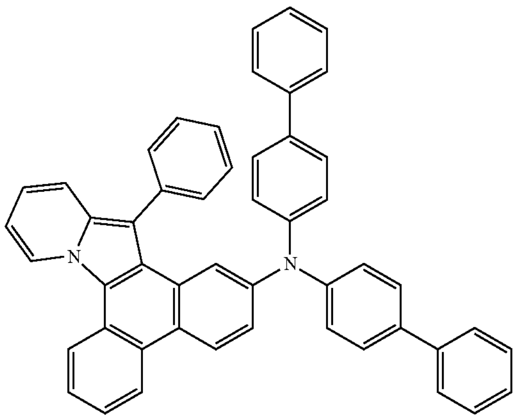
F22
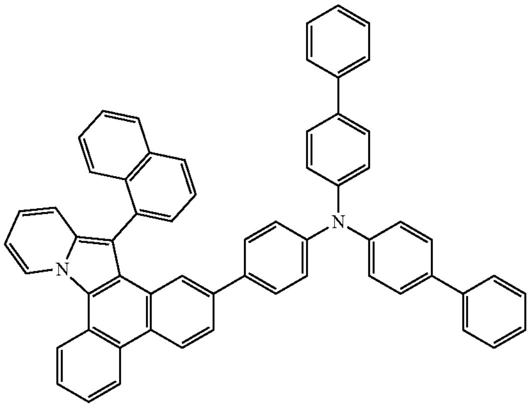
F23
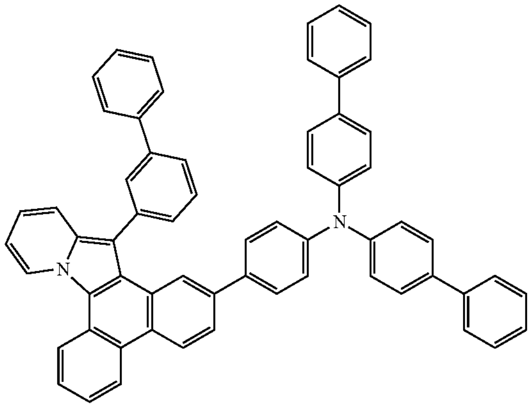

-continued
F24
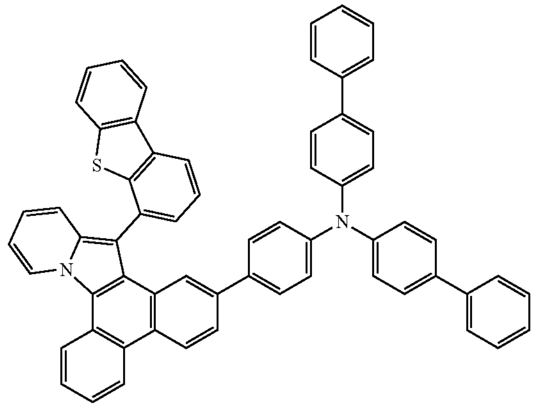
F25
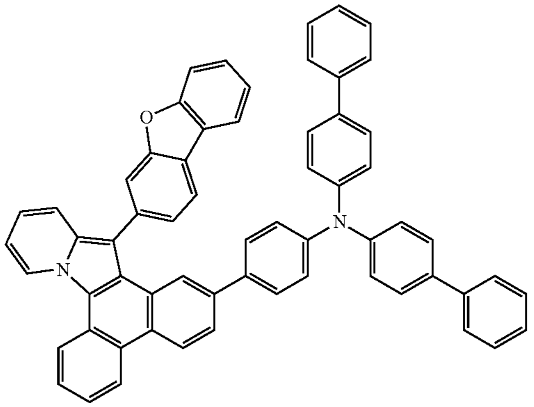
F26
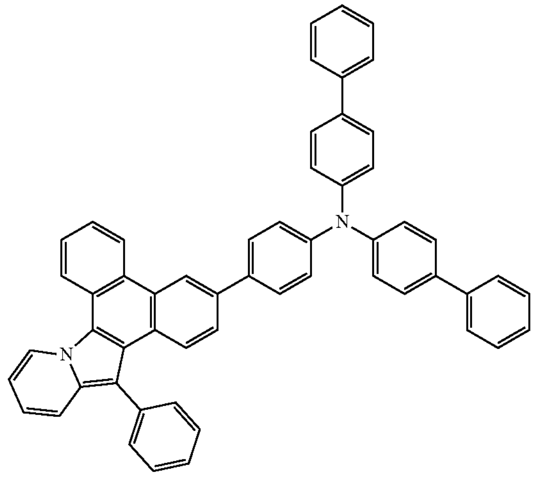
F27
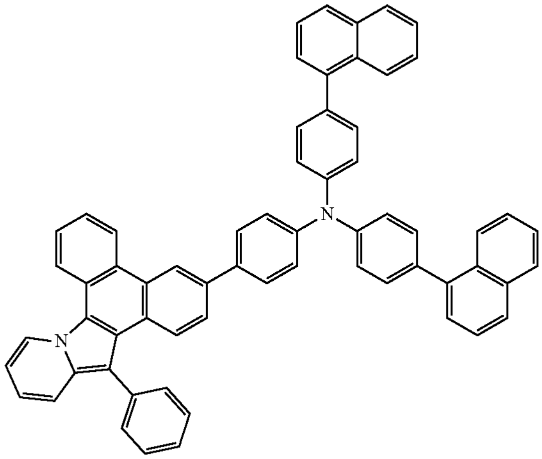
F28
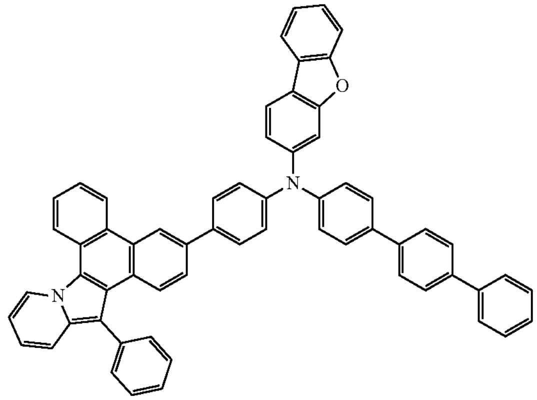
F29
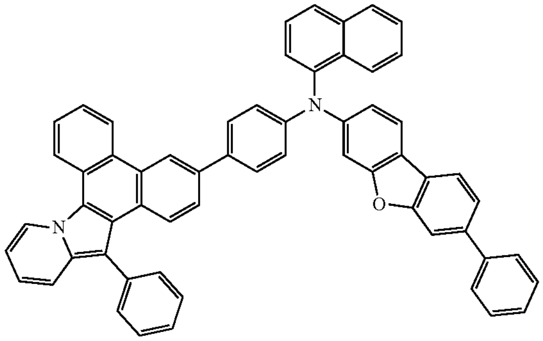
F30
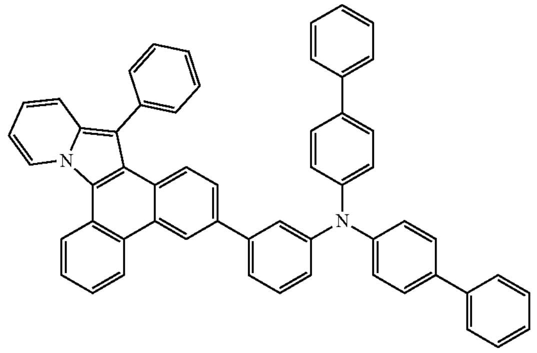
F31
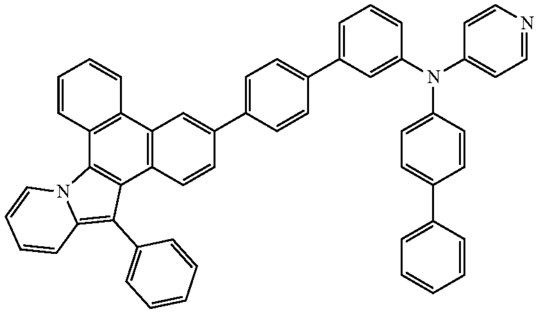

-continued
F32
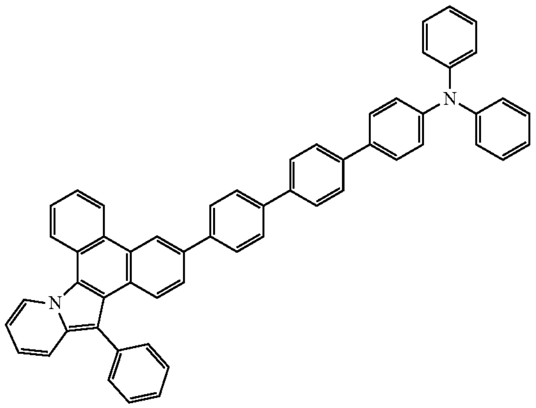
F33
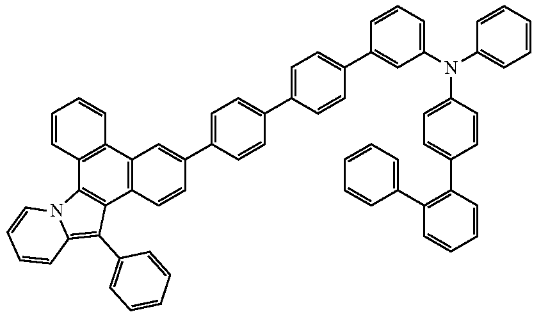
F34
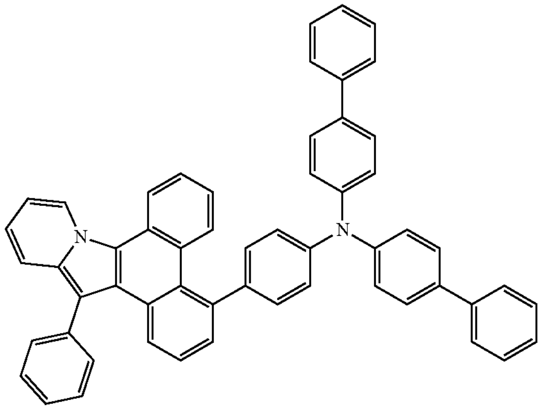
F35
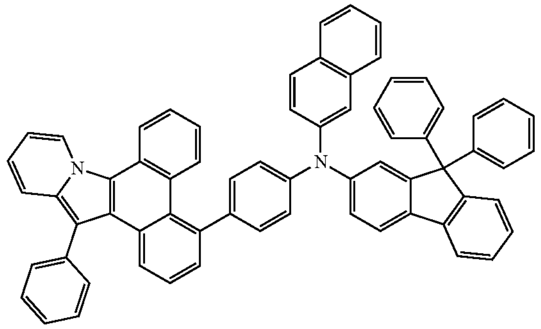
F36
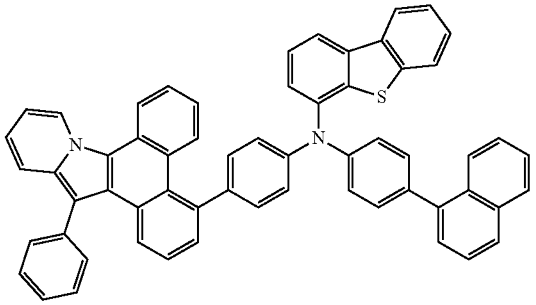
F37
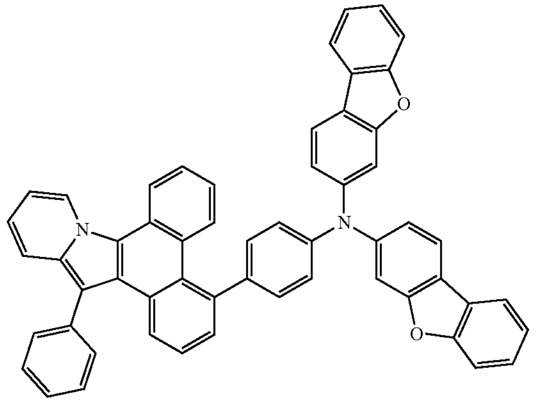
F38
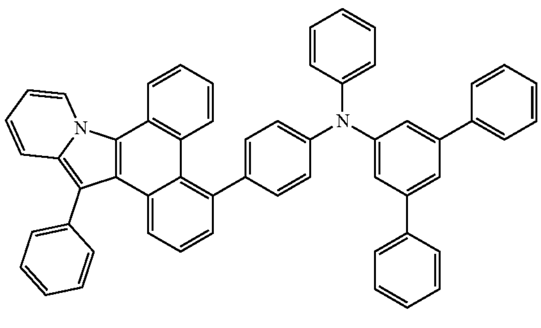
F39
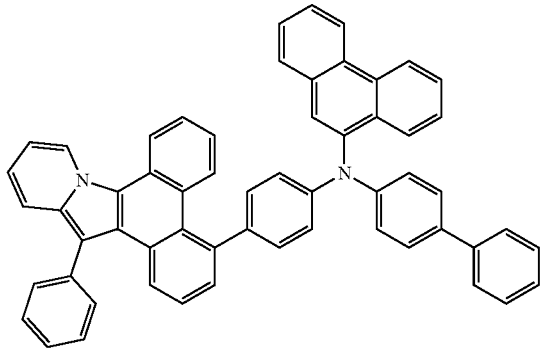

-continued
F40
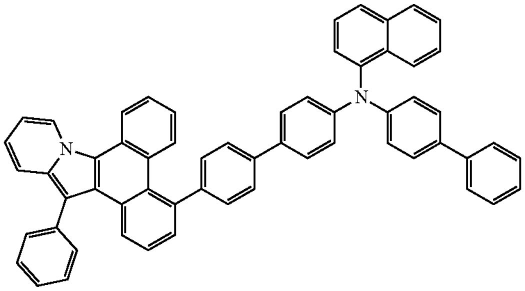
F41
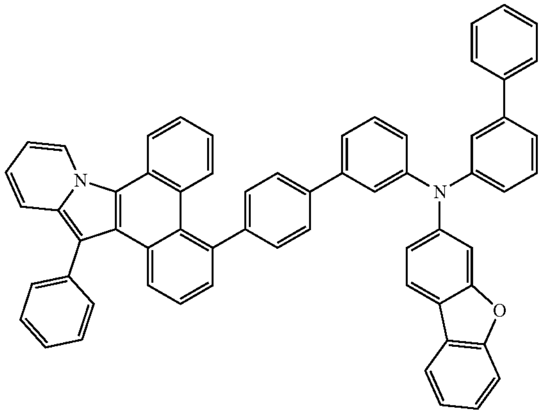
F42
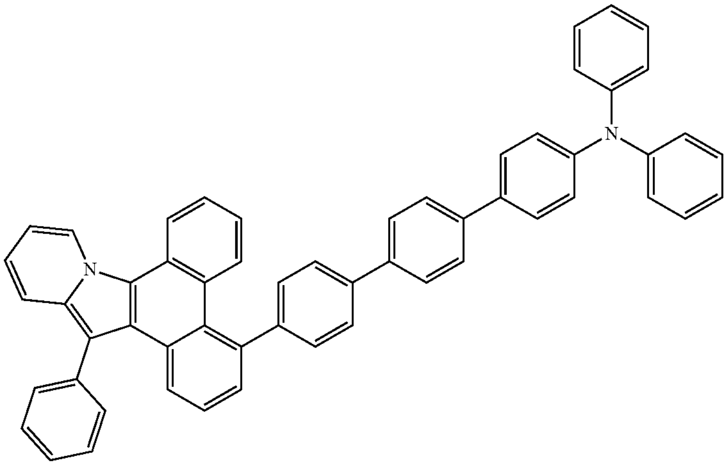
F43
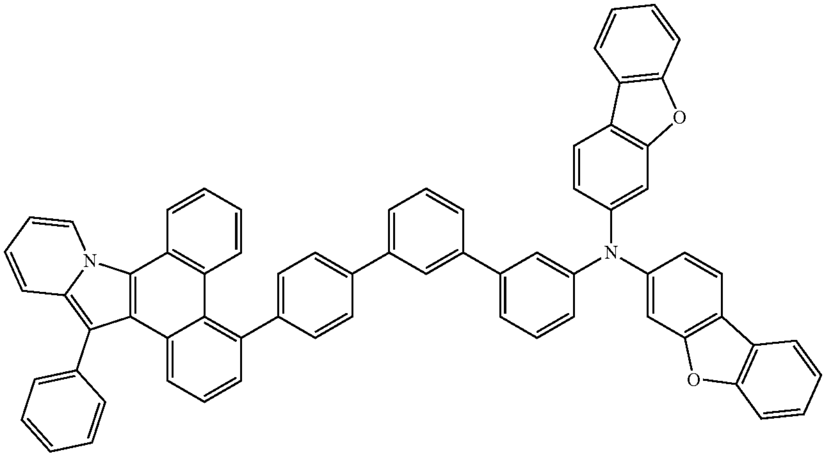

-continued
F44
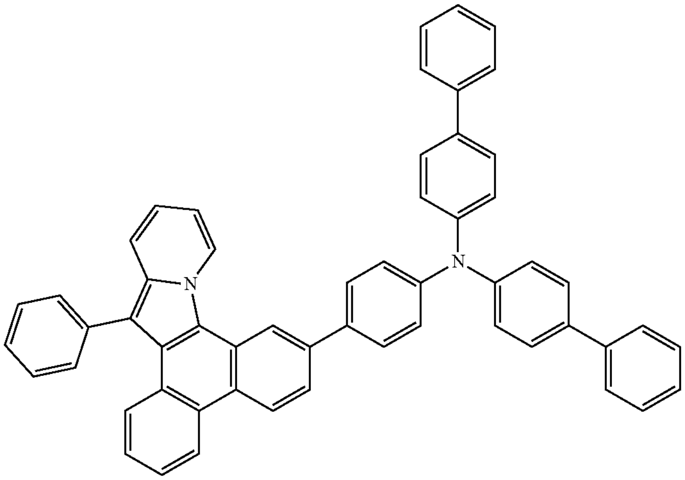
F45
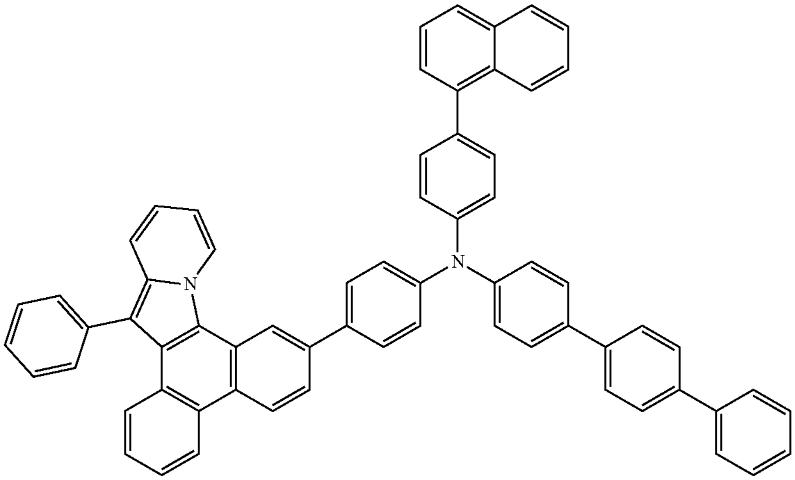
F46
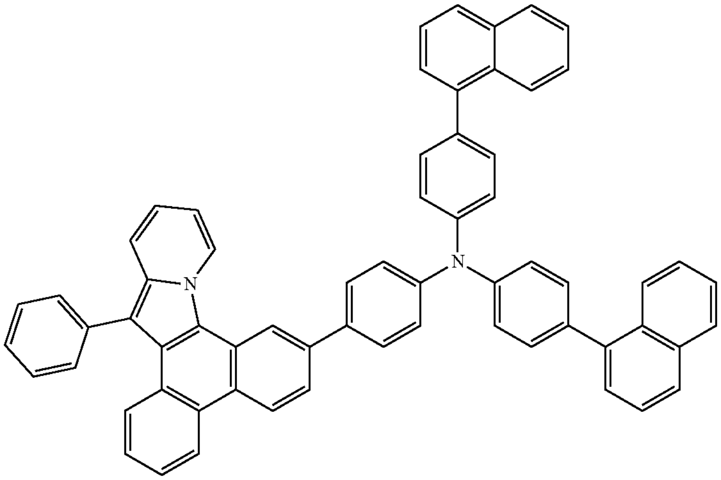

-continued
F47
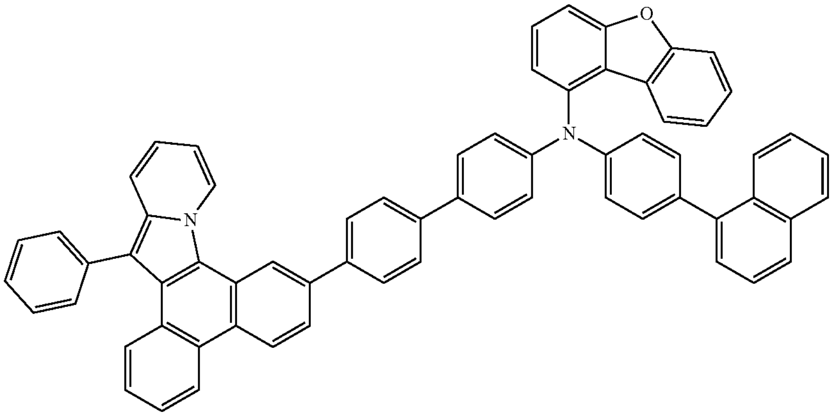
F48
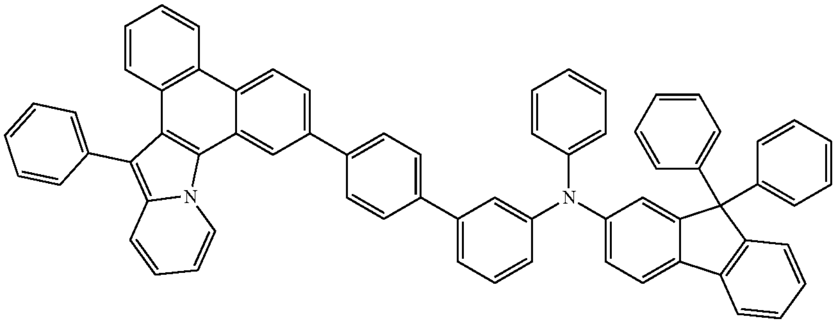
F49
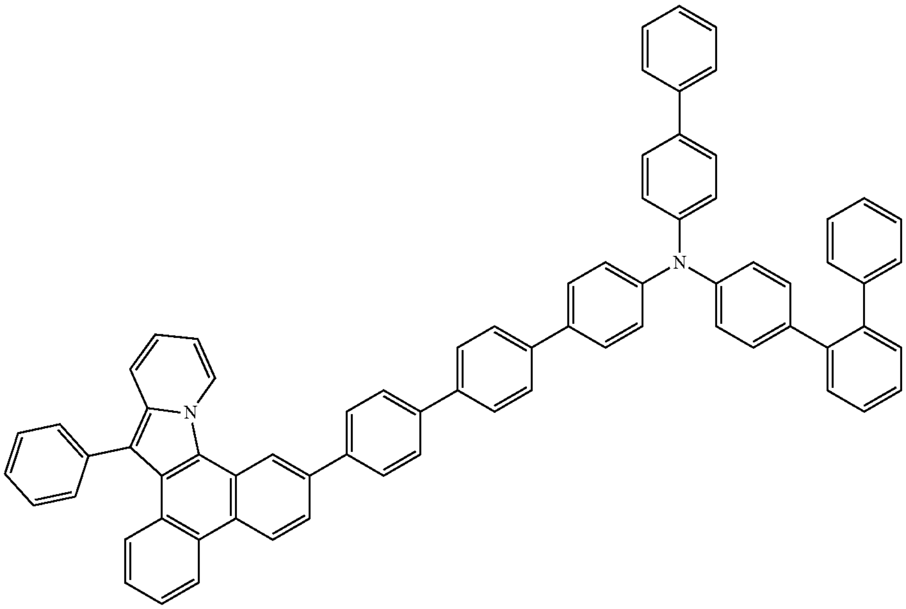

-continued
F50
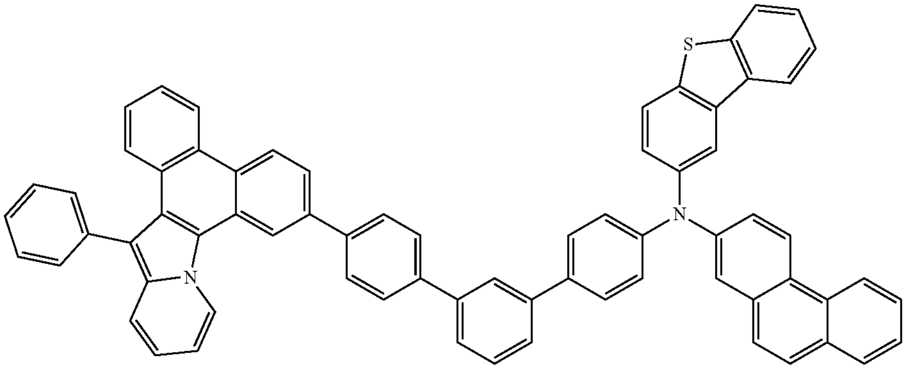
F51
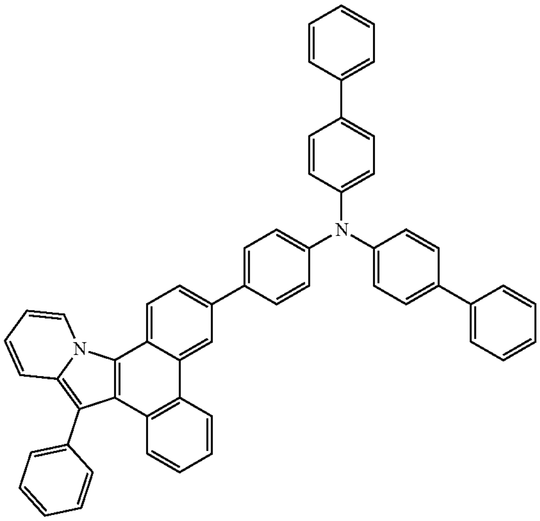
F52
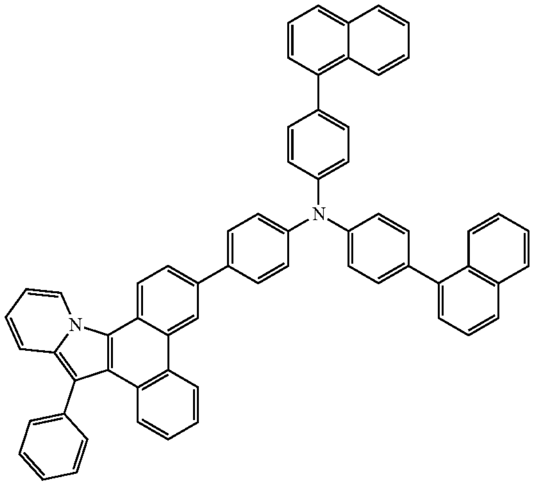
F53
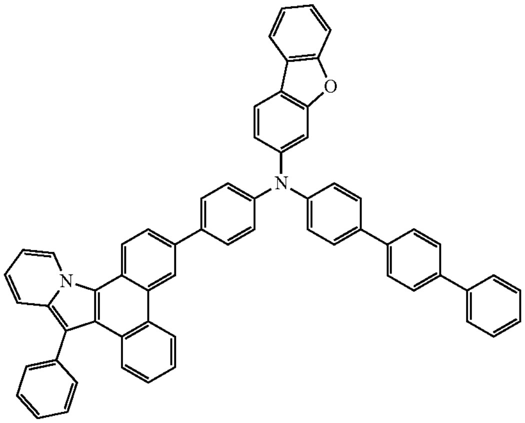
F54
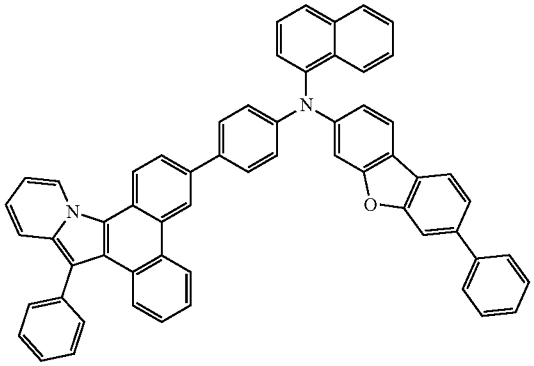

-continued
F55
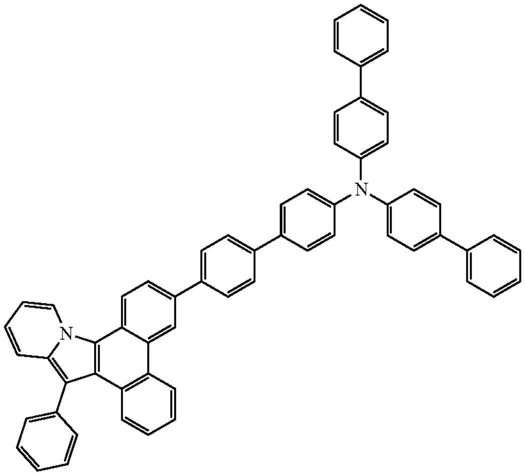
F56
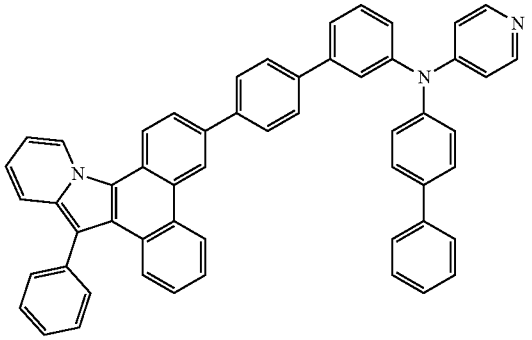
F57
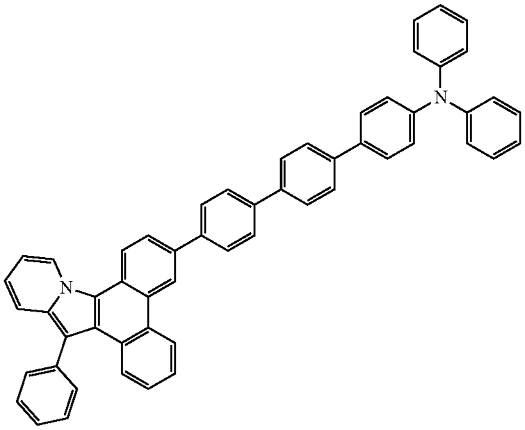
F58
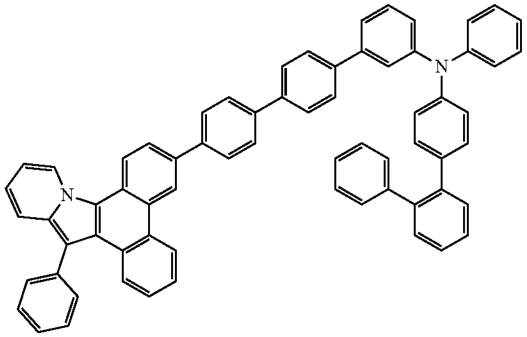
F59
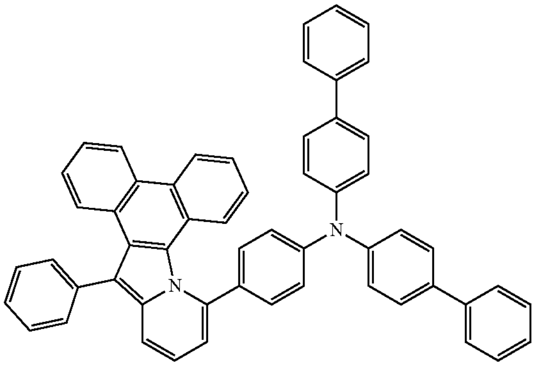
F60
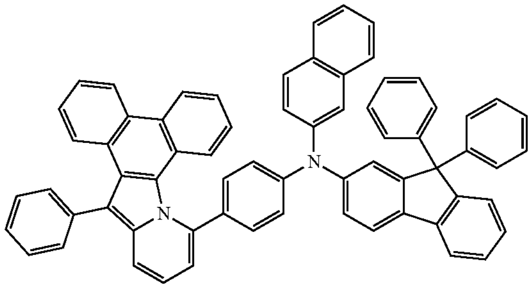
F61
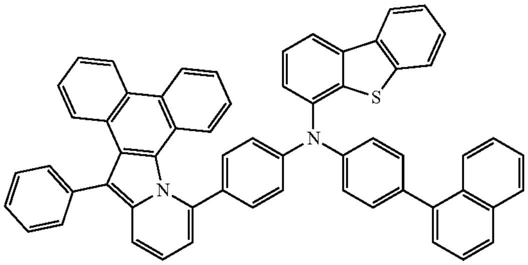
F62
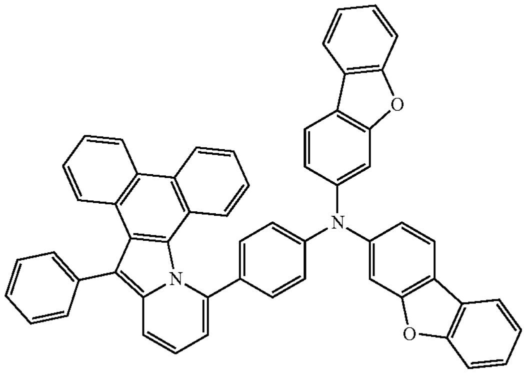

-continued
F63
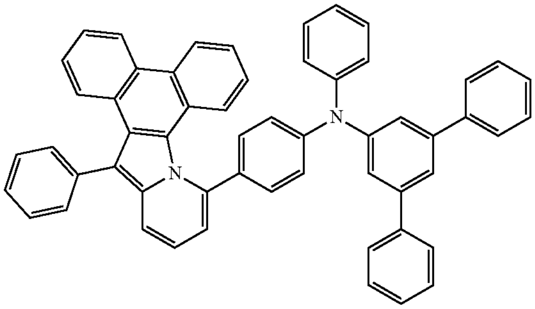
F64
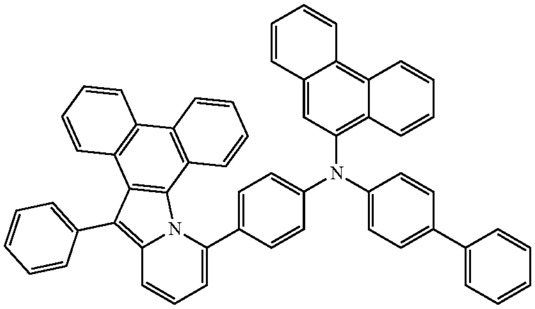
F65
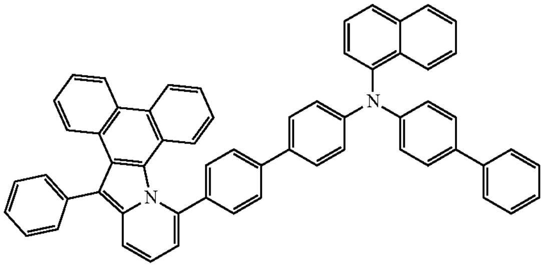
F66
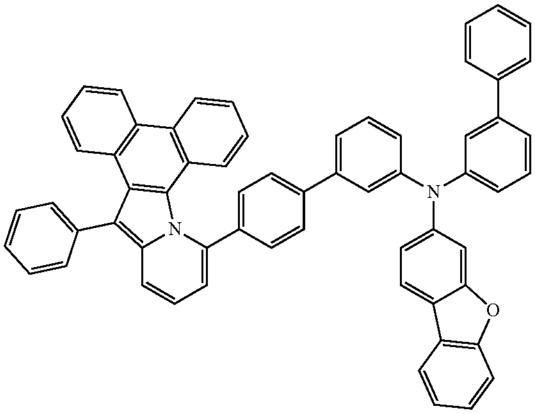
F67
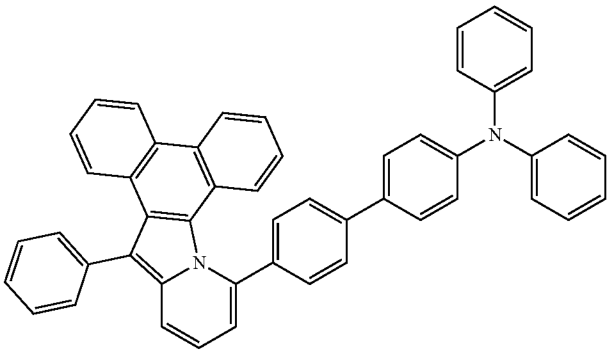
F68
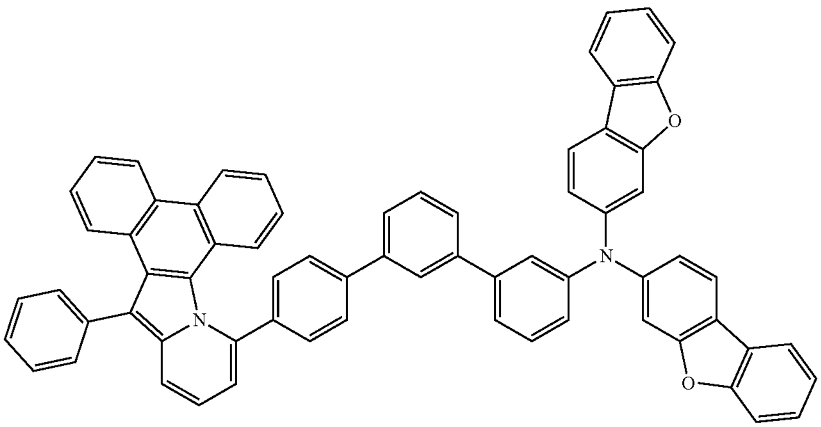

-continued
F69
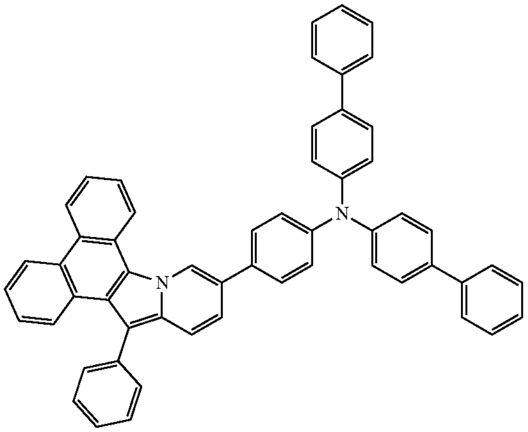
F70
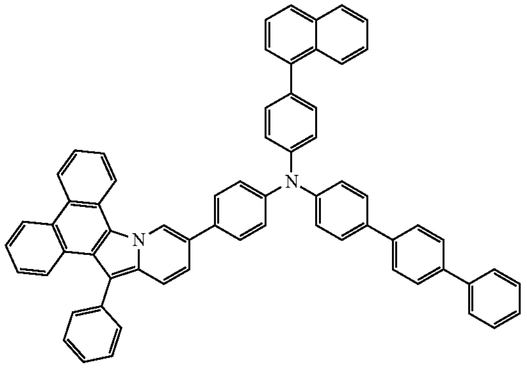
F71
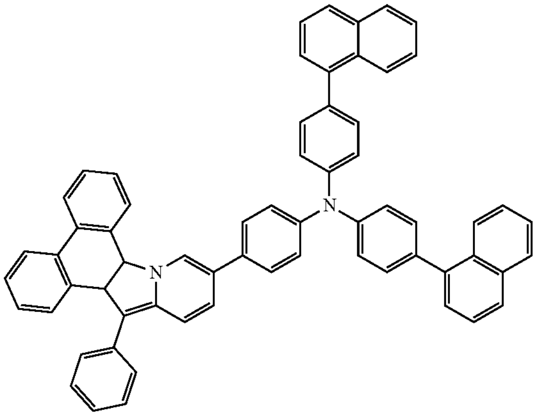
F72
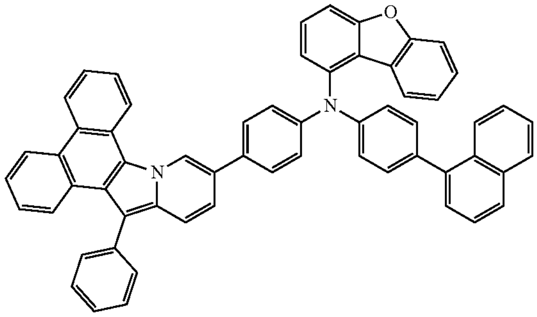
F73
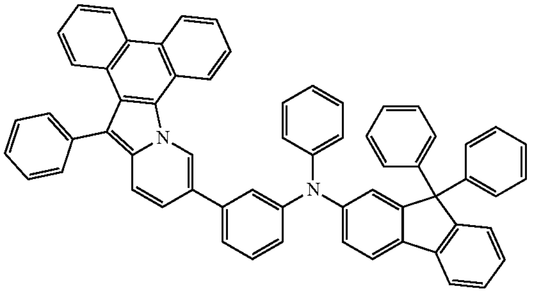
F74
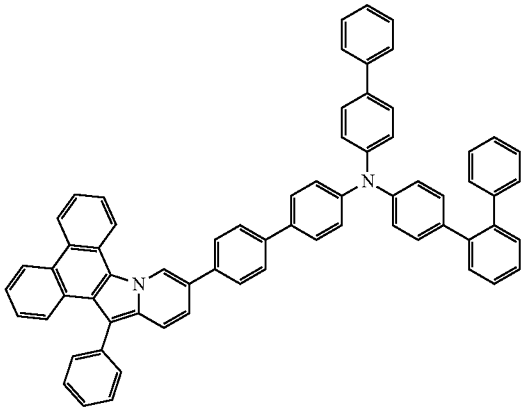

-continued
F75
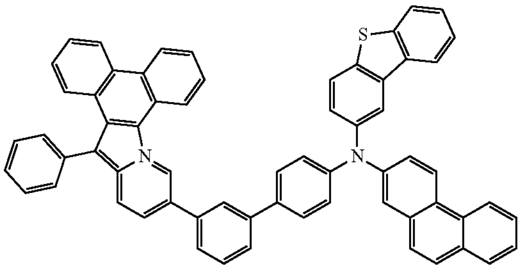
F76
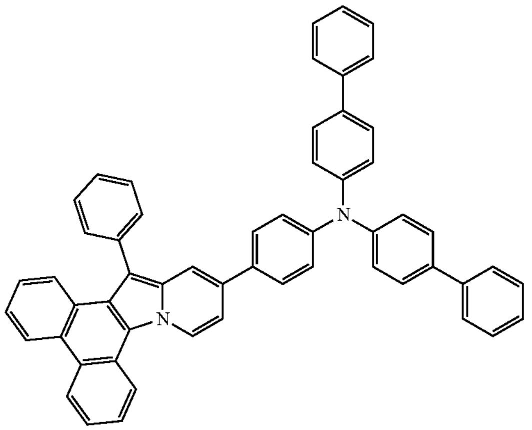
F77
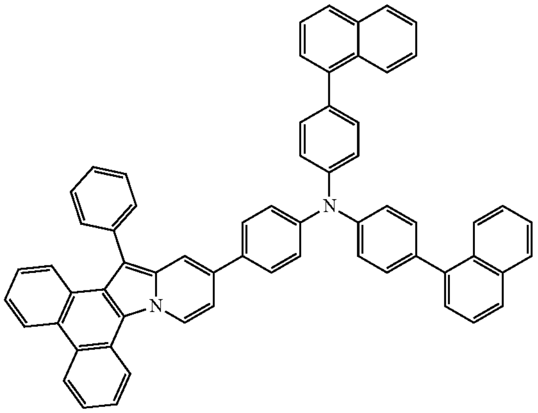
F78
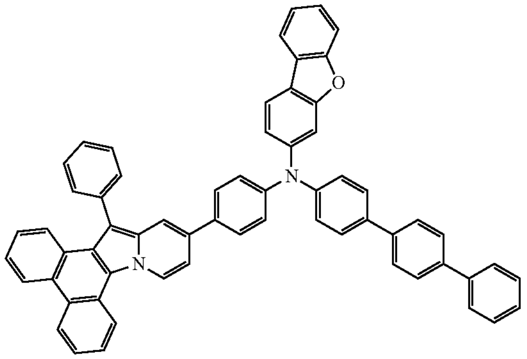
F79
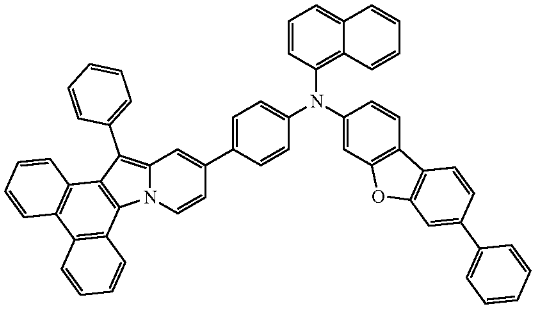
F80
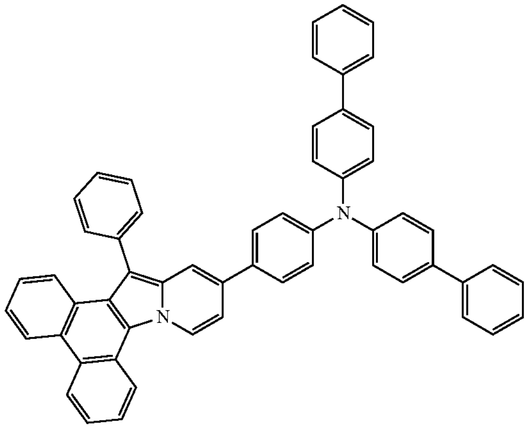

-continued
F81
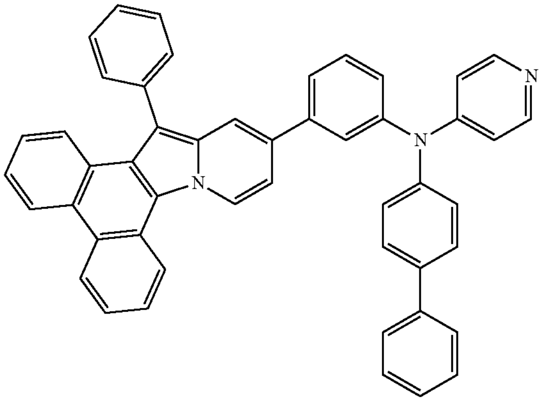
F82
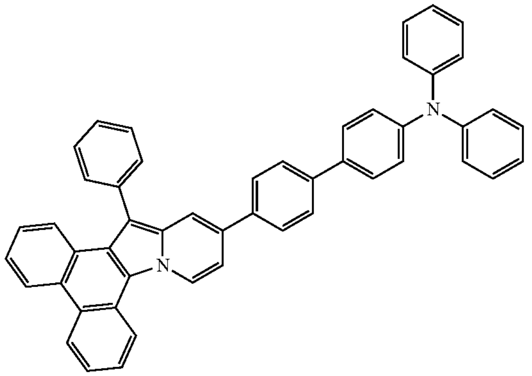
F83
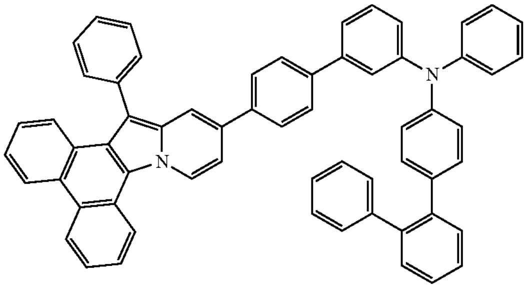
F84
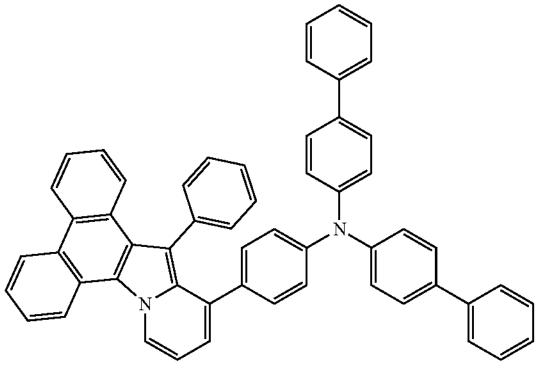
F85
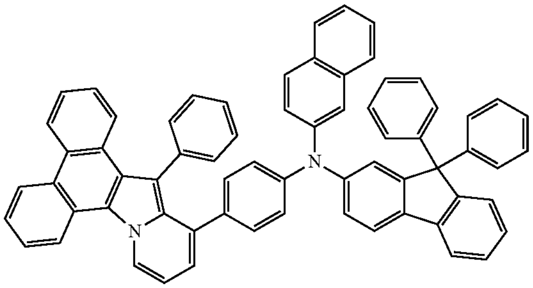
F86
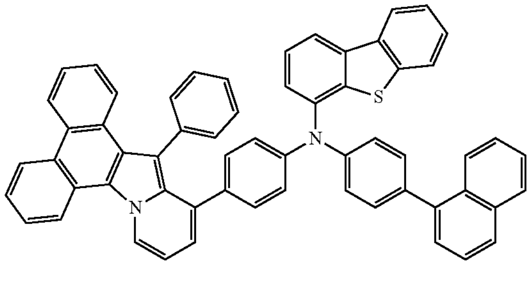
F87
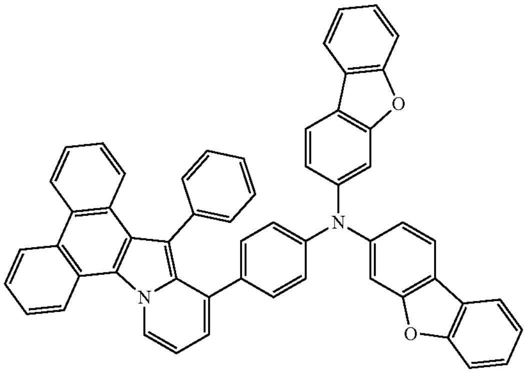
F88
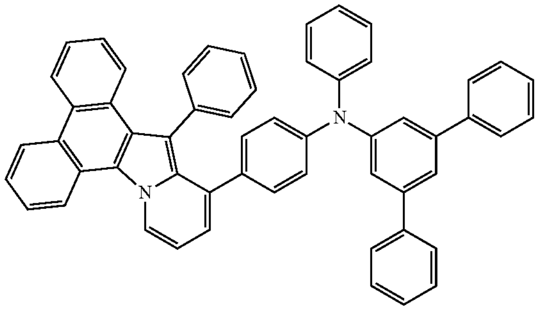

-continued
F89
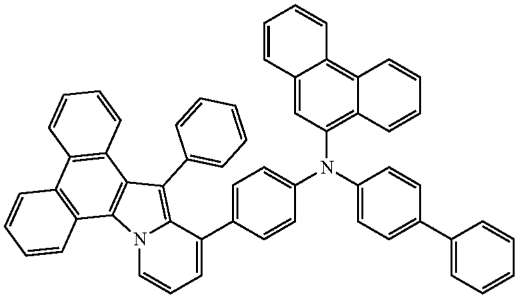
F90
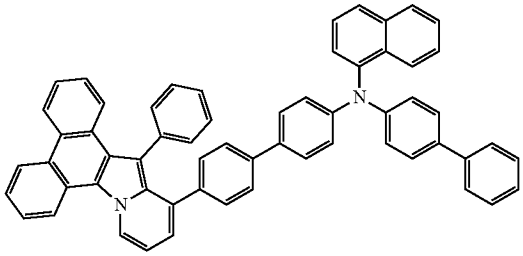
F91
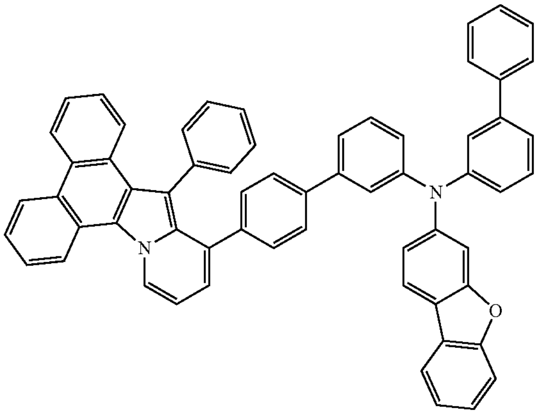
F92
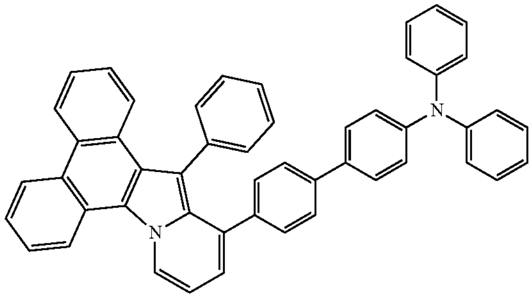
F93
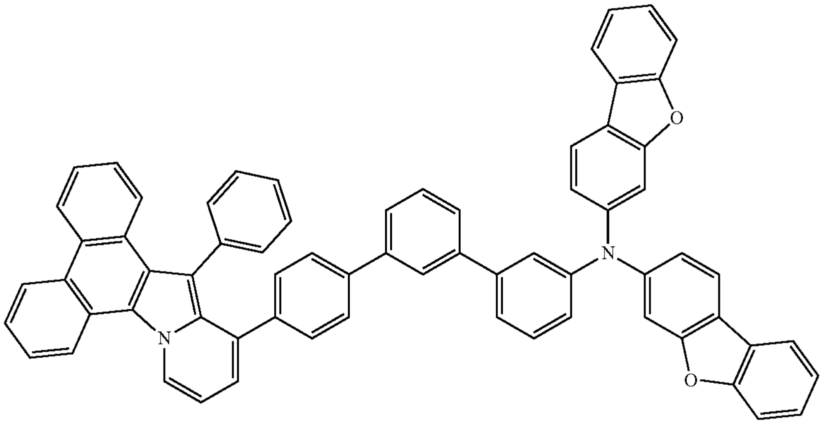
F94
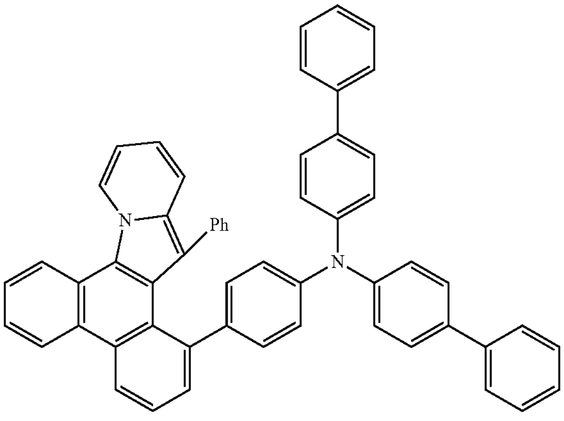
F95
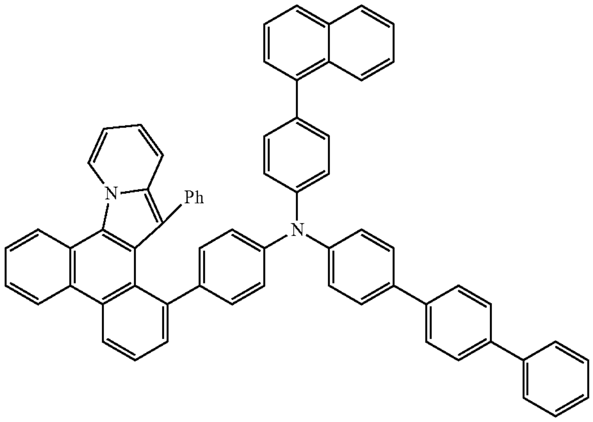

-continued
F96
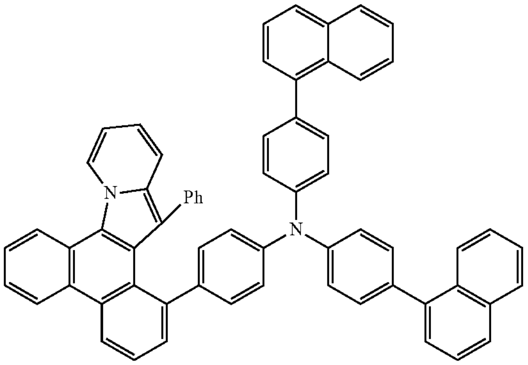
F97
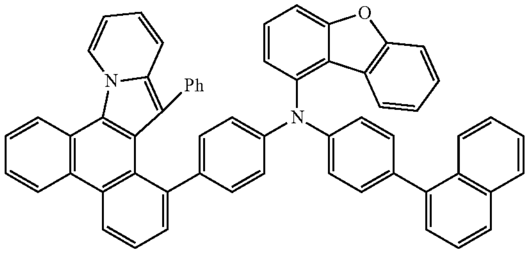
F98
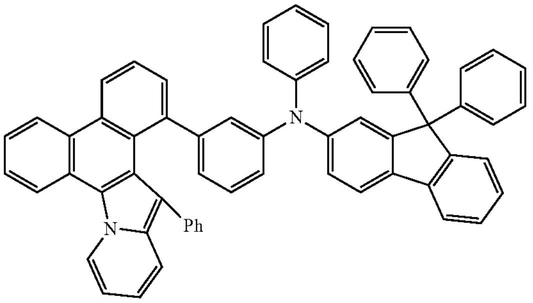
F99
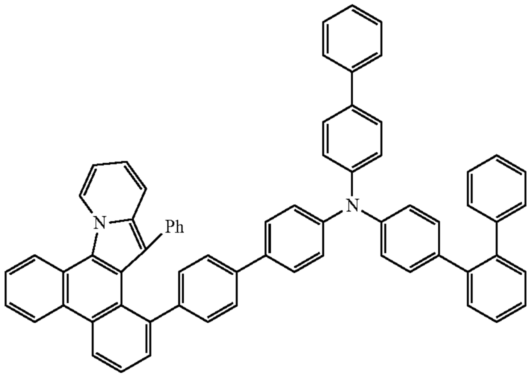
F100
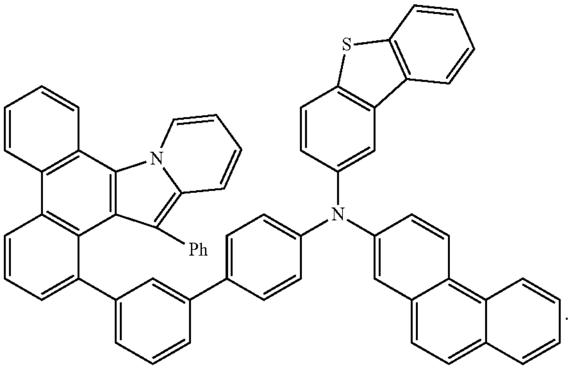
* * * * *

UNITED STATES PATENT AND TRADEMARK OFFICE

CERTIFICATE OF CORRECTION

PATENT NO. : 11,737,355 B2
APPLICATION NO. : 16/455353
DATED : August 22, 2023
INVENTOR(S) : Takuya Uno It is certified that error appears in the above-identified patent and that said Letters Patent is hereby corrected as shown below:

In the Claims

In Column 294, Line 61, in Claim 7, delete “ring forming” and insert -- ring-forming --.

In Column 365, Line 2, in Claim 13, after “ 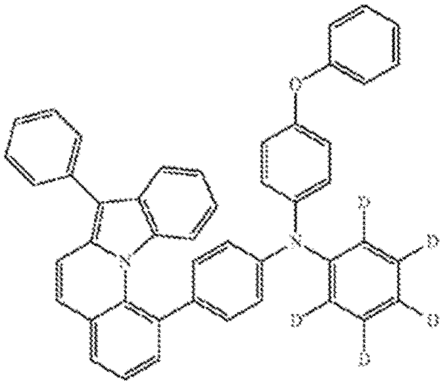 ” insert -- C13 --.

In Column 378, Line 1, in Claim 13, in Compound Group 1 - C51, delete

“ 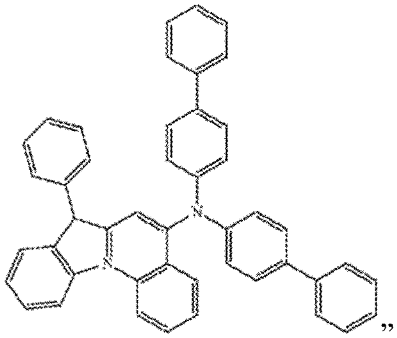 ” and insert -- 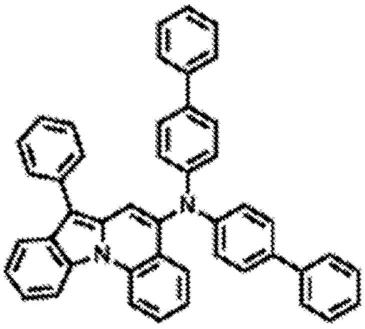 --.

In Columns 427-428, Line 1, in Claim 13, in Compound Group 1 - D100, delete

Signed and Sealed this
Thirtieth Day of April, 2024

Katherine Kelly Vidal
*Director of the United States Patent and Trademark Office*

“ 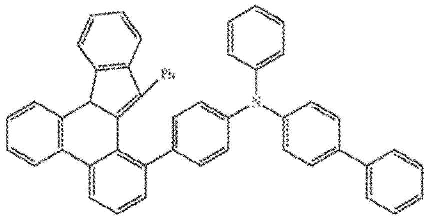 ” and insert -- 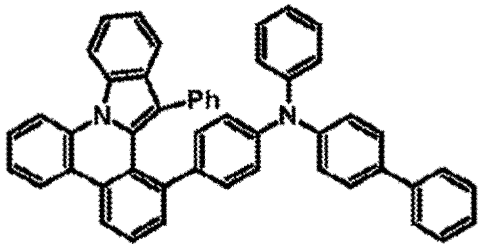 --.

In Column 428, Line 1, in Claim 13, in Compound Group 1 - D99, delete

“ 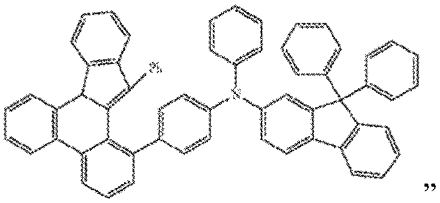 ” and insert -- 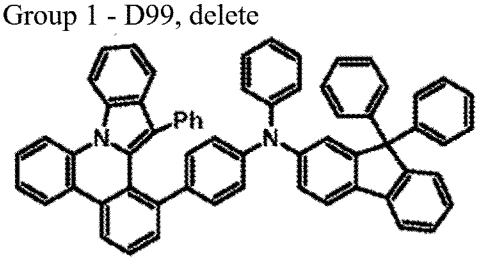 --.

In Column 495, Line 1, in Claim 13, in Compound Group 2 - F87, delete

“ 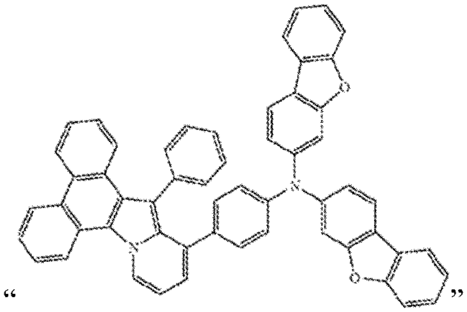 ” and insert -- 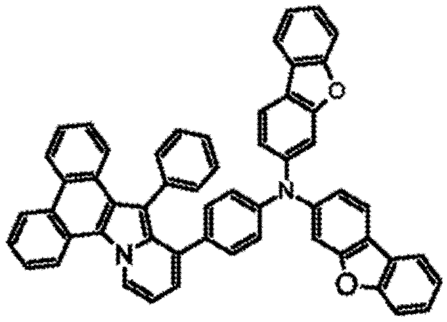 --.

In Columns 499-500, Line 1, in Claim 13, in Compound Group 2 - F100, after

“ 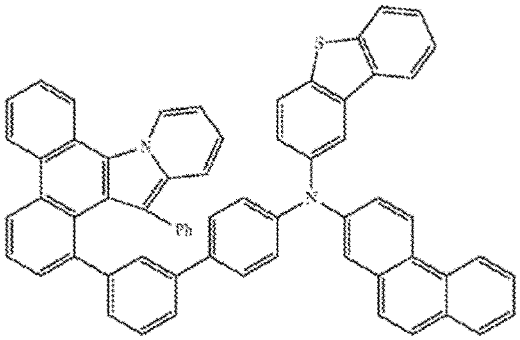 ” insert -- . --.

In Column 501, Line 18, in Claim 16, delete “$R_5$” and insert -- $R_8$ --.

In Column 501, Line 40, in Claim 17, delete “on” and insert -- or --.

In Column 501, Line 41, in Claim 17, delete “ring forming” and insert -- ring-forming --.

In Column 504, Line 34, in Claim 24, delete “ring forming” and insert -- ring-forming --.

In Column 521, Line 1, in Claim 25, in Compound Group 1 - A50, delete
“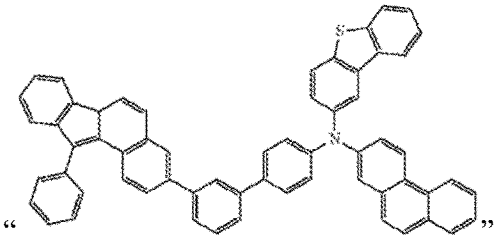” and insert -- 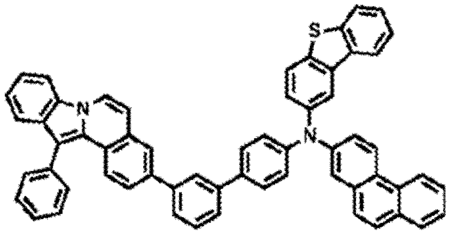 --.
In Column 619, Line 1, in Claim 25, in Compound Group 1 - E53, delete “E53” and insert -- D53 --.
In Column 645, Line 1, in Claim 25, in Compound Group 2 - E44, delete
“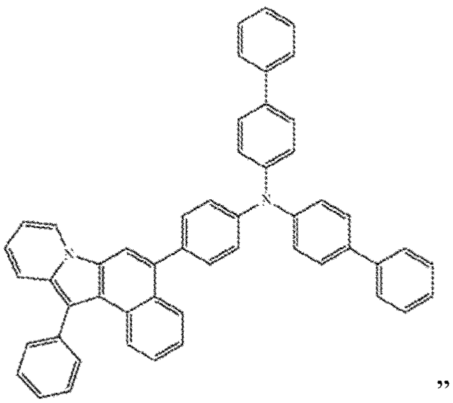” and insert -- 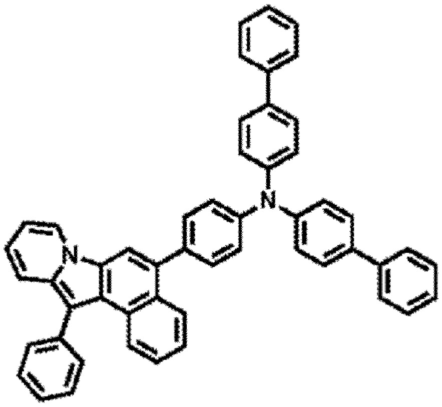 --.
In Column 645, Line 1, in Claim 25, in Compound Group 2 - E46, delete
“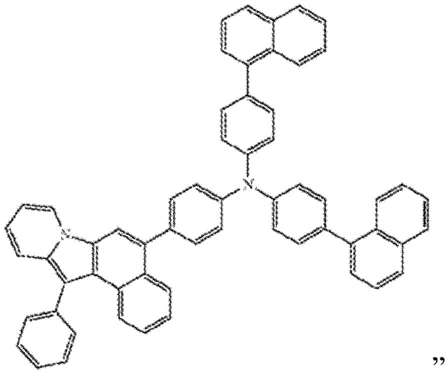” and insert -- 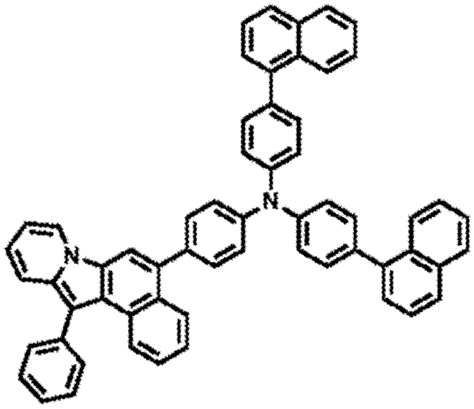 --.
In Column 646, Line 1, in Claim 25, in Compound Group 2 - E45, delete " 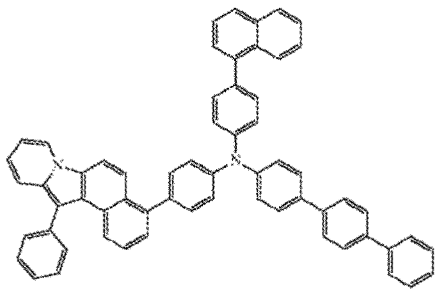 " and insert -- 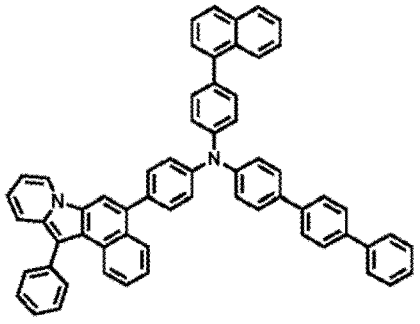 --.
In Column 646, Line 1, in Claim 25, in Compound Group 2 - E47, delete
" 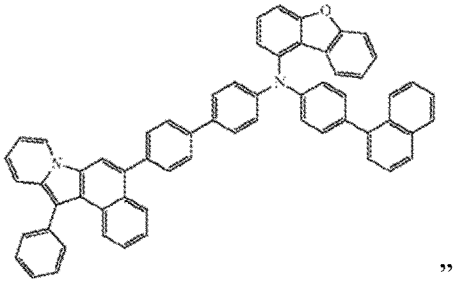 " and insert -- 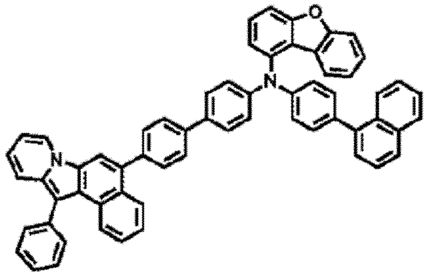 --.
In Column 664, Line 1, in Claim 25, in Compound Group 2 - F5, delete
" 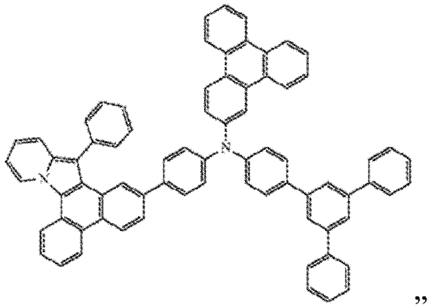 " and insert -- 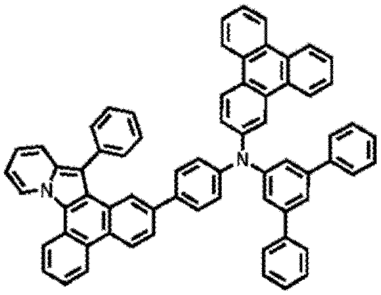 --.
In Column 689, Line 1, in Claim 25, in Compound Group 2 - F87, delete
" 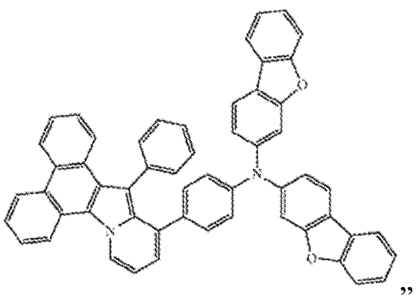 " and insert -- 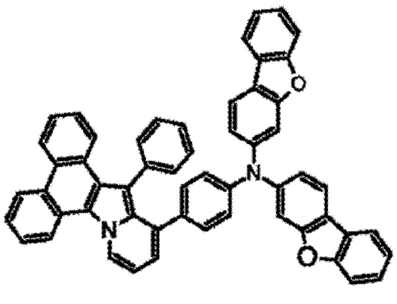 --.